US010487324B2

(12) United States Patent
Miller et al.

(10) Patent No.: US 10,487,324 B2
(45) Date of Patent: Nov. 26, 2019

(54) METHODS TO DETECT MOTOR NEURON DISEASE COMPRISING MICRO-RNAS

(71) Applicant: Washington University, St. Louis, MO (US)

(72) Inventors: Timothy M. Miller, St. Louis, MO (US); Mariah Lawler, St. Louis, MO (US); Ted Hyman, St. Louis, MO (US); Erica Koval, St. Louis, MO (US); Joseph Dougherty, St. Louis, MO (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 0 days.

(21) Appl. No.: 15/553,922

(22) PCT Filed: Feb. 25, 2016

(86) PCT No.: PCT/US2016/019602

§ 371 (c)(1),
(2) Date: Aug. 25, 2017

(87) PCT Pub. No.: WO2016/138287

PCT Pub. Date: Sep. 1, 2016

(65) Prior Publication Data

US 2018/0094259 A1 Apr. 5, 2018

Related U.S. Application Data

(60) Provisional application No. 62/120,654, filed on Feb. 25, 2015.

(51) Int. Cl.
*C12N 15/11* (2006.01)
*A61K 48/00* (2006.01)
(Continued)

(52) U.S. Cl.
CPC ........ *C12N 15/113* (2013.01); *A61K 31/7105* (2013.01); *A61P 25/28* (2018.01);
(Continued)

(58) Field of Classification Search
CPC ........... C12N 15/113; C12N 2310/141; C12N 2320/30; A61P 25/28; C12Q 2600/178
See application file for complete search history.

(56) References Cited

U.S. PATENT DOCUMENTS 4,522,811 A 6/1985 Eppstein et al.
4,880,635 A 11/1989 Janoff et al.
(Continued)

FOREIGN PATENT DOCUMENTS

WO 1988009810 A1 12/1988
WO 1989010134 A1 11/1989
(Continued)

OTHER PUBLICATIONS miRGeneDB, for MIR-218 Family Name. Downloaded from http://mirgenedb.org/show/dre/Mir-218-P1 on Jun. 9, 2018.*
(Continued)

*Primary Examiner* — Terra C Gibbs
(74) *Attorney, Agent, or Firm* — Polsinelli PC

(57) ABSTRACT

The present invention relates to compositions and methods for detecting motor neuron-specific miRNAs in a population of cells or subject. More particularly, the invention relates to detecting motor neuron-specific miRNAs to detect and treat motor neuron diseases associated with dysregulation of motor neuron-specific miRNAs, such as Amyotrophic Lateral Sclerosis (ALS).

5 Claims, 17 Drawing Sheets
(8 of 17 Drawing Sheet(s) Filed in Color)

Syn / ChAT / GFAP / Lyz2
Cre recombinase
STOP
GFP-myc-Ago2
loxP loxP

| Cell Promoter | Targeted Cells |
|---|---|
| Synapsin1 **(Syn)** | Pan-neuronal |
| Choline acetyltransferase **(ChAT)** | Cholinergic neurons including all motor neurons |
| Glial fibrillary acidic protein **(GFAP)** | Astrocytes, oligodendroglia, ependyma, and few neurons |
| Lysozyme 2 **(Lyz2, LysM)** | Myeloid cells including monocytes, microglia, macrophages, granulocytes |

(51) Int. Cl.

| | |
|---|---|
| ***C07H 21/02*** | (2006.01) |
| ***C07H 21/04*** | (2006.01) |
| ***C12N 15/113*** | (2010.01) |
| ***A61P 25/28*** | (2006.01) |
| ***A61K 31/7105*** | (2006.01) |
| ***C12Q 1/6883*** | (2018.01) |

(52) U.S. Cl.

CPC .......... *C12N 15/111* (2013.01); *C12Q 1/6883* (2013.01); *C12N 2310/141* (2013.01); *C12N 2320/10* (2013.01); *C12N 2320/30* (2013.01); *C12Q 2600/178* (2013.01)

(56) References Cited

U.S. PATENT DOCUMENTS

| | | | |
|---|---|---|---|
| 4,906,477 | A | 3/1990 | Kurono et al. |
| 4,911,928 | A | 3/1990 | Wallach |
| 4,917,951 | A | 4/1990 | Wallach |
| 4,920,016 | A | 4/1990 | Allen et al. |
| 4,921,757 | A | 5/1990 | Wheatley et al. |
| 5,328,470 | A | 7/1994 | Nabel et al. |
| 2008/0306006 | A1 | 12/2008 | Croce et al. |
| 2010/0167948 | A1 | 7/2010 | Krichevsky et al. |
| 2014/0120545 | A1 | 5/2014 | Umansky et al. |
| 2014/0235697 | A1 | 8/2014 | Weiner et al. |
| 2015/0037299 | A1 | 2/2015 | Brodie et al. |

FOREIGN PATENT DOCUMENTS

| | | | |
|---|---|---|---|
| WO | 2008153692 | A2 | 12/2008 |
| WO | 2009043353 | A2 | 4/2009 |
| WO | 2014020608 | A1 | 2/2014 |
| WO | 2014192907 | A1 | 12/2014 |
| WO | 2016138287 | A1 | 9/2016 |

OTHER PUBLICATIONS

Butovsky et al. (Ann Neurol, Jan. 2015 vol. 77:75-99).*
Zhou et al. (Int J Clin Exp Pathol, 2013 vol. 6(9):pp. 1826-1838).*
Packer et al. (J. Neurosci. 28, 14341-14346 (2008).*
Ricci et al. (Cells 2018 vol. 7:pp. 1-19).*
Aluise, C. et al., "Peptides and proteins in plasma and cerebrospinal fluid as biomarkers for the prediction, diagnosis, and monitoring of therapeutic efficacy of Alzheimer's disease," Biochim. Biophys. Acta, 2008, pp. 549-558, vol. 1782, Elsevier B.V.
Amin, N. et al., "Loss of motoneuron-specific microRNA-218 causes systemic neuromuscular failure," Sci., Dec. 18, 2015, pp. 1525-1529, vol. 350, No. 6267.
Ardekani, A. et al., "The Role of MicroRNAs in Human Diseases," Avicenna J. Med. Biotechnol., 2010, pp. 161-179, vol. 2, No. 4.
Arroyo, J. et al., "Argonaute2 complexes carry a population of circulating microRNAs independent of vesicles in human plasma," PNAS, Mar. 22, 2011, pp. 5003-5008, vol. 108, No. 12.
Bartel, D. et al., "Isolation of New Ribozymes from a Large Pool of Random Sequences," Sci., Sep. 10, 1993, pp. 1411-1418, vol. 261, No. 5127.
Boillee, S. et al., "Onset and Progression in Inherited ALS Determined by Motor Neurons and Microglia," Sci., Jun. 2, 2006, pp. 1389-1392, vol. 312, No. 5778.
Butovsky, O. et al., "Targeting miR-155 restores abnormal microglia and attenuates disease in SOD1 mice," HHS Public Access Author Manuscript, available in PMC Jan. 1, 2016, pp. 1-38, Published in final edited form as: Ann. Neurol., Jan. 2015, pp. 75-99, vol. 77, No. 1.
Chen, S-H. et al., "Gene therapy for brain tumors: Regression of experimental gliomas by adenovirus-mediated gene transfer in vivo," PNAS, Apr. 1994, pp. 3054-3057, vol. 91.
Chen, X. et al., "Characterization of microRNAs in serum: a novel class of biomarkers for diagnosis of cancer and other diseases," Cell Res., 2008, pp. 997-1006, vol. 18, No. 10, Nature Publishing Group.
Dougherty, J. et al., "Analytical approaches to RNA profiling data for the identification of genes enriched in specific cells," Nucl. Acids Res., 2010, pp. 4218-4230, vol. 38, No. 13, Oxford University Press.
Doyle, J. et al., "Application of a Translational Profiling Approach for the Comparative Analysis of CNS Cell Types," Cell, Nov. 14, 2008, pp. 749-762, vol. 135, No. 4, Elsevier Inc.
Fiore, R. et al., "MicroRNA function in neuronal development, plasticity and disease," Biochim. Biophys. Acta, 2008, pp. 471-478, vol. 1779, No. 8.
Gaughwin, P. et al., "Stage-Specific Modulation of Cortical Neuronal Development by Mmu-miR-134," Cereb. Cortex, Aug. 2011, pp. 1857-1869, vol. 21, No. 8, Oxford University Press.
Haseloff, J. et al., "Simple RNA enzymes with new and highly specific endoribonuclease activities," Nature, Aug. 18, 1988, pp. 585-591, vol. 334, No. 6183, Nature Publishing Group.
He, M. et al., "Cell-Type-Based Analysis of MicroRNA Profiles in the Mouse Brain," Neuron, Jan. 12, 2012, pp. 35-48, vol. 73, No. 1, Elsevier Inc.
Helene, C., "The anti-gene strategy: control of gene expression by triplex-forming-oligonucleotides," Anti-Cancer Drug Design, Dec. 1, 1991, pp. 569-584, vol. 6, No. 6, Macmillan Press Ltd.
Helene, C. et al., "Control of Gene Expression by Triple Helix-Forming Oligonucleotides. The Antigene Strategy," Ann. New York Acad. Sci., Oct. 1992, pp. 27-36, vol. 660, No. 1.
Howland, D. et al., "Focal loss of the glutamate transporter EAAT2 in a transgenic rat model of SOD1 mutant-mediated amyotrophic lateral sclerosis (ALS)," PNAS, Feb. 5, 2002, pp. 1604-1609, vol. 99, No. 3.
Hoye, M. et al., "MicroRNA Profiling Reveals Marker of Motor Neuron Disease in ALS Models," J. Neurosci., May 31, 2017, pp. 5574-5586, vol. 37, No. 22.
Hyrup, B. et al., "Peptide Nucleic Acids (PNA): Synthesis, Properties and Potential Applications," Bioorg. Med. Chem., Jan. 1996, pp. 5-23, vol. 4, No. 1, Elsevier Science Ltd., Great Britain.
Ilieva, H. et al., "Non-cell autonomous toxicity in neurodegenerative disorders: ALS and beyond," J. Cell Biol., 2009, pp. 761-772, vol. 187, No. 6, The Rockefeller University Press.
International Search Report and Written Opinion dated May 17, 2016 from related PCT Application No. PCT/US2016/019602, 12 pgs.
Kaalund, S. et al., "Aberrant expression of miR-218 and miR-204 in human mesial temporal lobe epilepsy and hippocampal sclerosis—Convergence on axonal guidance," Epilepsia, 2014, pp. 2017-2027, vol. 55, No. 12.
Klipper-Aurbach, Y. et al., "Mathematical Formulae for the Prediction of the Residual Beta Cell Function During the First Two Years of Disease in Children and Adolescents with Insulin-Dependent Diabetes Mellitus," Med. Hypotheses, Nov. 1995, pp. 486-490, vol. 45, No. 5, Pearson Professional Ltd.
Kocerha, J. et al., "MicroRNA-219 modulates NMDA receptor-mediated neurobehavioral dysfunction," PNAS, Mar. 3, 2009, pp. 3507-3512, vol. 106, No. 9.
Koval, E. et al., "Method for widespread microRNA-155 inhibition prolongs survival in ALS-model mice," Human Molecular Genetics, 2013, pp. 4127-4135, vol. 22, No. 20, Oxford University Press.
Lemaitre, M. et al., "Specific antiviral activity of a poly(L-lysine)-conjugated oligodeoxyribonucleotide sequence complementary to vesicular stomatitis virus N protein mRNA initiation site," PNAS, Feb. 1987, pp. 648-652, vol. 84.
Letsinger, R. et al., "Cholesteryl-conjugated oligonucleotides: Synthesis, properties, and activity as inhibitors of replication of human immunodeficiency virus in cell cultures," PNAS, Sep. 1989, pp. 6553-6556, vol. 86.
Lu, X. et al., "miR-142-3p regulates the formation and differentiation of hematopoietic stem cells in vertebrates," Cell Res., 2013, pp. 1356-1368, vol. 23, No. 12.
Maher, J., "DNA Triple-Helix Formation: An Approach to Artificial Gene Repressors?," BioEssays, Dec. 1992, pp. 807-815, vol. 14, No. 12.
Mitchell, P. et al., "Circulating microRNAs as stable blood-based markers for cancer detection," PNAS, Jul. 29, 2008, pp. 10513-10518, vol. 105, No. 30.

(56) References Cited

OTHER PUBLICATIONS

O'Connell, R. et al., "Physiological and pathological roles for microRNAs in the immune system," Nat. Rev. Immunol., Feb. 2010, pp. 111-122, vol. 10, No. 2, Macmillan Publishers Limited.
Peltier, H.et al., "Normalization of microRNA expression levels in quantitative RT-PCR assays: Identification of suitable reference RNA targets in normal and cancerous human solid tissues," RNA, 2008, pp. 844-852, vol. 14, No. 5, Cold Spring Harbor Laboratory Press.
Perry-O'Keefe, H. et al., "Peptide nucleic acid pre-gel hybridization: An alternative to Southern hybridization," PNAS, Dec. 1996, pp. 14670-14675, vol. 93.
Risso, D. et al., "A modified LOESS normalization applied to microRNA arrays: a comparative evaluation," Bioinformatics, 2009, pp. 2685-2691, vol. 25, No. 20, Oxford University Press.
Sayed, D. et al., "MicroRNAs in Development and Disease," Physiol. Rev., 2011, pp. 827-887, vol. 91, No. 3.
Smith, R. et al., "Antisense oligonucleotide therapy for neurodegenerative disease," J. Clin. Invest., Aug. 2006, pp. 2290-2296, vol. 116, No. 8.
Smyth, G. et al., "Linear Models and Empirical Bayes Methods for Assessing Differential Expression in Microarray Experiments," Stat. Appl. Genet. Mol. Biol., 2004, pp. 1-25, vol. 3, No. 1, Article 3, The Berkeley Electronic Press.
Su, Z. et al., "Discovery of a Biomarker and Lead Small Molecules to Target r(GGGGCC)-Associated Defects in c9FTD/ALS," Neuron, Sep. 3, 2014, pp. 1043-1050, vol. 83, No. 5, Elsevier Inc.
Suryawanshi, H. et al., "Modulation of microRNA function by synthetic ribozymes," Mol. BioSyst., 2010, pp. 1807-1809, vol. 6, The Royal Society of Chemistry.
Thiebes, K. et al., "miR-218 is Essential to Establish Motor Neuron Fate as a Downstream Effector of Isl1-Lhx3," HHS Public Access Author Manuscript, available in PMC Jan. 27, 2016, pp. 1-34, Published in final edited form as: Nat. Commun., 2015, pp. 7718, vol. 6.
Valadi, H. et al., "Exosome-mediated transfer of mRNAs and microRNAs is a novel mechanism of genetic exchange between cells," Nat. Cell Biol., Jun. 2007, pp. 654-659, vol. 9, No. 6, Nature Publishing Group.
Van Der Krol, A. et al., "Modulation of Eukaryotic Gene Expression by Complementary RNA or DNA Sequences," BioTechniques, Nov.-Dec. 1988, pp. 958-976, vol. 6, No. 10.
Wang, K. et al., "Export of microRNAs and microRNA-protective protein by mammalian cells," Nucl. Acids Res., 2010, pp. 7248-7259, vol. 38, No. 20, Oxford University Press.
Wooley, C. et al., "Gait Analysis Detects Early Changes in Transgenic SOD1(G93A) Mice," NIH Public Access Author Manuscript, available in PMC Jul. 1, 2006, pp. 1-15, Published in final edited form as: Muscle Nerve., Jul. 2005, pp. 43-50, vol. 32, No. 1.
Xu, X. et al., "Cell Type-Specific Expression Analysis to Identify Putative Cellular Mechanisms for Neurogenetic Disorders," J. Neurosci., Jan. 22, 2014, pp. 1420-1431, vol. 34, No. 4.
Ying. Z. et al., "(2013) Loss of miR-204 Expression Enhances Glioma Migration and Stem Cell-like Phenotype," Cancer Res., Jan. 15, 2013, pp. 990-999, vol. 73, No. 2.
Zelphati, O. et al., "PNA-Dependent Gene Chemistry: Stable Coupling of Peptides and OAligonucleotides to Plasmid DNA," BioTechniques, Feb. 2000, pp. 304-316, vol. 28, No. 2.
Zon, G., "Oligonucleotide Analogues as Potential Chemotherapeutic Agents," Pharmaceutical Research, Sep. 1988, pp. 539-549, vol. 5, No. 9, Plenum Publishing Corporation.

* cited by examiner

| Cell Promoter | Targeted Cells |
|---|---|
| Synapsin1 **(Syn)** | Pan-neuronal |
| Choline acetyltransferase **(ChAT)** | Cholinergic neurons including all motor neurons |
| Glial fibrillary acidic protein **(GFAP)** | Astrocytes, oligodendroglia, ependyma, and few neurons |
| Lysozyme 2 **(Lyz2, LysM)** | Myeloid cells including monocytes, microglia, macrophages, granulocytes |

| | miRNA | pSI bs | pSI sc |
|---|---|---|---|
| ChAT | miR-218 | 0.053 | 0.016 |
| | miR-218-2 | 0.029 | 0.002 |
| | miR-138 | 0.11 | 0.087 |
| Syn | miR-431 | 0.003 | 0.006 |
| | miR-672 | 0.014 | 0.030 |
| | miR-382 | 0.051 | 0.019 |
| GFAP | miR-365 | 0.008 | 0.013 |
| | miR-497 | 0.004 | 0.017 |
| | miR-130a | 0.006 | 0.06 |
| Lyz2 | miR-223 | 0.0001 | <0.0001 |
| | miR-142-3p | 0.001 | 0.005 |
| | miR-142-5p | 0.004 | 0.027 |

FIG. 3C

METHODS TO DETECT MOTOR NEURON DISEASE COMPRISING MICRO-RNAS

CROSS REFERENCE TO RELATED APPLICATIONS

This application claims the benefit of PCT Application PCT/US2016/019602, filed Feb. 25, 2016, which claims the benefit of U.S. Provisional Application No. 62/120,654, filed Feb. 25, 2015, each of the disclosures of which is hereby incorporated by reference in its entirety.

GOVERNMENTAL RIGHTS

This invention was made with government support under grant NS078398 awarded by the National Institute of Health. The government has certain rights in the invention.

FIELD OF THE INVENTION

The present invention relates to compositions and methods for detecting motor neuron-specific miRNAs in a population of cells or subject. More particularly, the invention relates to detecting motor neuron-specific miRNAs to detect and treat motor neuron diseases associated with dysregulation of motor neuron-specific miRNAs, such as Amyotrophic Lateral Sclerosis (ALS).

BACKGROUND OF THE INVENTION

MicroRNAs (miRNAs) are single-stranded, non-coding RNAs that regulate transcription and translation of coding RNAs (mRNA). Since their discovery in 1993, miRNAs have emerged as key regulators in numerous physiological and pathological processes. miRNAs are highly conserved and are about 18-25 nucleotides in length. Typically, miRNAs direct translational repression by binding to the 3' untranslated region (UTR) of mRNAs. Because only partial complementarity is required for miRNA-mRNA interactions, a single miRNA can potentially regulate hundreds of mRNA transcripts.

Motor neuron diseases are those involving progressive loss of structure or function of motor neurons, including death of motor neurons. Such diseases include Amyotrophic Lateral Sclerosis (ALS), primary lateral sclerosis, progressive muscular atrophy, progressive bulbar palsy and pseudobulbar palsy. Most motor neuron diseases have no cure and available therapeutics are targeted at improving symptoms, relieving pain, and slowing degeneration. Motor neuron diseases, such as ALS, need novel, innovative approaches to drug development since many traditional therapeutics have failed or only shown marginal benefits. Further, there are no specific tests to diagnose motor neuron diseases. Early diagnosis or detection of motor neuron disease may facilitate earlier treatment thus slowing degeneration. Thus, in addition to novel drugs, there is a need for early, accurate detection of motor neuron disease.

While miRNAs are known regulators of physiological and pathological processes, little is known about their involvement in motor neuron conditions or diseases. Further, knowledge of motor neuron-specific miRNAs may enhance the detection and treatment of motor neuron diseases. Compositions and methods exploiting motor neuron-specific miRNA regulation in motor neuron conditions or diseases are needed to further medical research and provide diagnostic and therapeutic resources for such conditions and diseases. The present invention provides compositions and methods for detecting and treating conditions and diseases associated with aberrant motor neuron-specific miRNA regulation.

SUMMARY OF THE INVENTION

In an aspect, the disclosure provides a method to detect motor neuron disease. The method comprises measuring the amount of miR-218 in a biological sample obtained from a subject, and comparing the amount of miR-218 in the biological sample to a reference value, wherein dysregulation of miR-218 relative to the reference value indicates motor neuron disease.

In another aspect, the disclosure provides a method to detect motor neuron disease. The method comprises measuring the amount of miR-218 and at least one additional miRNA selected from the group consisting of miR-138, miR-133a, miR-133b, miR-1193, miR-34b, miR-380, and miR-379 in a biological sample obtained from a subject, and comparing the amount of miR-218 and at least one additional miRNA selected from the group consisting of miR-138, miR-133a, miR-133b, miR-1193, miR-34b, miR-380, and miR-379 in the biological sample to a reference value, wherein dysregulation of miR-218 and at least one additional miRNA selected from the group consisting of miR-138, miR-133a, miR-133b, miR-1193, miR-34b, miR-380, and miR-379 relative to the reference value indicates motor neuron disease.

In still another aspect, the disclosure provides a method to detect the efficacy of treatment or the progression of motor neuron disease. The method comprises: measuring the amount of miR-218 in a first biological sample obtained from a subject; then at a later time measuring the amount of miR-218 in a second biological sample obtained from a subject; and comparing the amount of miR-218 in the first biological sample to the amount of miR-218 in the second biological sample, wherein a change in miR-218 indicates effectiveness of treatment or progression of motor neuron disease.

In still yet another aspect, the disclosure provides a method to detect the efficacy of treatment or the progression of motor neuron disease. The method comprises: measuring the amount of miR-218 and at least one additional miRNA selected from the group consisting of miR-138, miR-133a, miR-133b, miR-1193, miR-34b, miR-380, and miR-379 in a first biological sample obtained from a subject; then at a later time measuring the amount of miR-218 and at least one additional miRNA selected from the group consisting of miR-138, miR-133a, miR-133b, miR-1193, miR-34b, miR-380, and miR-379 in a second biological sample obtained from a subject; and comparing the amount of miR-218 and at least one additional miRNA selected from the group consisting of miR-138, miR-133a, miR-133b, miR-1193, miR-34b, miR-380, and miR-379 in the first biological sample to the amount of miR-218 and at least one additional miRNA selected from the group consisting of miR-138, miR-133a, miR-133b, miR-1193, miR-34b, miR-380, and miR-379 in the second biological sample, wherein a change in miR-218 and at least one additional miRNA selected from the group consisting of miR-138, miR-133a, miR-133b, miR-1193, miR-34b, miR-380, and miR-379 indicates effectiveness of treatment or progression of motor neuron disease.

In a different aspect, the disclosure provides a method to improve motor neuron function in a subject diagnosed with a motor neuron disease, suspected of having a motor neuron disease or at risk for a motor neuron disease. The method comprises administering a miR-218, miR-138, miR-133a, miR-133b, miR-1193, miR-34b, miR-380, or miR-379 composition, or combination thereof, to the subject.

In another different aspect, the disclosure provides a method of treating a subject diagnosed with a motor neuron disease, suspected of having a motor neuron disease or at risk for a motor neuron disease. The method comprises administering miR-218, miR-138, miR-133a, miR-133b, miR-1193, miR-34b, miR-380, or miR-379 composition, or combination thereof, to the subject.

BRIEF DESCRIPTION OF THE DRAWINGS

The application file contains at least one photograph executed in color. Copies of this patent application publication with color photographs will be provided by the Office upon request and payment of the necessary fee.

(FIG. 1A, FIG. 1B) Mice were generated to express Cre recombinase under one of four specific cell type promoters: synapsin 1 (Syn) for all neurons; choline acetyltransferase (ChAT) for motor neurons, glial acidic fibrillary protein (GFAP) for astrocytes or lysozyme M (Lyz2, LysM) for microglia. Cre recombinase drives expression of a tagged miRNA binding protein, Ago2, in the desired cell type. (FIG. 1C, FIG. 1D, FIG. 1E, FIG. 1F) Spinal cord sections from transgenic mice were stained for NeuN (red; neurons) or ChAT (red; MNs) or GFAP (red; astrocytes) or Iba1 (red; microglia) and GFP (green). Scale bars, 50 μm.

(FIG. 2A) Schematic of miRAP demonstrating selective expression of myc-GFP-tagged Ago2 in motor neurons, which allows for IP of myc to isolate miRNAs from only motor neurons or IP of Ago2 to isolate miRNA from all spinal cord cell types. (FIG. 2B) miRAP from genetically labeled mice produces miRNA expression profiles that are expected of all neurons, motor neurons, astrocytes and microglia in the brainstem. Relative expression normalized to geomean of endogenous miRNA controls: miR-30c, 24, and 191. n=6/line. Values are expressed as mean±SEM.

FIG. 3A, FIG. 3B and FIG. 3C depicts a graph, a heatmap and a schematic showing that CNS cell types cluster according to their miRNA expression profiles. (FIG. 3A) 3-Dimensional Principal Component Analysis illustrating the variation in our samples. The replicates of each spinal cord cell type cluster with each other moreso than any other cell type. miRNA expression from Ago2 IP from one of each of these four mice cluster, indicating global miRNA signatures are comparable. (FIG. 3B) Hierarchical heatmap clustering demonstrates spinal cord CNS cell types can be identified by their unique miRNA expression profiles and that neuronal miRNA expression is distinct from astrocytes and microglia. (FIG. 3C) The top 3 miRNAs exhibiting cell type specificity in each CNS cell type of the brainstem and spinal cord (CT<30 in both tissues). The specificity index (pSI) was calculated as described in the supplemental methods.

(FIG. 4A, FIG. 4B) MN-enriched miRNAs, miR-218 and miR-138, are significantly depleted in ALS mouse model spinal cord. This depletion occurs temporally and is maximized at end-stage. N=3-4. (FIG. 4C, FIG. 4D) Pan-Neuronal Enriched miRNAs are not significantly depleted in ALS mouse model spinal cord, even at end-stage. N=3-4. (FIG. 4E, FIG. 4F) MN-enriched miRNAs, miR-218 and miR-138, are significantly depleted in patient autopsy spinal cord as compared to age-matched controls. N=4-10. Values are expressed as mean±SEM. p≤0.01, *p≤0.001, **p≤0.0001. Student's two-tailed, unpaired t-test. Relative expression is normalized to RNA input and endogenous miRNA control, miR-24, (FIG. 4A, FIG. 4B, FIG. 4C, FIG. 4D) or U6 snRNA (FIG. 4E, FIG. 4**F).

(FIG. 5A) miR-218 expression is temporally increased in ALS rat model CSF. N=5-7/timepoint. 115d and 130d timepoints included rats ranging from 112-119d and 126-134d, respectively. End-stage rats ranged from 160-242d; average=192±30d. (FIG. 5B, FIG. 5C) Neuronal miRNAs, miR-132 and miR-124, are not increased in ALS rat model CSF. (FIG. 5D) miR-218 is reduced in rats treated with SOD1-lowering ASO as compared to a CSF-treated controls. N=4/group. (FIG. 5E, FIG. 5F) miR-132 and miR-124 are not responsive to ALS therapy. Relative expression is normalized to endogenous miRNA biological fluid control, miR-103a-3p. Values are expressed at mean±SEM. *p≤0.05, p≤0.01. Student's unpaired t-test two-tailed (FIG. 5A) or one-tailed (FIG. 5**D).

DETAILED DESCRIPTION

Figures 1A, 1B:
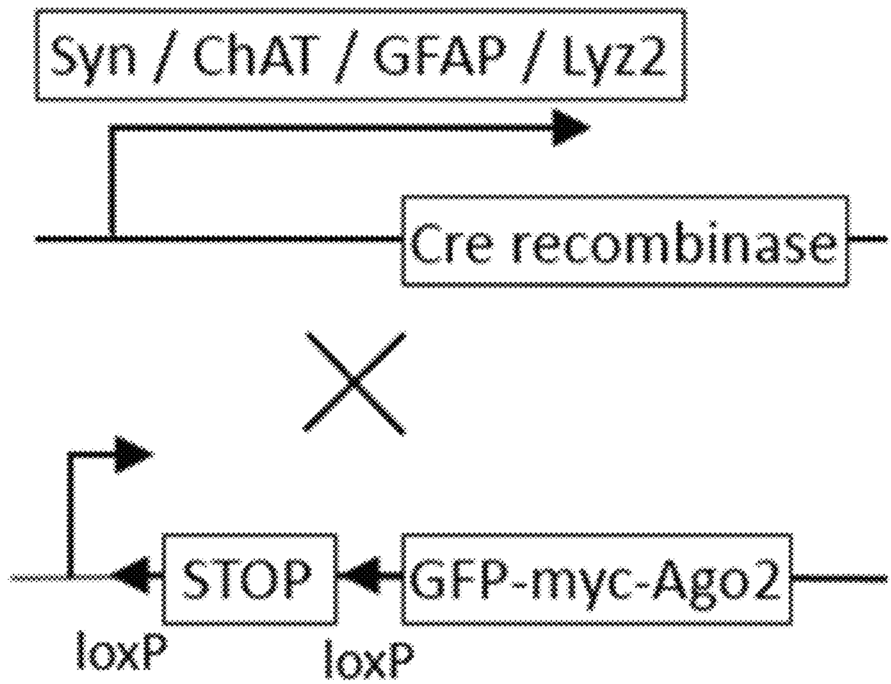
FIG. 1A, FIG. 1B, FIG. 1C, FIG. 1D, FIG. 1E and FIG. 1F depict schematics and images describing and validating the promoters used to drive cell type specific GFP-myc-Ago2 expression.

In accordance with the present invention, motor neuron (MN)-specific miRNAs selected from the group consisting of miR-218, miR-138, miR-133a, miR-133b, miR-1193, miR-34b, miR-380, and miR-379 have been discovered. In particular, the present invention provides compositions and methods useful in research, diagnostics, and therapeutics for conditions and diseases associated with dysregulation of miR-218, miR-138, miR-133a, miR-133b, miR-1193, miR-34b, miR-380, and/or miR-379. The compositions and methods are directed at modulating the activity of miR-218, miR-138, miR-133a, miR-133b, miR-1193, miR-34b, miR-380, and/or miR-379.

Various aspects of the invention are described in further detail in the following sections.

I. Compositions (a) Nucleic Acid Molecules

One aspect of the invention pertains to isolated nucleic acid molecules that encode miR-218, miR-138, miR-133a, miR-133b, miR-1193, miR-34b, miR-380, or miR-379 or biologically active portions thereof, as well as nucleic acid molecules sufficient for use as hybridization probes to identify miR-218, miR-138, miR-133a, miR-133b, miR-1193, miR-34b, miR-380, or miR-379-encoding nucleic acids (e.g., miRNA, pri-miRNA, pre-mRNA) and fragments for use as PCR primers for the amplification or mutation of miR-218, miR-138, miR-133a, miR-133b, miR-1193, miR-34b, miR-380, or miR-379 nucleic acid molecules.

A nucleic acid molecule of the present invention, or a complement of any of these nucleotide sequences, may be isolated using standard molecular biology techniques. For instance, using all or a portion of the nucleic acid sequences of miR-218, miR-138, miR-133a, miR-133b, miR-1193, miR-34b, miR-380, or miR-379, nucleic acid molecules may be isolated using standard hybridization and cloning techniques (e.g., as described in Sambrook et al., eds., Molecular Cloning: A Laboratory Manual. 2nd ed., Cold Spring Harbor Laboratory, Cold Spring Harbor Laboratory Press, Cold Spring Harbor, N.Y., 1989).

A nucleic acid of the invention may be amplified using cDNA, mRNA or genomic DNA as a template and appropriate oligonucleotide primers according to standard PCR amplification techniques. The nucleic acid so amplified may be cloned into an appropriate vector and characterized by DNA sequence analysis. Furthermore, oligonucleotides corresponding to miR-218, miR-138, miR-133a, miR-133b, miR-1193, miR-34b, miR-380, or miR-379 nucleotide sequences may be prepared by standard synthetic techniques known in the art, such as using an automated DNA synthesizer.

In another embodiment, an isolated nucleic acid molecule of the invention comprises a nucleic acid molecule which is a complement of a nucleotide sequence of miR-218, miR-138, miR-133a, miR-133b, miR-1193, miR-34b, miR-380, or miR-379, or portion thereof. A nucleic acid molecule which is complementary to a given nucleotide sequence is one which is sufficiently complementary to the given nucleotide sequence that it can hybridize to the given nucleotide sequence, thereby forming a stable duplex.

Moreover, the nucleic acid molecule of the invention may comprise only a portion of a nucleic acid sequence encoding miR-218, miR-138, miR-133a, miR-133b, miR-1193, miR-34b, miR-380, or miR-379. By way of example, a fragment of the nucleic acid coding sequence may be used as a probe, primer, or a fragment encoding a biologically active portion of miR-218, miR-138, miR-133a, miR-133b, miR-1193, miR-34b, miR-380, or miR-379. The nucleotide sequence determined from the cloning of miR-218, miR-138, miR-133a, miR-133b, miR-1193, miR-34b, miR-380, or miR-379 allows for the generation of probes and primers designed for use in identifying and/or cloning miR-218, miR-138, miR-133a, miR-133b, miR-1193, miR-34b, miR-380, or miR-379 homologues in other cell types, as well as miR-218, miR-138, miR-133a, miR-133b, miR-1193, miR-34b, miR-380, or miR-379 homologues and orthologs from other species. The probe/primer typically comprises substantially purified oligonucleotides. The oligonucleotides typically comprise a region of nucleotide sequence that hybridizes under stringent conditions to at least about 6, 7, 8, 9, 10, 11, 12, 13, 14, 15, 16, 17, 18, 19, 20, 21, 22, 23, 24, 25, 26, 27, 28, 29, 30 or more consecutive nucleotides of the sense or antisense sequence of miR-218, miR-138, miR-133a, miR-133b, miR-1193, miR-34b, miR-380, or miR-379, or of a naturally occurring mutant.

Probes based on the miR-218, miR-138, miR-133a, miR-133b, miR-1193, miR-34b, miR-380, or miR-379 nucleotide sequence may be used to detect transcripts or genomic sequences encoding the same or similar miRNA. The probe comprises a label group attached thereto, such as a radioisotope, a fluorescent compound, an enzyme, or an enzyme co-factor. Such probes may be used in diagnostic or screening assays.

A nucleic acid fragment encoding a "biologically active portion" of miR-218, miR-138, miR-133a, miR-133b, miR-1193, miR-34b, miR-380, or miR-379 may be prepared by isolating a portion of a nucleotide sequence having miR-218, miR-138, miR-133a, miR-133b, miR-1193, miR-34b, miR-380, or miR-379 biological activity, expressing the encoded portion of miR-218, miR-138, miR-133a, miR-133b, miR-1193, miR-34b, miR-380, or miR-379 (e.g., by recombinant expression in vitro), and assessing the activity of the encoded portion of miR-218, miR-138, miR-133a, miR-133b, miR-1193, miR-34b, miR-380, or miR-379. For example, a nucleic acid fragment encoding a biologically active portion of miR-218, miR-138, miR-133a, miR-133b, miR-1193, miR-34b, miR-380, or miR-379 includes the seed region, or an RNA binding site.

The invention further encompasses nucleic acid molecules that differ from the nucleotide sequence of the native miR-218, miR-138, miR-133a, miR-133b, miR-1193, miR-34b, miR-380, or miR-379, due to degeneracy of the genetic code and thus encode the same miR-218, miR-138, miR-133a, miR-133b, miR-1193, miR-34b, miR-380, or miR-379 as that encoded by the native nucleotide sequence.

In addition, it will be appreciated by those skilled in the art that nucleotide sequence polymorphisms may exist within a population (e.g., the human population). Such genetic polymorphism in the miR-218, miR-138, miR-133a, miR-133b, miR-1193, miR-34b, miR-380, or miR-379 coding sequence may exist among individuals within a population due to natural allelic variation. Such natural allelic variations may result in as much as 15% variance in the nucleotide sequence. Any and all such nucleotide variations and resulting polymorphisms in miR-218, miR-138, miR-133a, miR-133b, miR-1193, miR-34b, miR-380, or miR-379 that are the result of natural allelic variation and that do not alter the functional activity of the miRNA are intended to be within the scope of the invention. Thus, e.g., 1%, 2%, 3%, 4%, or 5% of the nucleotide bases in miR-218, miR-138, miR-133a, miR-133b, miR-1193, miR-34b, miR-380, or miR-379 (e.g., 1, 2, 3, 4, 5, 6, 8, 10, 15, 20, 25, 30, 35, 40, 45, 50, or 55) may be replaced by another nucleotide base.

Moreover, nucleic acid molecules encoding miR-218, miR-138, miR-133a, miR-133b, miR-1193, miR-34b, miR-380, or miR-379 from other species (miR-218, miR-138, miR-133a, miR-133b, miR-1193, miR-34b, miR-380, or miR-379 orthologs/homologues), which have a nucleotide sequence which differs from that of a miR-218, miR-138, miR-133a, miR-133b, miR-1193, miR-34b, miR-380, or miR-379 disclosed herein, are intended to be within the scope of the invention.

In addition to naturally occurring allelic variants of the miR-218, miR-138, miR-133a, miR-133b, miR-1193, miR-34b, miR-380, or miR-379 sequence that may exist in the population, the skilled artisan will further appreciate that changes may be introduced by mutation into the native nucleotide sequence, thereby leading to changes in the sequence of the encoded miRNA without altering the functional ability of the miRNA. For example, such mutations may include nucleotide substitutions at "nonessential" nucleotide bases. A "nonessential" nucleotide base is one that may be altered from the wildtype sequence of miR-218, miR-138, miR-133a, miR-133b, miR-1193, miR-34b, miR-380, or miR-379 without altering the biological activity, whereas an "essential" nucleotide base is required for biological activity.

Accordingly, another aspect of the invention pertains to nucleic acid molecules encoding miR-218, miR-138, miR-133a, miR-133b, miR-1193, miR-34b, miR-380, or miR-379 that contain changes in nucleotide bases that may or may not be essential for activity. Such miR-218, miR-138, miR-133a, miR-133b, miR-1193, miR-34b, miR-380, or miR-379 sequences differ from the native sequences. In specific embodiments, the isolated nucleic acid molecule includes a nucleotide sequence encoding miRNA that is at least about 45% identical, 65%, 75%, 85%, 90%, 91%, 92%, 93%, 94%, 95%, 96%, 97%, 98%, or more identical to the sequence of miR-218, miR-138, miR-133a, miR-133b, miR-1193, miR-34b, miR-380, or miR-379. An isolated nucleic acid molecule encoding miR-218, miR-138, miR-133a, miR-133b, miR-1193, miR-34b, miR-380, or miR-379 having a sequence which differs from that of the naturally occurring sequence may be created by introducing one or more nucleotide substitutions, additions or deletions into the native nucleotide sequence of miR-218, miR-138, miR-133a, miR-133b, miR-1193, miR-34b, miR-380, or miR-379 such that one or more substitutions, additions or deletions are introduced into the encoded miRNA. Mutations may be introduced by standard techniques known in the art, such as site-directed mutagenesis and PCR-mediated mutagenesis.

As will be recognized by individuals skilled in the art, both arms of a pre-miRNA hairpin encoding miR-218, miR-138, miR-133a, miR-133b, miR-1193, miR-34b, miR-380, or miR-379 may give rise to a mature miR-218, miR-138, miR-133a, miR-133b, miR-1193, miR-34b, miR-380, or miR-379 miRNA. For instance, two mature miRNAs that may result from a pre-miRNA encoding a miR-218, miR-138, miR-133a, miR-133b, miR-1193, miR-34b, miR-380, or miR-379 miRNA may be miR-218-3p, miR-138-3p, miR-133a-3p, miR-133b-3p, miR-1193-3p, miR-34b-3p, miR-380-3p, or miR-379-3p and miR-218-5p, miR-138-5p, miR-133a-5p, miR-133b-5p, miR-1193-5p, miR-34b-5p, miR-380-5p, or miR-379-5p, respectively. Specifically, a nucleic acid may be miR-218-3p, miR-218-5p, miR-138-5p, miR-138-3p, miR-133a-3p, miR-133b-3p, miR-34b-3p, miR-380-3p, or miR-380-5p. As used herein, miR-218 refers to miR-218-1 and miR-218-2.

(b) miR-218, miR-138, miR-133a, miR-133b, miR-1193, miR-34b, miR-380, or miR-379 Agents Another aspect of the invention pertains to miR-218, miR-138, miR-133a, miR-133b, miR-1193, miR-34b, miR-380, or miR-379 agents. As used herein, the term "miR-218, miR-138, miR-133a, miR-133b, miR-1193, miR-34b, miR-380, or miR-379 agent" refers to any molecule capable of modulating one or more activities of miR-218, miR-138, miR-133a, miR-133b, miR-1193, miR-34b, miR-380, or miR-379. A miR-218, miR-138, miR-133a, miR-133b, miR-1193, miR-34b, miR-380, or miR-379 agent may respectively modulate one or more activities of miR-218, miR-138, miR-133a, miR-133b, miR-1193, miR-34b, miR-380, or miR-379 by increasing or decreasing expression of the respective miR-218, miR-138, miR-133a, miR-133b, miR-1193, miR-34b, miR-380, or miR-379 in a subject. In some embodiments, a miR-218, miR-138, miR-133a, miR-133b, miR-1193, miR-34b, miR-380, or miR-379 agent respectively modulates a miR-218, miR-138, miR-133a, miR-133b, miR-1193, miR-34b, miR-380, or miR-379 activity by increasing the respective expression of a miR-218, miR-138, miR-133a, miR-133b, miR-1193, miR-34b, miR-380, or miR-379 in a subject. In other embodiments, a miR-218, miR-138, miR-133a, miR-133b, miR-1193, miR-34b, miR-380, or miR-379 agent respectively modulates a miR-218, miR-138, miR-133a, miR-133b, miR-1193, miR-34b, miR-380, or miR-379 activity by decreasing expression of a miR-218, miR-138, miR-133a, miR-133b, miR-1193, miR-34b, miR-380, or miR-379 in a subject. In a specific embodiment, a miR-218 agent modulates miR-218 activity by decreasing expression of miR-218 in a subject. In another specific embodiment, a miR-138 agent modulates miR-138 activity by decreasing expression of miR-138 in a subject.

Exemplary miR-218, miR-138, miR-133a, miR-133b, miR-1193, miR-34b, miR-380, or miR-379 agents may include, without limitation, a compound, a drug, a small molecule, a peptide, a nucleic acid molecule, a protein, an antibody, and combinations thereof. miR-218, miR-138, miR-133a, miR-133b, miR-1193, miR-34b, miR-380, or miR-379 agents may be synthetic or naturally occurring.

In some embodiments, a miR-218, miR-138, miR-133a, miR-133b, miR-1193, miR-34b, miR-380, or miR-379 agent is a compound. In another embodiment, a miR-218, miR-138, miR-133a, miR-133b, miR-1193, miR-34b, miR-380, or miR-379 agent is a drug. In yet another embodiment, a miR-218, miR-138, miR-133a, miR-133b, miR-1193, miR-34b, miR-380, or miR-379 agent is a small molecule. In another embodiment, a miR-218, miR-138, miR-133a, miR-133b, miR-1193, miR-34b, miR-380, or miR-379 agent is a peptide. In another embodiment, a miR-218, miR-138, miR-133a, miR-133b, miR-1193, miR-34b, miR-380, or miR-379 agent is a protein. In still another embodiment, a miR-218, miR-138, miR-133a, miR-133b, miR-1193, miR-34b, miR-380, or miR-379 agent is an antibody. In another embodiment, a miR-218, miR-138, miR-133a, miR-133b, miR-1193, miR-34b, miR-380, or miR-379 agent is a combination of miR-218, miR-138, miR-133a, miR-133b, miR-1193, miR-34b, miR-380, or miR-379 agents capable of respectively modulating miR-218, miR-138, miR-133a, miR-133b, miR-1193, miR-34b, miR-380, or miR-379 activity.

In preferred embodiments, a miR-218, miR-138, miR-133a, miR-133b, miR-1193, miR-34b, miR-380, or miR-379 agent is a nucleic acid molecule. For instance, a miR-218, miR-138, miR-133a, miR-133b, miR-1193, miR-34b, miR-380, or miR-379 nucleic acid agent may be an antisense oligonucleotide, a ribozyme, a small nuclear RNA (snRNA), a long noncoding RNA (LncRNA), or a nucleic acid molecule which forms triple helical structures.

In some embodiments, a miR-218, miR-138, miR-133a, miR-133b, miR-1193, miR-34b, miR-380, or miR-379 agent is a ribozyme. Ribozymes are catalytic RNA molecules with ribonuclease activity which are capable of cleaving a single-stranded nucleic acid, such as miRNA, to which they have a complementary region. Thus, ribozymes (e.g., hammerhead ribozymes (described in Haselhoff and Gerlach (1988) Nature 334:585-591)) may be used to catalytically cleave miR-218, miR-138, miR-133a, miR-133b, miR-1193, miR-34b, miR-380, or miR-379 to thereby respectively inhibit activity of miR-218, miR-138, miR-133a, miR-133b, miR-1193, miR-34b, miR-380, or miR-379. A ribozyme having specificity for a miR-218, miR-138, miR-133a, miR-133b, miR-1193, miR-34b, miR-380, or miR-379-encoding nucleic acid may be designed based upon the nucleotide sequence of a respective miR-218, miR-138, miR-133a, miR-133b, miR-1193, miR-34b, miR-380, or miR-379 cDNA. For example, miR-218, miR-138, miR-133a, miR-133b, miR-1193, miR-34b, miR-380, or miR-379 may be used to select a catalytic RNA having a specific ribonuclease activity from a pool of RNA molecules. See, e.g., Bartel and Szostak (1993) Science 261:1411-1418; Suryawanshi, Scaria, and Maiti (2010) Mol Biosyst. 6:1807-1809.

In other embodiments, a miR-218, miR-138, miR-133a, miR-133b, miR-1193, miR-34b, miR-380, or miR-379 agent is a snRNA. For instance, a miR-218, miR-138, miR-133a, miR-133b, miR-1193, miR-34b, miR-380, or miR-379 snRNA agent may be a snRNA capable of regulating transcription of a nucleic acid sequence respectively encoding miR-218, miR-138, miR-133a, miR-133b, miR-1193, miR-34b, miR-380, or miR-379. Alternatively, a miR-218, miR-138, miR-133a, miR-133b, miR-1193, miR-34b, miR-380, or miR-379 snRNA agent may be a snRNA capable of regulating splicing of a mirtron encoding miR-218, miR-138, miR-133a, miR-133b, miR-1193, miR-34b, miR-380, or miR-379.

In yet other embodiments, a miR-218, miR-138, miR-133a, miR-133b, miR-1193, miR-34b, miR-380, or miR-379 agent is a LncRNA. A miR-218, miR-138, miR-133a, miR-133b, miR-1193, miR-34b, miR-380, or miR-379 LncRNA agent may be a LncRNA capable of regulating transcription of a nucleic acid sequence respectively encoding miR-218, miR-138, miR-133a, miR-133b, miR-1193, miR-34b, miR-380, or miR-379.

In other embodiments, a miR-218, miR-138, miR-133a, miR-133b, miR-1193, miR-34b, miR-380, or miR-379 agent is a nucleic acid molecule which forms triple helical structures. For example, miR-218, miR-138, miR-133a, miR-133b, miR-1193, miR-34b, miR-380, or miR-379 expression may be modulated by targeting nucleotide sequences complementary to the regulatory region of miR-218, miR-138, miR-133a, miR-133b, miR-1193, miR-34b, miR-380, or miR-379 (e.g., promoter and/or enhancers) to form triple helical structures that respectively prevent transcription of miR-218, miR-138, miR-133a, miR-133b, miR-1193, miR-34b, miR-380, or miR-379 in target cells. See generally, Helene (1991) Anticancer Drug Des. 6(6):569-84; Helene (1992) Ann. N.Y. Acad. Sci. 660:27-36; and Maher (1992) Bioassays 14(12):807-15.

In preferred embodiments, a miR-218, miR-138, miR-133a, miR-133b, miR-1193, miR-34b, miR-380, or miR-379 agent is an antisense oligonucleotide. Antisense molecules are oligonucleotides comprising nucleic acid sequences complementary to a sense nucleic acid sequence. A miR-218, miR-138, miR-133a, miR-133b, miR-1193, miR-34b, miR-380, or miR-379 antisense oligonucleotide agent comprises nucleic acid sequences complementary to a miRNA encoding miR-218, miR-138, miR-133a, miR-133b, miR-1193, miR-34b, miR-380, or miR-379, and may modulate the respective expression of miR-218, miR-138, miR-133a, miR-133b, miR-1193, miR-34b, miR-380, or miR-379 by binding to a miRNA respectively encoding miR-218, miR-138, miR-133a, miR-133b, miR-1193, miR-34b, miR-380, or miR-379. The expression of miR-218, miR-138, miR-133a, miR-133b, miR-1193, miR-34b, miR-380, or miR-379 may be modulated by blocking the respective activity of miR-218, miR-138, miR-133a, miR-133b, miR-1193, miR-34b, miR-380, or miR-379, and respectively reducing the effective amount of miR-218, miR-138, miR-133a, miR-133b, miR-1193, miR-34b, miR-380, or miR-379 in a cell.

An antisense oligonucleotide may bind through hydrogen bonds to a sense nucleic acid. As used herein, the term "sense nucleic acid sequence" is a nucleic acid sequence corresponding to an RNA sequence expressed in a cell. For instance, a sense nucleic acid sequence may be an expressed mRNA nucleic acid sequence, or a DNA nucleic acid sequence corresponding to an expressed mRNA nucleic acid sequence. As such, an antisense molecule of the invention comprises a nucleic acid sequence complementary to an expressed miRNA encoding miR-218, miR-138, miR-133a, miR-133b, miR-1193, miR-34b, miR-380, or miR-379.

A miRNA encoding miR-218, miR-138, miR-133a, miR-133b, miR-1193, miR-34b, miR-380, or miR-379 may be a mature miR-218, miR-138, miR-133a, miR-133b, miR-1193, miR-34b, miR-380, or miR-379 or a miRNA processing intermediate encoding a miR-218, miR-138, miR-133a, miR-133b, miR-1193, miR-34b, miR-380, or miR-379 miRNA. As such, an antisense nucleic acid may comprise nucleic acid sequences complementary to a mature miR-218, miR-138, miR-133a, miR-133b, miR-1193, miR-34b, miR-380, or miR-379 or to a miRNA processing intermediate encoding a miR-218, miR-138, miR-133a, miR-133b, miR-1193, miR-34b, miR-380, or miR-379 miRNA. Non-limiting examples of miRNA processing intermediates encoding a miR-218, miR-138, miR-133a, miR-133b, miR-1193, miR-34b, miR-380, or miR-379 miRNA include a pre-miRNA encoding miR-218, miR-138, miR-133a, miR-133b, miR-1193, miR-34b, miR-380, or miR-379, a pri-miRNA encoding miR-218, miR-138, miR-133a, miR-133b, miR-1193, miR-34b, miR-380, or miR-379, or a mirtron encoding miR-218, miR-138, miR-133a, miR-133b, miR-1193, miR-34b, miR-380, or miR-379. In some embodiments, an antisense oligonucleotide comprises nucleic acid sequences complementary to a pri-miRNA encoding miR-218, miR-138, miR-133a, miR-133b, miR-1193, miR-34b, miR-380, or miR-379. In other embodiments, an antisense oligonucleotide comprises nucleic acid sequences complementary to a mirtron encoding miR-218, miR-138, miR-133a, miR-133b, miR-1193, miR-34b, miR-380, or miR-379. In some embodiments, an antisense oligonucleotide comprises nucleic acid sequences complementary to a pre-miRNA encoding miR-218, miR-138, miR-133a, miR-133b, miR-1193, miR-34b, miR-380, or miR-379. In yet other embodiments, an antisense oligonucleotide comprises nucleic acid sequences complementary to a mature miR-218, miR-138, miR-133a, miR-133b, miR-1193, miR-34b, miR-380, or miR-379.

An antisense oligonucleotide may comprise nucleic acid sequences complementary to a noncoding region in a miRNA processing intermediate encoding a miR-218, miR-138, miR-133a, miR-133b, miR-1193, miR-34b, miR-380, or miR-379 miRNA. For instance, an antisense oligonucleotide may comprise nucleic acid sequences complementary to a noncoding region of a pri-miRNA, a pre-miRNA, or a mirtron encoding miR-218, miR-138, miR-133a, miR-133b, miR-1193, miR-34b, miR-380, or miR-379. As used herein, the term "noncoding region" is used to describe nucleic acid sequences that flank a mature miR-218, miR-138, miR-133a, miR-133b, miR-1193, miR-34b, miR-380, or miR-379 sequence in a miRNA processing intermediate encoding a miR-218, miR-138, miR-133a, miR-133b, miR-1193, miR-34b, miR-380, or miR-379 miRNA.

In some embodiments, an antisense oligonucleotide comprises nucleic acid sequences complementary to a noncoding region of a pri-miRNA encoding miR-218, miR-138, miR-133a, miR-133b, miR-1193, miR-34b, miR-380, or miR-379. In other embodiments, an antisense oligonucleotide comprises nucleic acid sequences complementary to a noncoding region of a mirtron encoding miR-218, miR-138, miR-133a, miR-133b, miR-1193, miR-34b, miR-380, or miR-379. In yet other embodiments, an antisense oligonucleotide comprises nucleic acid sequences complementary to a noncoding region of a pre-miRNA encoding miR-218, miR-138, miR-133a, miR-133b, miR-1193, miR-34b, miR-380, or miR-379.

In yet other embodiments, an antisense oligonucleotide comprises nucleic acid sequences complementary to coding and noncoding regions of a miRNA encoding miR-218, miR-138, miR-133a, miR-133b, miR-1193, miR-34b, miR-380, or miR-379. In one alternative of the embodiments, an antisense oligonucleotide comprises nucleic acid sequences complementary to the stem-loop of a pre-miRNA encoding miR-218, miR-138, miR-133a, miR-133b, miR-1193, miR-34b, miR-380, or miR-379.

In preferred embodiments, an antisense oligonucleotide comprises nucleic acid sequences complementary to a coding region in a miR-218, miR-138, miR-133a, miR-133b, miR-1193, miR-34b, miR-380, or miR-379 miRNA. As used herein, the term "coding region" is used to describe a nucleic acid sequence present in a mature miR-218, miR-138, miR-133a, miR-133b, miR-1193, miR-34b, miR-380, or miR-379 miRNA. As will be recognized by those of skill in the art, a nucleic acid sequence present in a mature miR-218, miR-138, miR-133a, miR-133b, miR-1193, miR-34b, miR-380, or miR-379 is also present in a pri-miRNA encoding miR-218, miR-138, miR-133a, miR-133b, miR-1193, miR-34b, miR-380, or miR-379, a pre-miRNA encoding miR-218, miR-138, miR-133a, miR-133b, miR-1193, miR-34b, miR-380, or miR-379, and a mirtron encoding miR-218, miR-138, miR-133a, miR-133b, miR-1193, miR-34b, miR-380, or miR-379. As such, an antisense oligonucleotide comprising nucleic acid sequences complementary to a nucleic acid sequence present in a mature miR-218, miR-138, miR-133a, miR-133b, miR-1193, miR-34b, miR-380, or miR-379, may be complementary to a mature miR-218, miR-138, miR-133a, miR-133b, miR-1193, miR-34b, miR-380, or miR-379, as well as to a pri-miRNA encoding miR-218, miR-138, miR-133a, miR-133b, miR-1193, miR-34b, miR-380, or miR-379, a pre-miRNA encoding miR-218, miR-138, miR-133a, miR-133b, miR-1193, miR-34b, miR-380, or miR-379, and a mirtron encoding miR-218, miR-138, miR-133a, miR-133b, miR-1193, miR-34b, miR-380, or miR-379. In some embodiments, an antisense oligonucleotide comprises nucleic acid sequences complementary to a coding region of a pri-miRNA encoding miR-218, miR-138, miR-133a, miR-133b, miR-1193, miR-34b, miR-380, or miR-379. In other embodiments, an antisense oligonucleotide comprises nucleic acid sequences complementary to a coding region of a mirtron encoding miR-218, miR-138, miR-133a, miR-133b, miR-1193, miR-34b, miR-380, or miR-379. In some embodiments, an antisense oligonucleotide comprises nucleic acid sequences complementary to a coding region of a pre-miRNA encoding miR-218, miR-138, miR-133a, miR-133b, miR-1193, miR-34b, miR-380, or miR-379. In yet other embodiments, an antisense oligonucleotide comprises nucleic acid sequences complementary to a mature miR-218, miR-138, miR-133a, miR-133b, miR-1193, miR-34b, miR-380, or miR-379.

An antisense oligonucleotide molecule may comprise nucleic acid sequences complementary to the entire coding region of a miR-218, miR-138, miR-133a, miR-133b, miR-1193, miR-34b, miR-380, or miR-379 miRNA. Alternatively, an antisense oligonucleotide molecule may comprise nucleic acid sequences complementary to only a portion of the coding or noncoding region of a miR-218, miR-138, miR-133a, miR-133b, miR-1193, miR-34b, miR-380, or miR-379 miRNA. As such, an antisense oligonucleotide may comprise nucleic acid sequences complementary to 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 80, 90, 100 or more nucleotides of the coding or noncoding region of miR-218, miR-138, miR-133a, miR-133b, miR-1193, miR-34b, miR-380, or miR-379. In some embodiments, an antisense oligonucleotide comprises nucleic acid sequences complementary to 4, 5, 6, 7, 8, 9, or 10 nucleotides of the coding or noncoding region of miR-218, miR-138, miR-133a, miR-133b, miR-1193, miR-34b, miR-380, or miR-379. In other embodiments, an antisense oligonucleotide comprises nucleic acid sequences complementary to 10, 11, 12, 13, 14, 15, 16, 17, 18, 19, or 20 nucleotides of the coding or noncoding region of miR-218, miR-138, miR-133a, miR-133b, miR-1193, miR-34b, miR-380, or miR-379. In yet other embodiments, an antisense oligonucleotide comprises nucleic acid sequences complementary to 20, 21, 22, 23, 24, 25, 26, 27, 28, 29, or 30 nucleotides of the coding or noncoding region of miR-218, miR-138, miR-133a, miR-133b, miR-1193, miR-34b, miR-380, or miR-379. In yet other embodiments, an antisense oligonucleotide comprises nucleic acid sequences complementary to 30, 35, 40, 45, 50, 55, 60, 65, 70, 80, 90, 100 or more nucleotides of the coding or noncoding region of miR-218, miR-138, miR-133a, miR-133b, miR-1193, miR-34b, miR-380, or miR-379. In preferred embodiments, an antisense oligonucleotide comprises nucleic acid sequences complementary to 8, 9, 10, 11, 12, 13, 14, 15, 16, 17, 18, 19, 20, 21, 22, 23, 24, or 25 nucleotides of the coding or noncoding region of miR-218, miR-138, miR-133a, miR-133b, miR-1193, miR-34b, miR-380, or miR-379.

In particularly preferred embodiments, an antisense oligonucleotide of the invention comprises nucleic acid sequences complementary to a seed region of a miRNA encoding miR-218, miR-138, miR-133a, miR-133b, miR-1193, miR-34b, miR-380, or miR-379. In other particularly preferred embodiments, an antisense oligonucleotide consists of nucleic acid sequences complementary to a seed region of a miR-218, miR-138, miR-133a, miR-133b, miR-1193, miR-34b, miR-380, or miR-379. The seed region is a 7-8 nucleotide motif in the miRNA that determines specificity of binding of an miRNA to a target mRNA regulated by the miRNA. In most miRNAs, the seed region is within nucleotides 1-9 of the mature miRNA sequence. Antisense oligonucleotides comprising nucleic acid sequences complementary to the seed sequence of a miRNA have been shown to inhibit activity of the miRNA. Such inhibitory activity is described in PCT Publication No. WO 2009/043353, which is herein incorporated by reference in its entirety for its description of modified oligonucleotides targeting miRNA seed sequences.

As will be recognized by individuals skilled in the art, both arms of a pre-miRNA hairpin encoding miR-218, miR-138, miR-133a, miR-133b, miR-1193, miR-34b, miR-380, or miR-379 may give rise to a mature miR-218, miR-138, miR-133a, miR-133b, miR-1193, miR-34b, miR-380, or miR-379 miRNA. For instance, two mature miRNAs that may result from a pre-miRNA encoding a miR-218, miR-138, miR-133a, miR-133b, miR-1193, miR-34b, miR-380, or miR-379 miRNA may be miR-218-3p, miR-138-3p, miR-133a-3p, miR-133b-3p, miR-1193-3p, miR-34b-3p, miR-380-3p, or miR-379-3p and miR-218-5p, miR-138-5p, miR-133a-5p, miR-133b-5p, miR-1193-5p, miR-34b-5p, miR-380-5p, or miR-379-5p, respectively. As such, when an antisense nucleic acid comprises nucleic acid sequences complementary to a coding region of miR-380-3p, or miR-379-3p, an antisense nucleic acid may comprise nucleic acid sequences complementary to a miR-218-3p, miR-138-3p, miR-133a-3p, miR-133b-3p, miR-1193-3p, miR-34b-3p, miR-380-3p, or miR-379-3p coding region of miR-218, miR-138, miR-133a, miR-133b, miR-1193, miR-34b, miR-380, or miR-379, respectively, or to a miR-218-5p, miR-138-5p, miR-133a-5p, miR-133b-5p, miR-1193-5p, miR-34b-5p, miR-380-5p, or miR-379-5p coding region of miR-218, miR-138, miR-133a, miR-133b, miR-1193, miR-34b, miR-380, or miR-379, respectively. In some embodiments, an antisense nucleic acid comprises nucleic acid sequences complementary to a miR-218-3p, miR-138-3p, miR-133a-3p, miR-133b-3p, miR-1193-3p, miR-34b-3p, miR-380-3p, or miR-379-3p coding region of miR-218, miR-138, miR-133a, miR-133b, miR-1193, miR-34b, miR-380, or miR-379, respectively. In other embodiments, an antisense nucleic acid comprises nucleic acid sequences complementary to a miR-218-5p, miR-138-5p, miR-133a-5p, miR-133b-5p, miR-1193-5p, miR-34b-5p, miR-380-5p, or miR-379-5p coding region of miR-218, miR-138, miR-133a, miR-133b, miR-1193, miR-34b, miR-380, or miR-379, respectively.

The size of a miR-218, miR-138, miR-133a, miR-133b, miR-1193, miR-34b, miR-380, or miR-379 antisense agent of the invention can and will vary depending on the target miRNA encoding a miR-218, miR-138, miR-133a, miR-133b, miR-1193, miR-34b, miR-380, or miR-379, the size of the nucleic acid sequence complementary to a region of miR-218, miR-138, miR-133a, miR-133b, miR-1193, miR-34b, miR-380, or miR-379, and whether the antisense oligonucleotide comprises nucleic acid sequences in addition to the sequences complementary to a miR-218, miR-138, miR-133a, miR-133b, miR-1193, miR-34b, miR-380, or miR-379 miRNA. An antisense oligonucleotide may be about 5, 6, 7, 8, 9, 10, 11, 12, 13, 14, 15, 16, 17, 18, 19, 20, 21, 22, 23, 24, 25, 26, 27, 28, 29, 30, 35, 40, 45 or about 50 nucleotides in length. In some embodiments, an antisense oligonucleotide is about 5, 6, 7, 8, 9, 10, 11, 12, 13, 14, or about 15 nucleotides in length. In other embodiments, an antisense oligonucleotide is about 15, 16, 17, 18, 19, 20, 21, 22, 23, 24, or about 25 nucleotides in length. In yet other embodiments, an antisense oligonucleotide is about 25, 26, 27, 28, 29, 30, 35, 40, 45, or about 50 nucleotides in length. In some preferred embodiments, an antisense oligonucleotide is about 5, 6, 7, 8, 9, or about 10 nucleotides in length. In other preferred embodiments, an antisense oligonucleotide is about 19, 20, 21, 22, 23, 24, or about 25 nucleotides in length. In exemplary embodiments, an antisense oligonucleotide is 22 nucleotides in length.

In certain embodiments, a nucleic acid sequence of an antisense oligonucleotide comprising nucleic acid sequences complementary to a miR-218, miR-138, miR-133a, miR-133b, miR-1193, miR-34b, miR-380, or miR-379 miRNA may have one or more mismatched base pairs with respect to its target miRNA or precursor sequence, and remains capable of hybridizing to its target sequence. For instance, a nucleic acid sequence of an antisense oligonucleotide comprising nucleic acid sequences complementary to a miR-218, miR-138, miR-133a, miR-133b, miR-1193, miR-34b, miR-380, or miR-379 miRNA may have 1, 2, 3, 4, 5, 6, 7, 8, 9, 10 or more mismatched base pairs with respect to its target miRNA or precursor sequence, and remains capable of hybridizing to its target sequence.

In certain embodiments, an antisense oligonucleotide comprises 8-25 nucleotides at least 85% complementary to a miR-218, miR-138, miR-133a, miR-133b, miR-1193, miR-34b, miR-380, or miR-379 miRNA. In other embodiments, an antisense oligonucleotide consists of 8-25 nucleotides at least 85% complementary to a miR-218, miR-138, miR-133a, miR-133b, miR-1193, miR-34b, miR-380, or miR-379. In still other embodiments, an antisense oligonucleotide consists of 8-25 nucleotides at least 85% complementary to a mature miR-218, miR-138, miR-133a, miR-133b, miR-1193, miR-34b, miR-380, or miR-379 miRNA.

In certain embodiments, an antisense oligonucleotide comprises 8-25 nucleotides at least 90% complementary to a miR-218, miR-138, miR-133a, miR-133b, miR-1193, miR-34b, miR-380, or miR-379 miRNA. In other embodiments, an antisense oligonucleotide consists of 8-25 nucleotides at least 90% complementary to a miR-218, miR-138, miR-133a, miR-133b, miR-1193, miR-34b, miR-380, or miR-379 miRNA. In still other embodiments, an antisense oligonucleotide consists of 8-25 nucleotides at least 90% complementary to a mature miR-218, miR-138, miR-133a, miR-133b, miR-1193, miR-34b, miR-380, or miR-379 miRNA.

An antisense oligonucleotide of the invention may be synthesized using chemical synthesis and enzymatic ligation reactions using procedures known in the art. For example, an oligonucleotide (e.g., an antisense oligonucleotide) may be chemically synthesized using naturally occurring ribonucleotides, deoxyribonucleotides, variously modified nucleotides designed to increase the biological stability of the molecules or to increase the physical stability of the duplex formed between the antisense and sense nucleic acids, or combinations thereof. For example, phosphorothioate derivatives and acridine substituted nucleotides may be used. Other examples of modified nucleotides which may be used to generate an antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-aino-3-N-2-carboxypropyl) uracil, (acp3)w, and 2,6-diaminopurine. Alternatively, the oligonucleotide may be produced biologically using an expression vector into which a nucleic acid has been subcloned in an antisense orientation.

In certain embodiments, antisense oligonucleotides provided herein may include one or more modifications to a nucleobase, sugar, and/or internucleoside linkage, and as such is a modified oligonucleotide. A modified nucleobase, sugar, or internucleoside linkage may be selected over an unmodified form because of desirable properties such as, for example, enhanced cellular uptake, enhanced affinity for other oligonucleotides or nucleic acid targets, and increased stability in the presence of nucleases. In certain embodiments, a modified nucleoside is a sugar-modified nucleoside. In certain such embodiments, sugar-modified nucleosides may further comprise a natural or modified heterocyclic base moiety or natural or modified internucleoside linkage and may include further modifications independent from the sugar modification. In certain embodiments, a sugar modified nucleoside is a 2'-modified nucleoside, wherein the sugar ring is modified at the 2' carbon from natural ribose or 2'-deoxy-ribose. In certain embodiments, a 2'-modified nucleoside comprises a 2'-substituent group selected from F, O—$CH_3$, and $OCH_2CH_2OCH_3$. In certain embodiments, a 2'-modified nucleoside has a bicyclic sugar moiety. In certain embodiments, a bicyclic sugar moiety comprises a bridge group between the 2' and the 4' carbon atoms.

In certain embodiments, a modified oligonucleotide comprises one or more internucleoside modifications. In certain such embodiments, each internucleoside linkage of an oligonucleotide is a modified internucleoside linkage. In certain embodiments, a modified internucleoside linkage comprises a phosphorus atom.

In certain embodiments, a modified oligonucleotide comprises at least one phosphorothioate internucleoside linkage. In preferred embodiments, each internucleoside linkage of a modified oligonucleotide is a phosphorothioate internucleoside linkage.

In certain embodiments, a modified oligonucleotide comprises one or more modified nucleobases. In certain embodiments, a modified oligonucleotide comprises one or more 5-methylcytosines. In certain embodiments, each cytosine of a modified oligonucleotide comprises a 5-methylcytosine.

In certain embodiments, a modified nucleobase is selected from 5-hydroxymethyl cytosine, 7-deazaguanine and 7-deazaadenine. In certain embodiments, a modified nucleobase is selected from 7-deaza-adenine, 7-deazaguanosine, 2-aminopyridine and 2-pyridone.

In some embodiments, the antisense molecules of the invention may be modified at the base moiety, sugar moiety or phosphate backbone to improve, e.g., the stability, hybridization, or solubility of the molecule. By way of another example, the deoxyribose phosphate backbone of the nucleic acids may be modified to generate peptide nucleic acids (see Hyrup et al. (1996) Bioorganic & Medicinal Chemistry 4(I):5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of a PNA has been shown to allow for specific hybridization to DNA and RNA under conditions of low ionic strength. The synthesis of PNA oligomers may be performed using standard solid phase peptide synthesis protocols as described in Hyrup et al. (1996) supra; Perry-O'Keefe et al. (1996) Proc. Natl. Acad. Sci. USA 93:14670-675.

PNAs of miR-218, miR-138, miR-133a, miR-133b, miR-1193, miR-34b, miR-380, or miR-379 may be used for therapeutic and diagnostic applications. For example, PNAs may be used as antisense or miR-218, miR-138, miR-133a, miR-133b, miR-1193, miR-34b, miR-380, or miR-379 agents for sequence-specific modulation of expression by inducing transcription arrest or inhibiting replication. PNAs of miR-218, miR-138, miR-133a, miR-133b, miR-1193, miR-34b, miR-380, or miR-379 may also be used in the analysis of single base pair mutations in a gene by PNA-directed PCR clamping; as artificial restriction enzymes when used in combination with other enzymes, such as S1 nucleases (Hyrup (1996) supra); or as probes or primers for DNA sequence and hybridization (Hyrup (1996) supra; Perry-O'Keefe et al. (1996) Proc. Natl. Acad. Sci. USA 93: 14670-675).

In other embodiments, the oligonucleotides of the invention may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553-6556; Lemaitre et al. (1987) Proc. Natl. Acad. Sci. USA 84:648-652; PCT Publication No. WO 88/09810) or the blood-brain barrier (see, e.g., PCT Publication No. WO 89/10134). In addition, oligonucleotides may be modified with hybridization-triggered cleavage agents (see, e.g., Krol et al. (1988) Bio/Techniques 6:958-976) or intercalating agents (see, e.g., Zon (1988) Pharm. Res. 5:539-549). To this end, the oligonucleotide may be conjugated to another molecule, e.g., a peptide, hybridization triggered cross-linking agent, transport agent, hybridization-triggered cleavage agent, etc.

In certain embodiments, an antisense oligonucleotide of the invention is synthesized with a full phosphorothioate backbone with alternating blocks of 2'-MOE and 2'fluoro sugar-modified nucleosides.

(c) Pharmaceutical Compositions

The miR-218, miR-138, miR-133a, miR-133b, miR-1193, miR-34b, miR-380, or miR-379 agents (also referred to herein as "active compounds") of the invention may be incorporated into pharmaceutical compositions suitable for administration. Such compositions typically comprise the agent and a pharmaceutically acceptable carrier. As used herein, the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds may also be incorporated into the compositions.

The invention includes methods for preparing pharmaceutical compositions for modulating the expression or activity of miR-218, miR-138, miR-133a, miR-133b, miR-1193, miR-34b, miR-380, or miR-379. Such methods comprise formulating a pharmaceutically acceptable carrier with an agent which modulates expression or activity of miR-218, miR-138, miR-133a, miR-133b, miR-1193, miR-34b, miR-380, or miR-379. Such compositions can further include additional active agents. Thus, the invention further includes methods for preparing a pharmaceutical composition by formulating a pharmaceutically acceptable carrier with an agent which modulates expression or activity of miR-218, miR-138, miR-133a, miR-133b, miR-1193, miR-34b, miR-380, or miR-379 and one or more additional active compounds.

An agent which modulates expression or activity may, for example, be a small molecule. For example, such small molecules include peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the knowledge of the ordinarily skilled artisan. The dose(s) of the small molecule will vary, for example, depending upon the identity, size, and condition of the subject or sample being treated, further depending upon the route by which the composition is to be administered, if applicable, and the effect which the practitioner desires the small molecule to have. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of miR-155, a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention may be formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use may include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.), or phosphate buffered saline (PBS). In all cases, a composition may be sterile and may be fluid to the extent that easy syringeability exists. A composition may be stable under the conditions of manufacture and storage and may be preserved against the contaminating action of microorganisms such as bacteria and fungi. The carrier may be a solvent or dispersion medium containing, for example, water, ethanol, polyol (for example, glycerol, propylene glycol, and liquid polyetheylene glycol, and the like), and suitable mixtures thereof. The proper fluidity may be maintained, for example, by the use of a coating such as lecithin, by the maintenance of the required particle size in the case of dispersion, and by the use of surfactants. Prevention of the action of microorganisms may be achieved by various antibacterial and antifungal agents, for example, parabens, chlorobutanol, phenol, ascorbic acid, thimerosal, and the like. In many cases, it may be preferable to include isotonic agents, for example, sugars, polyalcohols such as mannitol, sorbitol, or sodium chloride, in the composition. Prolonged absorption of the injectable compositions may be brought about by including in the composition an agent which delays absorption, for example, aluminum monostearate and gelatin.

Sterile injectable solutions may be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally may include an inert diluent or an edible carrier. Oral compositions may be enclosed in gelatin capsules or compressed into tablets. For the purpose of oral therapeutic administration, the active compound may be incorporated with excipients and used in the form of tablets, troches, or capsules. Oral compositions may also be prepared using a fluid carrier for use as a mouthwash, wherein the compound in the fluid carrier is applied orally and swished and expectorated or swallowed. Pharmaceutically compatible binding agents and/or adjuvant materials may be included as part of the composition. The tablets, pills, capsules, troches, and the like, may contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressured container or dispenser which contains a suitable propellant, e.g., a gas such as carbon dioxide, or a nebulizer.

Systemic administration may also be by transmucosal or transdermal means. For transmucosal or transdermal administration, penetrants appropriate to the barrier to be permeated are used in the formulation. Such penetrants are generally known in the art, and may include, for example, for transmucosal administration, detergents, bile salts, and fusidic acid derivatives. Transmucosal administration may be accomplished through the use of nasal sprays or suppositories. For transdermal administration, the active compounds are formulated into ointments, salves, gels, or creams as generally known in the art. The compounds may also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, and polylactic acid. Methods for preparation of such formulations will be apparent to those skilled in the art. These may be prepared according to methods known to those skilled in the art, for example, as described in U.S. Pat. No. 4,522,811.

The nucleic acid molecules of the invention may be inserted into vectors and used as gene therapy vectors. Gene therapy vectors may be delivered to a subject by, for example, intravenous injection, local administration (U.S. Pat. No. 5,328,470) or by stereotactic injection (see, e.g., Chen et al. (1994) Proc. Natl. Acad. Sci. USA 91:3054-3057). The pharmaceutical preparation of the gene therapy vector may include the gene therapy vector in an acceptable diluent, or can comprise a slow release matrix in which the gene delivery vehicle is imbedded.

The gene therapy vectors of the invention may be either viral or non-viral. Examples of plasmid-based, non-viral vectors are discussed in Huang et al. (1999) Nonviral Vectors for Gene Therapy. A modified plasmid is one example of a non-viral gene delivery system. Peptides, proteins (including antibodies), and oligonucleotides may be stably conjugated to plasmid DNA by methods that do not interfere with the transcriptional activity of the plasmid (Zelphati et al. (2000) BioTechniques 28:304-315). The attachment of proteins and/or oligonucleotides may influence the delivery and trafficking of the plasmid and thus render it a more effective pharmaceutical composition.

II. Methods

In an aspect, the present invention encompasses a method to detect a motor neuron disease. The method comprises measuring the amount of miR-218 in a biological sample obtained from a subject, and comparing the amount of miR-218 in the biological sample to a reference value, wherein dysregulation of miR-218 relative to the reference value indicates motor neuron disease. In a specific embodiment, miR-218 is increased relative to a reference value. The method may further comprise treatment of the subject if motor neuron disease is detected. In a specific embodiment, the motor neuron disease is amyotrophic lateral sclerosis (ALS).

In another aspect, the present invention encompasses a method to detect a motor neuron disease. The method comprises measuring the amount of miR-218 and at least one additional miRNA selected from the group consisting of miR-138, miR-133a, miR-133b, miR-1193, miR-34b, miR-380, and miR-379 in a biological sample obtained from a subject, and comparing the amount of miR-218 and at least one additional miRNA selected from the group consisting of miR-138, miR-133a, miR-133b, miR-1193, miR-34b, miR-380, and miR-379 in the biological sample to a reference value, wherein dysregulation of miR-218 and at least one additional miRNA selected from the group consisting of miR-138, miR-133a, miR-133b, miR-1193, miR-34b, miR-380, and miR-379 relative to the reference value indicates motor neuron disease. In a specific embodiment, miR-218 is increased relative to a reference value. In another specific embodiment, method comprises measuring the amount of miR-218 and miR-138 in a biological sample obtained from a subject, and comparing the amount of miR-218 and miR-138 in the biological sample to a reference value, wherein dysregulation of miR-218 and miR-138 relative to the reference value indicates motor neuron disease. In a specific embodiment, miR-138 is increased relative to a reference value. The method may further comprise treatment of the subject if motor neuron disease is detected. In a specific embodiment, the motor neuron disease is ALS.

In still another aspect, the present invention encompasses a method to detect the efficacy of treatment or the progression of motor neuron disease. The method comprises measuring the amount of miR-218 in a first biological sample obtained from a subject; then at a later time measuring the amount of miR-218 in a second biological sample obtained from a subject; and comparing the amount of miR-218 in the first biological sample to the amount of miR-218 in the second biological sample, wherein a change in miR-218 indicates effectiveness of treatment or progression of motor neuron disease. For example, the second biological sample may be obtained days, weeks, months or years following the first biological sample. In a specific embodiment, ineffectiveness of treatment or progression of motor neuron disease is indicated if miR-218 is increased in the second biological sample relative to the first biological sample. The method may further comprise altering treatment modality if ineffectiveness of treatment or progression of motor neuron disease is detected. In a specific embodiment, the motor neuron disease is amyotrophic lateral sclerosis (ALS).

In yet still another aspect, the present invention encompasses a method to detect the efficacy of treatment or the progression of motor neuron disease. The method comprises measuring the amount of miR-218 and at least one additional miRNA selected from the group consisting of miR-138, miR-133a, miR-133b, miR-1193, miR-34b, miR-380, and miR-379 in a first biological sample obtained from a subject; then at a later time measuring the amount of miR-218 and at least one additional miRNA selected from the group consisting of miR-138, miR-133a, miR-133b, miR-1193, miR-34b, miR-380, and miR-379 in a second biological sample obtained from a subject; and comparing the amount of miR-218 and at least one additional miRNA selected from the group consisting of miR-138, miR-133a, miR-133b, miR-1193, miR-34b, miR-380, and miR-379 in the first biological sample to the amount of miR-218 and at least one additional miRNA selected from the group consisting of miR-138, miR-133a, miR-133b, miR-1193, miR-34b, miR-380, and miR-379 in the second biological sample, wherein a change in miR-218 and at least one additional miRNA selected from the group consisting of miR-138, miR-133a, miR-133b, miR-1193, miR-34b, miR-380, and miR-379 indicates effectiveness of treatment or progression of motor neuron disease. In a specific embodiment, ineffectiveness of treatment or progression of motor neuron disease is indicated if miR-218 in the second biological sample is increased relative to the first biological sample. In another specific embodiment, method comprises measuring the amount of miR-218 and miR-138 in a first biological sample obtained from a subject; then at a later time measuring the amount of miR-218 and miR-138 in a second biological sample obtained from a subject; and comparing the amount of miR-218 and miR-138 in the first biological sample to the amount of miR-218 and miR-138 in the second biological sample, wherein a change in miR-218 and miR-138 indicates effectiveness of treatment or progression of motor neuron disease. For example, the second biological sample may be obtained days, weeks, months or years following the first biological sample. In a specific embodiment, ineffectiveness of treatment or progression of motor neuron disease is indicated if miR-138 is increased in the second biological sample relative to the first biological sample. The method may further comprise altering treatment modality if ineffectiveness of treatment or progression of motor neuron disease is detected. In a specific embodiment, the motor neuron disease is ALS.

In a different aspect, the present invention encompasses a method to improve motor neuron function in a subject diagnosed with a motor neuron disease, suspected of having a motor neuron disease or at risk for a motor neuron disease. The method comprises administering a miR-218, miR-138, miR-133a, miR-133b, miR-1193, miR-34b, miR-380, or miR-379 composition, or combinations thereof. A miR-218, miR-138, miR-133a, miR-133b, miR-1193, miR-34b, miR-380, or miR-379 composition is as described in Section I. In a specific embodiment, a miR-218 composition is administered, wherein the composition decreases the amount or expression of miR-218. In another specific embodiment, a miR-138 composition is administered, wherein the composition decreases the amount or expression of miR-138. In still another specific embodiment, the motor neuron disease is ALS. Methods of diagnosing or determining risk of motor neuron disease are described in Section II(a).

In other aspects, the present invention encompasses a method of treating a subject diagnosed with a motor neuron disease, suspected of having a motor neuron disease or at risk for a motor neuron disease. The method comprises administering a miR-218, miR-138, miR-133a, miR-133b, miR-1193, miR-34b, miR-380, or miR-379 composition, or combinations thereof. In a specific embodiment, a miR-218 composition is administered, wherein the composition decreases the amount or expression of miR-218. In another specific embodiment, a miR-138 composition is administered, wherein the composition decreases the amount or expression of miR-138. In still another specific embodiment, the motor neuron disease is ALS. As used herein, the terms "treating" or "treatment" include prevention, attenuation, reversal, or improvement in at least one symptom or sign of symptoms associated with a motor neuron disease. Symptoms may be as described in Section 11(a).

In some embodiments, methods of the invention may be utilized to treat a population of cells that would benefit from a miR-218, miR-138, miR-133a, miR-133b, miR-1193, miR-34b, miR-380, or miR-379 composition, or combinations thereof. Such cells include those in a subject as well as those removed from a subject for therapeutic treatment, cultured cells, those used in gene therapy practices, and any other cell that may benefit from a miR-218, miR-138, miR-133a, miR-133b, miR-1193, miR-34b, miR-380, or miR-379 composition, or combinations thereof.

(a) Motor Neuron Disease

Motor neuron-specific miRNAs have been identified. Accordingly, one or more MN-specific miRNA may be used to detect or diagnose a motor neuron disease, improve the function of motor neurons, treat a symptom associated with a motor neuron disease or prevent, delay progression or treat a motor neuron disease. A motor neuron disease (MND) is a progressive neurological disorder that destroys motor neurons, the cells that control essential voluntary muscle activity such as speaking, walking, breathing, and swallowing. Non-limiting examples of motor neuron diseases include amyotrophic lateral sclerosis (ALS), also called Lou Gehrig's disease or classical motor neuron disease, progressive bulbar palsy, also called progressive bulbar atrophy, pseudobulbar palsy, primary lateral sclerosis (PLS), progressive muscular atrophy, spinal muscular atrophy (SMA), SMA type I, also called Werdnig-Hoffmann disease, SMA type II, SMA type III (Kugelberg-Welander disease), congenital SMA with arthrogryposis, Kennedy's disease, also known as progressive spinobulbar muscular atrophy, post-polio syndrome (PPS), spinal cord injury as well as others known in the art or yet to be discovered. A motor neuron disease of the invention may result from dysregulated miR-218, miR-138, miR-133a, miR-133b, miR-1193, miR-34b, miR-380, or miR-379. A dysregulated miR-218, miR-138, miR-133a, miR-133b, miR-1193, miR-34b, miR-380, or miR-379 may result from overexpression or underexpression of miR-138, miR-133a, miR-133b, miR-1193, miR-34b, miR-380, or miR-379. In some embodiments, a motor neuron disease may result from overexpression of miR-218, miR-138, miR-133a, miR-133b, miR-1193, miR-34b, miR-380, or miR-379. In a specific embodiment, a motor neuron disease results from overexpression of miR-218. In another specific embodiment, a motor neuron disease results from overexpression of miR-218 and mIR-138. In a specific embodiment, the motor neuron disease is ALS.

A subject may or may not be having a symptom associated with motor neuron disease. Exemplary symptoms of motor neuron diseases include muscle weakness including a weakened grip, weakness at the shoulder, tripping up over a foot, twitching of the muscles (fasciculations) or muscle cramps. A skilled artisan will appreciate that specific diseases are defined by specific symptoms. For example, ALS is recognized by weakness and wasting of the bulbar muscles (muscles that control speech, swallowing, and chewing), loss of strength and the ability to move arms and legs, and to hold the body upright, spasticity, spasms, muscle cramps, fasciculations, slurred or nasal speech, loss of the ability to breathe without mechanical support. Symptoms of progressive bulbar palsy (progressive bulbar atrophy) include pharyngeal muscle weakness (involved with swallowing), weak jaw and facial muscles, progressive loss of speech, and tongue muscle atrophy, limb weakness with both lower and upper motor neuron signs, outbursts of laughing or crying (called emotional lability). Pseudobulbar palsy, which shares many symptoms of progressive bulbar palsy, is recognized by progressive loss of the ability to speak, chew, and swallow, progressive weakness in facial muscles leading to an expressionless face, a gravelly voice and an increased gag reflex, an immobile tongue that may be unable to protrude from the mouth, outbursts of laughing or crying. Primary lateral sclerosis (PLS) shows symptoms of slow and effortful movements, slowed and slurred speech, stiff, clumsy, slow and weak legs and arms, leading to an inability to walk or carry out tasks requiring fine hand coordination, difficulty with balance may lead to falls, overactive startle response. Progressive muscular atrophy is marked by slow but progressive degeneration of only the lower motor neurons, weakness in the hands that spreads into the lower body, muscle wasting, clumsy hand movements, fasciculations, and muscle cramps. Spinal muscular atrophy (SMA) produces weakness and wasting of the skeletal muscles which is more severe in the trunk and upper leg and arm muscles than in muscles of the hands and feet. Symptoms of SMA type I, also called Werdnig-Hoffmann disease may include hypotonia (severely reduced muscle tone), diminished limb movements, lack of tendon reflexes, fasciculations, tremors, swallowing and feeding difficulties, and impaired breathing, scoliosis (curvature of the spine) or other skeletal abnormalities. Symptoms of SMA type II, the intermediate form, are inability to stand or walk unaided, and respiratory difficulties. Symptoms of SMA type III (Kugelberg-Welander disease) include abnormal gait; difficulty running, climbing steps, or rising from a chair; and a fine tremor of the fingers, scoliosis and joint contractures—chronic shortening of muscles or tendons around joints, abnormal muscle tone and weakness. Congenital SMA with arthrogryposis (persistent contracture of joints with fixed abnormal posture of the limb) is associated with severe contractures, scoliosis, chest deformity, respiratory problems, unusually small jaws, and drooping of the upper eyelids. Symptoms of Kennedy's disease, also known as progressive spinobulbar muscular atrophy, include weakness and atrophy of the facial, jaw, and tongue muscles, leading to problems with chewing, swallowing, and changes in speech, muscle pain and fatigue, weakness in arm and leg muscles closest to the trunk of the body, muscle atrophy and fasciculations, sensory loss in the feet and hands, sensory neuropathy (pain from sensory nerve inflammation or degeneration), enlargement of the male breasts or develop noninsulin-dependent diabetes mellitus. Post-polio syndrome (PPS) symptoms include fatigue, slowly progressive muscle weakness, muscle atrophy, fasciculations, cold intolerance, and muscle and joint pain, difficulty breathing, swallowing, or sleeping.

A subject may or may not be diagnosed with motor neuron disease. There are no specific tests to diagnose most MNDs. However, MNDs may be diagnosed using a physical exam followed by a thorough neurological exam. The neurological exam may assess motor and sensory skills, nerve function, hearing and speech, vision, coordination and balance, mental status, and changes in mood or behavior. Additionally, tests may be conducted to rule out other muscle disorders such as electromyography (EMG), laboratory tests of blood, urine, or other substances, magnetic resonance imaging (MRI), muscle or nerve biopsy, and transcranial magnetic stimulation.

Some MNDs are inherited, but the causes of most MNDs are not known. In sporadic or noninherited MNDs, environmental, toxic, viral, or genetic factors may be implicated. Accordingly, a subject may be at risk of or suspected of having a motor neuron disease based on environmental exposure or familial history. If the MND is inherited, it is also classified according to the mode of inheritance which is associated with varying risks. Autosomal dominant means that a person needs to inherit only one copy of the defective gene from one affected parent to be at risk of the disease. There is a 50 percent chance that each child of an affected person will be affected. Autosomal recessive means the individual must inherit a copy of the defective gene from both parents. These parents are likely to be asymptomatic (without symptoms of the disease). Autosomal recessive diseases often affect more than one person in the same generation (siblings or cousins). In X-linked inheritance, the mother carries the defective gene on one of her X chromosomes and passes the disorder along to her sons. Males inherit an X chromosome from their mother and a Y chromosome from their father, while females inherit an X chromosome from each parent. Daughters have a 50 percent chance of inheriting their mother's faulty X chromosome and a safe X chromosome from their father, which would make them asymptomatic carriers of the mutation.

(b) Biological Sample

In an aspect, the invention provides a method to detect dysregulation of miR-218 or miR-218 and at least one additional miRNA selected from the group consisting of miR-138, miR-133a, miR-133b, miR-1193, miR-34b, miR-380, and miR-379 in a biological sample obtained from a subject. Further, miR-409 and miR-34c may be detected. The method generally comprises (i) obtaining a biological sample from the subject, and (ii) measuring the amount of miR-218 or miR-218 and at least one additional miRNA selected from the group consisting of miR-138, miR-133a, miR-133b, miR-1193, miR-34b, miR-380, and miR-379 in the biological sample. Further, miR-409 and/or miR-34c may be measured.

As used herein, the term "biological sample" refers to a sample obtained from a subject. Any biological sample comprising a miRNA of the invention is suitable. Non-limiting examples include blood, plasma, serum, urine, cerebrospinal fluid (CSF) and interstitial fluid (ISF). In a specific embodiment, the biological sample is selected from the group consisting of CSF, serum and urine. In another specific embodiment, the biological sample is CSF. In a specific embodiment, the biological sample comprises motor neurons. The sample may be used "as is", the cellular components may be isolated from the sample, or a protein fraction may be isolated from the sample using standard techniques.

As will be appreciated by a skilled artisan, the method of collecting a biological sample can and will vary depending upon the nature of the biological sample and the type of analysis to be performed. Any of a variety of methods generally known in the art may be utilized to collect a biological sample. Generally speaking, the method preferably maintains the integrity of the sample such that the miRNA can be accurately detected and the amount measured according to the invention.

In some embodiments, a single sample is obtained from a subject to detect miRNAs in the sample. Alternatively, miRNAs may be detected in samples obtained over time from a subject. As such, more than one sample may be collected from a subject over time. For instance, 2, 3, 4, 5, 6, 7, 8, 9, 10, 11, 12, 13, 14, 15, 16 or more samples may be collected from a subject over time. In some embodiments, 2, 3, 4, 5, or 6 samples are collected from a subject over time. In other embodiments, 6, 7, 8, 9, or 10 samples are collected from a subject over time. In yet other embodiments, 10, 11, 12, 13, or 14 samples are collected from a subject over time. In other embodiments, 14, 15, 16 or more samples are collected from a subject over time.

When more than one sample is collected from a subject over time, samples may be collected every 0.5, 1, 2, 3, 4, 5, 6, 7, 8, 9, 10, 11, 12 or more hours. In some embodiments, samples are collected every 0.5, 1, 2, 3, or 4 hours. In other embodiments, samples are collected every 4, 5, 6, or 7 hours. In yet other embodiments, samples are collected every 7, 8, 9, or 10 hours. In other embodiments, samples are collected every 10, 11, 12 or more hours. Additionally, samples may be collected every 1, 2, 3, 4, 5, 6, 7, 8, 9, 10, 11, 12 or more days. In some embodiments, a sample is collected about every 6 days. In some embodiments, samples are collected every 1, 2, 3, 4, or 5 days. In other embodiments, samples are collected every 5, 6, 7, 8, or 9 days. In yet other embodiments, samples are collected every 9, 10, 11, 12 or more days.

(c) Detecting miRNAs miR-218, miR-138, miR-133a, miR-133b, miR-1193, miR-34b, miR-380, miR-379, miR-409 and miR-34c or a complement thereof, may be detected using standard molecular biology techniques. For instance, using all or a portion of the nucleic acid sequences of miR-218, miR-138, miR-133a, miR-133b, miR-1193, miR-34b, miR-380, miR-379, miR-409 and miR-34c, nucleic acid molecules may be detected using standard hybridization and cloning techniques (e.g., as described in Sambrook et al., eds., Molecular Cloning: A Laboratory Manual. 2nd ed., Cold Spring Harbor Laboratory, Cold Spring Harbor Laboratory Press, Cold Spring Harbor, N.Y., 1989). As used herein, miR-218 refers to miR-218-1 and miR-218-2. Accordingly, miR-218-1 and/or miR-218-2 may be detected. As will be recognized by individuals skilled in the art, both arms of a pre-miRNA hairpin encoding miR-218, miR-138, miR-133a, miR-133b, miR-1193, miR-34b, miR-380, miR-379, miR-409, and miR-34c may give rise to a mature miR-218, miR-138, miR-133a, miR-133b, miR-1193, miR-34b, miR-380, miR-379, miR-409 or miR-34c miRNA. For instance, two mature miRNAs that may result from a pre-miRNA encoding a miR-218, miR-138, miR-133a, miR-133b, miR-1193, miR-34b, miR-380, miR-379, miR-409, and miR-34c miRNA may be miR-218-3p, miR-138-3p, miR-133a-3p, miR-133b-3p, miR-1193-3p, miR-34b-3p, miR-380-3p, miR-379-3p, miR-409-3p, and miR-34c-3p and miR-218-5p, miR-138-5p, miR-133a-5p, miR-133b-5p, miR-1193-5p, miR-34b-5p, miR-380-5p, miR-379-5p, miR-409-5p, and miR-34c-5p, respectively. Specifically, miR-218-3p, miR-218-5p, miR-138-5p, miR-138-3p, miR-133a-3p, miR-133b-3p, miR-34b-3p, miR-380-3p, miR-380-5p, miR-409-3p, miR-409-5p, miR-34c-3p, and/or miR-34c-5p may be detected.

Methods for assessing an amount of nucleic acid expression in cells are well known in the art, and all suitable methods for assessing an amount of nucleic acid expression known to one of skill in the art are contemplated within the scope of the invention. The term "amount of nucleic acid expression" or "level of nucleic acid expression" as used herein refers to a measurable level of expression of the nucleic acids, such as, without limitation, the level of miRNA transcript expressed or a specific variant or other portion of the miRNA. The term "nucleic acid" includes DNA and RNA and can be either double stranded or single stranded. Non-limiting examples of suitable methods to assess an amount of nucleic acid expression may include arrays, such as microarrays, PCR, such as RT-PCR (including quantitative RT-PCR), nuclease protection assays and Northern blot analyses. In a specific embodiment, determining the amount of a miRNA comprises, in part, measuring the level of miRNA expression.

In one embodiment, the amount of nucleic acid expression may be determined by using an array, such as a microarray. Methods of using a nucleic acid microarray are well and widely known in the art. For example, a nucleic acid probe that is complementary or hybridizable to an expression product of a target gene may be used in the array. The term "hybridize" or "hybridizable" refers to the sequence specific non-covalent binding interaction with a complementary nucleic acid. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. The term "probe" as used herein refers to a nucleic acid sequence that will hybridize to a nucleic acid target sequence. In one example, the probe hybridizes to an RNA product of the nucleic acid or a nucleic acid sequence complementary thereof. The length of probe depends on the hybridization conditions and the sequences of the probe and nucleic acid target sequence. In one embodiment, the probe is at least 8, 10, 15, 20, 25, 50, 75, 100, 150, 200, 250, 400, 500 or more nucleotides in length.

In another embodiment, the amount of nucleic acid expression may be determined using PCR. A nucleic acid may be amplified using cDNA, mRNA or genomic DNA as a template and appropriate oligonucleotide primers according to standard PCR amplification techniques. Methods of PCR are well and widely known in the art, and may include quantitative PCR, semi-quantitative PCR, multiplex PCR, or any combination thereof. Specifically, the amount of nucleic expression may be determined using quantitative RT-PCR. Methods of performing quantitative RT-PCR are common in the art. In such an embodiment, the primers used for quantitative RT-PCR may comprise a forward and reverse primer for a target gene. The term "primer" as used herein refers to a nucleic acid sequence, whether occurring naturally as in a purified restriction digest or produced synthetically, which is capable of acting as a point of synthesis when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less or more. The factors involved in determining the appropriate length of primer are readily known to one of ordinary skill in the art.

The amount of nucleic acid expression may be measured by measuring an entire miRNA transcript for a nucleic acid sequence, or measuring a portion of the miRNA transcript for a nucleic acid sequence. For instance, if a nucleic acid array is utilized to measure the amount of miRNA expression, the array may comprise a probe for a portion of the miRNA of the nucleic acid sequence of interest, or the array may comprise a probe for the full miRNA of the nucleic acid sequence of interest. Similarly, in a PCR reaction, the primers may be designed to amplify the entire cDNA sequence of the nucleic acid sequence of interest, or a portion of the cDNA sequence. One of skill in the art will recognize that there is more than one set of primers that may be used to amplify either the entire cDNA or a portion of the cDNA for a nucleic acid sequence of interest. Methods of designing primers are known in the art. Methods of extracting RNA from a biological sample are known in the art.

The level of expression may or may not be normalized to the level of a control nucleic acid. Such a control nucleic acid should not specifically hybridize with an miRNA nucleotide sequence of the invention. This allows comparisons between assays that are performed on different occasions. In certain embodiments, the level of expression is normalized to a control nucleic acid. In a specific embodiment, a control nucleic acid is selected from the group consisting of miR-191, miR-24 and miR-30c.

(d) Reference Level

According to the invention, a motor neuron disease may be detected based on dysregulation of miR-218 or miR-218 and at least one additional miRNA selected from the group consisting of miR-138, miR-133a, miR-133b, miR-1193, miR-34b, miR-380, and miR-379 relative to a reference value. Detecting dysregulation of miR-218 or miR-218 and at least one additional miRNA selected from the group consisting of miR-138, miR-133a, miR-133b, miR-1193, miR-34b, miR-380, and miR-379 relative to a reference value in the subject may be used to diagnose a motor neuron disease or determine the efficacy of treatment or determine the progression of motor neuron disease. Additionally, at least one miRNA selected from the group consisting of miR-409 and miR-34c may be detected.

Generally speaking, a miRNA disclosed herein may be classified as dysregulated when it has an increased or decreased amount relative to a reference value. Any suitable reference value known in the art may be used. For example, a suitable reference value may be the amount of miRNA in a biological sample obtained from a subject, or group of subjects, of the same species that has no clinically detectable symptom of MND. In another example, a suitable reference value may be the amount of miRNA in a biological sample obtained from a subject, or group of subjects, of the same species that has no detectable MND pathology. In another example, a suitable reference value may be the background signal of the assay as determined by methods known in the art. In another example, a suitable reference value may be a measurement of the amount of miRNA in a reference sample obtained from the same subject. The reference sample comprises the same type of biological sample as the test sample, and may be obtained from a subject when the subject had no clinically detectable symptom of MND. A skilled artisan will appreciate that it is not always possible or desirable to obtain a reference sample from a subject when the subject is otherwise healthy. For example, when monitoring the effectiveness of a therapy or progression of disease, a reference sample may be a sample obtained from a subject before therapy or at an earlier point in the disease. In such an example, a subject may have a risk of MND (familial or environmental) but may not have other symptoms of MND (e.g. muscle weakness) or the subject may have one or more other symptom of MND. In an additional example, a suitable reference sample may be a biological sample from an individual or group of individuals that has been shown not to have MND. In an embodiment, the reference value may be a sample of the same type of biological sample obtained from one or more individuals that has not been administered therapy but has a MND.

In certain embodiments, to classify the amount of miRNA as increased in a biological sample, the amount of miRNA in the biological sample compared to the reference value is increased at least 2-fold. For example, the amount of miRNA in the sample compared to the reference value is increased at least 2-fold, at least 5-fold, at least 10-fold, at least 15-fold, at least 20-fold, at least 25-fold, at least 30-fold, at least 35-fold, at least 40-fold, at least 45-fold, at least 50-fold, at least 100-fold, at least 200-fold, at least 300-fold, at least 400-fold, at least 500-fold, at least 1000-fold, at least 5000-fold, or at least 10000-fold. In a specific embodiment, the amount of miR-218 in the sample compared to the reference value is increased at least 10-fold. In another specific embodiment, the amount of miR-138, miR-133a, miR-1193, and/or miR-34b in the sample compared to the reference value is increased at least 3-fold.

In certain embodiments, to classify the amount of miRNA as decreased in a biological sample, the amount of miRNA in the biological sample compared to the reference value is decreased at least 2-fold. For example, the amount of miRNA in the sample compared to the reference value is decreased at least 2-fold, at least 5-fold, at least 10-fold, at least 15-fold, at least 20-fold, at least 25-fold, at least 30-fold, at least 35-fold, at least 40-fold, at least 45-fold, at least 50-fold, at least 100-fold, at least 200-fold, at least 300-fold, at least 400-fold, at least 500-fold, at least 1000-fold, at least 5000-fold, or at least 10000-fold.

In another embodiment, the increase or decrease in the amount of miRNA is measured using p-value. For instance, when using p-value, a miRNA is identified as being differentially expressed between a a biological sample and a reference value when the p-value is less than 0.1, preferably less than 0.05, more preferably less than 0.01, even more preferably less than 0.005, the most preferably less than 0.001.

(e) Treatment

According to the disclosure, the subject may be treated if motor neuron disease is detected. Additionally, the treatment modality may be altered if ineffectiveness of treatment or progression of motor neuron disease is detected. The term "treatment" or "therapy" as used herein means any treatment suitable for the treatment of MND. Treatment may consist of standard treatments for MND. Non-limiting examples of standard treatment for MND include Riluzole (Rilutek), Tizanidine (Zanaflex), Baclofen, quinine, hyoscine hydrobromide skin patch, NSAIDs, gabapentin, physical therapy, acupuncture, immunotherapy, gene transfer therapy, stem cell and progenitor cell based cellular replacement therapy, antisense oligonucleotide therapy, antioxidant therapy, antidepressant therapy, antibody therapy, autophagy control therapy, drug therapy (small-molecule inhibitor of kynurenine 3-monooxygenase JM6), and any therapeutic agent known in the art or yet to be discovered. Still further, treatment may be as described below or with an agent as described in Section I.

(f) Administration

The present invention also provides for both prophylactic and therapeutic methods of treating a subject at risk of, or susceptible to a MND. In a specific embodiment, the MND may be associated with aberrant miR-218, miR-138, miR-133a, miR-133b, miR-1193, miR-34b, miR-380, and/or miR-379 expression or activity. Generally, methods of the present invention include administering to a subject a miR-218, miR-138, miR-133a, miR-133b, miR-1193, miR-34b, miR-380, or miR-379 composition respectively comprising at least miR-218 miR-138, miR-133a, miR-133b, miR-1193, miR-34b, miR-380, or miR-379 agent. For instance, 1, 2, 3, 4, 5, 6, 7, 8, 9, 10 or more miR-218, miR-138, miR-133a, miR-133b, miR-1193, miR-34b, miR-380, or miR-379 agents may be administered. In some embodiments, 1, 2, 3, 4, or 5 miR-218, miR-138, miR-133a, miR-133b, miR-1193, miR-34b, miR-380, or miR-379 agents are administered. In other embodiments, 5, 6, 7, 8, 9, 10 or more miR-218, miR-138, miR-133a, miR-133b, miR-1193, miR-34b, miR-380, or miR-379 agents are administered. In one embodiment, one miR-218, miR-138, miR-133a, miR-133b, miR-1193, miR-34b, miR-380, or miR-379 agent is administered. In another embodiment, two miR-218, miR-138, miR-133a, miR-133b, miR-1193, miR-34b, miR-380, or miR-379 agents are administered. In yet another embodiment, the miR-218, miR-138, miR-133a, miR-133b, miR-1193, miR-34b, miR-380, or miR-379 agent is delivered in combination with additional therapeutic agents known in the art. miR-218, miR-138, miR-133a, miR-133b, miR-1193, miR-34b, miR-380, or miR-379 agents may be as described in Section I(b).

In certain embodiments, a miR-218, miR-138, miR-133a, miR-133b, miR-1193, miR-34b, miR-380, or miR-379 composition is administered in combination with at least one additional therapeutic agent. In certain embodiments, miR-218, miR-138, miR-133a, miR-133b, miR-1193, miR-34b, miR-380, or miR-379 composition is administered sequential to an additional therapeutic agent. In other embodiments, a miR-218, miR-138, miR-133a, miR-133b, miR-1193, miR-34b, miR-380, or miR-379 composition is administered prior to the administration of an additional therapeutic agent. In certain embodiments, a miR-218, miR-138, miR-133a, miR-133b, miR-1193, miR-34b, miR-380, or miR-379 composition is administered prior to and after the administration of an additional therapeutic agent. In other embodiments, a miR-218, miR-138, miR-133a, miR-133b, miR-1193, miR-34b, miR-380, or miR-379 composition is administered at the same time as at least one therapeutic agent. In certain embodiments, a miR-218, miR-138, miR-133a, miR-133b, miR-1193, miR-34b, miR-380, or miR-379 composition may be administered without additional therapeutic agents.

Additional therapeutic agents may include those used in immunotherapy, gene transfer therapy, stem cell and progenitor cell based cellular replacement therapy, antisense oligonucleotide therapy, antioxidant therapy, antidepressant therapy, antibody therapy, autophagy control therapy, drug therapy (small-molecule inhibitor of kynurenine 3-monooxygenase JM6), and any therapeutic agent known in the art or yet to be discovered.

A miR-218, miR-138, miR-133a, miR-133b, miR-1193, miR-34b, miR-380, or miR-379 composition of the invention may be administered to a subject by several different means. For instance, compositions may generally be administered in dosage unit formulations containing conventional nontoxic pharmaceutically acceptable carriers, adjuvants, and vehicles as desired.

Methods of administration include any method known in the art or yet to be discovered. Exemplary administration methods include intravenous, intraocular, intratracheal, intratumoral, oral, rectal, topical, intramuscular, intraarterial, intrahepatic, intrathoracic, intrathecal, intracranial, intraperitoneal, intrapancreatic, intrapulmonary, or subcutaneously. A composition of the invention may also be administered directly by infusion into central nervous system fluid. One skilled in the art will appreciate that the route of administration and method of administration depend upon the intended use of the compositions, the location of the target area, and the condition being treated, in addition to other factors known in the art such as subject health, age, and physiological status.

In a preferred embodiment, the oligonucleotide may be administered parenterally. The term "parenteral" as used herein describes administration into the body via a route other than the mouth, especially via infusion, injection, or implantation, and includes intradermal, subcutaneous, transdermal implant, intracavernous, intravitreal, intra-articular or intrasynovial injection, transscleral, intracerebral, intrathecal, epidural, intravenous, intracardiac, intramuscular, intraosseous, intraperitoneal, intravenous, intrasternal injection, or nanocell injection. Formulation of pharmaceutical compositions is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

In some embodiments, a miR-218, miR-138, miR-133a, miR-133b, miR-1193, miR-34b, miR-380, or miR-379 composition of the invention is administered parenterally. When a miR-218, miR-138, miR-133a, miR-133b, miR-1193, miR-34b, miR-380, or miR-379 composition is administered parenterally, delivery methods are preferably those that are effective to circumvent the blood-brain barrier, and are effective to deliver agents to the central nervous system. For example, delivery methods may include the use of nanoparticles. The particles may be of any suitable structure, such as unilamellar or plurilamellar, so long as the antisense oligonucleotide is contained therein. Positively charged lipids such as N-[1-(2,3-dioleoyloxi)propyl]-N, N,N-trimethylamoniummethylsulfate, or "DOTAP," are particularly preferred for such particles and vesicles. The preparation of such lipid particles is well known in the art. See, e.g., U.S. Pat. No. 4,880,635 to Janoff et al.; U.S. Pat. No. 4,906,477 to Kurono et al.; U.S. Pat. No. 4,911,928 to Wallach; U.S. Pat. No. 4,917,951 to Wallach; U.S. Pat. No. 4,920,016 to Allen et al.; U.S. Pat. No. 4,921,757 to Wheatley et al.; etc.

In preferred embodiments, a miR-218, miR-138, miR-133a, miR-133b, miR-1193, miR-34b, miR-380, or miR-379 composition of the invention is administered into the central nervous system. Methods of administering a miR-218, miR-138, miR-133a, miR-133b, miR-1193, miR-34b, miR-380, or miR-379 composition of the invention to the central nervous system are known in the art. For instance, a miR-218, miR-138, miR-133a, miR-133b, miR-1193, miR-34b, miR-380, or miR-379 composition of the invention may be administered in a bolus directly into the central nervous system. A miR-218, miR-138, miR-133a, miR-133b, miR-1193, miR-34b, miR-380, or miR-379 composition may be administered to the subject in a bolus once or multiple times. In some preferred embodiments, a miR-218, miR-138, miR-133a, miR-133b, miR-1193, miR-34b, miR-380, or miR-379 composition may be administered in a bolus once. In other preferred embodiments, a miR-218, miR-138, miR-133a, miR-133b, miR-1193, miR-34b, miR-380, or miR-379 composition may be administered in a bolus multiple times. When administered multiple times, a miR-218 miR-138, miR-133a, miR-133b, miR-1193, miR-34b, miR-380, or miR-379 composition may be administered at regular intervals or at intervals that may vary during the treatment of a subject. In some embodiments, a miR-218, miR-138, miR-133a, miR-133b, miR-1193, miR-34b, miR-380, or miR-379 composition is administered multiple times at intervals that may vary during the treatment of a subject. In other embodiments, a miR-218, miR-138, miR-133a, miR-133b, miR-1193, miR-34b, miR-380, or miR-379 composition is administered multiple times at regular intervals.

In another preferred embodiment, a miR-218, miR-138, miR-133a, miR-133b, miR-1193, miR-34b, miR-380, or miR-379 composition is administered by continuous infusion into the central nervous system. Non-limiting examples of methods that may be used to deliver a miR-218, miR-138, miR-133a, miR-133b, miR-1193, miR-34b, miR-380, or miR-379 composition into the central nervous system by continuous infusion may include pumps, wafers, gels, foams and fibrin clots. In a preferred embodiment, a miR-218, miR-138, miR-133a, miR-133b, miR-1193, miR-34b, miR-380, or miR-379 composition is delivered into the central nervous system by continuous infusion using an osmotic pump. An osmotic minipump contains a high-osmolality chamber that surrounds a flexible, yet impermeable, reservoir filled with the targeted delivery composition-containing vehicle. Subsequent to the subcutaneous implantation of this minipump, extracellular fluid enters through an outer semi-permeable membrane into the high-osmolality chamber, thereby compressing the reservoir to release the targeted delivery composition at a controlled, pre-determined rate. The targeted delivery composition, released from the pump, may be directed via a catheter to a stereotaxically placed cannula for infusion into the cerebroventricular space.

Compositions of the invention are typically administered to a subject in an amount sufficient to provide a benefit to the subject. This amount is defined as a "therapeutically effective amount." A therapeutically effective amount may be determined by the efficacy or potency of the particular composition, the MND being treated, the duration or frequency of administration, the method of administration, and the size and condition of the subject, including that subject's particular treatment response. A therapeutically effective amount may be determined using methods known in the art, and may be determined experimentally, derived from therapeutically effective amounts determined in model animals such as the mouse, or a combination thereof. Additionally, the route of administration may be considered when determining the therapeutically effective amount. In determining the therapeutically effective amounts, one skilled in the art may also consider the existence, nature, and extent of any adverse effects that accompany the administration of a particular compound in a particular subject.

In some embodiments, when a miR-218, miR-138, miR-133a, miR-133b, miR-1193, miR-34b, miR-380, or miR-379 composition is administered in a bolus into the central nervous system, the miR-218, miR-138, miR-133a, miR-133b, miR-1193, miR-34b, miR-380, or miR-379 composition may be administered to the subject in an amount of about 0.1, 0.2, 0.3, 0.4, 0.5, 1, 1.5, 2, 2.5, 3, 3.5, 4, 4.5, 5, 6.5, 7, 7.5, 8, 8.5, 9, 9.5, 10, 10.5, 11, 11.5, 12, 12.5, 13, 13.5, 14, 14.5, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or about 100 mg/kg or more. In one embodiment, when a miR-218, miR-138, miR-133a, miR-133b, miR-1193, miR-34b, miR-380, or miR-379 composition is administered in a bolus into the central nervous system, the miR-218, miR-138, miR-133a, miR-133b, miR-1193, miR-34b, miR-380, or miR-379 composition is administered to the subject in an amount of about 0.1, 0.2, 0.3, 0.4, 0.5, or about 1 mg/kg. In another embodiment, when a miR-218, miR-138, miR-133a, miR-133b, miR-1193, miR-34b, miR-380, or miR-379 composition is administered in a bolus into the central nervous system, the miR-218, miR-138, miR-133a, miR-133b, miR-1193, miR-34b, miR-380, or miR-379 composition is administered to the subject in an amount of about 1, 1.5, 2, 2.5, 3, 3.5, 4, 4.5, 5, 6.5, 7, 7.5, 8, 8.5, 9, 9.5, or about 10 mg/kg. In yet another embodiment, when a miR-218, miR-138, miR-133a, miR-133b, miR-1193, miR-34b, miR-380, or miR-379 composition is administered in a bolus into the central nervous system, the miR-218, miR-138, miR-133a, miR-133b, miR-1193, miR-34b, miR-380, or miR-379 composition is administered to the subject in an amount of about 10, 10.5, 11, 11.5, 12, 12.5, 13, 13.5, 14, 14.5, 15, 16, 17, 18, 19, or about 20 mg/kg. In another embodiment, when miR-218, miR-138, miR-133a, miR-133b, miR-1193, miR-34b, miR-380, or miR-379 composition is administered in a bolus into the central nervous system, the miR-218, miR-138, miR-133a, miR-133b, miR-1193, miR-34b, miR-380, or miR-379 composition is administered to the subject in an amount of about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or about 50 mg/kg. In an additional embodiment, when a miR-218, miR-138, miR-133a, miR-133b, miR-1193, miR-34b, miR-380, or miR-379 composition is administered in a bolus into the central nervous system, the miR-218, miR-138, miR-133a, miR-133b, miR-1193, miR-34b, miR-380, or miR-379 composition is administered to the subject in an amount of about 50, 60, 70, 80, 90, or about 100 mg/kg. In a preferred embodiment, when a miR-218, miR-138, miR-133a, miR-133b, miR-1193, miR-34b, miR-380, or miR-379 composition is administered in a bolus into the central nervous system, miR-218, miR-138, miR-133a, miR-133b, miR-1193, miR-34b, miR-380, or miR-379 composition is administered to the subject in an amount of about 23, 24, 25, 26, or about 27 mg/kg.

In some embodiments, when a miR-218, miR-138, miR-133a, miR-133b, miR-1193, miR-34b, miR-380, or miR-379 composition is administered by continuous infusion into the central nervous system, the miR-218, miR-138, miR-133a, miR-133b, miR-1193, miR-34b, miR-380, or miR-379 composition may be administered to the subject in an amount of about 0.1, 0.2, 0.3, 0.4, 0.5, 1, 1.5, 2, 2.5, 3, 3.5, 4, 4.5, 5, 6.5, 7, 7.5, 8, 8.5, 9, 9.5, 10, 10.5, 11, 11.5, 12, 12.5, 13, 13.5, 14, 14.5, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or about 100 μg/day or more. In one embodiment, when a miR-218, miR-138, miR-133a, miR-133b, miR-1193, miR-34b, miR-380, or miR-379 composition is administered by continuous infusion into the central nervous system, the miR-218, miR-138, miR-133a, miR-133b, miR-1193, miR-34b, miR-380, or miR-379 composition is administered to the subject in an amount of about 0.1, 0.2, 0.3, 0.4, 0.5, or about 1 μg/day. In another embodiment, when a miR-218, miR-138, miR-133a, miR-133b, miR-1193, miR-34b, miR-380, or miR-379 composition is administered by continuous infusion into the central nervous system, the miR-218, miR-138, miR-133a, miR-133b, miR-1193, miR-34b, miR-380, or miR-379 composition is administered to the subject in an amount of about 1, 1.5, 2, 2.5, 3, 3.5, 4, 4.5, 5, 6.5, 7, 7.5, 8, 8.5, 9, 9.5, or about 10 μg/day. In yet another embodiment, when a miR-218, miR-138, miR-133a, miR-133b, miR-1193, miR-34b, miR-380, or miR-379 composition is administered by continuous infusion into the central nervous system, the miR-218, miR-138, miR-133a, miR-133b, miR-1193, miR-34b, miR-380, or miR-379 is administered to the subject in an amount of about 10, 10.5, 11, 11.5, 12, 12.5, 13, 13.5, 14, 14.5, 15, 16, 17, 18, 19, or about 20 μg/day. In another embodiment, when a miR-218, miR-miR-138, miR-133a, miR-133b, miR-1193, miR-34b, miR-380, or miR-379 composition is administered by continuous infusion into the central nervous system, the miR-218, miR-138, miR-133a, miR-133b, miR-1193, miR-34b, miR-380, or miR-379 composition is administered to the subject in an amount of about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or about 50 μg/day. In an additional embodiment, when a miR-218, miR-138, miR-133a, miR-133b, miR-1193, miR-34b, miR-380, or miR-379 composition is administered by continuous infusion into the central nervous system, the miR-218, miR-138, miR-133a, miR-133b, miR-1193, miR-34b, miR-380, or miR-379 composition is administered to the subject in an amount of about 50, 60, 70, 80, 90, or about 100 μg/day. In a preferred embodiment, when a miR-218, miR-138, miR-133a, miR-133b, miR-1193, miR-34b, miR-380, or miR-379 composition is administered by continuous infusion into the central nervous system, the miR-218, miR-138, miR-133a, miR-133b, miR-1193, miR-34b, miR-380, or miR-379 composition is administered to the subject in an amount of about 17, 18, 19, 20, 21, 22, or about 23 μg/day.

One of skill in the art will also recognize that the duration of the administration by continuous infusion can and will vary, and will depend in part on the subject, the MND, and the severity, progression and improvement of the condition of the subject, and may be determined experimentally. In some embodiments, a miR-218, miR-138, miR-133a, miR-133b, miR-1193, miR-34b, miR-380, or miR-379 composition is administered by continuous infusion for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 days or longer. In one embodiment, a miR-218, miR-138, miR-133a, miR-133b, miR-1193, miR-34b, miR-380, or miR-379 composition is administered by continuous infusion for 20, 21, 22, 23, 24, 25, 26, 27, 28, 29, 30, 31, 32, 33, 34, 35 days or longer. In another embodiment, a miR-218, miR-138, miR-133a, miR-133b, miR-1193, miR-34b, miR-380, or miR-379 composition is administered by continuous infusion for 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65 days or longer. In yet another embodiment, a miR-218, miR-138, miR-133a, miR-133b, miR-1193, miR-34b, miR-380, or miR-379 composition is administered by continuous infusion for 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95 days or longer. Longer continuous infusions of the antisense oligonucleotide may also be envisioned using existing pump technology as is known in the art.

When a miR-218, miR-138, miR-133a, miR-133b, miR-1193, miR-34b, miR-380, or miR-379 composition of the invention is an antisense oligonucleotide, molecules of the invention are typically administered to a subject or generated in situ such that they hybridize with or bind to miR-218, miR-138, miR-133a, miR-133b, miR-1193, miR-34b, miR-380, or miR-379 or the coding sequence of miR-218, miR-138, miR-133a, miR-133b, miR-1193, miR-34b, miR-380, or miR-379 inhibiting the respective biological activity of miR-218, miR-138, miR-133a, miR-133b, miR-1193, miR-34b, miR-380, or miR-379. The hybridization may be by conventional nucleotide complementarity to form a stable duplex, or, for example, in the case of an antisense nucleic acid molecule which binds to DNA duplexes, through specific interactions in the major groove of the double helix. An antisense nucleic acid molecule of the invention may be administered by direct injection at a tissue site. Alternatively, antisense nucleic acid molecules may be modified to target selected cells and then administered systemically. For example, for systemic administration, antisense molecules may be modified such that they specifically bind to receptors or antigens expressed on a selected cell surface, e.g., by linking the antisense nucleic acid molecules to peptides or antibodies which bind to cell surface receptors or antigens. The antisense nucleic acid molecules may also be delivered by direct infusion into a subject. The antisense nucleic acid molecules may also be delivered to cells using gene therapy vectors known in the art. To achieve sufficient intracellular concentrations of the antisense molecules, vectors in which the antisense nucleic acid molecule is placed under the control of a strong pol II or pol III promoter are preferred.

(g) Restoring Motor Neuron Function and/or Treatment

A method of the invention comprises improving motor neuron function in a subject diagnosed with a motor neuron disease, suspected of having a motor neuron disease or at risk for a motor neuron disease by administering a miR-218, miR-138, miR-133a, miR-133b, miR-1193, miR-34b, miR-380, or miR-379 composition to the subject. The miR-218, miR-138, miR-133a, miR-133b, miR-1193, miR-34b, miR-380, or miR-379 composition may decrease the amount or expression of miR-218, miR-138, miR-133a, miR-133b, miR-1193, miR-34b, miR-380, or miR-379, respectively. In a specific embodiment, a miR-218 composition may decrease the amount or expression of miR-218. In another specific embodiment, a miR-138 composition may decrease the amount or expression of miR-138.

An improvement in motor neuron function may be measured by several means, including an increase in motor neurons, an improvement in symptoms associated with a motor neuron disease, and/or an improvement or restoration of miR-218, miR-138, miR-133a, miR-133b, miR-1193, miR-34b, miR-380, or miR-379 amount to that of a reference value, wherein the reference value is that of a subject without motor neuron disease.

A method of the invention also comprises treating a subject by administering to the subject a therapeutically effective amount of a composition comprising a miR-218, miR-138, miR-133a, miR-133b, miR-1193, miR-34b, miR-380, or miR-379 agent that decreases the expression of miR-218, miR-138, miR-133a, miR-133b, miR-1193, miR-34b, miR-380, or miR-379. In a specific embodiment, a method of the invention comprises treating a subject by administering to the subject a therapeutically effective amount of a composition comprising a miR-218 agent that decreases the expression of miR-218. In another specific embodiment, a method of the invention comprises treating a subject by administering to the subject a therapeutically effective amount of a composition comprising a miR-138 agent that decreases the expression of miR-138. As used herein, "subject" may refer to a living organism having a central nervous system. In particular, subjects may include, but are not limited to, human subjects or patients and companion animals. Exemplary companion animals may include domesticated mammals (e.g., dogs, cats, horses), mammals with significant commercial value (e.g., dairy cows, beef cattle, sporting animals), mammals with significant scientific value (e.g., captive or free specimens of endangered species), or mammals which otherwise have value. Suitable subjects may also include: mice, rats, dogs, cats, ungulates such as cattle, swine, sheep, horses, and goats, lagomorphs such as rabbits and hares, other rodents, and primates such as monkeys, chimps, and apes. In some preferred embodiments, a subject is a human. In other preferred embodiments, a subject is a rat. In yet other preferred embodiments, a subject is a mouse. Subjects may be of any age including newborn, adolescent, adult, middle age, or elderly.

A subject may be at risk for developing a MND resulting from dysregulation of miR-218, miR-138, miR-133a, miR-133b, miR-1193, miR-34b, miR-380, or miR-379. In a specific embodiment, a subject may be at risk for developing a MND resulting from dysregulation of miR-218 and/or miR-138. In another specific embodiment, a subject may be at risk for developing a MND resulting from overexpression of miR-218. In still another specific embodiment, a subject may be at risk for developing a MND resulting from overrexpression of miR-138. As such, in some embodiments, treating a MND prevents a disorder from developing in a subject at risk of developing a MND resulting from dysregulation of miR-218, miR-138, miR-133a, miR-133b, miR-1193, miR-34b, miR-380, or miR-379. In other embodiments, treating a MND prevents a disorder from developing in a subject at risk of developing a MND resulting from dysregulation of miR-218 and/or miR-138. In specific embodiments, treating a MND prevents a disorder from developing in a subject at risk of developing a MND resulting from overexpression of miR-218. In other specific embodiments, treating a MND prevents a disorder from developing in a subject at risk of developing a MND resulting from overexpression of miR-138. Subjects at risk for a MND which is caused or contributed to by dysregulation of miR-218, miR-138, miR-133a, miR-133b, miR-1193, miR-34b, miR-380, or miR-379 activity may be identified by, for example, any or a combination of diagnostic or prognostic assays for detecting miR-218, miR-138, miR-133a, miR-133b, miR-1193, miR-34b, miR-380, or miR-379 mutation or activity. A prophylactic agent may be administered prior to the manifestation of symptoms characteristic of the miR-218, miR-138, miR-133a, miR-133b, miR-1193, miR-34b, miR-380, or miR-379 aberrancy, such that a disease or disorder is prevented, or delayed in its progression.

A subject may also be diagnosed as having a MND resulting from dysregulation of miR-218, miR-138, miR-133a, miR-133b, miR-1193, miR-34b, miR-380, or miR-379. In other embodiments, a subject may also be diagnosed as having a MND resulting from dysregulation of miR-218 and/or miR-138. In a specific embodiment, a subject may also be diagnosed as having a MND resulting from overexpression of miR-218. In another specific embodiment, a subject may also be diagnosed as having a MND resulting from overexpression of miR-138. In some embodiments, treating a MND treats a disorder in a subject having a MND resulting from dysregulation of miR-218, miR-138, miR-133a, miR-133b, miR-1193, miR-34b, miR-380, or miR-379. In other embodiments, treating a MND treats a disorder in a subject having a MND resulting from dysregulation of miR-218 and/or miR-138. In a specific, treating a MND treats a disorder in a subject having a MND resulting from overexpression of miR-218. In another specific embodiment, treating a MND treats a disorder in a subject having a MND resulting from overexpression of miR-138. As such, the present invention provides methods of treating an individual afflicted with a disease or disorder characterized by dysregulation of miR-218, miR-138, miR-133a, miR-133b, miR-1193, miR-34b, miR-380, or miR-379.

Treating a subject using a method of the invention may extend the survival of the subject. Alternatively, treating a subject using a method of the invention may extend the disease duration of the subject.

In some embodiments, treating a subject extends the survival of the subject. A method of the invention may extend the survival of a subject by days, weeks, months, or years, when compared to the survival of a subject that was not treated using a method of the invention. As will be recognized by individuals skilled in the art, the number of days, months, or years that a method of the invention may extend the survival of a subject can and will vary depending on the subject, the MND, and the condition of the subject when treatment was initiated among other factors.

In other embodiments, treating a subject extends the disease duration of a subject. As used herein, the term "disease duration" is used to describe the length of time between onset of symptoms and death caused by the disease. A method of the invention may extend the disease duration of a subject by days, weeks, months, or years, when compared to the survival of the subject that was not treated using a method of the invention. The number of days, months, or years that a method of the invention may extend the disease duration of a subject can and will vary depending on the subject, the MND, and the condition of the subject when treatment was initiated among other factors.

III. Kits

In still other aspects, the present invention provides articles of manufacture and kits containing materials useful for treating the conditions described herein. The article of manufacture may include a container of a composition as described herein with a label. Suitable containers include, for example, bottles, vials, and test tubes. The containers may be formed from a variety of materials such as glass or plastic. The container holds a composition having an active agent which is effective for treating, for example, conditions that benefit from miR-218, miR-138, miR-133a, miR-133b, miR-1193, miR-34b, miR-380, or miR-379 therapy. The active agent is at least one miR-218, miR-138, miR-133a, miR-133b, miR-1193, miR-34b, miR-380, or miR-379 agent of the invention and may further include additional bioactive agents known in the art for treating the specific condition. The label on the container may indicate that the composition is useful for treating specific conditions and may also indicate directions for administration.

DEFINITIONS

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

As used herein, "administering" is used in its broadest sense to mean contacting a subject with a composition of the invention.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1-6.3.6. A non-limiting example of stringent hybridization conditions are hybridization in 6× sodium chloride/sodium citrate (SSC) at about 45° C., followed by one or more washes in 0.2×SSC, 0.1% SDS at 50-65° C. (e.g., 50° C. or 60° C. or 65° C.). Preferably, the isolated nucleic acid molecule of the invention that hybridizes under stringent conditions corresponds to a naturally-occurring nucleic acid molecule. As used herein, a "naturally-occurring" nucleic acid molecule refers to a RNA or DNA molecule having a nucleotide sequence that occurs in a human cell in nature (e.g., encodes a natural protein).

As used herein, the term "nucleic acid molecule" is intended to include DNA molecules (e.g., cDNA or genomic DNA) and RNA molecules (e.g., mRNA or miRNA) and analogs of the DNA or RNA generated using nucleotide analogs. The nucleic acid molecule may be single-stranded or double-stranded.

An "isolated nucleic acid molecule" means that the material is removed from its original environment (e.g., the natural environment if it is naturally occurring). For example, a naturally occurring polynucleotide present in a living animal is not isolated, but the same polynucleotide or polypeptide, separated from some or all of the coexisting materials in the natural system, is isolated, even if subsequently reintroduced into the natural system. Such polynucleotides may be part of a vector or other composition and still be isolated in that such vector or composition is not part of its natural environment.

A "nucleic acid vector" is a nucleic acid sequence designed to be propagated and or transcribed upon exposure to a cellular environment, such as a cell lysate or a whole cell. A "gene therapy vector" refers to a nucleic acid vector that also carries functional aspects for transfection into whole cells, with the intent of increasing expression of one or more genes or proteins. In each case, such vectors usually contain a "vector propagation sequence" which is commonly an origin of replication recognized by the cell to permit the propagation of the vector inside the cell. A wide range of nucleic acid vectors and gene therapy vectors are familiar to those skilled in the art.

A miRNA is a small non-coding RNA molecule which functions in transcriptional and post-transcriptional regulation of gene expression. A miRNA functions via base-pairing with complementary sequences within mRNA molecules, usually resulting in gene silencing via translational repression or target degradation. A mature miRNA is processed through a series of steps from a larger primary RNA transcript (pri-miRNA), or from an intron comprising a miRNA (mirtron), to generate a stem loop pre-miRNA structure comprising the miRNA sequence. A pre-miRNA is then cleaved to generate the mature miRNA.

Primary miRNA transcripts are transcribed by RNA polymerase II and may range in size from hundreds to thousands of nucleotides in length (pri-mRNA). Pri-miRNAs may encode for a single miRNA but may also contain clusters of several miRNAs. The pri-miRNA is subsequently processed into an about 70 nucleotide hairpin (pre-miRNA) by the nuclear ribonuclease III (RNase III) endonuclease, Drosha. Thus, isolated nucleic acid molecules of the invention have various preferred lengths, depending on their intended targets. When targeted to pri-miRNA, preferred lengths vary between 100 and 200 nucleotides, e.g., 100, 120, 150, 180 or 200 nucleotides. In the cytoplasm, a second RNAse III, Dicer, together with its dsRBD protein partner, cuts the pre-miRNA in the stem region of the hairpin thereby liberating an about 21 nucleotide RNA-duplex. Thus, isolated polynucleotides of about 80, 70, 60, 50, 40, 30, 25, 21, 20, 19, 18, 17, 16, 15, 14, 13, 12, 11, 10, 9, 8, 7, or 6 nucleotides in length are also considered in one embodiment of the invention.

As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences have a common structural domain and/or common functional activity. For example, amino acid or nucleotide sequences which contain a common structural domain having about 65% identity, preferably 75% identity, more preferably 85%, 95%, or 98% identity are defined herein as sufficiently identical.

As used interchangeably herein, a "miR-218, miR-138, miR-133a, miR-133b, miR-1193, miR-34b, miR-380, or miR-379 activity", "biological activity of miR-218, miR-138, miR-133a, miR-133b, miR-1193, miR-34b, miR-380, or miR-379" or "functional activity of miR-218, miR-138, miR-133a, miR-133b, miR-1193, miR-34b, miR-380, or miR-379" refers to an activity exerted by a miR-218, miR-138, miR-133a, miR-133b, miR-1193, miR-34b, miR-380, or miR-379 respectively on a miR-218, miR-138, miR-133a, miR-133b, miR-1193, miR-34b, miR-380, or miR-379 responsive cell, target mRNA, or target protein as determined in vivo or in vitro, according to standard techniques. A miR-218, miR-138, miR-133a, miR-133b, miR-1193, miR-34b, miR-380, or miR-379 activity may be a direct activity such as an association with a second protein or mRNA. A miR-218, miR-138, miR-133a, miR-133b, miR-1193, miR-34b, miR-380, or miR-379 activity may be an indirect activity such as a cellular signaling activity mediated by interaction of the miR-218, miR-138, miR-133a, miR-133b, miR-1193, miR-34b, miR-380, or miR-379 protein with a second protein or mRNA.

The term "sample" refers to a cell, a population of cells, biological samples, and subjects, such as mammalian subjects. The term "biological sample" refers to tissues, cells and biological fluids isolated from a subject, as well as tissues, cells and fluids present within a subject.

As used herein, "subject" refers to a living organism having a central nervous system. In particular, subjects may include, but are not limited to, human subjects or patients and companion animals. Exemplary companion animals may include domesticated mammals (e.g., dogs, cats, horses), mammals with significant commercial value (e.g., dairy cows, beef cattle, sporting animals), mammals with significant scientific value (e.g., captive or free specimens of endangered species), or mammals which otherwise have value. Suitable subjects may also include: mice, rats, dogs, cats, ungulates such as cattle, swine, sheep, horses, and goats, lagomorphs such as rabbits and hares, other rodents, and primates such as monkeys, chimps, and apes. In some embodiments, subjects may be diagnosed with a fibroblastic condition, may be at risk for a fibroblastic condition, or may be experiencing a fibroblastic condition. Subjects may be of any age including newborn, adolescent, adult, middle age, or elderly.

The term "miR-218, miR-138, miR-133a, miR-133b, miR-1193, miR-34b, miR-380, or miR-379 agent" refers to any molecule capable of respectively modulating miR-218, miR-138, miR-133a, miR-133b, miR-1193, miR-34b, miR-380, or miR-379 activity. Exemplary miR-218, miR-138, miR-133a, miR-133b, miR-1193, miR-34b, miR-380, or miR-379 agents may include, without limitation, a compound, drug, small molecule, peptide, oligonucleotide, protein, antibody, and combinations thereof. miR-218, miR-138, miR-133a, miR-133b, miR-1193, miR-34b, miR-380, or miR-379 agents may be synthetic or naturally occurring. A miR-218, miR-138, miR-133a, miR-133b, miR-1193, miR-34b, miR-380, or miR-379 agent may be a molecule identified in a screening assay as described herein.

The term "miR-218, miR-138, miR-133a, miR-133b, miR-1193, miR-34b, miR-380, or miR-379 indicator" refers to any molecule capable of detecting, respectively, the presence of miR-218, miR-138, miR-133a, miR-133b, miR-1193, miR-34b, miR-380, or miR-379. A suitable miR-218, miR-138, miR-133a, miR-133b, miR-1193, miR-34b, miR-380, or miR-379 indicator may be a compound, drug, small molecule, peptide, oligonucleotide, protein, antibody, and combinations thereof.

As used herein, the phrases "therapeutically effective amount" and "prophylactically effective amount" refer to an amount that provides a therapeutic benefit in the treatment, prevention, or management of pathological processes mediated by dysregulation of miR-218, miR-138, miR-133a, miR-133b, miR-1193, miR-34b, miR-380, or miR-379. The specific amount that is therapeutically effective may be readily determined by ordinary medical practitioners, and may vary depending on factors known in the art, such as the type of disorder being treated, the subject's history and age, the stage of the disorder, and administration of other agents in combination.

As used herein, a "pharmaceutical composition" includes a pharmacologically effective amount of a therapeutic agent of the invention and a pharmaceutically acceptable carrier. As used herein, "pharmacologically effective amount," "therapeutically effective amount" or simply "effective amount" refers to that amount of an agent effective to produce the intended pharmacological, therapeutic or preventive result. For example, if a given clinical treatment is considered effective when there is at least a 15% reduction in a measurable parameter associated with a disease or disorder, a therapeutically effective amount of an agent for the treatment of that disorder or disease is the amount necessary to effect at least a 15% reduction in that parameter.

The term "pharmaceutically acceptable carrier" refers to a carrier for administration of a therapeutic agent. Such carriers may include, but are not limited to, saline, buffered saline, dextrose, water, glycerol, ethanol, and combinations thereof. The term specifically excludes cell culture medium. For drugs administered orally, pharmaceutically acceptable carriers may include, but are not limited to, pharmaceutically acceptable excipients such as inert diluents, disintegrating agents, binding agents, lubricating agents, sweetening agents, flavoring agents, coloring agents and preservatives. Suitable inert diluents may include sodium and calcium carbonate, sodium and calcium phosphate, and lactose, while corn starch and alginic acid are suitable disintegrating agents. Binding agents may include starch and gelatin, while the lubricating agent, if present, may generally be magnesium stearate, stearic acid or talc. If desired, the tablets may be coated with a material such as glyceryl monostearate or glyceryl distearate to delay absorption in the gastrointestinal tract.

As used herein, "percent complementarity" means the percentage of nucleotides of a modified oligonucleotide that are complementary to a microRNA. Percent complementarity may be calculated by dividing the number of nucleotides of the modified oligonucleotide that are complementary to nucleotides at corresponding positions in the microRNA by the total length of the modified oligonucleotide.

As used herein, "oligonucleotide" means a polymer of linked nucleosides, each of which may be modified or unmodified, independent from one another.

As used herein, "anti-miR" means an oligonucleotide having a nucleotides sequence complementary to a microRNA. In certain embodiments, an anti-miR is a modified oligonucleotide.

As used herein, "internucleoside linkage" means a covalent linkage between adjacent nucleosides.

As used herein, "linked nucleosides" means nucleosides joined by a covalent linkage.

As used herein, "nucleobase" means a heterocyclic moiety capable of non-covalently pairing with another nucleobase.

As used herein, "nucleoside" means a nucleobase linked to a sugar.

As used herein, "nucleotide" means a nucleoside having a phosphate group or other internucleoside linkage forming group covalently linked to the sugar portion of a nucleoside.

As used herein, "modified oligonucleotide" means an oligonucleotide having one or more modifications relative to a naturally occurring terminus, sugar, nucleobase, and/or internucleoside linkage.

As used herein, "modified internucleoside linkage" means any change from a naturally occurring internucleoside linkage.

As used herein, "phosphorothioate internucleoside linkage" means a linkage between nucleosides where one of the non-bridging atoms is a sulfur atom.

As used herein, "modified sugar" means substitution and/or any change from a natural sugar.

As used herein, "modified nucleobase" means any substitution and/or change from a natural nucleobase.

As used herein, "5-methylcytosine" means a cytosine modified with a methyl group attached to the 5' position.

As used herein, "2'fluoro sugar" means a sugar having a fluorine modification at the 2' position.

As used herein, "2'-O-methyl sugar" or "2'-OMe sugar" means a sugar having an O-methyl modification at the 2' position.

As used herein, "2'-O-methoxyethyl sugar" or "2'-MOE sugar" means a sugar having an O-methoxyethyl modification at the 2' position.

As used herein, "2'-O-fluoro" or "2'-F" means a sugar having a fluoro modification at the 2' position.

As used herein, "bicyclic sugar moiety" means a sugar modified by the bridging of two non-geminal ring atoms.

As used herein, "locked nucleic acid (LNA) sugar moiety" means a substituted sugar moiety having a $(CH_2)$—O bridge between the 4' and 2' furanose ring atoms.

In practicing the present invention, many conventional techniques in molecular biology, microbiology, and recombinant DNA may be used. These techniques are well known and are explained in, for example, Current Protocols in Molecular Biology, Volumes I, II, and III, 1997 (F. M. Ausubel ed.); Sambrook et al., 1989, Molecular Cloning: A Laboratory Manual, Second Edition, Cold Spring Harbor Laboratory Press, Cold Spring Harbor, N.Y.; DNA Cloning: A Practical Approach, Volumes I and II, 1985 (D. N. Glover ed.); Oligonucleotide Synthesis, 1984 (M. L. Gait ed.); Nucleic Acid Hybridization, 1985, (Hames and Higgins eds.); Transcription and Translation, 1984 (Hames and Higgins eds.); Animal Cell Culture, 1986 (R. I. Freshney ed.); Immobilized Cells and Enzymes, 1986 (IRL Press); Perbal, 1984, A Practical Guide to Molecular Cloning; the series, Methods in Enzymology (Academic Press, Inc.); Gene Transfer Vectors for Mammalian cells, 1987 (J. H. Miller and M. P. Calos eds., Cold Spring Harbor Laboratory); and Methods in Enzymology, Vol. 154 and Vol. 155 (Wu and Grossman, and Wu, eds., respectively).

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction to the Examples.

Amyotrophic Lateral Sclerosis (ALS) is a fatal, adult-onset neurodegenerative disease in which motor neurons (MNs) are selectively lost. This progressive loss of MNs results in denervation and muscle atrophy, where most patients die within 3-5 years of symptom onset. Nearly 4 in 100,000 people in the US are affected by ALS. The majority of ALS cases are sporadic with age being the highest risk factor for disease. The remaining 10% of ALS cases are familial. Mutations in superoxide dismutase 1 (SOD1) were the first identified genetic cause of ALS and are attributed to 20% of familial ALS; recently, a hexanucleotide repeat expansion in chromosome 9 open reading frame 72 (C9orf72) is now associated with 20-40% of familial ALS cases. Currently mouse and rat models containing mutated human SOD1 are still the most widely used and most faithfully recapitulate the disease pathology.

microRNAs (miRNAs) are small, regulatory RNAs that, canonically, regulate translation of protein-coding RNAs. miRNAs direct translational repression by partial binding to the 3' UTR of mRNAs after first being incorporated into a RNA-induced silencing complex (RISC), containing Argonaute-2 (Ago2). Because only partial complementarity is required for miRNA-mRNA interactions, a single miRNA can potentially regulate hundreds of mRNA transcripts. Emerging data demonstrate miRNAs are powerful regulators of physiological and pathological cellular processes. Consequently, miRNA expression is often dysregulated in disease and miRNAs have been used as therapeutic and diagnostic targets.

miR-155, a glial-enriched miRNA, is upregulated in the spinal cords of end-stage ALS model ($SOD1^{G93A}$) mice and human autopsy. Inhibiting miR-155 significantly delays disease progression in $SOD1^{G93A}$ mice. Non-cell autonomous disease mechanisms are important and targeting an immunomodulatory miRNA may be an effective therapy for ALS. Despite enthusiasm for this glial miRNA therapeutic approach, we hypothesized that MN miRNA changes in ALS may be equally or more important, as MN loss and pathology define the onset of disease and ultimately death. However, since MNs represent approximately 4% of the total mouse spinal cord volume, probing miRNA changes in MNs is challenging and must be done utilizing a MN-targeted approach.

To date, most cell type enriched expression data have been generated though fluorescence activated cell sorting (FACS), laser capture microdissections (LCMs), and in situ histology. Each of these methods has significant limitations, which can be overcome with the advent of biochemical purification systems such as, translating ribosome affinity purification (TRAP) for mRNA, or miRNA tagging and affinity purification (miRAP) for miRNA.

To assess miRNA expression in CNS cell types, we employed miRAP, in which tagged-Argonaute2 (Ago2) is expressed in particular cell types under the control of the Cre-Lox system. Because catalytically functional miRNAs must first be loaded into the miRNA processing protein Ago2, affinity purification via antibodies against Ago2 serves to also isolate active miRNAs from tissue lysates. Furthermore, by expressing a GFP-myc-tagged version of Ago2 only in particular cell types, miRNAs from distinct cell populations may be isolated via myc or GFP immunoprecipitation (IP). To determine enriched miRNA expression in MNs, we crossed miRAP reporter mice (with a lox-stop-lox-GFP-myc-Ago2 (LSL-tAgo2)) to mice expressing Cre under promoters targeting all neurons, MNs, astrocytes, and myeloid cells including microglia. With these experiments we were able to generate a physiologically relevant database of well-validated miRNAs enriched in these CNS cell types and, via comparative analysis, discriminate MN-enriched miRNAs. We predict these MN-enriched miRNA expression profiles will broadly inform on studies of diseases and injuries specific to MNs. Here, we focused on ALS disease mechanisms. By probing the expression of MN-enriched miRNAs in ALS rodent models, we have identified a new CSF, drug-responsive biomarker of MN disease.

Example 1. Generation and Validation of Cell Specific Expression of GFP-Myc-Ago2 in CNS Tissues We adapted the miRAP method developed by He, et al to express tagged-Ago2 in specific cell populations relevant to ALS (He et al. Neuron 2012; 73(1): 35-48). Double transgenic mice carrying alleles of Cre recombinase under various promoters and lox-stop-lox-GFP-myc-Ago2 (LSL-tAgo2) in the Rosa26 locus were generated (FIG. 1A). To target cell type specific expression of Cre recombinase, and thus cell type specific expression of tAgo2, we used existing Cre lines with the following promoters: Synapsin 1 (Syn), choline acetyltransferase (ChAT), glial fibrillary acidic protein (GFAP), or lysozyme 2 (Lyz2, LysM) targeting a pan neuronal, MN, astrocyte, or microglia cell population, respectively (FIG. 1B).

Figure 1C:
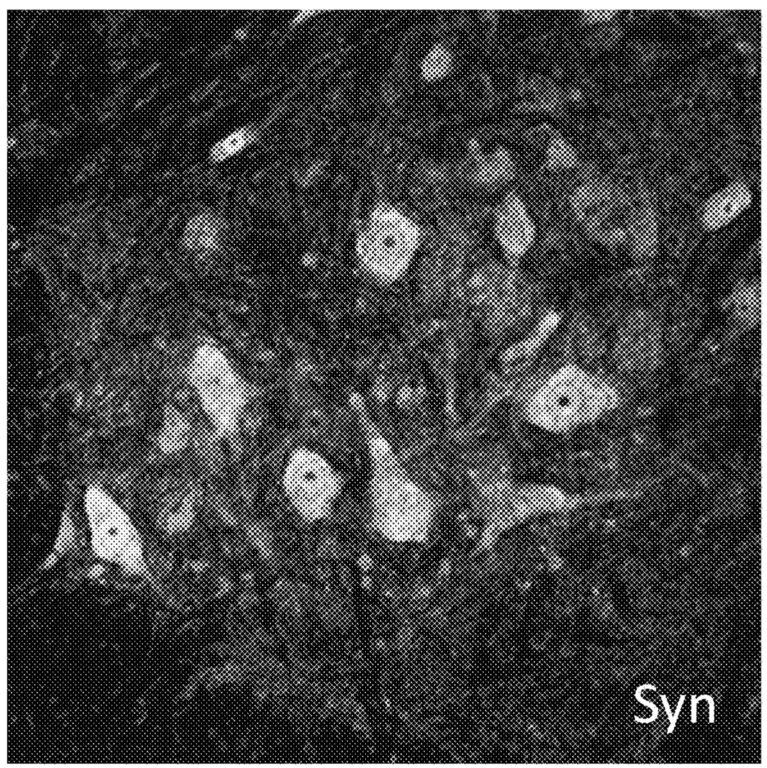
Figure 1D:
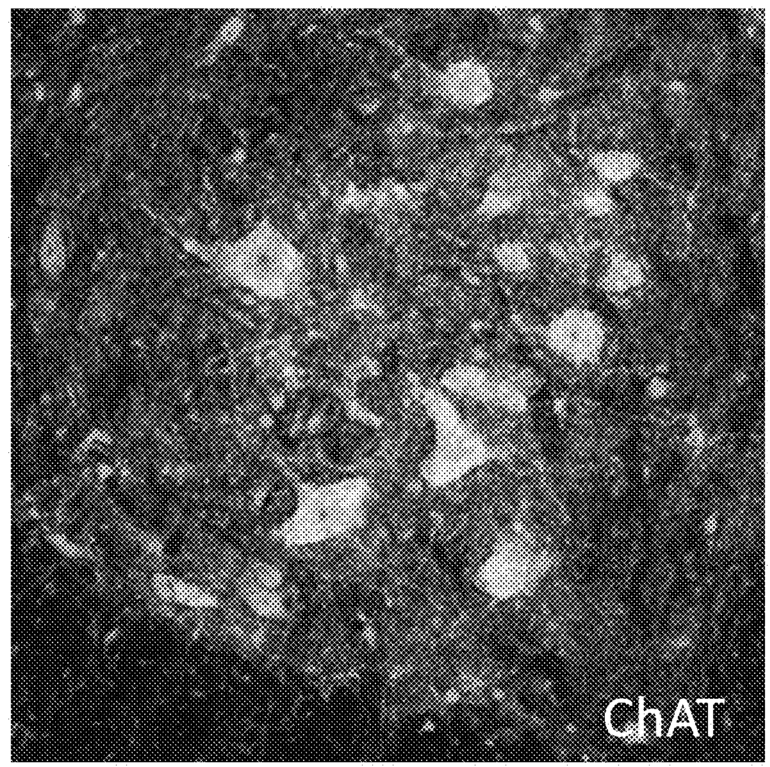
Figure 1E:
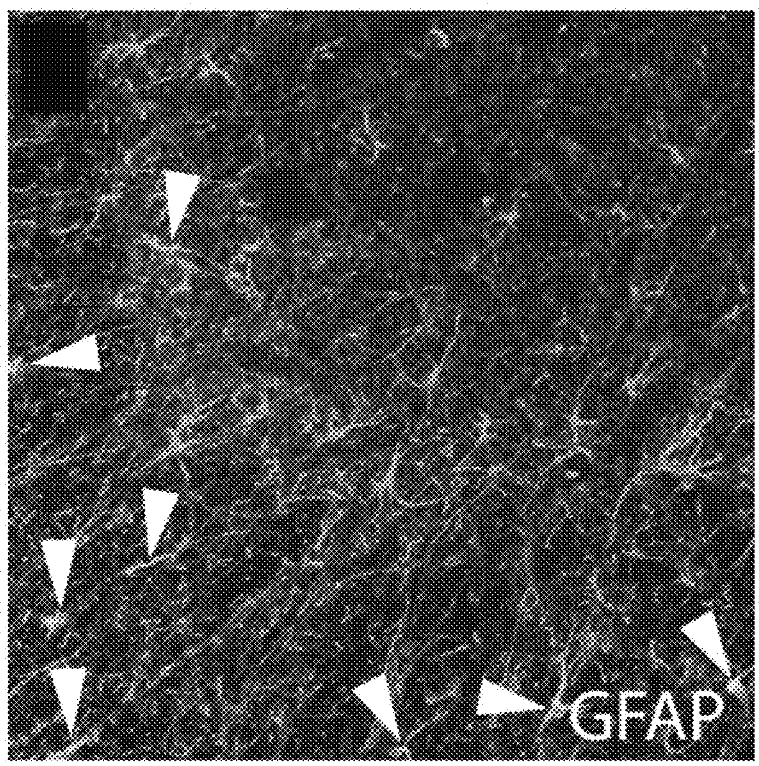
Figure 1F:
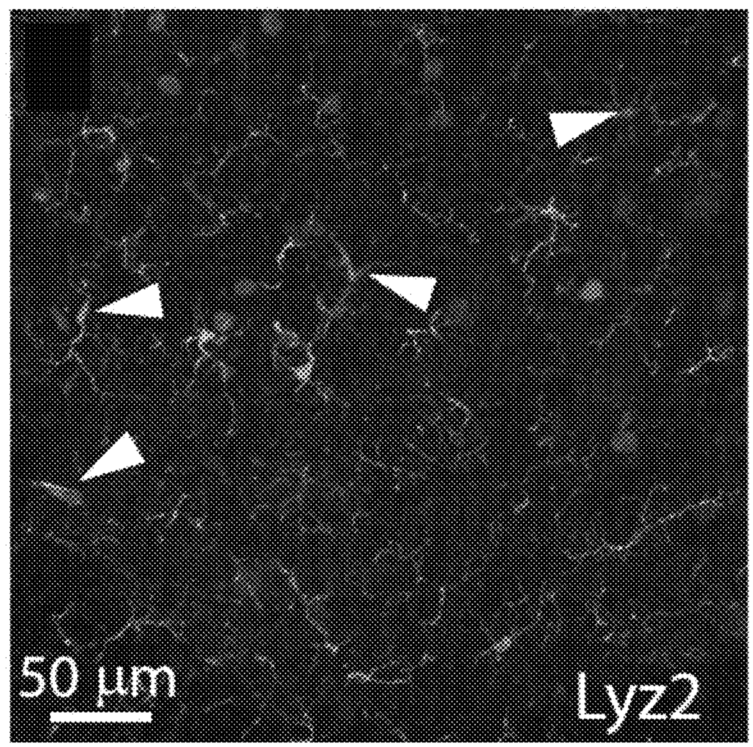
Figure 6:
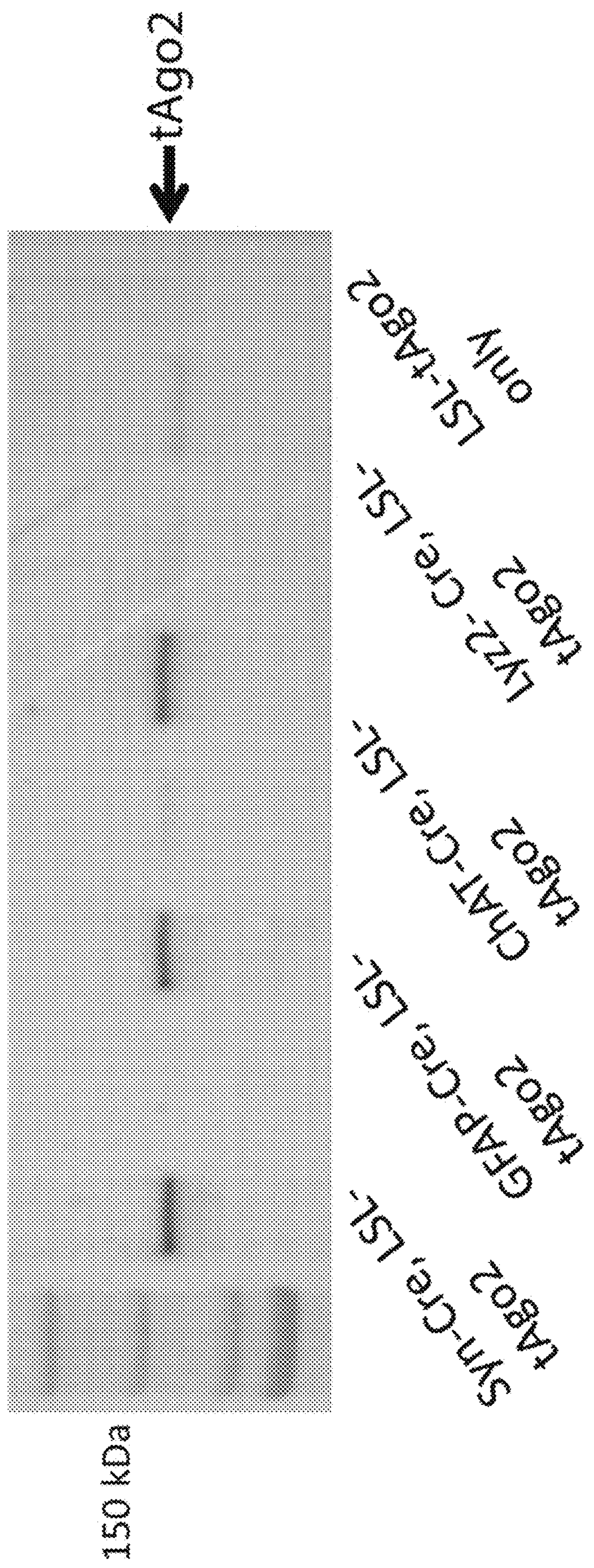
FIG. 6 depicts an immunoblot showing biochemical validation of cell type specific tAgo2 expression. Myc immunoprecipitation and subsequent immunoblot to confirm tagged-Ago2 expression in each transgenic mouse. GFP-myc-Ago2 (tAgo2; ~130 kDa) is only expressed when LSL-tAgo2 mice are crossed with mice expressing Cre recombinase under a cell type specific promoter. One well was intentionally left blank between each mouse, with exception to LSL-tAgo2 only.

In order to validate tAgo2 expression in the desired cell types, we isolated brainstem or spinal cord and immunoprecipitated (IP'ed) with myc antibodies from each transgenic mouse. As confirmed by Western blot, each double transgenic mouse expresses tAgo2 (~130 kDa) in the brain and spinal cord, but LSL-tAgo2+, Cre-littermates do not (FIG. 6). Double-label immunofluorescence histology using a cell-specific antibody and with an antibody against GFP indicated tAgo2 was being expressed in the desired neuronal cell types. The Syn-Cre, LSL-tAgo2 mouse showed strong expression of GFP in NeuN+ cells throughout the brain and spinal cord including in the brainstem (FIG. 1C). In ChAT-Cre double transgenic mice, tAgo2 expression was isolated to the ChAT+ brainstem motor nuclei and spinal MNs (FIG. 1D). For both of these lines, GFP expression appeared cytoplasmic and not nuclear, in agreement with known Ago2 localization. To visualize the cell types marked by GFAP- and Lyz2-Cre, we crossed these drivers with LSL-tdTomato/Ai9 mice. As anticipated, the LSL-tdTomato, GFAP-Cre mice showed robust Cre activity in astrocytes (labeled with anti-GFAP, FIG. 1E). And, as previously reported for GFAP-Cre drivers, there was sparse labeling of neurons, many of which are likely late born neuronal progeny of GFAP+ neural stem cells. As expected LSL-tdTomato, Lyz2-Cre mice showed recombinase activity in some microglia (labeled with anti-Iba1, FIG. 1F). Unexpectedly, given their widespread use in targeting microglia for functional studies in the CNS, we also saw robust Cre activity in sparse subsets of neurons. Nonetheless, as the neuronal Cre lines both had high specificity, and only the Lyz2 line showed any microglial Cre activity, we reasoned that we would still be able to identify miRNA enriched in each cell type via a comparative strategy similar to that previously used to control for background in TRAP studies (Dougherty et al. *Nucleic Acids Research* 2010; 38(13): 4218-4230).

Figure 2A:
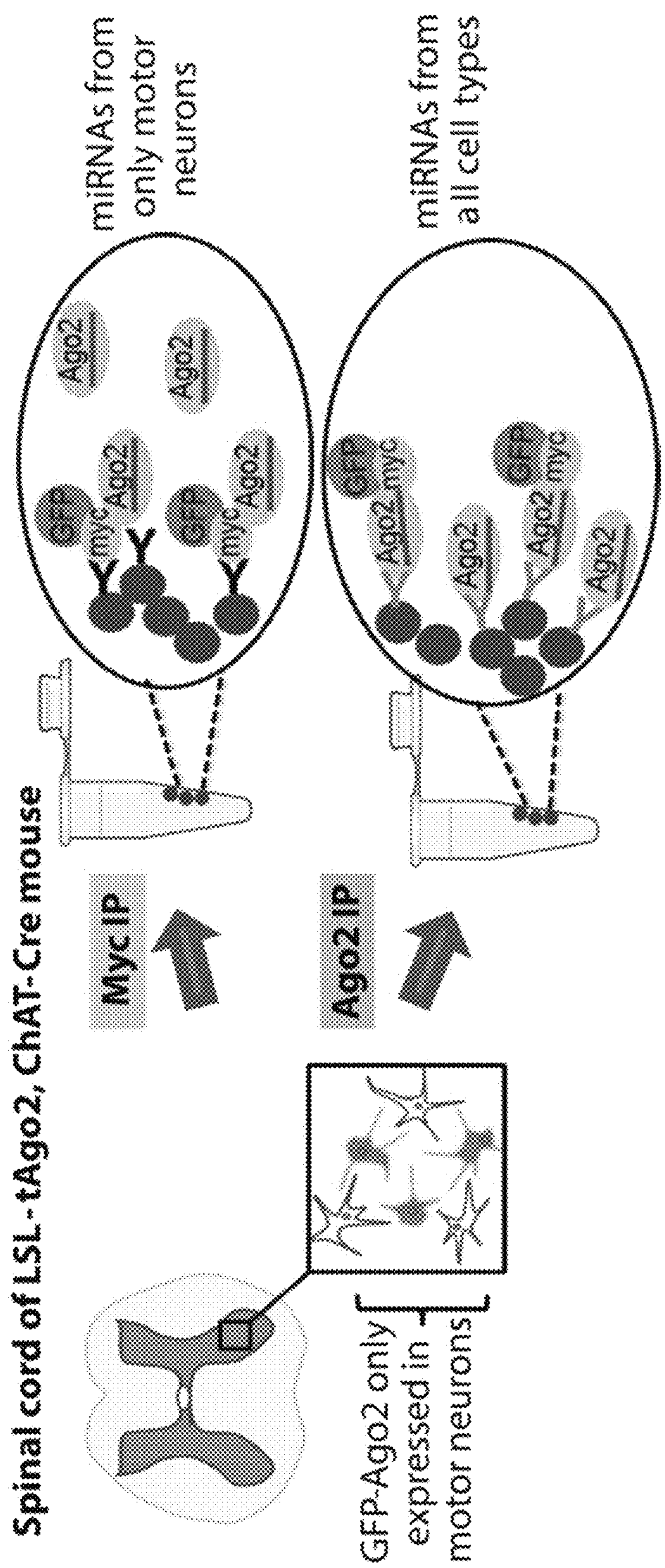
FIG. 2A and FIG. 2B depict a schematic and graph showing that miRNA Affinity Purification recapitulates cell type specific miRNA expression.

Therefore, we harvested the brainstems and spinal cords from replicate transgenic mice that carried both Cre-recombinase and LSL-tAgo2 alleles (experimental mice) or only LSL-tAgo2 (negative controls). Following BCA normalization for protein input, miRAP was performed on these tissues using either myc or Ago2 antibodies (FIG. 2A). The resulting miRNAs were isolated and assayed via TaqMan miRNA microarrays v3.0 (A+B cards). To account for background miRNA expression associated with the myc-IP, we performed Taqman miRNA microarrays on RNA from myc IP of both brainstem and spinal cord of littermate controls not expressing tAgo2. To this end, we empirically determined background cycle threshold (CT) cut-offs for each individual miRNA. We used these data to eliminate any miRNA not significantly enriched over background. Table 1 indicates the number of miRNAs in each cell type that were found to be expressed significantly over noise in either brainstem or spinal cord.

TABLE 1

The number of miRNAs differentially expressed from non-transgenic in brainstem and spinal cord following miRAP. A total of 672 miRNAs were queried. The criteria for a miRNA to be expressed above background were 1) the miRNA must be expressed (CT < 40) in 2 of 3 replicates (3 of 4 for Ago2); 2) the median expression for a miRNA of the triplicates must be CT < 35 (CT < 37 for Ago2); 3) the highest CT of the replicates must be 2 CT < the median of the non-transgenics. The number of miRNAs expressed above background in an untagged Ago2 immunoprecipiation represents an estimate of the number of all miRNAs expressed above background in each tissue-type.

| Sample | Brainstem | Spinal Cord |
| --- | --- | --- |
| ChAT | 257 | 295 |
| Syn | 406 | 417 |
| GFAP | 325 | 295 |
| Lyz2 | 123 | 56 |
| Ago2 | 484 | 467 |

Figure 2B:
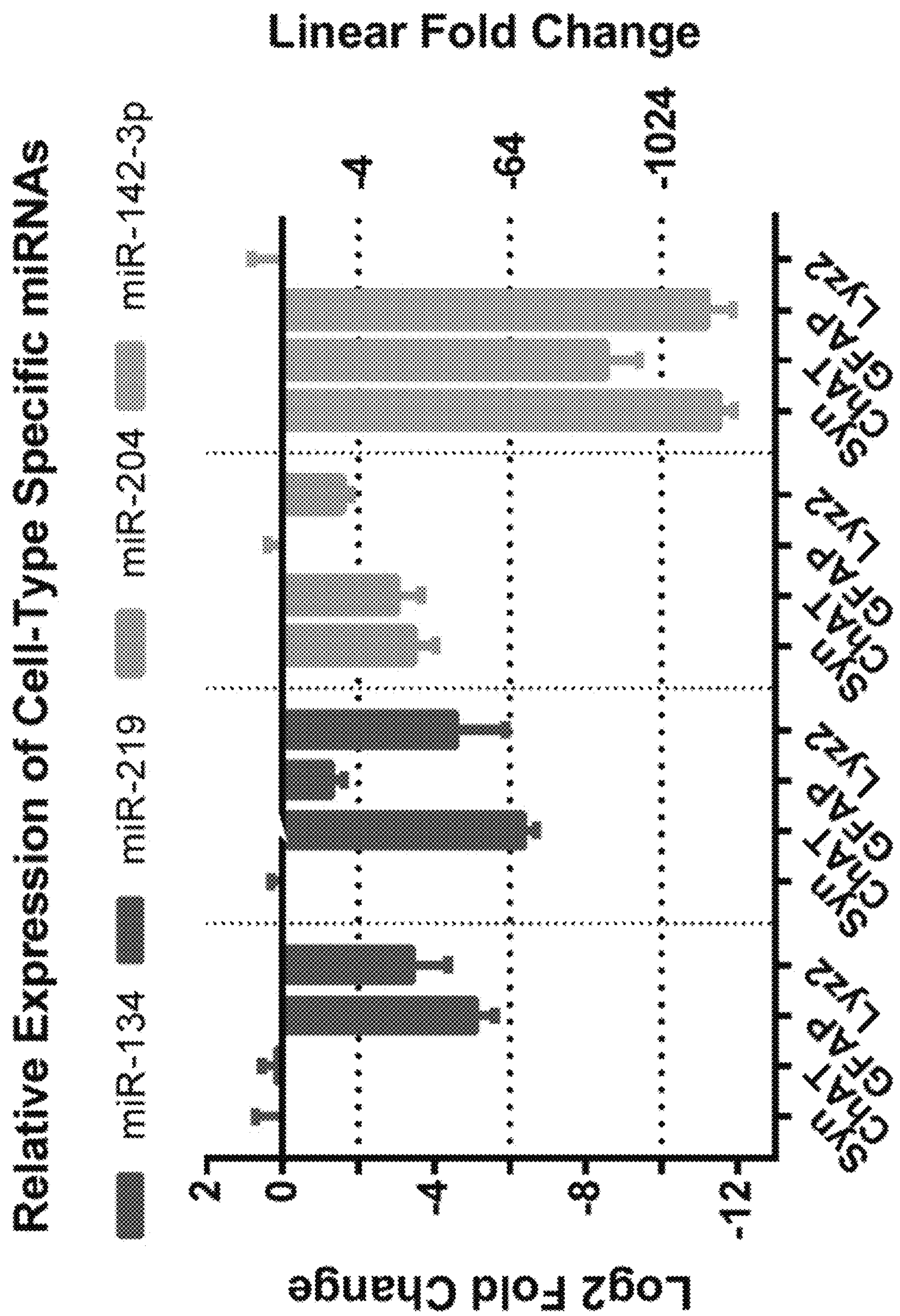

To confirm that miRAP from brainstem and spinal cord tissue was accurately recapitulating miRNA expression in each distinct cell type, we assessed the expression of miRNAs previously reported to exhibit cell type specificity or enrichment (FIG. 2B). miR-134, a miRNA involved in cortical neuronal development, was robustly expressed in our Syn and ChAT mice and greatly depleted in GFAP and Lyz2 mice. Expression of miR-219, which is known to act on NMDA receptors, was absent in MNs, consistent with lack of NMDA receptors. Only astrocytes exhibited high expression of miR-204, a miRNA that has been extensively studied in gliomas. Finally, perfused Lyz2 tissue showed strong expression of miR-142-3p, a miRNA involved in hematopoetic cell differentiation, consistent with the lineage of microglia.

Figure 3A:
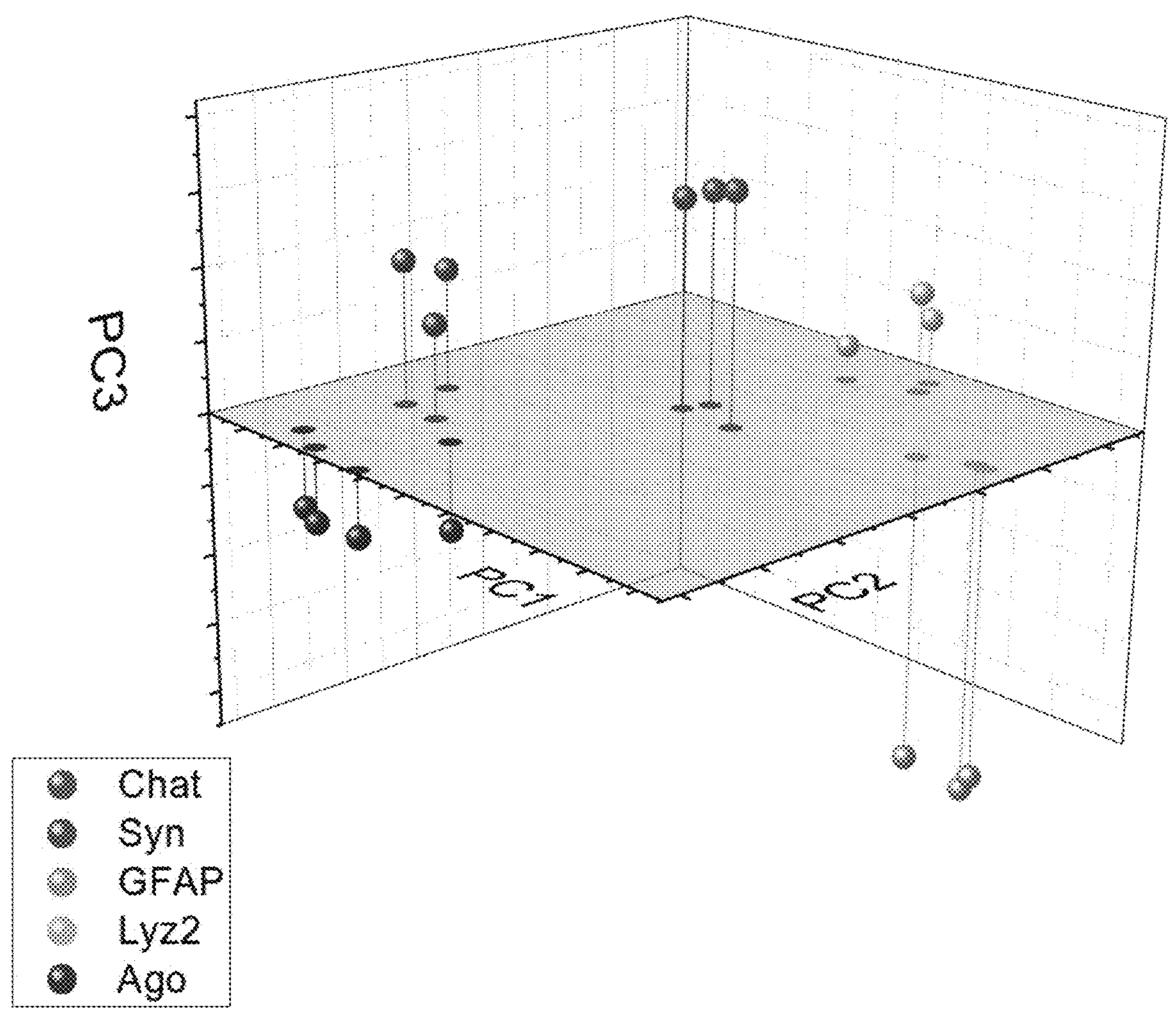
Figure 3B:
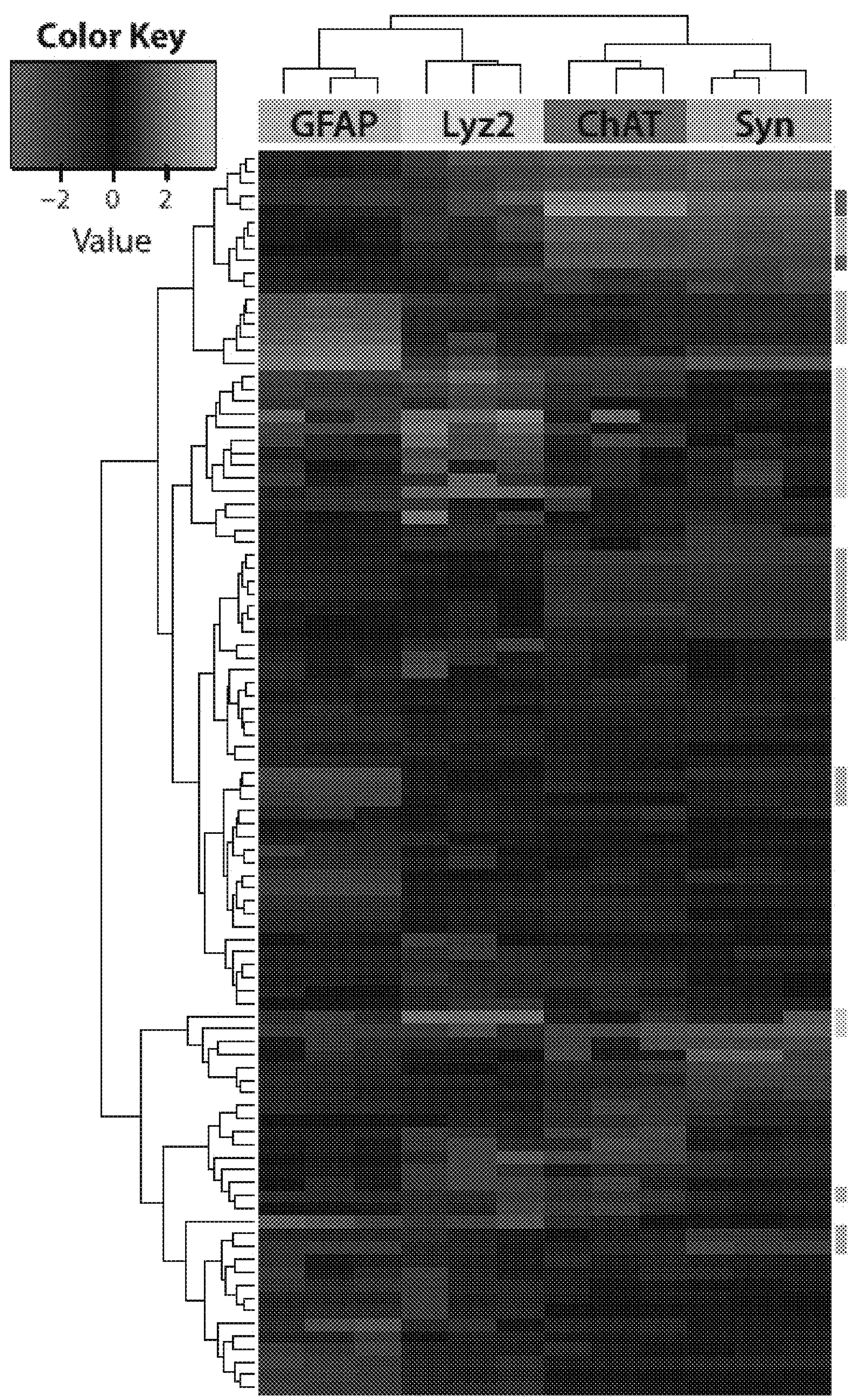

On a global level, the miRNA expression profiles for CNS cell types are distinct. Following unsupervised 3D principal component analysis (PCA), we found that miRNA expression profiles were sufficient to cluster samples by their cell type of origin (FIG. 3A). Furthermore, the miRNA expression profiles from IP of tagged and untagged Ago2 from each transgenic mouse clustered together in PCA, indicating global miRNA expression in these mice is comparable (FIG. 3A). Hierarchical heatmaps also demonstrate that these CNS cell types can be identified by their unique miRNA expression profiles (FIG. 3B).

Figure 7:
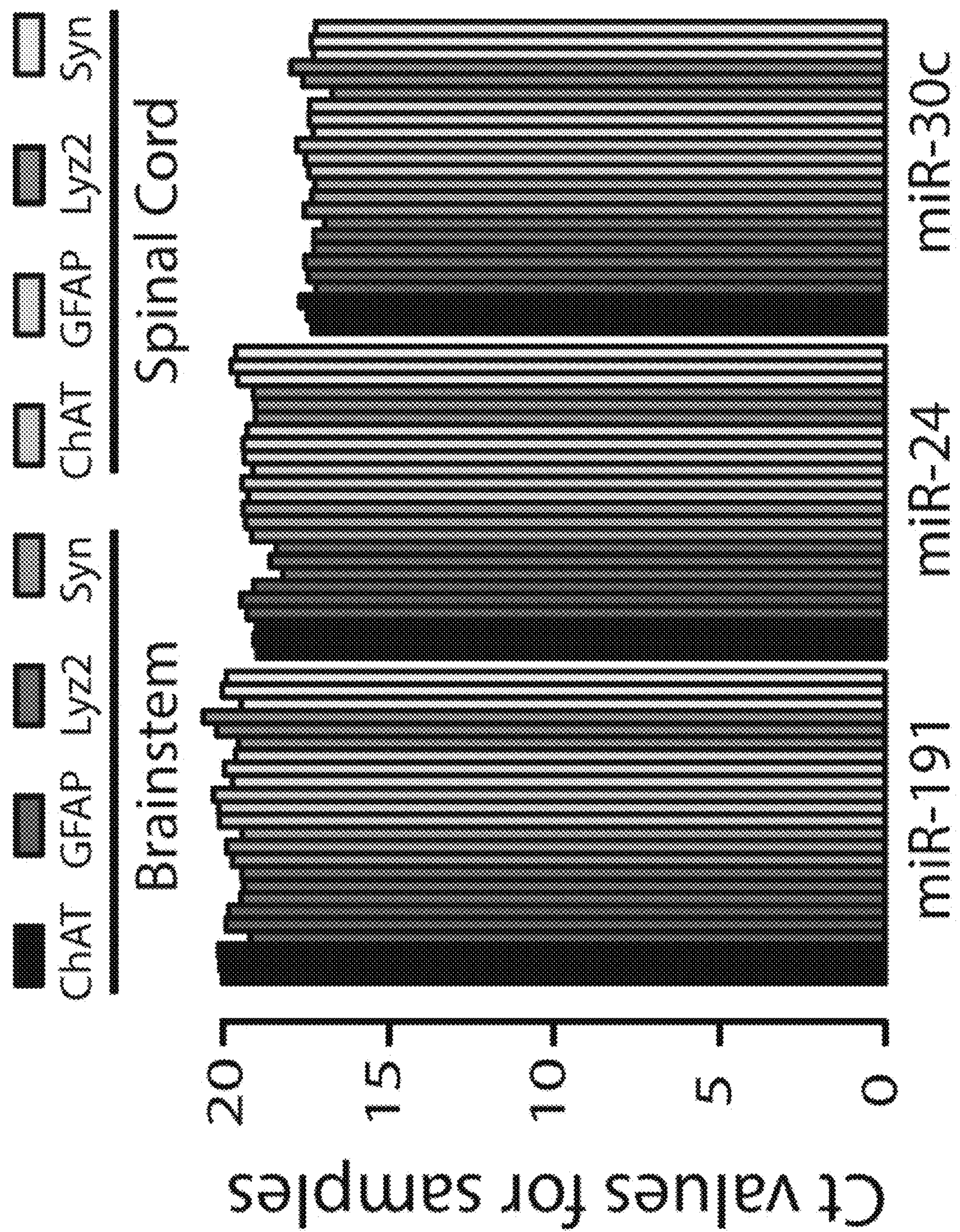
FIG. 7 depicts a graph showing putative endogenous miRNA controls for CNS cell types. Using global LoessM normalization of the miRNA microarray data, miR-191, 24 and 30c were found to be consistently expressed across CNS cell types in both brainstem (bs) and spinal cord (sc). For the CNS cell types analyzed here, these miRNAs could serve as controls for normalizing miRNA RT-qPCR data.

Using this global miRNA array data, we identified miRNAs that are consistently expressed across CNS cell types: miR-24, 30c and 191 (FIG. 7). The use of these miRNAs as putative endogenous controls for normalizing RT-qPCR data will greatly aid in future studies of miRNAs in the CNS. Furthermore, these results align well with previous reports identifying putative housekeeping miRNAs. Because U6 snRNA is not typically loaded into Ago2, miRAP studies must employ endogenous miRNA controls for normalization of RT-qPCR data.

We have confirmed the validity of our approach by ensuring the transgenic mice employed in these studies express tAgo2 in the desired cell types and that miRAP produces a miRNA signature for these distinct CNS cell types that is consistent with previous reports.

Example 2. Identification of MN-Enriched miRNAs

To discriminate MN-enriched miRNA expression, we performed pairwise comparisons with other CNS cell types. FIG. 3C indicates the top 3 miRNAs in each cell type exhibiting enriched expression and the associated specificity index for both brainstem and spinal cord. We then validated the MN-enrichment of the top 8 miRNAs using the original 3 samples from the arrays (technical replicate) and an additional 3 samples (biological replicate) to confirm the array findings at a higher power using individual RT-qPCR assays (Table 2). miR-218-5p and its lesser abundant 3p strand exhibited the strongest enrichment in MNs (Table 2). The MN-enrichment of miR-544 and miR-380-5p could not be confirmed due to low expression (CT>35) and non-specificity of Taqman primers (repeated amplification in no-template control), respectively. All comparisons made using LoessM normalized array data are included in Table 3 (spinal cord) and Table 4 (brain stem).

TABLE 2

Confirmation of MN-enrichment of miRNAs in the spinal cord as compared to all other neurons. The MN-enrichment of 6 of 8 miRNAs was validated with individual RT-qPCR assays. Student's unpaired, two-tailed t-test, Bonferroni correction for multiple (6) comparisons. Values are normalized to a geomean of endogenous miRNA controls, miR-30c, 24 and 191, and expressed as the mean of N = 6.

| miRNA | Fold-Change | P-value |
|---|---|---|
| miR-218 | 11.9 | 0.0002 |
| miR-218-2 | 11.9 | <0.0001 |
| miR-138 | 3.2 | <0.0001 |
| miR-133a | 2.8 | <0.0001 |
| miR-1193 | 3.7 | 0.0008 |
| miR-34b-3p | 3.1 | 0.045 |

Figure 4A:
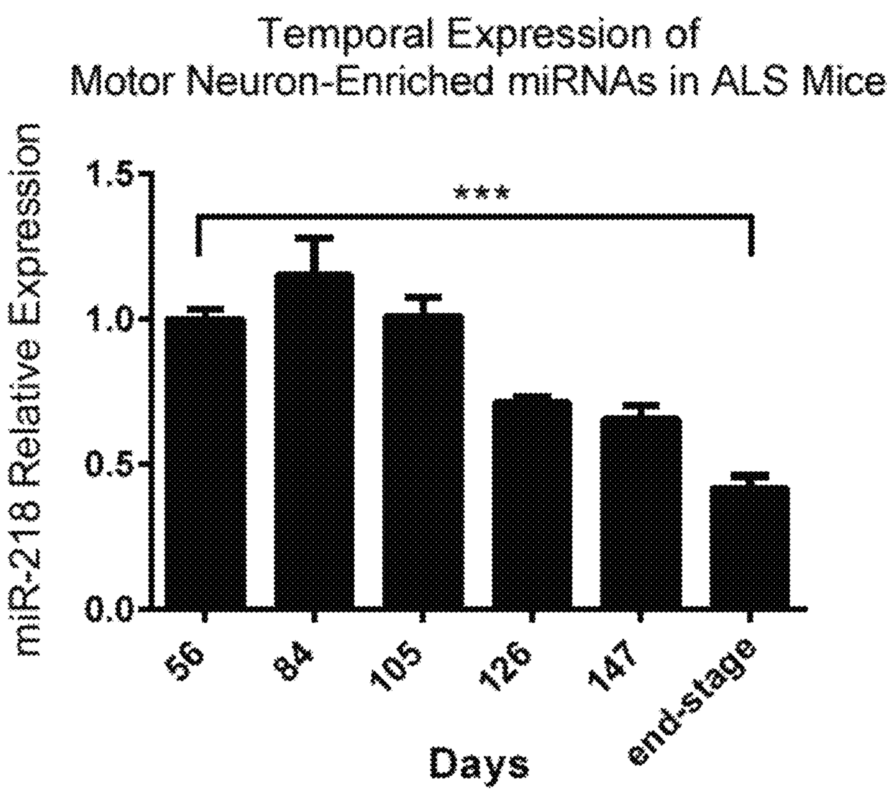
FIG. 4A, FIG. 4B, FIG. 4C, FIG. 4D, FIG. 4E and FIG. 4F depict graphs showing that MN-Enriched miRNAs are temporally depleted in ALS mouse model and human patient spinal cord.
Figure 4B:
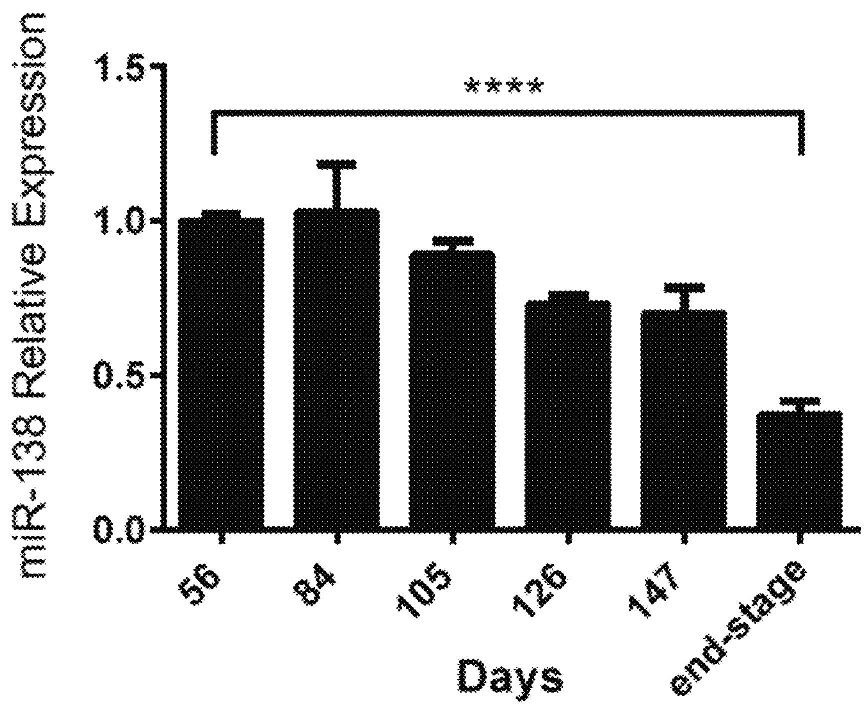
Figure 4C:
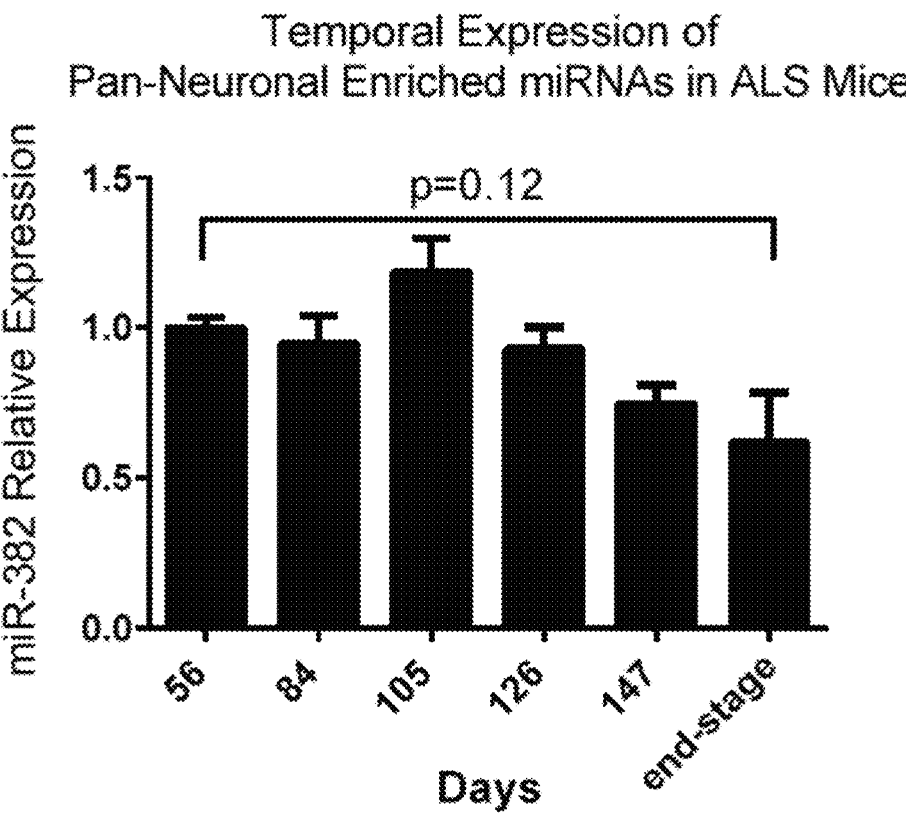
Figure 4D:
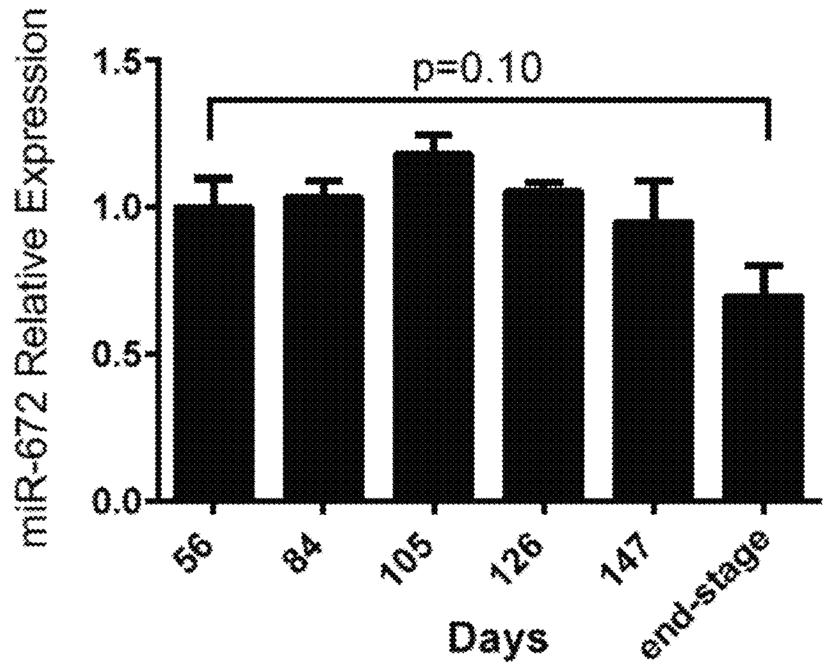
Figure 4E:
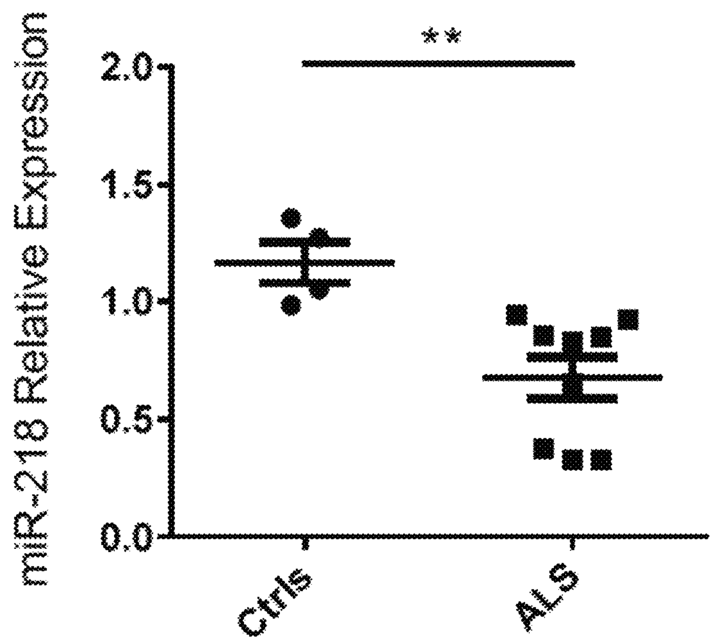
Figure 4F:
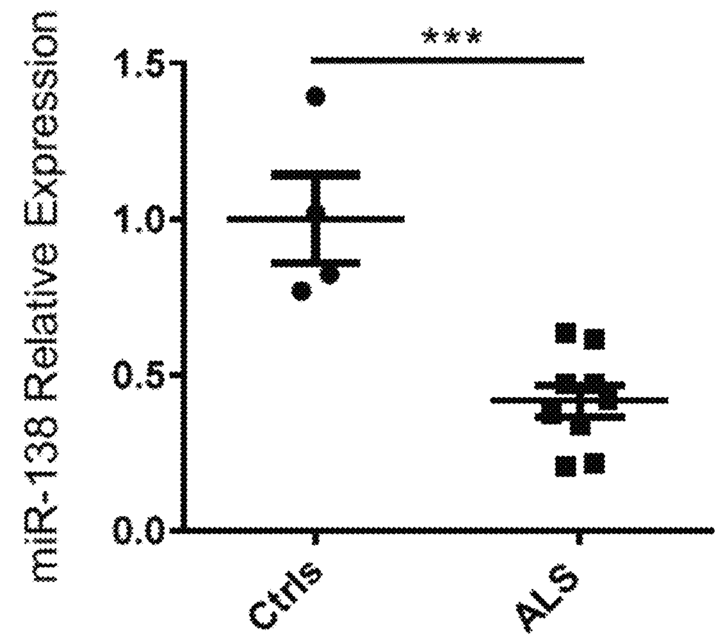

Example 3. Depletion of MN-Enriched miRNAs in Spinal Cord from ALS Mouse Models and Patients To determine whether MN-enriched miRNAs are relevant for MN disease, we characterized their expression in the spinal cords of an ALS mouse model and human ALS patient autopsies. In our congenic ALS mouse model (B6.Cg-Tg (SOD1$^{G93A}$)1Gur/J) colony, disease onset typically occurs at 100-110 days, as marked by time to peak weight. We performed RT-qPCR on SOD1$^{G93A}$ spinal cord harvested at 56, 84, 105, 126, and 147 days, as well as end-stage (inability to right itself within 30 seconds). There was a robust and highly significant temporal depletion of MN-enriched miRNAs, miR-218 and miR-138, in SOD1$^{G93A}$ spinal cord beginning at 126 days (FIG. 4A, FIG. 4B). This depletion was maximized in end-stage ALS mouse model spinal cord. Following a similar trend, pan-neuronal enriched miRNAs, miR-382 and miR-672, are decreased, but not significantly depleted in ALS mouse model spinal cord, even at end-stage (FIG. 4C, FIG. 4D). Finally, miR-218 and miR-138 are also depleted in ALS patient autopsy spinal cord as compared to non-diseased autopsy spinal cord controls (FIG. 4E, FIG. 4F).

Example 4. Dysregulation of MN-Enriched miRNAs as Biomarkers of MN Disease

Figure 5A:
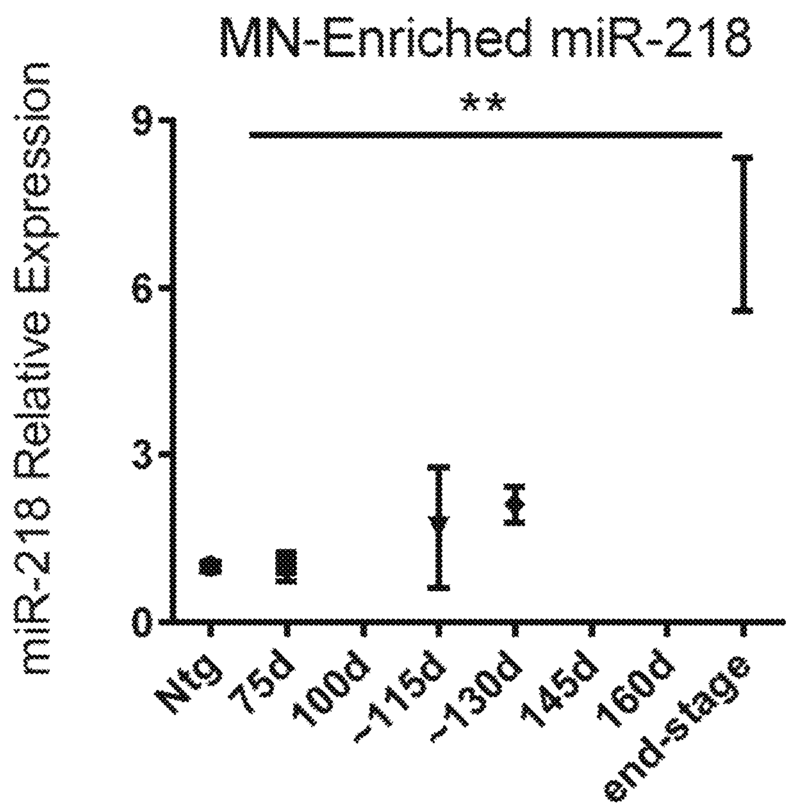
FIG. 5A, FIG. 5B, FIG. 5C, FIG. 5D, FIG. 5E and FIG. 5F depict graphs showing that MN-enriched miRNAs are increased in ALS rat model CSF and are responsive to ALS therapy.
Figure 5B:
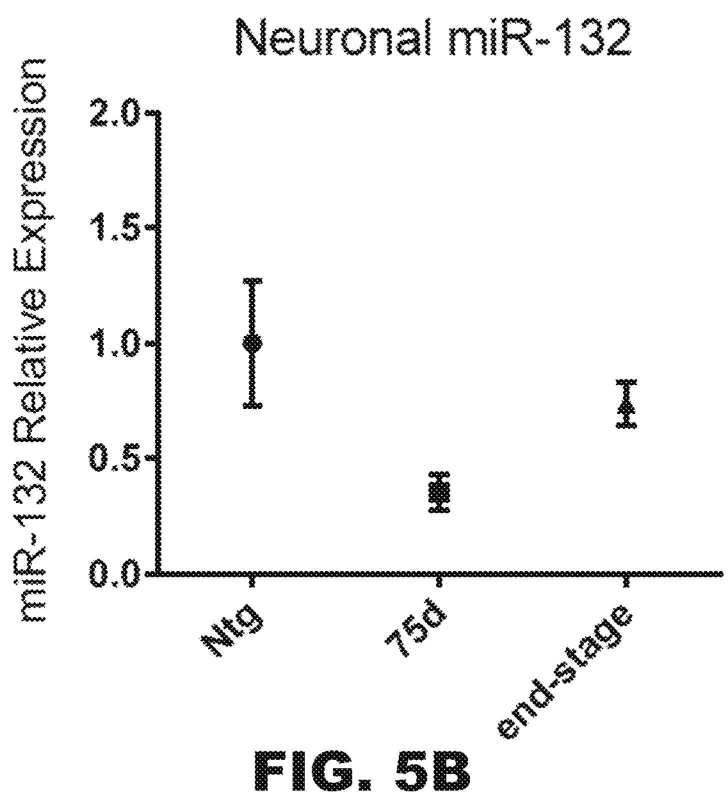
Figure 5C:
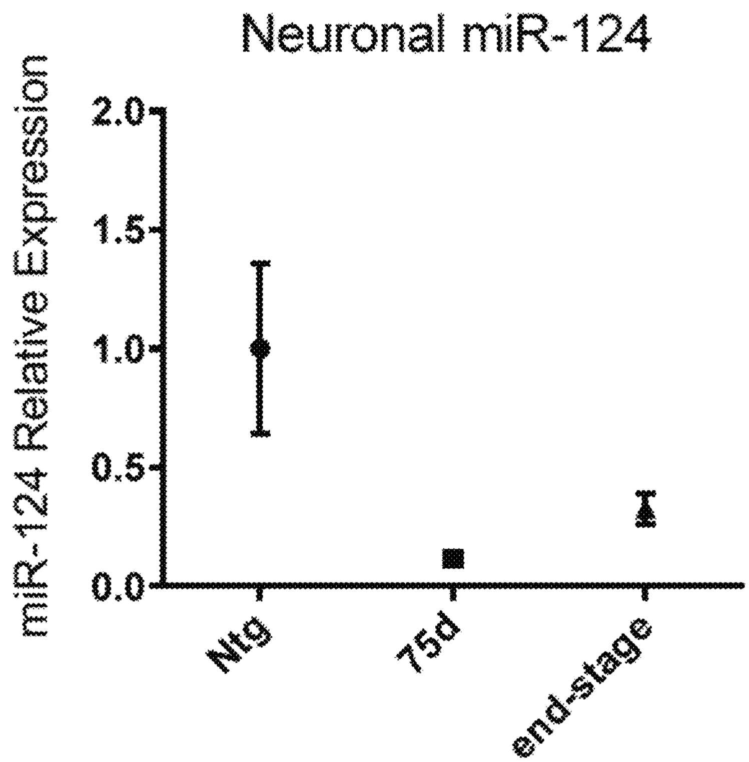
Figure 8:
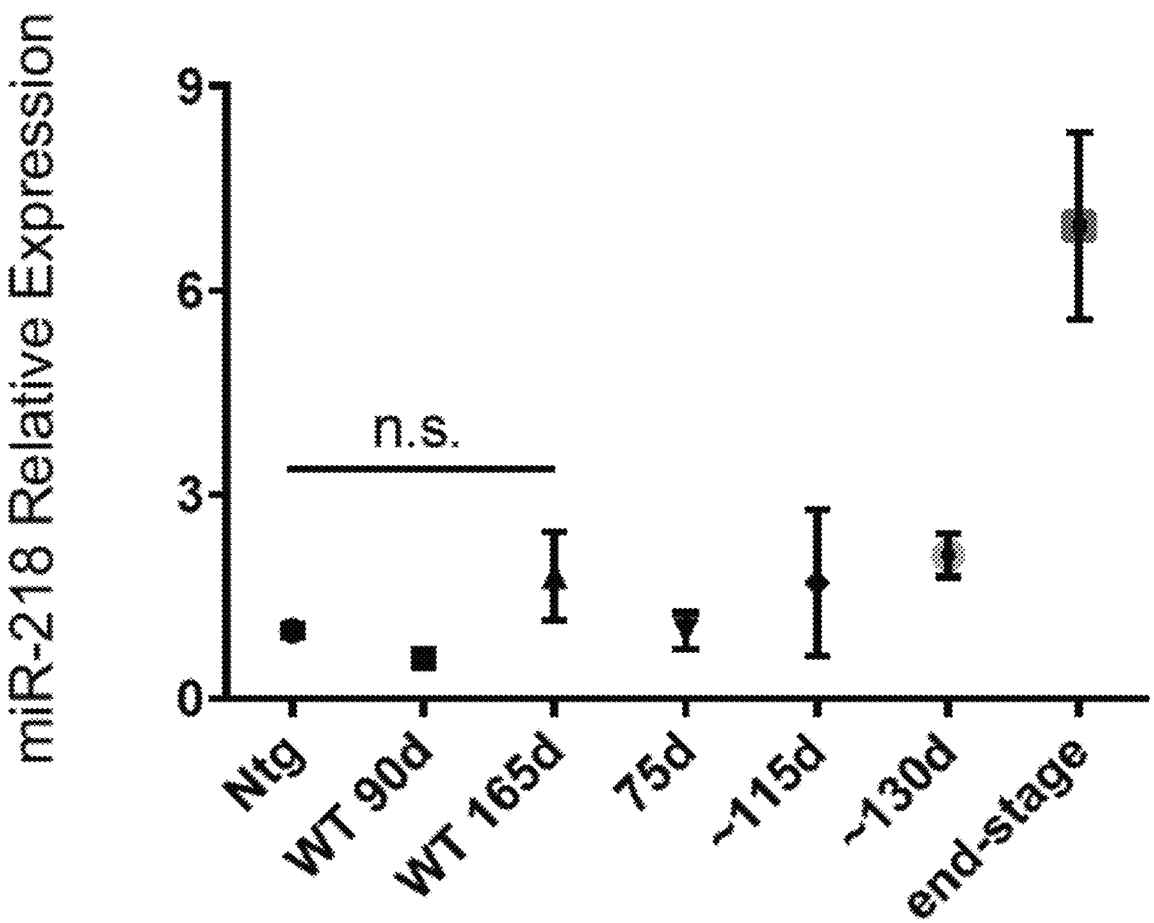
FIG. 8 depicts a graph showing increased miR-218 levels in ALS rat model CSF are not due solely to hSOD1 overexpression. miR-218 CSF levels are not significantly increased at either 90 or 165 days in hSOD1 wildtype overexpressing rats. N=2-7/timepoint. Values are expressed at mean±SEM. Student's unpaired, two-tailed t-test.

Because MN-enriched miRNAs are depleted temporally in ALS mouse model and patient autopsy spinal cord, we hypothesized these miRNAs might also be dysregulated in cerebrospinal fluid (CSF) as MNs are lost throughout ALS disease progression. Furthermore, as CSF bathes the brain and spinal cord, it might contain a detectable MN miRNA biomarker. Here, we used ALS SOD1$^{G93A}$ rats for these CSF studies because of the larger volume of CSF obtained from rats as compared to mice. Surprisingly, rather than decreased, as in mouse and patient spinal cord tissues, miR-218 increases throughout disease progression in ALS rat model CSF as compared to non-transgenic rats (FIG. 5A). To ensure this effect was not simply due to human SOD1 (hSOD1) overexpression, we measured miR-218 levels in CSF from rats overexpressing wildtype hSOD1 at 95 and 165 days. miR-218 CSF levels were not significantly different in hSOD1WT rats as compared to non-transgenics at either timepoint (FIG. 8). However, there is a trend towards increased miR-218 CSF levels at 165 days in hSOD1 WT rats, which could be reflective of the MN loss and decreased survival that is associated hSOD1 WT mice. Furthermore, increased expression of miR-218 in ALS rat model CSF is not due to global increases in miRNA expression in CSF, as a neuronal miRNAs, miR-132 and miR-124, were decreased in rat SOD1$^{G93A}$ CSF as compared with non-transgenic controls (FIG. 5B, FIG. 5C).

Figure 5D:
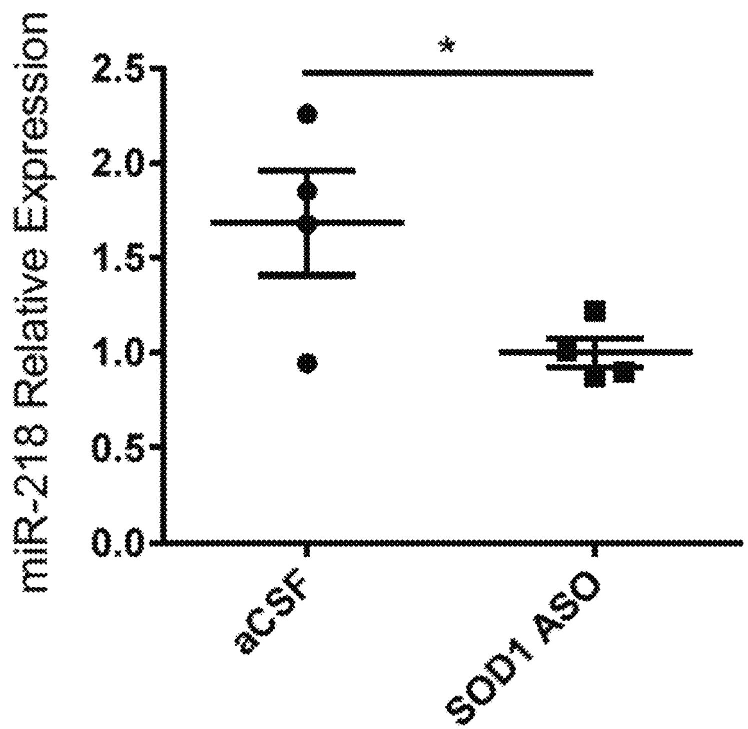
Figure 5E:
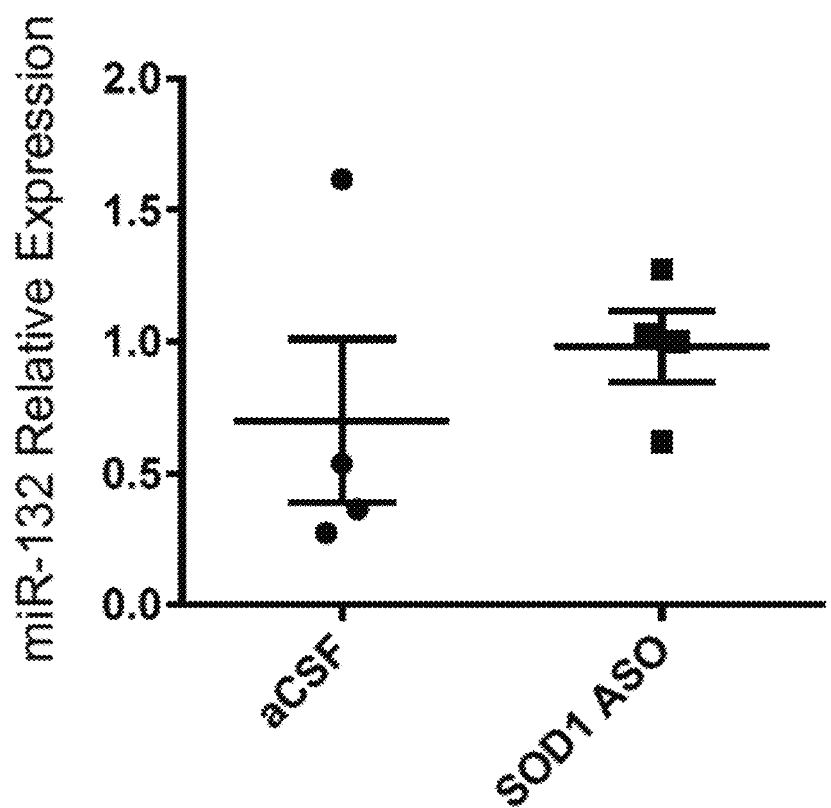
Figure 5F:
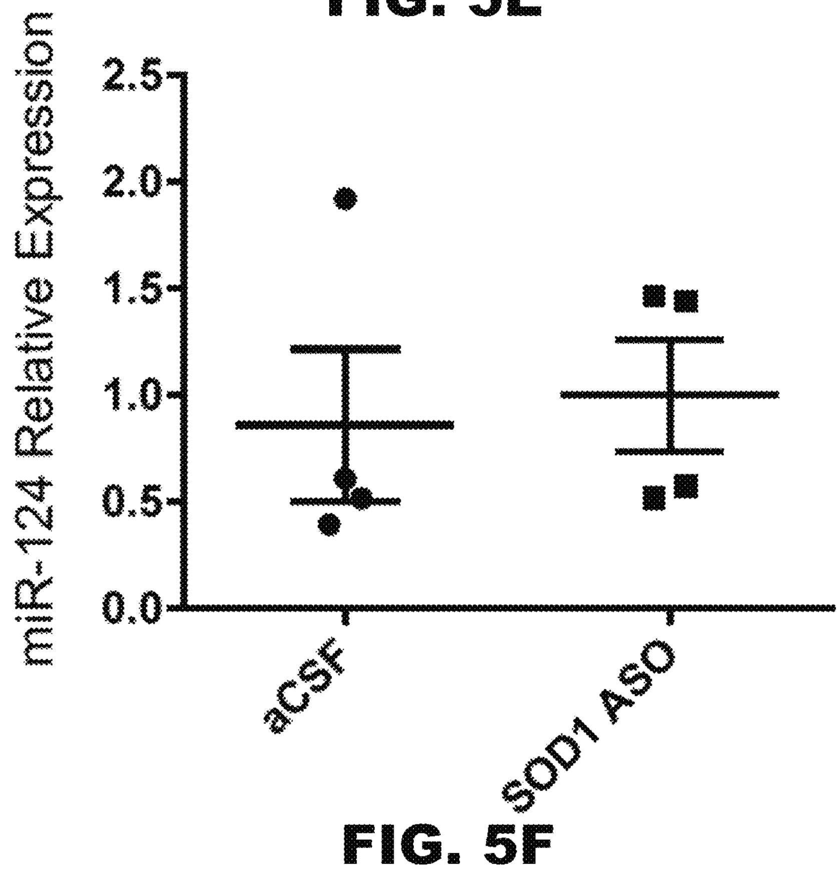

Because these data show that rats expressing human SOD1$^{G93A}$ transgene have increased levels of miR-218 in their CSF, we hypothesized that decreasing the levels of toxic transgene, SOD1$^{G93A}$ would also decrease the miR-218 levels in CSF. Antisense oligonucleotides (ASOs) against SOD1 are well-tolerated, effectively and specifically lower human SOD1$^{G93A}$ and extend survival in this rat model. To this end, we treated ALS SOD1$^{G93A}$ rats with SOD1 ASO. As predicted, hSOD1 mRNA was significantly lowered in the lumbar spinal cord of these animals (as assessed 50 days post-treatment). Strikingly, miR-218 CSF levels were reduced in SOD1 ASO-treated rats as compared to artificial CSF (aCSF)-treated littermate controls (FIG. 5D), but the levels of neuronal miR-132 and 124 were not (FIG. 5E, FIG. 5F). These data establish miR-218 as the first MN-specific and drug-responsive biomarker of MN disease.

Discussion for the Examples.

This study employs tools to assess in vivo miRNA expression in a cell type specific manner to discriminate MN-enriched miRNA expression relative to other CNS cell types. By focusing on MN-enriched miRNA expression in models of MN disease, we defined the first drug-responsive biomarker in an ALS disease model. In addition, we anticipate this dataset of MN-enriched miRNAs will facilitate other insights into MN disease mechanisms, risk factors and genetics underlying MN vulnerability.

In vivo cell type specific expression profiling techniques allow high-throughput access to key disease-relevant cell types, yet preserve physiological relevance as compared to ex vivo methods. This in vivo approach is particularly relevant for MNs, which represent roughly 4% of the spinal cord volume and may not be easily isolated from neighboring cells. We adopted a comparative, systematic approach to define MN-enriched miRNA expression relative to other CNS cell types. Inclusion of a pan-neuronal line allowed us to define which miRNAs distinguish MNs specifically from neurons in general, while assessment of microglial and astrocyte profiles provided key controls and baseline data to facilitate future analyses with understanding the molecular correlates of the well-known histological response of these cell types to disease pathology. The ability to define in vivo, cell type-enriched expression enables broad application of the concept of profiling the cell type most affected by a particular disease to understand disease mechanism and identify biomarkers. For example, we hypothesize that understanding brainstem dopaminergic miRNA profiles would reveal miRNA biomarkers for Parkinson's disease. Likewise, miRNA profiles of pancreatic beta islet cells would reveal serum miRNA biomarkers for diabetes.

As a first application of MN-enriched miRNA data in MN disease, we have defined a drug-responsive marker in CSF. Beyond this, we anticipate these MN-enriched miRNAs may provide a window into understanding of MN development and disease. The dataset generated here could inform novel miRNAs involved in cell fate specification, particularly those exhibiting enriched expression in a single CNS cell type. Furthermore, this study may provide insight into another emerging area of research interest: understanding the regulatory mechanisms that lead to cell type specific expression. Oftentimes, miRNAs are embedded within introns of genes, and while their transcription is sometimes dictated by the host gene promoter, there is increasing evidence that many miRNAs have their own promoters. Our dataset also enables probing regional differences in miRNA expression among the same cell type, which is of particular interest in ALS as glia are the main drivers of disease progression.

Our data demonstrate miR-218 is a marker of MN loss and/or injury in ALS rat model CSF. miR-218 exists at two different genomic loci within the introns of SLIT2 and SLIT3, which are important for axonal guidance. Our work highlights the importance of miR-218 and its relation to MN health and disease.

Currently, the regulation of miR-218 deposition into the CSF throughout ALS disease progression is unknown. It is possible that deposition of miR-218 into the CSF may reflect a pathological disease mechanism beyond just MN loss. While clearance of proteins and other molecules into the CSF can result from normal physiological processes, there is also increasing evidence that deposition into the CSF can be pathological as well. Disease-associated deposition could result from leakiness and permeability of the blood brain barrier, pathological signaling in response to cellular stress or cellular damage that is incurred from misfolded proteins and other neurological disease hallmarks. Future studies will help delineate whether the increased expression of miR-218 in ALS rat CSF is due to MN loss and subsequent clearance or an active signal or homeostatic attempt from diseased MNs. Understanding whether miR-218 is also changed in spinal muscular atrophy, spinal cord injury, or other disease of the spinal cord may provide insights into the miR-218 CSF signal.

miRNAs have been increasingly used as biomarkers of disease because they are measurable in biofluids, including CSF, serum and urine. Their stability in biofluid likely arises from their extracellular association with Argonaute or presence exosomes, making them more resistant to degradation. However, the relatively low abundance of miRNA in biofluids has made profiling miRNAs challenging. By defining miRNAs that were enriched in our cell type of interest, that being the predominantly affected cell type in ALS, we were able to develop a miRNA biomarker who presence in CSF reflected the progression of the disease.

Unlike multiple sclerosis with an imaging marker, muscles diseases with creatine kinase, or HIV with viral load, ALS clinical trials are hampered by the lack of a disease responsive biomarker that may be used as a proxy for MN health. Our data in animal models suggests that miR-218 in CSF may be such a marker. In clinical trials, if miR-218 levels could be used as an early signal regarding efficacy of the drug, drugs could be assessed much more rapidly for their likelihood of affecting MNs, thus potentially selecting a more promising candidate for a much longer trial.

This study has identified the first MN-specific, drug-responsive biomarker of MN disease. Our approach highlights a new pipeline for hypothesis-driven development of cell type specific miRNA biomarkers of diseases. miRNAs are ideal biomarkers because they are readily quantifiable, stable in biofluids and report on physiological and pathological processes. A MN-specific, drug-responsive biomarker would revolutionize the design and assessment of efficacy of MN disease therapies.

Methods for the Examples.

Animals.

All mice were bred on a congenic C57BL/6J background. To generate cell-specific GFP-Ago2 expressing mice, a homozygous (ROSA)26Sortm1(CAG-GFP/EiF2c2)Zjh (LSL-tAgo2) mouse (Jax ID: 017626) was bred to one of four Cre lines: Syn-Cre (Jax ID: 003966), ChAT-Cre (Jax ID: 006410), GFAP-Cre (a gift from David H. Gutmann), Lyz2-Cre (Jax ID: 004781). To visualize the cell types marked by GFAP and Lyz2, we used LSL-tdTomato mice (JAX: 007905). Mice used in experiments were heterozygous for LSL-tAgo2 and for a cell-specific Cre driver, while control mice were only positive for LSL-tAgo2. C57Bl/6J SOD1$^{G93A}$ mice were purchased from Jackson Laboratories (ID: 004435). For CSF studies, Sprague-Dawley non-transgenic, hSOD1 WT (provided by Pak Chan, Stanford University) and the SOD1$^{G93A}$ (Taconic model 2148) rat lines were used.

At 9 weeks of age, mice were anesthetized with an overdose of inhaled isoflurane before being perfused with 20-30 mL of cold PBS. Perfusion was critical for elimination of Lyz2-labeled monocytes in the blood. Following visual examination for complete exsanguination, whole spinal cords and whole brainstems were isolated and flash frozen in liquid nitrogen. Brainstem tissue included the pons and medulla with care to exclude any cortical, cerebellar, or spinal cord tissue. Tissues were stored at −80° C. until ready for miRNA isolation.

Histology: Double Label Cell Type Expression.

Free-floating 50 μm sections of brain and spinal cord were washed in TBS and blocked in 5% normal horse serum, 0.1% triton, in TBS for one half hour. Goat-anti-ChAT (1:200, Millipore AB144) or rabbit anti-NeuN antibody (1:1000, Cell Signaling, 12943), both with chicken-anti-GFP (1:250, Ayes, GFP-1020) in blocking solution were applied to the tissues overnight at 4° C. AlexaFluor 488-conjugated donkey anti-chicken (1:500, Jackson Immuno Research, 703-545-155) was added with DyLight 550 goat anti-rabbit (1:500, Thermo Scientific, 84541) or DyLight 550 donkey anti-goat (1:500, Thermo Scientific, SA5-10087) in blocking buffer to the tissue for one hour. Chicken anti-GFAP (1:1000, Abcam, ab4674) and rabbit anti-Iba1 (1:250, Wako, 019-19741) were used to label Td tomato tissue. No antibody was necessary to visualize Td tomato expression. DyLight 488 goat anti-chicken 1:500, Thermo Scientific, SA5-10070) or DyLight 488 donkey anti-rabbit (1:500, Thermo Scientific, SA5-10038) in blocking buffer to the tissue for one hour. All sections were stained with DAPI. Slides were washed 3 times in TBS, mounted on superfrost slides, and coverslipped with Fluoromount (Southern Biotech, 0100-01). All slides were observed at 20× objectives using a Nikon A1Rsi Confocal. All images were taken at ambient temperature with a 405, 488 and 561 nm lasers. For image acquisition and formatting, ImageJ and Adobe Photoshop CS6 Extended were used.

miRAP.

Brainstem and spinal cords from perfused, 63 day-old mice were harvested and flash frozen in liquid nitrogen and stored at −80° C. For array experiments, IPs were conducted on 3 double positive mice from each of the 4-cre driver lines and from an additional 4 negative control mice at the same time for a given tissue type. Whole brainstem or spinal cord was homogenized using a hand blender in 1 ml of lysis buffer and miRAP was conducted as previously described (He et al. Neuron 2012; 73(1): 35-48). Briefly, Whole brainstem or spinal cord was lysed in 1 mL of ice-cold lysis buffer (10 mM HEPES [pH 7.4], 100 mM KCl, 5 mM $MgCl_2$, 0.5% NP-40, 1 mM DTT, 100 U/mL RNasin Plus (Promega), and EDTA-free protease inhibitors (Roche)). Tissue was lysed using a hand blender before centrifuging at +4° C. for 30 min at 13,000 g. 10 μg of mouse-anti-Myc (sc-40; Santa Cruz Biotechnology) or 5 μg of mouse-anti-Ago2 (2E12-1C9; Anova) in 350 μL of PBS-Tween was conjugated to 50 μL of protein G Dynabeads (Invitrogen) for 45 min, rotating at RT. Antibody-conjugated beads were washed three times with 1 mL of PBS-Tween to remove any excess antibody. A BCA assay was performed on all tissue homogenates to normalize input to the lowest protein concentration. 850 μL of supernatant or supernatant diluted with lysis buffer were applied to the antibody-conjugated beads and incubated at +4° C. for 4 hours with end-over-end rotation. Beads were washed twice with low-salt buffer (50 mMTris-HCl [pH 7.5], 150 mM NaCl, 1 mM $MgCl_2$, 0.5% NP-40, 1 mM DTT, 100 U/mL RNasin Plus) and twice with high-salt buffer (50 mMTris-HCl [pH 7.5], 600 mM NaCl, 1 mM $MgCl_2$, 0.5% NP-40, 1 mM DTT, 100 U/ml RNasin Plus). 700 μL of Qiazol was added directly to the beads, and samples were vortexed for 30 sec and stored at −20° C.

miRNA Extraction and Quantification.

RNA was isolated using miRNeasy kits per manufacturer's instructions (Qiagen). miRNA microarrays were performed using 3 μL with pre-amplification using low density Rodent MiRNA A+B cards sets 3.0 (Life Technologies) on a 7900HT qPCR machine for 40 cycles. Analysis was conducted on SDSv2.2 software with automatic thresholding. Microarray miRNA targets were confirmed with individual TaqMan miRNA assays (Life Technologies) as per the manufacturer's instructions. qPCR samples were quantified in technical duplicates on an Applied Biosystems 7500 fast Real-Time PCR System.

Data Analysis and Statistics.

Data are presented as mean±SEM. All statistical tests were conducted using R's Bioconductor toolkit, MS Excel, or with Graphpad Prism 6 Software. Array data was normalized by global LoessM in R studio as previously described (Risso et al. *Bioinformatics* 2009; 25(20): 2685-2691).

Differentially Expressed from Non-Transgenic:

For a given sample, data was excluded for a miRNA if it failed to be expressed at a significant level over the corresponding microarray data from three myc-IP miRNA extractions from negative control mice, matched by tissue type. The criteria for differential expression were 1) the miRNA must be expressed in at least two of three replicates (three of four for Ago2); 2) The median expression of the triplicates for a given miRNA must be CT<35 (CT<37 for Ago2); 3) The highest CT of the triplicates for a given miRNA must be 2 CT< the median CT of the non-transgenics.

Endogenous miRNA Controls:

To identify putative housekeeping miRNAs, we used the following criteria: 1) Using the LoessM normalized CTs, we subsetted for miRNAs with a low standard deviation (<1) among the triplicates; 2) The mean CT of the triplicates had to be <24 for all cell types. miR-24, 30c, and 191 were the top three miRNAs that met these criteria.

Pairwise Comparisons:

For the miRNAs that met these criteria, relative expression data was generated for all pairwise comparisons between cell types in both tissues. Significant changes in miRNA expression profiles were determined by empirical Bayes given the low sample number, the large number of targets (672 miRNAs), and the inability to assume normal distribution (Smyth et al. *Stat Appl Genet Mol Biol* 2004; 3: Article3). These data are included in completion in Table 3 (spinal cord) and Table 4 (brain stem). Adjusted p values were calculated using the Benjamini-Hochberg correction (Klipper-Aurbach et al. *Med Hypotheses* 1995; 45(5): 486-490).

Heatmap:

miRNAs were included in the heatmap illustration (FIG. 3B) if a given miRNA was found to have significant differential expression (Log 2FC>2 and p<0.01) in at least one comparison.

Specificity Index:

We used the R Package pSI (Xu et al. *Journal of Neuroscience* 2014; 34(4): 1420-1431) to define which miRNAs were enriched in each cell type when compared to all others, with minor adaptations to the input for use with qPCR microarrays. Briefly, we converted CTs into a relative expression values, x, for each gene as x=2(40-CT), such that genes with lower CTs had higher relative expression and expression was in linear scale. This was then provided to the function specificity.index as was a filter to remove those miRNAs not expressed above background for each type, allowing calculation of a p-value for the enrichment of each miRNA in each cell type (pSI, in Table 1).

MN-Enriched miRNAs:

The top 8 miRNAs enriched in MNs were defined by the following criteria: 1) The geomean of the ChAT triplicates from the arrays<30 CT; 2) Fold-change>1.75 in all spinal cord comparisons; 3) unadjusted p-value<0.01 in ChAT versus Syn comparison.

CSF Collection and miRNA Extraction and Quantification.

CSF was obtained from rats anesthetized with 5% isoflurane via puncture of the cisterna magna and spun at 16,000 g for 10 mins at +4° C. prior to freezing the supernatant at −80° C. miRNA was extracted from CSF using the miRcury RNA Isolation Kit-Biofluids (Exiqon). RT-qPCR was performed using the miRCURY LNA Universal RT and ExiLENT SYBR green kit (Exiqon). 6 μL of undiluted RNA was used for RT using the miRCURY LNA Universal RT kit (Exiqon). The cDNA was diluted 1:20 in 17 μL of water and 2 μL of ROX reference dye (Invitrogen). 4 μL of diluted cDNA was used for each qPCR reaction using the ExiLENT SYBR Green kit (Exiqon). The data was analyzed using the 2^(−ddCT) method and miR-103a-3p was used as a normalization control (as per manufactuer's recommendation for biological fluid). qPCR samples were quantified in technical duplicates on an Applied Biosystems 7500 fast Real-Time PCR System.

SOD1 ASO Treatment.

$SOD1^{G93A}$ rats at 65 days of age were anesthetized with 5% isoflurane and given a 30 μL intrathecal bolus injection of 1000 μg of ASO or artificial CSF (aCSF) within their lumbar spinal region. Cohorts were gender- and litter-matched. CSF and spinal cord were harvested at 115 days of age. All surgeries and downstream analyses were done by personnel blinded to the treatment groups.

TABLE 3

Spinal Cord miRNA data.

| | mean_ sc.ChAT | mean_ sc.GFAP | mean_ sc.Lyz2 | mean_ sc.Syn | pSI_ sc.ChAT | pSI_ sc.GFAP | pSI_ sc.Lyz2 | pSI_ sc.Syn | detect_ SC.ChAT | detect_ SC.GFAP | detect_ SC.Lyz2 | detect_ SC.Syn |
|---|---|---|---|---|---|---|---|---|---|---|---|---|
| hsa_let_7b_002404 | 30.879 | 35.020 | 31.267 | 36.072 | 0.152 | 0.811 | 0.263 | 0.927 | TRUE | TRUE | TRUE | TRUE |
| hsa_let_7e_002407 | 30.955 | 30.486 | 30.064 | 31.333 | 0.588 | 0.574 | 0.377 | 0.703 | TRUE | TRUE | TRUE | TRUE |
| hsa_let_7f_1_002417 | 36.988 | 36.524 | 38.053 | 34.173 | NA | NA | 0.913 | 0.050 | FALSE | FALSE | TRUE | TRUE |
| hsa_let_7i_002172 | 33.472 | 30.838 | 34.523 | 35.180 | 0.458 | 0.072 | 0.755 | 0.908 | TRUE | TRUE | TRUE | TRUE |
| hsa_miR_106b_002380 | 30.817 | 27.576 | 29.987 | 27.067 | 0.909 | 0.326 | 0.809 | 0.089 | TRUE | TRUE | TRUE | TRUE |
| hsa_miR_10a_002288 | 35.055 | 35.056 | 37.102 | 36.059 | 0.300 | 0.444 | 0.888 | 0.597 | TRUE | TRUE | TRUE | TRUE |
| hsa_miR_1197_002810 | 32.465 | 35.963 | 34.449 | 33.050 | 0.210 | NA | 0.721 | 0.370 | TRUE | FALSE | TRUE | TRUE |
| hsa_miR_124_002197 | 35.423 | 35.842 | 35.382 | 37.266 | NA | NA | 0.402 | 0.868 | FALSE | FALSE | TRUE | TRUE |
| hsa_miR_127_5p_002229 | 31.428 | 35.136 | 34.115 | 32.536 | 0.117 | NA | 0.798 | 0.403 | TRUE | FALSE | TRUE | TRUE |
| hsa_miR_136_000592 | 29.264 | 33.332 | 27.628 | 28.940 | 0.548 | 0.967 | 0.162 | 0.418 | TRUE | TRUE | TRUE | TRUE |
| hsa_miR_136_002100 | 21.563 | 27.320 | 24.145 | 22.028 | 0.109 | 0.963 | 0.748 | 0.240 | TRUE | TRUE | TRUE | TRUE |
| hsa_miR_140_3p_002234 | 28.995 | 27.836 | 28.290 | 28.065 | 0.769 | 0.539 | 0.561 | 0.399 | TRUE | TRUE | TRUE | TRUE |
| hsa_miR_143_000466 | 27.619 | 28.159 | 21.533 | 29.701 | 0.554 | 0.759 | 0.010 | 0.947 | TRUE | TRUE | TRUE | TRUE |
| hsa_miR_144_002676 | 37.549 | 37.458 | 38.284 | 39.542 | NA | NA | 0.589 | NA | FALSE | FALSE | TRUE | FALSE |
| hsa_miR_148a_002134 | 37.722 | 34.727 | 38.858 | 39.554 | NA | NA | 0.766 | NA | FALSE | FALSE | TRUE | FALSE |
| hsa_miR_149_002255 | 19.790 | 20.672 | 21.481 | 19.353 | 0.447 | 0.688 | 0.872 | 0.239 | TRUE | TRUE | TRUE | TRUE |
| hsa_miR_151_5P_002642 | 30.948 | 27.369 | 26.408 | 29.995 | 0.953 | 0.292 | 0.164 | 0.719 | TRUE | TRUE | TRUE | TRUE |
| hsa_miR_154_000478 | 25.101 | 29.523 | 26.728 | 26.622 | 0.138 | 0.914 | 0.571 | 0.542 | TRUE | TRUE | TRUE | TRUE |
| hsa_miR_15b_002173 | 36.618 | 36.061 | 35.342 | 40.824 | NA | NA | NA | NA | FALSE | FALSE | FALSE | FALSE |
| hsa_miR_183_002270 | 27.187 | 33.259 | 25.842 | 26.869 | 0.471 | NA | 0.160 | 0.364 | TRUE | FALSE | TRUE | TRUE |
| hsa_miR_189_000488 | 34.202 | 33.163 | 31.920 | 30.879 | NA | 0.709 | 0.446 | 0.149 | FALSE | TRUE | TRUE | TRUE |
| hsa_miR_190b_002263 | 28.285 | 27.710 | 26.596 | 30.132 | 0.527 | 0.480 | 0.242 | 0.944 | TRUE | TRUE | TRUE | TRUE |
| hsa_miR_196a_241070_mat | 22.898 | 20.685 | 23.004 | 22.343 | 0.740 | 0.233 | 0.740 | 0.510 | TRUE | TRUE | TRUE | TRUE |
| hsa_miR_200a_001011 | 37.942 | 37.898 | 39.681 | 39.675 | NA | 0.386 | 0.791 | NA | FALSE | TRUE | TRUE | FALSE |
| hsa_miR_200b_001800 | 32.621 | 32.764 | 31.536 | 35.312 | NA | NA | NA | NA | FALSE | FALSE | FALSE | FALSE |
| hsa_miR_200b_002274 | 41.058 | 40.840 | 34.869 | 40.479 | NA | NA | 0.022 | NA | FALSE | FALSE | TRUE | FALSE |
| hsa_miR_200c_000505 | 29.521 | 28.937 | 24.555 | 28.936 | 0.855 | 0.759 | 0.057 | 0.596 | TRUE | TRUE | TRUE | TRUE |
| hsa_miR_200c_002286 | 39.357 | 39.448 | 39.774 | 39.626 | NA | NA | 0.623 | NA | FALSE | FALSE | TRUE | FALSE |
| hsa_miR_206_000510 | 32.580 | 26.994 | 25.742 | 29.679 | 0.996 | 0.255 | 0.120 | 0.640 | TRUE | TRUE | TRUE | TRUE |
| hsa_miR_213_000516 | 28.312 | 26.353 | 27.318 | 27.441 | 0.818 | 0.375 | 0.545 | 0.502 | TRUE | TRUE | TRUE | TRUE |
| hsa_miR_214_000517 | 32.027 | 28.745 | 29.776 | 31.372 | 0.897 | 0.202 | 0.398 | 0.696 | TRUE | TRUE | TRUE | TRUE |
| hsa_miR_214_002293 | 36.503 | 34.840 | 37.066 | 38.480 | NA | 0.175 | 0.644 | NA | FALSE | TRUE | TRUE | FALSE |
| hsa_miR_218_2_002294 | 25.488 | 35.935 | 30.916 | 29.525 | 0.002 | NA | 0.674 | 0.418 | TRUE | FALSE | TRUE | TRUE |
| hsa_miR_223_000526 | 24.678 | 28.611 | 15.981 | 28.679 | 0.408 | 0.925 | 0.000 | 0.893 | TRUE | TRUE | TRUE | TRUE |
| hsa_miR_22_000398 | 24.765 | 23.723 | 23.861 | 24.624 | 0.691 | 0.510 | 0.439 | 0.607 | TRUE | TRUE | TRUE | TRUE |
| hsa_miR_22_002301 | 28.491 | 28.403 | 28.568 | 29.796 | 0.419 | 0.521 | 0.473 | 0.812 | TRUE | TRUE | TRUE | TRUE |
| hsa_miR_23a_002439 | 35.070 | 32.073 | 24.625 | 41.740 | NA | 0.370 | 0.000 | NA | FALSE | TRUE | TRUE | FALSE |
| hsa_miR_26b_002444 | 33.164 | 30.729 | 29.582 | 34.928 | 0.690 | 0.302 | 0.155 | 0.982 | TRUE | TRUE | TRUE | TRUE |
| hsa_miR_27a_002445 | 34.867 | 33.503 | 35.742 | 37.360 | NA | 0.180 | 0.656 | 0.956 | FALSE | TRUE | TRUE | TRUE |
| hsa_miR_27b_002174 | 35.044 | 33.956 | 34.215 | 34.349 | NA | 0.539 | 0.503 | 0.466 | FALSE | TRUE | TRUE | TRUE |
| hsa_miR_28_3p_002446 | 36.072 | 37.158 | 37.479 | 36.676 | NA | NA | NA | NA | FALSE | FALSE | FALSE | FALSE |
| hsa_miR_299_5p_000600 | 34.556 | 36.641 | 36.116 | 34.620 | 0.346 | NA | 0.748 | 0.327 | TRUE | FALSE | TRUE | TRUE |
| hsa_miR_29a_002447 | 28.575 | 27.217 | 29.270 | 26.827 | 0.744 | 0.452 | 0.885 | 0.158 | TRUE | TRUE | TRUE | TRUE |
| hsa_miR_29b_2_002166 | 28.849 | 30.240 | 25.085 | 30.194 | 0.536 | 0.863 | 0.051 | 0.802 | TRUE | TRUE | TRUE | TRUE |
| hsa_miR_30a_3p_000416 | 20.965 | 20.170 | 21.278 | 20.687 | 0.621 | 0.486 | 0.699 | 0.465 | TRUE | TRUE | TRUE | TRUE |
| hsa_miR_30c_1_002108 | 35.948 | 32.956 | 39.089 | 39.727 | NA | 0.021 | 0.871 | NA | FALSE | TRUE | TRUE | FALSE |

TABLE 3-continued

| Spinal Cord miRNA data. | | | | | | | | | | | | |
|---|---|---|---|---|---|---|---|---|---|---|---|---|
| hsa_miR_30c_2_002110 | 32.808 | 38.297 | 37.811 | 40.585 | 0.004 | NA | NA | NA | TRUE | FALSE | FALSE | FALSE |
| hsa_miR_30d_002305 | 24.046 | 27.665 | 28.018 | 30.140 | 0.029 | 0.556 | 0.653 | 0.952 | TRUE | TRUE | TRUE | TRUE |
| hsa_miR_30e_3p_000422 | 20.710 | 19.830 | 20.973 | 20.639 | 0.597 | 0.457 | 0.677 | 0.531 | TRUE | TRUE | TRUE | TRUE |
| hsa_miR_324_3p_000579 | 29.427 | 24.147 | 26.753 | 25.193 | 0.981 | 0.161 | 0.682 | 0.239 | TRUE | TRUE | TRUE | TRUE |
| hsa_miR_338_000548 | 26.821 | 23.285 | 24.875 | 25.198 | 0.932 | 0.200 | 0.522 | 0.520 | TRUE | TRUE | TRUE | TRUE |
| hsa_miR_338_5P_002658 | 26.074 | 23.052 | 23.289 | 24.223 | 0.949 | 0.359 | 0.351 | 0.502 | TRUE | TRUE | TRUE | TRUE |
| hsa_miR_33a_002136 | 31.918 | 29.590 | 30.539 | 30.621 | 0.878 | 0.364 | 0.526 | 0.460 | TRUE | TRUE | TRUE | TRUE |
| hsa_miR_340_000550 | 23.475 | 22.875 | 23.973 | 23.292 | 0.589 | 0.502 | 0.730 | 0.462 | TRUE | TRUE | TRUE | TRUE |
| hsa_miR_363_001283 | 39.170 | 40.277 | 38.929 | 35.354 | NA | NA | 0.650 | 0.013 | FALSE | FALSE | TRUE | TRUE |
| hsa_miR_376a_001287 | 24.086 | 31.048 | 26.324 | 25.302 | 0.071 | 0.986 | 0.611 | 0.386 | TRUE | TRUE | TRUE | TRUE |
| hsa_miR_378_000567 | 25.843 | 25.735 | 22.340 | 27.387 | NA | NA | NA | NA | FALSE | FALSE | FALSE | FALSE |
| hsa_miR_411_002238 | 24.845 | 31.212 | 26.382 | 25.055 | 0.196 | 0.989 | 0.589 | 0.259 | TRUE | TRUE | TRUE | TRUE |
| hsa_miR_412_001023 | 29.401 | 33.999 | 31.660 | 30.565 | 0.114 | NA | 0.691 | 0.428 | TRUE | FALSE | TRUE | TRUE |
| hsa_miR_421_002700 | 22.275 | 22.096 | 23.281 | 23.044 | 0.414 | 0.484 | 0.738 | 0.638 | TRUE | TRUE | TRUE | TRUE |
| hsa_miR_423_3P_002626 | 30.184 | 25.943 | 28.472 | 28.527 | 0.937 | 0.095 | 0.598 | 0.532 | TRUE | TRUE | TRUE | TRUE |
| hsa_miR_425_001104 | 31.256 | 27.795 | 28.489 | 30.517 | 0.917 | 0.216 | 0.343 | 0.707 | TRUE | TRUE | TRUE | TRUE |
| hsa_miR_431_002312 | 31.094 | 36.118 | 34.404 | 31.738 | 0.104 | NA | 0.820 | 0.257 | TRUE | FALSE | TRUE | TRUE |
| hsa_miR_455_001280 | 31.927 | 26.562 | 27.804 | 29.967 | 0.985 | 0.108 | 0.342 | 0.654 | TRUE | TRUE | TRUE | TRUE |
| hsa_miR_485_5p_001036 | 35.893 | 35.904 | 35.951 | 36.172 | NA | NA | 0.525 | 0.583 | FALSE | FALSE | TRUE | TRUE |
| hsa_miR_493_3p_001282 | 38.550 | 29.485 | 34.151 | 34.931 | NA | 0.004 | 0.499 | 0.587 | FALSE | TRUE | TRUE | TRUE |
| hsa_miR_590_3P_002677 | 40.354 | 40.711 | 40.447 | 39.055 | NA | NA | NA | NA | FALSE | FALSE | TRUE | FALSE |
| hsa_miR_653_002292 | 33.569 | 37.039 | 33.565 | 36.984 | 0.213 | NA | 0.258 | 0.834 | TRUE | FALSE | TRUE | TRUE |
| hsa_miR_671_5p_197646_mat | 33.621 | 32.414 | 27.096 | 34.593 | NA | NA | 0.017 | NA | FALSE | FALSE | TRUE | FALSE |
| hsa_miR_708_002342 | 40.439 | 40.391 | 40.302 | 39.815 | NA | NA | NA | NA | FALSE | FALSE | TRUE | FALSE |
| hsa_miR_744_002325 | 30.577 | 30.629 | 30.064 | 30.735 | 0.560 | 0.666 | 0.430 | 0.592 | TRUE | TRUE | TRUE | TRUE |
| hsa_miR_875_5p_002203 | 25.517 | 28.405 | 20.202 | 35.659 | 0.391 | 0.651 | 0.005 | NA | TRUE | TRUE | TRUE | FALSE |
| hsa_miR_935_002178 | 35.947 | 34.504 | 35.791 | 34.312 | NA | NA | 0.734 | 0.228 | FALSE | FALSE | TRUE | TRUE |
| hsa_miR_93_002139 | 27.499 | 24.585 | 26.984 | 26.362 | 0.832 | 0.188 | 0.706 | 0.471 | TRUE | TRUE | TRUE | TRUE |
| hsa_miR_99b_002196 | 29.619 | 30.180 | 30.703 | 30.506 | 0.353 | 0.629 | NA | 0.605 | TRUE | TRUE | FALSE | TRUE |
| hsa_miR_9_002231 | 21.119 | 17.033 | 19.942 | 19.886 | 0.900 | 0.077 | 0.637 | 0.568 | TRUE | TRUE | TRUE | TRUE |
| mmu_let_7a_000377 | 26.605 | 22.901 | 29.543 | 23.721 | 0.710 | 0.144 | 0.999 | 0.144 | TRUE | TRUE | TRUE | TRUE |
| mmu_let_7a_002478 | 33.879 | 26.482 | 32.333 | 36.299 | NA | 0.000 | NA | NA | FALSE | TRUE | FALSE | FALSE |
| mmu_let_7b_000378 | 21.022 | 18.952 | 20.591 | 21.083 | 0.683 | 0.252 | 0.588 | 0.702 | TRUE | TRUE | TRUE | TRUE |
| mmu_let_7c_000379 | 20.247 | 18.747 | 20.629 | 20.101 | 0.641 | 0.321 | 0.743 | 0.544 | TRUE | TRUE | TRUE | TRUE |
| mmu_let_7c_1_002479 | 34.745 | 31.257 | 26.064 | 33.303 | NA | 0.476 | 0.014 | 0.698 | FALSE | TRUE | TRUE | TRUE |
| mmu_let_7d_001178 | 35.310 | 35.617 | 32.794 | 32.821 | NA | NA | 0.302 | 0.231 | FALSE | FALSE | TRUE | TRUE |
| mmu_let_7d_002283 | 21.114 | 20.892 | 22.375 | 21.161 | 0.481 | 0.520 | 0.835 | 0.439 | TRUE | TRUE | TRUE | TRUE |
| mmu_let_7e_002406 | 18.883 | 18.865 | 20.928 | 19.214 | 0.365 | 0.495 | 0.927 | 0.441 | TRUE | TRUE | TRUE | TRUE |
| mmu_let_7f_000382 | 28.133 | 25.503 | 27.217 | 24.260 | 0.900 | 0.424 | NA | 0.070 | TRUE | TRUE | FALSE | TRUE |
| mmu_let_7g_002282 | 20.587 | 21.067 | 21.987 | 21.300 | 0.340 | 0.608 | 0.776 | 0.546 | TRUE | TRUE | TRUE | TRUE |
| mmu_let_7g_002492 | 30.813 | 35.502 | 33.242 | 33.315 | 0.059 | NA | 0.617 | 0.621 | TRUE | FALSE | TRUE | TRUE |
| mmu_let_7i_002221 | 22.420 | 20.344 | 23.094 | 21.890 | 0.691 | 0.234 | 0.848 | 0.461 | TRUE | TRUE | TRUE | TRUE |
| mmu_miR_100_000437 | 21.277 | 18.539 | 20.865 | 21.116 | 0.736 | 0.162 | 0.639 | 0.674 | TRUE | TRUE | TRUE | TRUE |
| mmu_miR_101a_002253 | 21.391 | 22.078 | 22.549 | 22.492 | 0.316 | 0.630 | 0.687 | 0.647 | TRUE | TRUE | TRUE | TRUE |
| mmu_miR_101a_002507 | 35.607 | 35.338 | 35.313 | 34.185 | NA | 0.666 | 0.611 | 0.240 | FALSE | TRUE | TRUE | TRUE |
| mmu_miR_101b_002531 | 23.593 | 23.284 | 24.919 | 23.229 | 0.536 | 0.522 | 0.877 | 0.321 | TRUE | TRUE | TRUE | TRUE |
| mmu_miR_103_000439 | 23.842 | 23.307 | 25.438 | 23.785 | 0.478 | 0.450 | 0.905 | 0.406 | TRUE | TRUE | TRUE | TRUE |
| mmu_miR_105_002465 | 32.153 | 33.607 | 31.208 | 40.714 | 0.295 | 0.506 | 0.157 | NA | TRUE | TRUE | TRUE | FALSE |
| mmu_miR_106a_002459 | 25.321 | 21.039 | 26.750 | 22.667 | 0.806 | 0.081 | 0.980 | 0.216 | TRUE | TRUE | TRUE | TRUE |
| mmu_miR_106b_000442 | 24.829 | 22.708 | 23.579 | 23.942 | 0.844 | 0.364 | 0.498 | 0.530 | TRUE | TRUE | TRUE | TRUE |
| mmu_miR_107_000443 | 25.595 | 25.491 | 21.860 | 25.747 | 0.719 | 0.756 | 0.098 | 0.696 | TRUE | TRUE | TRUE | TRUE |

TABLE 3-continued

| Spinal Cord miRNA data. | | | | | | | | | | | | |
|---|---|---|---|---|---|---|---|---|---|---|---|---|
| mmu_miR_10a_000387 | 22.311 | 20.705 | 21.958 | 21.852 | 0.724 | 0.365 | 0.624 | 0.531 | TRUE | TRUE | TRUE | TRUE |
| mmu_miR_10b_001181 | 24.756 | 23.502 | 24.193 | 23.460 | 0.787 | 0.531 | 0.622 | 0.318 | TRUE | TRUE | TRUE | TRUE |
| mmu_miR_10b_002218 | 19.724 | 19.901 | 22.288 | 18.429 | 0.497 | 0.556 | 0.982 | 0.113 | TRUE | TRUE | TRUE | TRUE |
| mmu_miR_10b_002572 | 30.867 | 31.253 | 33.468 | 31.829 | 0.240 | 0.492 | 0.948 | 0.513 | TRUE | TRUE | TRUE | TRUE |
| mmu_miR_1186_002825 | 35.674 | 34.292 | 35.448 | 37.548 | NA | NA | 0.498 | NA | FALSE | FALSE | TRUE | FALSE |
| mmu_miR_1188_002866 | 34.066 | 36.573 | 36.296 | 35.675 | 0.152 | NA | 0.737 | 0.568 | TRUE | FALSE | TRUE | TRUE |
| mmu_miR_1191_002892 | 33.993 | 31.206 | 26.053 | 32.943 | NA | 0.524 | 0.017 | 0.708 | FALSE | TRUE | TRUE | TRUE |
| mmu_miR_1192_002806 | 39.297 | 39.488 | 39.624 | 39.611 | NA | NA | 0.587 | NA | FALSE | FALSE | TRUE | FALSE |
| mmu_miR_1193_002794 | 29.446 | 31.092 | 31.622 | 32.179 | 0.137 | 0.599 | 0.695 | 0.815 | TRUE | TRUE | TRUE | TRUE |
| mmu_miR_1194_002793 | 38.551 | 38.752 | 38.938 | 38.326 | NA | NA | 0.645 | NA | FALSE | FALSE | TRUE | FALSE |
| mmu_miR_1195_002839 | 36.882 | 36.650 | 36.988 | 39.681 | NA | NA | 0.432 | NA | FALSE | FALSE | TRUE | FALSE |
| mmu_miR_1198_002780 | 28.387 | 26.877 | 29.951 | 26.235 | 0.705 | 0.393 | 0.967 | 0.102 | TRUE | TRUE | TRUE | TRUE |
| mmu_miR_1199_240984_mat | 40.800 | 40.976 | 40.660 | 39.599 | NA | NA | NA | NA | FALSE | FALSE | TRUE | FALSE |
| mmu_miR_1224_240985_mat | 40.588 | 40.830 | 40.479 | 38.692 | NA | NA | NA | NA | FALSE | FALSE | TRUE | FALSE |
| mmu_miR_122_002245 | 36.718 | 32.391 | 27.033 | 38.251 | NA | 0.313 | 0.005 | NA | FALSE | TRUE | TRUE | FALSE |
| mmu_miR_124_001182 | 22.915 | 27.716 | 24.414 | 22.536 | 0.326 | 0.953 | 0.672 | 0.149 | TRUE | TRUE | TRUE | TRUE |
| mmu_miR_125a_3p_002199 | 26.710 | 27.123 | 26.352 | 26.339 | 0.602 | 0.736 | 0.486 | 0.431 | TRUE | TRUE | TRUE | TRUE |
| mmu_miR_125a_5p_002198 | 19.531 | 20.109 | 21.013 | 19.923 | 0.359 | 0.637 | 0.805 | 0.474 | TRUE | TRUE | TRUE | TRUE |
| mmu_miR_125b_002508 | 28.814 | 28.271 | 30.011 | 29.716 | 0.409 | 0.383 | NA | 0.683 | TRUE | TRUE | FALSE | TRUE |
| mmu_miR_125b_3p_002378 | 31.665 | 29.295 | 28.707 | 32.283 | 0.758 | 0.322 | 0.213 | 0.900 | TRUE | TRUE | TRUE | TRUE |
| mmu_miR_125b_5p_000449 | 19.134 | 18.277 | 17.962 | 19.210 | 0.673 | 0.541 | 0.362 | 0.667 | TRUE | TRUE | TRUE | TRUE |
| mmu_miR_126_3p_002228 | 21.436 | 24.546 | 19.796 | 22.934 | 0.390 | 0.919 | 0.138 | 0.724 | TRUE | TRUE | TRUE | TRUE |
| mmu_miR_126_5p_000451 | 23.217 | 26.593 | 22.386 | 24.760 | 0.324 | NA | 0.202 | 0.708 | TRUE | FALSE | TRUE | TRUE |
| mmu_miR_1274a_121150_mat | 32.404 | 33.863 | 28.270 | 35.143 | 0.477 | 0.794 | 0.030 | 0.942 | TRUE | TRUE | TRUE | TRUE |
| mmu_miR_127_000452 | 17.984 | 22.141 | 18.143 | 17.627 | 0.433 | 0.953 | 0.446 | 0.283 | TRUE | TRUE | TRUE | TRUE |
| mmu_miR_128a_002216 | 21.459 | 23.311 | 21.623 | 20.888 | 0.535 | 0.848 | 0.541 | 0.292 | TRUE | TRUE | TRUE | TRUE |
| mmu_miR_129_3p_001184 | 20.069 | 22.271 | 20.910 | 19.403 | 0.491 | 0.849 | 0.670 | 0.206 | TRUE | TRUE | TRUE | TRUE |
| mmu_miR_129_5p_000590 | 27.145 | 29.775 | 29.925 | 27.053 | 0.266 | 0.789 | 0.896 | 0.209 | TRUE | TRUE | TRUE | TRUE |
| mmu_miR_1306_121155_mat | 33.892 | 35.991 | 35.909 | 34.131 | NA | NA | 0.810 | 0.336 | FALSE | FALSE | TRUE | TRUE |
| mmu_miR_130a_000454 | 28.162 | 23.051 | 28.262 | 24.955 | 0.894 | 0.062 | 0.910 | 0.229 | TRUE | TRUE | TRUE | TRUE |
| mmu_miR_130b_000456 | 30.362 | 27.283 | 28.242 | 29.307 | 0.907 | 0.251 | 0.425 | 0.607 | TRUE | TRUE | TRUE | TRUE |
| mmu_miR_130b_002460 | 34.518 | 34.829 | 27.920 | 29.072 | 0.910 | 0.941 | 0.062 | 0.191 | TRUE | TRUE | TRUE | TRUE |
| mmu_miR_132_000457 | 18.750 | 22.630 | 18.745 | 17.460 | 0.539 | 0.955 | 0.492 | 0.126 | TRUE | TRUE | TRUE | TRUE |
| mmu_miR_133a_001637 | 37.169 | 39.184 | 39.128 | 36.680 | NA | NA | 0.835 | 0.183 | FALSE | FALSE | TRUE | TRUE |
| mmu_miR_133a_002246 | 18.284 | 25.610 | 20.344 | 19.099 | 0.102 | 0.993 | 0.603 | 0.318 | TRUE | TRUE | TRUE | TRUE |
| mmu_miR_133b_002247 | 22.228 | 30.028 | 24.044 | 23.931 | 0.069 | 0.995 | 0.488 | 0.477 | TRUE | TRUE | TRUE | TRUE |
| mmu_miR_134_001186 | 24.455 | 29.430 | 25.829 | 24.328 | 0.291 | 0.954 | 0.636 | 0.215 | TRUE | TRUE | TRUE | TRUE |
| mmu_miR_135a_000460 | 23.965 | 20.438 | 22.637 | 21.522 | 0.929 | 0.228 | 0.682 | 0.317 | TRUE | TRUE | TRUE | TRUE |
| mmu_miR_135b_002261 | 25.636 | 22.688 | 26.516 | 23.650 | 0.801 | 0.203 | 0.943 | 0.210 | TRUE | TRUE | TRUE | TRUE |
| mmu_miR_136_002511 | 23.198 | 31.431 | 25.603 | 23.459 | 0.123 | NA | 0.663 | 0.186 | TRUE | FALSE | TRUE | TRUE |
| mmu_miR_136_002512 | 30.751 | 31.041 | 30.171 | 31.783 | 0.461 | 0.647 | 0.359 | 0.760 | TRUE | TRUE | TRUE | TRUE |
| mmu_miR_137_001129 | 21.829 | 26.038 | 21.266 | 22.713 | 0.329 | 0.953 | 0.231 | 0.575 | TRUE | TRUE | TRUE | TRUE |
| mmu_miR_138_002284 | 15.816 | 20.940 | 18.263 | 16.941 | 0.087 | 0.935 | 0.705 | 0.398 | TRUE | TRUE | TRUE | TRUE |
| mmu_miR_138_002554 | 24.601 | 28.346 | 26.566 | 25.101 | 0.212 | 0.890 | 0.714 | 0.344 | TRUE | TRUE | TRUE | TRUE |
| mmu_miR_139_3p_002546 | 34.023 | 33.445 | 31.486 | 29.227 | 0.900 | NA | 0.489 | 0.035 | TRUE | FALSE | TRUE | TRUE |
| mmu_miR_139_5p_002289 | 19.948 | 22.750 | 19.943 | 19.486 | 0.507 | 0.896 | 0.471 | 0.301 | TRUE | TRUE | TRUE | TRUE |
| mmu_miR_140_001187 | 22.521 | 21.960 | 24.091 | 22.526 | 0.479 | 0.437 | 0.901 | 0.422 | TRUE | TRUE | TRUE | TRUE |
| mmu_miR_141_000463 | 31.253 | 32.458 | 30.061 | 37.665 | 0.337 | 0.522 | 0.156 | 1.000 | TRUE | TRUE | TRUE | TRUE |
| mmu_miR_141_002513 | 28.856 | 30.454 | 28.179 | 34.222 | NA | NA | NA | NA | FALSE | FALSE | FALSE | FALSE |
| mmu_miR_142_3p_000464 | 27.484 | 26.708 | 20.479 | 32.121 | 0.596 | 0.521 | 0.005 | NA | TRUE | TRUE | TRUE | FALSE |
| mmu_miR_142_5p_002248 | 32.748 | 34.090 | 28.889 | 38.300 | 0.444 | 0.632 | 0.027 | NA | TRUE | TRUE | TRUE | FALSE |

TABLE 3-continued

Spinal Cord miRNA data.

| | | | | | | | | | | | | |
|---|---|---|---|---|---|---|---|---|---|---|---|---|
| mmu_miR_143_002249 | 30.354 | 27.693 | 27.746 | 33.991 | 0.627 | 0.200 | 0.220 | 0.998 | TRUE | TRUE | TRUE | TRUE |
| mmu_miR_145_002278 | 28.267 | 25.943 | 25.032 | 32.452 | NA | NA | NA | NA | FALSE | FALSE | FALSE | FALSE |
| mmu_miR_145_002514 | 39.598 | 36.221 | 39.871 | 39.625 | NA | NA | 0.764 | NA | FALSE | FALSE | TRUE | FALSE |
| mmu_miR_146a_000468 | 20.205 | 20.612 | 18.294 | 23.316 | 0.440 | 0.570 | 0.167 | 0.978 | TRUE | TRUE | TRUE | TRUE |
| mmu_miR_146b_001097 | 22.698 | 21.903 | 21.670 | 22.024 | 0.759 | 0.599 | 0.431 | 0.468 | TRUE | TRUE | TRUE | TRUE |
| mmu_miR_146b_002453 | 35.118 | 34.458 | 31.011 | 32.893 | NA | NA | 0.136 | 0.387 | FALSE | FALSE | TRUE | TRUE |
| mmu_miR_147_002262 | 28.214 | 30.341 | 34.695 | 39.546 | 0.033 | NA | 0.765 | NA | TRUE | FALSE | TRUE | FALSE |
| mmu_miR_148a_000470 | 27.498 | 25.528 | 29.408 | 26.749 | 0.628 | 0.224 | 0.973 | 0.316 | TRUE | TRUE | TRUE | TRUE |
| mmu_miR_148b_000471 | 26.707 | 26.805 | 25.776 | 26.507 | 0.642 | 0.708 | 0.381 | 0.522 | TRUE | TRUE | TRUE | TRUE |
| mmu_miR_150_000473 | 23.612 | 24.661 | 20.531 | 26.976 | 0.455 | NA | 0.071 | NA | TRUE | FALSE | TRUE | FALSE |
| mmu_miR_150_002570 | 39.157 | 37.146 | 32.653 | 38.636 | NA | 0.568 | 0.034 | 0.729 | FALSE | TRUE | TRUE | TRUE |
| mmu_miR_151_3p_001190 | 29.393 | 24.392 | 28.688 | 27.117 | 0.913 | 0.047 | 0.805 | 0.379 | TRUE | TRUE | TRUE | TRUE |
| mmu_miR_152_000475 | 27.431 | 22.005 | 23.831 | 27.291 | 0.907 | 0.050 | 0.357 | 0.855 | TRUE | TRUE | TRUE | TRUE |
| mmu_miR_153_001191 | 29.827 | 33.226 | 27.820 | 30.060 | 0.510 | 0.950 | 0.122 | 0.552 | TRUE | TRUE | TRUE | TRUE |
| mmu_miR_154_000477 | 30.215 | 35.952 | 31.332 | 29.029 | 0.389 | NA | 0.623 | 0.058 | TRUE | FALSE | TRUE | TRUE |
| mmu_miR_155_002571 | 29.516 | 25.108 | 24.640 | 31.805 | 0.751 | 0.147 | 0.132 | NA | TRUE | TRUE | TRUE | FALSE |
| mmu_miR_15a_000389 | 25.684 | 23.551 | 26.442 | 25.119 | 0.693 | 0.221 | 0.864 | 0.452 | TRUE | TRUE | TRUE | TRUE |
| mmu_miR_15a_002488 | 35.500 | 33.636 | 32.562 | 35.057 | NA | 0.470 | 0.217 | 0.682 | FALSE | TRUE | TRUE | TRUE |
| mmu_miR_15b_000390 | 24.047 | 22.118 | 22.240 | 24.231 | 0.739 | 0.361 | 0.339 | 0.786 | TRUE | TRUE | TRUE | TRUE |
| mmu_miR_16_000391 | 19.478 | 19.323 | 19.314 | 19.828 | 0.527 | 0.604 | 0.486 | 0.635 | TRUE | TRUE | TRUE | TRUE |
| mmu_miR_16_002489 | 34.399 | 30.663 | 32.622 | 34.433 | NA | 0.097 | 0.464 | 0.820 | FALSE | TRUE | TRUE | TRUE |
| mmu_miR_17_002308 | 24.571 | 21.219 | 23.448 | 22.552 | 0.913 | 0.210 | 0.677 | 0.369 | TRUE | TRUE | TRUE | TRUE |
| mmu_miR_17_002543 | 34.661 | 32.484 | 32.602 | 38.723 | NA | 0.219 | 0.249 | 0.998 | FALSE | TRUE | TRUE | TRUE |
| mmu_miR_181A_2_002687 | 40.456 | 38.366 | 40.505 | 39.603 | NA | NA | NA | NA | FALSE | FALSE | TRUE | FALSE |
| mmu_miR_181a_000480 | 23.838 | 21.402 | 23.184 | 22.734 | 0.825 | 0.281 | 0.658 | 0.458 | TRUE | TRUE | TRUE | TRUE |
| mmu_miR_181c_000482 | 28.956 | 28.208 | 27.870 | 27.191 | 0.821 | 0.655 | 0.511 | 0.254 | TRUE | TRUE | TRUE | TRUE |
| mmu_miR_182_002599 | 22.935 | 24.346 | 22.552 | 22.881 | 0.510 | 0.826 | 0.410 | 0.484 | TRUE | TRUE | TRUE | TRUE |
| mmu_miR_1839_3p_121203_mat | 24.704 | 24.328 | 27.016 | 25.038 | 0.367 | 0.407 | 0.961 | 0.448 | TRUE | TRUE | TRUE | TRUE |
| mmu_miR_1839_5p_121135_mat | 26.728 | 25.648 | 28.582 | 25.394 | 0.627 | 0.418 | 0.968 | 0.156 | TRUE | TRUE | TRUE | TRUE |
| mmu_miR_183_002269 | 29.532 | 33.817 | 27.068 | 29.281 | 0.571 | NA | 0.093 | 0.456 | TRUE | FALSE | TRUE | TRUE |
| mmu_miR_184_000485 | 27.527 | 32.548 | 27.199 | 30.752 | 0.184 | 0.954 | 0.175 | 0.781 | TRUE | TRUE | TRUE | TRUE |
| mmu_miR_185_002271 | 26.194 | 29.218 | 29.561 | 25.105 | 0.343 | 0.813 | 0.929 | 0.067 | TRUE | TRUE | TRUE | TRUE |
| mmu_miR_186_002285 | 22.785 | 21.581 | 21.943 | 22.370 | 0.733 | 0.489 | 0.484 | 0.547 | TRUE | TRUE | TRUE | TRUE |
| mmu_miR_186_002574 | 29.676 | 29.459 | 27.346 | 30.002 | 0.665 | 0.677 | 0.192 | 0.720 | TRUE | TRUE | TRUE | TRUE |
| mmu_miR_187_001193 | 31.217 | 25.654 | 30.275 | 26.191 | 0.949 | 0.140 | 0.859 | 0.110 | TRUE | TRUE | TRUE | TRUE |
| mmu_miR_188_3p_002106 | 38.923 | 38.713 | 39.440 | 39.453 | NA | NA | 0.657 | NA | FALSE | FALSE | TRUE | FALSE |
| mmu_miR_188_5p_002320 | 25.421 | 23.733 | 19.030 | 25.431 | NA | NA | NA | NA | FALSE | FALSE | FALSE | FALSE |
| mmu_miR_1893_121170_mat | 41.067 | 40.807 | 40.667 | 39.923 | NA | NA | NA | NA | FALSE | FALSE | TRUE | FALSE |
| mmu_miR_1894_3p_241002_mat | 27.754 | 27.636 | 24.011 | 33.056 | 0.513 | 0.493 | 0.056 | NA | TRUE | TRUE | TRUE | FALSE |
| mmu_miR_1894_5p_121144_mat | 38.132 | 37.626 | 38.700 | 38.771 | NA | NA | 0.680 | NA | FALSE | FALSE | TRUE | FALSE |
| mmu_miR_1896_121128_mat | 23.931 | 22.339 | 20.892 | 30.141 | 0.571 | 0.306 | 0.114 | NA | TRUE | TRUE | TRUE | FALSE |
| mmu_miR_1897_3p_121126_mat | 40.727 | 40.894 | 40.614 | 39.596 | NA | NA | NA | NA | FALSE | FALSE | TRUE | FALSE |
| mmu_miR_1897_5p_121199_mat | 20.325 | 19.912 | 15.717 | 23.724 | NA | NA | 0.038 | NA | FALSE | FALSE | TRUE | FALSE |
| mmu_miR_1898_121195_mat | 40.765 | 40.949 | 40.633 | 39.458 | NA | NA | NA | NA | FALSE | FALSE | TRUE | FALSE |
| mmu_miR_1899_121198_mat | 40.059 | 40.154 | 40.223 | 39.589 | NA | NA | NA | NA | FALSE | FALSE | TRUE | FALSE |
| mmu_miR_18a_002422 | 27.873 | 27.994 | 28.076 | 27.983 | 0.520 | 0.650 | 0.572 | 0.522 | TRUE | TRUE | TRUE | TRUE |
| mmu_miR_18a_002490 | 34.460 | 32.829 | 32.514 | 33.417 | NA | 0.514 | 0.353 | 0.505 | FALSE | TRUE | TRUE | TRUE |
| mmu_miR_18b_002466 | 34.967 | 40.959 | 40.289 | 39.992 | 0.005 | NA | NA | NA | TRUE | FALSE | TRUE | FALSE |
| mmu_miR_1900_121143_mat | 40.350 | 40.477 | 40.406 | 39.601 | NA | NA | NA | NA | FALSE | FALSE | TRUE | FALSE |
| mmu_miR_1901_121183_mat | 36.706 | 36.929 | 35.814 | 38.354 | NA | NA | 0.301 | 0.875 | FALSE | FALSE | TRUE | TRUE |
| mmu_miR_1902_121197_mat | 40.582 | 40.743 | 40.538 | 39.592 | NA | NA | NA | NA | FALSE | FALSE | TRUE | FALSE |

TABLE 3-continued

Spinal Cord miRNA data.

| | | | | | | | | | | | | |
|---|---|---|---|---|---|---|---|---|---|---|---|---|
| mmu_miR_1903_121153_mat | 37.136 | 37.793 | 39.222 | 37.513 | NA | NA | NA | NA | FALSE | FALSE | FALSE | FALSE |
| mmu_miR_1904_121162_mat | 16.565 | 18.004 | 13.193 | 20.893 | NA | NA | NA | NA | FALSE | FALSE | FALSE | FALSE |
| mmu_miR_1905_121196_mat | 27.519 | 30.772 | 23.772 | 33.607 | 0.373 | 0.755 | 0.014 | 0.993 | TRUE | TRUE | TRUE | TRUE |
| mmu_miR_1906_121169_mat | 39.986 | 38.551 | 40.095 | 39.687 | NA | NA | NA | NA | FALSE | FALSE | TRUE | FALSE |
| mmu_miR_190_000489 | 26.020 | 24.836 | 23.901 | 25.434 | 0.821 | 0.568 | 0.283 | 0.572 | TRUE | TRUE | TRUE | TRUE |
| mmu_miR_191_002299 | 20.171 | 19.761 | 20.100 | 19.787 | 0.645 | 0.599 | 0.588 | 0.438 | TRUE | TRUE | TRUE | TRUE |
| mmu_miR_191_002576 | 30.096 | 30.591 | 30.703 | 31.638 | 0.333 | 0.591 | 0.543 | 0.788 | TRUE | TRUE | TRUE | TRUE |
| mmu_miR_1927_121193_mat | 37.263 | 36.434 | 37.663 | 37.542 | NA | NA | 0.686 | NA | FALSE | FALSE | TRUE | FALSE |
| mmu_miR_1928_121164_mat | 21.073 | 21.447 | 17.307 | 24.884 | 0.505 | 0.605 | 0.049 | NA | TRUE | TRUE | TRUE | FALSE |
| mmu_miR_192_000491 | 25.821 | 24.640 | 27.611 | 24.923 | 0.607 | 0.378 | 0.963 | 0.228 | TRUE | TRUE | TRUE | TRUE |
| mmu_miR_1930_121201_mat | 27.711 | 29.487 | 28.858 | 29.873 | 0.213 | 0.724 | 0.536 | 0.775 | TRUE | TRUE | TRUE | TRUE |
| mmu_miR_1931_121168_mat | 40.049 | 40.269 | 40.120 | 39.375 | NA | NA | NA | NA | FALSE | FALSE | TRUE | FALSE |
| mmu_miR_1932_121172_mat | 34.483 | 30.920 | 35.361 | 34.291 | NA | 0.055 | 0.884 | 0.593 | FALSE | TRUE | TRUE | TRUE |
| mmu_miR_1933_3p_121145_mat | 40.460 | 40.620 | 40.478 | 39.589 | NA | NA | NA | NA | FALSE | FALSE | TRUE | FALSE |
| mmu_miR_1933_5p_121133_mat | 36.958 | 31.287 | 33.447 | 36.139 | NA | 0.046 | 0.385 | 0.762 | FALSE | TRUE | TRUE | TRUE |
| mmu_miR_1934_121185_mat | 36.253 | 38.565 | 38.642 | 38.408 | 0.118 | NA | 0.735 | NA | TRUE | FALSE | TRUE | FALSE |
| mmu_miR_1935_121192_mat | 40.374 | 40.629 | 40.327 | 39.848 | NA | NA | NA | NA | FALSE | FALSE | TRUE | FALSE |
| mmu_miR_1936_121158_mat | 38.865 | 38.937 | 39.344 | 39.702 | NA | NA | 0.594 | NA | FALSE | FALSE | TRUE | FALSE |
| mmu_miR_1937b_241023_mat | 20.223 | 20.471 | 17.105 | 24.382 | 0.492 | 0.541 | 0.081 | NA | TRUE | TRUE | TRUE | FALSE |
| mmu_miR_1937c_241011_mat | 21.727 | 22.012 | 18.017 | 25.595 | NA | NA | 0.055 | NA | FALSE | FALSE | TRUE | FALSE |
| mmu_miR_1938_121194_mat | 38.639 | 38.671 | 39.202 | 39.535 | NA | NA | 0.620 | NA | FALSE | FALSE | TRUE | FALSE |
| mmu_miR_1939_121180_mat | 35.897 | 35.198 | 36.959 | 37.323 | NA | NA | 0.712 | 0.816 | FALSE | FALSE | TRUE | TRUE |
| mmu_miR_193_002250 | 35.129 | 33.877 | 33.044 | 36.199 | 0.637 | 0.434 | 0.243 | 0.894 | TRUE | TRUE | TRUE | TRUE |
| mmu_miR_193_002577 | 31.827 | 29.274 | 30.764 | 33.235 | 0.615 | 0.160 | 0.451 | 0.945 | TRUE | TRUE | TRUE | TRUE |
| mmu_miR_193b_002467 | 21.195 | 20.017 | 23.182 | 22.324 | 0.359 | 0.222 | 0.907 | 0.705 | TRUE | TRUE | TRUE | TRUE |
| mmu_miR_1940_121187_mat | 37.494 | 38.721 | 39.788 | 37.955 | 0.268 | 0.663 | 0.903 | 0.396 | TRUE | TRUE | TRUE | TRUE |
| mmu_miR_1941_3p_121130_mat | 38.707 | 38.733 | 39.267 | 39.559 | NA | NA | 0.623 | NA | FALSE | FALSE | TRUE | FALSE |
| mmu_miR_1941_5p_121140_mat | 32.911 | 31.434 | 31.722 | 32.165 | 0.806 | 0.486 | 0.450 | 0.506 | TRUE | TRUE | TRUE | TRUE |
| mmu_miR_1942_121136_mat | 37.383 | 35.682 | 32.572 | 40.377 | NA | 0.393 | 0.058 | NA | FALSE | TRUE | TRUE | FALSE |
| mmu_miR_1943_121174_mat | 34.219 | 31.433 | 33.667 | 34.136 | NA | 0.157 | 0.607 | 0.710 | FALSE | TRUE | TRUE | TRUE |
| mmu_miR_1944_121189_mat | 40.038 | 38.885 | 40.224 | 36.979 | NA | NA | NA | NA | FALSE | FALSE | TRUE | FALSE |
| mmu_miR_1945_121166_mat | 38.445 | 38.543 | 38.984 | 39.087 | NA | NA | 0.631 | NA | FALSE | FALSE | TRUE | FALSE |
| mmu_miR_1946a_121178_mat | 41.375 | 40.616 | 40.439 | 40.411 | NA | NA | NA | NA | FALSE | FALSE | TRUE | FALSE |
| mmu_miR_1947_121156_mat | 37.774 | 35.276 | 38.705 | 39.625 | NA | 0.079 | 0.726 | NA | FALSE | TRUE | TRUE | FALSE |
| mmu_miR_1948_121171_mat | 35.099 | 34.784 | 37.053 | 35.673 | 0.369 | 0.411 | 0.911 | 0.531 | TRUE | TRUE | TRUE | TRUE |
| mmu_miR_1949_121182_mat | 40.135 | 40.342 | 40.234 | 39.610 | NA | NA | NA | NA | FALSE | FALSE | TRUE | FALSE |
| mmu_miR_194_000493 | 26.330 | 25.568 | 23.924 | 25.839 | 0.799 | 0.655 | 0.231 | 0.571 | TRUE | TRUE | TRUE | TRUE |
| mmu_miR_1950_121146_mat | 40.526 | 37.767 | 39.581 | 39.600 | NA | NA | 0.604 | NA | FALSE | FALSE | TRUE | FALSE |
| mmu_miR_1951_121165_mat | 35.079 | 35.529 | 36.820 | 40.704 | NA | NA | 0.614 | NA | FALSE | FALSE | TRUE | FALSE |
| mmu_miR_1952_121167_mat | 40.678 | 40.848 | 40.591 | 39.596 | NA | NA | NA | NA | FALSE | FALSE | TRUE | FALSE |
| mmu_miR_1953_121159_mat | 39.401 | 39.472 | 39.822 | 39.556 | NA | NA | 0.639 | NA | FALSE | FALSE | TRUE | FALSE |
| mmu_miR_1954_121137_mat | 29.035 | 29.632 | 26.449 | 36.272 | 0.422 | 0.504 | 0.083 | NA | TRUE | TRUE | TRUE | FALSE |
| mmu_miR_1956_121129_mat | 34.837 | 32.972 | 37.649 | 38.751 | NA | 0.064 | NA | NA | FALSE | TRUE | FALSE | FALSE |
| mmu_miR_1957_121163_mat | 40.800 | 40.976 | 40.660 | 39.599 | NA | NA | NA | NA | FALSE | FALSE | TRUE | FALSE |
| mmu_miR_1958_121181_mat | 38.727 | 35.735 | 39.186 | 39.621 | NA | NA | 0.723 | NA | FALSE | FALSE | TRUE | FALSE |
| mmu_miR_1959_121132_mat | 27.370 | 28.292 | 25.195 | 34.862 | 0.395 | 0.511 | 0.097 | NA | TRUE | TRUE | TRUE | FALSE |
| mmu_miR_195_000494 | 23.651 | 20.103 | 23.001 | 22.685 | 0.850 | 0.107 | 0.691 | 0.542 | TRUE | TRUE | TRUE | TRUE |
| mmu_miR_1960_121148_mat | 36.303 | 34.907 | 37.184 | 37.489 | NA | NA | 0.736 | 0.817 | FALSE | FALSE | TRUE | TRUE |
| mmu_miR_1961_197391_mat | 25.571 | 26.372 | 21.891 | 33.930 | 0.441 | NA | 0.035 | NA | TRUE | FALSE | TRUE | FALSE |
| mmu_miR_1962_121173_mat | 40.135 | 39.765 | 40.222 | 38.982 | NA | NA | NA | NA | FALSE | FALSE | TRUE | FALSE |
| mmu_miR_1963_121191_mat | 40.800 | 40.976 | 40.660 | 39.599 | NA | NA | NA | NA | FALSE | FALSE | TRUE | FALSE |

TABLE 3-continued

| Spinal Cord miRNA data. | | | | | | | | | | | | |
|---|---|---|---|---|---|---|---|---|---|---|---|---|
| mmu_miR_1964_121138_mat | 37.371 | 36.401 | 38.090 | 38.242 | NA | NA | 0.711 | NA | FALSE | FALSE | TRUE | FALSE |
| mmu_miR_1965_121186_mat | 40.817 | 40.947 | 40.655 | 39.615 | NA | NA | NA | NA | FALSE | FALSE | TRUE | FALSE |
| mmu_miR_1966_121134_mat | 40.522 | 40.884 | 40.557 | 38.864 | NA | NA | NA | NA | FALSE | FALSE | TRUE | FALSE |
| mmu_miR_1967_121151_mat | 40.791 | 40.969 | 40.662 | 39.651 | NA | NA | NA | NA | FALSE | FALSE | TRUE | FALSE |
| mmu_miR_1968_121179_mat | 38.202 | 33.226 | 38.270 | 40.336 | NA | 0.005 | 0.626 | NA | FALSE | TRUE | TRUE | FALSE |
| mmu_miR_1969_121131_mat | 22.677 | 22.813 | 19.052 | 26.253 | 0.514 | 0.573 | 0.066 | NA | TRUE | TRUE | TRUE | FALSE |
| mmu_miR_196a_002477 | 23.463 | 23.683 | 26.769 | 28.784 | 0.123 | 0.212 | NA | NA | TRUE | TRUE | FALSE | FALSE |
| mmu_miR_196b_002215 | 26.664 | 24.959 | 29.268 | 26.734 | 0.452 | 0.187 | 0.989 | 0.468 | TRUE | TRUE | TRUE | TRUE |
| mmu_miR_1970_121202_mat | 37.158 | 40.486 | 37.291 | 35.218 | 0.588 | NA | 0.575 | 0.051 | TRUE | FALSE | TRUE | TRUE |
| mmu_miR_1971_121161_mat | 31.867 | 26.827 | 28.458 | 28.504 | 0.983 | 0.170 | 0.505 | 0.433 | TRUE | TRUE | TRUE | TRUE |
| mmu_miR_197_000497 | 25.970 | 31.605 | 25.145 | 36.074 | 0.149 | NA | 0.073 | NA | TRUE | FALSE | TRUE | FALSE |
| mmu_miR_1981_121200_mat | 28.861 | 29.731 | 27.985 | 28.723 | 0.586 | 0.793 | 0.353 | 0.506 | TRUE | TRUE | TRUE | TRUE |
| mmu_miR_1982.1_121157_mat | 32.471 | 30.251 | 29.215 | 31.222 | 0.921 | 0.480 | 0.227 | 0.563 | TRUE | TRUE | TRUE | TRUE |
| mmu_miR_1982.2_121154_mat | 31.162 | 32.098 | 28.473 | 30.835 | 0.705 | 0.848 | 0.149 | 0.542 | TRUE | TRUE | TRUE | TRUE |
| mmu_miR_199a_3p_002304 | 33.229 | 27.600 | 25.700 | 29.693 | 0.997 | 0.311 | 0.095 | 0.604 | TRUE | TRUE | TRUE | TRUE |
| mmu_miR_199a_5p_000498 | 34.977 | 35.802 | 35.689 | 34.177 | 0.567 | NA | 0.717 | 0.227 | TRUE | FALSE | TRUE | TRUE |
| mmu_miR_199b_001131 | 34.903 | 34.917 | 36.895 | 36.159 | NA | NA | 0.866 | 0.665 | FALSE | FALSE | TRUE | TRUE |
| mmu_miR_19a_000395 | 26.653 | 23.770 | 23.913 | 26.348 | 0.866 | 0.283 | 0.288 | 0.759 | TRUE | TRUE | TRUE | TRUE |
| mmu_miR_19a_002544 | 39.970 | 40.091 | 40.183 | 39.587 | NA | NA | NA | NA | FALSE | FALSE | TRUE | FALSE |
| mmu_miR_19b_000396 | 23.455 | 20.176 | 21.772 | 21.905 | 0.917 | 0.221 | 0.553 | 0.501 | TRUE | TRUE | TRUE | TRUE |
| mmu_miR_1_002222 | 20.609 | 24.439 | 22.001 | 21.881 | 0.177 | 0.892 | 0.569 | 0.541 | TRUE | TRUE | TRUE | TRUE |
| mmu_miR_1_2_AS_002882 | 33.789 | 30.701 | 29.589 | 35.511 | 0.736 | 0.254 | 0.133 | 0.984 | TRUE | TRUE | TRUE | TRUE |
| mmu_miR_200a_000502 | 37.374 | 35.908 | 36.797 | 40.028 | NA | NA | NA | NA | FALSE | FALSE | FALSE | FALSE |
| mmu_miR_200b_002251 | 34.157 | 30.147 | 31.994 | 38.092 | NA | 0.053 | NA | NA | FALSE | TRUE | FALSE | FALSE |
| mmu_miR_200c_002300 | 35.038 | 34.544 | 34.569 | 34.087 | NA | NA | NA | 0.347 | FALSE | FALSE | FALSE | TRUE |
| mmu_miR_201_002578 | 39.119 | 38.981 | 39.419 | 39.702 | NA | NA | 0.582 | NA | FALSE | FALSE | TRUE | FALSE |
| mmu_miR_202_3p_001195 | 34.130 | 35.598 | 29.818 | 38.508 | NA | NA | 0.020 | NA | FALSE | FALSE | TRUE | FALSE |
| mmu_miR_202_5p_002579 | 36.557 | 36.487 | 36.622 | 38.051 | NA | NA | NA | NA | FALSE | FALSE | FALSE | FALSE |
| mmu_miR_203_000507 | 30.904 | 23.633 | 24.671 | 26.032 | 0.999 | 0.141 | 0.323 | 0.532 | TRUE | TRUE | TRUE | TRUE |
| mmu_miR_203_002580 | 38.162 | 33.989 | 38.656 | 39.162 | NA | 0.019 | 0.742 | NA | FALSE | TRUE | TRUE | FALSE |
| mmu_miR_204_000508 | 21.639 | 17.844 | 20.130 | 21.552 | 0.823 | 0.083 | 0.508 | 0.786 | TRUE | TRUE | TRUE | TRUE |
| mmu_miR_205_000509 | 36.168 | 36.173 | 29.195 | 31.628 | NA | NA | 0.034 | 0.274 | FALSE | FALSE | TRUE | TRUE |
| mmu_miR_207_001198 | 39.609 | 39.847 | 39.859 | 38.772 | NA | NA | 0.645 | NA | FALSE | FALSE | TRUE | FALSE |
| mmu_miR_208_000511 | 36.655 | 39.691 | 32.832 | 34.276 | NA | NA | 0.079 | 0.252 | FALSE | FALSE | TRUE | TRUE |
| mmu_miR_208b_002290 | 37.345 | 36.626 | 34.475 | 40.825 | NA | NA | 0.123 | NA | FALSE | FALSE | TRUE | FALSE |
| mmu_miR_20a_000580 | 23.510 | 20.560 | 20.501 | 22.040 | 0.941 | 0.360 | 0.288 | 0.574 | TRUE | TRUE | TRUE | TRUE |
| mmu_miR_20a_002491 | 33.464 | 33.864 | 31.505 | 33.131 | NA | 0.783 | NA | 0.539 | FALSE | TRUE | FALSE | TRUE |
| mmu_miR_20b_001014 | 26.251 | 22.328 | 23.702 | 24.708 | 0.949 | 0.175 | 0.440 | 0.589 | TRUE | TRUE | TRUE | TRUE |
| mmu_miR_20b_002524 | 36.450 | 39.946 | 39.831 | 39.368 | NA | NA | 0.764 | NA | FALSE | FALSE | TRUE | FALSE |
| mmu_miR_210_000512 | 35.507 | 25.807 | 29.748 | 29.925 | 0.999 | 0.012 | 0.513 | 0.519 | TRUE | TRUE | TRUE | TRUE |
| mmu_miR_211_001199 | 23.729 | 22.214 | 22.798 | 23.652 | 0.714 | 0.398 | 0.466 | 0.667 | TRUE | TRUE | TRUE | TRUE |
| mmu_miR_212_002551 | 21.787 | 26.550 | 24.396 | 20.210 | 0.342 | 0.942 | 0.817 | 0.022 | TRUE | TRUE | TRUE | TRUE |
| mmu_miR_2134_241120_mat | 25.220 | 26.216 | 21.255 | 30.207 | 0.467 | NA | 0.030 | NA | TRUE | FALSE | TRUE | FALSE |
| mmu_miR_2135_241140_mat | 38.826 | 37.734 | 31.165 | 39.755 | NA | NA | 0.006 | NA | FALSE | FALSE | TRUE | FALSE |
| mmu_miR_2136_241133_mat | 39.360 | 37.795 | 37.095 | 38.837 | NA | NA | 0.277 | NA | FALSE | FALSE | TRUE | FALSE |
| mmu_miR_2138_241080_mat | 30.825 | 31.356 | 25.456 | 37.511 | 0.486 | 0.585 | 0.009 | NA | TRUE | TRUE | TRUE | FALSE |
| mmu_miR_2139_241130_mat | 38.024 | 38.095 | 38.487 | 39.682 | NA | NA | 0.539 | NA | FALSE | FALSE | TRUE | FALSE |
| mmu_miR_2146_241082_mat | 27.401 | 26.323 | 23.305 | 30.057 | 0.613 | 0.456 | 0.080 | NA | TRUE | TRUE | TRUE | FALSE |
| mmu_miR_214_002306 | 35.017 | 33.128 | 34.592 | 35.114 | 0.665 | 0.285 | 0.572 | 0.706 | TRUE | TRUE | TRUE | TRUE |
| mmu_miR_215_001200 | 34.222 | 33.059 | 27.880 | 34.179 | NA | 0.662 | 0.026 | 0.772 | FALSE | TRUE | TRUE | TRUE |
| mmu_miR_216a_002220 | 30.592 | 35.327 | 28.474 | 31.164 | 0.438 | NA | 0.092 | 0.579 | TRUE | FALSE | TRUE | TRUE |

TABLE 3-continued

| Spinal Cord miRNA data. | | | | | | | | | | | | |
|---|---|---|---|---|---|---|---|---|---|---|---|---|
| mmu_miR_216b_002326 | 25.938 | 36.270 | 26.110 | 26.554 | 0.217 | 1.000 | 0.284 | 0.429 | TRUE | TRUE | TRUE | TRUE |
| mmu_miR_217_001133 | 29.524 | 35.038 | 33.026 | 32.032 | 0.023 | NA | 0.725 | 0.513 | TRUE | FALSE | TRUE | TRUE |
| mmu_miR_217_002556 | 29.147 | 34.378 | 29.282 | 31.591 | 0.166 | NA | 0.236 | 0.715 | TRUE | FALSE | TRUE | TRUE |
| mmu_miR_2182_241119_mat | 31.894 | 32.813 | 34.424 | 37.603 | NA | NA | NA | NA | FALSE | FALSE | FALSE | FALSE |
| mmu_miR_2183_241095_mat | 28.181 | 28.424 | 24.513 | 34.224 | 0.485 | 0.524 | 0.049 | NA | TRUE | TRUE | TRUE | FALSE |
| mmu_miR_218_000521 | 15.157 | 22.592 | 18.977 | 17.487 | 0.016 | 0.971 | 0.719 | 0.411 | TRUE | TRUE | TRUE | TRUE |
| mmu_miR_218_1_002552 | 27.310 | 32.810 | 28.424 | 27.609 | 0.232 | 0.980 | 0.542 | 0.323 | TRUE | TRUE | TRUE | TRUE |
| mmu_miR_219_000522 | 28.768 | 22.724 | 26.704 | 24.160 | 0.975 | 0.087 | 0.779 | 0.211 | TRUE | TRUE | TRUE | TRUE |
| mmu_miR_21_000397 | 21.854 | 20.412 | 19.267 | 22.577 | 0.697 | 0.446 | 0.207 | 0.871 | TRUE | TRUE | TRUE | TRUE |
| mmu_miR_21_002493 | 36.703 | 36.669 | 37.067 | 38.292 | NA | NA | 0.524 | NA | FALSE | FALSE | TRUE | FALSE |
| mmu_miR_220_002468 | 40.664 | 40.854 | 40.565 | 39.599 | NA | NA | NA | NA | FALSE | FALSE | TRUE | FALSE |
| mmu_miR_221_000524 | 24.562 | 21.642 | 23.828 | 23.363 | 0.849 | 0.210 | 0.671 | 0.475 | TRUE | TRUE | TRUE | TRUE |
| mmu_miR_222_002276 | 22.440 | 21.967 | 21.100 | 21.187 | 0.798 | 0.682 | 0.413 | 0.362 | TRUE | TRUE | TRUE | TRUE |
| mmu_miR_223_002295 | 29.696 | 29.533 | 19.004 | 34.351 | 0.570 | 0.596 | 0.000 | NA | TRUE | TRUE | TRUE | FALSE |
| mmu_miR_224_002553 | 33.739 | 29.622 | 30.948 | 30.549 | 0.975 | 0.265 | 0.536 | 0.347 | TRUE | TRUE | TRUE | TRUE |
| mmu_miR_23a_000399 | 38.101 | 35.621 | 38.758 | 39.498 | NA | NA | 0.715 | NA | FALSE | FALSE | TRUE | FALSE |
| mmu_miR_23b_000400 | 23.589 | 24.287 | 24.723 | 24.319 | 0.350 | 0.658 | 0.708 | 0.564 | TRUE | TRUE | TRUE | TRUE |
| mmu_miR_24_000402 | 19.249 | 19.332 | 19.042 | 19.636 | 0.508 | 0.645 | 0.465 | 0.629 | TRUE | TRUE | TRUE | TRUE |
| mmu_miR_24_2_002494 | 28.004 | 25.903 | 26.784 | 28.749 | 0.664 | 0.260 | 0.420 | 0.873 | TRUE | TRUE | TRUE | TRUE |
| mmu_miR_25_000403 | 24.910 | 23.155 | 28.754 | 26.164 | 0.300 | 0.112 | NA | 0.632 | TRUE | TRUE | FALSE | TRUE |
| mmu_miR_26a_000405 | 19.400 | 18.349 | 19.799 | 18.864 | 0.661 | 0.453 | 0.750 | 0.406 | TRUE | TRUE | TRUE | TRUE |
| mmu_miR_26b_000407 | 21.965 | 19.982 | 20.984 | 21.864 | 0.740 | 0.314 | 0.490 | 0.689 | TRUE | TRUE | TRUE | TRUE |
| mmu_miR_27a_000408 | 22.205 | 21.250 | 21.075 | 25.023 | 0.486 | 0.357 | 0.296 | 0.984 | TRUE | TRUE | TRUE | TRUE |
| mmu_miR_27b_000409 | 22.543 | 21.142 | 21.638 | 21.953 | 0.768 | 0.469 | 0.505 | 0.516 | TRUE | TRUE | TRUE | TRUE |
| mmu_miR_28_000411 | 23.530 | 23.280 | 19.520 | 26.346 | 0.565 | 0.557 | 0.063 | 0.988 | TRUE | TRUE | TRUE | TRUE |
| mmu_miR_28_002545 | 33.734 | 29.672 | 29.004 | 30.874 | NA | 0.360 | 0.210 | 0.512 | FALSE | TRUE | TRUE | TRUE |
| mmu_miR_290_000187 | 34.568 | 38.332 | 32.703 | 37.070 | 0.329 | NA | 0.093 | 0.799 | TRUE | FALSE | TRUE | TRUE |
| mmu_miR_290_3p_002591 | 40.715 | 40.888 | 40.610 | 39.599 | NA | NA | NA | NA | FALSE | FALSE | TRUE | FALSE |
| mmu_miR_290_5p_002590 | 38.539 | 38.292 | 38.763 | 39.370 | NA | NA | 0.551 | 0.723 | FALSE | FALSE | TRUE | TRUE |
| mmu_miR_291_3p_001135 | 39.716 | 40.918 | 40.536 | 39.670 | NA | NA | NA | NA | FALSE | FALSE | TRUE | FALSE |
| mmu_miR_291_5p_001202 | 40.679 | 40.889 | 40.559 | 38.886 | NA | NA | NA | NA | FALSE | FALSE | TRUE | FALSE |
| mmu_miR_291a_3p_002592 | 40.725 | 40.893 | 40.617 | 39.598 | NA | NA | NA | NA | FALSE | FALSE | TRUE | FALSE |
| mmu_miR_291b_3p_002538 | 40.228 | 40.364 | 40.319 | 39.593 | NA | NA | NA | NA | FALSE | FALSE | TRUE | FALSE |
| mmu_miR_291b_5p_002537 | 40.827 | 40.974 | 40.102 | 39.630 | NA | NA | NA | NA | FALSE | FALSE | TRUE | FALSE |
| mmu_miR_292_3p_001054 | 36.543 | 40.991 | 40.487 | 39.557 | NA | NA | NA | NA | FALSE | FALSE | TRUE | FALSE |
| mmu_miR_292_3p_002593 | 37.337 | 37.261 | 31.933 | 38.244 | NA | NA | 0.026 | NA | FALSE | FALSE | TRUE | FALSE |
| mmu_miR_292_5p_001055 | 32.090 | 39.133 | 38.466 | 35.412 | NA | NA | NA | NA | FALSE | FALSE | FALSE | FALSE |
| mmu_miR_293_001794 | 30.545 | 33.985 | 36.927 | 37.689 | NA | NA | NA | NA | FALSE | FALSE | FALSE | FALSE |
| mmu_miR_293_002594 | 39.185 | 39.336 | 39.466 | 39.619 | NA | NA | 0.566 | NA | FALSE | FALSE | TRUE | FALSE |
| mmu_miR_294_001056 | 35.345 | 33.862 | 38.747 | 39.926 | NA | 0.074 | 0.844 | NA | FALSE | TRUE | TRUE | FALSE |
| mmu_miR_294_002595 | 40.800 | 40.976 | 40.660 | 39.599 | NA | NA | NA | NA | FALSE | FALSE | TRUE | FALSE |
| mmu_miR_295_000189 | 38.865 | 38.753 | 37.345 | 39.773 | NA | NA | 0.258 | NA | FALSE | FALSE | TRUE | FALSE |
| mmu_miR_295_002596 | 41.230 | 40.887 | 40.649 | 39.990 | NA | NA | NA | NA | FALSE | FALSE | TRUE | FALSE |
| mmu_miR_296_3p_002101 | 34.506 | 35.537 | 36.603 | 36.656 | NA | NA | 0.770 | 0.765 | FALSE | FALSE | TRUE | TRUE |
| mmu_miR_296_5p_000527 | 23.767 | 22.719 | 27.116 | 25.004 | 0.274 | 0.201 | 0.989 | 0.619 | TRUE | TRUE | TRUE | TRUE |
| mmu_miR_297a_002454 | 32.589 | 27.503 | 31.143 | 32.654 | 0.820 | 0.021 | NA | 0.832 | TRUE | TRUE | FALSE | TRUE |
| mmu_miR_297b_5p_001626 | 37.991 | 37.973 | 38.582 | 39.563 | NA | NA | 0.584 | NA | FALSE | FALSE | TRUE | FALSE |
| mmu_miR_297c_002480 | 34.923 | 34.760 | 35.370 | 34.027 | NA | NA | 0.738 | 0.267 | FALSE | FALSE | TRUE | TRUE |
| mmu_miR_298_002598 | 30.511 | 34.138 | 29.386 | 28.972 | 0.639 | 0.962 | 0.331 | 0.174 | TRUE | TRUE | TRUE | TRUE |
| mmu_miR_299_002612 | 40.800 | 40.976 | 40.660 | 39.599 | NA | NA | NA | NA | FALSE | FALSE | TRUE | FALSE |
| mmu_miR_29a_002112 | 18.880 | 20.272 | 20.631 | 18.663 | 0.396 | 0.736 | 0.839 | 0.265 | TRUE | TRUE | TRUE | TRUE |

TABLE 3-continued

Spinal Cord miRNA data.

| | | | | | | | | | | | | |
|---|---|---|---|---|---|---|---|---|---|---|---|---|
| mmu_miR_29b_000413 | 22.096 | 23.254 | 19.985 | 23.180 | 0.508 | 0.814 | 0.161 | 0.749 | TRUE | TRUE | TRUE | TRUE |
| mmu_miR_29b_002497 | 25.948 | 25.957 | 22.206 | 29.062 | NA | NA | 0.067 | NA | FALSE | FALSE | TRUE | FALSE |
| mmu_miR_29c_000587 | 20.948 | 22.083 | 22.585 | 21.339 | 0.325 | 0.695 | 0.803 | 0.439 | TRUE | TRUE | TRUE | TRUE |
| mmu_miR_300_000191 | 26.672 | 30.547 | 23.857 | 27.574 | 0.465 | 0.961 | 0.062 | 0.651 | TRUE | TRUE | TRUE | TRUE |
| mmu_miR_300_002613 | 30.068 | 35.836 | 33.223 | 31.684 | 0.040 | NA | 0.741 | 0.400 | TRUE | FALSE | TRUE | TRUE |
| mmu_miR_301a_000528 | 24.988 | 24.431 | 24.259 | 24.762 | 0.667 | 0.598 | 0.447 | 0.543 | TRUE | TRUE | TRUE | TRUE |
| mmu_miR_301b_002600 | 23.806 | 23.233 | 24.592 | 23.643 | 0.566 | 0.492 | 0.784 | 0.440 | TRUE | TRUE | TRUE | TRUE |
| mmu_miR_302a_000529 | 26.452 | 28.091 | 29.988 | 31.762 | 0.069 | 0.361 | 0.753 | 0.967 | TRUE | TRUE | TRUE | TRUE |
| mmu_miR_302a_002615 | 36.954 | 35.943 | 37.319 | 37.084 | NA | NA | 0.697 | NA | FALSE | FALSE | TRUE | FALSE |
| mmu_miR_302b_000531 | 36.591 | 34.482 | 36.252 | 34.708 | NA | NA | 0.752 | 0.228 | FALSE | FALSE | TRUE | TRUE |
| mmu_miR_302b_001307 | 39.525 | 39.366 | 39.773 | 39.983 | NA | NA | 0.576 | NA | FALSE | FALSE | TRUE | FALSE |
| mmu_miR_302c_002557 | 37.155 | 40.917 | 40.494 | 40.085 | 0.050 | NA | NA | NA | TRUE | FALSE | TRUE | FALSE |
| mmu_miR_302c_002558 | 36.032 | 37.229 | 38.700 | 37.763 | NA | NA | 0.887 | NA | FALSE | FALSE | TRUE | FALSE |
| mmu_miR_302d_000535 | 34.905 | 36.994 | 34.892 | 37.028 | NA | NA | 0.327 | 0.794 | FALSE | FALSE | TRUE | TRUE |
| mmu_miR_30a_000417 | 21.643 | 20.660 | 21.029 | 21.372 | 0.683 | 0.513 | 0.505 | 0.555 | TRUE | TRUE | TRUE | TRUE |
| mmu_miR_30b_000602 | 17.560 | 17.349 | 17.415 | 17.264 | 0.619 | 0.638 | 0.553 | 0.455 | TRUE | TRUE | TRUE | TRUE |
| mmu_miR_30b_002498 | 36.136 | 34.542 | 36.464 | 37.099 | NA | NA | 0.644 | NA | FALSE | FALSE | TRUE | FALSE |
| mmu_miR_30c_000419 | 17.295 | 17.157 | 16.745 | 16.935 | 0.644 | 0.669 | 0.472 | 0.472 | TRUE | TRUE | TRUE | TRUE |
| mmu_miR_30d_000420 | 24.417 | 22.754 | 23.617 | 24.391 | 0.698 | 0.361 | 0.500 | 0.685 | TRUE | TRUE | TRUE | TRUE |
| mmu_miR_30e_002223 | 21.865 | 20.533 | 21.461 | 21.738 | 0.669 | 0.408 | 0.566 | 0.606 | TRUE | TRUE | TRUE | TRUE |
| mmu_miR_31_000185 | 25.113 | 24.578 | 25.846 | 26.116 | NA | 0.405 | NA | NA | FALSE | TRUE | FALSE | FALSE |
| mmu_miR_31_002495 | 26.718 | 27.680 | 28.770 | 27.077 | 0.308 | 0.645 | 0.891 | 0.398 | TRUE | TRUE | TRUE | TRUE |
| mmu_miR_320_002277 | 21.617 | 19.602 | 22.107 | 21.161 | 0.687 | 0.243 | 0.811 | 0.493 | TRUE | TRUE | TRUE | TRUE |
| mmu_miR_322_001059 | 32.711 | 27.863 | 28.295 | 29.519 | NA | 0.251 | 0.311 | 0.512 | FALSE | TRUE | TRUE | TRUE |
| mmu_miR_322_001076 | 34.886 | 26.816 | 29.866 | 27.636 | NA | 0.136 | 0.672 | 0.174 | FALSE | TRUE | TRUE | TRUE |
| mmu_miR_322_002506 | 35.754 | 28.144 | 29.024 | 29.855 | NA | 0.188 | 0.334 | 0.470 | FALSE | TRUE | TRUE | TRUE |
| mmu_miR_323_3p_002227 | 25.679 | 34.949 | 28.564 | 24.974 | 0.208 | 0.999 | 0.703 | 0.047 | TRUE | TRUE | TRUE | TRUE |
| mmu_miR_324_3p_002509 | 28.000 | 25.700 | 28.198 | 25.696 | 0.823 | 0.351 | 0.857 | 0.152 | TRUE | TRUE | TRUE | TRUE |
| mmu_miR_324_5p_000539 | 26.356 | 24.861 | 25.898 | 25.099 | 0.789 | 0.473 | 0.655 | 0.331 | TRUE | TRUE | TRUE | TRUE |
| mmu_miR_325_001060 | 34.452 | 30.685 | 25.031 | 30.002 | NA | 0.653 | 0.020 | 0.436 | FALSE | TRUE | TRUE | TRUE |
| mmu_miR_325_002510 | 25.983 | 27.615 | 27.307 | 25.724 | 0.423 | 0.783 | 0.754 | 0.274 | TRUE | TRUE | TRUE | TRUE |
| mmu_miR_326_001061 | 36.939 | 28.374 | 35.872 | 35.442 | NA | 0.000 | 0.714 | 0.570 | FALSE | TRUE | TRUE | TRUE |
| mmu_miR_327_002481 | 39.083 | 40.737 | 40.499 | 39.740 | NA | NA | NA | NA | FALSE | FALSE | FALSE | FALSE |
| mmu_miR_328_000543 | 19.844 | 20.826 | 20.752 | 20.004 | 0.422 | 0.730 | 0.681 | 0.440 | TRUE | TRUE | TRUE | TRUE |
| mmu_miR_329_000192 | 25.077 | 30.111 | 27.321 | 25.846 | 0.131 | 0.935 | 0.704 | 0.344 | TRUE | TRUE | TRUE | TRUE |
| mmu_miR_32_002109 | 31.024 | 27.794 | 23.494 | 32.717 | 0.763 | 0.356 | 0.019 | 0.989 | TRUE | TRUE | TRUE | TRUE |
| mmu_miR_330_001062 | 32.387 | 34.544 | 31.881 | 34.615 | NA | NA | 0.262 | 0.817 | FALSE | FALSE | TRUE | TRUE |
| mmu_miR_330_002230 | 33.769 | 35.687 | 33.609 | 32.897 | 0.585 | NA | 0.502 | 0.254 | TRUE | FALSE | TRUE | TRUE |
| mmu_miR_331_3p_000545 | 21.121 | 21.839 | 23.389 | 22.266 | 0.227 | 0.556 | 0.888 | 0.567 | TRUE | TRUE | TRUE | TRUE |
| mmu_miR_331_5p_002233 | 26.447 | 30.018 | 24.235 | 28.002 | 0.401 | 0.942 | 0.085 | 0.730 | TRUE | TRUE | TRUE | TRUE |
| mmu_miR_335_3p_002185 | 24.204 | 32.080 | 29.145 | 24.623 | 0.065 | NA | NA | 0.157 | TRUE | FALSE | FALSE | TRUE |
| mmu_miR_335_5p_000546 | 20.019 | 24.151 | 22.165 | 21.066 | 0.146 | 0.896 | 0.699 | 0.422 | TRUE | TRUE | TRUE | TRUE |
| mmu_miR_337_000193 | 24.808 | 27.742 | 26.572 | 25.866 | 0.200 | 0.840 | 0.679 | 0.494 | TRUE | TRUE | TRUE | TRUE |
| mmu_miR_337_3p_002532 | 24.335 | 29.317 | 26.350 | 25.540 | 0.115 | 0.933 | 0.642 | 0.444 | TRUE | TRUE | TRUE | TRUE |
| mmu_miR_337_5p_002515 | 22.502 | 24.118 | 22.776 | 24.779 | 0.274 | 0.729 | 0.389 | 0.833 | TRUE | TRUE | TRUE | TRUE |
| mmu_miR_338_3p_002252 | 27.975 | 23.944 | 25.100 | 25.953 | 0.968 | 0.201 | 0.422 | 0.539 | TRUE | TRUE | TRUE | TRUE |
| mmu_miR_339_3p_002533 | 28.323 | 27.527 | 26.418 | 30.378 | 0.542 | 0.439 | 0.226 | 0.966 | TRUE | TRUE | TRUE | TRUE |
| mmu_miR_339_5p_002257 | 30.435 | 26.331 | 29.808 | 28.775 | 0.891 | 0.081 | 0.752 | 0.440 | TRUE | TRUE | TRUE | TRUE |
| mmu_miR_340_3p_002259 | 23.365 | 23.616 | 23.577 | 23.956 | 0.448 | 0.644 | 0.520 | 0.637 | TRUE | TRUE | TRUE | TRUE |
| mmu_miR_340_5p_002258 | 22.205 | 21.848 | 22.815 | 22.211 | 0.536 | 0.534 | 0.727 | 0.491 | TRUE | TRUE | TRUE | TRUE |
| mmu_miR_342_3p_002260 | 21.321 | 23.880 | 21.751 | 20.813 | 0.490 | 0.873 | 0.571 | 0.264 | TRUE | TRUE | TRUE | TRUE |

TABLE 3-continued

| Spinal Cord miRNA data. | | | | | | | | | | | | |
|---|---|---|---|---|---|---|---|---|---|---|---|---|
| mmu_miR_342_5p_002527 | 30.184 | 36.101 | 30.724 | 31.060 | 0.207 | NA | NA | 0.478 | TRUE | FALSE | FALSE | TRUE |
| mmu_miR_343_002483 | 40.797 | 40.943 | 39.789 | 39.404 | NA | NA | 0.457 | NA | FALSE | FALSE | TRUE | FALSE |
| mmu_miR_344_001063 | 28.289 | 26.961 | 29.952 | 26.321 | 0.680 | 0.410 | 0.969 | 0.108 | TRUE | TRUE | TRUE | TRUE |
| mmu_miR_345_001137 | 26.501 | 25.026 | 26.910 | 26.797 | 0.567 | 0.297 | 0.717 | 0.667 | TRUE | TRUE | TRUE | TRUE |
| mmu_miR_345_3p_002529 | 30.626 | 30.462 | 32.136 | 32.339 | 0.300 | 0.381 | 0.752 | 0.804 | TRUE | TRUE | TRUE | TRUE |
| mmu_miR_345_5p_002528 | 29.401 | 26.673 | 30.028 | 28.619 | 0.744 | 0.158 | 0.874 | 0.440 | TRUE | TRUE | TRUE | TRUE |
| mmu_miR_346_001064 | 35.482 | 36.613 | 36.919 | 37.432 | NA | NA | 0.633 | 0.772 | FALSE | FALSE | TRUE | TRUE |
| mmu_miR_34a_000426 | 18.255 | 23.341 | 19.478 | 18.546 | 0.240 | 0.962 | 0.573 | 0.333 | TRUE | TRUE | TRUE | TRUE |
| mmu_miR_34b_001065 | 30.158 | 32.933 | 33.550 | 32.506 | 0.078 | 0.716 | 0.860 | 0.586 | TRUE | TRUE | TRUE | TRUE |
| mmu_miR_34b_3p_002618 | 21.772 | 23.190 | 23.803 | 23.280 | 0.200 | 0.668 | 0.783 | 0.610 | TRUE | TRUE | TRUE | TRUE |
| mmu_miR_34b_5p_002617 | 29.445 | 30.853 | 29.802 | 31.524 | 0.284 | 0.706 | 0.422 | 0.819 | TRUE | TRUE | TRUE | TRUE |
| mmu_miR_34c_000428 | 24.217 | 26.464 | 28.795 | 25.613 | 0.108 | 0.618 | NA | 0.401 | TRUE | TRUE | FALSE | TRUE |
| mmu_miR_34c_002584 | 24.789 | 26.008 | 24.762 | 25.940 | 0.372 | 0.762 | 0.395 | 0.698 | TRUE | TRUE | TRUE | TRUE |
| mmu_miR_350_002530 | 27.855 | 24.200 | 25.686 | 26.607 | 0.928 | 0.173 | 0.464 | 0.609 | TRUE | TRUE | TRUE | TRUE |
| mmu_miR_351_001067 | 36.981 | 37.207 | 37.323 | 34.907 | NA | NA | 0.735 | 0.094 | FALSE | FALSE | TRUE | TRUE |
| mmu_miR_361_000554 | 22.743 | 23.747 | 26.542 | 23.436 | 0.209 | 0.547 | 0.989 | 0.367 | TRUE | TRUE | TRUE | TRUE |
| mmu_miR_362_3p_002616 | 26.200 | 26.560 | 25.174 | 27.972 | 0.439 | 0.624 | 0.266 | 0.886 | TRUE | TRUE | TRUE | TRUE |
| mmu_miR_362_5p_002614 | 27.713 | 26.227 | 29.748 | 27.733 | 0.493 | 0.239 | 0.965 | 0.467 | TRUE | TRUE | TRUE | TRUE |
| mmu_miR_363_001271 | 35.112 | 31.763 | 35.278 | 32.752 | NA | 0.188 | NA | 0.216 | FALSE | TRUE | FALSE | TRUE |
| mmu_miR_365_001020 | 26.691 | 21.520 | 27.434 | 25.577 | 0.809 | 0.013 | 0.928 | 0.460 | TRUE | TRUE | TRUE | TRUE |
| mmu_miR_367_000555 | 24.098 | 21.615 | 22.812 | 22.630 | 0.884 | 0.337 | 0.572 | 0.430 | TRUE | TRUE | TRUE | TRUE |
| mmu_miR_369_3p_000557 | 25.252 | 30.681 | 26.357 | 25.051 | 0.309 | 0.979 | 0.575 | 0.211 | TRUE | TRUE | TRUE | TRUE |
| mmu_miR_369_5p_001021 | 27.346 | 33.699 | 27.481 | 29.284 | 0.158 | 0.986 | 0.229 | 0.638 | TRUE | TRUE | TRUE | TRUE |
| mmu_miR_370_001068 | 36.845 | 36.916 | 37.275 | 38.519 | NA | NA | 0.529 | 0.846 | FALSE | FALSE | TRUE | TRUE |
| mmu_miR_370_002275 | 27.812 | 37.320 | 30.071 | 25.383 | 0.322 | 1.000 | NA | 0.005 | TRUE | TRUE | FALSE | TRUE |
| mmu_miR_374_002043 | 35.888 | 35.949 | 31.764 | 38.675 | NA | NA | 0.049 | 0.985 | FALSE | FALSE | TRUE | TRUE |
| mmu_miR_374_5p_001319 | 28.990 | 24.221 | 24.822 | 25.278 | 0.990 | 0.286 | 0.375 | 0.417 | TRUE | TRUE | TRUE | TRUE |
| mmu_miR_375_000564 | 27.239 | 30.166 | 30.012 | 27.378 | 0.228 | NA | NA | 0.249 | TRUE | FALSE | FALSE | TRUE |
| mmu_miR_376a_001069 | 20.511 | 26.028 | 22.102 | 20.927 | 0.179 | 0.972 | 0.609 | 0.322 | TRUE | TRUE | TRUE | TRUE |
| mmu_miR_376a_002482 | 26.417 | 32.304 | 28.456 | 26.618 | 0.170 | 0.976 | 0.682 | 0.222 | TRUE | TRUE | TRUE | TRUE |
| mmu_miR_376b_002451 | 22.440 | 26.856 | 27.602 | 22.368 | 0.172 | 0.824 | NA | 0.136 | TRUE | TRUE | FALSE | TRUE |
| mmu_miR_376b_002452 | 24.914 | 33.500 | 27.221 | 25.424 | 0.103 | 0.998 | 0.632 | 0.238 | TRUE | TRUE | TRUE | TRUE |
| mmu_miR_376c_002450 | 21.249 | 24.932 | 23.650 | 22.212 | 0.145 | 0.866 | 0.757 | 0.407 | TRUE | TRUE | TRUE | TRUE |
| mmu_miR_376c_002523 | 38.621 | 40.718 | 38.370 | 38.732 | 0.459 | NA | 0.393 | 0.491 | TRUE | FALSE | TRUE | TRUE |
| mmu_miR_377_000566 | 32.710 | 34.245 | 34.053 | 33.271 | 0.315 | NA | 0.703 | 0.477 | TRUE | FALSE | TRUE | TRUE |
| mmu_miR_379_001138 | 21.972 | 26.362 | 26.134 | 22.919 | 0.090 | 0.854 | 0.899 | 0.278 | TRUE | TRUE | TRUE | TRUE |
| mmu_miR_380_3p_001071 | 30.254 | 35.033 | 33.354 | 31.918 | 0.064 | NA | 0.760 | 0.435 | TRUE | FALSE | TRUE | TRUE |
| mmu_miR_380_5p_002601 | 23.589 | 30.331 | 25.748 | 25.525 | 0.051 | 0.978 | 0.552 | 0.512 | TRUE | TRUE | TRUE | TRUE |
| mmu_miR_381_000571 | 28.445 | 33.389 | 26.658 | 28.385 | 0.491 | 0.983 | 0.128 | 0.459 | TRUE | TRUE | TRUE | TRUE |
| mmu_miR_382_000572 | 20.937 | 29.384 | 24.871 | 19.561 | 0.237 | 0.991 | 0.768 | 0.019 | TRUE | TRUE | TRUE | TRUE |
| mmu_miR_383_001767 | 22.534 | 29.975 | 25.067 | 23.078 | 0.094 | NA | 0.684 | 0.231 | TRUE | FALSE | TRUE | TRUE |
| mmu_miR_384_3p_002603 | 23.280 | 25.392 | 24.325 | 23.128 | 0.417 | 0.826 | 0.674 | 0.316 | TRUE | TRUE | TRUE | TRUE |
| mmu_miR_384_5p_002602 | 18.262 | 21.020 | 19.033 | 18.127 | 0.411 | 0.871 | 0.603 | 0.325 | TRUE | TRUE | TRUE | TRUE |
| mmu_miR_409_3p_002332 | 21.286 | 26.031 | 24.446 | 22.315 | 0.093 | 0.902 | 0.808 | 0.323 | TRUE | TRUE | TRUE | TRUE |
| mmu_miR_409_5p_002331 | 26.908 | 35.390 | 30.555 | 28.663 | 0.022 | NA | 0.703 | 0.329 | TRUE | FALSE | TRUE | TRUE |
| mmu_miR_410_001274 | 19.898 | 25.075 | 22.390 | 19.982 | 0.173 | 0.948 | 0.761 | 0.194 | TRUE | TRUE | TRUE | TRUE |
| mmu_miR_411_001610 | 20.429 | 24.068 | 22.266 | 20.705 | 0.250 | 0.893 | 0.717 | 0.298 | TRUE | TRUE | TRUE | TRUE |
| mmu_miR_412_002575 | 25.523 | 34.189 | 25.255 | 25.460 | 0.332 | 0.999 | 0.273 | 0.333 | TRUE | TRUE | TRUE | TRUE |
| mmu_miR_423_5p_002340 | 30.360 | 27.126 | 28.185 | 29.617 | 0.900 | 0.212 | 0.410 | 0.669 | TRUE | TRUE | TRUE | TRUE |
| mmu_miR_425_001516 | 21.123 | 22.834 | 16.568 | 25.320 | 0.453 | 0.737 | 0.016 | 0.986 | TRUE | TRUE | TRUE | TRUE |
| mmu_miR_429_001077 | 33.809 | 36.377 | 34.473 | 36.700 | 0.205 | NA | 0.404 | 0.830 | TRUE | FALSE | TRUE | TRUE |

TABLE 3-continued

| Spinal Cord miRNA data. | | | | | | | | | | | | |
|---|---|---|---|---|---|---|---|---|---|---|---|---|
| mmu_miR_431_001979 | 32.503 | 34.726 | 30.760 | 27.887 | 0.760 | 0.951 | 0.473 | 0.006 | TRUE | TRUE | TRUE | TRUE |
| mmu_miR_432_241135_mat | 38.490 | 37.084 | 35.029 | 36.021 | NA | NA | 0.225 | 0.353 | FALSE | FALSE | TRUE | TRUE |
| mmu_miR_433_001028 | 20.259 | 25.289 | 21.589 | 20.396 | 0.256 | 0.957 | 0.604 | 0.289 | TRUE | TRUE | TRUE | TRUE |
| mmu_miR_433_5p_001078 | 30.228 | 32.245 | 26.982 | 30.885 | 0.553 | 0.911 | 0.070 | 0.686 | TRUE | TRUE | TRUE | TRUE |
| mmu_miR_434_3p_002604 | 18.243 | 23.286 | 19.240 | 18.182 | 0.308 | 0.969 | 0.559 | 0.264 | TRUE | TRUE | TRUE | TRUE |
| mmu_miR_434_5p_002581 | 24.430 | 31.736 | 26.828 | 24.087 | 0.203 | 0.991 | 0.703 | 0.096 | TRUE | TRUE | TRUE | TRUE |
| mmu_miR_448_001029 | 28.223 | 36.293 | 30.417 | 27.635 | 0.245 | NA | 0.669 | 0.070 | TRUE | FALSE | TRUE | TRUE |
| mmu_miR_449a_001030 | 27.142 | 30.045 | 25.134 | 28.069 | 0.461 | 0.924 | 0.121 | 0.668 | TRUE | TRUE | TRUE | TRUE |
| mmu_miR_449b_001667 | 29.405 | 33.682 | 28.480 | 31.605 | 0.268 | 0.948 | 0.155 | 0.744 | TRUE | TRUE | TRUE | TRUE |
| mmu_miR_449b_002539 | 40.727 | 40.899 | 40.619 | 39.597 | NA | NA | NA | NA | FALSE | FALSE | TRUE | FALSE |
| mmu_miR_450B_3P_00263_2 | 35.959 | 33.054 | 30.636 | 33.766 | NA | 0.522 | 0.113 | 0.523 | FALSE | TRUE | TRUE | TRUE |
| mmu_miR_450a_3p_00252_5 | 40.800 | 40.976 | 40.660 | 39.599 | NA | NA | NA | NA | FALSE | FALSE | TRUE | FALSE |
| mmu_miR_450a_5p_00230_3 | 35.187 | 32.418 | 33.647 | 32.204 | NA | 0.415 | 0.655 | 0.188 | FALSE | TRUE | TRUE | TRUE |
| mmu_miR_450b_5p_00196_2 | 40.525 | 40.670 | 40.489 | 39.589 | NA | NA | NA | NA | FALSE | FALSE | TRUE | FALSE |
| mmu_miR_451_001141 | 37.033 | 32.191 | 30.809 | 37.857 | NA | 0.191 | 0.087 | 0.966 | FALSE | TRUE | TRUE | TRUE |
| mmu_miR_452_001032 | 36.411 | 37.134 | 37.605 | 40.297 | NA | NA | 0.550 | NA | FALSE | FALSE | TRUE | FALSE |
| mmu_miR_453_002484 | 39.483 | 39.595 | 39.828 | 39.597 | NA | NA | 0.613 | NA | FALSE | FALSE | TRUE | FALSE |
| mmu_miR_455_002455 | 34.584 | 27.062 | 30.417 | 30.333 | NA | 0.035 | 0.550 | 0.486 | FALSE | TRUE | TRUE | TRUE |
| mmu_miR_463_002582 | 26.304 | 26.350 | 22.867 | 31.467 | 0.498 | 0.505 | 0.069 | NA | TRUE | TRUE | TRUE | FALSE |
| mmu_miR_463_002662 | 38.057 | 34.632 | 30.192 | 36.726 | NA | NA | 0.026 | NA | FALSE | FALSE | TRUE | FALSE |
| mmu_miR_464_001081 | 40.237 | 40.439 | 40.280 | 38.634 | NA | NA | NA | NA | FALSE | FALSE | TRUE | FALSE |
| mmu_miR_465C_5P_002654 | 30.464 | 32.392 | 25.806 | 35.592 | 0.439 | 0.716 | 0.012 | NA | TRUE | TRUE | TRUE | FALSE |
| mmu_miR_465a_3p_002040 | 34.515 | 36.175 | 34.166 | 34.299 | NA | NA | 0.424 | 0.430 | FALSE | FALSE | TRUE | TRUE |
| mmu_miR_465a_5p_001082 | 34.974 | 26.714 | 32.320 | 31.671 | NA | 0.004 | NA | 0.481 | FALSE | TRUE | FALSE | TRUE |
| mmu_miR_465b_5p_002485 | 30.420 | 35.363 | 34.766 | 32.266 | 0.039 | NA | 0.869 | 0.383 | TRUE | FALSE | TRUE | TRUE |
| mmu_miR_466E_5P_002718 | 30.162 | 27.858 | 24.607 | 31.113 | 0.774 | 0.408 | 0.058 | 0.946 | TRUE | TRUE | TRUE | TRUE |
| mmu_miR_466J_002817 | 35.226 | 28.322 | 32.504 | 31.986 | NA | 0.021 | 0.642 | 0.471 | FALSE | TRUE | TRUE | TRUE |
| mmu_miR_466a_3p_002586 | 30.538 | 26.507 | 30.484 | 29.971 | 0.800 | 0.049 | 0.759 | 0.594 | TRUE | TRUE | TRUE | TRUE |
| mmu_miR_466b_3_3p_002500 | 31.942 | 27.874 | 30.752 | 31.264 | 0.876 | 0.072 | 0.582 | 0.660 | TRUE | TRUE | TRUE | TRUE |
| mmu_miR_466d_5p_002534 | 35.029 | 38.645 | 32.541 | 39.543 | NA | NA | NA | NA | FALSE | FALSE | FALSE | FALSE |
| mmu_miR_466g_241015_mat | 34.038 | 31.760 | 37.315 | 38.056 | NA | 0.042 | 0.866 | 0.953 | FALSE | TRUE | TRUE | TRUE |
| mmu_miR_466h_002516 | 36.735 | 35.344 | 36.958 | 38.103 | NA | 0.256 | 0.590 | 0.882 | FALSE | TRUE | TRUE | TRUE |
| mmu_miR_466k_240990_mat | 35.911 | 31.450 | 34.810 | 37.035 | NA | NA | NA | NA | FALSE | FALSE | FALSE | FALSE |
| mmu_miR_467F_002886 | 33.166 | 27.244 | 25.592 | 32.470 | NA | 0.185 | 0.074 | NA | FALSE | TRUE | TRUE | FALSE |
| mmu_miR_467H_002809 | 33.764 | 29.697 | 34.739 | 33.705 | NA | 0.028 | 0.889 | 0.636 | FALSE | TRUE | TRUE | TRUE |
| mmu_miR_467a_001826 | 30.022 | 24.813 | 25.330 | 29.406 | 0.955 | 0.121 | 0.235 | 0.805 | TRUE | TRUE | TRUE | TRUE |
| mmu_miR_467a_002587 | 27.603 | 23.878 | 28.942 | 26.271 | 0.763 | 0.070 | 0.967 | 0.344 | TRUE | TRUE | TRUE | TRUE |
| mmu_miR_467b_001671 | 32.002 | 26.872 | 30.360 | 29.231 | 0.954 | 0.070 | 0.714 | 0.384 | TRUE | TRUE | TRUE | TRUE |
| mmu_miR_467b_001684 | 31.650 | 27.444 | 23.596 | 34.258 | NA | 0.262 | 0.020 | NA | FALSE | TRUE | TRUE | FALSE |
| mmu_miR_467c_002517 | 34.187 | 27.763 | 32.178 | 32.692 | 0.953 | 0.010 | 0.582 | 0.636 | TRUE | TRUE | TRUE | TRUE |
| mmu_miR_467d_002518 | 32.355 | 29.522 | 31.398 | 32.574 | 0.724 | 0.161 | 0.522 | 0.802 | TRUE | TRUE | TRUE | TRUE |
| mmu_miR_467e_002568 | 29.762 | 26.215 | 26.113 | 29.740 | 0.870 | 0.228 | 0.220 | 0.851 | TRUE | TRUE | TRUE | TRUE |
| mmu_miR_467e_002569 | 39.174 | 37.658 | 39.443 | 36.066 | NA | 0.484 | 0.855 | 0.067 | FALSE | TRUE | TRUE | TRUE |
| mmu_miR_468_001085 | 40.269 | 40.531 | 40.150 | 36.928 | NA | NA | NA | NA | FALSE | FALSE | TRUE | FALSE |
| mmu_miR_469_001086 | 39.224 | 39.642 | 39.042 | 36.826 | NA | NA | 0.651 | NA | FALSE | FALSE | TRUE | FALSE |
| mmu_miR_470_002588 | 38.923 | 38.435 | 39.442 | 39.595 | NA | NA | 0.659 | NA | FALSE | FALSE | TRUE | FALSE |
| mmu_miR_470_002589 | 34.203 | 31.339 | 26.021 | 40.506 | 0.673 | 0.356 | 0.006 | NA | TRUE | TRUE | TRUE | TRUE |
| mmu_miR_471_002605 | 40.344 | 40.523 | 40.377 | 39.598 | NA | NA | NA | NA | FALSE | FALSE | TRUE | FALSE |
| mmu_miR_483_001291 | 37.285 | 35.015 | 34.326 | 38.790 | NA | NA | 0.195 | 0.966 | FALSE | FALSE | TRUE | TRUE |
| mmu_miR_483_002560 | 36.869 | 36.615 | 37.237 | 39.476 | NA | NA | 0.509 | NA | FALSE | FALSE | TRUE | FALSE |
| mmu_miR_484_001821 | 22.322 | 20.136 | 21.311 | 21.207 | 0.843 | 0.348 | 0.576 | 0.465 | TRUE | TRUE | TRUE | TRUE |

TABLE 3-continued

Spinal Cord miRNA data.

| | | | | | | | | | | | | |
|---|---|---|---|---|---|---|---|---|---|---|---|---|
| mmu_miR_485_3p_001943 | 21.149 | 25.388 | 22.849 | 22.303 | 0.154 | 0.910 | 0.617 | 0.478 | TRUE | TRUE | TRUE | TRUE |
| mmu_miR_486_001278 | 31.827 | 25.420 | 30.227 | 24.428 | 0.970 | 0.192 | 0.839 | 0.048 | TRUE | TRUE | TRUE | TRUE |
| mmu_miR_487b_001285 | 21.627 | 26.731 | 22.936 | 22.429 | 0.183 | 0.958 | 0.551 | 0.423 | TRUE | TRUE | TRUE | TRUE |
| mmu_miR_487b_001306 | 23.180 | 30.278 | 26.332 | 23.456 | 0.108 | 0.984 | 0.752 | 0.165 | TRUE | TRUE | TRUE | TRUE |
| mmu_miR_488_001659 | 28.771 | 28.129 | 29.898 | 29.135 | 0.470 | 0.411 | 0.812 | 0.568 | TRUE | TRUE | TRUE | TRUE |
| mmu_miR_488_002014 | 32.195 | 34.737 | 36.969 | 36.800 | 0.052 | NA | 0.890 | 0.829 | TRUE | FALSE | TRUE | TRUE |
| mmu_miR_489_001302 | 27.089 | 33.366 | 27.996 | 25.652 | 0.415 | NA | 0.588 | 0.047 | TRUE | FALSE | TRUE | TRUE |
| mmu_miR_490_001037 | 31.465 | 36.157 | 30.035 | 29.794 | 0.637 | NA | NA | 0.157 | TRUE | FALSE | FALSE | TRUE |
| mmu_miR_491_001630 | 24.874 | 29.530 | 28.835 | 25.402 | 0.115 | 0.879 | 0.881 | 0.233 | TRUE | TRUE | TRUE | TRUE |
| mmu_miR_493_002519 | 34.511 | 36.255 | 33.004 | 33.016 | NA | NA | NA | NA | FALSE | FALSE | FALSE | FALSE |
| mmu_miR_494_001293 | 34.753 | 36.588 | 36.252 | 33.580 | NA | NA | 0.805 | 0.103 | FALSE | FALSE | TRUE | TRUE |
| mmu_miR_494_002365 | 31.658 | 31.997 | 30.406 | 29.946 | 0.778 | 0.790 | 0.434 | 0.242 | TRUE | TRUE | TRUE | TRUE |
| mmu_miR_495_001663 | 18.622 | 23.718 | 20.524 | 18.665 | 0.227 | 0.952 | 0.696 | 0.215 | TRUE | TRUE | TRUE | TRUE |
| mmu_miR_496_001953 | 33.201 | 34.770 | 31.100 | 29.598 | 0.789 | NA | NA | 0.051 | TRUE | FALSE | FALSE | TRUE |
| mmu_miR_497_001346 | 29.107 | 23.568 | 29.597 | 27.202 | 0.861 | 0.017 | NA | 0.373 | TRUE | TRUE | FALSE | TRUE |
| mmu_miR_499_001352 | 33.880 | 35.631 | 34.285 | 35.037 | 0.314 | NA | 0.462 | 0.660 | TRUE | FALSE | TRUE | TRUE |
| mmu_miR_500_002606 | 29.012 | 29.215 | 29.250 | 27.924 | 0.645 | 0.700 | NA | 0.240 | TRUE | TRUE | FALSE | TRUE |
| mmu_miR_501_001356 | 37.050 | 37.050 | 37.450 | 37.737 | NA | NA | 0.591 | NA | FALSE | FALSE | TRUE | FALSE |
| mmu_miR_501_3p_001651 | 27.999 | 27.676 | 29.219 | 26.327 | 0.655 | 0.569 | 0.908 | 0.112 | TRUE | TRUE | TRUE | TRUE |
| mmu_miR_503_002456 | 35.674 | 35.308 | 35.416 | 35.057 | NA | NA | 0.565 | 0.393 | FALSE | FALSE | TRUE | TRUE |
| mmu_miR_503_002536 | 35.491 | 31.627 | 33.805 | 33.992 | NA | 0.139 | 0.568 | 0.540 | FALSE | TRUE | TRUE | TRUE |
| mmu_miR_504_002084 | 34.407 | 35.651 | 33.908 | 31.961 | NA | NA | 0.578 | 0.072 | FALSE | FALSE | TRUE | TRUE |
| mmu_miR_505_001655 | 37.364 | 38.370 | 38.988 | 39.577 | NA | NA | 0.670 | NA | FALSE | FALSE | TRUE | FALSE |
| mmu_miR_509_3p_002521 | 36.861 | 37.575 | 34.121 | 36.583 | NA | NA | 0.150 | 0.561 | FALSE | FALSE | TRUE | TRUE |
| mmu_miR_509_5p_002520 | 36.180 | 40.548 | 40.305 | 38.916 | NA | NA | NA | NA | FALSE | FALSE | TRUE | FALSE |
| mmu_miR_511_002549 | 37.004 | 37.841 | 38.555 | 39.656 | NA | NA | 0.641 | NA | FALSE | FALSE | TRUE | FALSE |
| mmu_miR_532_3p_002355 | 24.847 | 23.964 | 22.996 | 24.388 | 0.774 | 0.604 | 0.304 | 0.569 | TRUE | TRUE | TRUE | TRUE |
| mmu_miR_532_5p_001518 | 23.624 | 21.738 | 22.501 | 22.843 | 0.816 | 0.396 | 0.503 | 0.527 | TRUE | TRUE | TRUE | TRUE |
| mmu_miR_539_001286 | 22.424 | 27.391 | 26.557 | 23.046 | 0.096 | 0.889 | 0.879 | 0.233 | TRUE | TRUE | TRUE | TRUE |
| mmu_miR_540_3p_001310 | 32.548 | 35.708 | 33.102 | 33.145 | 0.315 | NA | 0.498 | 0.499 | TRUE | FALSE | TRUE | TRUE |
| mmu_miR_540_5p_002561 | 29.978 | 35.672 | 32.671 | 31.383 | 0.054 | NA | 0.708 | 0.409 | TRUE | FALSE | TRUE | TRUE |
| mmu_miR_541_002562 | 26.457 | 31.737 | 25.784 | 25.739 | 0.488 | 0.991 | 0.299 | 0.246 | TRUE | TRUE | TRUE | TRUE |
| mmu_miR_542_3p_001284 | 35.613 | 32.934 | 35.172 | 33.911 | NA | 0.273 | 0.746 | 0.322 | FALSE | TRUE | TRUE | TRUE |
| mmu_miR_542_5p_002563 | 35.612 | 37.261 | 36.674 | 33.012 | NA | NA | 0.788 | 0.027 | FALSE | FALSE | TRUE | TRUE |
| mmu_miR_543_001298 | 21.458 | 26.589 | 22.913 | 21.577 | 0.239 | 0.962 | 0.623 | 0.271 | TRUE | TRUE | TRUE | TRUE |
| mmu_miR_543_002376 | 20.323 | 25.773 | 22.272 | 20.621 | 0.179 | 0.963 | 0.679 | 0.255 | TRUE | TRUE | TRUE | TRUE |
| mmu_miR_544_002550 | 21.890 | 28.591 | 26.732 | 23.829 | 0.017 | NA | NA | 0.331 | TRUE | FALSE | FALSE | TRUE |
| mmu_miR_546_001312 | 31.935 | 34.193 | 27.745 | 36.252 | NA | NA | 0.018 | NA | FALSE | FALSE | TRUE | FALSE |
| mmu_miR_547_002564 | 26.138 | 27.187 | 28.096 | 25.517 | 0.449 | 0.696 | NA | 0.182 | TRUE | TRUE | FALSE | TRUE |
| mmu_miR_551b_001535 | 26.945 | 27.292 | 24.796 | 27.345 | 0.610 | 0.756 | 0.189 | 0.698 | TRUE | TRUE | TRUE | TRUE |
| mmu_miR_574_3p_002349 | 30.890 | 25.042 | 26.552 | 26.317 | 0.995 | 0.188 | 0.497 | 0.368 | TRUE | TRUE | TRUE | TRUE |
| mmu_miR_582_3p_002567 | 32.076 | 30.934 | 33.779 | 33.073 | 0.390 | 0.246 | 0.876 | 0.698 | TRUE | TRUE | TRUE | TRUE |
| mmu_miR_582_5p_002566 | 28.701 | 29.070 | 29.917 | 28.437 | 0.490 | 0.644 | 0.813 | 0.333 | TRUE | TRUE | TRUE | TRUE |
| mmu_miR_590_5p_001984 | 37.534 | 37.840 | 37.755 | 36.904 | NA | NA | 0.620 | 0.325 | FALSE | FALSE | TRUE | TRUE |
| mmu_miR_592_002017 | 27.354 | 30.566 | 28.369 | 27.732 | 0.309 | 0.882 | 0.591 | 0.419 | TRUE | TRUE | TRUE | TRUE |
| mmu_miR_598_002476 | 24.686 | 27.608 | 27.022 | 24.559 | 0.287 | 0.832 | 0.835 | 0.210 | TRUE | TRUE | TRUE | TRUE |
| mmu_miR_599_241117_mat | 37.161 | 34.690 | 37.474 | 35.386 | NA | 0.283 | 0.861 | 0.232 | FALSE | TRUE | TRUE | TRUE |
| mmu_miR_615_3p_001960 | 28.547 | 29.223 | 32.805 | 28.065 | 0.359 | 0.527 | 0.998 | 0.175 | TRUE | TRUE | TRUE | TRUE |
| mmu_miR_615_5p_002353 | 38.761 | 38.892 | 39.278 | 38.865 | NA | NA | 0.662 | NA | FALSE | FALSE | TRUE | FALSE |
| mmu_miR_652_002352 | 27.051 | 23.635 | 27.536 | 24.383 | 0.843 | 0.193 | 0.929 | 0.167 | TRUE | TRUE | TRUE | TRUE |
| mmu_miR_654_3p_002239 | 40.150 | 40.294 | 40.254 | 39.223 | NA | NA | NA | NA | FALSE | FALSE | TRUE | FALSE |

TABLE 3-continued

| Spinal Cord miRNA data. | | | | | | | | | | | | |
|---|---|---|---|---|---|---|---|---|---|---|---|---|
| mmu_miR_654_5p_002522 | 40.354 | 40.524 | 40.388 | 39.672 | NA | NA | NA | NA | FALSE | FALSE | TRUE | FALSE |
| mmu_miR_665_002607 | 34.066 | 35.858 | 34.916 | 32.957 | 0.534 | NA | 0.716 | 0.143 | TRUE | FALSE | TRUE | TRUE |
| mmu_miR_666_3p_002448 | 36.520 | 37.135 | 36.562 | 39.885 | NA | NA | 0.365 | NA | FALSE | FALSE | TRUE | FALSE |
| mmu_miR_666_5p_001952 | 30.140 | 35.696 | 32.684 | 31.593 | 0.059 | NA | 0.688 | 0.435 | TRUE | FALSE | TRUE | TRUE |
| mmu_miR_667_001949 | 21.751 | 26.723 | 24.269 | 21.917 | 0.175 | 0.934 | 0.767 | 0.213 | TRUE | TRUE | TRUE | TRUE |
| mmu_miR_668_001947 | 27.669 | 31.073 | 29.300 | 27.434 | 0.339 | 0.890 | 0.724 | 0.208 | TRUE | TRUE | TRUE | TRUE |
| mmu_miR_669C_002646 | 34.778 | 29.582 | 32.826 | 32.985 | NA | 0.046 | 0.593 | 0.559 | FALSE | TRUE | TRUE | TRUE |
| mmu_miR_669D_002808 | 34.298 | 30.155 | 34.051 | 33.795 | 0.806 | 0.043 | 0.732 | 0.624 | TRUE | TRUE | TRUE | TRUE |
| mmu_miR_669E_002774 | 36.536 | 33.561 | 36.941 | 37.575 | NA | 0.071 | 0.702 | 0.865 | FALSE | TRUE | TRUE | TRUE |
| mmu_miR_669G_002813 | 40.400 | 40.565 | 40.423 | 39.587 | NA | NA | NA | NA | FALSE | FALSE | TRUE | FALSE |
| mmu_miR_669H_5P_002906 | 34.460 | 35.317 | 36.314 | 34.848 | NA | NA | 0.856 | 0.430 | FALSE | FALSE | TRUE | TRUE |
| mmu_miR_669a_001683 | 29.042 | 28.049 | 30.063 | 30.180 | 0.420 | 0.300 | 0.746 | 0.778 | TRUE | TRUE | TRUE | TRUE |
| mmu_miR_669l_121149_mat | 34.317 | 29.902 | 34.264 | 33.931 | NA | 0.025 | 0.752 | 0.643 | FALSE | TRUE | TRUE | TRUE |
| mmu_miR_669m_121190_mat | 29.699 | 28.157 | 27.789 | 31.750 | 0.586 | 0.337 | 0.254 | 0.974 | TRUE | TRUE | TRUE | TRUE |
| mmu_miR_669n_197143_mat | 34.800 | 30.775 | 33.800 | 34.005 | NA | 0.073 | 0.625 | 0.623 | FALSE | TRUE | TRUE | TRUE |
| mmu_miR_669o_121176_mat | 32.436 | 29.443 | 33.191 | 32.963 | 0.586 | 0.077 | 0.810 | 0.751 | TRUE | TRUE | TRUE | TRUE |
| mmu_miR_670_002020 | 32.716 | 28.377 | 26.694 | 31.199 | NA | 0.283 | 0.108 | 0.710 | FALSE | TRUE | TRUE | TRUE |
| mmu_miR_671_3p_002322 | 28.747 | 27.118 | 27.966 | 29.041 | 0.655 | 0.344 | 0.483 | 0.756 | TRUE | TRUE | TRUE | TRUE |
| mmu_miR_672_002327 | 24.410 | 33.554 | 29.922 | 23.538 | 0.183 | 0.985 | NA | 0.030 | TRUE | TRUE | FALSE | TRUE |
| mmu_miR_673_001954 | 22.449 | 23.321 | 18.775 | 27.082 | NA | NA | 0.043 | NA | FALSE | FALSE | TRUE | FALSE |
| mmu_miR_673_3p_002449 | 26.805 | 35.820 | 24.527 | 29.511 | 0.253 | NA | 0.053 | 0.684 | TRUE | FALSE | TRUE | TRUE |
| mmu_miR_674_001956 | 28.166 | 25.112 | 27.887 | 27.705 | 0.776 | 0.126 | 0.695 | 0.606 | TRUE | TRUE | TRUE | TRUE |
| mmu_miR_674_002021 | 34.540 | 27.577 | 27.210 | 31.675 | 0.997 | 0.151 | 0.143 | 0.693 | TRUE | TRUE | TRUE | TRUE |
| mmu_miR_675_3p_001941 | 35.413 | 32.390 | 28.177 | 35.510 | NA | 0.411 | 0.026 | 0.890 | FALSE | TRUE | TRUE | TRUE |
| mmu_miR_675_5p_001940 | 37.050 | 35.095 | 33.268 | 36.332 | NA | NA | 0.153 | 0.646 | FALSE | FALSE | TRUE | TRUE |
| mmu_miR_676_001958 | 28.640 | 28.417 | 29.646 | 29.728 | 0.389 | 0.442 | 0.713 | 0.722 | TRUE | TRUE | TRUE | TRUE |
| mmu_miR_676_001959 | 28.483 | 24.952 | 30.121 | 26.862 | 0.749 | 0.095 | 0.981 | 0.281 | TRUE | TRUE | TRUE | TRUE |
| mmu_miR_677_001660 | 37.303 | 37.402 | 37.637 | 35.148 | NA | NA | 0.746 | 0.092 | FALSE | FALSE | TRUE | TRUE |
| mmu_miR_679_001662 | 37.078 | 34.383 | 35.587 | 38.860 | NA | NA | 0.401 | 0.970 | FALSE | FALSE | TRUE | TRUE |
| mmu_miR_680_001664 | 38.404 | 34.109 | 33.469 | 34.865 | NA | 0.385 | 0.224 | 0.446 | FALSE | TRUE | TRUE | TRUE |
| mmu_miR_682_001666 | 33.216 | 35.557 | 32.287 | 38.360 | NA | NA | 0.172 | 0.988 | FALSE | FALSE | TRUE | TRUE |
| mmu_miR_683_001668 | 38.963 | 37.814 | 39.189 | 37.954 | NA | NA | 0.748 | NA | FALSE | FALSE | TRUE | FALSE |
| mmu_miR_684_001669 | 40.800 | 40.976 | 40.660 | 39.599 | NA | NA | NA | NA | FALSE | FALSE | TRUE | FALSE |
| mmu_miR_685_001670 | 32.878 | 35.470 | 35.005 | 40.913 | 0.080 | 0.478 | 0.492 | NA | TRUE | TRUE | TRUE | FALSE |
| mmu_miR_686_001672 | 40.863 | 38.311 | 40.736 | 39.560 | NA | NA | NA | NA | FALSE | FALSE | TRUE | FALSE |
| mmu_miR_687_001674 | 39.989 | 39.280 | 40.194 | 39.568 | NA | NA | NA | NA | FALSE | FALSE | FALSE | FALSE |
| mmu_miR_688_001675 | 38.490 | 40.710 | 36.581 | 39.679 | NA | NA | 0.145 | NA | FALSE | FALSE | TRUE | FALSE |
| mmu_miR_690_001677 | 38.523 | 38.415 | 39.023 | 39.682 | NA | NA | 0.591 | NA | FALSE | FALSE | TRUE | FALSE |
| mmu_miR_691_001678 | 36.677 | 38.815 | 31.505 | 38.336 | NA | NA | 0.015 | NA | FALSE | FALSE | TRUE | FALSE |
| mmu_miR_692_001679 | 40.794 | 40.381 | 36.138 | 37.213 | NA | NA | 0.126 | 0.265 | FALSE | FALSE | TRUE | TRUE |
| mmu_miR_693_001680 | 37.646 | 37.043 | 32.245 | 37.684 | NA | 0.726 | 0.037 | 0.732 | FALSE | TRUE | TRUE | TRUE |
| mmu_miR_693_3p_002036 | 40.395 | 39.668 | 34.766 | 39.556 | NA | NA | 0.041 | NA | FALSE | FALSE | TRUE | FALSE |
| mmu_miR_694_001681 | 31.451 | 30.650 | 26.077 | 37.038 | NA | NA | 0.020 | NA | FALSE | FALSE | TRUE | FALSE |
| mmu_miR_695_001627 | 38.256 | 39.781 | 35.674 | 38.668 | NA | NA | 0.124 | NA | FALSE | FALSE | TRUE | FALSE |
| mmu_miR_696_001628 | 36.609 | 32.104 | 27.580 | 37.553 | 0.843 | 0.290 | 0.012 | 0.973 | TRUE | TRUE | TRUE | TRUE |
| mmu_miR_697_001631 | 36.200 | 35.923 | 40.046 | 38.002 | 0.195 | 0.259 | NA | 0.646 | TRUE | TRUE | TRUE | TRUE |
| mmu_miR_698_001632 | 40.328 | 40.366 | 40.363 | 39.643 | NA | NA | NA | NA | FALSE | FALSE | FALSE | FALSE |
| mmu_miR_700_001634 | 26.172 | 25.761 | 28.528 | 25.500 | 0.503 | 0.467 | 0.978 | 0.207 | TRUE | TRUE | TRUE | TRUE |
| mmu_miR_701_001635 | 31.771 | 29.862 | 32.818 | 33.616 | 0.417 | 0.129 | 0.729 | 0.914 | TRUE | TRUE | TRUE | TRUE |
| mmu_miR_702_001636 | 30.963 | 35.116 | 31.276 | 32.756 | 0.211 | 0.925 | 0.323 | 0.674 | TRUE | TRUE | TRUE | TRUE |
| mmu_miR_704_001639 | 35.571 | 37.012 | 37.447 | 35.512 | NA | NA | 0.849 | 0.298 | FALSE | FALSE | TRUE | TRUE |

TABLE 3-continued

| Spinal Cord miRNA data. | | | | | | | | | | | | |
|---|---|---|---|---|---|---|---|---|---|---|---|---|
| mmu_miR_706_001641 | 32.189 | 33.896 | 32.173 | 40.404 | 0.229 | 0.504 | 0.242 | NA | TRUE | TRUE | TRUE | FALSE |
| mmu_miR_707_001642 | 40.353 | 40.496 | 40.419 | 39.590 | NA | NA | NA | NA | FALSE | FALSE | TRUE | FALSE |
| mmu_miR_708_002341 | 24.115 | 22.834 | 24.270 | 23.436 | 0.711 | 0.429 | 0.714 | 0.401 | TRUE | TRUE | TRUE | TRUE |
| mmu_miR_710_001645 | 33.815 | 35.216 | 36.312 | 38.961 | 0.103 | 0.400 | 0.665 | NA | TRUE | TRUE | TRUE | FALSE |
| mmu_miR_711_001646 | 39.085 | 38.578 | 36.256 | 40.123 | NA | NA | 0.150 | NA | FALSE | FALSE | TRUE | FALSE |
| mmu_miR_712_001961 | 39.661 | 39.959 | 39.931 | 37.770 | NA | NA | 0.711 | 0.109 | FALSE | FALSE | TRUE | TRUE |
| mmu_miR_712_002636 | 33.431 | 32.443 | 25.894 | 34.968 | 0.681 | 0.609 | 0.005 | 0.961 | TRUE | TRUE | TRUE | TRUE |
| mmu_miR_713_001648 | 39.497 | 39.231 | 38.729 | 40.164 | NA | NA | 0.375 | NA | FALSE | FALSE | TRUE | FALSE |
| mmu_miR_715_001649 | 38.597 | 37.149 | 39.004 | 39.787 | NA | NA | NA | NA | FALSE | FALSE | FALSE | FALSE |
| mmu_miR_717_001652 | 41.436 | 34.738 | 35.058 | 40.122 | NA | 0.105 | 0.179 | NA | FALSE | TRUE | TRUE | FALSE |
| mmu_miR_718_001656 | 35.000 | 38.914 | 39.870 | 40.369 | 0.022 | NA | 0.774 | NA | TRUE | FALSE | TRUE | FALSE |
| mmu_miR_719_001673 | 39.496 | 39.436 | 39.653 | 37.089 | NA | NA | 0.728 | 0.079 | FALSE | FALSE | TRUE | TRUE |
| mmu_miR_720_001629 | 24.167 | 24.633 | 20.593 | 28.777 | NA | NA | 0.056 | NA | FALSE | FALSE | TRUE | FALSE |
| mmu_miR_721_001657 | 26.336 | 24.283 | 20.781 | 31.059 | 0.648 | 0.346 | 0.034 | 1.000 | TRUE | TRUE | TRUE | TRUE |
| mmu_miR_741_002457 | 37.878 | 37.765 | 32.527 | 38.222 | NA | NA | 0.033 | 0.761 | FALSE | FALSE | TRUE | TRUE |
| mmu_miR_742_002038 | 38.576 | 36.894 | 39.163 | 39.500 | NA | NA | 0.713 | NA | FALSE | FALSE | TRUE | FALSE |
| mmu_miR_742_002458 | 33.534 | 36.917 | 31.984 | 34.619 | 0.404 | NA | 0.143 | 0.667 | TRUE | FALSE | TRUE | TRUE |
| mmu_miR_743a_002469 | 29.264 | 32.391 | 29.746 | 30.572 | 0.263 | 0.877 | 0.422 | 0.634 | TRUE | TRUE | TRUE | TRUE |
| mmu_miR_743b_3p_002471 | 39.757 | 39.876 | 40.034 | 39.436 | NA | NA | NA | NA | FALSE | FALSE | TRUE | FALSE |
| mmu_miR_743b_5p_002470 | 34.649 | 30.215 | 30.014 | 34.708 | NA | NA | NA | NA | FALSE | FALSE | FALSE | FALSE |
| mmu_miR_744_002324 | 24.023 | 25.380 | 24.182 | 24.195 | 0.455 | 0.793 | 0.499 | 0.494 | TRUE | TRUE | TRUE | TRUE |
| mmu_miR_758_002025 | 35.957 | 36.206 | 35.942 | 32.714 | NA | NA | 0.703 | 0.031 | FALSE | FALSE | TRUE | TRUE |
| mmu_miR_759_002034 | 35.605 | 35.482 | 38.134 | 36.619 | 0.272 | 0.386 | 0.951 | 0.569 | TRUE | TRUE | TRUE | TRUE |
| mmu_miR_761_002030 | 37.353 | 36.994 | 33.659 | 38.451 | NA | NA | 0.098 | 0.881 | FALSE | FALSE | TRUE | TRUE |
| mmu_miR_762_002028 | 35.244 | 35.637 | 38.051 | 38.204 | 0.142 | NA | 0.852 | NA | TRUE | FALSE | TRUE | FALSE |
| mmu_miR_763_002033 | 37.229 | 35.932 | 32.342 | 37.048 | NA | NA | 0.075 | NA | FALSE | FALSE | TRUE | FALSE |
| mmu_miR_764_3p_002032 | 34.648 | 36.164 | 34.809 | 33.470 | NA | NA | 0.593 | 0.191 | FALSE | FALSE | TRUE | TRUE |
| mmu_miR_764_5p_002031 | 32.356 | 34.427 | 33.719 | 30.814 | 0.515 | 0.836 | 0.787 | 0.067 | TRUE | TRUE | TRUE | TRUE |
| mmu_miR_767_241081_mat | 40.800 | 40.975 | 40.660 | 39.602 | NA | NA | NA | NA | FALSE | FALSE | TRUE | FALSE |
| mmu_miR_770_3p_002027 | 30.569 | 35.966 | 31.873 | 31.275 | 0.185 | NA | 0.546 | 0.400 | TRUE | FALSE | TRUE | TRUE |
| mmu_miR_770_5p_002608 | 32.645 | 35.829 | 34.391 | 32.846 | 0.278 | NA | 0.725 | 0.308 | TRUE | FALSE | TRUE | TRUE |
| mmu_miR_7a_000268 | 27.027 | 30.847 | 23.932 | 25.453 | 0.722 | NA | 0.090 | 0.289 | TRUE | FALSE | TRUE | TRUE |
| mmu_miR_7b_002555 | 27.123 | 32.566 | 24.728 | 26.755 | 0.545 | 0.995 | 0.093 | 0.405 | TRUE | TRUE | TRUE | TRUE |
| mmu_miR_802_002029 | 35.431 | 33.970 | 34.657 | 35.564 | NA | NA | 0.483 | 0.708 | FALSE | FALSE | TRUE | TRUE |
| mmu_miR_804_002044 | 39.061 | 31.348 | 32.156 | 36.554 | NA | 0.082 | 0.222 | 0.709 | FALSE | TRUE | TRUE | TRUE |
| mmu_miR_805_002045 | 32.731 | 29.465 | 30.868 | 37.361 | NA | 0.088 | 0.348 | NA | FALSE | TRUE | TRUE | FALSE |
| mmu_miR_871_002354 | 39.297 | 39.390 | 39.632 | 38.895 | NA | NA | 0.651 | NA | FALSE | FALSE | TRUE | FALSE |
| mmu_miR_872_002264 | 24.637 | 23.514 | 26.865 | 24.808 | 0.438 | 0.288 | 0.967 | 0.470 | TRUE | TRUE | TRUE | TRUE |
| mmu_miR_872_002542 | 24.608 | 22.415 | 25.909 | 24.040 | 0.662 | 0.193 | 0.934 | 0.407 | TRUE | TRUE | TRUE | TRUE |
| mmu_miR_873_002356 | 32.250 | 35.550 | 33.231 | 31.401 | 0.470 | NA | 0.663 | 0.141 | TRUE | FALSE | TRUE | TRUE |
| mmu_miR_874_002268 | 38.004 | 37.796 | 38.534 | 39.585 | NA | NA | 0.582 | NA | FALSE | FALSE | TRUE | FALSE |
| mmu_miR_875_3p_002547 | 36.814 | 37.733 | 34.232 | 39.656 | NA | NA | 0.110 | NA | FALSE | FALSE | TRUE | FALSE |
| mmu_miR_876_3p_002464 | 36.338 | 38.484 | 37.176 | 38.533 | NA | NA | 0.468 | NA | FALSE | FALSE | TRUE | FALSE |
| mmu_miR_876_5p_002463 | 36.405 | 38.658 | 38.726 | 36.765 | 0.238 | NA | 0.846 | 0.336 | TRUE | FALSE | TRUE | TRUE |
| mmu_miR_877_002548 | 23.304 | 19.708 | 16.429 | 23.453 | NA | 0.323 | 0.046 | NA | FALSE | TRUE | TRUE | FALSE |
| mmu_miR_878_3p_002541 | 33.157 | 31.722 | 29.189 | 39.450 | NA | NA | NA | NA | FALSE | FALSE | FALSE | FALSE |
| mmu_miR_878_5p_002540 | 37.798 | 37.893 | 32.419 | 37.402 | NA | NA | 0.031 | 0.604 | FALSE | FALSE | TRUE | TRUE |
| mmu_miR_879_002472 | 34.015 | 34.055 | 34.827 | 34.343 | NA | NA | 0.717 | 0.534 | FALSE | FALSE | TRUE | TRUE |
| mmu_miR_879_002473 | 28.646 | 28.606 | 27.363 | 27.211 | 0.780 | 0.746 | 0.423 | 0.310 | TRUE | TRUE | TRUE | TRUE |
| mmu_miR_880_002665 | 35.770 | 29.151 | 33.468 | 38.671 | NA | 0.003 | 0.434 | NA | FALSE | TRUE | TRUE | FALSE |
| mmu_miR_881_002475 | 38.590 | 38.635 | 33.232 | 39.302 | NA | NA | 0.027 | 0.808 | FALSE | FALSE | TRUE | TRUE |

TABLE 3-continued

Spinal Cord miRNA data.

| | | | | | | | | | | | | |
|---|---|---|---|---|---|---|---|---|---|---|---|---|
| mmu_miR_881_002609 | 34.675 | 37.061 | 35.055 | 39.877 | NA | NA | 0.317 | NA | FALSE | FALSE | TRUE | FALSE |
| mmu_miR_882_002610 | 40.800 | 40.976 | 40.660 | 39.599 | NA | NA | NA | NA | FALSE | FALSE | TRUE | FALSE |
| mmu_miR_883B_5P_002669 | 34.843 | 35.469 | 32.374 | 38.205 | 0.454 | 0.598 | 0.122 | 0.983 | TRUE | TRUE | TRUE | TRUE |
| mmu_miR_883a_3p_002461 | 36.395 | 38.086 | 38.457 | 37.598 | NA | NA | 0.791 | NA | FALSE | FALSE | TRUE | FALSE |
| mmu_miR_883a_5p_002611 | 40.646 | 40.806 | 40.576 | 39.599 | NA | NA | NA | NA | FALSE | FALSE | TRUE | FALSE |
| mmu_miR_883b_3p_002565 | 35.970 | 40.249 | 39.498 | 35.101 | NA | NA | 0.883 | 0.057 | FALSE | FALSE | TRUE | TRUE |
| mmu_miR_92a_000430 | 19.851 | 20.028 | 17.119 | 22.167 | 0.513 | 0.604 | 0.124 | 0.959 | TRUE | TRUE | TRUE | TRUE |
| mmu_miR_92a_002496 | 40.488 | 40.630 | 40.455 | 39.676 | NA | NA | NA | NA | FALSE | FALSE | TRUE | FALSE |
| mmu_miR_93_001090 | 23.262 | 21.456 | 24.556 | 22.792 | 0.633 | 0.245 | 0.922 | 0.407 | TRUE | TRUE | TRUE | TRUE |
| mmu_miR_96_000186 | 29.835 | 34.889 | 26.262 | 31.653 | 0.367 | 0.980 | 0.034 | 0.727 | TRUE | TRUE | TRUE | TRUE |
| mmu_miR_98_000577 | 28.720 | 31.651 | 28.038 | 26.315 | 0.655 | 0.938 | 0.498 | 0.054 | TRUE | TRUE | TRUE | TRUE |
| mmu_miR_99a_000435 | 21.378 | 18.906 | 19.610 | 21.071 | 0.822 | 0.290 | 0.405 | 0.710 | TRUE | TRUE | TRUE | TRUE |
| mmu_miR_99b_000436 | 23.084 | 21.118 | 23.632 | 23.366 | 0.585 | 0.205 | 0.773 | 0.674 | TRUE | TRUE | TRUE | TRUE |
| mmu_miR_9_000583 | 19.271 | 16.500 | 18.698 | 18.273 | 0.825 | 0.213 | 0.676 | 0.496 | TRUE | TRUE | TRUE | TRUE |

| | log2FC_ ChATvsGFAP_sc | adj.p.value_ ChATvsGFAP_sc | log2FC_ ChATvsLyz2_sc | adj.p.value_ ChATvsLyz2_sc | log2FC_ ChATvsSyn_sc | adj.p.value_ ChATvsSyn_sc |
|---|---|---|---|---|---|---|
| hsa_let_7b_002404 | 4.141 | 0.299 | 0.388 | 0.957 | 5.193 | 0.227 |
| hsa_let_7e_002407 | −0.470 | 0.836 | −0.892 | 0.558 | 0.377 | 0.868 |
| hsa_let_7f_1_002417 | −0.464 | 0.945 | 1.065 | 0.767 | −2.815 | 0.343 |
| hsa_let_7i_002172 | −2.634 | 0.009 | 1.052 | 0.363 | 1.708 | 0.159 |
| hsa_miR_106b_002380 | −3.241 | 0.009 | −0.830 | 0.616 | −3.750 | 0.007 |
| hsa_miR_10a_002288 | 0.000 | 1.000 | 2.047 | 0.390 | 1.004 | 0.759 |
| hsa_miR_1197_002810 | 3.498 | 0.031 | 1.984 | 0.280 | 0.585 | 0.839 |
| hsa_miR_124_002197 | 0.419 | 0.943 | −0.041 | 0.986 | 1.842 | 0.501 |
| hsa_miR_127_5p_002229 | 3.709 | 0.001 | 2.688 | 0.017 | 1.108 | 0.437 |
| hsa_miR_136_000592 | 4.068 | 0.000 | −1.636 | 0.082 | −0.325 | 0.836 |
| hsa_miR_136_002100 | 5.757 | 0.002 | 2.581 | 0.213 | 0.465 | 0.900 |
| hsa_miR_140_3p_002234 | −1.159 | 0.156 | −0.705 | 0.445 | −0.930 | 0.360 |
| hsa_miR_143_000466 | 0.540 | 0.961 | −6.086 | 0.079 | 2.082 | 0.668 |
| hsa_miR_144_002676 | −0.092 | 0.975 | 0.735 | 0.360 | 1.993 | 0.011 |
| hsa_miR_148a_002134 | −2.995 | 0.190 | 1.136 | 0.728 | 1.832 | 0.548 |
| hsa_miR_149_002255 | 0.882 | 0.180 | 1.692 | 0.011 | −0.436 | 0.633 |
| hsa_miR_151_5P_002642 | −3.579 | 0.001 | −4.540 | 0.000 | −0.953 | 0.517 |
| hsa_miR_154_000478 | 4.422 | 0.000 | 1.627 | 0.192 | 1.520 | 0.279 |
| hsa_miR_15b_002173 | −0.557 | 0.969 | −1.276 | 0.855 | 4.206 | 0.437 |
| hsa_miR_183_002270 | 6.072 | 0.003 | −1.345 | 0.633 | −0.318 | 0.927 |
| hsa_miR_189_000488 | −1.039 | 0.907 | −2.282 | 0.656 | −3.323 | 0.521 |
| hsa_miR_190b_002263 | −0.575 | 0.835 | −1.689 | 0.298 | 1.847 | 0.309 |
| hsa_miR_196a_241070_mat | −2.212 | 0.054 | 0.106 | 0.968 | −0.554 | 0.759 |
| hsa_miR_200a_001011 | −0.044 | 0.996 | 1.739 | 0.298 | 1.733 | 0.367 |
| hsa_miR_200b_001800 | 0.144 | 0.996 | −1.084 | 0.815 | 2.691 | 0.478 |
| hsa_miR_200b_002274 | −0.219 | 0.996 | −6.190 | 0.187 | −0.580 | 0.933 |
| hsa_miR_200c_000505 | −0.584 | 0.853 | −4.965 | 0.004 | −0.585 | 0.836 |
| hsa_miR_200c_002286 | 0.090 | 0.994 | 0.417 | 0.860 | 0.268 | 0.914 |
| hsa_miR_206_000510 | −5.586 | 0.002 | −6.838 | 0.001 | −2.901 | 0.182 |
| hsa_miR_213_000516 | −1.959 | 0.066 | −0.994 | 0.420 | −0.871 | 0.560 |
| hsa_miR_214_000517 | −3.282 | 0.017 | −2.251 | 0.141 | −0.656 | 0.768 |
| hsa_miR_214_002293 | −1.663 | 0.239 | 0.563 | 0.787 | 1.978 | 0.205 |
| hsa_miR_218_2_002294 | 10.447 | 0.000 | 5.428 | 0.000 | 4.037 | 0.003 |

TABLE 3-continued

Spinal Cord miRNA data.

| | | | | | | |
|---|---|---|---|---|---|---|
| hsa_miR_223_000526 | 3.932 | 0.187 | −8.698 | 0.004 | 4.001 | 0.243 |
| hsa_miR_22_000398 | −1.043 | 0.774 | −0.905 | 0.791 | −0.141 | 0.974 |
| hsa_miR_22_002301 | −0.088 | 0.987 | 0.078 | 0.968 | 1.305 | 0.205 |
| hsa_miR_23a_002439 | −2.997 | 0.565 | −10.445 | 0.012 | 6.670 | 0.151 |
| hsa_miR_26b_002444 | −2.435 | 0.379 | −3.583 | 0.174 | 1.764 | 0.610 |
| hsa_miR_27a_002445 | −1.365 | 0.647 | 0.874 | 0.788 | 2.493 | 0.346 |
| hsa_miR_27b_002174 | −1.088 | 0.238 | −0.829 | 0.398 | −0.695 | 0.561 |
| hsa_miR_28_3p_002446 | 1.086 | 0.716 | 1.407 | 0.558 | 0.604 | 0.868 |
| hsa_miR_299_5p_000600 | 2.085 | 0.534 | 1.561 | 0.664 | 0.064 | 0.992 |
| hsa_miR_29a_002447 | −1.359 | 0.684 | 0.695 | 0.855 | −1.749 | 0.568 |
| hsa_miR_29b_2_002166 | 1.391 | 0.736 | −3.764 | 0.186 | 1.344 | 0.740 |
| hsa_miR_30a_3p_000416 | −0.796 | 0.072 | 0.313 | 0.578 | −0.278 | 0.674 |
| hsa_miR_30c_1_002108 | −2.992 | 0.439 | 3.142 | 0.390 | 3.779 | 0.360 |
| hsa_miR_30c_2_002110 | 5.489 | 0.190 | 5.003 | 0.262 | 7.777 | 0.095 |
| hsa_miR_30d_002305 | 3.619 | 0.244 | 3.972 | 0.205 | 6.093 | 0.065 |
| hsa_miR_30e_3p_000422 | −0.881 | 0.057 | 0.263 | 0.692 | −0.071 | 0.927 |
| hsa_miR_324_3p_000579 | −5.280 | 0.010 | −2.673 | 0.254 | −4.234 | 0.082 |
| hsa_miR_338_000548 | −3.535 | 0.055 | −1.946 | 0.354 | −1.623 | 0.529 |
| hsa_miR_338_5P_002658 | −3.022 | 0.001 | −2.785 | 0.004 | −1.851 | 0.074 |
| hsa_miR_33a_002136 | −2.328 | 0.147 | −1.379 | 0.445 | −1.298 | 0.548 |
| hsa_miR_340_000550 | −0.601 | 0.599 | 0.498 | 0.671 | −0.183 | 0.912 |
| hsa_miR_363_001283 | 1.107 | 0.841 | −0.241 | 0.970 | −3.816 | 0.295 |
| hsa_miR_376a_001287 | 6.962 | 0.000 | 2.238 | 0.072 | 1.216 | 0.441 |
| hsa_miR_378_000567 | −0.109 | 0.996 | −3.504 | 0.063 | 1.544 | 0.531 |
| hsa_miR_411_002238 | 6.367 | 0.000 | 1.536 | 0.322 | 0.210 | 0.927 |
| hsa_miR_412_001023 | 4.597 | 0.007 | 2.258 | 0.246 | 1.163 | 0.650 |
| hsa_miR_421_002700 | −0.179 | 0.889 | 1.006 | 0.110 | 0.769 | 0.295 |
| hsa_miR_423_3P_002626 | −4.241 | 0.001 | −1.713 | 0.232 | −1.657 | 0.310 |
| hsa_miR_425_001104 | −3.461 | 0.075 | −2.767 | 0.192 | −0.739 | 0.830 |
| hsa_miR_431_002312 | 5.024 | 0.002 | 3.310 | 0.059 | 0.644 | 0.827 |
| hsa_miR_455_001280 | −5.364 | 0.001 | −4.123 | 0.016 | −1.960 | 0.340 |
| hsa_miR_485_5p_001036 | 0.011 | 0.998 | 0.058 | 0.979 | 0.279 | 0.912 |
| hsa_miR_493_3p_001282 | −9.065 | 0.046 | −4.399 | 0.401 | −3.619 | 0.571 |
| hsa_miR_590_3P_002677 | 0.357 | 0.690 | 0.092 | 0.939 | −1.300 | 0.061 |
| hsa_miR_653_002292 | 3.470 | 0.318 | −0.004 | 0.999 | 3.415 | 0.402 |
| hsa_miR_671_5p_197646_mat | −1.207 | 0.889 | −6.525 | 0.122 | 0.972 | 0.899 |
| hsa_miR_708_002342 | −0.048 | 0.996 | −0.137 | 0.972 | −0.624 | 0.875 |
| hsa_miR_744_002325 | 0.053 | 0.996 | −0.512 | 0.728 | 0.158 | 0.924 |
| hsa_miR_875_5p_002203 | 2.888 | 0.806 | −5.315 | 0.488 | 10.142 | 0.185 |
| hsa_miR_935_002178 | −1.443 | 0.572 | −0.156 | 0.970 | −1.636 | 0.539 |
| hsa_miR_93_002139 | −2.914 | 0.003 | −0.515 | 0.726 | −1.137 | 0.367 |
| hsa_miR_99b_002196 | 0.561 | 0.835 | 1.084 | 0.542 | 0.887 | 0.679 |
| hsa_miR_9_002231 | −4.086 | 0.000 | −1.177 | 0.011 | −1.233 | 0.010 |
| mmu_let_7a_000377 | −3.703 | 0.011 | 2.938 | 0.063 | −2.884 | 0.096 |
| mmu_let_7a_002478 | −7.397 | 0.169 | −1.546 | 0.871 | 2.421 | 0.768 |
| mmu_let_7b_000378 | −2.070 | 0.000 | −0.431 | 0.377 | 0.061 | 0.929 |
| mmu_let_7c_000379 | −1.501 | 0.000 | 0.382 | 0.434 | −0.146 | 0.842 |
| mmu_let_7c_1_002479 | −3.489 | 0.299 | −8.681 | 0.007 | −1.442 | 0.761 |
| mmu_let_7d_001178 | 0.308 | 0.855 | −2.515 | 0.006 | −2.489 | 0.008 |
| mmu_let_7d_002283 | −0.222 | 0.833 | 1.261 | 0.028 | 0.047 | 0.963 |
| mmu_let_7e_002406 | −0.017 | 0.997 | 2.046 | 0.036 | 0.331 | 0.839 |

TABLE 3-continued

Spinal Cord miRNA data.

| | | | | | | |
|---|---|---|---|---|---|---|
| mmu_let_7f_000382 | −2.629 | 0.459 | −0.916 | 0.855 | −3.873 | 0.279 |
| mmu_let_7g_002282 | 0.479 | 0.646 | 1.400 | 0.067 | 0.712 | 0.462 |
| mmu_let_7g_002492 | 4.689 | 0.002 | 2.429 | 0.141 | 2.502 | 0.163 |
| mmu_let_7i_002221 | −2.076 | 0.000 | 0.674 | 0.248 | −0.530 | 0.455 |
| mmu_miR_100_000437 | −2.738 | 0.000 | −0.412 | 0.654 | −0.161 | 0.902 |
| mmu_miR_101a_002253 | 0.688 | 0.184 | 1.158 | 0.025 | 1.102 | 0.049 |
| mmu_miR_101a_002507 | −0.269 | 0.867 | −0.294 | 0.823 | −1.421 | 0.117 |
| mmu_miR_101b_002531 | −0.309 | 0.757 | 1.326 | 0.036 | −0.364 | 0.686 |
| mmu_miR_103_000439 | −0.535 | 0.641 | 1.596 | 0.059 | −0.057 | 0.971 |
| mmu_miR_105_002465 | 1.454 | 0.907 | −0.945 | 0.924 | 8.561 | 0.162 |
| mmu_miR_106a_002459 | −4.282 | 0.062 | 1.429 | 0.651 | −2.654 | 0.367 |
| mmu_miR_106b_000442 | −2.121 | 0.002 | −1.250 | 0.084 | −0.887 | 0.301 |
| mmu_miR_107_000443 | −0.104 | 0.994 | −3.735 | 0.022 | 0.152 | 0.958 |
| mmu_miR_10a_000387 | −1.605 | 0.238 | −0.353 | 0.882 | −0.459 | 0.836 |
| mmu_miR_10b_001181 | −1.254 | 0.410 | −0.564 | 0.784 | −1.296 | 0.456 |
| mmu_miR_10b_002218 | 0.177 | 0.983 | 2.564 | 0.146 | −1.295 | 0.568 |
| mmu_miR_10b_002572 | 0.386 | 0.961 | 2.602 | 0.298 | 0.962 | 0.795 |
| mmu_miR_1186_002825 | −1.382 | 0.813 | −0.227 | 0.972 | 1.874 | 0.687 |
| mmu_miR_1188_002866 | 2.507 | 0.422 | 2.230 | 0.471 | 1.609 | 0.679 |
| mmu_miR_1191_002892 | −2.787 | 0.563 | −7.940 | 0.036 | −1.050 | 0.875 |
| mmu_miR_1192_002806 | 0.192 | 0.981 | 0.327 | 0.918 | 0.314 | 0.914 |
| mmu_miR_1193_002794 | 1.645 | 0.017 | 2.175 | 0.004 | 2.732 | 0.001 |
| mmu_miR_1194_002793 | 0.201 | 0.945 | 0.388 | 0.811 | −0.225 | 0.906 |
| mmu_miR_1195_002839 | −0.232 | 0.994 | 0.105 | 0.979 | 2.799 | 0.458 |
| mmu_miR_1198_002780 | −1.510 | 0.063 | 1.564 | 0.070 | −2.152 | 0.016 |
| mmu_miR_1199_240984_mat | 0.175 | 0.690 | −0.141 | 0.754 | −1.201 | 0.000 |
| mmu_miR_1224_240985_mat | 0.242 | 0.823 | −0.110 | 0.920 | −1.896 | 0.003 |
| mmu_miR_122_002245 | −4.328 | 0.371 | −9.685 | 0.027 | 1.533 | 0.836 |
| mmu_miR_124_001182 | 4.801 | 0.000 | 1.499 | 0.172 | −0.379 | 0.830 |
| mmu_miR_125a_3p_002199 | 0.413 | 0.890 | −0.358 | 0.882 | −0.371 | 0.884 |
| mmu_miR_125a_5p_002198 | 0.578 | 0.262 | 1.482 | 0.003 | 0.392 | 0.554 |
| mmu_miR_125b_002508 | −0.543 | 0.690 | 1.197 | 0.238 | 0.902 | 0.464 |
| mmu_miR_125b_3p_002378 | −2.370 | 0.009 | −2.958 | 0.003 | 0.618 | 0.650 |
| mmu_miR_125b_5p_000449 | −0.857 | 0.077 | −1.172 | 0.021 | 0.076 | 0.925 |
| mmu_miR_126_3p_002228 | 3.110 | 0.000 | −1.640 | 0.002 | 1.498 | 0.005 |
| mmu_miR_126_5p_000451 | 3.376 | 0.000 | −0.831 | 0.157 | 1.544 | 0.009 |
| mmu_miR_1274a_121150_mat | 1.460 | 0.672 | −4.133 | 0.094 | 2.740 | 0.360 |
| mmu_miR_127_000452 | 4.157 | 0.000 | 0.159 | 0.834 | −0.357 | 0.561 |
| mmu_miR_128a_002216 | 1.852 | 0.001 | 0.164 | 0.874 | −0.571 | 0.444 |
| mmu_miR_129_3p_001184 | 2.203 | 0.000 | 0.841 | 0.184 | −0.666 | 0.367 |
| mmu_miR_129_5p_000590 | 2.630 | 0.017 | 2.780 | 0.020 | −0.093 | 0.963 |
| mmu_miR_1306_121155_mat | 2.099 | 0.139 | 2.016 | 0.184 | 0.239 | 0.920 |
| mmu_miR_130a_000454 | −5.111 | 0.001 | 0.100 | 0.972 | −3.207 | 0.065 |
| mmu_miR_130b_000456 | −3.079 | 0.001 | −2.119 | 0.024 | −1.054 | 0.360 |
| mmu_miR_130b_002460 | 0.310 | 0.959 | −6.598 | 0.001 | −5.447 | 0.005 |
| mmu_miR_132_000457 | 3.880 | 0.000 | −0.005 | 0.994 | −1.290 | 0.007 |
| mmu_miR_133a_001637 | 2.015 | 0.273 | 1.958 | 0.298 | −0.489 | 0.875 |
| mmu_miR_133a_002246 | 7.326 | 0.000 | 2.060 | 0.000 | 0.815 | 0.159 |
| mmu_miR_133b_002247 | 7.800 | 0.000 | 1.816 | 0.184 | 1.703 | 0.256 |
| mmu_miR_134_001186 | 4.975 | 0.000 | 1.373 | 0.138 | −0.127 | 0.928 |
| mmu_miR_135a_000460 | −3.527 | 0.000 | −1.329 | 0.020 | −2.443 | 0.000 |

TABLE 3-continued

| Spinal Cord miRNA data. | | | | | | |
|---|---|---|---|---|---|---|
| mmu_miR_135b_002261 | −2.949 | 0.003 | 0.879 | 0.454 | −1.987 | 0.089 |
| mmu_miR_136_002511 | 8.233 | 0.000 | 2.405 | 0.238 | 0.261 | 0.929 |
| mmu_miR_136_002512 | 0.290 | 0.975 | −0.581 | 0.882 | 1.031 | 0.771 |
| mmu_miR_137_001129 | 4.209 | 0.004 | −0.562 | 0.826 | 0.884 | 0.699 |
| mmu_miR_138_002284 | 5.124 | 0.000 | 2.447 | 0.000 | 1.125 | 0.099 |
| mmu_miR_138_002554 | 3.745 | 0.001 | 1.965 | 0.084 | 0.500 | 0.768 |
| mmu_miR_139_3p_002546 | −0.578 | 0.952 | −2.537 | 0.487 | −4.795 | 0.187 |
| mmu_miR_139_5p_002289 | 2.803 | 0.000 | −0.004 | 0.998 | −0.462 | 0.699 |
| mmu_miR_140_001187 | −0.561 | 0.586 | 1.571 | 0.051 | 0.005 | 0.995 |
| mmu_miR_141_000463 | 1.205 | 0.867 | −1.192 | 0.845 | 6.412 | 0.114 |
| mmu_miR_141_002513 | 1.598 | 0.764 | −0.677 | 0.918 | 5.367 | 0.159 |
| mmu_miR_142_3p_000464 | −0.776 | 0.823 | −7.005 | 0.001 | 4.637 | 0.025 |
| mmu_miR_142_5p_002248 | 1.343 | 0.850 | −3.859 | 0.353 | 5.552 | 0.202 |
| mmu_miR_143_002249 | −2.661 | 0.022 | −2.608 | 0.036 | 3.637 | 0.005 |
| mmu_miR_145_002278 | −2.324 | 0.069 | −3.235 | 0.017 | 4.184 | 0.003 |
| mmu_miR_145_002514 | −3.377 | 0.180 | 0.273 | 0.953 | 0.027 | 0.993 |
| mmu_miR_146a_000468 | 0.407 | 0.469 | −1.911 | 0.000 | 3.111 | 0.000 |
| mmu_miR_146b_001097 | −0.796 | 0.084 | −1.028 | 0.032 | −0.675 | 0.217 |
| mmu_miR_146b_002453 | −0.660 | 0.936 | −4.107 | 0.184 | −2.225 | 0.568 |
| mmu_miR_147_002262 | 2.127 | 0.617 | 6.481 | 0.043 | 11.332 | 0.001 |
| mmu_miR_148a_000470 | −1.970 | 0.113 | 1.910 | 0.153 | −0.749 | 0.679 |
| mmu_miR_148b_000471 | 0.098 | 0.988 | −0.931 | 0.415 | −0.200 | 0.914 |
| mmu_miR_150_000473 | 1.049 | 0.299 | −3.081 | 0.002 | 3.363 | 0.001 |
| mmu_miR_150_002570 | −2.011 | 0.570 | −6.503 | 0.020 | −0.521 | 0.914 |
| mmu_miR_151_3p_001190 | −5.001 | 0.000 | −0.705 | 0.477 | −2.276 | 0.014 |
| mmu_miR_152_000475 | −5.426 | 0.000 | −3.600 | 0.000 | −0.140 | 0.914 |
| mmu_miR_153_001191 | 3.399 | 0.007 | −2.008 | 0.153 | 0.232 | 0.917 |
| mmu_miR_154_000477 | 5.737 | 0.000 | 1.117 | 0.471 | −1.186 | 0.517 |
| mmu_miR_155_002571 | −4.409 | 0.000 | −4.876 | 0.000 | 2.289 | 0.027 |
| mmu_miR_15a_000389 | −2.134 | 0.087 | 0.757 | 0.656 | −0.566 | 0.771 |
| mmu_miR_15a_002488 | −1.864 | 0.017 | −2.938 | 0.001 | −0.443 | 0.721 |
| mmu_miR_15b_000390 | −1.930 | 0.000 | −1.807 | 0.001 | 0.184 | 0.826 |
| mmu_miR_16_000391 | −0.155 | 0.855 | −0.165 | 0.823 | 0.349 | 0.564 |
| mmu_miR_16_002489 | −3.736 | 0.002 | −1.777 | 0.189 | 0.034 | 0.992 |
| mmu_miR_17_002308 | −3.351 | 0.000 | −1.123 | 0.190 | −2.019 | 0.020 |
| mmu_miR_17_002543 | −2.176 | 0.667 | −2.059 | 0.664 | 4.063 | 0.360 |
| mmu_miR_181A_2_002687 | −2.090 | 0.116 | 0.048 | 0.979 | −0.853 | 0.657 |
| mmu_miR_181a_000480 | −2.436 | 0.000 | −0.654 | 0.316 | −1.104 | 0.102 |
| mmu_miR_181c_000482 | −0.748 | 0.374 | −1.086 | 0.174 | −1.765 | 0.028 |
| mmu_miR_182_002599 | 1.411 | 0.690 | −0.383 | 0.933 | −0.055 | 0.992 |
| mmu_miR_1839_3p_121203_mat | −0.375 | 0.835 | 2.313 | 0.021 | 0.335 | 0.841 |
| mmu_miR_1839_5p_121135_mat | −1.080 | 0.641 | 1.854 | 0.302 | −1.334 | 0.552 |
| mmu_miR_183_002269 | 4.285 | 0.013 | −2.463 | 0.199 | −0.251 | 0.929 |
| mmu_miR_184_000485 | 5.021 | 0.012 | −0.328 | 0.933 | 3.225 | 0.187 |
| mmu_miR_185_002271 | 3.024 | 0.003 | 3.368 | 0.003 | −1.089 | 0.444 |
| mmu_miR_186_002285 | −1.204 | 0.312 | −0.842 | 0.511 | −0.415 | 0.827 |
| mmu_miR_186_002574 | −0.216 | 0.957 | −2.330 | 0.069 | 0.327 | 0.884 |
| mmu_miR_187_001193 | −5.563 | 0.000 | −0.942 | 0.351 | −5.026 | 0.000 |
| mmu_miR_188_3p_002106 | −0.210 | 0.941 | 0.518 | 0.695 | 0.530 | 0.703 |
| mmu_miR_188_5p_002320 | −1.688 | 0.357 | −6.391 | 0.000 | 0.010 | 0.995 |
| mmu_miR_1893_121170_mat | −0.259 | 0.983 | −0.400 | 0.932 | −1.144 | 0.759 |

TABLE 3-continued

| Spinal Cord miRNA data. | | | | | | |
|---|---|---|---|---|---|---|
| mmu_miR_1894_3p_241002_mat | −0.118 | 0.996 | −3.743 | 0.293 | 5.302 | 0.159 |
| mmu_miR_1894_5p_121144_mat | −0.506 | 0.854 | 0.568 | 0.798 | 0.639 | 0.771 |
| mmu_miR_1896_121128_mat | −1.592 | 0.823 | −3.039 | 0.508 | 6.210 | 0.167 |
| mmu_miR_1897_3p_121126_mat | 0.167 | 0.757 | −0.113 | 0.844 | −1.131 | 0.002 |
| mmu_miR_1897_5p_121199_mat | −0.413 | 0.945 | −4.607 | 0.035 | 3.400 | 0.167 |
| mmu_miR_1898_121195_mat | 0.184 | 0.748 | −0.131 | 0.826 | −1.307 | 0.001 |
| mmu_miR_1899_121198_mat | 0.095 | 0.983 | 0.164 | 0.918 | −0.470 | 0.717 |
| mmu_miR_18a_002422 | 0.121 | 0.988 | 0.203 | 0.933 | 0.110 | 0.963 |
| mmu_miR_18a_002490 | −1.631 | 0.370 | −1.945 | 0.267 | −1.043 | 0.650 |
| mmu_miR_18b_002466 | 5.992 | 0.017 | 5.322 | 0.050 | 5.025 | 0.095 |
| mmu_miR_1900_121143_mat | 0.127 | 0.961 | 0.056 | 0.972 | −0.749 | 0.487 |
| mmu_miR_1901_121183_mat | 0.223 | 0.994 | −0.892 | 0.882 | 1.648 | 0.743 |
| mmu_miR_1902_121197_mat | 0.161 | 0.820 | −0.044 | 0.953 | −0.990 | 0.016 |
| mmu_miR_1903_121153_mat | 0.657 | 0.961 | 2.086 | 0.745 | 0.377 | 0.963 |
| mmu_miR_1904_121162_mat | 1.439 | 0.040 | −3.372 | 0.000 | 4.328 | 0.000 |
| mmu_miR_1905_121196_mat | 3.253 | 0.399 | −3.747 | 0.312 | 6.088 | 0.111 |
| mmu_miR_1906_121169_mat | −1.435 | 0.540 | 0.109 | 0.973 | −0.298 | 0.924 |
| mmu_miR_190_000489 | −1.183 | 0.376 | −2.119 | 0.084 | −0.586 | 0.742 |
| mmu_miR_191_002299 | −0.410 | 0.345 | −0.071 | 0.922 | −0.384 | 0.453 |
| mmu_miR_191_002576 | 0.495 | 0.736 | 0.607 | 0.616 | 1.543 | 0.159 |
| mmu_miR_1927_121193_mat | −0.829 | 0.823 | 0.400 | 0.918 | 0.279 | 0.929 |
| mmu_miR_1928_121164_mat | 0.373 | 0.961 | −3.766 | 0.138 | 3.811 | 0.167 |
| mmu_miR_192_000491 | −1.181 | 0.169 | 1.790 | 0.038 | −0.897 | 0.412 |
| mmu_miR_1930_121201_mat | 1.776 | 0.306 | 1.147 | 0.556 | 2.163 | 0.251 |
| mmu_miR_1931_121168_mat | 0.220 | 0.961 | 0.071 | 0.978 | −0.674 | 0.742 |
| mmu_miR_1932_121172_mat | −3.562 | 0.374 | 0.878 | 0.885 | −0.191 | 0.978 |
| mmu_miR_1933_3p_121145_mat | 0.161 | 0.890 | 0.019 | 0.979 | −0.871 | 0.171 |
| mmu_miR_1933_5p_121133_mat | −5.671 | 0.385 | −3.511 | 0.650 | −0.819 | 0.929 |
| mmu_miR_1934_121185_mat | 2.311 | 0.558 | 2.389 | 0.506 | 2.155 | 0.619 |
| mmu_miR_1935_121192_mat | 0.255 | 0.969 | −0.047 | 0.985 | −0.526 | 0.875 |
| mmu_miR_1936_121158_mat | 0.072 | 0.996 | 0.479 | 0.840 | 0.837 | 0.677 |
| mmu_miR_1937b_241023_mat | 0.248 | 0.996 | −3.117 | 0.792 | 4.159 | 0.721 |
| mmu_miR_1937c_241011_mat | 0.285 | 0.776 | −3.710 | 0.000 | 3.868 | 0.000 |
| mmu_miR_1938_121194_mat | 0.032 | 0.997 | 0.564 | 0.855 | 0.897 | 0.740 |
| mmu_miR_1939_121180_mat | −0.699 | 0.936 | 1.062 | 0.834 | 1.427 | 0.759 |
| mmu_miR_193_002250 | −1.252 | 0.823 | −2.085 | 0.579 | 1.070 | 0.836 |
| mmu_miR_193_002577 | −2.553 | 0.001 | −1.062 | 0.198 | 1.408 | 0.108 |
| mmu_miR_193b_002467 | −1.179 | 0.075 | 1.986 | 0.005 | 1.129 | 0.151 |
| mmu_miR_1940_121187_mat | 1.227 | 0.767 | 2.295 | 0.426 | 0.461 | 0.916 |
| mmu_miR_1941_3p_121130_mat | 0.026 | 0.996 | 0.560 | 0.392 | 0.852 | 0.213 |
| mmu_miR_1941_5p_121140_mat | −1.478 | 0.525 | −1.189 | 0.616 | −0.746 | 0.808 |
| mmu_miR_1942_121136_mat | −1.701 | 0.885 | −4.811 | 0.440 | 2.994 | 0.716 |
| mmu_miR_1943_121174_mat | −2.786 | 0.004 | −0.552 | 0.704 | −0.083 | 0.963 |
| mmu_miR_1944_121189_mat | −1.152 | 0.747 | 0.187 | 0.970 | −3.058 | 0.252 |
| mmu_miR_1945_121166_mat | 0.098 | 0.979 | 0.540 | 0.600 | 0.642 | 0.561 |
| mmu_miR_1946a_121178_mat | −0.759 | 0.941 | −0.936 | 0.882 | −0.964 | 0.875 |
| mmu_miR_1947_121156_mat | −2.499 | 0.247 | 0.931 | 0.763 | 1.851 | 0.504 |
| mmu_miR_1948_121171_mat | −0.315 | 0.964 | 1.954 | 0.406 | 0.573 | 0.876 |
| mmu_miR_1949_121182_mat | 0.207 | 0.907 | 0.099 | 0.948 | −0.525 | 0.626 |
| mmu_miR_194_000493 | −0.762 | 0.618 | −2.406 | 0.036 | −0.490 | 0.782 |
| mmu_miR_1950_121146_mat | −2.759 | 0.110 | −0.945 | 0.703 | −0.926 | 0.726 |

TABLE 3-continued

| Spinal Cord miRNA data. | | | | | | |
|---|---|---|---|---|---|---|
| mmu_miR_1951_121165_mat | 0.450 | 0.994 | 1.741 | 0.882 | 5.624 | 0.548 |
| mmu_miR_1952_121167_mat | 0.170 | 0.764 | −0.087 | 0.885 | −1.082 | 0.004 |
| mmu_miR_1953_121159_mat | 0.071 | 0.994 | 0.421 | 0.784 | 0.155 | 0.924 |
| mmu_miR_1954_121137_mat | 0.597 | 0.918 | −2.586 | 0.314 | 7.237 | 0.004 |
| mmu_miR_1956_121129_mat | −1.865 | 0.806 | 2.812 | 0.603 | 3.914 | 0.492 |
| mmu_miR_1957_121163_mat | 0.175 | 0.690 | −0.141 | 0.754 | −1.201 | 0.000 |
| mmu_miR_1958_121181_mat | −2.992 | 0.185 | 0.459 | 0.917 | 0.893 | 0.807 |
| mmu_miR_1959_121132_mat | 0.923 | 0.690 | −2.175 | 0.194 | 7.493 | 0.000 |
| mmu_miR_195_000494 | −3.548 | 0.000 | −0.650 | 0.354 | −0.966 | 0.187 |
| mmu_miR_1960_121148_mat | −1.397 | 0.539 | 0.881 | 0.744 | 1.185 | 0.645 |
| mmu_miR_1961_197391_mat | 0.801 | 0.945 | −3.680 | 0.434 | 8.359 | 0.071 |
| mmu_miR_1962_121173_mat | −0.370 | 0.886 | 0.087 | 0.972 | −1.153 | 0.463 |
| mmu_miR_1963_121191_mat | 0.175 | 0.690 | −0.141 | 0.754 | −1.201 | 0.000 |
| mmu_miR_1964_121138_mat | −0.971 | 0.456 | 0.718 | 0.605 | 0.871 | 0.560 |
| mmu_miR_1965_121186_mat | 0.130 | 0.846 | −0.162 | 0.760 | −1.202 | 0.002 |
| mmu_miR_1966_121134_mat | 0.362 | 0.572 | 0.034 | 0.972 | −1.658 | 0.002 |
| mmu_miR_1967_121151_mat | 0.178 | 0.835 | −0.129 | 0.882 | −1.140 | 0.025 |
| mmu_miR_1968_121179_mat | −4.976 | 0.114 | 0.069 | 0.986 | 2.134 | 0.637 |
| mmu_miR_1969_121131_mat | 0.136 | 0.994 | −3.625 | 0.071 | 3.576 | 0.105 |
| mmu_miR_196a_002477 | 0.220 | 0.996 | 3.305 | 0.692 | 5.321 | 0.508 |
| mmu_miR_196b_002215 | −1.705 | 0.456 | 2.604 | 0.199 | 0.070 | 0.984 |
| mmu_miR_1970_121202_mat | 3.328 | 0.270 | 0.134 | 0.979 | −1.939 | 0.629 |
| mmu_miR_1971_121161_mat | −5.039 | 0.129 | −3.409 | 0.354 | −3.363 | 0.442 |
| mmu_miR_197_000497 | 5.635 | 0.190 | −0.825 | 0.918 | 10.105 | 0.027 |
| mmu_miR_1981_121200_mat | 0.870 | 0.385 | −0.876 | 0.369 | −0.137 | 0.925 |
| mmu_miR_1982.1_121157_mat | −2.220 | 0.106 | −3.256 | 0.022 | −1.249 | 0.506 |
| mmu_miR_1982.2_121154_mat | 0.936 | 0.820 | −2.690 | 0.265 | −0.327 | 0.927 |
| mmu_miR_199a_3p_002304 | −5.629 | 0.000 | −7.529 | 0.000 | −3.536 | 0.027 |
| mmu_miR_199a_5p_000498 | 0.824 | 0.835 | 0.712 | 0.845 | −0.800 | 0.830 |
| mmu_miR_199b_001131 | 0.014 | 0.998 | 1.992 | 0.360 | 1.256 | 0.657 |
| mmu_miR_19a_000395 | −2.883 | 0.000 | −2.740 | 0.000 | −0.305 | 0.742 |
| mmu_miR_19a_002544 | 0.121 | 0.936 | 0.213 | 0.791 | −0.383 | 0.603 |
| mmu_miR_19b_000396 | −3.279 | 0.000 | −1.683 | 0.027 | −1.550 | 0.063 |
| mmu_miR_1_002222 | 3.831 | 0.023 | 1.392 | 0.502 | 1.272 | 0.610 |
| mmu_miR_1_2_AS_002882 | −3.088 | 0.484 | −4.200 | 0.293 | 1.722 | 0.759 |
| mmu_miR_200a_000502 | −1.466 | 0.715 | −0.577 | 0.911 | 2.654 | 0.444 |
| mmu_miR_200b_002251 | −4.009 | 0.378 | −2.162 | 0.706 | 3.936 | 0.456 |
| mmu_miR_200c_002300 | −0.494 | 0.961 | −0.469 | 0.933 | −0.951 | 0.855 |
| mmu_miR_201_002578 | −0.139 | 0.994 | 0.300 | 0.943 | 0.583 | 0.875 |
| mmu_miR_202_3p_001195 | 1.468 | 0.774 | −4.312 | 0.193 | 4.378 | 0.230 |
| mmu_miR_202_5p_002579 | −0.069 | 0.996 | 0.066 | 0.979 | 1.495 | 0.519 |
| mmu_miR_203_000507 | −7.272 | 0.002 | −6.233 | 0.012 | −4.873 | 0.067 |
| mmu_miR_203_002580 | −4.173 | 0.153 | 0.494 | 0.927 | 1.000 | 0.839 |
| mmu_miR_204_000508 | −3.795 | 0.000 | −1.509 | 0.008 | −0.087 | 0.924 |
| mmu_miR_205_000509 | 0.005 | 1.000 | −6.973 | 0.019 | −4.539 | 0.171 |
| mmu_miR_207_001198 | 0.238 | 0.944 | 0.250 | 0.915 | −0.837 | 0.613 |
| mmu_miR_208_000511 | 3.037 | 0.649 | −3.823 | 0.487 | −2.379 | 0.741 |
| mmu_miR_208b_002290 | −0.719 | 0.957 | −2.870 | 0.558 | 3.480 | 0.521 |
| mmu_miR_20a_000580 | −2.949 | 0.000 | −3.009 | 0.000 | −1.470 | 0.032 |
| mmu_miR_20a_002491 | 0.400 | 0.943 | −1.959 | 0.360 | −0.333 | 0.920 |
| mmu_miR_20b_001014 | −3.923 | 0.012 | −2.550 | 0.141 | −1.544 | 0.473 |

TABLE 3-continued

Spinal Cord miRNA data.

| | | | | | | |
|---|---|---|---|---|---|---|
| mmu_miR_20b_002524 | 3.495 | 0.088 | 3.380 | 0.123 | 2.918 | 0.233 |
| mmu_miR_210_000512 | −9.700 | 0.000 | −5.759 | 0.000 | −5.582 | 0.001 |
| mmu_miR_211_001199 | −1.515 | 0.907 | −0.931 | 0.930 | −0.077 | 0.993 |
| mmu_miR_212_002551 | 4.763 | 0.000 | 2.609 | 0.024 | −1.577 | 0.236 |
| mmu_miR_2134_241120_mat | 0.996 | 0.687 | −3.964 | 0.020 | 4.988 | 0.005 |
| mmu_miR_2135_241140_mat | −1.092 | 0.961 | −7.661 | 0.319 | 0.929 | 0.933 |
| mmu_miR_2136_241133_mat | −1.565 | 0.941 | −2.265 | 0.855 | −0.523 | 0.970 |
| mmu_miR_2138_241080_mat | 0.531 | 0.961 | −5.369 | 0.123 | 6.687 | 0.071 |
| mmu_miR_2139_241130_mat | 0.071 | 0.996 | 0.463 | 0.882 | 1.657 | 0.464 |
| mmu_miR_2146_241082_mat | −1.079 | 0.885 | −4.096 | 0.279 | 2.655 | 0.579 |
| mmu_miR_214_002306 | −1.889 | 0.256 | −0.425 | 0.882 | 0.097 | 0.974 |
| mmu_miR_215_001200 | −1.162 | 0.690 | −6.341 | 0.003 | −0.043 | 0.992 |
| mmu_miR_216a_002220 | 4.735 | 0.001 | −2.118 | 0.190 | 0.573 | 0.827 |
| mmu_miR_216b_002326 | 10.332 | 0.000 | 0.172 | 0.955 | 0.616 | 0.822 |
| mmu_miR_217_001133 | 5.514 | 0.001 | 3.502 | 0.047 | 2.509 | 0.209 |
| mmu_miR_217_002556 | 5.231 | 0.000 | 0.135 | 0.961 | 2.444 | 0.110 |
| mmu_miR_2182_241119_mat | 0.919 | 0.882 | 2.530 | 0.445 | 5.709 | 0.082 |
| mmu_miR_2183_241095_mat | 0.244 | 0.983 | −3.668 | 0.121 | 6.044 | 0.013 |
| mmu_miR_218_000521 | 7.436 | 0.000 | 3.821 | 0.000 | 2.330 | 0.000 |
| mmu_miR_218_1_002552 | 5.499 | 0.000 | 1.113 | 0.401 | 0.299 | 0.891 |
| mmu_miR_219_000522 | −6.044 | 0.000 | −2.064 | 0.075 | −4.608 | 0.000 |
| mmu_miR_21_000397 | −1.442 | 0.076 | −2.587 | 0.003 | 0.723 | 0.521 |
| mmu_miR_21_002493 | −0.033 | 0.996 | 0.365 | 0.882 | 1.589 | 0.355 |
| mmu_miR_220_002468 | 0.190 | 0.736 | −0.100 | 0.882 | −1.065 | 0.006 |
| mmu_miR_221_000524 | −2.920 | 0.000 | −0.734 | 0.112 | −1.199 | 0.012 |
| mmu_miR_222_002276 | −0.473 | 0.156 | −1.340 | 0.000 | −1.253 | 0.001 |
| mmu_miR_223_002295 | −0.163 | 0.945 | −10.692 | 0.000 | 4.655 | 0.000 |
| mmu_miR_224_002553 | −4.117 | 0.000 | −2.791 | 0.014 | −3.191 | 0.007 |
| mmu_miR_23a_000399 | −2.479 | 0.110 | 0.658 | 0.786 | 1.397 | 0.508 |
| mmu_miR_23b_000400 | 0.698 | 0.599 | 1.135 | 0.298 | 0.730 | 0.603 |
| mmu_miR_24_000402 | 0.083 | 0.889 | −0.207 | 0.538 | 0.387 | 0.239 |
| mmu_miR_24_2_002494 | −2.101 | 0.010 | −1.220 | 0.184 | 0.744 | 0.521 |
| mmu_miR_25_000403 | −1.754 | 0.157 | 3.844 | 0.003 | 1.255 | 0.437 |
| mmu_miR_26a_000405 | −1.051 | 0.003 | 0.399 | 0.329 | −0.536 | 0.215 |
| mmu_miR_26b_000407 | −1.983 | 0.000 | −0.981 | 0.030 | −0.101 | 0.903 |
| mmu_miR_27a_000408 | −0.955 | 0.489 | −1.130 | 0.369 | 2.818 | 0.024 |
| mmu_miR_27b_000409 | −1.401 | 0.009 | −0.905 | 0.125 | −0.590 | 0.417 |
| mmu_miR_28_000411 | −0.251 | 0.967 | −4.011 | 0.027 | 2.816 | 0.170 |
| mmu_miR_28_002545 | −4.062 | 0.019 | −4.730 | 0.012 | −2.860 | 0.173 |
| mmu_miR_290_000187 | 3.765 | 0.346 | −1.864 | 0.715 | 2.503 | 0.621 |
| mmu_miR_290_3p_002591 | 0.172 | 0.732 | −0.105 | 0.850 | −1.116 | 0.002 |
| mmu_miR_290_5p_002590 | −0.247 | 0.994 | 0.225 | 0.972 | 0.832 | 0.901 |
| mmu_miR_291_3p_001135 | 1.202 | 0.108 | 0.821 | 0.321 | −0.046 | 0.974 |
| mmu_miR_291_5p_001202 | 0.210 | 0.790 | −0.119 | 0.882 | −1.793 | 0.001 |
| mmu_miR_291a_3p_002592 | 0.168 | 0.730 | −0.108 | 0.841 | −1.127 | 0.001 |
| mmu_miR_291b_3p_002538 | 0.136 | 0.935 | 0.091 | 0.933 | −0.635 | 0.391 |
| mmu_miR_291b_5p_002537 | 0.148 | 0.877 | −0.725 | 0.133 | −1.196 | 0.015 |
| mmu_miR_292_3p_001054 | 4.448 | 0.063 | 3.944 | 0.128 | 3.014 | 0.318 |
| mmu_miR_292_3p_002593 | −0.076 | 0.997 | −5.404 | 0.299 | 0.907 | 0.914 |
| mmu_miR_292_5p_001055 | 7.043 | 0.122 | 6.376 | 0.192 | 3.322 | 0.608 |
| mmu_miR_293_001794 | 3.441 | 0.586 | 6.383 | 0.214 | 7.145 | 0.203 |

TABLE 3-continued

| Spinal Cord miRNA data. | | | | | | |
|---|---|---|---|---|---|---|
| mmu_miR_293_002594 | 0.151 | 0.991 | 0.282 | 0.932 | 0.434 | 0.891 |
| mmu_miR_294_001056 | −1.483 | 0.828 | 3.402 | 0.415 | 4.580 | 0.313 |
| mmu_miR_294_002595 | 0.175 | 0.690 | −0.141 | 0.754 | −1.201 | 0.000 |
| mmu_miR_295_000189 | −0.112 | 0.994 | −1.520 | 0.365 | 0.908 | 0.679 |
| mmu_miR_295_002596 | −0.343 | 0.961 | −0.581 | 0.882 | −1.239 | 0.679 |
| mmu_miR_296_3p_002101 | 1.031 | 0.690 | 2.097 | 0.270 | 2.149 | 0.316 |
| mmu_miR_296_5p_000527 | −1.047 | 0.461 | 3.350 | 0.006 | 1.237 | 0.421 |
| mmu_miR_297a_002454 | −5.086 | 0.000 | −1.446 | 0.157 | 0.065 | 0.971 |
| mmu_miR_297b_5p_001626 | −0.017 | 0.997 | 0.592 | 0.767 | 1.573 | 0.339 |
| mmu_miR_297c_002480 | −0.163 | 0.988 | 0.447 | 0.882 | −0.896 | 0.737 |
| mmu_miR_298_002598 | 3.627 | 0.016 | −1.125 | 0.558 | −1.539 | 0.458 |
| mmu_miR_299_002612 | 0.175 | 0.690 | −0.141 | 0.754 | −1.201 | 0.000 |
| mmu_miR_29a_002112 | 1.393 | 0.002 | 1.752 | 0.001 | −0.217 | 0.767 |
| mmu_miR_29b_000413 | 1.158 | 0.306 | −2.112 | 0.048 | 1.083 | 0.421 |
| mmu_miR_29b_002497 | 0.008 | 0.998 | −3.742 | 0.001 | 3.114 | 0.007 |
| mmu_miR_29c_000587 | 1.135 | 0.004 | 1.636 | 0.000 | 0.391 | 0.468 |
| mmu_miR_300_000191 | 3.875 | 0.118 | −2.815 | 0.301 | 0.902 | 0.836 |
| mmu_miR_300_002613 | 5.768 | 0.000 | 3.155 | 0.019 | 1.616 | 0.309 |
| mmu_miR_301a_000528 | −0.556 | 0.353 | −0.729 | 0.199 | −0.225 | 0.793 |
| mmu_miR_301b_002600 | −0.573 | 0.468 | 0.785 | 0.274 | −0.163 | 0.895 |
| mmu_miR_302a_000529 | 1.639 | 0.857 | 3.536 | 0.531 | 5.310 | 0.369 |
| mmu_miR_302a_002615 | −1.010 | 0.835 | 0.365 | 0.945 | 0.130 | 0.978 |
| mmu_miR_302b_000531 | −2.108 | 0.462 | −0.339 | 0.943 | −1.883 | 0.564 |
| mmu_miR_302b_001307 | −0.158 | 0.996 | 0.249 | 0.971 | 0.458 | 0.929 |
| mmu_miR_302c_002557 | 3.762 | 0.100 | 3.339 | 0.182 | 2.930 | 0.301 |
| mmu_miR_302c_002558 | 1.198 | 0.882 | 2.668 | 0.558 | 1.731 | 0.767 |
| mmu_miR_302d_000535 | 2.089 | 0.588 | −0.013 | 0.998 | 2.123 | 0.608 |
| mmu_miR_30a_000417 | −0.982 | 0.009 | −0.613 | 0.141 | −0.270 | 0.628 |
| mmu_miR_30b_000602 | −0.211 | 0.690 | −0.145 | 0.791 | −0.297 | 0.539 |
| mmu_miR_30b_002498 | −1.594 | 0.418 | 0.328 | 0.918 | 0.962 | 0.702 |
| mmu_miR_30c_000419 | −0.138 | 0.797 | −0.551 | 0.084 | −0.360 | 0.352 |
| mmu_miR_30d_000420 | −1.663 | 0.006 | −0.800 | 0.238 | −0.026 | 0.983 |
| mmu_miR_30e_002223 | −1.332 | 0.000 | −0.403 | 0.197 | −0.126 | 0.787 |
| mmu_miR_31_000185 | −0.535 | 0.570 | 0.732 | 0.359 | 1.002 | 0.236 |
| mmu_miR_31_002495 | 0.961 | 0.764 | 2.051 | 0.353 | 0.359 | 0.916 |
| mmu_miR_320_002277 | −2.015 | 0.000 | 0.490 | 0.259 | −0.456 | 0.361 |
| mmu_miR_322_001059 | −4.848 | 0.209 | −4.416 | 0.279 | −3.192 | 0.529 |
| mmu_miR_322_001076 | −8.070 | 0.000 | −5.020 | 0.003 | −7.250 | 0.000 |
| mmu_miR_322_002506 | −7.610 | 0.000 | −6.730 | 0.000 | −5.900 | 0.001 |
| mmu_miR_323_3p_002227 | 9.271 | 0.000 | 2.885 | 0.001 | −0.704 | 0.544 |
| mmu_miR_324_3p_002509 | −2.299 | 0.017 | 0.199 | 0.918 | −2.304 | 0.037 |
| mmu_miR_324_5p_000539 | −1.495 | 0.194 | −0.458 | 0.791 | −1.257 | 0.373 |
| mmu_miR_325_001060 | −3.766 | 0.345 | −9.421 | 0.011 | −4.450 | 0.309 |
| mmu_miR_325_002510 | 1.632 | 0.075 | 1.324 | 0.187 | −0.258 | 0.875 |
| mmu_miR_326_001061 | −8.565 | 0.088 | −1.067 | 0.917 | −1.497 | 0.871 |
| mmu_miR_327_002481 | 1.654 | 0.154 | 1.417 | 0.256 | 0.657 | 0.699 |
| mmu_miR_328_000543 | 0.982 | 0.013 | 0.909 | 0.033 | 0.160 | 0.826 |
| mmu_miR_329_000192 | 5.034 | 0.000 | 2.245 | 0.034 | 0.769 | 0.599 |
| mmu_miR_32_002109 | −3.230 | 0.216 | −7.530 | 0.004 | 1.693 | 0.637 |
| mmu_miR_330_001062 | 2.157 | 0.721 | −0.505 | 0.948 | 2.228 | 0.706 |
| mmu_miR_330_002230 | 1.918 | 0.120 | −0.160 | 0.948 | −0.872 | 0.620 |

TABLE 3-continued

| Spinal Cord miRNA data. | | | | | | |
|---|---|---|---|---|---|---|
| mmu_miR_331_3p_000545 | 0.717 | 0.218 | 2.268 | 0.000 | 1.145 | 0.067 |
| mmu_miR_331_5p_002233 | 3.571 | 0.152 | −2.213 | 0.426 | 1.555 | 0.661 |
| mmu_miR_335_3p_002185 | 7.875 | 0.000 | 4.941 | 0.000 | 0.419 | 0.851 |
| mmu_miR_335_5p_000546 | 4.132 | 0.000 | 2.146 | 0.001 | 1.047 | 0.108 |
| mmu_miR_337_000193 | 2.934 | 0.017 | 1.763 | 0.199 | 1.057 | 0.548 |
| mmu_miR_337_3p_002532 | 4.982 | 0.000 | 2.015 | 0.084 | 1.205 | 0.411 |
| mmu_miR_337_5p_002515 | 1.616 | 0.492 | 0.274 | 0.943 | 2.277 | 0.350 |
| mmu_miR_338_3p_002252 | −4.032 | 0.000 | −2.876 | 0.013 | −2.023 | 0.110 |
| mmu_miR_339_3p_002533 | −0.796 | 0.822 | −1.905 | 0.365 | 2.055 | 0.402 |
| mmu_miR_339_5p_002257 | −4.104 | 0.000 | −0.627 | 0.706 | −1.661 | 0.229 |
| mmu_miR_340_3p_002259 | 0.251 | 0.652 | 0.212 | 0.706 | 0.591 | 0.200 |
| mmu_miR_340_5p_002258 | −0.357 | 0.462 | 0.609 | 0.158 | 0.006 | 0.993 |
| mmu_miR_342_3p_002260 | 2.559 | 0.000 | 0.430 | 0.321 | −0.507 | 0.293 |
| mmu_miR_342_5p_002527 | 5.917 | 0.000 | 0.540 | 0.803 | 0.876 | 0.657 |
| mmu_miR_343_002483 | 0.146 | 0.924 | −1.008 | 0.101 | −1.393 | 0.030 |
| mmu_miR_344_001063 | −1.328 | 0.239 | 1.663 | 0.145 | −1.968 | 0.107 |
| mmu_miR_345_001137 | −1.476 | 0.125 | 0.409 | 0.784 | 0.296 | 0.868 |
| mmu_miR_345_3p_002529 | −0.164 | 0.967 | 1.510 | 0.225 | 1.713 | 0.204 |
| mmu_miR_345_5p_002528 | −2.728 | 0.000 | 0.627 | 0.449 | −0.782 | 0.402 |
| mmu_miR_346_001064 | 1.131 | 0.513 | 1.437 | 0.354 | 1.950 | 0.236 |
| mmu_miR_34a_000426 | 5.086 | 0.000 | 1.223 | 0.044 | 0.291 | 0.742 |
| mmu_miR_34b_001065 | 2.775 | 0.041 | 3.392 | 0.020 | 2.348 | 0.151 |
| mmu_miR_34b_3p_002618 | 1.417 | 0.002 | 2.030 | 0.000 | 1.508 | 0.004 |
| mmu_miR_34b_5p_002617 | 1.409 | 0.345 | 0.357 | 0.882 | 2.079 | 0.177 |
| mmu_miR_34c_000428 | 2.246 | 0.004 | 4.578 | 0.000 | 1.396 | 0.139 |
| mmu_miR_34c_002584 | 1.218 | 0.037 | −0.027 | 0.979 | 1.151 | 0.095 |
| mmu_miR_350_002530 | −3.655 | 0.000 | −2.169 | 0.000 | −1.249 | 0.036 |
| mmu_miR_351_001067 | 0.225 | 0.944 | 0.342 | 0.855 | −2.075 | 0.098 |
| mmu_miR_361_000554 | 1.003 | 0.583 | 3.799 | 0.009 | 0.693 | 0.742 |
| mmu_miR_362_3p_002616 | 0.360 | 0.840 | −1.026 | 0.336 | 1.773 | 0.107 |
| mmu_miR_362_5p_002614 | −1.486 | 0.070 | 2.035 | 0.019 | 0.021 | 0.992 |
| mmu_miR_363_001271 | −3.349 | 0.190 | 0.166 | 0.972 | −2.360 | 0.473 |
| mmu_miR_365_001020 | −5.171 | 0.000 | 0.743 | 0.441 | −1.114 | 0.273 |
| mmu_miR_367_000555 | −2.483 | 0.737 | −1.287 | 0.882 | −1.469 | 0.868 |
| mmu_miR_369_3p_000557 | 5.429 | 0.000 | 1.105 | 0.299 | −0.201 | 0.912 |
| mmu_miR_369_5p_001021 | 6.353 | 0.000 | 0.135 | 0.948 | 1.938 | 0.095 |
| mmu_miR_370_001068 | 0.071 | 0.996 | 0.430 | 0.899 | 1.674 | 0.504 |
| mmu_miR_370_002275 | 9.508 | 0.000 | 2.260 | 0.002 | −2.429 | 0.001 |
| mmu_miR_374_002043 | 0.061 | 0.997 | −4.124 | 0.472 | 2.787 | 0.707 |
| mmu_miR_374_5p_001319 | −4.769 | 0.187 | −4.168 | 0.279 | −3.711 | 0.418 |
| mmu_miR_375_000564 | 2.926 | 0.011 | 2.773 | 0.024 | 0.139 | 0.946 |
| mmu_miR_376a_001069 | 5.517 | 0.000 | 1.592 | 0.003 | 0.416 | 0.548 |
| mmu_miR_376a_002482 | 5.887 | 0.001 | 2.039 | 0.334 | 0.201 | 0.951 |
| mmu_miR_376b_002451 | 4.416 | 0.306 | 5.162 | 0.225 | −0.071 | 0.992 |
| mmu_miR_376b_002452 | 8.585 | 0.000 | 2.307 | 0.028 | 0.510 | 0.742 |
| mmu_miR_376c_002450 | 3.682 | 0.000 | 2.401 | 0.000 | 0.963 | 0.053 |
| mmu_miR_376c_002523 | 2.097 | 0.395 | −0.250 | 0.953 | 0.111 | 0.978 |
| mmu_miR_377_000566 | 1.534 | 0.471 | 1.343 | 0.525 | 0.561 | 0.863 |
| mmu_miR_379_001138 | 4.389 | 0.000 | 4.162 | 0.001 | 0.947 | 0.531 |
| mmu_miR_380_3p_001071 | 4.779 | 0.000 | 3.099 | 0.003 | 1.664 | 0.146 |
| mmu_miR_380_5p_002601 | 6.742 | 0.000 | 2.159 | 0.002 | 1.936 | 0.007 |

TABLE 3-continued

| Spinal Cord miRNA data. | | | | | | |
|---|---|---|---|---|---|---|
| mmu_miR_381_000571 | 4.944 | 0.001 | −1.787 | 0.289 | −0.060 | 0.983 |
| mmu_miR_382_000572 | 8.447 | 0.000 | 3.934 | 0.005 | −1.376 | 0.441 |
| mmu_miR_383_001767 | 7.441 | 0.000 | 2.533 | 0.000 | 0.544 | 0.539 |
| mmu_miR_384_3p_002603 | 2.112 | 0.000 | 1.046 | 0.084 | −0.152 | 0.884 |
| mmu_miR_384_5p_002602 | 2.758 | 0.000 | 0.771 | 0.050 | −0.135 | 0.836 |
| mmu_miR_409_3p_002332 | 4.745 | 0.000 | 3.160 | 0.004 | 1.029 | 0.458 |
| mmu_miR_409_5p_002331 | 8.482 | 0.000 | 3.647 | 0.001 | 1.755 | 0.111 |
| mmu_miR_410_001274 | 5.178 | 0.000 | 2.492 | 0.000 | 0.084 | 0.916 |
| mmu_miR_411_001610 | 3.639 | 0.000 | 1.837 | 0.009 | 0.275 | 0.807 |
| mmu_miR_412_002575 | 8.665 | 0.000 | −0.268 | 0.882 | −0.063 | 0.973 |
| mmu_miR_423_5p_002340 | −3.233 | 0.000 | −2.175 | 0.021 | −0.743 | 0.551 |
| mmu_miR_425_001516 | 1.711 | 0.488 | −4.554 | 0.029 | 4.197 | 0.066 |
| mmu_miR_429_001077 | 2.568 | 0.378 | 0.664 | 0.882 | 2.891 | 0.370 |
| mmu_miR_431_001979 | 2.223 | 0.028 | −1.743 | 0.117 | −4.616 | 0.000 |
| mmu_miR_432_241135_mat | −1.407 | 0.833 | −3.461 | 0.384 | −2.469 | 0.628 |
| mmu_miR_433_001028 | 5.030 | 0.000 | 1.330 | 0.009 | 0.137 | 0.875 |
| mmu_miR_433_5p_001078 | 2.017 | 0.649 | −3.246 | 0.354 | 0.657 | 0.912 |
| mmu_miR_434_3p_002604 | 5.044 | 0.000 | 0.998 | 0.048 | −0.060 | 0.943 |
| mmu_miR_434_5p_002581 | 7.306 | 0.000 | 2.398 | 0.048 | −0.342 | 0.874 |
| mmu_miR_448_001029 | 8.071 | 0.000 | 2.194 | 0.218 | −0.588 | 0.836 |
| mmu_miR_449a_001030 | 2.903 | 0.036 | −2.008 | 0.190 | 0.927 | 0.650 |
| mmu_miR_449b_001667 | 4.277 | 0.020 | −0.925 | 0.754 | 2.201 | 0.364 |
| mmu_miR_449b_002539 | 0.172 | 0.719 | −0.108 | 0.841 | −1.130 | 0.001 |
| mmu_miR_450B_3P_002632 | −2.905 | 0.394 | −5.323 | 0.084 | −2.193 | 0.603 |
| mmu_miR_450a_3p_002525 | 0.175 | 0.690 | −0.141 | 0.754 | −1.201 | 0.000 |
| mmu_miR_450a_5p_002303 | −2.769 | 0.048 | −1.540 | 0.334 | −2.984 | 0.065 |
| mmu_miR_450b_5p_001962 | 0.145 | 0.918 | −0.036 | 0.972 | −0.936 | 0.151 |
| mmu_miR_451_001141 | −4.842 | 0.154 | −6.224 | 0.073 | 0.824 | 0.896 |
| mmu_miR_452_001032 | 0.723 | 0.943 | 1.195 | 0.841 | 3.886 | 0.380 |
| mmu_miR_453_002484 | 0.112 | 0.991 | 0.344 | 0.882 | 0.113 | 0.963 |
| mmu_miR_455_002455 | −7.521 | 0.000 | −4.167 | 0.004 | −4.250 | 0.005 |
| mmu_miR_463_002582 | 0.046 | 0.996 | −3.437 | 0.014 | 5.163 | 0.001 |
| mmu_miR_463_002662 | −3.425 | 0.185 | −7.865 | 0.003 | −1.331 | 0.729 |
| mmu_miR_464_001081 | 0.202 | 0.939 | 0.044 | 0.979 | −1.603 | 0.112 |
| mmu_miR_465C_5P_002654 | 1.929 | 0.369 | −4.658 | 0.018 | 5.129 | 0.012 |
| mmu_miR_465a_3p_002040 | 1.660 | 0.652 | −0.350 | 0.948 | −0.217 | 0.963 |
| mmu_miR_465a_5p_001082 | −8.260 | 0.194 | −2.654 | 0.784 | −3.303 | 0.727 |
| mmu_miR_465b_5p_002485 | 4.942 | 0.256 | 4.345 | 0.339 | 1.846 | 0.771 |
| mmu_miR_466E_5P_00278 | −2.304 | 0.729 | −5.556 | 0.230 | 0.951 | 0.906 |
| mmu_miR_466J_002817 | −6.904 | 0.000 | −2.722 | 0.067 | −3.240 | 0.039 |
| mmu_miR_466a_3p_002586 | −4.030 | 0.000 | −0.053 | 0.972 | −0.566 | 0.599 |
| mmu_miR_466b_3_3p_002500 | −4.068 | 0.000 | −1.190 | 0.354 | −0.678 | 0.686 |
| mmu_miR_466d_5p_002534 | 3.616 | 0.540 | −2.488 | 0.706 | 4.514 | 0.458 |
| mmu_miR_466g_241015_mat | −2.278 | 0.379 | 3.276 | 0.184 | 4.018 | 0.124 |
| mmu_miR_466h_002516 | −1.391 | 0.599 | 0.223 | 0.953 | 1.368 | 0.629 |
| mmu_miR_466k_240990_mat | −4.461 | 0.090 | −1.100 | 0.791 | 1.124 | 0.795 |
| mmu_miR_467F_002886 | −5.922 | 0.051 | −7.574 | 0.019 | −0.696 | 0.906 |
| mmu_miR_467H_002809 | −4.066 | 0.000 | 0.975 | 0.470 | −0.059 | 0.978 |
| mmu_miR_467a_001826 | −5.209 | 0.000 | −4.692 | 0.001 | −0.616 | 0.768 |
| mmu_miR_467a_002587 | −3.725 | 0.001 | 1.339 | 0.278 | −1.333 | 0.346 |
| mmu_miR_467b_001671 | −5.130 | 0.000 | −1.642 | 0.184 | −2.771 | 0.027 |

TABLE 3-continued

| Spinal Cord miRNA data. | | | | | | |
|---|---|---|---|---|---|---|
| mmu_miR_467b_001684 | −4.205 | 0.037 | −8.053 | 0.000 | 2.608 | 0.309 |
| mmu_miR_467c_002517 | −6.425 | 0.000 | −2.009 | 0.317 | −1.495 | 0.548 |
| mmu_miR_467d_002518 | −2.833 | 0.022 | −0.957 | 0.539 | 0.219 | 0.920 |
| mmu_miR_467e_002568 | −3.548 | 0.062 | −3.650 | 0.070 | −0.023 | 0.993 |
| mmu_miR_467e_002569 | −1.516 | 0.565 | 0.270 | 0.948 | −3.108 | 0.186 |
| mmu_miR_468_001085 | 0.262 | 0.961 | −0.119 | 0.972 | −3.341 | 0.067 |
| mmu_miR_469_001086 | 0.418 | 0.979 | −0.181 | 0.978 | −2.397 | 0.628 |
| mmu_miR_470_002588 | −0.488 | 0.828 | 0.519 | 0.784 | 0.672 | 0.712 |
| mmu_miR_470_002589 | −2.865 | 0.721 | −8.182 | 0.144 | 6.303 | 0.339 |
| mmu_miR_471_002605 | 0.180 | 0.852 | 0.033 | 0.972 | −0.746 | 0.203 |
| mmu_miR_483_001291 | −2.270 | 0.547 | −2.959 | 0.363 | 1.505 | 0.738 |
| mmu_miR_483_002560 | −0.254 | 0.941 | 0.368 | 0.855 | 2.606 | 0.046 |
| mmu_miR_484_001821 | −2.187 | 0.000 | −1.011 | 0.029 | −1.115 | 0.024 |
| mmu_miR_485_3p_001943 | 4.239 | 0.000 | 1.700 | 0.003 | 1.155 | 0.064 |
| mmu_miR_486_001278 | −6.407 | 0.000 | −1.600 | 0.318 | −7.399 | 0.000 |
| mmu_miR_487b_001285 | 5.104 | 0.000 | 1.309 | 0.022 | 0.802 | 0.220 |
| mmu_miR_487b_001306 | 7.099 | 0.000 | 3.152 | 0.000 | 0.276 | 0.741 |
| mmu_miR_488_001659 | −0.642 | 0.757 | 1.127 | 0.445 | 0.364 | 0.875 |
| mmu_miR_488_002014 | 2.542 | 0.371 | 4.774 | 0.067 | 4.604 | 0.107 |
| mmu_miR_489_001302 | 6.276 | 0.001 | 0.907 | 0.765 | −1.437 | 0.611 |
| mmu_miR_490_001037 | 4.692 | 0.000 | −1.430 | 0.277 | −1.670 | 0.236 |
| mmu_miR_491_001630 | 4.656 | 0.000 | 3.961 | 0.000 | 0.528 | 0.728 |
| mmu_miR_493_002519 | 1.745 | 0.558 | −1.507 | 0.606 | −1.494 | 0.650 |
| mmu_miR_494_001293 | 1.835 | 0.285 | 1.500 | 0.401 | −1.173 | 0.603 |
| mmu_miR_494_002365 | 0.339 | 0.908 | −1.252 | 0.364 | −1.713 | 0.246 |
| mmu_miR_495_001663 | 5.096 | 0.000 | 1.903 | 0.000 | 0.043 | 0.950 |
| mmu_miR_496_001953 | 1.569 | 0.649 | −2.101 | 0.452 | −3.603 | 0.205 |
| mmu_miR_497_001346 | −5.540 | 0.000 | 0.490 | 0.784 | −1.905 | 0.151 |
| mmu_miR_499_001352 | 1.750 | 0.468 | 0.405 | 0.918 | 1.157 | 0.698 |
| mmu_miR_500_002606 | 0.203 | 0.948 | 0.238 | 0.908 | −1.089 | 0.439 |
| mmu_miR_501_001356 | 0.000 | 1.000 | 0.400 | 0.918 | 0.687 | 0.847 |
| mmu_miR_501_3p_001651 | −0.323 | 0.771 | 1.220 | 0.084 | −1.672 | 0.024 |
| mmu_miR_503_002456 | −0.366 | 0.924 | −0.259 | 0.927 | −0.617 | 0.800 |
| mmu_miR_503_002536 | −3.864 | 0.000 | −1.686 | 0.111 | −1.499 | 0.203 |
| mmu_miR_504_002084 | 1.244 | 0.261 | −0.500 | 0.754 | −2.447 | 0.031 |
| mmu_miR_505_001655 | 1.006 | 0.484 | 1.624 | 0.199 | 2.213 | 0.102 |
| mmu_miR_509_3p_002521 | 0.714 | 0.967 | −2.740 | 0.706 | −0.278 | 0.978 |
| mmu_miR_509_5p_002520 | 4.369 | 0.370 | 4.125 | 0.390 | 2.736 | 0.657 |
| mmu_miR_511_002549 | 0.837 | 0.764 | 1.551 | 0.423 | 2.651 | 0.182 |
| mmu_miR_532_3p_002355 | −0.882 | 0.179 | −1.851 | 0.005 | −0.459 | 0.611 |
| mmu_miR_532_5p_001518 | −1.886 | 0.000 | −1.123 | 0.023 | −0.781 | 0.162 |
| mmu_miR_539_001286 | 4.967 | 0.000 | 4.133 | 0.000 | 0.623 | 0.669 |
| mmu_miR_540_3p_001310 | 3.160 | 0.003 | 0.555 | 0.733 | 0.597 | 0.721 |
| mmu_miR_540_5p_002561 | 5.694 | 0.000 | 2.693 | 0.023 | 1.405 | 0.330 |
| mmu_miR_541_002562 | 5.280 | 0.000 | −0.673 | 0.302 | −0.718 | 0.338 |
| mmu_miR_542_3p_001284 | −2.679 | 0.039 | −0.440 | 0.849 | −1.702 | 0.301 |
| mmu_miR_542_5p_002563 | 1.648 | 0.721 | 1.062 | 0.835 | −2.600 | 0.529 |
| mmu_miR_543_001298 | 5.130 | 0.000 | 1.455 | 0.022 | 0.119 | 0.914 |
| mmu_miR_543_002376 | 5.450 | 0.000 | 1.949 | 0.000 | 0.298 | 0.677 |
| mmu_miR_544_002550 | 6.701 | 0.000 | 4.842 | 0.000 | 1.939 | 0.062 |
| mmu_miR_546_001312 | 2.258 | 0.882 | −4.191 | 0.664 | 4.317 | 0.677 |

TABLE 3-continued

| Spinal Cord miRNA data. | | | | | | |
|---|---|---|---|---|---|---|
| mmu_miR_547_002564 | 1.049 | 0.835 | 1.958 | 0.558 | −0.621 | 0.906 |
| mmu_miR_551b_001535 | 0.347 | 0.889 | −2.149 | 0.073 | 0.399 | 0.839 |
| mmu_miR_574_3p_002349 | −5.848 | 0.000 | −4.339 | 0.000 | −4.573 | 0.000 |
| mmu_miR_582_3p_002567 | −1.142 | 0.646 | 1.703 | 0.384 | 0.997 | 0.702 |
| mmu_miR_582_5p_002566 | 0.369 | 0.820 | 1.216 | 0.192 | −0.264 | 0.868 |
| mmu_miR_590_5p_001984 | 0.306 | 0.972 | 0.221 | 0.966 | −0.630 | 0.880 |
| mmu_miR_592_002017 | 3.212 | 0.000 | 1.015 | 0.212 | 0.378 | 0.742 |
| mmu_miR_598_002476 | 2.922 | 0.011 | 2.336 | 0.061 | −0.127 | 0.951 |
| mmu_miR_599_241117_mat | −2.471 | 0.410 | 0.313 | 0.953 | −1.775 | 0.630 |
| mmu_miR_615_3p_001960 | 0.676 | 0.618 | 4.258 | 0.000 | −0.483 | 0.748 |
| mmu_miR_615_5p_002353 | 0.131 | 0.918 | 0.517 | 0.363 | 0.104 | 0.913 |
| mmu_miR_652_002352 | −3.416 | 0.001 | 0.485 | 0.772 | −2.667 | 0.025 |
| mmu_miR_654_3p_002239 | 0.144 | 0.957 | 0.104 | 0.948 | −0.927 | 0.367 |
| mmu_miR_654_5p_002522 | 0.170 | 0.957 | 0.034 | 0.979 | −0.682 | 0.619 |
| mmu_miR_665_002607 | 1.792 | 0.110 | 0.850 | 0.530 | −1.109 | 0.456 |
| mmu_miR_666_3p_002448 | 0.615 | 0.889 | 0.042 | 0.986 | 3.364 | 0.162 |
| mmu_miR_666_5p_001952 | 5.556 | 0.000 | 2.544 | 0.001 | 1.453 | 0.092 |
| mmu_miR_667_001949 | 4.972 | 0.000 | 2.518 | 0.000 | 0.166 | 0.868 |
| mmu_miR_668_001947 | 3.404 | 0.073 | 1.630 | 0.466 | −0.235 | 0.943 |
| mmu_miR_669C_002646 | −5.195 | 0.000 | −1.952 | 0.174 | −1.793 | 0.258 |
| mmu_miR_669D_002808 | −4.143 | 0.001 | −0.247 | 0.920 | −0.503 | 0.827 |
| mmu_miR_669E_002774 | −2.975 | 0.052 | 0.405 | 0.882 | 1.039 | 0.646 |
| mmu_miR_669G_002813 | 0.164 | 0.870 | 0.022 | 0.979 | −0.814 | 0.156 |
| mmu_miR_669H_5P_002906 | 0.857 | 0.822 | 1.855 | 0.423 | 0.388 | 0.914 |
| mmu_miR_669a_001683 | −0.992 | 0.649 | 1.021 | 0.605 | 1.139 | 0.603 |
| mmu_miR_669l_121149_mat | −4.415 | 0.000 | −0.053 | 0.979 | −0.386 | 0.868 |
| mmu_miR_669m_121190_mat | −1.542 | 0.570 | −1.911 | 0.415 | 2.051 | 0.455 |
| mmu_miR_669n_197143_mat | −4.025 | 0.000 | −1.000 | 0.413 | −0.795 | 0.603 |
| mmu_miR_669o_121176_mat | −2.992 | 0.030 | 0.756 | 0.712 | 0.527 | 0.833 |
| mmu_miR_670_002020 | −4.339 | 0.368 | −6.021 | 0.186 | −1.516 | 0.836 |
| mmu_miR_671_3p_002322 | −1.629 | 0.071 | −0.780 | 0.461 | 0.295 | 0.861 |
| mmu_miR_672_002327 | 9.144 | 0.000 | 5.512 | 0.002 | −0.872 | 0.738 |
| mmu_miR_673_001954 | 0.873 | 0.874 | −3.674 | 0.196 | 4.634 | 0.129 |
| mmu_miR_673_3p_002449 | 9.016 | 0.001 | −2.277 | 0.469 | 2.706 | 0.451 |
| mmu_miR_674_001956 | −3.054 | 0.000 | −0.279 | 0.823 | −0.461 | 0.677 |
| mmu_miR_674_002021 | −6.963 | 0.000 | −7.330 | 0.000 | −2.865 | 0.112 |
| mmu_miR_675_3p_001941 | −3.023 | 0.764 | −7.236 | 0.288 | 0.097 | 0.993 |
| mmu_miR_675_5p_001940 | −1.956 | 0.658 | −3.782 | 0.264 | −0.719 | 0.903 |
| mmu_miR_676_001958 | −0.224 | 0.941 | 1.006 | 0.380 | 1.088 | 0.417 |
| mmu_miR_676_001959 | −3.531 | 0.006 | 1.638 | 0.260 | −1.621 | 0.329 |
| mmu_miR_677_001660 | 0.099 | 0.994 | 0.333 | 0.882 | −2.155 | 0.151 |
| mmu_miR_679_001662 | −2.695 | 0.707 | −1.491 | 0.855 | 1.782 | 0.830 |
| mmu_miR_680_001664 | −4.295 | 0.513 | −4.935 | 0.408 | −3.539 | 0.643 |
| mmu_miR_682_001666 | 2.340 | 0.737 | −0.929 | 0.917 | 5.144 | 0.360 |
| mmu_miR_683_001668 | −1.149 | 0.889 | 0.227 | 0.973 | −1.009 | 0.884 |
| mmu_miR_684_001669 | 0.175 | 0.690 | −0.141 | 0.754 | −1.201 | 0.000 |
| mmu_miR_685_001670 | 2.592 | 0.582 | 2.127 | 0.660 | 8.034 | 0.041 |
| mmu_miR_686_001672 | −2.552 | 0.098 | −0.127 | 0.970 | −1.303 | 0.539 |
| mmu_miR_687_001674 | −0.709 | 0.484 | 0.205 | 0.887 | −0.421 | 0.742 |
| mmu_miR_688_001675 | 2.220 | 0.374 | −1.908 | 0.449 | 1.189 | 0.721 |
| mmu_miR_690_001677 | −0.108 | 0.994 | 0.500 | 0.823 | 1.159 | 0.531 |

TABLE 3-continued

| Spinal Cord miRNA data. | | | | | | |
|---|---|---|---|---|---|---|
| mmu_miR_691_001678 | 2.138 | 0.774 | −5.171 | 0.298 | 1.659 | 0.834 |
| mmu_miR_692_001679 | −0.413 | 0.950 | −4.656 | 0.039 | −3.581 | 0.160 |
| mmu_miR_693_001680 | −0.603 | 0.967 | −5.401 | 0.223 | 0.038 | 0.994 |
| mmu_miR_693_3p_002036 | −0.728 | 0.961 | −5.630 | 0.260 | −0.840 | 0.916 |
| mmu_miR_694_001681 | −0.801 | 0.941 | −5.374 | 0.182 | 5.587 | 0.200 |
| mmu_miR_695_001627 | 1.525 | 0.830 | −2.582 | 0.592 | 0.412 | 0.950 |
| mmu_miR_696_001628 | −4.505 | 0.477 | −9.029 | 0.099 | 0.944 | 0.916 |
| mmu_miR_697_001631 | −0.277 | 0.988 | 3.846 | 0.225 | 1.803 | 0.677 |
| mmu_miR_698_001632 | 0.038 | 0.996 | 0.035 | 0.979 | −0.685 | 0.595 |
| mmu_miR_700_001634 | −0.410 | 0.882 | 2.356 | 0.082 | −0.672 | 0.737 |
| mmu_miR_701_001635 | −1.908 | 0.581 | 1.048 | 0.798 | 1.845 | 0.620 |
| mmu_miR_702_001636 | 4.154 | 0.050 | 0.314 | 0.943 | 1.794 | 0.548 |
| mmu_miR_704_001639 | 1.441 | 0.386 | 1.877 | 0.236 | −0.059 | 0.983 |
| mmu_miR_706_001641 | 1.707 | 0.855 | −0.016 | 0.998 | 8.215 | 0.146 |
| mmu_miR_707_001642 | 0.143 | 0.918 | 0.066 | 0.953 | −0.762 | 0.243 |
| mmu_miR_708_002341 | −1.282 | 0.023 | 0.155 | 0.882 | −0.679 | 0.360 |
| mmu_miR_710_001645 | 1.401 | 0.941 | 2.496 | 0.811 | 5.146 | 0.563 |
| mmu_miR_711_001646 | −0.507 | 0.994 | −2.830 | 0.778 | 1.038 | 0.924 |
| mmu_miR_712_001961 | 0.298 | 0.936 | 0.270 | 0.917 | −1.892 | 0.211 |
| mmu_miR_712_002636 | −0.988 | 0.908 | −7.537 | 0.047 | 1.537 | 0.797 |
| mmu_miR_713_001648 | −0.266 | 0.996 | −0.769 | 0.953 | 0.666 | 0.958 |
| mmu_miR_715_001649 | −1.448 | 0.824 | 0.406 | 0.953 | 1.189 | 0.849 |
| mmu_miR_717_001652 | −6.698 | 0.245 | −6.378 | 0.285 | −1.314 | 0.900 |
| mmu_miR_718_001656 | 3.915 | 0.252 | 4.870 | 0.157 | 5.369 | 0.151 |
| mmu_miR_719_001673 | −0.059 | 0.996 | 0.157 | 0.968 | −2.407 | 0.246 |
| mmu_miR_720_001629 | 0.466 | 0.764 | −3.574 | 0.001 | 4.610 | 0.000 |
| mmu_miR_721_001657 | −2.053 | 0.889 | −5.555 | 0.488 | 4.723 | 0.629 |
| mmu_miR_741_002457 | −0.113 | 0.996 | −5.351 | 0.097 | 0.344 | 0.949 |
| mmu_miR_742_002038 | −1.682 | 0.419 | 0.587 | 0.849 | 0.924 | 0.737 |
| mmu_miR_742_002458 | 3.383 | 0.582 | −1.550 | 0.845 | 1.085 | 0.903 |
| mmu_miR_743a_002469 | 3.127 | 0.157 | 0.482 | 0.909 | 1.307 | 0.679 |
| mmu_miR_743b_3p_002471 | 0.120 | 0.983 | 0.277 | 0.882 | −0.320 | 0.871 |
| mmu_miR_743b_5p_002470 | −4.433 | 0.184 | −4.635 | 0.184 | 0.059 | 0.992 |
| mmu_miR_744_002324 | 1.357 | 0.105 | 0.159 | 0.920 | 0.172 | 0.912 |
| mmu_miR_758_002025 | 0.249 | 0.918 | −0.015 | 0.990 | −3.243 | 0.002 |
| mmu_miR_759_002034 | −0.123 | 0.996 | 2.529 | 0.579 | 1.014 | 0.875 |
| mmu_miR_761_002030 | −0.359 | 0.994 | −3.694 | 0.558 | 1.098 | 0.912 |
| mmu_miR_762_002028 | 0.393 | 0.983 | 2.806 | 0.524 | 2.959 | 0.559 |
| mmu_miR_763_002033 | −1.298 | 0.889 | −4.887 | 0.306 | −0.181 | 0.983 |
| mmu_miR_764_3p_002032 | 1.515 | 0.771 | 0.161 | 0.979 | −1.179 | 0.830 |
| mmu_miR_764_5p_002031 | 2.071 | 0.306 | 1.363 | 0.542 | −1.542 | 0.544 |
| mmu_miR_767_241081_mat | 0.175 | 0.690 | −0.140 | 0.754 | −1.197 | 0.000 |
| mmu_miR_770_3p_002027 | 5.398 | 0.000 | 1.304 | 0.271 | 0.707 | 0.650 |
| mmu_miR_770_5p_002608 | 3.184 | 0.000 | 1.746 | 0.063 | 0.200 | 0.906 |
| mmu_miR_7a_000268 | 3.819 | 0.110 | −3.096 | 0.232 | −1.574 | 0.650 |
| mmu_miR_7b_002555 | 5.443 | 0.002 | −2.396 | 0.208 | −0.369 | 0.912 |
| mmu_miR_802_002029 | −1.461 | 0.455 | −0.774 | 0.754 | 0.133 | 0.963 |
| mmu_miR_804_002044 | −7.713 | 0.201 | −6.905 | 0.280 | −2.508 | 0.790 |
| mmu_miR_805_002045 | −3.266 | 0.456 | −1.863 | 0.728 | 4.631 | 0.304 |
| mmu_miR_871_002354 | 0.093 | 0.996 | 0.335 | 0.918 | −0.401 | 0.903 |
| mmu_miR_872_002264 | −1.123 | 0.041 | 2.227 | 0.000 | 0.170 | 0.870 |

TABLE 3-continued

Spinal Cord miRNA data.

| | log2FC_ GFAPvsLyz2_sc | adj.p.value_ GFAPvsLyz2_sc | log2FC_ GFAPvsSyn_sc | adj.p.value_ GFAPvsSyn_sc | log2FC_ Lyz2vsSyn_sc | adj.p.value_ Lyz_2vsSyn_sc |
|---|---|---|---|---|---|---|
| mmu_miR_872_002542 | −2.193 | 0.000 | 1.300 | 0.020 | −0.568 | 0.418 |
| mmu_miR_873_002356 | 3.300 | 0.003 | 0.981 | 0.461 | −0.849 | 0.603 |
| mmu_miR_874_002268 | −0.207 | 0.984 | 0.530 | 0.882 | 1.581 | 0.561 |
| mmu_miR_875_3p_002547 | 0.919 | 0.941 | −2.582 | 0.654 | 2.843 | 0.645 |
| mmu_miR_876_3p_002464 | 2.146 | 0.481 | 0.838 | 0.845 | 2.195 | 0.521 |
| mmu_miR_876_5p_002463 | 2.253 | 0.098 | 2.320 | 0.107 | 0.359 | 0.884 |
| mmu_miR_877_002548 | −3.597 | 0.184 | −6.876 | 0.012 | 0.149 | 0.978 |
| mmu_miR_878_3p_002541 | −1.435 | 0.835 | −3.968 | 0.336 | 6.293 | 0.148 |
| mmu_miR_878_5p_002540 | 0.095 | 0.996 | −5.379 | 0.140 | −0.396 | 0.946 |
| mmu_miR_879_002472 | 0.040 | 0.996 | 0.812 | 0.749 | 0.328 | 0.914 |
| mmu_miR_879_002473 | −0.039 | 0.996 | −1.282 | 0.426 | −1.435 | 0.444 |
| mmu_miR_880_002665 | −6.619 | 0.261 | −2.302 | 0.788 | 2.901 | 0.732 |
| mmu_miR_881_002475 | 0.045 | 0.997 | −5.358 | 0.203 | 0.712 | 0.916 |
| mmu_miR_881_002609 | 2.386 | 0.599 | 0.380 | 0.953 | 5.202 | 0.190 |
| mmu_miR_882_002610 | 0.175 | 0.690 | −0.141 | 0.754 | −1.201 | 0.000 |
| mmu_miR_883B_5P_002669 | 0.625 | 0.961 | −2.469 | 0.607 | 3.361 | 0.512 |
| mmu_miR_883a_3p_002461 | 1.691 | 0.479 | 2.062 | 0.349 | 1.204 | 0.677 |
| mmu_miR_883a_5p_002611 | 0.160 | 0.823 | −0.070 | 0.923 | −1.047 | 0.013 |
| mmu_miR_883b_3p_002565 | 4.279 | 0.150 | 3.529 | 0.270 | −0.869 | 0.871 |
| mmu_miR_92a_000430 | 0.177 | 0.822 | −2.732 | 0.000 | 2.316 | 0.000 |
| mmu_miR_92a_002496 | 0.142 | 0.983 | −0.033 | 0.985 | −0.812 | 0.677 |
| mmu_miR_93_001090 | −1.806 | 0.013 | 1.295 | 0.105 | −0.470 | 0.674 |
| mmu_miR_96_000186 | 5.054 | 0.004 | −3.573 | 0.063 | 1.819 | 0.456 |
| mmu_miR_98_000577 | 2.930 | 0.062 | −0.682 | 0.784 | −2.405 | 0.200 |
| mmu_miR_99a_000435 | −2.472 | 0.001 | −1.768 | 0.022 | −0.306 | 0.807 |
| mmu_miR_99b_000436 | −1.966 | 0.035 | 0.548 | 0.681 | 0.283 | 0.871 |
| mmu_miR_9_000583 | −2.772 | 0.000 | −0.573 | 0.169 | −0.998 | 0.017 |
| hsa_let_7b_002404 | −3.753 | 0.324 | 1.052 | 0.794 | 4.805 | 0.184 |
| hsa_let_7e_002407 | −0.422 | 0.810 | 0.847 | 0.501 | 1.269 | 0.318 |
| hsa_let_7f_1_002417 | 1.529 | 0.571 | −2.351 | 0.316 | −3.880 | 0.095 |
| hsa_let_7i_002172 | 3.686 | 0.000 | 4.342 | 0.000 | 0.656 | 0.563 |
| hsa_miR_106b_002380 | 2.412 | 0.054 | −0.509 | 0.714 | −2.920 | 0.022 |
| hsa_miR_10a_002288 | 2.047 | 0.367 | 1.004 | 0.659 | −1.043 | 0.673 |
| hsa_miR_1197_002810 | −1.514 | 0.401 | −2.912 | 0.065 | −1.399 | 0.434 |
| hsa_miR_124_002197 | −0.460 | 0.887 | 1.424 | 0.485 | 1.883 | 0.366 |
| hsa_miR_127_5p_002229 | −1.021 | 0.378 | −2.600 | 0.011 | −1.580 | 0.138 |
| hsa_miR_136_000592 | −5.704 | 0.000 | −4.393 | 0.000 | 1.312 | 0.138 |
| hsa_miR_136_002100 | −3.175 | 0.093 | −5.292 | 0.004 | −2.117 | 0.282 |
| hsa_miR_140_3p_002234 | 0.454 | 0.639 | 0.229 | 0.794 | −0.225 | 0.839 |
| hsa_miR_143_000466 | −6.626 | 0.040 | 1.542 | 0.664 | 8.168 | 0.013 |
| hsa_miR_144_002676 | 0.827 | 0.276 | 2.084 | 0.003 | 1.257 | 0.077 |
| hsa_miR_148a_002134 | 4.131 | 0.056 | 4.827 | 0.022 | 0.696 | 0.814 |
| hsa_miR_149_002255 | 0.810 | 0.216 | −1.318 | 0.029 | −2.128 | 0.001 |
| hsa_miR_151_5P_002642 | −0.961 | 0.407 | 2.625 | 0.010 | 3.586 | 0.001 |
| hsa_miR_154_000478 | −2.795 | 0.013 | −2.902 | 0.009 | −0.107 | 0.948 |
| hsa_miR_15b_002173 | −0.719 | 0.912 | 4.763 | 0.231 | 5.482 | 0.178 |
| hsa_miR_183_002270 | −7.417 | 0.001 | −6.390 | 0.002 | 1.027 | 0.680 |

TABLE 3-continued

| Spinal Cord miRNA data. | | | | | | |
|---|---|---|---|---|---|---|
| hsa_miR_189_000488 | −1.243 | 0.813 | −2.285 | 0.558 | −1.041 | 0.841 |
| hsa_miR_190b_002263 | −1.114 | 0.493 | 2.422 | 0.079 | 3.536 | 0.016 |
| hsa_miR_196a_241070_mat | 2.319 | 0.042 | 1.658 | 0.136 | −0.661 | 0.609 |
| hsa_miR_200a_001011 | 1.783 | 0.258 | 1.777 | 0.229 | −0.006 | 0.996 |
| hsa_miR_200b_001800 | −1.228 | 0.746 | 2.548 | 0.373 | 3.776 | 0.183 |
| hsa_miR_200b_002274 | −5.971 | 0.173 | −0.361 | 0.943 | 5.610 | 0.197 |
| hsa_miR_200c_000505 | −4.382 | 0.006 | −0.001 | 0.999 | 4.381 | 0.007 |
| hsa_miR_200c_002286 | 0.327 | 0.885 | 0.178 | 0.904 | −0.149 | 0.937 |
| hsa_miR_206_000510 | −1.252 | 0.553 | 2.685 | 0.130 | 3.937 | 0.031 |
| hsa_miR_213_000516 | 0.964 | 0.408 | 1.087 | 0.313 | 0.123 | 0.934 |
| hsa_miR_214_000517 | 1.031 | 0.517 | 2.626 | 0.052 | 1.595 | 0.275 |
| hsa_miR_214_002293 | 2.226 | 0.089 | 3.641 | 0.004 | 1.415 | 0.303 |
| hsa_miR_218_2_002294 | −5.019 | 0.000 | −6.410 | 0.000 | −1.391 | 0.276 |
| hsa_miR_223_000526 | 12.630 | 0.000 | 0.068 | 0.986 | 12.698 | 0.000 |
| hsa_miR_22_000398 | 0.138 | 0.968 | 0.902 | 0.707 | 0.764 | 0.790 |
| hsa_miR_22_002301 | 0.165 | 0.912 | 1.393 | 0.093 | 1.227 | 0.157 |
| hsa_miR_23a_002439 | −7.449 | 0.054 | 9.667 | 0.011 | 17.115 | 0.000 |
| hsa_miR_26b_002444 | −1.148 | 0.717 | 4.199 | 0.067 | 5.347 | 0.026 |
| hsa_miR_27a_002445 | 2.239 | 0.312 | 3.858 | 0.052 | 1.618 | 0.480 |
| hsa_miR_27b_002174 | 0.259 | 0.840 | 0.393 | 0.676 | 0.134 | 0.913 |
| hsa_miR_28_3p_002446 | 0.321 | 0.918 | −0.482 | 0.822 | −0.803 | 0.743 |
| hsa_miR_299_5p_000600 | −0.524 | 0.911 | −2.021 | 0.448 | −1.497 | 0.608 |
| hsa_miR_29a_002447 | 2.054 | 0.392 | −0.390 | 0.877 | −2.444 | 0.285 |
| hsa_miR_29b_2_002166 | −5.155 | 0.045 | −0.046 | 0.988 | 5.109 | 0.048 |
| hsa_miR_30a_3p_000416 | 1.109 | 0.012 | 0.518 | 0.238 | −0.591 | 0.187 |
| hsa_miR_30c_1_002108 | 6.133 | 0.054 | 6.771 | 0.028 | 0.637 | 0.895 |
| hsa_miR_30c_2_002110 | −0.486 | 0.936 | 2.288 | 0.591 | 2.774 | 0.531 |
| hsa_miR_30d_002305 | 0.353 | 0.936 | 2.474 | 0.400 | 2.122 | 0.505 |
| hsa_miR_30e_3p_000422 | 1.144 | 0.013 | 0.810 | 0.068 | −0.334 | 0.513 |
| hsa_miR_324_3p_000579 | 2.607 | 0.235 | 1.047 | 0.645 | −1.560 | 0.505 |
| hsa_miR_338_000548 | 1.590 | 0.436 | 1.913 | 0.305 | 0.323 | 0.905 |
| hsa_miR_338_5P_002658 | 0.236 | 0.873 | 1.171 | 0.183 | 0.935 | 0.323 |
| hsa_miR_33a_002136 | 0.949 | 0.610 | 1.031 | 0.521 | 0.081 | 0.971 |
| hsa_miR_340_000550 | 1.099 | 0.209 | 0.417 | 0.645 | −0.681 | 0.462 |
| hsa_miR_363_001283 | −1.348 | 0.728 | −4.923 | 0.077 | −3.575 | 0.233 |
| hsa_miR_376a_001287 | −4.724 | 0.000 | −5.746 | 0.000 | −1.022 | 0.421 |
| hsa_miR_378_000567 | −3.395 | 0.054 | 1.652 | 0.361 | 5.047 | 0.005 |
| hsa_miR_411_002238 | −4.830 | 0.001 | −6.157 | 0.000 | −1.326 | 0.366 |
| hsa_miR_412_001023 | −2.339 | 0.199 | −3.434 | 0.042 | −1.095 | 0.575 |
| hsa_miR_421_002700 | 1.185 | 0.042 | 0.948 | 0.093 | −0.236 | 0.752 |
| hsa_miR_423_3P_002626 | 2.529 | 0.050 | 2.584 | 0.039 | 0.055 | 0.976 |
| hsa_miR_425_001104 | 0.694 | 0.799 | 2.722 | 0.146 | 2.028 | 0.318 |
| hsa_miR_431_002312 | −1.714 | 0.333 | −4.380 | 0.007 | −2.666 | 0.108 |
| hsa_miR_455_001280 | 1.242 | 0.492 | 3.405 | 0.028 | 2.163 | 0.183 |
| hsa_miR_485_5p_001036 | 0.046 | 0.976 | 0.267 | 0.856 | 0.221 | 0.906 |
| hsa_miR_493_3p_001282 | 4.666 | 0.340 | 5.446 | 0.229 | 0.780 | 0.906 |
| hsa_miR_590_3P_002677 | −0.265 | 0.746 | −1.657 | 0.005 | −1.392 | 0.022 |
| hsa_miR_653_002292 | −3.475 | 0.296 | −0.055 | 0.988 | 3.420 | 0.289 |
| hsa_miR_671_5p_197646_mat | −5.318 | 0.189 | 2.179 | 0.597 | 7.497 | 0.055 |
| hsa_miR_708_002342 | −0.089 | 0.974 | −0.576 | 0.811 | −0.487 | 0.874 |
| hsa_miR_744_002325 | −0.565 | 0.640 | 0.106 | 0.926 | 0.670 | 0.539 |

TABLE 3-continued

| Spinal Cord miRNA data. | | | | | | |
|---|---|---|---|---|---|---|
| hsa_miR_875_5p_002203 | −8.203 | 0.220 | 7.254 | 0.259 | 15.457 | 0.017 |
| hsa_miR_935_002178 | 1.287 | 0.562 | −0.193 | 0.932 | −1.479 | 0.486 |
| hsa_miR_93_002139 | 2.399 | 0.013 | 1.777 | 0.060 | −0.622 | 0.570 |
| hsa_miR_99b_002196 | 0.524 | 0.796 | 0.327 | 0.838 | −0.197 | 0.926 |
| hsa_miR_9_002231 | 2.909 | 0.000 | 2.853 | 0.000 | −0.056 | 0.928 |
| mmu_let_7a_000377 | 6.642 | 0.000 | 0.819 | 0.600 | −5.822 | 0.000 |
| mmu_let_7a_002478 | 5.851 | 0.289 | 9.818 | 0.048 | 3.966 | 0.488 |
| mmu_let_7b_000378 | 1.639 | 0.000 | 2.131 | 0.000 | 0.492 | 0.271 |
| mmu_let_7c_000379 | 1.883 | 0.000 | 1.354 | 0.001 | −0.529 | 0.218 |
| mmu_let_7c_1_002479 | −5.193 | 0.085 | 2.046 | 0.512 | 7.239 | 0.017 |
| mmu_let_7d_001178 | −2.823 | 0.001 | −2.797 | 0.001 | 0.026 | 0.983 |
| mmu_let_7d_002283 | 1.483 | 0.007 | 0.269 | 0.650 | −1.214 | 0.027 |
| mmu_let_7e_002406 | 2.063 | 0.025 | 0.348 | 0.736 | −1.715 | 0.065 |
| mmu_let_7f_000382 | 1.713 | 0.626 | −1.244 | 0.696 | −2.957 | 0.331 |
| mmu_let_7g_002282 | 0.920 | 0.219 | 0.233 | 0.777 | −0.688 | 0.366 |
| mmu_let_7g_002492 | −2.260 | 0.144 | −2.187 | 0.136 | 0.073 | 0.972 |
| mmu_let_7i_002221 | 2.750 | 0.000 | 1.546 | 0.003 | −1.204 | 0.023 |
| mmu_miR_100_000437 | 2.326 | 0.001 | 2.577 | 0.000 | 0.252 | 0.769 |
| mmu_miR_101a_002253 | 0.470 | 0.383 | 0.414 | 0.412 | −0.056 | 0.934 |
| mmu_miR_101a_002507 | −0.025 | 0.977 | −1.152 | 0.129 | −1.127 | 0.150 |
| mmu_miR_101b_002531 | 1.635 | 0.007 | −0.055 | 0.940 | −1.690 | 0.006 |
| mmu_miR_103_000439 | 2.131 | 0.007 | 0.478 | 0.567 | −1.653 | 0.038 |
| mmu_miR_105_002465 | −2.399 | 0.728 | 7.108 | 0.156 | 9.506 | 0.067 |
| mmu_miR_106a_002459 | 5.711 | 0.012 | 1.627 | 0.493 | −4.083 | 0.076 |
| mmu_miR_106b_000442 | 0.871 | 0.220 | 1.234 | 0.061 | 0.363 | 0.646 |
| mmu_miR_107_000443 | −3.631 | 0.018 | 0.256 | 0.883 | 3.887 | 0.013 |
| mmu_miR_10a_000387 | 1.252 | 0.359 | 1.146 | 0.373 | −0.106 | 0.953 |
| mmu_miR_10b_001181 | 0.690 | 0.669 | −0.042 | 0.980 | −0.732 | 0.614 |
| mmu_miR_10b_002218 | 2.388 | 0.148 | −1.472 | 0.373 | −3.859 | 0.018 |
| mmu_miR_10b_002572 | 2.215 | 0.359 | 0.576 | 0.818 | −1.639 | 0.505 |
| mmu_miR_1186_002825 | 1.156 | 0.795 | 3.256 | 0.302 | 2.100 | 0.544 |
| mmu_miR_1188_002866 | −0.277 | 0.943 | −0.898 | 0.759 | −0.621 | 0.868 |
| mmu_miR_1191_002892 | −5.153 | 0.164 | 1.737 | 0.659 | 6.890 | 0.056 |
| mmu_miR_1192_002806 | 0.135 | 0.957 | 0.122 | 0.950 | −0.013 | 0.994 |
| mmu_miR_1193_002794 | 0.530 | 0.503 | 1.087 | 0.111 | 0.557 | 0.479 |
| mmu_miR_1194_002793 | 0.187 | 0.912 | −0.425 | 0.695 | −0.612 | 0.575 |
| mmu_miR_1195_002839 | 0.337 | 0.936 | 3.031 | 0.285 | 2.694 | 0.366 |
| mmu_miR_1198_002780 | 3.074 | 0.000 | −0.642 | 0.442 | −3.716 | 0.000 |
| mmu_miR_1199_240984_mat | −0.316 | 0.314 | −1.377 | 0.000 | −1.061 | 0.001 |
| mmu_miR_1224_240985_mat | −0.351 | 0.609 | −2.138 | 0.000 | −1.786 | 0.003 |
| mmu_miR_122_002245 | −5.358 | 0.216 | 5.860 | 0.145 | 11.218 | 0.008 |
| mmu_miR_124_001182 | −3.302 | 0.001 | −5.180 | 0.000 | −1.878 | 0.059 |
| mmu_miR_125a_3p_002199 | −0.771 | 0.653 | −0.784 | 0.594 | −0.013 | 0.994 |
| mmu_miR_125a_5p_002198 | 0.904 | 0.054 | −0.186 | 0.726 | −1.090 | 0.023 |
| mmu_miR_125b_002508 | 1.740 | 0.056 | 1.445 | 0.103 | −0.295 | 0.813 |
| mmu_miR_125b_3p_002378 | −0.588 | 0.598 | 2.988 | 0.001 | 3.576 | 0.000 |
| mmu_miR_125b_5p_000449 | −0.316 | 0.577 | 0.933 | 0.045 | 1.248 | 0.011 |
| mmu_miR_126_3p_002228 | −4.750 | 0.000 | −1.612 | 0.001 | 3.138 | 0.000 |
| mmu_miR_126_5p_000451 | −4.207 | 0.000 | −1.833 | 0.001 | 2.374 | 0.000 |
| mmu_miR_1274a_121150_mat | −5.593 | 0.015 | 1.280 | 0.600 | 6.873 | 0.004 |
| mmu_miR_127_000452 | −3.998 | 0.000 | −4.514 | 0.000 | −0.516 | 0.255 |

TABLE 3-continued

| Spinal Cord miRNA data. | | | | | | |
|---|---|---|---|---|---|---|
| mmu_miR_128a_002216 | −1.687 | 0.003 | −2.423 | 0.000 | −0.735 | 0.192 |
| mmu_miR_129_3p_001184 | −1.362 | 0.017 | −2.868 | 0.000 | −1.507 | 0.010 |
| mmu_miR_129_5p_000590 | 0.150 | 0.936 | −2.723 | 0.012 | −2.873 | 0.012 |
| mmu_miR_1306_121155_mat | −0.082 | 0.968 | −1.860 | 0.162 | −1.778 | 0.205 |
| mmu_miR_130a_000454 | 5.211 | 0.001 | 1.904 | 0.201 | −3.307 | 0.029 |
| mmu_miR_130b_000456 | 0.960 | 0.314 | 2.024 | 0.019 | 1.065 | 0.252 |
| mmu_miR_130b_002460 | −6.908 | 0.000 | −5.757 | 0.001 | 1.152 | 0.551 |
| mmu_miR_132_000457 | −3.885 | 0.000 | −5.170 | 0.000 | −1.285 | 0.004 |
| mmu_miR_133a_001637 | −0.057 | 0.976 | −2.504 | 0.126 | −2.448 | 0.147 |
| mmu_miR_133a_002246 | −5.266 | 0.000 | −6.511 | 0.000 | −1.245 | 0.012 |
| mmu_miR_133b_002247 | −5.985 | 0.000 | −6.097 | 0.000 | −0.113 | 0.948 |
| mmu_miR_134_001186 | −3.602 | 0.000 | −5.102 | 0.000 | −1.500 | 0.078 |
| mmu_miR_135a_000460 | 2.199 | 0.000 | 1.084 | 0.038 | −1.115 | 0.040 |
| mmu_miR_135b_002261 | 3.828 | 0.000 | 0.962 | 0.347 | −2.866 | 0.005 |
| mmu_miR_136_002511 | −5.828 | 0.002 | −7.972 | 0.000 | −2.144 | 0.263 |
| mmu_miR_136_002512 | −0.871 | 0.780 | 0.741 | 0.769 | 1.612 | 0.513 |
| mmu_miR_137_001129 | −4.772 | 0.002 | −3.325 | 0.022 | 1.446 | 0.366 |
| mmu_miR_138_002284 | −2.677 | 0.000 | −3.998 | 0.000 | −1.321 | 0.025 |
| mmu_miR_138_002554 | −1.780 | 0.095 | −3.245 | 0.002 | −1.465 | 0.176 |
| mmu_miR_139_3p_002546 | −1.959 | 0.589 | −4.218 | 0.154 | −2.258 | 0.505 |
| mmu_miR_139_5p_002289 | −2.807 | 0.001 | −3.264 | 0.000 | −0.457 | 0.608 |
| mmu_miR_140_001187 | 2.132 | 0.005 | 0.566 | 0.474 | −1.565 | 0.040 |
| mmu_miR_141_000463 | −2.397 | 0.553 | 5.207 | 0.126 | 7.604 | 0.030 |
| mmu_miR_141_002513 | −2.275 | 0.538 | 3.768 | 0.238 | 6.044 | 0.060 |
| mmu_miR_142_3p_000464 | −6.229 | 0.001 | 5.413 | 0.003 | 11.642 | 0.000 |
| mmu_miR_142_5p_002248 | −5.202 | 0.163 | 4.210 | 0.244 | 9.412 | 0.011 |
| mmu_miR_143_002249 | 0.053 | 0.972 | 6.298 | 0.000 | 6.245 | 0.000 |
| mmu_miR_145_002278 | −0.911 | 0.534 | 6.509 | 0.000 | 7.420 | 0.000 |
| mmu_miR_145_002514 | 3.650 | 0.134 | 3.404 | 0.143 | −0.246 | 0.940 |
| mmu_miR_146a_000468 | −2.319 | 0.000 | 2.704 | 0.000 | 5.023 | 0.000 |
| mmu_miR_146b_001097 | −0.233 | 0.691 | 0.121 | 0.814 | 0.354 | 0.486 |
| mmu_miR_146b_002453 | −3.446 | 0.238 | −1.565 | 0.596 | 1.882 | 0.544 |
| mmu_miR_147_002262 | 4.353 | 0.163 | 9.205 | 0.002 | 4.852 | 0.113 |
| mmu_miR_148a_000470 | 3.880 | 0.002 | 1.222 | 0.324 | −2.659 | 0.029 |
| mmu_miR_148b_000471 | −1.029 | 0.331 | −0.298 | 0.790 | 0.730 | 0.505 |
| mmu_miR_150_000473 | −4.130 | 0.000 | 2.314 | 0.009 | 6.445 | 0.000 |
| mmu_miR_150_002570 | −4.493 | 0.089 | 1.490 | 0.596 | 5.983 | 0.025 |
| mmu_miR_151_3p_001190 | 4.296 | 0.000 | 2.725 | 0.001 | −1.571 | 0.060 |
| mmu_miR_152_000475 | 1.826 | 0.009 | 5.286 | 0.000 | 3.460 | 0.000 |
| mmu_miR_153_001191 | −5.407 | 0.000 | −3.167 | 0.011 | 2.240 | 0.082 |
| mmu_miR_154_000477 | −4.620 | 0.001 | −6.923 | 0.000 | −2.303 | 0.080 |
| mmu_miR_155_002571 | −0.468 | 0.695 | 6.697 | 0.000 | 7.165 | 0.000 |
| mmu_miR_15a_000389 | 2.891 | 0.018 | 1.568 | 0.195 | −1.323 | 0.307 |
| mmu_miR_15a_002488 | −1.074 | 0.197 | 1.421 | 0.065 | 2.495 | 0.003 |
| mmu_miR_15b_000390 | 0.122 | 0.873 | 2.114 | 0.000 | 1.991 | 0.000 |
| mmu_miR_16_000391 | −0.009 | 0.983 | 0.505 | 0.241 | 0.514 | 0.253 |
| mmu_miR_16_002489 | 1.958 | 0.114 | 3.770 | 0.002 | 1.811 | 0.143 |
| mmu_miR_17_002308 | 2.228 | 0.004 | 1.332 | 0.075 | −0.896 | 0.271 |
| mmu_miR_17_002543 | 0.117 | 0.976 | 6.239 | 0.059 | 6.122 | 0.075 |
| mmu_miR_181A_2_002687 | 2.138 | 0.102 | 1.237 | 0.352 | −0.902 | 0.533 |
| mmu_miR_181a_000480 | 1.782 | 0.002 | 1.332 | 0.017 | −0.450 | 0.486 |

TABLE 3-continued

Spinal Cord miRNA data.

| | | | | | | |
|---|---|---|---|---|---|---|
| mmu_miR_181c_000482 | −0.338 | 0.726 | −1.018 | 0.145 | −0.679 | 0.375 |
| mmu_miR_182_002599 | −1.794 | 0.503 | −1.466 | 0.558 | 0.328 | 0.926 |
| mmu_miR_1839_3p_121203_mat | 2.688 | 0.005 | 0.710 | 0.474 | −1.978 | 0.038 |
| mmu_miR_1839_5p_121135_mat | 2.934 | 0.066 | −0.254 | 0.887 | −3.187 | 0.047 |
| mmu_miR_183_002269 | −6.749 | 0.000 | −4.536 | 0.008 | 2.213 | 0.220 |
| mmu_miR_184_000485 | −5.349 | 0.009 | −1.796 | 0.393 | 3.553 | 0.083 |
| mmu_miR_185_002271 | 0.344 | 0.819 | −4.112 | 0.000 | −4.456 | 0.000 |
| mmu_miR_186_002285 | 0.362 | 0.812 | 0.789 | 0.474 | 0.428 | 0.752 |
| mmu_miR_186_002574 | −2.114 | 0.079 | 0.543 | 0.682 | 2.657 | 0.027 |
| mmu_miR_187_001193 | 4.621 | 0.000 | 0.537 | 0.564 | −4.084 | 0.000 |
| mmu_miR_188_3p_002106 | 0.727 | 0.478 | 0.740 | 0.433 | 0.012 | 0.994 |
| mmu_miR_188_5p_002320 | −4.703 | 0.003 | 1.698 | 0.288 | 6.401 | 0.000 |
| mmu_miR_1893_121170_mat | −0.140 | 0.968 | −0.885 | 0.737 | −0.744 | 0.817 |
| mmu_miR_1894_3p_241002_mat | −3.625 | 0.286 | 5.420 | 0.074 | 9.045 | 0.005 |
| mmu_miR_1894_5p_121144_mat | 1.074 | 0.493 | 1.145 | 0.424 | 0.071 | 0.971 |
| mmu_miR_1896_121128_mat | −1.447 | 0.788 | 7.802 | 0.033 | 9.249 | 0.016 |
| mmu_miR_1897_3p_121126_mat | −0.280 | 0.437 | −1.298 | 0.000 | −1.018 | 0.003 |
| mmu_miR_1897_5p_121199_mat | −4.194 | 0.042 | 3.813 | 0.057 | 8.007 | 0.000 |
| mmu_miR_1898_121195_mat | −0.315 | 0.415 | −1.491 | 0.000 | −1.176 | 0.002 |
| mmu_miR_1899_121198_mat | 0.069 | 0.958 | −0.565 | 0.516 | −0.634 | 0.496 |
| mmu_miR_18a_002422 | 0.082 | 0.968 | −0.011 | 0.995 | −0.093 | 0.958 |
| mmu_miR_18a_002490 | −0.314 | 0.911 | 0.588 | 0.736 | 0.902 | 0.608 |
| mmu_miR_18b_002466 | −0.670 | 0.873 | −0.967 | 0.736 | −0.297 | 0.934 |
| mmu_miR_1900_121143_mat | −0.071 | 0.952 | −0.876 | 0.267 | −0.805 | 0.330 |
| mmu_miR_1901_121183_mat | −1.115 | 0.812 | 1.425 | 0.695 | 2.540 | 0.486 |
| mmu_miR_1902_121197_mat | −0.205 | 0.658 | −1.151 | 0.002 | −0.946 | 0.012 |
| mmu_miR_1903_121153_mat | 1.429 | 0.810 | −0.280 | 0.955 | −1.709 | 0.745 |
| mmu_miR_1904_121162_mat | −4.810 | 0.000 | 2.889 | 0.000 | 7.700 | 0.000 |
| mmu_miR_1905_121196_mat | −7.000 | 0.033 | 2.835 | 0.400 | 9.835 | 0.004 |
| mmu_miR_1906_121169_mat | 1.544 | 0.437 | 1.136 | 0.547 | −0.408 | 0.874 |
| mmu_miR_190_000489 | −0.935 | 0.466 | 0.598 | 0.632 | 1.533 | 0.190 |
| mmu_miR_191_002299 | 0.339 | 0.414 | 0.026 | 0.955 | −0.313 | 0.451 |
| mmu_miR_191_002576 | 0.112 | 0.936 | 1.047 | 0.255 | 0.936 | 0.334 |
| mmu_miR_1927_121193_mat | 1.229 | 0.605 | 1.108 | 0.596 | −0.122 | 0.964 |
| mmu_miR_1928_121164_mat | −4.139 | 0.075 | 3.437 | 0.129 | 7.576 | 0.002 |
| mmu_miR_192_000491 | 2.971 | 0.000 | 0.283 | 0.758 | −2.688 | 0.002 |
| mmu_miR_1930_121201_mat | −0.629 | 0.774 | 0.386 | 0.822 | 1.015 | 0.555 |
| mmu_miR_1931_121168_mat | −0.149 | 0.939 | −0.894 | 0.512 | −0.745 | 0.615 |
| mmu_miR_1932_121172_mat | 4.441 | 0.216 | 3.371 | 0.337 | −1.069 | 0.817 |
| mmu_miR_1933_3p_121145_mat | −0.142 | 0.873 | −1.032 | 0.046 | −0.889 | 0.099 |
| mmu_miR_1933_5p_121133_mat | 2.160 | 0.785 | 4.852 | 0.399 | 2.692 | 0.688 |
| mmu_miR_1934_121185_mat | 0.077 | 0.982 | −0.156 | 0.965 | −0.234 | 0.956 |
| mmu_miR_1935_121192_mat | −0.302 | 0.922 | −0.781 | 0.703 | −0.479 | 0.854 |
| mmu_miR_1936_121158_mat | 0.407 | 0.840 | 0.765 | 0.595 | 0.358 | 0.850 |
| mmu_miR_1937b_241023_mat | −3.366 | 0.740 | 3.911 | 0.631 | 7.277 | 0.362 |
| mmu_miR_1937c_241011_mat | −3.995 | 0.000 | 3.583 | 0.000 | 7.578 | 0.000 |
| mmu_miR_1938_121194_mat | 0.531 | 0.837 | 0.864 | 0.643 | 0.333 | 0.898 |
| mmu_miR_1939_121180_mat | 1.761 | 0.621 | 2.126 | 0.485 | 0.365 | 0.931 |
| mmu_miR_193_002250 | −0.834 | 0.856 | 2.322 | 0.446 | 3.155 | 0.307 |
| mmu_miR_193_002577 | 1.490 | 0.046 | 3.961 | 0.000 | 2.471 | 0.002 |
| mmu_miR_193b_002467 | 3.165 | 0.000 | 2.307 | 0.001 | −0.858 | 0.203 |

TABLE 3-continued

Spinal Cord miRNA data.

| | | | | | | |
|---|---|---|---|---|---|---|
| mmu_miR_1940_121187_mat | 1.067 | 0.754 | −0.766 | 0.788 | −1.834 | 0.505 |
| mmu_miR_1941_3p_121130_mat | 0.534 | 0.393 | 0.826 | 0.136 | 0.292 | 0.666 |
| mmu_miR_1941_5p_121140_mat | 0.288 | 0.924 | 0.732 | 0.714 | 0.443 | 0.861 |
| mmu_miR_1942_121136_mat | −3.110 | 0.632 | 4.696 | 0.389 | 7.806 | 0.145 |
| mmu_miR_1943_121174_mat | 2.233 | 0.023 | 2.702 | 0.005 | 0.469 | 0.694 |
| mmu_miR_1944_121189_mat | 1.339 | 0.615 | −1.906 | 0.399 | −3.245 | 0.143 |
| mmu_miR_1945_121166_mat | 0.442 | 0.653 | 0.544 | 0.508 | 0.102 | 0.928 |
| mmu_miR_1946a_121178_mat | −0.177 | 0.968 | −0.206 | 0.959 | −0.028 | 0.994 |
| mmu_miR_1947_121156_mat | 3.430 | 0.085 | 4.349 | 0.024 | 0.920 | 0.704 |
| mmu_miR_1948_121171_mat | 2.269 | 0.301 | 0.888 | 0.695 | −1.381 | 0.542 |
| mmu_miR_1949_121182_mat | −0.108 | 0.932 | −0.733 | 0.327 | −0.624 | 0.436 |
| mmu_miR_194_000493 | −1.644 | 0.140 | 0.272 | 0.822 | 1.915 | 0.081 |
| mmu_miR_1950_121146_mat | 1.815 | 0.314 | 1.833 | 0.283 | 0.019 | 0.994 |
| mmu_miR_1951_121165_mat | 1.291 | 0.912 | 5.174 | 0.456 | 3.884 | 0.608 |
| mmu_miR_1952_121167_mat | −0.256 | 0.502 | −1.252 | 0.000 | −0.995 | 0.004 |
| mmu_miR_1953_121159_mat | 0.350 | 0.795 | 0.085 | 0.941 | −0.266 | 0.842 |
| mmu_miR_1954_121137_mat | −3.184 | 0.174 | 6.640 | 0.003 | 9.823 | 0.000 |
| mmu_miR_1956_121129_mat | 4.677 | 0.292 | 5.779 | 0.148 | 1.102 | 0.850 |
| mmu_miR_1957_121163_mat | −0.316 | 0.314 | −1.377 | 0.000 | −1.061 | 0.001 |
| mmu_miR_1958_121181_mat | 3.452 | 0.109 | 3.886 | 0.060 | 0.434 | 0.893 |
| mmu_miR_1959_121132_mat | −3.098 | 0.042 | 6.570 | 0.000 | 9.668 | 0.000 |
| mmu_miR_195_000494 | 2.898 | 0.000 | 2.582 | 0.000 | −0.317 | 0.663 |
| mmu_miR_1960_121148_mat | 2.278 | 0.211 | 2.582 | 0.128 | 0.305 | 0.905 |
| mmu_miR_1961_197391_mat | −4.481 | 0.301 | 7.558 | 0.052 | 12.039 | 0.004 |
| mmu_miR_1962_121173_mat | 0.458 | 0.780 | −0.783 | 0.518 | −1.240 | 0.310 |
| mmu_miR_1963_121191_mat | −0.316 | 0.314 | −1.377 | 0.000 | −1.061 | 0.001 |
| mmu_miR_1964_121138_mat | 1.689 | 0.114 | 1.841 | 0.071 | 0.152 | 0.923 |
| mmu_miR_1965_121186_mat | −0.292 | 0.443 | −1.332 | 0.000 | −1.040 | 0.004 |
| mmu_miR_1966_121134_mat | −0.327 | 0.553 | −2.019 | 0.000 | −1.692 | 0.001 |
| mmu_miR_1967_121151_mat | −0.307 | 0.560 | −1.318 | 0.003 | −1.011 | 0.027 |
| mmu_miR_1968_121179_mat | 5.044 | 0.104 | 7.110 | 0.017 | 2.065 | 0.547 |
| mmu_miR_1969_121131_mat | −3.761 | 0.045 | 3.440 | 0.059 | 7.201 | 0.000 |
| mmu_miR_196a_002477 | 3.085 | 0.669 | 5.101 | 0.391 | 2.016 | 0.796 |
| mmu_miR_196b_002215 | 4.309 | 0.019 | 1.774 | 0.349 | −2.535 | 0.181 |
| mmu_miR_1970_121202_mat | −3.194 | 0.280 | −5.268 | 0.048 | −2.073 | 0.499 |
| mmu_miR_1971_121161_mat | 1.631 | 0.695 | 1.676 | 0.633 | 0.045 | 0.994 |
| mmu_miR_197_000497 | −6.459 | 0.118 | 4.470 | 0.280 | 10.929 | 0.009 |
| mmu_miR_1981_121200_mat | −1.747 | 0.042 | −1.008 | 0.240 | 0.739 | 0.431 |
| mmu_miR_1982.1_121157_mat | −1.036 | 0.495 | 0.970 | 0.487 | 2.007 | 0.139 |
| mmu_miR_1982.2_121154_mat | −3.626 | 0.093 | −1.263 | 0.579 | 2.363 | 0.294 |
| mmu_miR_199a_3p_002304 | −1.900 | 0.204 | 2.093 | 0.134 | 3.993 | 0.007 |
| mmu_miR_199a_5p_000498 | −0.113 | 0.968 | −1.624 | 0.448 | −1.512 | 0.510 |
| mmu_miR_199b_001131 | 1.979 | 0.334 | 1.242 | 0.535 | −0.737 | 0.766 |
| mmu_miR_19a_000395 | 0.143 | 0.885 | 2.578 | 0.000 | 2.435 | 0.000 |
| mmu_miR_19a_002544 | 0.092 | 0.912 | −0.504 | 0.329 | −0.596 | 0.259 |
| mmu_miR_19b_000396 | 1.596 | 0.026 | 1.729 | 0.013 | 0.133 | 0.903 |
| mmu_miR_1_002222 | −2.438 | 0.167 | −2.559 | 0.126 | −0.120 | 0.960 |
| mmu_miR_1_2_AS_002882 | −1.112 | 0.834 | 4.810 | 0.162 | 5.922 | 0.098 |
| mmu_miR_200a_000502 | 0.889 | 0.810 | 4.120 | 0.098 | 3.231 | 0.221 |
| mmu_miR_200b_002251 | 1.847 | 0.723 | 7.945 | 0.035 | 6.098 | 0.123 |
| mmu_miR_200c_002300 | 0.025 | 0.992 | −0.457 | 0.887 | −0.482 | 0.906 |

TABLE 3-continued

Spinal Cord miRNA data.

| | | | | | | |
|---|---|---|---|---|---|---|
| mmu_miR_201_002578 | 0.438 | 0.905 | 0.721 | 0.754 | 0.283 | 0.926 |
| mmu_miR_202_3p_001195 | −5.780 | 0.054 | 2.910 | 0.347 | 8.690 | 0.005 |
| mmu_miR_202_5p_002579 | 0.135 | 0.959 | 1.564 | 0.355 | 1.429 | 0.429 |
| mmu_miR_203_000507 | 1.039 | 0.741 | 2.399 | 0.307 | 1.360 | 0.606 |
| mmu_miR_203_002580 | 4.667 | 0.097 | 5.173 | 0.056 | 0.506 | 0.904 |
| mmu_miR_204_000508 | 2.286 | 0.000 | 3.708 | 0.000 | 1.422 | 0.009 |
| mmu_miR_205_000509 | −6.978 | 0.012 | −4.544 | 0.092 | 2.434 | 0.424 |
| mmu_miR_207_001198 | 0.012 | 0.991 | −1.075 | 0.356 | −1.087 | 0.368 |
| mmu_miR_208_000511 | −6.859 | 0.144 | −5.415 | 0.237 | 1.444 | 0.817 |
| mmu_miR_208b_002290 | −2.151 | 0.661 | 4.199 | 0.288 | 6.351 | 0.107 |
| mmu_miR_20a_000580 | −0.059 | 0.948 | 1.479 | 0.013 | 1.539 | 0.013 |
| mmu_miR_20a_002491 | −2.358 | 0.233 | −0.732 | 0.727 | 1.626 | 0.429 |
| mmu_miR_20b_001014 | 1.374 | 0.435 | 2.380 | 0.125 | 1.006 | 0.571 |
| mmu_miR_20b_002524 | −0.115 | 0.968 | −0.577 | 0.799 | −0.462 | 0.874 |
| mmu_miR_210_000512 | 3.940 | 0.005 | 4.117 | 0.003 | 0.177 | 0.931 |
| mmu_miR_211_001199 | 0.584 | 0.941 | 1.438 | 0.814 | 0.854 | 0.913 |
| mmu_miR_212_002551 | −2.154 | 0.049 | −6.340 | 0.000 | −4.186 | 0.000 |
| mmu_miR_2134_241120_mat | −4.961 | 0.002 | 3.991 | 0.011 | 8.952 | 0.000 |
| mmu_miR_2135_241140_mat | −6.569 | 0.380 | 2.021 | 0.793 | 8.590 | 0.220 |
| mmu_miR_2136_241133_mat | −0.700 | 0.948 | 1.042 | 0.893 | 1.742 | 0.861 |
| mmu_miR_2138_241080_mat | −5.900 | 0.066 | 6.155 | 0.048 | 12.055 | 0.001 |
| mmu_miR_2139_241130_mat | 0.392 | 0.887 | 1.586 | 0.355 | 1.194 | 0.523 |
| mmu_miR_2146_241082_mat | −3.017 | 0.415 | 3.734 | 0.271 | 6.751 | 0.046 |
| mmu_miR_214_002306 | 1.464 | 0.382 | 1.986 | 0.183 | 0.522 | 0.799 |
| mmu_miR_215_001200 | −5.179 | 0.008 | 1.120 | 0.592 | 6.299 | 0.002 |
| mmu_miR_216a_002220 | −6.853 | 0.000 | −4.162 | 0.004 | 2.691 | 0.068 |
| mmu_miR_216b_002326 | 10.159 | 0.000 | −9.716 | 0.000 | 0.443 | 0.838 |
| mmu_miR_217_001133 | −2.012 | 0.254 | −3.006 | 0.061 | −0.993 | 0.599 |
| mmu_miR_217_002556 | −5.097 | 0.000 | −2.787 | 0.028 | 2.310 | 0.080 |
| mmu_miR_2182_241119_mat | 1.611 | 0.645 | 4.791 | 0.077 | 3.179 | 0.281 |
| mmu_miR_2183_241095_mat | −3.912 | 0.073 | 5.800 | 0.007 | 9.712 | 0.000 |
| mmu_miR_218_000521 | −3.615 | 0.000 | −5.105 | 0.000 | −1.490 | 0.003 |
| mmu_miR_218_1_002552 | −4.386 | 0.000 | −5.201 | 0.000 | −0.815 | 0.525 |
| mmu_miR_219_000522 | 3.980 | 0.000 | 1.437 | 0.175 | −2.543 | 0.020 |
| mmu_miR_21_000397 | −1.145 | 0.169 | 2.165 | 0.006 | 3.310 | 0.000 |
| mmu_miR_21_002493 | 0.398 | 0.840 | 1.622 | 0.216 | 1.224 | 0.387 |
| mmu_miR_220_002468 | −0.289 | 0.460 | −1.255 | 0.000 | −0.965 | 0.007 |
| mmu_miR_221_000524 | 2.186 | 0.000 | 1.721 | 0.000 | −0.465 | 0.303 |
| mmu_miR_222_002276 | −0.867 | 0.007 | −0.780 | 0.012 | 0.087 | 0.848 |
| mmu_miR_223_002295 | 10.529 | 0.000 | 4.818 | 0.000 | 15.347 | 0.000 |
| mmu_miR_224_002553 | 1.326 | 0.235 | 0.926 | 0.399 | −0.400 | 0.771 |
| mmu_miR_23a_000399 | 3.137 | 0.038 | 3.876 | 0.009 | 0.739 | 0.682 |
| mmu_miR_23b_000400 | 0.437 | 0.740 | 0.032 | 0.980 | −0.404 | 0.744 |
| mmu_miR_24_000402 | −0.290 | 0.317 | 0.304 | 0.267 | 0.594 | 0.029 |
| mmu_miR_24_2_002494 | 0.882 | 0.322 | 2.846 | 0.001 | 1.964 | 0.020 |
| mmu_miR_25_000403 | 5.598 | 0.000 | 3.009 | 0.009 | −2.589 | 0.030 |
| mmu_miR_26a_000405 | 1.450 | 0.000 | 0.515 | 0.143 | −0.935 | 0.011 |
| mmu_miR_26b_000407 | 1.001 | 0.019 | 1.881 | 0.000 | 0.880 | 0.042 |
| mmu_miR_27a_000408 | −0.175 | 0.926 | 3.773 | 0.001 | 3.948 | 0.001 |
| mmu_miR_27b_000409 | 0.496 | 0.407 | 0.811 | 0.126 | 0.315 | 0.608 |
| mmu_miR_28_000411 | −3.760 | 0.028 | 3.066 | 0.065 | 6.826 | 0.000 |

TABLE 3-continued

Spinal Cord miRNA data.

| | | | | | | |
|---|---|---|---|---|---|---|
| mmu_miR_28_002545 | −0.668 | 0.790 | 1.202 | 0.512 | 1.870 | 0.313 |
| mmu_miR_290_000187 | −5.629 | 0.107 | −1.262 | 0.746 | 4.367 | 0.221 |
| mmu_miR_290_3p_002591 | −0.278 | 0.426 | −1.289 | 0.000 | −1.011 | 0.002 |
| mmu_miR_290_5p_002590 | 0.471 | 0.935 | 1.079 | 0.785 | 0.607 | 0.905 |
| mmu_miR_291_3p_001135 | −0.381 | 0.681 | −1.248 | 0.076 | −0.866 | 0.255 |
| mmu_miR_291_5p_001202 | −0.330 | 0.520 | −2.003 | 0.000 | −1.673 | 0.001 |
| mmu_miR_291a_3p_002592 | −0.276 | 0.414 | −1.295 | 0.000 | −1.019 | 0.002 |
| mmu_miR_291b_3p_002538 | −0.045 | 0.959 | −0.771 | 0.158 | −0.726 | 0.208 |
| mmu_miR_291b_5p_002537 | −0.873 | 0.047 | −1.344 | 0.002 | −0.471 | 0.310 |
| mmu_miR_292_3p_001054 | −0.505 | 0.906 | −1.435 | 0.568 | −0.930 | 0.766 |
| mmu_miR_292_3p_002593 | −5.329 | 0.284 | 0.983 | 0.851 | 6.312 | 0.182 |
| mmu_miR_292_5p_001055 | −0.667 | 0.932 | −3.721 | 0.416 | −3.054 | 0.537 |
| mmu_miR_293_001794 | 2.942 | 0.600 | 3.704 | 0.444 | 0.762 | 0.910 |
| mmu_miR_293_002594 | 0.130 | 0.960 | 0.282 | 0.881 | 0.152 | 0.948 |
| mmu_miR_294_001056 | 4.885 | 0.192 | 6.063 | 0.079 | 1.178 | 0.809 |
| mmu_miR_294_002595 | −0.316 | 0.314 | −1.377 | 0.000 | −1.061 | 0.001 |
| mmu_miR_295_000189 | −1.408 | 0.388 | 1.020 | 0.509 | 2.428 | 0.105 |
| mmu_miR_295_002596 | −0.238 | 0.936 | −0.897 | 0.689 | −0.659 | 0.810 |
| mmu_miR_296_3p_002101 | 1.066 | 0.600 | 1.119 | 0.527 | 0.053 | 0.983 |
| mmu_miR_296_5p_000527 | 4.397 | 0.000 | 2.284 | 0.041 | −2.113 | 0.068 |
| mmu_miR_297a_002454 | 3.640 | 0.000 | 5.151 | 0.000 | 1.511 | 0.107 |
| mmu_miR_297b_5p_001626 | 0.609 | 0.721 | 1.590 | 0.208 | 0.981 | 0.491 |
| mmu_miR_297c_002480 | 0.610 | 0.799 | −0.733 | 0.695 | −1.343 | 0.479 |
| mmu_miR_298_002598 | −4.752 | 0.002 | −5.165 | 0.001 | −0.414 | 0.848 |
| mmu_miR_299_002612 | −0.316 | 0.314 | −1.377 | 0.000 | −1.061 | 0.001 |
| mmu_miR_29a_002112 | 0.359 | 0.487 | −1.609 | 0.001 | −1.969 | 0.000 |
| mmu_miR_29b_000413 | −3.269 | 0.001 | −0.074 | 0.953 | 3.195 | 0.002 |
| mmu_miR_29b_002497 | −3.751 | 0.000 | 3.105 | 0.002 | 6.856 | 0.000 |
| mmu_miR_29c_000587 | 0.501 | 0.231 | −0.744 | 0.054 | −1.245 | 0.003 |
| mmu_miR_300_000191 | −6.690 | 0.006 | −2.973 | 0.216 | 3.717 | 0.128 |
| mmu_miR_300_002613 | −2.614 | 0.037 | −4.152 | 0.001 | −1.538 | 0.235 |
| mmu_miR_301a_000528 | −0.172 | 0.815 | 0.331 | 0.543 | 0.503 | 0.362 |
| mmu_miR_301b_002600 | 1.359 | 0.033 | 0.410 | 0.542 | −0.949 | 0.141 |
| mmu_miR_302a_000529 | 1.897 | 0.769 | 3.671 | 0.439 | 1.774 | 0.766 |
| mmu_miR_302a_002615 | 1.376 | 0.669 | 1.140 | 0.689 | −0.236 | 0.948 |
| mmu_miR_302b_000531 | 1.770 | 0.502 | 0.226 | 0.935 | −1.544 | 0.551 |
| mmu_miR_302b_001307 | 0.407 | 0.936 | 0.616 | 0.859 | 0.209 | 0.961 |
| mmu_miR_302c_002557 | −0.424 | 0.912 | −0.832 | 0.739 | −0.409 | 0.904 |
| mmu_miR_302c_002558 | 1.470 | 0.774 | 0.533 | 0.893 | −0.937 | 0.856 |
| mmu_miR_302d_000535 | −2.102 | 0.517 | 0.033 | 0.993 | 2.136 | 0.500 |
| mmu_miR_30a_000417 | 0.369 | 0.378 | 0.712 | 0.053 | 0.343 | 0.403 |
| mmu_miR_30b_000602 | 0.065 | 0.912 | −0.086 | 0.822 | −0.151 | 0.724 |
| mmu_miR_30b_002498 | 1.922 | 0.279 | 2.556 | 0.111 | 0.634 | 0.766 |
| mmu_miR_30c_000419 | −0.413 | 0.182 | −0.222 | 0.474 | 0.191 | 0.568 |
| mmu_miR_30d_000420 | 0.863 | 0.171 | 1.637 | 0.006 | 0.775 | 0.218 |
| mmu_miR_30e_002223 | 0.928 | 0.001 | 1.205 | 0.000 | 0.277 | 0.362 |
| mmu_miR_31_000185 | 1.267 | 0.070 | 1.537 | 0.023 | 0.270 | 0.766 |
| mmu_miR_31_002495 | 1.090 | 0.649 | −0.602 | 0.786 | −1.693 | 0.420 |
| mmu_miR_320_002277 | 2.505 | 0.000 | 1.559 | 0.000 | −0.946 | 0.016 |
| mmu_miR_322_001059 | 0.432 | 0.936 | 1.656 | 0.680 | 1.224 | 0.804 |
| mmu_miR_322_001076 | 3.051 | 0.054 | 0.820 | 0.635 | −2.231 | 0.168 |

TABLE 3-continued

| Spinal Cord miRNA data. | | | | | | |
|---|---|---|---|---|---|---|
| mmu_miR_322_002506 | 0.880 | 0.667 | 1.711 | 0.300 | 0.831 | 0.667 |
| mmu_miR_323_3p_002227 | −6.385 | 0.000 | −9.975 | 0.000 | −3.590 | 0.000 |
| mmu_miR_324_3p_002509 | 2.498 | 0.010 | −0.004 | 0.998 | −2.502 | 0.012 |
| mmu_miR_324_5p_000539 | 1.037 | 0.388 | 0.237 | 0.846 | −0.800 | 0.510 |
| mmu_miR_325_001060 | −5.655 | 0.104 | −0.683 | 0.859 | 4.971 | 0.154 |
| mmu_miR_325_002510 | −0.308 | 0.813 | −1.891 | 0.032 | −1.582 | 0.083 |
| mmu_miR_326_001061 | 7.498 | 0.140 | 7.069 | 0.143 | −0.430 | 0.952 |
| mmu_miR_327_002481 | −0.238 | 0.905 | −0.997 | 0.385 | −0.759 | 0.541 |
| mmu_miR_328_000543 | −0.073 | 0.912 | −0.822 | 0.035 | −0.749 | 0.065 |
| mmu_miR_329_000192 | −2.789 | 0.006 | −4.265 | 0.000 | −1.475 | 0.145 |
| mmu_miR_32_002109 | −4.301 | 0.079 | 4.923 | 0.037 | 9.223 | 0.001 |
| mmu_miR_330_001062 | −2.663 | 0.553 | 0.071 | 0.988 | 2.733 | 0.525 |
| mmu_miR_330_002230 | −2.078 | 0.086 | −2.790 | 0.017 | −0.712 | 0.603 |
| mmu_miR_331_3p_000545 | 1.551 | 0.005 | 0.427 | 0.448 | −1.123 | 0.040 |
| mmu_miR_331_5p_002233 | −5.784 | 0.015 | −2.017 | 0.412 | 3.767 | 0.119 |
| mmu_miR_335_3p_002185 | −2.935 | 0.017 | −7.457 | 0.000 | −4.522 | 0.001 |
| mmu_miR_335_5p_000546 | −1.987 | 0.001 | −3.085 | 0.000 | −1.098 | 0.049 |
| mmu_miR_337_000193 | −1.171 | 0.393 | −1.876 | 0.125 | −0.706 | 0.616 |
| mmu_miR_337_3p_002532 | −2.967 | 0.007 | −3.778 | 0.001 | −0.811 | 0.505 |
| mmu_miR_337_5p_002515 | −1.343 | 0.538 | 0.661 | 0.755 | 2.003 | 0.311 |
| mmu_miR_338_3p_002252 | 1.156 | 0.318 | 2.009 | 0.056 | 0.853 | 0.482 |
| mmu_miR_339_3p_002533 | −1.109 | 0.622 | 2.851 | 0.114 | 3.960 | 0.033 |
| mmu_miR_339_5p_002257 | 3.477 | 0.003 | 2.444 | 0.027 | −1.034 | 0.401 |
| mmu_miR_340_3p_002259 | −0.040 | 0.944 | 0.340 | 0.389 | 0.380 | 0.353 |
| mmu_miR_340_5p_002258 | 0.966 | 0.013 | 0.363 | 0.370 | −0.604 | 0.129 |
| mmu_miR_342_3p_002260 | −2.129 | 0.000 | −3.066 | 0.000 | −0.937 | 0.016 |
| mmu_miR_342_5p_002527 | −5.377 | 0.000 | −5.041 | 0.000 | 0.336 | 0.861 |
| mmu_miR_343_002483 | −1.154 | 0.043 | −1.538 | 0.006 | −0.385 | 0.546 |
| mmu_miR_344_001063 | 2.991 | 0.004 | −0.640 | 0.561 | −3.631 | 0.001 |
| mmu_miR_345_001137 | 1.884 | 0.043 | 1.772 | 0.051 | −0.113 | 0.932 |
| mmu_miR_345_3p_002529 | 1.674 | 0.146 | 1.877 | 0.083 | 0.203 | 0.904 |
| mmu_miR_345_5p_002528 | 3.355 | 0.000 | 1.946 | 0.005 | −1.409 | 0.046 |
| mmu_miR_346_001064 | 0.306 | 0.896 | 0.819 | 0.567 | 0.513 | 0.769 |
| mmu_miR_34a_000426 | −3.863 | 0.000 | −4.795 | 0.000 | −0.931 | 0.108 |
| mmu_miR_34b_001065 | 0.617 | 0.740 | −0.427 | 0.786 | −1.044 | 0.493 |
| mmu_miR_34b_3p_002618 | 0.613 | 0.212 | 0.091 | 0.862 | −0.523 | 0.288 |
| mmu_miR_34b_5p_002617 | −1.052 | 0.466 | 0.670 | 0.633 | 1.722 | 0.192 |
| mmu_miR_34c_000428 | 2.331 | 0.003 | −0.851 | 0.288 | −3.182 | 0.000 |
| mmu_miR_34c_002584 | −1.245 | 0.034 | −0.067 | 0.922 | 1.178 | 0.046 |
| mmu_miR_350_002530 | 1.486 | 0.005 | 2.406 | 0.000 | 0.920 | 0.083 |
| mmu_miR_351_001067 | 0.117 | 0.941 | −2.300 | 0.027 | −2.417 | 0.025 |
| mmu_miR_361_000554 | 2.795 | 0.038 | −0.311 | 0.837 | −3.106 | 0.023 |
| mmu_miR_362_3p_002616 | −1.386 | 0.148 | 1.412 | 0.124 | 2.799 | 0.004 |
| mmu_miR_362_5p_002614 | 3.521 | 0.000 | 1.507 | 0.056 | −2.015 | 0.015 |
| mmu_miR_363_001271 | 3.515 | 0.159 | 0.989 | 0.714 | −2.526 | 0.323 |
| mmu_miR_365_001020 | 5.914 | 0.000 | 4.057 | 0.000 | −1.857 | 0.025 |
| mmu_miR_367_000555 | 1.197 | 0.874 | 1.015 | 0.845 | −0.182 | 0.977 |
| mmu_miR_369_3p_000557 | −4.324 | 0.000 | −5.631 | 0.000 | −1.307 | 0.176 |
| mmu_miR_369_5p_001021 | −6.219 | 0.000 | −4.415 | 0.000 | 1.803 | 0.071 |
| mmu_miR_370_001068 | 0.359 | 0.911 | 1.603 | 0.385 | 1.244 | 0.533 |
| mmu_miR_370_002275 | −7.248 | 0.000 | −11.937 | 0.000 | −4.689 | 0.000 |

TABLE 3-continued

Spinal Cord miRNA data.

| | | | | | | |
|---|---|---|---|---|---|---|
| mmu_miR_374_002043 | −4.185 | 0.436 | 2.726 | 0.596 | 6.911 | 0.158 |
| mmu_miR_374_5p_001319 | 0.601 | 0.912 | 1.057 | 0.788 | 0.456 | 0.928 |
| mmu_miR_375_000564 | −0.153 | 0.936 | −2.788 | 0.014 | −2.634 | 0.025 |
| mmu_miR_376a_001069 | −3.926 | 0.000 | −5.101 | 0.000 | −1.175 | 0.019 |
| mmu_miR_376a_002482 | −3.847 | 0.038 | −5.686 | 0.002 | −1.838 | 0.353 |
| mmu_miR_376b_002451 | 0.745 | 0.912 | −4.488 | 0.242 | −5.233 | 0.182 |
| mmu_miR_376b_002452 | −6.279 | 0.000 | −8.075 | 0.000 | −1.797 | 0.074 |
| mmu_miR_376c_002450 | −1.281 | 0.003 | −2.719 | 0.000 | −1.438 | 0.002 |
| mmu_miR_376c_002523 | −2.348 | 0.301 | −1.986 | 0.355 | 0.361 | 0.906 |
| mmu_miR_377_000566 | −0.191 | 0.941 | −0.974 | 0.596 | −0.782 | 0.711 |
| mmu_miR_379_001138 | −0.228 | 0.906 | −3.442 | 0.001 | −3.215 | 0.004 |
| mmu_miR_380_3p_001071 | −1.680 | 0.079 | −3.116 | 0.001 | −1.436 | 0.138 |
| mmu_miR_380_5p_002601 | −4.583 | 0.000 | −4.806 | 0.000 | −0.223 | 0.796 |
| mmu_miR_381_000571 | −6.732 | 0.000 | −5.004 | 0.001 | 1.728 | 0.270 |
| mmu_miR_382_000572 | −4.513 | 0.001 | −9.823 | 0.000 | −5.310 | 0.000 |
| mmu_miR_383_001767 | −4.909 | 0.000 | −6.897 | 0.000 | −1.988 | 0.003 |
| mmu_miR_384_3p_002603 | −1.066 | 0.058 | −2.264 | 0.000 | −1.197 | 0.036 |
| mmu_miR_384_5p_002602 | −1.987 | 0.000 | −2.893 | 0.000 | −0.906 | 0.016 |
| mmu_miR_409_3p_002332 | −1.585 | 0.130 | −3.716 | 0.000 | −2.131 | 0.039 |
| mmu_miR_409_5p_002331 | −4.835 | 0.000 | −6.727 | 0.000 | −1.892 | 0.046 |
| mmu_miR_410_001274 | −2.686 | 0.000 | −5.093 | 0.000 | −2.408 | 0.000 |
| mmu_miR_411_001610 | −1.802 | 0.007 | −3.363 | 0.000 | −1.562 | 0.020 |
| mmu_miR_412_002575 | −8.934 | 0.000 | −8.729 | 0.000 | 0.205 | 0.881 |
| mmu_miR_423_5p_002340 | 1.058 | 0.263 | 2.491 | 0.004 | 1.433 | 0.110 |
| mmu_miR_425_001516 | −6.265 | 0.002 | 2.486 | 0.203 | 8.752 | 0.000 |
| mmu_miR_429_001077 | −1.904 | 0.502 | 0.324 | 0.907 | 2.227 | 0.412 |
| mmu_miR_431_001979 | −3.966 | 0.000 | −6.840 | 0.000 | −2.873 | 0.006 |
| mmu_miR_432_241135_mat | −2.055 | 0.627 | −1.063 | 0.789 | 0.992 | 0.839 |
| mmu_miR_433_001028 | −3.700 | 0.000 | −4.893 | 0.000 | −1.193 | 0.013 |
| mmu_miR_433_5p_001078 | −5.263 | 0.086 | −1.360 | 0.689 | 3.903 | 0.214 |
| mmu_miR_434_3p_002604 | −4.046 | 0.000 | −5.104 | 0.000 | −1.058 | 0.027 |
| mmu_miR_434_5p_002581 | −4.908 | 0.000 | −7.648 | 0.000 | −2.741 | 0.019 |
| mmu_miR_448_001029 | −5.876 | 0.000 | −8.659 | 0.000 | −2.782 | 0.086 |
| mmu_miR_449a_001030 | −4.911 | 0.001 | −1.976 | 0.144 | 2.935 | 0.036 |
| mmu_miR_449b_001667 | −5.202 | 0.006 | −2.077 | 0.271 | 3.125 | 0.099 |
| mmu_miR_449b_002539 | −0.280 | 0.406 | −1.302 | 0.000 | −1.022 | 0.002 |
| mmu_miR_450B_3P_002632 | −2.418 | 0.452 | 0.712 | 0.823 | 3.130 | 0.306 |
| mmu_miR_450a_3p_002525 | −0.316 | 0.314 | −1.377 | 0.000 | −1.061 | 0.001 |
| mmu_miR_450a_5p_002303 | 1.228 | 0.429 | −0.215 | 0.892 | −1.443 | 0.330 |
| mmu_miR_450b_5p_001962 | −0.181 | 0.817 | −1.081 | 0.042 | −0.900 | 0.105 |
| mmu_miR_451_001141 | −1.382 | 0.758 | 5.665 | 0.070 | 7.048 | 0.031 |
| mmu_miR_452_001032 | 0.471 | 0.935 | 3.163 | 0.365 | 2.691 | 0.480 |
| mmu_miR_453_002484 | 0.233 | 0.912 | 0.002 | 0.999 | −0.231 | 0.898 |
| mmu_miR_455_002455 | 3.355 | 0.013 | 3.271 | 0.013 | −0.084 | 0.964 |
| mmu_miR_463_002582 | −3.483 | 0.008 | 5.117 | 0.000 | 8.600 | 0.000 |
| mmu_miR_463_002662 | −4.440 | 0.070 | 2.094 | 0.407 | 6.534 | 0.009 |
| mmu_miR_464_001081 | −0.158 | 0.912 | −1.805 | 0.031 | −1.646 | 0.059 |
| mmu_miR_465C_5P_002654 | −6.587 | 0.001 | 3.200 | 0.070 | 9.787 | 0.000 |
| mmu_miR_465a_3p_002040 | −2.010 | 0.482 | −1.877 | 0.475 | 0.133 | 0.971 |
| mmu_miR_465a_5p_001082 | 5.606 | 0.398 | 4.957 | 0.426 | −0.649 | 0.938 |
| mmu_miR_465b_5p_002485 | −0.597 | 0.932 | −3.097 | 0.454 | −2.500 | 0.575 |

TABLE 3-continued

Spinal Cord miRNA data.

| | | | | | | |
|---|---|---|---|---|---|---|
| mmu_miR_466E_5P_00278 | −3.252 | 0.492 | 3.255 | 0.452 | 6.507 | 0.124 |
| mmu_miR_466J_002817 | 4.182 | 0.003 | 3.665 | 0.007 | −0.518 | 0.773 |
| mmu_miR_466a_3p_002586 | 3.977 | 0.000 | 3.464 | 0.000 | −0.513 | 0.532 |
| mmu_miR_466b_3_3p_002500 | 2.878 | 0.010 | 3.389 | 0.002 | 0.511 | 0.711 |
| mmu_miR_466d_5p_002534 | −6.104 | 0.195 | 0.898 | 0.859 | 7.002 | 0.125 |
| mmu_miR_466g_241015_mat | 5.554 | 0.012 | 6.296 | 0.004 | 0.742 | 0.806 |
| mmu_miR_466h_002516 | 1.614 | 0.452 | 2.760 | 0.143 | 1.145 | 0.603 |
| mmu_miR_466k_240990_mat | 3.361 | 0.216 | 5.585 | 0.027 | 2.225 | 0.434 |
| mmu_miR_467F_002886 | −1.653 | 0.665 | 5.226 | 0.073 | 6.878 | 0.025 |
| mmu_miR_467H_002809 | 5.041 | 0.000 | 4.007 | 0.001 | −1.034 | 0.398 |
| mmu_miR_467a_001826 | 0.517 | 0.780 | 4.593 | 0.001 | 4.076 | 0.003 |
| mmu_miR_467a_002587 | 5.064 | 0.000 | 2.392 | 0.024 | −2.671 | 0.016 |
| mmu_miR_467b_001671 | 3.488 | 0.002 | 2.360 | 0.029 | −1.128 | 0.339 |
| mmu_miR_467b_001684 | −3.848 | 0.057 | 6.813 | 0.001 | 10.661 | 0.000 |
| mmu_miR_467c_002517 | 4.416 | 0.012 | 4.929 | 0.005 | 0.514 | 0.838 |
| mmu_miR_467d_002518 | 1.876 | 0.145 | 3.052 | 0.012 | 1.176 | 0.379 |
| mmu_miR_467e_002568 | −0.102 | 0.968 | 3.525 | 0.054 | 3.627 | 0.056 |
| mmu_miR_467e_002569 | 1.785 | 0.409 | −1.592 | 0.433 | −3.377 | 0.087 |
| mmu_miR_468_001085 | −0.381 | 0.885 | −3.603 | 0.019 | −3.222 | 0.043 |
| mmu_miR_469_001086 | −0.600 | 0.912 | −2.816 | 0.419 | −2.216 | 0.555 |
| mmu_miR_470_002588 | 1.007 | 0.441 | 1.160 | 0.337 | 0.153 | 0.928 |
| mmu_miR_470_002589 | −5.318 | 0.334 | 9.168 | 0.063 | 14.485 | 0.006 |
| mmu_miR_471_002605 | −0.147 | 0.840 | −0.926 | 0.051 | −0.779 | 0.115 |
| mmu_miR_483_001291 | −0.689 | 0.885 | 3.775 | 0.177 | 4.464 | 0.123 |
| mmu_miR_483_002560 | 0.622 | 0.667 | 2.860 | 0.010 | 2.238 | 0.052 |
| mmu_miR_484_001821 | 1.175 | 0.008 | 1.071 | 0.012 | −0.104 | 0.868 |
| mmu_miR_485_3p_001943 | −2.539 | 0.000 | −3.085 | 0.000 | −0.545 | 0.339 |
| mmu_miR_486_001278 | 4.807 | 0.001 | −0.992 | 0.501 | −5.799 | 0.000 |
| mmu_miR_487b_001285 | −3.795 | 0.000 | −4.302 | 0.000 | −0.507 | 0.380 |
| mmu_miR_487b_001306 | −3.946 | 0.000 | −6.822 | 0.000 | −2.876 | 0.000 |
| mmu_miR_488_001659 | 1.769 | 0.172 | 1.006 | 0.439 | −0.762 | 0.590 |
| mmu_miR_488_002014 | 2.232 | 0.407 | 2.063 | 0.411 | −0.169 | 0.960 |
| mmu_miR_489_001302 | −5.370 | 0.006 | −7.714 | 0.000 | −2.344 | 0.248 |
| mmu_miR_490_001037 | −6.122 | 0.000 | −6.363 | 0.000 | −0.240 | 0.891 |
| mmu_miR_491_001630 | −0.695 | 0.534 | −4.128 | 0.000 | −3.433 | 0.001 |
| mmu_miR_493_002519 | −3.252 | 0.156 | −3.239 | 0.136 | 0.013 | 0.995 |
| mmu_miR_494_001293 | −0.336 | 0.904 | −3.009 | 0.045 | −2.673 | 0.086 |
| mmu_miR_494_002365 | −1.591 | 0.211 | −2.051 | 0.079 | −0.460 | 0.769 |
| mmu_miR_495_001663 | −3.194 | 0.000 | −5.053 | 0.000 | −1.860 | 0.000 |
| mmu_miR_496_001953 | −3.670 | 0.128 | −5.172 | 0.024 | −1.502 | 0.572 |
| mmu_miR_497_001346 | 6.029 | 0.000 | 3.634 | 0.001 | −2.395 | 0.032 |
| mmu_miR_499_001352 | −1.345 | 0.553 | −0.593 | 0.790 | 0.752 | 0.766 |
| mmu_miR_500_002606 | 0.035 | 0.976 | −1.291 | 0.208 | −1.327 | 0.214 |
| mmu_miR_501_001356 | 0.400 | 0.911 | 0.687 | 0.758 | 0.287 | 0.923 |
| mmu_miR_501_3p_001651 | 1.543 | 0.018 | −1.349 | 0.034 | −2.892 | 0.000 |
| mmu_miR_503_002456 | 0.107 | 0.962 | −0.251 | 0.879 | −0.358 | 0.861 |
| mmu_miR_503_002536 | 2.178 | 0.026 | 2.365 | 0.013 | 0.187 | 0.898 |
| mmu_miR_504_002084 | −1.744 | 0.086 | −3.691 | 0.000 | −1.947 | 0.056 |
| mmu_miR_505_001655 | 0.618 | 0.669 | 1.207 | 0.303 | 0.589 | 0.667 |
| mmu_miR_509_3p_002521 | −3.454 | 0.553 | −0.992 | 0.859 | 2.462 | 0.679 |
| mmu_miR_509_5p_002520 | −0.243 | 0.968 | −1.633 | 0.727 | −1.389 | 0.806 |

TABLE 3-continued

| Spinal Cord miRNA data. | | | | | | |
|---|---|---|---|---|---|---|
| mmu_miR_511_002549 | 0.714 | 0.754 | 1.815 | 0.280 | 1.101 | 0.551 |
| mmu_miR_532_3p_002355 | −0.969 | 0.125 | 0.424 | 0.512 | 1.392 | 0.026 |
| mmu_miR_532_5p_001518 | 0.763 | 0.105 | 1.106 | 0.015 | 0.342 | 0.510 |
| mmu_miR_539_001286 | −0.834 | 0.437 | −4.345 | 0.000 | −3.511 | 0.001 |
| mmu_miR_540_3p_001310 | −2.606 | 0.014 | −2.563 | 0.013 | 0.043 | 0.977 |
| mmu_miR_540_5p_002561 | −3.001 | 0.008 | −4.289 | 0.000 | −1.288 | 0.275 |
| mmu_miR_541_002562 | −5.953 | 0.000 | −5.998 | 0.000 | −0.045 | 0.956 |
| mmu_miR_542_3p_001284 | 2.238 | 0.087 | 0.977 | 0.474 | −1.262 | 0.366 |
| mmu_miR_542_5p_002563 | −0.586 | 0.911 | −4.248 | 0.137 | −3.662 | 0.228 |
| mmu_miR_543_001298 | −3.676 | 0.000 | −5.012 | 0.000 | −1.336 | 0.027 |
| mmu_miR_543_002376 | −3.501 | 0.000 | −5.152 | 0.000 | −1.651 | 0.001 |
| mmu_miR_544_002550 | −1.859 | 0.038 | −4.762 | 0.000 | −2.903 | 0.002 |
| mmu_miR_546_001312 | −6.449 | 0.397 | 2.059 | 0.793 | 8.508 | 0.235 |
| mmu_miR_547_002564 | 0.909 | 0.813 | −1.670 | 0.554 | −2.579 | 0.366 |
| mmu_miR_551b_001535 | −2.496 | 0.025 | 0.052 | 0.970 | 2.548 | 0.025 |
| mmu_miR_574_3p_002349 | 1.510 | 0.040 | 1.275 | 0.073 | −0.234 | 0.817 |
| mmu_miR_582_3p_002567 | 2.845 | 0.098 | 2.139 | 0.205 | −0.706 | 0.745 |
| mmu_miR_582_5p_002566 | 0.846 | 0.359 | −0.634 | 0.474 | −1.480 | 0.082 |
| mmu_miR_590_5p_001984 | −0.085 | 0.976 | −0.936 | 0.711 | −0.851 | 0.771 |
| mmu_miR_592_002017 | −2.197 | 0.003 | −2.834 | 0.000 | −0.637 | 0.429 |
| mmu_miR_598_002476 | −0.586 | 0.697 | −3.049 | 0.007 | −2.463 | 0.036 |
| mmu_miR_599_241117_mat | 2.784 | 0.307 | 0.696 | 0.807 | −2.088 | 0.454 |
| mmu_miR_615_3p_001960 | 3.582 | 0.000 | −1.158 | 0.229 | −4.740 | 0.000 |
| mmu_miR_615_5p_002353 | 0.386 | 0.494 | −0.027 | 0.965 | −0.413 | 0.454 |
| mmu_miR_652_002352 | 3.901 | 0.000 | 0.749 | 0.500 | −3.152 | 0.004 |
| mmu_miR_654_3p_002239 | −0.040 | 0.969 | −1.072 | 0.166 | −1.031 | 0.206 |
| mmu_miR_654_5p_002522 | −0.137 | 0.933 | −0.852 | 0.375 | −0.716 | 0.493 |
| mmu_miR_665_002607 | −0.942 | 0.437 | −2.901 | 0.007 | −1.959 | 0.076 |
| mmu_miR_666_3p_002448 | −0.573 | 0.856 | 2.749 | 0.162 | 3.323 | 0.105 |
| mmu_miR_666_5p_001952 | −3.012 | 0.000 | −4.103 | 0.000 | −1.091 | 0.141 |
| mmu_miR_667_001949 | −2.454 | 0.000 | −4.807 | 0.000 | −2.352 | 0.000 |
| mmu_miR_668_001947 | −1.773 | 0.392 | −3.639 | 0.046 | −1.866 | 0.353 |
| mmu_miR_669C_002646 | 3.244 | 0.012 | 3.402 | 0.007 | 0.158 | 0.932 |
| mmu_miR_669D_002808 | 3.896 | 0.003 | 3.640 | 0.004 | −0.256 | 0.896 |
| mmu_miR_669E_002774 | 3.380 | 0.026 | 4.015 | 0.007 | 0.634 | 0.745 |
| mmu_miR_669G_002813 | −0.142 | 0.845 | −0.978 | 0.035 | −0.836 | 0.083 |
| mmu_miR_669H_5P_002906 | 0.998 | 0.696 | −0.469 | 0.832 | −1.467 | 0.505 |
| mmu_miR_669a_001683 | 2.013 | 0.199 | 2.131 | 0.145 | 0.118 | 0.956 |
| mmu_miR_669l_121149_mat | 4.362 | 0.001 | 4.030 | 0.001 | −0.332 | 0.848 |
| mmu_miR_669m_121190_mat | −0.369 | 0.912 | 3.593 | 0.065 | 3.961 | 0.051 |
| mmu_miR_669n_197143_mat | 3.025 | 0.004 | 3.230 | 0.002 | 0.205 | 0.898 |
| mmu_miR_669o_121176_mat | 3.748 | 0.007 | 3.520 | 0.010 | −0.229 | 0.910 |
| mmu_miR_670_002020 | −1.683 | 0.774 | 2.822 | 0.512 | 4.505 | 0.298 |
| mmu_miR_671_3p_002322 | 0.848 | 0.389 | 1.923 | 0.027 | 1.075 | 0.249 |
| mmu_miR_672_002327 | −3.632 | 0.027 | −10.016 | 0.000 | −6.384 | 0.000 |
| mmu_miR_673_001954 | −4.546 | 0.079 | 3.761 | 0.135 | 8.307 | 0.002 |
| mmu_miR_673_3p_002449 | 11.293 | 0.000 | −6.309 | 0.014 | 4.984 | 0.060 |
| mmu_miR_674_001956 | 2.775 | 0.000 | 2.593 | 0.001 | −0.182 | 0.861 |
| mmu_miR_674_002021 | −0.367 | 0.886 | 4.098 | 0.007 | 4.465 | 0.005 |
| mmu_miR_675_3p_001941 | −4.213 | 0.550 | 3.120 | 0.634 | 7.333 | 0.243 |
| mmu_miR_675_5p_001940 | −1.827 | 0.618 | 1.237 | 0.712 | 3.064 | 0.336 |

TABLE 3-continued

Spinal Cord miRNA data.

| | | | | | | |
|---|---|---|---|---|---|---|
| mmu_miR_676_001958 | 1.230 | 0.244 | 1.311 | 0.182 | 0.082 | 0.955 |
| mmu_miR_676_001959 | 5.169 | 0.000 | 1.911 | 0.130 | −3.258 | 0.013 |
| mmu_miR_677_001660 | 0.235 | 0.912 | −2.254 | 0.064 | −2.488 | 0.049 |
| mmu_miR_679_001662 | 1.203 | 0.874 | 4.477 | 0.349 | 3.273 | 0.529 |
| mmu_miR_680_001664 | −0.640 | 0.936 | 0.756 | 0.893 | 1.396 | 0.848 |
| mmu_miR_682_001666 | −3.269 | 0.508 | 2.804 | 0.541 | 6.073 | 0.170 |
| mmu_miR_683_001668 | 1.375 | 0.795 | 0.140 | 0.979 | −1.235 | 0.807 |
| mmu_miR_684_001669 | −0.316 | 0.314 | −1.377 | 0.000 | −1.061 | 0.001 |
| mmu_miR_685_001670 | −0.465 | 0.936 | 5.443 | 0.108 | 5.908 | 0.092 |
| mmu_miR_686_001672 | 2.425 | 0.113 | 1.249 | 0.425 | −1.176 | 0.486 |
| mmu_miR_687_001674 | 0.914 | 0.299 | 0.288 | 0.754 | −0.625 | 0.491 |
| mmu_miR_688_001675 | −4.128 | 0.054 | −1.031 | 0.660 | 3.097 | 0.152 |
| mmu_miR_690_001677 | 0.607 | 0.734 | 1.267 | 0.349 | 0.660 | 0.676 |
| mmu_miR_691_001678 | −7.309 | 0.100 | −0.479 | 0.926 | 6.831 | 0.127 |
| mmu_miR_692_001679 | −4.243 | 0.047 | −3.168 | 0.129 | 1.075 | 0.673 |
| mmu_miR_693_001680 | −4.798 | 0.260 | 0.642 | 0.887 | 5.439 | 0.183 |
| mmu_miR_693_3p_002036 | −4.902 | 0.308 | −0.112 | 0.986 | 4.790 | 0.307 |
| mmu_miR_694_001681 | −4.573 | 0.229 | 6.388 | 0.067 | 10.961 | 0.004 |
| mmu_miR_695_001627 | −4.107 | 0.306 | −1.113 | 0.793 | 2.994 | 0.470 |
| mmu_miR_696_001628 | −4.524 | 0.420 | 5.448 | 0.290 | 9.973 | 0.051 |
| mmu_miR_697_001631 | 4.124 | 0.163 | 2.080 | 0.485 | −2.044 | 0.523 |
| mmu_miR_698_001632 | −0.002 | 0.997 | −0.723 | 0.430 | −0.720 | 0.464 |
| mmu_miR_700_001634 | 2.766 | 0.027 | −0.262 | 0.855 | −3.028 | 0.018 |
| mmu_miR_701_001635 | 2.956 | 0.280 | 3.753 | 0.130 | 0.798 | 0.817 |
| mmu_miR_702_001636 | −3.840 | 0.070 | −2.360 | 0.269 | 1.480 | 0.531 |
| mmu_miR_704_001639 | 0.435 | 0.840 | −1.500 | 0.300 | −1.935 | 0.183 |
| mmu_miR_706_001641 | −1.724 | 0.796 | 6.507 | 0.156 | 8.231 | 0.083 |
| mmu_miR_707_001642 | −0.077 | 0.933 | −0.906 | 0.080 | −0.828 | 0.128 |
| mmu_miR_708_002341 | 1.437 | 0.012 | 0.603 | 0.302 | −0.834 | 0.150 |
| mmu_miR_710_001645 | 1.095 | 0.914 | 3.745 | 0.577 | 2.650 | 0.744 |
| mmu_miR_711_001646 | −2.322 | 0.795 | 1.545 | 0.823 | 3.867 | 0.584 |
| mmu_miR_712_001961 | −0.028 | 0.983 | −2.190 | 0.071 | −2.162 | 0.087 |
| mmu_miR_712_002636 | −6.550 | 0.067 | 2.525 | 0.499 | 9.074 | 0.013 |
| mmu_miR_713_001648 | −0.503 | 0.962 | 0.932 | 0.900 | 1.435 | 0.884 |
| mmu_miR_715_001649 | 1.855 | 0.669 | 2.638 | 0.465 | 0.783 | 0.874 |
| mmu_miR_717_001652 | 0.320 | 0.968 | 5.384 | 0.320 | 5.064 | 0.368 |
| mmu_miR_718_001656 | 0.955 | 0.840 | 1.455 | 0.675 | 0.499 | 0.913 |
| mmu_miR_719_001673 | 0.217 | 0.936 | −2.348 | 0.158 | −2.564 | 0.138 |
| mmu_miR_720_001629 | −4.040 | 0.000 | 4.144 | 0.000 | 8.184 | 0.000 |
| mmu_miR_721_001657 | −3.502 | 0.679 | 6.777 | 0.321 | 10.279 | 0.128 |
| mmu_miR_741_002457 | −5.238 | 0.082 | 0.456 | 0.892 | 5.694 | 0.059 |
| mmu_miR_742_002038 | 2.269 | 0.215 | 2.606 | 0.126 | 0.337 | 0.898 |
| mmu_miR_742_002458 | −4.933 | 0.313 | −2.298 | 0.640 | 2.635 | 0.608 |
| mmu_miR_743a_002469 | −2.645 | 0.235 | −1.820 | 0.405 | 0.826 | 0.766 |
| mmu_miR_743b_3p_002471 | 0.158 | 0.932 | −0.440 | 0.709 | −0.598 | 0.616 |
| mmu_miR_743b_5p_002470 | −0.202 | 0.968 | 4.492 | 0.144 | 4.694 | 0.141 |
| mmu_miR_744_002324 | −1.198 | 0.155 | −1.185 | 0.137 | 0.013 | 0.994 |
| mmu_miR_758_002025 | −0.264 | 0.861 | −3.493 | 0.000 | −3.228 | 0.001 |
| mmu_miR_759_002034 | 2.651 | 0.515 | 1.137 | 0.783 | −1.514 | 0.739 |
| mmu_miR_761_002030 | −3.335 | 0.573 | 1.456 | 0.797 | 4.791 | 0.370 |
| mmu_miR_762_002028 | 2.414 | 0.564 | 2.566 | 0.492 | 0.153 | 0.976 |

TABLE 3-continued

| Spinal Cord miRNA data. | | | | | | |
|---|---|---|---|---|---|---|
| mmu_miR_763_002033 | −3.589 | 0.445 | 1.117 | 0.816 | 4.706 | 0.289 |
| mmu_miR_764_3p_002032 | −1.355 | 0.748 | −2.694 | 0.399 | −1.339 | 0.731 |
| mmu_miR_764_5p_002031 | −0.708 | 0.780 | −3.612 | 0.039 | −2.904 | 0.111 |
| mmu_miR_767_241081_mat | −0.315 | 0.312 | −1.373 | 0.000 | −1.057 | 0.001 |
| mmu_miR_770_3p_002027 | −4.093 | 0.000 | −4.691 | 0.000 | −0.598 | 0.616 |
| mmu_miR_770_5p_002608 | −1.438 | 0.105 | −2.983 | 0.001 | −1.545 | 0.082 |
| mmu_miR_7a_000268 | −6.915 | 0.003 | −5.393 | 0.017 | 1.522 | 0.558 |
| mmu_miR_7b_002555 | −7.838 | 0.000 | −5.811 | 0.001 | 2.027 | 0.262 |
| mmu_miR_802_002029 | 0.687 | 0.752 | 1.595 | 0.324 | 0.907 | 0.614 |
| mmu_miR_804_002044 | 0.808 | 0.933 | 5.205 | 0.373 | 4.397 | 0.489 |
| mmu_miR_805_002045 | 1.403 | 0.780 | 7.896 | 0.022 | 6.493 | 0.070 |
| mmu_miR_871_002354 | 0.242 | 0.933 | −0.494 | 0.794 | −0.737 | 0.729 |
| mmu_miR_872_002264 | 3.351 | 0.000 | 1.294 | 0.015 | −2.057 | 0.001 |
| mmu_miR_872_002542 | 3.494 | 0.000 | 1.625 | 0.002 | −1.869 | 0.001 |
| mmu_miR_873_002356 | −2.319 | 0.039 | −4.150 | 0.000 | −1.830 | 0.108 |
| mmu_miR_874_002268 | 0.738 | 0.788 | 1.789 | 0.368 | 1.051 | 0.636 |
| mmu_miR_875_3p_002547 | −3.501 | 0.449 | 1.924 | 0.676 | 5.425 | 0.205 |
| mmu_miR_876_3p_002464 | −1.308 | 0.669 | 0.050 | 0.988 | 1.357 | 0.625 |
| mmu_miR_876_5p_002463 | 0.067 | 0.969 | −1.894 | 0.145 | −1.961 | 0.146 |
| mmu_miR_877_002548 | −3.279 | 0.220 | 3.745 | 0.134 | 7.025 | 0.007 |
| mmu_miR_878_3p_002541 | −2.533 | 0.550 | 7.727 | 0.028 | 10.261 | 0.006 |
| mmu_miR_878_5p_002540 | −5.474 | 0.102 | −0.491 | 0.893 | 4.983 | 0.138 |
| mmu_miR_879_002472 | 0.771 | 0.722 | 0.287 | 0.877 | −0.484 | 0.830 |
| mmu_miR_879_002473 | −1.243 | 0.414 | −1.396 | 0.322 | −0.152 | 0.937 |
| mmu_miR_880_002665 | 4.317 | 0.476 | 9.520 | 0.067 | 5.203 | 0.366 |
| mmu_miR_881_002475 | −5.403 | 0.173 | 0.667 | 0.879 | 6.070 | 0.118 |
| mmu_miR_881_002609 | −2.006 | 0.619 | 2.817 | 0.411 | 4.823 | 0.150 |
| mmu_miR_882_002610 | −0.316 | 0.314 | −1.377 | 0.000 | −1.061 | 0.001 |
| mmu_miR_883B_5P_002669 | −3.095 | 0.447 | 2.736 | 0.474 | 5.830 | 0.116 |
| mmu_miR_883a_3p_002461 | 0.371 | 0.912 | −0.488 | 0.822 | −0.858 | 0.718 |
| mmu_miR_883a_5p_002611 | −0.231 | 0.616 | −1.208 | 0.001 | −0.977 | 0.012 |
| mmu_miR_883b_3p_002565 | −0.751 | 0.873 | −5.148 | 0.061 | −4.397 | 0.127 |
| mmu_miR_92a_000430 | −2.909 | 0.000 | 2.139 | 0.000 | 5.048 | 0.000 |
| mmu_miR_92a_002496 | −0.175 | 0.936 | −0.954 | 0.482 | −0.779 | 0.599 |
| mmu_miR_93_001090 | 3.100 | 0.000 | 1.336 | 0.062 | −1.764 | 0.019 |
| mmu_miR_96_000186 | −8.627 | 0.000 | −3.235 | 0.062 | 5.392 | 0.004 |
| mmu_miR_98_000577 | −3.613 | 0.020 | −5.336 | 0.001 | −1.723 | 0.292 |
| mmu_miR_99a_000435 | 0.704 | 0.381 | 2.165 | 0.003 | 1.461 | 0.046 |
| mmu_miR_99b_000436 | 2.514 | 0.007 | 2.248 | 0.013 | −0.266 | 0.840 |
| mmu_miR_9_000583 | 2.198 | 0.000 | 1.773 | 0.000 | −0.425 | 0.281 |

TABLE 4

| Brain Stem miRNA data. | | | | | | |
| --- | --- | --- | --- | --- | --- | --- |
| | mean__bs.ChAT | mean__bs.GFAP | mean__bs.Lyz2 | mean__bs.Syn | pSI__BS.ChAT | pSI__BS.GFAP |
| hsa__let__7b__002404 | 30.434 | 30.568 | 32.311 | 34.174 | 0.263 | 0.220 |
| hsa__let__7e__002407 | 29.845 | 30.485 | 29.490 | 30.383 | 0.495 | 0.708 |
| hsa__let__7f__1__002417 | 38.091 | 34.575 | 38.321 | 37.593 | NA | 0.033 |
| hsa__let__7i__002172 | 35.202 | 31.683 | 33.850 | 34.880 | NA | 0.054 |
| hsa__miR__106b__002380 | 31.761 | 28.527 | 31.863 | 27.336 | 0.879 | 0.273 |
| hsa__miR__10a__002288 | 37.788 | 38.584 | 38.553 | 39.428 | NA | NA |
| hsa__miR__1197__002810 | 31.437 | 35.563 | 33.740 | 32.817 | 0.125 | NA |
| hsa__miR__124__002197 | 33.367 | 35.516 | 35.026 | 35.695 | NA | NA |
| hsa__miR__127__5p__002229 | 33.808 | 34.690 | 33.263 | 33.401 | NA | 0.786 |
| hsa__miR__136__000592 | 28.841 | 32.218 | 27.819 | 29.145 | 0.442 | 0.971 |
| hsa__miR__136__002100 | 21.421 | 24.050 | 24.092 | 21.782 | 0.261 | 0.779 |
| hsa__miR__140__3p__002234 | 29.226 | 27.686 | 28.505 | 27.789 | 0.821 | 0.431 |
| hsa__miR__143__000466 | 27.198 | 26.694 | 26.214 | 29.246 | 0.509 | 0.396 |
| hsa__miR__144__002676 | 37.700 | 37.852 | 38.215 | 39.548 | NA | NA |
| hsa__miR__148a__002134 | 38.518 | 38.580 | 38.824 | 37.837 | NA | NA |
| hsa__miR__149__002255 | 19.540 | 21.538 | 21.293 | 19.270 | 0.416 | 0.793 |
| hsa__miR__151__5P__002642 | 33.956 | 28.970 | 30.520 | 29.653 | 0.991 | 0.173 |
| hsa__miR__154__000478 | 26.477 | 27.881 | 27.338 | 26.423 | 0.459 | 0.772 |
| hsa__miR__15b__002173 | 34.070 | 35.301 | 26.617 | 37.222 | NA | NA |
| hsa__miR__183__002270 | 25.794 | 32.436 | 25.214 | 26.665 | 0.252 | 1.000 |
| hsa__miR__189__000488 | 28.951 | 28.688 | 25.020 | 31.972 | 0.604 | 0.504 |
| hsa__miR__190b__002263 | 27.724 | 27.463 | 27.813 | 30.158 | 0.408 | 0.330 |
| hsa__miR__196a__241070__mat | 32.372 | 37.264 | 33.308 | 30.122 | 0.441 | NA |
| hsa__miR__200a__001011 | 39.485 | 36.945 | 39.735 | 39.687 | NA | NA |
| hsa__miR__200b__001800 | 28.278 | 33.939 | 27.140 | 33.967 | 0.196 | 0.942 |
| hsa__miR__200b__002274 | 35.926 | 39.292 | 40.372 | 40.499 | NA | NA |
| hsa__miR__200c__000505 | 31.975 | 30.255 | 25.288 | 31.441 | 0.915 | 0.555 |
| hsa__miR__200c__002286 | 38.694 | 39.262 | 39.873 | 39.630 | NA | NA |
| hsa__miR__206__000510 | 28.359 | 27.407 | 27.323 | 26.978 | 0.818 | 0.564 |
| hsa__miR__213__000516 | 28.920 | 26.020 | 26.931 | 26.933 | 0.939 | 0.256 |
| hsa__miR__214__000517 | 28.917 | 31.861 | 25.809 | 32.003 | 0.424 | 0.882 |
| hsa__miR__214__002293 | 36.550 | 35.972 | 36.817 | 38.637 | NA | NA |
| hsa__miR__218__2__002294 | 26.211 | 31.344 | 30.326 | 29.884 | 0.029 | 0.905 |
| hsa__miR__223__000526 | 27.468 | 28.773 | 15.220 | 34.785 | 0.495 | 0.597 |
| hsa__miR__22__000398 | 27.805 | 24.403 | 30.737 | 25.335 | 0.724 | 0.097 |
| hsa__miR__22__002301 | 29.328 | 29.533 | 29.132 | 30.107 | 0.482 | 0.575 |
| hsa__miR__23a__002439 | 38.796 | 39.294 | 28.613 | 41.955 | NA | NA |
| hsa__miR__26b__002444 | 33.572 | 32.024 | 31.236 | 33.868 | NA | 0.404 |
| hsa__miR__27a__002445 | 33.991 | 35.349 | 35.233 | 37.296 | NA | NA |
| hsa__miR__27b__002174 | 34.186 | 33.247 | 33.389 | 34.129 | NA | 0.429 |
| hsa__miR__28__3p__002446 | 37.121 | 37.725 | 37.345 | 37.774 | NA | NA |
| hsa__miR__299__5p__000600 | 29.902 | 37.773 | 32.238 | 36.179 | 0.028 | NA |
| hsa__miR__29a__002447 | 26.052 | 27.242 | 24.052 | 26.836 | 0.559 | 0.819 |
| hsa__miR__29b__2__002166 | 25.519 | 29.022 | 27.905 | 29.466 | 0.096 | 0.778 |
| hsa__miR__30a__3p__000416 | 20.644 | 20.331 | 20.356 | 20.776 | 0.588 | 0.511 |
| hsa__miR__30c__1__002108 | 37.944 | 35.826 | 39.076 | 38.526 | NA | NA |
| hsa__miR__30c__2__002110 | 28.241 | 38.668 | 37.794 | 34.723 | 0.001 | NA |

TABLE 4-continued

| Brain Stem miRNA data. | | | | | | |
|---|---|---|---|---|---|---|
| hsa_miR_30d_002305 | 30.742 | 28.457 | 29.160 | 30.321 | 0.849 | 0.240 |
| hsa_miR_30e_3p_000422 | 20.190 | 20.373 | 18.882 | 20.676 | 0.599 | 0.659 |
| hsa_miR_324_3p_000579 | 28.368 | 25.541 | 25.449 | 25.655 | 0.966 | 0.412 |
| hsa_miR_338_000548 | 27.266 | 22.604 | 25.289 | 23.537 | 0.971 | 0.118 |
| hsa_miR_338_5P_002658 | 24.029 | 22.551 | 24.232 | 23.233 | 0.723 | 0.302 |
| hsa_miR_33a_002136 | 35.133 | 29.937 | 30.568 | 29.366 | NA | 0.355 |
| hsa_miR_340_000550 | 23.506 | 23.449 | 24.239 | 23.647 | 0.511 | 0.506 |
| hsa_miR_363_001283 | 40.095 | 33.199 | 37.805 | 37.736 | NA | 0.004 |
| hsa_miR_376a_001287 | 24.347 | 28.975 | 25.870 | 25.621 | 0.149 | 0.976 |
| hsa_miR_378_000567 | 23.620 | 25.178 | 21.652 | 27.299 | 0.435 | 0.645 |
| hsa_miR_411_002238 | 24.657 | 28.970 | 29.827 | 25.309 | 0.100 | 0.827 |
| hsa_miR_412_001023 | 30.780 | 35.319 | 24.951 | 31.354 | 0.504 | 0.997 |
| hsa_miR_421_002700 | 22.200 | 22.945 | 23.999 | 23.005 | 0.329 | 0.531 |
| hsa_miR_423_3P_002626 | 29.568 | 27.930 | 27.157 | 28.221 | 0.901 | 0.528 |
| hsa_miR_425_001104 | 32.387 | 31.046 | 26.712 | 29.362 | 0.955 | 0.767 |
| hsa_miR_431_002312 | 32.157 | 37.151 | 32.333 | 34.027 | 0.184 | NA |
| hsa_miR_455_001280 | 31.707 | 27.390 | 26.382 | 28.677 | 0.993 | 0.335 |
| hsa_miR_485_5p_001036 | 35.747 | 36.568 | 34.541 | 35.670 | NA | 0.790 |
| hsa_miR_493_3p_001282 | 33.823 | 39.803 | 35.837 | 40.403 | 0.037 | NA |
| hsa_miR_590_3P_002677 | 40.553 | 39.781 | 40.129 | 39.642 | NA | NA |
| hsa_miR_653_002292 | 35.570 | 38.640 | 35.155 | 37.152 | 0.298 | NA |
| hsa_miR_671_5p_197646_mat | 29.677 | 32.567 | 29.854 | 38.221 | 0.172 | 0.586 |
| hsa_miR_708_002342 | 40.436 | 40.199 | 36.808 | 39.872 | NA | NA |
| hsa_miR_744_002325 | 29.906 | 32.132 | 29.147 | 31.138 | 0.398 | 0.869 |
| hsa_miR_875_5p_002203 | 29.170 | 31.613 | 23.935 | 37.191 | 0.414 | 0.639 |
| hsa_miR_935_002178 | 35.689 | 35.255 | 35.413 | 35.777 | NA | 0.486 |
| hsa_miR_93_002139 | 26.818 | 24.833 | 25.487 | 25.510 | 0.875 | 0.352 |
| hsa_miR_99b_002196 | 32.682 | 29.792 | 31.883 | 31.331 | 0.878 | 0.138 |
| hsa_miR_9_002231 | 20.922 | 17.339 | 19.345 | 19.660 | 0.921 | 0.082 |
| mmu_let_7a_000377 | 25.121 | 22.205 | 26.424 | 22.828 | 0.794 | 0.152 |
| mmu_let_7a_002478 | 27.040 | 24.472 | 25.460 | 26.910 | 0.820 | 0.165 |
| mmu_let_7b_000378 | 21.087 | 19.336 | 20.589 | 21.251 | 0.671 | 0.211 |
| mmu_let_7c_000379 | 20.610 | 18.852 | 20.133 | 20.102 | 0.763 | 0.252 |
| mmu_let_7c_1_002479 | 35.061 | 33.804 | 33.692 | 35.897 | NA | 0.353 |
| mmu_let_7d_001178 | 34.147 | 31.554 | 32.490 | 31.230 | NA | 0.382 |
| mmu_let_7d_002283 | 21.499 | 20.703 | 21.447 | 21.426 | 0.618 | 0.414 |
| mmu_let_7e_002406 | 19.033 | 19.032 | 18.704 | 19.049 | 0.591 | 0.618 |
| mmu_let_7f_000382 | 28.381 | 23.278 | 26.668 | 24.450 | 0.969 | 0.081 |
| mmu_let_7g_002282 | 20.687 | 20.748 | 22.080 | 21.362 | 0.409 | 0.415 |
| mmu_let_7g_002492 | 31.538 | 33.480 | 30.996 | 33.693 | 0.361 | 0.781 |
| mmu_let_7i_002221 | 22.310 | 20.755 | 22.444 | 22.311 | 0.642 | 0.226 |
| mmu_miR_100_000437 | 21.320 | 18.575 | 20.961 | 20.198 | 0.835 | 0.128 |
| mmu_miR_101a_002253 | 22.611 | 22.120 | 22.059 | 22.232 | 0.693 | 0.544 |
| mmu_miR_101a_002507 | 34.319 | 32.954 | 34.658 | 33.152 | 0.727 | 0.366 |
| mmu_miR_101b_002531 | 23.132 | 23.051 | 24.168 | 23.343 | 0.488 | 0.456 |
| mmu_miR_103_000439 | 23.062 | 23.983 | 23.456 | 23.342 | 0.468 | 0.721 |
| mmu_miR_105_002465 | 35.643 | 36.454 | 28.902 | 34.276 | NA | NA |
| mmu_miR_106a_002459 | 26.615 | 21.441 | 21.190 | 21.951 | 0.998 | 0.335 |
| mmu_miR_106b_000442 | 24.983 | 23.018 | 23.966 | 23.903 | 0.840 | 0.306 |
| mmu_miR_107_000443 | 25.300 | 25.893 | 27.235 | 25.745 | 0.373 | 0.516 |
| mmu_miR_10a_000387 | 23.708 | 26.102 | 24.476 | 24.291 | 0.346 | 0.866 |

TABLE 4-continued

Brain Stem miRNA data.

| | | | | | | |
|---|---|---|---|---|---|---|
| mmu_miR_10b_001181 | 29.264 | 32.944 | 32.007 | 28.448 | 0.336 | 0.934 |
| mmu_miR_10b_002218 | 26.421 | 35.293 | 31.249 | 22.367 | 0.277 | 0.997 |
| mmu_miR_10b_002572 | 34.529 | 37.263 | 34.417 | 35.584 | NA | NA |
| mmu_miR_1186_002825 | 32.523 | 35.271 | 35.084 | 37.786 | NA | 0.521 |
| mmu_miR_1188_002866 | 33.122 | 33.621 | 36.405 | 36.582 | 0.189 | 0.216 |
| mmu_miR_1191_002892 | 28.902 | 30.073 | 28.750 | 33.773 | 0.308 | 0.492 |
| mmu_miR_1192_002806 | 39.446 | 39.327 | 39.732 | 37.831 | NA | NA |
| mmu_miR_1193_002794 | 28.907 | 32.400 | 31.853 | 32.430 | 0.084 | 0.782 |
| mmu_miR_1194_002793 | 38.645 | 38.769 | 39.026 | 37.065 | NA | NA |
| mmu_miR_1195_002839 | 32.959 | 37.286 | 36.966 | 38.911 | NA | NA |
| mmu_miR_1198_002780 | 28.232 | 26.900 | 31.296 | 26.120 | 0.611 | 0.347 |
| mmu_miR_1199_240984_mat | 40.779 | 40.407 | 40.776 | 39.620 | NA | NA |
| mmu_miR_1224_240985_mat | 40.569 | 40.300 | 40.616 | 39.214 | NA | NA |
| mmu_miR_122_002245 | 36.227 | 37.637 | 32.106 | 38.209 | NA | NA |
| mmu_miR_124_001182 | 23.164 | 23.414 | 24.104 | 22.933 | 0.541 | 0.576 |
| mmu_miR_125a_3p_002199 | 26.699 | 26.213 | 26.085 | 26.534 | 0.664 | 0.532 |
| mmu_miR_125a_5p_002198 | 19.648 | 19.951 | 20.885 | 19.731 | 0.473 | 0.539 |
| mmu_miR_125b_002508 | 27.982 | 28.087 | 29.434 | 29.015 | 0.367 | 0.384 |
| mmu_miR_125b_3p_002378 | 31.114 | 30.269 | 29.950 | 32.016 | 0.591 | 0.415 |
| mmu_miR_125b_5p_000449 | 18.605 | 18.192 | 19.062 | 18.646 | 0.559 | 0.449 |
| mmu_miR_126_3p_002228 | 21.279 | 24.181 | 20.259 | 22.698 | 0.367 | 0.925 |
| mmu_miR_126_5p_000451 | 23.120 | 26.318 | 22.505 | 24.685 | 0.313 | NA |
| mmu_miR_1274a_121150_mat | 31.992 | 32.495 | 24.705 | 33.454 | NA | NA |
| mmu_miR_127_000452 | 17.757 | 20.818 | 19.687 | 17.827 | 0.298 | 0.913 |
| mmu_miR_128a_002216 | 21.223 | 21.008 | 20.910 | 20.653 | 0.677 | 0.599 |
| mmu_miR_129_3p_001184 | 19.707 | 21.808 | 20.868 | 19.585 | 0.430 | 0.839 |
| mmu_miR_129_5p_000590 | 27.010 | 28.204 | 30.022 | 27.169 | 0.325 | 0.559 |
| mmu_miR_1306_121155_mat | 35.808 | 35.958 | 35.514 | 35.068 | NA | NA |
| mmu_miR_130a_000454 | 28.741 | 22.626 | 28.602 | 24.793 | 0.913 | 0.022 |
| mmu_miR_130b_000456 | 29.944 | 27.093 | 26.578 | 29.185 | 0.937 | 0.296 |
| mmu_miR_130b_002460 | 28.591 | 31.823 | 29.783 | 28.383 | 0.371 | 0.939 |
| mmu_miR_132_000457 | 18.035 | 19.896 | 19.396 | 17.703 | 0.454 | 0.804 |
| mmu_miR_133a_001637 | 39.021 | 39.126 | 39.251 | 38.610 | NA | NA |
| mmu_miR_133a_002246 | 18.976 | 26.628 | 23.107 | 19.978 | 0.050 | 0.995 |
| mmu_miR_133b_002247 | 23.603 | 27.595 | 26.324 | 24.681 | 0.123 | 0.932 |
| mmu_miR_134_001186 | 24.953 | 28.914 | 28.803 | 24.447 | 0.256 | 0.891 |
| mmu_miR_135a_000460 | 22.296 | 21.720 | 22.947 | 21.224 | 0.670 | 0.481 |
| mmu_miR_135b_002261 | 22.920 | 23.363 | 25.387 | 22.631 | 0.446 | 0.503 |
| mmu_miR_136_002511 | 24.804 | 25.342 | 28.027 | 23.107 | 0.502 | 0.535 |
| mmu_miR_136_002512 | 27.928 | 33.354 | 26.670 | 33.230 | 0.209 | 0.946 |
| mmu_miR_137_001129 | 21.307 | 24.504 | 24.442 | 23.077 | 0.115 | 0.786 |
| mmu_miR_138_002284 | 16.359 | 20.181 | 19.959 | 17.325 | 0.112 | 0.874 |
| mmu_miR_138_002554 | 24.236 | 27.898 | 25.725 | 25.031 | 0.220 | 0.941 |
| mmu_miR_139_3p_002546 | 33.359 | 36.004 | 31.195 | 29.851 | NA | NA |
| mmu_miR_139_5p_002289 | 20.048 | 21.609 | 19.632 | 20.161 | 0.512 | 0.834 |
| mmu_miR_140_001187 | 23.036 | 22.725 | 22.684 | 22.970 | 0.621 | 0.541 |
| mmu_miR_141_000463 | 33.803 | 33.932 | 28.985 | 37.568 | 0.576 | 0.532 |
| mmu_miR_141_002513 | 28.188 | 32.907 | 24.416 | 35.162 | 0.296 | NA |
| mmu_miR_142_3p_000464 | 29.811 | 28.711 | 19.522 | 32.652 | NA | NA |
| mmu_miR_142_5p_002248 | 32.005 | 32.756 | 25.253 | 38.885 | 0.511 | 0.568 |
| mmu_miR_143_002249 | 28.060 | 28.450 | 25.414 | 30.750 | 0.535 | 0.568 |

TABLE 4-continued

| Brain Stem miRNA data. | | | | | | |
|---|---|---|---|---|---|---|
| mmu_miR_145_002278 | 27.756 | 27.402 | 23.963 | 29.597 | NA | NA |
| mmu_miR_145_002514 | 37.933 | 39.523 | 40.040 | 39.638 | NA | NA |
| mmu_miR_146a_000468 | 20.639 | 22.626 | 17.434 | 23.710 | 0.479 | 0.756 |
| mmu_miR_146b_001097 | 22.695 | 22.216 | 21.839 | 22.482 | 0.687 | 0.567 |
| mmu_miR_146b_002453 | 31.794 | 31.415 | 31.443 | 33.050 | 0.481 | 0.401 |
| mmu_miR_147_002262 | 36.016 | 33.798 | 33.587 | 38.816 | NA | NA |
| mmu_miR_148a_000470 | 26.811 | 25.080 | 30.850 | 26.539 | 0.497 | 0.136 |
| mmu_miR_148b_000471 | 27.647 | 25.405 | 30.954 | 26.787 | 0.600 | 0.121 |
| mmu_miR_150_000473 | 23.174 | 25.591 | 21.132 | 27.950 | 0.385 | NA |
| mmu_miR_150_002570 | 36.223 | 39.715 | 36.964 | 39.714 | 0.180 | NA |
| mmu_miR_151_3p_001190 | 30.840 | 24.438 | 31.063 | 26.117 | 0.907 | 0.032 |
| mmu_miR_152_000475 | 26.857 | 22.888 | 23.571 | 27.870 | 0.800 | 0.100 |
| mmu_miR_153_001191 | 29.396 | 30.050 | 29.135 | 29.692 | 0.512 | 0.720 |
| mmu_miR_154_000477 | 31.574 | 35.290 | 32.145 | 29.713 | 0.494 | NA |
| mmu_miR_155_002571 | 28.988 | 26.564 | 25.019 | 33.436 | 0.679 | 0.277 |
| mmu_miR_15a_000389 | 27.748 | 23.050 | 23.786 | 25.578 | 0.984 | 0.126 |
| mmu_miR_15a_002488 | 32.231 | 31.428 | 32.252 | 32.864 | 0.529 | 0.349 |
| mmu_miR_15b_000390 | 25.296 | 22.564 | 22.469 | 24.117 | 0.937 | 0.289 |
| mmu_miR_16_000391 | 20.727 | 18.380 | 17.503 | 18.919 | 0.946 | 0.467 |
| mmu_miR_16_002489 | 35.351 | 29.781 | 26.776 | 33.488 | NA | 0.261 |
| mmu_miR_17_002308 | 25.016 | 21.092 | 20.348 | 21.549 | 0.990 | 0.401 |
| mmu_miR_17_002543 | 30.979 | 37.822 | 27.821 | 34.399 | 0.301 | NA |
| mmu_miR_181A_2_002687 | 40.599 | 40.161 | 40.674 | 39.605 | NA | NA |
| mmu_miR_181a_000480 | 24.582 | 21.252 | 23.710 | 22.198 | 0.912 | 0.152 |
| mmu_miR_181c_000482 | 28.994 | 27.339 | 28.014 | 27.754 | 0.831 | 0.403 |
| mmu_miR_182_002599 | 22.728 | 26.575 | 23.162 | 23.594 | 0.255 | 0.969 |
| mmu_miR_1839_3p_121203_mat | 24.447 | 24.082 | 25.141 | 24.832 | 0.503 | 0.397 |
| mmu_miR_1839_5p_121135_mat | 24.912 | 24.707 | 28.820 | 25.164 | 0.353 | 0.322 |
| mmu_miR_183_002269 | 28.202 | 33.198 | 29.383 | 29.520 | 0.152 | 0.988 |
| mmu_miR_184_000485 | 28.731 | 33.046 | 25.242 | 30.157 | 0.402 | NA |
| mmu_miR_185_002271 | 26.081 | 26.282 | 32.052 | 25.770 | 0.382 | 0.406 |
| mmu_miR_186_002285 | 23.564 | 21.590 | 22.348 | 23.100 | 0.820 | 0.276 |
| mmu_miR_186_002574 | 28.670 | 30.838 | 26.330 | 30.285 | 0.474 | 0.880 |
| mmu_miR_187_001193 | 33.055 | 25.462 | 31.176 | 27.396 | 0.982 | 0.026 |
| mmu_miR_188_3p_002106 | 39.121 | 38.941 | 39.540 | 39.323 | NA | NA |
| mmu_miR_188_5p_002320 | 25.401 | 26.064 | 22.115 | 27.573 | NA | NA |
| mmu_miR_1893_121170_mat | 39.304 | 40.600 | 36.900 | 40.075 | NA | NA |
| mmu_miR_1894_3p_241002_mat | 27.801 | 30.706 | 25.968 | 33.332 | 0.335 | NA |
| mmu_miR_1894_5p_121144_mat | 38.271 | 36.354 | 38.706 | 39.612 | NA | NA |
| mmu_miR_1896_121128_mat | 22.791 | 25.156 | 19.203 | 30.938 | 0.393 | 0.620 |
| mmu_miR_1897_3p_121126_mat | 40.712 | 40.345 | 40.733 | 39.619 | NA | NA |
| mmu_miR_1897_5p_121199_mat | 17.358 | 20.450 | 17.629 | 22.211 | NA | NA |
| mmu_miR_1898_121195_mat | 40.754 | 40.130 | 40.752 | 39.621 | NA | NA |
| mmu_miR_1899_121198_mat | 40.114 | 39.769 | 40.350 | 39.621 | NA | NA |
| mmu_miR_18a_002422 | 31.352 | 27.187 | 25.283 | 27.985 | 0.994 | 0.407 |
| mmu_miR_18a_002490 | 33.913 | 32.190 | 29.459 | 33.745 | 0.865 | 0.482 |
| mmu_miR_18b_002466 | 40.650 | 38.742 | 40.323 | 39.953 | NA | NA |
| mmu_miR_1900_121143_mat | 40.382 | 40.016 | 40.523 | 39.626 | NA | NA |
| mmu_miR_1901_121183_mat | 33.367 | 34.836 | 38.448 | 36.561 | 0.127 | 0.304 |
| mmu_miR_1902_121197_mat | 40.597 | 40.228 | 40.662 | 39.611 | NA | NA |
| mmu_miR_1903_121153_mat | 40.379 | 36.811 | 35.263 | 40.133 | NA | NA |

TABLE 4-continued

| Brain Stem miRNA data. | | | | | | |
|---|---|---|---|---|---|---|
| mmu_miR_1904_121162_mat | 15.010 | 18.703 | 14.060 | 20.519 | NA | NA |
| mmu_miR_1905_121196_mat | 25.376 | 28.001 | 24.687 | 31.218 | 0.273 | 0.631 |
| mmu_miR_1906_121169_mat | 40.168 | 38.123 | 40.252 | 38.085 | NA | NA |
| mmu_miR_190_000489 | 26.239 | 24.859 | 25.449 | 25.666 | 0.770 | 0.387 |
| mmu_miR_191_002299 | 20.075 | 19.632 | 19.418 | 19.673 | 0.705 | 0.575 |
| mmu_miR_191_002576 | 31.390 | 30.572 | 30.354 | 31.978 | 0.618 | 0.434 |
| mmu_miR_1927_121193_mat | 37.418 | 34.176 | 37.493 | 36.762 | NA | 0.051 |
| mmu_miR_1928_121164_mat | 18.309 | 23.066 | 19.404 | 28.506 | 0.065 | 0.675 |
| mmu_miR_192_000491 | 25.904 | 23.854 | 25.070 | 25.323 | 0.809 | 0.230 |
| mmu_miR_1930_121201_mat | 29.247 | 29.979 | 27.194 | 28.980 | 0.710 | 0.816 |
| mmu_miR_1931_121168_mat | 40.109 | 38.542 | 40.241 | 38.119 | NA | NA |
| mmu_miR_1932_121172_mat | 32.634 | 29.164 | 34.172 | 35.153 | NA | 0.012 |
| mmu_miR_1933_3p_121145_mat | 40.509 | 40.133 | 40.605 | 39.601 | NA | NA |
| mmu_miR_1933_5p_121133_mat | 31.267 | 36.124 | 31.827 | 35.135 | 0.130 | NA |
| mmu_miR_1934_121185_mat | 38.764 | 30.581 | 38.675 | 39.556 | NA | 0.000 |
| mmu_miR_1935_121192_mat | 37.587 | 39.820 | 40.427 | 38.135 | NA | NA |
| mmu_miR_1936_121158_mat | 37.623 | 38.925 | 39.390 | 38.950 | NA | NA |
| mmu_miR_1937b_241023_mat | 19.684 | 21.650 | 18.534 | 24.192 | 0.359 | NA |
| mmu_miR_1937c_241011_mat | 20.764 | 22.957 | 19.748 | 25.354 | 0.335 | NA |
| mmu_miR_1938_121194_mat | 38.858 | 38.707 | 39.286 | 39.541 | NA | NA |
| mmu_miR_1939_121180_mat | 38.426 | 38.695 | 38.538 | 37.256 | NA | NA |
| mmu_miR_193_002250 | 35.294 | 32.650 | 35.316 | 35.961 | NA | NA |
| mmu_miR_193_002577 | 30.351 | 30.720 | 31.809 | 31.789 | 0.322 | 0.411 |
| mmu_miR_193b_002467 | 22.479 | 21.410 | 24.489 | 22.163 | 0.549 | 0.266 |
| mmu_miR_1940_121187_mat | 38.067 | 39.190 | 32.253 | 39.388 | NA | NA |
| mmu_miR_1941_3p_121130_mat | 38.834 | 38.716 | 39.340 | 39.579 | NA | NA |
| mmu_miR_1941_5p_121140_mat | 32.257 | 30.942 | 29.886 | 33.774 | 0.638 | 0.385 |
| mmu_miR_1942_121136_mat | 34.626 | 32.903 | 27.591 | 37.286 | 0.712 | 0.425 |
| mmu_miR_1943_121174_mat | 34.816 | 31.883 | 32.801 | 32.777 | NA | 0.253 |
| mmu_miR_1944_121189_mat | 39.858 | 38.519 | 40.370 | 38.606 | NA | NA |
| mmu_miR_1945_121166_mat | 38.586 | 38.632 | 39.052 | 38.188 | NA | NA |
| mmu_miR_1946a_121178_mat | 41.116 | 41.011 | 29.608 | 38.214 | NA | NA |
| mmu_miR_1947_121156_mat | 38.479 | 35.568 | 38.700 | 37.990 | NA | NA |
| mmu_miR_1948_121171_mat | 34.678 | 37.569 | 36.859 | 36.217 | 0.175 | NA |
| mmu_miR_1949_121182_mat | 40.209 | 39.917 | 40.385 | 38.679 | NA | NA |
| mmu_miR_194_000493 | 26.451 | 23.960 | 23.957 | 25.288 | 0.923 | 0.309 |
| mmu_miR_1950_121146_mat | 40.561 | 40.166 | 40.607 | 39.643 | NA | NA |
| mmu_miR_1951_121165_mat | 33.211 | 37.796 | 26.261 | 40.596 | 0.331 | NA |
| mmu_miR_1952_121167_mat | 40.666 | 40.303 | 40.709 | 39.621 | NA | NA |
| mmu_miR_1953_121159_mat | 39.568 | 39.198 | 39.936 | 39.588 | NA | NA |
| mmu_miR_1954_121137_mat | 30.339 | 32.215 | 26.346 | 38.985 | 0.419 | 0.593 |
| mmu_miR_1956_121129_mat | 37.850 | 36.225 | 37.633 | 35.738 | NA | NA |
| mmu_miR_1957_121163_mat | 40.779 | 40.407 | 40.776 | 39.620 | NA | NA |
| mmu_miR_1958_121181_mat | 38.999 | 39.003 | 39.333 | 37.052 | NA | NA |
| mmu_miR_1959_121132_mat | 27.990 | 31.239 | 25.584 | 33.686 | 0.337 | 0.721 |
| mmu_miR_195_000494 | 23.628 | 19.832 | 20.314 | 22.240 | 0.966 | 0.158 |
| mmu_miR_1960_121148_mat | 36.936 | 33.980 | 36.872 | 36.795 | NA | 0.056 |
| mmu_miR_1961_197391_mat | 23.108 | 29.697 | 27.375 | 37.545 | 0.002 | NA |
| mmu_miR_1962_121173_mat | 38.824 | 39.910 | 39.220 | 39.780 | NA | NA |
| mmu_miR_1963_121191_mat | 40.779 | 40.407 | 40.776 | 39.620 | NA | NA |
| mmu_miR_1964_121138_mat | 37.575 | 37.060 | 38.006 | 39.532 | NA | NA |

TABLE 4-continued

| Brain Stem miRNA data. | | | | | | |
|---|---|---|---|---|---|---|
| mmu_miR_1965_121186_mat | 40.795 | 40.410 | 40.366 | 39.649 | NA | NA |
| mmu_miR_1966_121134_mat | 40.660 | 40.345 | 40.680 | 39.620 | NA | NA |
| mmu_miR_1967_121151_mat | 40.021 | 40.401 | 40.778 | 39.673 | NA | NA |
| mmu_miR_1968_121179_mat | 30.248 | 36.761 | 36.635 | 37.643 | 0.002 | NA |
| mmu_miR_1969_121131_mat | 21.274 | 25.058 | 18.341 | 26.745 | 0.336 | 0.792 |
| mmu_miR_196a_002477 | 21.777 | 25.204 | 20.904 | 27.980 | NA | NA |
| mmu_miR_196b_002215 | 34.768 | 38.244 | 31.439 | 33.210 | NA | NA |
| mmu_miR_1970_121202_mat | 32.780 | 40.987 | 31.266 | 41.111 | 0.166 | NA |
| mmu_miR_1971_121161_mat | 29.699 | 38.627 | 31.814 | 35.040 | 0.035 | NA |
| mmu_miR_197_000497 | 32.912 | 34.297 | 26.123 | 35.535 | NA | 0.743 |
| mmu_miR_1981_121200_mat | 28.065 | 29.920 | 29.937 | 28.093 | 0.375 | 0.741 |
| mmu_miR_1982.1_121157_mat | 30.826 | 31.427 | 30.776 | 30.341 | 0.607 | 0.731 |
| mmu_miR_1982.2_121154_mat | 27.576 | 31.319 | 26.539 | 29.548 | 0.312 | 0.956 |
| mmu_miR_199a_3p_002304 | 29.777 | 28.047 | 26.523 | 29.533 | 0.858 | 0.452 |
| mmu_miR_199a_5p_000498 | 34.724 | 34.590 | 36.359 | 34.891 | NA | 0.410 |
| mmu_miR_199b_001131 | 35.176 | 37.688 | 36.650 | 36.005 | NA | NA |
| mmu_miR_19a_000395 | 27.188 | 23.586 | 23.321 | 25.452 | 0.972 | 0.255 |
| mmu_miR_19a_002544 | 40.034 | 39.695 | 40.309 | 39.617 | NA | NA |
| mmu_miR_19b_000396 | 23.294 | 20.144 | 19.669 | 20.797 | 0.975 | 0.386 |
| mmu_miR_1_002222 | 21.871 | 27.594 | 20.563 | 23.178 | 0.288 | 0.998 |
| mmu_miR_1_2_AS_002882 | 35.345 | 28.481 | 26.118 | 34.981 | 0.967 | 0.209 |
| mmu_miR_200a_000502 | 31.719 | 37.663 | 36.941 | 39.953 | 0.003 | NA |
| mmu_miR_200b_002251 | 31.231 | 31.741 | 30.026 | 34.919 | NA | 0.494 |
| mmu_miR_200c_002300 | 31.716 | 36.230 | 32.300 | 37.303 | NA | NA |
| mmu_miR_201_002578 | 36.148 | 38.928 | 39.538 | 39.763 | NA | NA |
| mmu_miR_202_3p_001195 | 36.927 | 36.113 | 33.539 | 38.039 | NA | NA |
| mmu_miR_202_5p_002579 | 33.390 | 31.430 | 36.135 | 37.191 | NA | NA |
| mmu_miR_203_000507 | 25.969 | 24.325 | 24.247 | 27.330 | 0.632 | 0.271 |
| mmu_miR_203_002580 | 35.108 | 36.643 | 37.195 | 39.914 | NA | NA |
| mmu_miR_204_000508 | 21.447 | 17.333 | 19.260 | 21.373 | 0.882 | 0.039 |
| mmu_miR_205_000509 | 34.048 | 37.286 | 34.959 | 34.082 | NA | NA |
| mmu_miR_207_001198 | 39.726 | 39.574 | 40.013 | 38.300 | NA | NA |
| mmu_miR_208_000511 | 39.616 | 34.309 | 38.909 | 39.531 | NA | 0.006 |
| mmu_miR_208b_002290 | 32.923 | 39.937 | 34.748 | 39.077 | 0.039 | NA |
| mmu_miR_20a_000580 | 23.656 | 20.751 | 19.671 | 21.382 | 0.974 | 0.439 |
| mmu_miR_20a_002491 | 34.777 | 30.027 | 29.243 | 32.265 | NA | 0.253 |
| mmu_miR_20b_001014 | 28.488 | 23.612 | 22.946 | 24.275 | 0.996 | 0.359 |
| mmu_miR_20b_002524 | 39.840 | 39.637 | 39.999 | 38.737 | NA | NA |
| mmu_miR_210_000512 | 35.629 | 29.576 | 31.132 | 30.080 | NA | 0.181 |
| mmu_miR_211_001199 | 24.145 | 22.814 | 22.479 | 24.265 | 0.734 | 0.416 |
| mmu_miR_212_002551 | 20.874 | 22.679 | 22.638 | 20.192 | 0.475 | 0.768 |
| mmu_miR_2134_241120_mat | 24.834 | 28.789 | 24.542 | 31.120 | 0.173 | NA |
| mmu_miR_2135_241140_mat | 33.806 | 38.244 | 37.114 | 39.303 | NA | NA |
| mmu_miR_2136_241133_mat | 37.318 | 39.436 | 35.632 | 37.052 | NA | NA |
| mmu_miR_2138_241080_mat | 30.888 | 30.392 | 24.701 | 38.642 | 0.567 | 0.473 |
| mmu_miR_2139_241130_mat | 36.927 | 38.347 | 38.463 | 37.743 | NA | NA |
| mmu_miR_2146_241082_mat | 25.772 | 30.577 | 26.557 | 34.080 | 0.078 | NA |
| mmu_miR_214_002306 | 34.389 | 35.010 | 32.191 | 36.076 | NA | 0.660 |
| mmu_miR_215_001200 | 35.445 | 31.877 | 31.067 | 33.831 | NA | 0.292 |
| mmu_miR_216a_002220 | 30.048 | 37.348 | 31.795 | 29.662 | 0.270 | NA |
| mmu_miR_216b_002326 | 26.065 | 32.405 | 28.652 | 25.902 | 0.203 | 0.996 |

TABLE 4-continued

| Brain Stem miRNA data. | | | | | | |
|---|---|---|---|---|---|---|
| mmu_miR_217_001133 | 31.554 | 35.319 | 29.570 | 32.348 | 0.427 | NA |
| mmu_miR_217_002556 | 31.155 | 32.594 | 29.283 | 30.120 | 0.732 | 0.900 |
| mmu_miR_2182_241119_mat | 31.778 | 35.018 | 35.966 | 36.266 | 0.055 | NA |
| mmu_miR_2183_241095_mat | 27.250 | 29.961 | 25.247 | 34.319 | 0.337 | NA |
| mmu_miR_218_000521 | 15.816 | 20.069 | 20.109 | 18.091 | 0.053 | 0.825 |
| mmu_miR_218_1_002552 | 27.788 | 31.808 | 30.423 | 28.279 | 0.177 | 0.945 |
| mmu_miR_219_000522 | 30.748 | 22.905 | 27.038 | 23.221 | NA | 0.117 |
| mmu_miR_21_000397 | 22.751 | 20.844 | 18.683 | 21.333 | 0.942 | 0.544 |
| mmu_miR_21_002493 | 36.705 | 35.839 | 36.208 | 35.769 | NA | NA |
| mmu_miR_220_002468 | 40.660 | 40.316 | 40.691 | 39.348 | NA | NA |
| mmu_miR_221_000524 | 24.001 | 21.593 | 22.265 | 23.310 | 0.881 | 0.245 |
| mmu_miR_222_002276 | 21.201 | 20.667 | 20.026 | 20.960 | 0.723 | 0.579 |
| mmu_miR_223_002295 | 29.089 | 31.997 | 17.947 | 35.498 | 0.428 | NA |
| mmu_miR_224_002553 | 32.228 | 29.991 | 32.008 | 31.560 | 0.779 | 0.169 |
| mmu_miR_23a_000399 | 38.256 | 37.681 | 38.710 | 39.541 | NA | NA |
| mmu_miR_23b_000400 | 24.939 | 23.136 | 23.435 | 24.304 | 0.843 | 0.336 |
| mmu_miR_24_000402 | 18.998 | 19.268 | 18.384 | 19.273 | 0.571 | 0.671 |
| mmu_miR_24_2_002494 | 27.423 | 26.213 | 25.855 | 28.226 | 0.639 | 0.386 |
| mmu_miR_25_000403 | 26.882 | 23.960 | 23.313 | 26.221 | 0.937 | 0.285 |
| mmu_miR_26a_000405 | 19.177 | 17.911 | 17.801 | 18.582 | 0.805 | 0.454 |
| mmu_miR_26b_000407 | 21.789 | 19.689 | 19.536 | 21.076 | 0.892 | 0.345 |
| mmu_miR_27a_000408 | 23.456 | 21.793 | 22.832 | 24.680 | 0.573 | 0.190 |
| mmu_miR_27b_000409 | 22.422 | 21.502 | 22.410 | 21.611 | 0.709 | 0.457 |
| mmu_miR_28_000411 | 24.637 | 23.164 | 23.167 | 26.535 | 0.590 | 0.265 |
| mmu_miR_28_002545 | 26.622 | 29.680 | 28.827 | 30.317 | 0.124 | 0.726 |
| mmu_miR_290_000187 | 39.287 | 39.601 | 24.958 | 41.533 | NA | NA |
| mmu_miR_290_3p_002591 | 40.705 | 40.334 | 40.729 | 39.619 | NA | NA |
| mmu_miR_290_5p_002590 | 37.325 | 36.079 | 33.962 | 38.083 | NA | 0.468 |
| mmu_miR_291_3p_001135 | 40.674 | 40.359 | 40.671 | 38.800 | NA | NA |
| mmu_miR_291_5p_001202 | 40.658 | 40.344 | 40.686 | 39.613 | NA | NA |
| mmu_miR_291a_3p_002592 | 40.712 | 40.343 | 40.735 | 39.620 | NA | NA |
| mmu_miR_291b_3p_002538 | 40.268 | 39.913 | 40.449 | 39.616 | NA | NA |
| mmu_miR_291b_5p_002537 | 40.802 | 40.420 | 40.795 | 39.653 | NA | NA |
| mmu_miR_292_3p_001054 | 39.757 | 40.471 | 40.569 | 39.822 | NA | NA |
| mmu_miR_292_3p_002593 | 37.329 | 35.768 | 33.538 | 36.540 | NA | 0.539 |
| mmu_miR_292_5p_001055 | 38.946 | 34.584 | 38.600 | 39.977 | NA | NA |
| mmu_miR_293_001794 | 35.456 | 36.244 | 30.953 | 36.610 | NA | NA |
| mmu_miR_293_002594 | 39.272 | 38.553 | 39.580 | 37.980 | NA | NA |
| mmu_miR_294_001056 | 38.715 | 36.370 | 34.327 | 40.025 | NA | NA |
| mmu_miR_294_002595 | 40.779 | 40.407 | 40.776 | 39.620 | NA | NA |
| mmu_miR_295_000189 | 38.981 | 38.889 | 37.797 | 39.785 | NA | NA |
| mmu_miR_295_002596 | 41.119 | 40.867 | 34.183 | 40.117 | NA | NA |
| mmu_miR_296_3p_002101 | 36.262 | 35.884 | 36.232 | 39.131 | NA | NA |
| mmu_miR_296_5p_000527 | 24.300 | 24.992 | 28.026 | 25.671 | 0.210 | 0.369 |
| mmu_miR_297a_002454 | 31.680 | 29.002 | 31.750 | 31.691 | 0.698 | 0.076 |
| mmu_miR_297b_5p_001626 | 38.154 | 36.702 | 38.584 | 39.546 | NA | NA |
| mmu_miR_297c_002480 | 35.366 | 34.247 | 35.620 | 36.814 | NA | 0.210 |
| mmu_miR_298_002598 | 31.634 | 34.349 | 31.848 | 28.722 | 0.598 | 0.953 |
| mmu_miR_299_002612 | 40.779 | 40.407 | 40.776 | 39.620 | NA | NA |
| mmu_miR_29a_002112 | 19.161 | 19.807 | 20.212 | 18.938 | 0.508 | 0.637 |
| mmu_miR_29b_000413 | 21.629 | 24.117 | 23.945 | 23.070 | 0.190 | 0.763 |

TABLE 4-continued

| Brain Stem miRNA data. | | | | | | |
|---|---|---|---|---|---|---|
| mmu_miR_29b_002497 | 25.614 | 26.667 | 22.986 | 29.804 | 0.474 | NA |
| mmu_miR_29c_000587 | 21.034 | 22.104 | 22.771 | 21.397 | 0.379 | 0.631 |
| mmu_miR_300_000191 | 27.480 | 30.709 | 30.748 | 27.987 | 0.184 | 0.823 |
| mmu_miR_300_002613 | 29.809 | 35.221 | 32.721 | 32.235 | 0.057 | NA |
| mmu_miR_301a_000528 | 24.920 | 23.709 | 24.178 | 24.297 | 0.762 | 0.428 |
| mmu_miR_301b_002600 | 23.624 | 22.973 | 24.039 | 23.249 | 0.634 | 0.430 |
| mmu_miR_302a_000529 | 26.977 | 31.723 | 25.356 | 28.214 | 0.334 | 0.993 |
| mmu_miR_302a_002615 | 34.844 | 37.421 | 37.131 | 37.606 | NA | NA |
| mmu_miR_302b_000531 | 33.904 | 33.174 | 35.800 | 34.292 | NA | 0.267 |
| mmu_miR_302b_001307 | 39.725 | 39.648 | 34.500 | 40.069 | NA | NA |
| mmu_miR_302c_002557 | 38.167 | 36.546 | 40.449 | 39.965 | NA | 0.082 |
| mmu_miR_302c_002558 | 37.423 | 36.512 | 33.955 | 38.827 | NA | NA |
| mmu_miR_302d_000535 | 35.291 | 36.049 | 36.792 | 36.616 | NA | NA |
| mmu_miR_30a_000417 | 21.698 | 20.137 | 20.265 | 21.016 | 0.832 | 0.393 |
| mmu_miR_30b_000602 | 17.475 | 17.380 | 17.142 | 17.355 | 0.614 | 0.606 |
| mmu_miR_30b_002498 | 36.132 | 34.886 | 36.121 | 35.905 | NA | 0.321 |
| mmu_miR_30c_000419 | 17.116 | 16.966 | 16.927 | 16.891 | 0.621 | 0.575 |
| mmu_miR_30d_000420 | 23.825 | 22.193 | 23.057 | 23.532 | 0.747 | 0.299 |
| mmu_miR_30e_002223 | 21.736 | 20.479 | 21.089 | 21.616 | 0.694 | 0.366 |
| mmu_miR_31_000185 | 25.626 | 27.069 | 26.014 | 26.001 | NA | NA |
| mmu_miR_31_002495 | 28.358 | 29.511 | 27.044 | 27.678 | 0.700 | 0.847 |
| mmu_miR_320_002277 | 21.156 | 19.411 | 20.620 | 20.927 | 0.727 | 0.245 |
| mmu_miR_322_001059 | 31.125 | 30.989 | 27.236 | 30.603 | 0.836 | 0.770 |
| mmu_miR_322_001076 | 35.284 | 27.169 | 26.585 | 26.663 | NA | 0.430 |
| mmu_miR_322_002506 | 33.990 | 30.829 | 28.704 | 28.871 | 0.992 | 0.614 |
| mmu_miR_323_3p_002227 | 25.537 | 28.141 | 28.960 | 25.195 | 0.313 | 0.758 |
| mmu_miR_324_3p_002509 | 27.420 | 25.593 | 28.723 | 25.850 | 0.725 | 0.262 |
| mmu_miR_324_5p_000539 | 25.924 | 24.992 | 25.826 | 24.829 | 0.732 | 0.483 |
| mmu_miR_325_001060 | 32.862 | 30.823 | 25.244 | 30.859 | 0.967 | 0.653 |
| mmu_miR_325_002510 | 26.745 | 27.111 | 32.150 | 26.365 | 0.389 | 0.430 |
| mmu_miR_326_001061 | 36.948 | 38.300 | 20.219 | 34.048 | NA | NA |
| mmu_miR_327_002481 | 39.744 | 39.792 | 40.626 | 39.733 | NA | NA |
| mmu_miR_328_000543 | 19.530 | 20.759 | 20.606 | 20.132 | 0.377 | 0.695 |
| mmu_miR_329_000192 | 25.707 | 28.477 | 29.202 | 26.116 | 0.214 | 0.755 |
| mmu_miR_32_002109 | 35.828 | 28.818 | 29.159 | 30.486 | NA | 0.174 |
| mmu_miR_330_001062 | 31.613 | 37.408 | 33.542 | 34.761 | NA | NA |
| mmu_miR_330_002230 | 33.887 | 35.398 | 31.767 | 33.041 | 0.739 | 0.903 |
| mmu_miR_331_3p_000545 | 21.656 | 22.319 | 23.293 | 22.730 | 0.320 | 0.504 |
| mmu_miR_331_5p_002233 | 27.229 | 27.501 | 25.159 | 31.110 | 0.496 | 0.484 |
| mmu_miR_335_3p_002185 | 25.593 | 29.003 | 31.297 | 24.093 | 0.318 | 0.738 |
| mmu_miR_335_5p_000546 | 20.861 | 24.311 | 23.122 | 21.683 | 0.189 | 0.914 |
| mmu_miR_337_000193 | 25.962 | 27.401 | 28.392 | 26.676 | 0.281 | 0.613 |
| mmu_miR_337_3p_002532 | 25.481 | 27.726 | 28.505 | 26.162 | 0.224 | 0.697 |
| mmu_miR_337_5p_002515 | 21.915 | 24.957 | 25.898 | 25.164 | 0.081 | 0.625 |
| mmu_miR_338_3p_002252 | 28.573 | 23.817 | 28.416 | 24.306 | 0.909 | 0.121 |
| mmu_miR_339_3p_002533 | 32.270 | 28.192 | 27.526 | 30.403 | 0.982 | 0.259 |
| mmu_miR_339_5p_002257 | 33.696 | 27.922 | 28.878 | 29.064 | 0.997 | 0.167 |
| mmu_miR_340_3p_002259 | 23.516 | 23.383 | 23.777 | 23.630 | 0.544 | 0.525 |
| mmu_miR_340_5p_002258 | 22.685 | 21.831 | 23.300 | 22.327 | 0.624 | 0.368 |
| mmu_miR_342_3p_002260 | 21.459 | 22.717 | 21.021 | 21.081 | 0.597 | 0.822 |
| mmu_miR_342_5p_002527 | 32.442 | 32.170 | 31.711 | 29.804 | 0.801 | 0.715 |

TABLE 4-continued

| Brain Stem miRNA data. | | | | | | |
|---|---|---|---|---|---|---|
| mmu_miR_343_002483 | 40.770 | 40.406 | 40.771 | 39.668 | NA | NA |
| mmu_miR_344_001063 | 26.914 | 26.244 | 29.304 | 25.831 | 0.582 | 0.392 |
| mmu_miR_345_001137 | 26.300 | 24.825 | 26.214 | 26.402 | 0.631 | 0.243 |
| mmu_miR_345_3p_002529 | 32.929 | 30.769 | 32.058 | 31.965 | NA | 0.234 |
| mmu_miR_345_5p_002528 | 30.664 | 26.774 | 31.071 | 27.911 | 0.862 | 0.087 |
| mmu_miR_346_001064 | 35.876 | 37.331 | 36.678 | 36.125 | NA | NA |
| mmu_miR_34a_000426 | 18.770 | 23.400 | 21.626 | 19.254 | 0.153 | 0.965 |
| mmu_miR_34b_001065 | 32.898 | 31.491 | 31.978 | 33.863 | 0.596 | 0.273 |
| mmu_miR_34b_3p_002618 | 22.661 | 21.800 | 24.385 | 23.644 | 0.403 | 0.211 |
| mmu_miR_34b_5p_002617 | 29.587 | 29.940 | 30.812 | 32.273 | 0.311 | 0.341 |
| mmu_miR_34c_000428 | 24.984 | 24.061 | 30.994 | 26.306 | 0.257 | 0.132 |
| mmu_miR_34c_002584 | 25.127 | 24.564 | 26.480 | 26.516 | 0.383 | 0.241 |
| mmu_miR_350_002530 | 28.443 | 24.742 | 25.919 | 25.830 | 0.970 | 0.189 |
| mmu_miR_351_001067 | 36.990 | 36.649 | 37.191 | 36.818 | NA | NA |
| mmu_miR_361_000554 | 23.226 | 23.218 | 23.997 | 23.240 | 0.526 | 0.526 |
| mmu_miR_362_3p_002616 | 29.143 | 26.046 | 24.541 | 27.146 | 0.974 | 0.407 |
| mmu_miR_362_5p_002614 | 27.218 | 26.025 | 25.038 | 26.850 | 0.815 | 0.522 |
| mmu_miR_363_001271 | 34.901 | 35.817 | 35.924 | 35.922 | NA | NA |
| mmu_miR_365_001020 | 28.515 | 22.801 | 28.738 | 26.247 | 0.875 | 0.008 |
| mmu_miR_367_000555 | 23.509 | 20.741 | 22.536 | 22.063 | 0.884 | 0.168 |
| mmu_miR_369_3p_000557 | 25.317 | 27.740 | 27.202 | 25.459 | 0.329 | 0.833 |
| mmu_miR_369_5p_001021 | 28.657 | 33.050 | 30.290 | 29.089 | 0.219 | 0.976 |
| mmu_miR_370_001068 | 36.861 | 36.610 | 37.089 | 36.043 | NA | NA |
| mmu_miR_370_002275 | 26.763 | 29.245 | 31.622 | 25.539 | 0.361 | 0.675 |
| mmu_miR_374_002043 | 35.132 | 35.764 | 36.212 | 40.845 | 0.253 | 0.329 |
| mmu_miR_374_5p_001319 | 34.579 | 25.126 | 28.482 | 25.368 | 1.000 | 0.135 |
| mmu_miR_375_000564 | 27.321 | 24.201 | 28.854 | 27.483 | 0.607 | 0.028 |
| mmu_miR_376a_001069 | 20.805 | 23.784 | 23.358 | 21.174 | 0.245 | 0.859 |
| mmu_miR_376a_002482 | 26.076 | 30.398 | 27.854 | 26.617 | 0.197 | 0.971 |
| mmu_miR_376b_002451 | 21.874 | 24.907 | 24.508 | 22.372 | 0.221 | 0.858 |
| mmu_miR_376b_002452 | 25.520 | 28.888 | 29.909 | 25.773 | 0.177 | 0.773 |
| mmu_miR_376c_002450 | 21.766 | 23.756 | 23.879 | 22.471 | 0.280 | 0.715 |
| mmu_miR_376c_002523 | 38.055 | 39.234 | 40.519 | 40.097 | NA | NA |
| mmu_miR_377_000566 | 32.446 | 32.807 | 33.196 | 33.281 | 0.407 | 0.527 |
| mmu_miR_379_001138 | 22.106 | 25.162 | 25.346 | 23.238 | 0.139 | 0.784 |
| mmu_miR_380_3p_001071 | 30.486 | 36.926 | 32.914 | 32.247 | 0.073 | NA |
| mmu_miR_380_5p_002601 | 24.184 | 28.762 | 27.336 | 25.226 | 0.094 | 0.953 |
| mmu_miR_381_000571 | 27.886 | 29.668 | 28.167 | 28.382 | 0.410 | 0.821 |
| mmu_miR_382_000572 | 20.778 | 24.724 | 28.808 | 20.142 | 0.237 | 0.700 |
| mmu_miR_383_001767 | 23.437 | 28.223 | 27.018 | 23.664 | 0.146 | 0.961 |
| mmu_miR_384_3p_002603 | 23.619 | 25.238 | 25.061 | 23.639 | 0.411 | 0.750 |
| mmu_miR_384_5p_002602 | 18.345 | 20.403 | 19.959 | 18.148 | 0.410 | 0.809 |
| mmu_miR_409_3p_002332 | 22.085 | 25.320 | 24.972 | 22.624 | 0.194 | NA |
| mmu_miR_409_5p_002331 | 29.518 | 34.225 | 31.925 | 29.316 | 0.246 | 0.977 |
| mmu_miR_410_001274 | 20.161 | 23.158 | 23.569 | 20.333 | 0.223 | 0.798 |
| mmu_miR_411_001610 | 20.584 | 22.914 | 23.126 | 21.221 | 0.249 | 0.741 |
| mmu_miR_412_002575 | 25.140 | 30.518 | 30.482 | 25.782 | 0.078 | 0.906 |
| mmu_miR_423_5p_002340 | 30.466 | 27.801 | 29.204 | 28.226 | 0.909 | 0.276 |
| mmu_miR_425_001516 | 18.851 | 21.662 | 16.661 | 25.634 | 0.346 | 0.647 |
| mmu_miR_429_001077 | 34.930 | 37.298 | 34.723 | 38.088 | NA | NA |
| mmu_miR_431_001979 | 33.814 | 32.845 | 31.658 | 27.380 | 0.921 | 0.782 |

TABLE 4-continued

Brain Stem miRNA data.

| | | | | | | |
|---|---|---|---|---|---|---|
| mmu_miR_432_241135_mat | 35.801 | 36.966 | 38.337 | 37.508 | NA | NA |
| mmu_miR_433_001028 | 20.179 | 23.825 | 23.439 | 20.606 | 0.178 | 0.888 |
| mmu_miR_433_5p_001078 | 30.375 | 35.965 | 29.787 | 31.137 | 0.286 | NA |
| mmu_miR_434_3p_002604 | 18.234 | 21.249 | 19.807 | 18.237 | 0.340 | 0.917 |
| mmu_miR_434_5p_002581 | 24.507 | 28.480 | 27.475 | 25.019 | 0.160 | 0.934 |
| mmu_miR_448_001029 | 28.304 | 33.346 | 30.590 | 28.353 | 0.212 | 0.986 |
| mmu_miR_449a_001030 | 27.725 | 28.761 | 25.362 | 29.015 | 0.541 | 0.769 |
| mmu_miR_449b_001667 | 29.951 | 32.432 | 29.427 | 32.241 | 0.327 | 0.844 |
| mmu_miR_449b_002539 | 40.711 | 40.345 | 40.736 | 39.620 | NA | NA |
| mmu_miR_450B_3P_002632 | 34.541 | 34.539 | 28.340 | 33.043 | NA | 0.845 |
| mmu_miR_450a_3p_002525 | 40.779 | 40.407 | 40.776 | 39.620 | NA | NA |
| mmu_miR_450a_5p_002303 | 33.816 | 31.468 | 32.812 | 32.601 | NA | 0.230 |
| mmu_miR_450b_5p_001962 | 40.528 | 40.169 | 40.614 | 39.617 | NA | NA |
| mmu_miR_451_001141 | 34.722 | 32.232 | 29.234 | 39.399 | NA | NA |
| mmu_miR_452_001032 | 36.669 | 35.070 | 32.301 | 34.894 | NA | NA |
| mmu_miR_453_002484 | 39.562 | 39.369 | 39.948 | 38.935 | NA | NA |
| mmu_miR_455_002455 | 34.544 | 27.947 | 29.791 | 28.553 | NA | 0.154 |
| mmu_miR_463_002582 | 27.834 | 30.557 | 26.058 | 34.186 | 0.332 | NA |
| mmu_miR_463_002662 | 32.696 | 35.615 | 30.031 | 37.548 | NA | NA |
| mmu_miR_464_001081 | 40.260 | 39.976 | 40.420 | 39.610 | NA | NA |
| mmu_miR_465C_5P_002654 | 27.488 | 34.074 | 26.941 | 35.262 | 0.121 | NA |
| mmu_miR_465a_3p_002040 | 32.197 | 35.521 | 35.325 | 33.223 | 0.140 | 0.840 |
| mmu_miR_465a_5p_001082 | 38.078 | 31.114 | 37.052 | 39.259 | NA | 0.001 |
| mmu_miR_465b_5p_002485 | 33.795 | 36.924 | 30.696 | 33.397 | NA | NA |
| mmu_miR_466E_5P_002718 | 34.009 | 32.512 | 25.828 | 34.785 | 0.783 | 0.516 |
| mmu_miR_466J_002817 | 32.158 | 30.298 | 31.384 | 32.447 | 0.690 | 0.207 |
| mmu_miR_466a_3p_002586 | 31.405 | 27.770 | 32.036 | 30.440 | 0.792 | 0.032 |
| mmu_miR_466b_3_3p_002500 | 32.011 | 28.743 | 31.912 | 30.742 | 0.839 | 0.074 |
| mmu_miR_466d_5p_002534 | 34.250 | 37.227 | 35.285 | 35.714 | NA | NA |
| mmu_miR_466g_241015_mat | 35.780 | 32.194 | 37.048 | 36.680 | NA | NA |
| mmu_miR_466h_002516 | 36.720 | 35.351 | 36.680 | 34.987 | NA | 0.428 |
| mmu_miR_466k_240990_mat | 31.869 | 36.174 | 29.194 | 35.851 | 0.322 | 0.942 |
| mmu_miR_467F_002886 | 30.823 | 28.068 | 25.607 | 30.661 | NA | NA |
| mmu_miR_467H_002809 | 35.688 | 31.163 | 34.289 | 33.569 | NA | 0.041 |
| mmu_miR_467a_001826 | 28.224 | 25.535 | 29.254 | 29.010 | 0.553 | 0.044 |
| mmu_miR_467a_002587 | 27.427 | 24.764 | 30.760 | 27.354 | 0.526 | 0.047 |
| mmu_miR_467b_001671 | 33.237 | 28.109 | 31.912 | 29.932 | 0.956 | 0.047 |
| mmu_miR_467b_001684 | 29.220 | 30.182 | 27.116 | 32.731 | 0.478 | 0.580 |
| mmu_miR_467c_002517 | 32.292 | 27.982 | 31.406 | 33.290 | 0.698 | 0.015 |
| mmu_miR_467d_002518 | 32.683 | 30.286 | 31.325 | 33.392 | 0.705 | 0.146 |
| mmu_miR_467e_002568 | 29.540 | 27.406 | 25.368 | 29.772 | 0.839 | 0.382 |
| mmu_miR_467e_002569 | 39.520 | 39.678 | 38.066 | 37.865 | NA | NA |
| mmu_miR_468_001085 | 40.237 | 40.133 | 40.332 | 39.662 | NA | NA |
| mmu_miR_469_001086 | 39.130 | 39.516 | 39.226 | 35.650 | NA | NA |
| mmu_miR_470_002588 | 39.083 | 38.984 | 39.534 | 39.024 | NA | NA |
| mmu_miR_470_002589 | 34.099 | 30.637 | 26.014 | 36.689 | 0.784 | 0.312 |
| mmu_miR_471_002605 | 40.363 | 40.038 | 40.509 | 39.206 | NA | NA |
| mmu_miR_483_001291 | 35.848 | 37.737 | 30.555 | 38.260 | NA | NA |
| mmu_miR_483_002560 | 36.720 | 37.308 | 37.096 | 39.545 | NA | NA |
| mmu_miR_484_001821 | 21.593 | 19.821 | 19.846 | 20.566 | 0.870 | 0.391 |
| mmu_miR_485_3p_001943 | 21.271 | 23.481 | 23.929 | 22.164 | 0.222 | 0.707 |

TABLE 4-continued

| Brain Stem miRNA data. | | | | | | |
|---|---|---|---|---|---|---|
| mmu_miR_486_001278 | 30.587 | 24.633 | 32.254 | 24.316 | 0.849 | 0.149 |
| mmu_miR_487b_001285 | 21.553 | 23.904 | 23.491 | 22.514 | 0.245 | 0.788 |
| mmu_miR_487b_001306 | 23.472 | 24.851 | 25.981 | 23.208 | 0.398 | 0.632 |
| mmu_miR_488_001659 | 30.015 | 29.381 | 31.520 | 29.927 | 0.532 | 0.339 |
| mmu_miR_488_002014 | 36.722 | 37.586 | 36.788 | 38.553 | NA | NA |
| mmu_miR_489_001302 | 24.782 | 30.644 | 26.602 | 26.022 | 0.115 | 0.994 |
| mmu_miR_490_001037 | 34.460 | 37.250 | 31.550 | 29.778 | 0.797 | NA |
| mmu_miR_491_001630 | 25.556 | 28.057 | 29.451 | 26.264 | 0.186 | 0.661 |
| mmu_miR_493_002519 | 32.532 | 35.276 | 34.029 | 35.663 | NA | NA |
| mmu_miR_494_001293 | 36.178 | 34.718 | 35.857 | 35.363 | NA | 0.343 |
| mmu_miR_494_002365 | 30.331 | 32.000 | 31.697 | 31.179 | 0.314 | 0.739 |
| mmu_miR_495_001663 | 18.735 | 21.612 | 21.168 | 18.746 | 0.302 | 0.862 |
| mmu_miR_496_001953 | 32.882 | 30.914 | 31.855 | 28.407 | 0.905 | 0.503 |
| mmu_miR_497_001346 | 29.645 | 23.883 | 26.612 | 27.522 | 0.979 | 0.019 |
| mmu_miR_499_001352 | 33.524 | 35.272 | 30.975 | 31.824 | 0.785 | 0.939 |
| mmu_miR_500_002606 | 31.136 | 27.449 | 26.448 | 27.684 | 0.989 | 0.449 |
| mmu_miR_501_001356 | 35.848 | 37.612 | 37.167 | 37.116 | NA | NA |
| mmu_miR_501_3p_001651 | 28.632 | 26.429 | 25.461 | 26.115 | 0.954 | 0.552 |
| mmu_miR_503_002456 | 35.490 | 33.449 | 34.926 | 33.837 | NA | 0.306 |
| mmu_miR_503_002536 | 34.909 | 32.622 | 30.234 | 33.746 | NA | 0.475 |
| mmu_miR_504_002084 | 33.539 | 35.757 | 33.286 | 33.431 | 0.499 | 0.895 |
| mmu_miR_505_001655 | 38.563 | 38.523 | 39.008 | 39.606 | NA | NA |
| mmu_miR_509_3p_002521 | 34.418 | 38.474 | 36.155 | 41.171 | NA | NA |
| mmu_miR_509_5p_002520 | 35.148 | 39.872 | 40.214 | 40.015 | NA | NA |
| mmu_miR_511_002549 | 38.873 | 38.235 | 36.445 | 39.701 | NA | NA |
| mmu_miR_532_3p_002355 | 24.706 | 23.419 | 22.585 | 24.339 | 0.817 | 0.495 |
| mmu_miR_532_5p_001518 | 23.871 | 21.515 | 21.110 | 22.417 | 0.935 | 0.400 |
| mmu_miR_539_001286 | 22.369 | 24.949 | 24.761 | 22.838 | 0.267 | 0.801 |
| mmu_miR_540_3p_001310 | 31.949 | 35.794 | 32.473 | 32.540 | 0.280 | NA |
| mmu_miR_540_5p_002561 | 32.086 | 34.072 | 32.194 | 32.494 | 0.424 | 0.846 |
| mmu_miR_541_002562 | 26.472 | 30.871 | 28.929 | 26.056 | 0.282 | 0.969 |
| mmu_miR_542_3p_001284 | 35.450 | 32.698 | 34.516 | 33.763 | NA | 0.190 |
| mmu_miR_542_5p_002563 | 36.846 | 36.483 | 36.662 | 36.574 | NA | NA |
| mmu_miR_543_001298 | 21.415 | 24.412 | 24.195 | 21.712 | 0.240 | 0.843 |
| mmu_miR_543_002376 | 20.547 | 23.579 | 23.312 | 21.084 | 0.212 | 0.847 |
| mmu_miR_544_002550 | 22.636 | 25.456 | 25.326 | 24.434 | NA | NA |
| mmu_miR_546_001312 | 33.281 | 33.170 | 27.376 | 24.877 | NA | NA |
| mmu_miR_547_002564 | 25.861 | 26.191 | 23.097 | 25.264 | 0.797 | 0.800 |
| mmu_miR_551b_001535 | 26.284 | 27.273 | 24.939 | 27.453 | 0.498 | 0.745 |
| mmu_miR_574_3p_002349 | 29.981 | 25.061 | 24.414 | 26.191 | 0.996 | 0.316 |
| mmu_miR_582_3p_002567 | 32.529 | 33.030 | 32.153 | 33.626 | 0.448 | 0.622 |
| mmu_miR_582_5p_002566 | 28.511 | 29.854 | 31.850 | 28.927 | 0.277 | 0.555 |
| mmu_miR_590_5p_001984 | 37.609 | 35.633 | 37.682 | 35.544 | NA | 0.326 |
| mmu_miR_592_002017 | 26.939 | 29.653 | 30.067 | 26.555 | 0.332 | 0.794 |
| mmu_miR_598_002476 | 25.089 | 25.609 | 26.502 | 25.281 | 0.436 | 0.565 |
| mmu_miR_599_241117_mat | 36.290 | 33.531 | 36.113 | 38.545 | 0.551 | 0.048 |
| mmu_miR_615_3p_001960 | 35.001 | 37.236 | 33.634 | 35.001 | NA | NA |
| mmu_miR_615_5p_002353 | 38.986 | 38.890 | 39.371 | 39.557 | NA | NA |
| mmu_miR_652_002352 | 25.804 | 22.996 | 24.210 | 24.716 | 0.903 | 0.173 |
| mmu_miR_654_3p_002239 | 40.173 | 39.881 | 40.391 | 39.630 | NA | NA |
| mmu_miR_654_5p_002522 | 39.725 | 40.059 | 40.519 | 39.661 | NA | NA |

TABLE 4-continued

| Brain Stem miRNA data. | | | | | | |
|---|---|---|---|---|---|---|
| mmu_miR_665_002607 | 35.224 | 35.286 | 34.309 | 33.107 | NA | NA |
| mmu_miR_666_3p_002448 | 36.724 | 38.190 | 37.855 | 39.859 | NA | NA |
| mmu_miR_666_5p_001952 | 32.047 | 36.100 | 32.384 | 32.174 | 0.333 | 0.982 |
| mmu_miR_667_001949 | 22.019 | 25.572 | 24.829 | 22.213 | 0.220 | 0.909 |
| mmu_miR_668_001947 | 29.405 | 29.162 | 29.431 | 27.281 | 0.727 | 0.632 |
| mmu_miR_669C_002646 | 33.789 | 30.714 | 32.462 | 33.516 | NA | 0.088 |
| mmu_miR_669D_002808 | 33.465 | 30.754 | 33.550 | 33.545 | NA | 0.071 |
| mmu_miR_669E_002774 | 36.634 | 34.066 | 36.607 | 36.517 | NA | 0.094 |
| mmu_miR_669G_002813 | 40.449 | 40.093 | 40.555 | 39.607 | NA | NA |
| mmu_miR_669H_5P_002906 | 36.086 | 36.354 | 33.693 | 35.622 | NA | NA |
| mmu_miR_669a_001683 | 30.472 | 27.744 | 31.263 | 29.861 | 0.734 | 0.082 |
| mmu_miR_669l_121149_mat | 33.168 | 30.704 | 33.709 | 33.675 | 0.595 | 0.073 |
| mmu_miR_669m_121190_mat | 30.825 | 28.346 | 31.895 | 31.620 | 0.539 | 0.056 |
| mmu_miR_669n_197143_mat | 34.946 | 30.901 | 33.100 | 33.241 | NA | 0.067 |
| mmu_miR_669o_121176_mat | 30.009 | 30.380 | 32.869 | 33.757 | 0.202 | 0.210 |
| mmu_miR_670_002020 | 32.275 | 31.355 | 25.955 | 31.268 | NA | 0.733 |
| mmu_miR_671_3p_002322 | 28.882 | 28.298 | 31.958 | 28.483 | 0.492 | 0.336 |
| mmu_miR_672_002327 | 26.448 | 28.627 | 30.095 | 24.158 | 0.438 | 0.711 |
| mmu_miR_673_001954 | 19.800 | 24.039 | 20.825 | 27.536 | 0.094 | 0.674 |
| mmu_miR_673_3p_002449 | 29.443 | 33.136 | 30.424 | 29.464 | 0.336 | 0.962 |
| mmu_miR_674_001956 | 27.953 | 24.617 | 26.055 | 26.867 | 0.924 | 0.112 |
| mmu_miR_674_002021 | 32.307 | 28.218 | 29.997 | 28.652 | 0.975 | 0.205 |
| mmu_miR_675_3p_001941 | 34.169 | 34.934 | 24.982 | 34.614 | 0.707 | 0.851 |
| mmu_miR_675_5p_001940 | 37.109 | 33.765 | 36.848 | 36.845 | NA | 0.042 |
| mmu_miR_676_001958 | 28.811 | 29.942 | 30.601 | 29.697 | 0.309 | 0.609 |
| mmu_miR_676_001959 | 28.905 | 25.575 | 27.909 | 27.668 | 0.890 | 0.091 |
| mmu_miR_677_001660 | 36.510 | 36.727 | 37.552 | 38.085 | NA | NA |
| mmu_miR_679_001662 | 35.212 | 35.308 | 31.862 | 31.518 | NA | NA |
| mmu_miR_680_001664 | 38.348 | 34.243 | 29.115 | 35.970 | NA | NA |
| mmu_miR_682_001666 | 37.348 | 34.625 | 36.994 | 39.107 | NA | 0.058 |
| mmu_miR_683_001668 | 39.278 | 34.231 | 34.118 | 40.413 | NA | 0.118 |
| mmu_miR_684_001669 | 40.779 | 40.407 | 40.776 | 39.620 | NA | NA |
| mmu_miR_685_001670 | 33.613 | 37.065 | 31.979 | 40.667 | 0.277 | NA |
| mmu_miR_686_001672 | 40.864 | 40.480 | 40.588 | 39.596 | NA | NA |
| mmu_miR_687_001674 | 40.104 | 39.787 | 40.335 | 39.226 | NA | NA |
| mmu_miR_688_001675 | 36.601 | 40.473 | 40.485 | 40.292 | 0.052 | NA |
| mmu_miR_690_001677 | 38.672 | 38.617 | 36.851 | 39.331 | NA | NA |
| mmu_miR_691_001678 | 32.428 | 36.683 | 32.718 | 38.078 | 0.138 | NA |
| mmu_miR_692_001679 | 39.842 | 40.402 | 37.586 | 40.218 | NA | NA |
| mmu_miR_693_001680 | 39.142 | 30.660 | 34.813 | 39.756 | NA | 0.001 |
| mmu_miR_693_3p_002036 | 40.503 | 34.490 | 33.491 | 37.948 | NA | NA |
| mmu_miR_694_001681 | 28.762 | 32.464 | 27.378 | 37.905 | 0.234 | 0.670 |
| mmu_miR_695_001627 | 33.397 | 38.315 | 39.404 | 38.315 | 0.013 | NA |
| mmu_miR_696_001628 | 32.814 | 39.178 | 28.941 | 37.917 | 0.293 | NA |
| mmu_miR_697_001631 | 34.315 | 40.466 | 38.642 | 38.706 | 0.015 | NA |
| mmu_miR_698_001632 | 40.366 | 39.987 | 39.633 | 39.688 | NA | NA |
| mmu_miR_700_001634 | 25.572 | 25.661 | 27.463 | 25.630 | 0.447 | 0.454 |
| mmu_miR_701_001635 | 31.511 | 31.838 | 28.773 | 33.711 | 0.558 | 0.585 |
| mmu_miR_702_001636 | 30.189 | 32.804 | 29.595 | 30.244 | 0.486 | 0.932 |
| mmu_miR_704_001639 | 36.886 | 35.390 | 37.248 | 37.178 | NA | 0.204 |
| mmu_miR_706_001641 | 26.138 | 35.476 | 33.207 | 38.592 | 0.000 | 0.685 |

TABLE 4-continued

| Brain Stem miRNA data. | | | | | | |
|---|---|---|---|---|---|---|
| mmu_miR_707_001642 | 40.405 | 40.031 | 40.542 | 39.608 | NA | NA |
| mmu_miR_708_002341 | 23.719 | 23.636 | 25.849 | 23.687 | 0.458 | 0.419 |
| mmu_miR_710_001645 | 32.320 | 36.476 | 38.806 | 40.606 | 0.009 | NA |
| mmu_miR_711_001646 | 31.956 | 37.169 | 37.270 | 40.300 | 0.004 | NA |
| mmu_miR_712_001961 | 39.482 | 38.272 | 40.076 | 39.598 | NA | NA |
| mmu_miR_712_002636 | 33.036 | 34.113 | 32.822 | 36.288 | 0.347 | 0.551 |
| mmu_miR_713_001648 | 33.397 | 39.304 | 38.922 | 40.154 | 0.005 | NA |
| mmu_miR_715_001649 | 33.695 | 38.619 | 39.129 | 39.784 | NA | NA |
| mmu_miR_717_001652 | 36.026 | 38.260 | 31.203 | 40.848 | 0.464 | NA |
| mmu_miR_718_001656 | 34.117 | 40.259 | 39.777 | 37.247 | 0.019 | NA |
| mmu_miR_719_001673 | 38.115 | 39.504 | 38.847 | 39.594 | NA | NA |
| mmu_miR_720_001629 | 24.232 | 25.498 | 21.867 | 27.961 | NA | NA |
| mmu_miR_721_001657 | 21.681 | 24.545 | 25.636 | 29.432 | 0.049 | 0.363 |
| mmu_miR_741_002457 | 37.816 | 38.432 | 37.835 | 36.176 | NA | NA |
| mmu_miR_742_002038 | 38.716 | 38.645 | 39.214 | 39.112 | NA | NA |
| mmu_miR_742_002458 | 34.365 | 36.092 | 35.923 | 36.772 | 0.241 | NA |
| mmu_miR_743a_002469 | 28.031 | 30.747 | 26.683 | 31.826 | 0.346 | 0.775 |
| mmu_miR_743b_3p_002471 | 39.893 | 39.575 | 40.160 | 39.607 | NA | NA |
| mmu_miR_743b_5p_002470 | 32.283 | 32.691 | 30.261 | 34.276 | NA | NA |
| mmu_miR_744_002324 | 24.223 | 25.567 | 25.414 | 25.042 | 0.340 | 0.698 |
| mmu_miR_758_002025 | 35.766 | 37.048 | 35.681 | 36.230 | NA | NA |
| mmu_miR_759_002034 | 33.250 | 34.639 | 35.261 | 39.970 | 0.161 | 0.353 |
| mmu_miR_761_002030 | 36.196 | 33.800 | 25.101 | 37.298 | NA | 0.422 |
| mmu_miR_762_002028 | 34.208 | 38.322 | 37.861 | 39.880 | NA | NA |
| mmu_miR_763_002033 | 37.647 | 37.969 | 38.912 | 39.345 | NA | NA |
| mmu_miR_764_3p_002032 | 31.727 | 37.035 | 34.675 | 33.315 | NA | NA |
| mmu_miR_764_5p_002031 | 31.117 | 37.576 | 30.762 | 33.600 | 0.183 | NA |
| mmu_miR_767_241081_mat | 40.729 | 40.407 | 40.776 | 39.623 | NA | NA |
| mmu_miR_770_3p_002027 | 31.720 | 36.098 | 32.238 | 31.202 | 0.399 | 0.990 |
| mmu_miR_770_5p_002608 | 31.861 | 35.790 | 33.555 | 32.904 | 0.175 | NA |
| mmu_miR_7a_000268 | 26.427 | 24.507 | 25.351 | 26.830 | 0.705 | 0.218 |
| mmu_miR_7b_002555 | 26.818 | 27.811 | 27.476 | 26.899 | 0.473 | NA |
| mmu_miR_802_002029 | 34.040 | 32.331 | 34.070 | 32.861 | NA | 0.302 |
| mmu_miR_804_002044 | 31.814 | 27.826 | 30.680 | 35.732 | 0.621 | 0.016 |
| mmu_miR_805_002045 | 27.298 | 30.778 | 25.563 | 33.185 | 0.293 | NA |
| mmu_miR_871_002354 | 39.458 | 37.370 | 39.742 | 39.615 | NA | NA |
| mmu_miR_872_002264 | 25.578 | 23.421 | 26.037 | 25.108 | 0.717 | 0.146 |
| mmu_miR_872_002542 | 24.241 | 22.853 | 25.342 | 23.868 | 0.627 | 0.245 |
| mmu_miR_873_002356 | 32.523 | 34.776 | 32.446 | 32.401 | 0.485 | 0.896 |
| mmu_miR_874_002268 | 36.393 | 38.081 | 38.527 | 39.642 | NA | NA |
| mmu_miR_875_3p_002547 | 40.325 | 37.253 | 35.978 | 38.715 | NA | NA |
| mmu_miR_876_3p_002464 | 39.267 | 39.203 | 39.445 | 39.858 | NA | NA |
| mmu_miR_876_5p_002463 | 38.519 | 37.965 | 38.792 | 38.611 | NA | NA |
| mmu_miR_877_002548 | 21.133 | 24.956 | 18.274 | 24.164 | 0.374 | 0.948 |
| mmu_miR_878_3p_002541 | 32.969 | 35.576 | 29.154 | 39.116 | NA | NA |
| mmu_miR_878_5p_002540 | 37.798 | 38.550 | 37.891 | 37.103 | NA | NA |
| mmu_miR_879_002472 | 34.099 | 33.900 | 34.127 | 33.819 | NA | 0.556 |
| mmu_miR_879_002473 | 27.117 | 28.411 | 30.022 | 26.658 | 0.412 | 0.599 |
| mmu_miR_880_002665 | 35.299 | 38.314 | 33.252 | 39.143 | NA | NA |
| mmu_miR_881_002475 | 35.896 | 39.013 | 38.933 | 39.810 | NA | NA |
| mmu_miR_881_002609 | 32.441 | 36.609 | 36.666 | 38.051 | 0.027 | NA |

TABLE 4-continued

| Brain Stem miRNA data. | | | | | | |
|---|---|---|---|---|---|---|
| mmu__miR__882__002610 | 40.779 | 40.407 | 40.776 | 39.620 | NA | NA |
| mmu__miR__883B__5P__002669 | 34.585 | 38.209 | 38.887 | 39.543 | 0.041 | NA |
| mmu__miR__883a__3p__002461 | 38.076 | 38.365 | 38.467 | 39.719 | NA | NA |
| mmu__miR__883a__5p__002611 | 40.644 | 40.273 | 40.692 | 39.621 | NA | NA |
| mmu__miR__883b__3p__002565 | 38.081 | 40.025 | 39.666 | 39.791 | NA | NA |
| mmu__miR__92a__000430 | 19.360 | 20.369 | 17.520 | 21.330 | 0.491 | 0.683 |
| mmu__miR__92a__002496 | 38.278 | 40.167 | 40.521 | 39.742 | NA | NA |
| mmu__miR__93__001090 | 23.794 | 21.212 | 22.453 | 22.527 | 0.892 | 0.212 |
| mmu__miR__96__000186 | 28.897 | 34.078 | 31.395 | 31.599 | 0.066 | 0.962 |
| mmu__miR__98__000577 | 30.069 | 29.061 | 31.357 | 27.704 | 0.706 | 0.436 |
| mmu__miR__99a__000435 | 21.605 | 19.498 | 20.893 | 20.744 | 0.822 | 0.226 |
| mmu__miR__99b__000436 | 22.549 | 21.380 | 23.717 | 22.913 | 0.513 | 0.230 |
| mmu__miR__9__000583 | 19.265 | 16.684 | 18.258 | 18.223 | 0.858 | 0.177 |
| | pSI__BS.Lyz2 | pSI__BS.Syn | detect__BS.ChAT | detect__BS.GFAP | detect__BS.Lyz2 | detect__BS.Syn |
| hsa__let__7b__002404 | 0.784 | 0.973 | TRUE | TRUE | TRUE | TRUE |
| hsa__let__7e__002407 | 0.518 | 0.638 | TRUE | TRUE | TRUE | TRUE |
| hsa__let__7f__1__002417 | NA | NA | FALSE | TRUE | FALSE | FALSE |
| hsa__let__7i__002172 | NA | 0.739 | FALSE | TRUE | FALSE | TRUE |
| hsa__miR__106b__002380 | NA | 0.057 | TRUE | TRUE | FALSE | TRUE |
| hsa__miR__10a__002288 | NA | NA | FALSE | FALSE | FALSE | FALSE |
| hsa__miR__1197__002810 | NA | 0.450 | TRUE | FALSE | FALSE | TRUE |
| hsa__miR__124__002197 | NA | 0.743 | FALSE | FALSE | FALSE | TRUE |
| hsa__miR__127__5p__002229 | NA | 0.395 | FALSE | TRUE | FALSE | TRUE |
| hsa__miR__136__000592 | 0.305 | 0.497 | TRUE | TRUE | TRUE | TRUE |
| hsa__miR__136__002100 | 0.909 | 0.289 | TRUE | TRUE | TRUE | TRUE |
| hsa__miR__140__3p__002234 | 0.731 | 0.326 | TRUE | TRUE | TRUE | TRUE |
| hsa__miR__143__000466 | 0.399 | 0.969 | TRUE | TRUE | TRUE | TRUE |
| hsa__miR__144__002676 | NA | NA | FALSE | FALSE | FALSE | FALSE |
| hsa__miR__148a__002134 | NA | NA | FALSE | FALSE | FALSE | TRUE |
| hsa__miR__149__002255 | 0.837 | 0.222 | TRUE | TRUE | TRUE | TRUE |
| hsa__miR__151__5P__002642 | 0.654 | 0.308 | TRUE | TRUE | TRUE | TRUE |
| hsa__miR__154__000478 | 0.724 | 0.359 | TRUE | TRUE | TRUE | TRUE |
| hsa__miR__15b__002173 | 0.003 | NA | FALSE | FALSE | TRUE | FALSE |
| hsa__miR__183__002270 | 0.266 | 0.514 | TRUE | TRUE | TRUE | TRUE |
| hsa__miR__189__000488 | 0.073 | 0.994 | TRUE | TRUE | TRUE | TRUE |
| hsa__miR__190b__002263 | 0.594 | 0.961 | TRUE | TRUE | TRUE | TRUE |
| hsa__miR__196a__241070__mat | NA | 0.019 | TRUE | FALSE | FALSE | TRUE |
| hsa__miR__200a__001011 | NA | NA | FALSE | TRUE | FALSE | FALSE |
| hsa__miR__200b__001800 | 0.112 | 0.897 | TRUE | TRUE | TRUE | TRUE |
| hsa__miR__200b__002274 | NA | NA | FALSE | FALSE | FALSE | FALSE |
| hsa__miR__200c__000505 | 0.036 | 0.733 | TRUE | TRUE | TRUE | TRUE |
| hsa__miR__200c__002286 | NA | NA | FALSE | FALSE | FALSE | FALSE |
| hsa__miR__206__000510 | 0.635 | 0.315 | TRUE | TRUE | TRUE | TRUE |
| hsa__miR__213__000516 | 0.626 | 0.446 | TRUE | TRUE | TRUE | TRUE |
| hsa__miR__214__000517 | 0.063 | 0.880 | TRUE | TRUE | TRUE | TRUE |
| hsa__miR__214__002293 | NA | NA | FALSE | FALSE | FALSE | FALSE |
| hsa__miR__218__2__002294 | NA | 0.584 | TRUE | TRUE | FALSE | TRUE |
| hsa__miR__223__000526 | 0.000 | NA | TRUE | TRUE | TRUE | FALSE |
| hsa__miR__22__000398 | 0.994 | 0.202 | TRUE | TRUE | TRUE | TRUE |

TABLE 4-continued

| Brain Stem miRNA data. | | | | | | |
|---|---|---|---|---|---|---|
| hsa_miR_22_002301 | 0.570 | 0.729 | TRUE | TRUE | TRUE | TRUE |
| hsa_miR_23a_002439 | 0.001 | NA | FALSE | FALSE | TRUE | FALSE |
| hsa_miR_26b_002444 | 0.311 | 0.838 | FALSE | TRUE | TRUE | TRUE |
| hsa_miR_27a_002445 | NA | NA | FALSE | FALSE | FALSE | TRUE |
| hsa_miR_27b_002174 | NA | 0.643 | FALSE | TRUE | FALSE | TRUE |
| hsa_miR_28_3p_002446 | NA | NA | FALSE | FALSE | FALSE | TRUE |
| hsa_miR_299_5p_000600 | NA | 0.798 | TRUE | FALSE | FALSE | TRUE |
| hsa_miR_29a_002447 | 0.222 | 0.719 | TRUE | TRUE | TRUE | TRUE |
| hsa_miR_29b_2_002166 | 0.622 | 0.844 | TRUE | TRUE | TRUE | TRUE |
| hsa_miR_30a_3p_000416 | 0.658 | 0.614 | TRUE | TRUE | TRUE | TRUE |
| hsa_miR_30c_1_002108 | NA | NA | FALSE | FALSE | FALSE | FALSE |
| hsa_miR_30c_2_002110 | NA | 0.362 | TRUE | FALSE | FALSE | TRUE |
| hsa_miR_30d_002305 | 0.554 | 0.677 | TRUE | TRUE | TRUE | TRUE |
| hsa_miR_30e_3p_000422 | 0.373 | 0.719 | TRUE | TRUE | TRUE | TRUE |
| hsa_miR_324_3p_000579 | 0.480 | 0.362 | TRUE | TRUE | TRUE | TRUE |
| hsa_miR_338_000548 | 0.789 | 0.274 | TRUE | TRUE | TRUE | TRUE |
| hsa_miR_338_5P_002658 | 0.851 | 0.409 | TRUE | TRUE | TRUE | TRUE |
| hsa_miR_33a_002136 | 0.564 | 0.163 | FALSE | TRUE | TRUE | TRUE |
| hsa_miR_340_000550 | 0.804 | 0.505 | TRUE | TRUE | TRUE | TRUE |
| hsa_miR_363_001283 | NA | NA | FALSE | TRUE | TRUE | FALSE |
| hsa_miR_376a_001287 | 0.610 | 0.471 | TRUE | TRUE | TRUE | TRUE |
| hsa_miR_378_000567 | 0.158 | 0.982 | TRUE | TRUE | TRUE | TRUE |
| hsa_miR_411_002238 | 0.973 | 0.215 | TRUE | TRUE | TRUE | TRUE |
| hsa_miR_412_001023 | 0.014 | 0.600 | TRUE | TRUE | TRUE | TRUE |
| hsa_miR_421_002700 | 0.884 | 0.538 | TRUE | TRUE | TRUE | TRUE |
| hsa_miR_423_3P_002626 | 0.375 | 0.488 | TRUE | TRUE | TRUE | TRUE |
| hsa_miR_425_001104 | 0.097 | 0.372 | TRUE | TRUE | TRUE | TRUE |
| hsa_miR_431_002312 | 0.362 | 0.622 | TRUE | FALSE | TRUE | TRUE |
| hsa_miR_455_001280 | 0.214 | 0.564 | TRUE | TRUE | TRUE | TRUE |
| hsa_miR_485_5p_001036 | 0.399 | 0.526 | FALSE | TRUE | TRUE | TRUE |
| hsa_miR_493_3p_001282 | 0.398 | NA | TRUE | FALSE | TRUE | FALSE |
| hsa_miR_590_3P_002677 | NA | NA | FALSE | FALSE | FALSE | FALSE |
| hsa_miR_653_002292 | 0.346 | NA | TRUE | FALSE | TRUE | TRUE |
| hsa_miR_671_5p_197646_mat | 0.278 | NA | TRUE | TRUE | TRUE | TRUE |
| hsa_miR_708_002342 | NA | NA | FALSE | FALSE | TRUE | FALSE |
| hsa_miR_744_002325 | 0.342 | 0.703 | TRUE | TRUE | TRUE | TRUE |
| hsa_miR_875_5p_002203 | 0.007 | NA | TRUE | TRUE | TRUE | TRUE |
| hsa_miR_935_002178 | NA | 0.617 | FALSE | TRUE | FALSE | TRUE |
| hsa_miR_93_002139 | 0.635 | 0.460 | TRUE | TRUE | TRUE | TRUE |
| hsa_miR_99b_002196 | NA | 0.468 | TRUE | TRUE | FALSE | TRUE |
| hsa_miR_9_002231 | 0.682 | 0.595 | TRUE | TRUE | TRUE | TRUE |
| mmu_let_7a_000377 | 0.961 | 0.200 | TRUE | TRUE | TRUE | TRUE |
| mmu_let_7a_002478 | 0.569 | 0.768 | TRUE | TRUE | TRUE | TRUE |
| mmu_let_7b_000378 | 0.708 | 0.746 | TRUE | TRUE | TRUE | TRUE |
| mmu_let_7c_000379 | 0.756 | 0.553 | TRUE | TRUE | TRUE | TRUE |
| mmu_let_7c_1_002479 | NA | 0.895 | FALSE | TRUE | FALSE | TRUE |
| mmu_let_7d_001178 | NA | 0.201 | FALSE | TRUE | FALSE | TRUE |
| mmu_let_7d_002283 | 0.740 | 0.579 | TRUE | TRUE | TRUE | TRUE |
| mmu_let_7e_002406 | 0.608 | 0.549 | TRUE | TRUE | TRUE | TRUE |
| mmu_let_7f_000382 | 0.829 | 0.266 | TRUE | TRUE | TRUE | TRUE |
| mmu_let_7g_002282 | 0.864 | 0.600 | TRUE | TRUE | TRUE | TRUE |

TABLE 4-continued

| Brain Stem miRNA data. | | | | | | |
|---|---|---|---|---|---|---|
| mmu_let_7g_002492 | 0.357 | 0.829 | TRUE | TRUE | TRUE | TRUE |
| mmu_let_7i_002221 | 0.810 | 0.631 | TRUE | TRUE | TRUE | TRUE |
| mmu_miR_100_000437 | 0.825 | 0.473 | TRUE | TRUE | TRUE | TRUE |
| mmu_miR_101a_002253 | 0.641 | 0.487 | TRUE | TRUE | TRUE | TRUE |
| mmu_miR_101a_002507 | NA | 0.294 | TRUE | TRUE | FALSE | TRUE |
| mmu_miR_101b_002531 | 0.848 | 0.510 | TRUE | TRUE | TRUE | TRUE |
| mmu_miR_103_000439 | 0.665 | 0.498 | TRUE | TRUE | TRUE | TRUE |
| mmu_miR_105_002465 | 0.024 | 0.459 | FALSE | FALSE | TRUE | TRUE |
| mmu_miR_106a_002459 | 0.341 | 0.413 | TRUE | TRUE | TRUE | TRUE |
| mmu_miR_106b_000442 | 0.699 | 0.478 | TRUE | TRUE | TRUE | TRUE |
| mmu_miR_107_000443 | 0.918 | 0.445 | TRUE | TRUE | TRUE | TRUE |
| mmu_miR_10a_000387 | 0.628 | 0.477 | TRUE | TRUE | TRUE | TRUE |
| mmu_miR_10b_001181 | NA | 0.062 | TRUE | TRUE | FALSE | TRUE |
| mmu_miR_10b_002218 | 0.826 | 0.001 | TRUE | TRUE | TRUE | TRUE |
| mmu_miR_10b_002572 | NA | 0.627 | FALSE | FALSE | FALSE | TRUE |
| mmu_miR_1186_002825 | 0.657 | NA | FALSE | TRUE | TRUE | FALSE |
| mmu_miR_1188_002866 | 0.917 | 0.899 | TRUE | TRUE | TRUE | TRUE |
| mmu_miR_1191_002892 | 0.375 | 0.996 | TRUE | TRUE | TRUE | TRUE |
| mmu_miR_1192_002806 | NA | NA | FALSE | FALSE | FALSE | FALSE |
| mmu_miR_1193_002794 | NA | 0.742 | TRUE | TRUE | FALSE | TRUE |
| mmu_miR_1194_002793 | NA | NA | FALSE | FALSE | FALSE | TRUE |
| mmu_miR_1195_002839 | NA | NA | FALSE | FALSE | FALSE | FALSE |
| mmu_miR_1198_002780 | 0.993 | 0.095 | TRUE | TRUE | TRUE | TRUE |
| mmu_miR_1199_240984_mat | NA | NA | FALSE | FALSE | FALSE | FALSE |
| mmu_miR_1224_240985_mat | NA | NA | FALSE | FALSE | FALSE | FALSE |
| mmu_miR_122_002245 | 0.052 | NA | FALSE | FALSE | TRUE | TRUE |
| mmu_miR_124_001182 | 0.826 | 0.360 | TRUE | TRUE | TRUE | TRUE |
| mmu_miR_125a_3p_002199 | 0.600 | 0.566 | TRUE | TRUE | TRUE | TRUE |
| mmu_miR_125a_5p_002198 | 0.857 | 0.426 | TRUE | TRUE | TRUE | TRUE |
| mmu_miR_125b_002508 | 0.860 | 0.685 | TRUE | TRUE | TRUE | TRUE |
| mmu_miR_125b_3p_002378 | 0.445 | 0.882 | TRUE | TRUE | TRUE | TRUE |
| mmu_miR_125b_5p_000449 | 0.797 | 0.534 | TRUE | TRUE | TRUE | TRUE |
| mmu_miR_126_3p_002228 | 0.271 | 0.708 | TRUE | TRUE | TRUE | TRUE |
| mmu_miR_126_5p_000451 | 0.309 | NA | TRUE | FALSE | TRUE | FALSE |
| mmu_miR_1274a_121150_mat | 0.006 | NA | FALSE | FALSE | TRUE | FALSE |
| mmu_miR_127_000452 | 0.794 | 0.245 | TRUE | TRUE | TRUE | TRUE |
| mmu_miR_128a_002216 | 0.686 | 0.387 | TRUE | TRUE | TRUE | TRUE |
| mmu_miR_129_3p_001184 | 0.734 | 0.287 | TRUE | TRUE | TRUE | TRUE |
| mmu_miR_129_5p_000590 | 0.971 | 0.298 | TRUE | TRUE | TRUE | TRUE |
| mmu_miR_1306_121155_mat | NA | 0.327 | FALSE | FALSE | FALSE | TRUE |
| mmu_miR_130a_000454 | 0.940 | 0.272 | TRUE | TRUE | TRUE | TRUE |
| mmu_miR_130b_000456 | 0.290 | 0.714 | TRUE | TRUE | TRUE | TRUE |
| mmu_miR_130b_002460 | 0.705 | 0.221 | TRUE | TRUE | TRUE | TRUE |
| mmu_miR_132_000457 | 0.787 | 0.237 | TRUE | TRUE | TRUE | TRUE |
| mmu_miR_133a_001637 | NA | NA | FALSE | FALSE | FALSE | FALSE |
| mmu_miR_133a_002246 | 0.813 | 0.238 | TRUE | TRUE | TRUE | TRUE |
| mmu_miR_133b_002247 | 0.809 | 0.378 | TRUE | TRUE | TRUE | TRUE |
| mmu_miR_134_001186 | 0.937 | 0.072 | TRUE | TRUE | TRUE | TRUE |
| mmu_miR_135a_000460 | 0.875 | 0.242 | TRUE | TRUE | TRUE | TRUE |
| mmu_miR_135b_002261 | 0.964 | 0.250 | TRUE | TRUE | TRUE | TRUE |
| mmu_miR_136_002511 | NA | 0.067 | TRUE | TRUE | FALSE | TRUE |

TABLE 4-continued

| Brain Stem miRNA data. | | | | | | |
|---|---|---|---|---|---|---|
| mmu_miR_136_002512 | 0.117 | 0.881 | TRUE | TRUE | TRUE | TRUE |
| mmu_miR_137_001129 | 0.879 | 0.492 | TRUE | TRUE | TRUE | TRUE |
| mmu_miR_138_002284 | 0.909 | 0.317 | TRUE | TRUE | TRUE | TRUE |
| mmu_miR_138_002554 | 0.669 | 0.417 | TRUE | TRUE | TRUE | TRUE |
| mmu_miR_139_3p_002546 | NA | 0.050 | FALSE | FALSE | FALSE | TRUE |
| mmu_miR_139_5p_002289 | 0.498 | 0.500 | TRUE | TRUE | TRUE | TRUE |
| mmu_miR_140_001187 | 0.647 | 0.559 | TRUE | TRUE | TRUE | TRUE |
| mmu_miR_141_000463 | 0.034 | NA | TRUE | TRUE | TRUE | TRUE |
| mmu_miR_141_002513 | 0.017 | NA | TRUE | FALSE | TRUE | FALSE |
| mmu_miR_142_3p_000464 | 0.001 | NA | FALSE | FALSE | TRUE | FALSE |
| mmu_miR_142_5p_002248 | 0.004 | NA | TRUE | TRUE | TRUE | FALSE |
| mmu_miR_143_002249 | 0.152 | NA | TRUE | TRUE | TRUE | FALSE |
| mmu_miR_145_002278 | 0.103 | NA | FALSE | FALSE | TRUE | FALSE |
| mmu_miR_145_002514 | NA | NA | FALSE | FALSE | FALSE | FALSE |
| mmu_miR_146a_000468 | 0.071 | 0.945 | TRUE | TRUE | TRUE | TRUE |
| mmu_miR_146b_001097 | 0.545 | 0.563 | TRUE | TRUE | TRUE | TRUE |
| mmu_miR_146b_002453 | NA | 0.878 | TRUE | TRUE | FALSE | TRUE |
| mmu_miR_147_002262 | NA | NA | FALSE | FALSE | FALSE | FALSE |
| mmu_miR_148a_000470 | NA | 0.390 | TRUE | TRUE | FALSE | TRUE |
| mmu_miR_148b_000471 | 0.994 | 0.323 | TRUE | TRUE | TRUE | TRUE |
| mmu_miR_150_000473 | 0.109 | NA | TRUE | FALSE | TRUE | FALSE |
| mmu_miR_150_002570 | NA | NA | TRUE | FALSE | FALSE | FALSE |
| mmu_miR_151_3p_001190 | 0.954 | 0.222 | TRUE | TRUE | TRUE | TRUE |
| mmu_miR_152_000475 | 0.350 | 0.970 | TRUE | TRUE | TRUE | TRUE |
| mmu_miR_153_001191 | 0.555 | 0.576 | TRUE | TRUE | TRUE | TRUE |
| mmu_miR_154_000477 | NA | 0.040 | TRUE | FALSE | FALSE | TRUE |
| mmu_miR_155_002571 | 0.115 | 1.000 | TRUE | TRUE | TRUE | TRUE |
| mmu_miR_15a_000389 | 0.409 | 0.641 | TRUE | TRUE | TRUE | TRUE |
| mmu_miR_15a_002488 | 0.713 | 0.760 | TRUE | TRUE | TRUE | TRUE |
| mmu_miR_15b_000390 | 0.398 | 0.627 | TRUE | TRUE | TRUE | TRUE |
| mmu_miR_16_000391 | 0.322 | 0.507 | TRUE | TRUE | TRUE | TRUE |
| mmu_miR_16_002489 | 0.053 | 0.763 | FALSE | TRUE | TRUE | TRUE |
| mmu_miR_17_002308 | 0.299 | 0.445 | TRUE | TRUE | TRUE | TRUE |
| mmu_miR_17_002543 | 0.039 | 0.727 | TRUE | FALSE | TRUE | TRUE |
| mmu_miR_181A_2_002687 | NA | NA | FALSE | FALSE | FALSE | FALSE |
| mmu_miR_181a_000480 | 0.833 | 0.308 | TRUE | TRUE | TRUE | TRUE |
| mmu_miR_181c_000482 | 0.690 | 0.402 | TRUE | TRUE | TRUE | TRUE |
| mmu_miR_182_002599 | 0.494 | 0.513 | TRUE | TRUE | TRUE | TRUE |
| mmu_miR_1839_3p_121203_mat | 0.814 | 0.610 | TRUE | TRUE | TRUE | TRUE |
| mmu_miR_1839_5p_121135_mat | 0.992 | 0.395 | TRUE | TRUE | TRUE | TRUE |
| mmu_miR_183_002269 | 0.535 | 0.497 | TRUE | TRUE | TRUE | TRUE |
| mmu_miR_184_000485 | 0.059 | 0.691 | TRUE | FALSE | TRUE | TRUE |
| mmu_miR_185_002271 | 0.999 | 0.208 | TRUE | TRUE | TRUE | TRUE |
| mmu_miR_186_002285 | 0.606 | 0.630 | TRUE | TRUE | TRUE | TRUE |
| mmu_miR_186_002574 | 0.141 | 0.793 | TRUE | TRUE | TRUE | TRUE |
| mmu_miR_187_001193 | 0.866 | 0.247 | TRUE | TRUE | TRUE | TRUE |
| mmu_miR_188_3p_002106 | NA | NA | FALSE | FALSE | FALSE | FALSE |
| mmu_miR_188_5p_002320 | NA | NA | FALSE | FALSE | FALSE | FALSE |
| mmu_miR_1893_121170_mat | NA | NA | FALSE | FALSE | TRUE | FALSE |
| mmu_miR_1894_3p_241002_mat | 0.109 | NA | TRUE | FALSE | TRUE | FALSE |
| mmu_miR_1894_5p_121144_mat | NA | NA | FALSE | FALSE | FALSE | FALSE |

TABLE 4-continued

| Brain Stem miRNA data. | | | | | | |
|---|---|---|---|---|---|---|
| mmu_miR_1896_121128_mat | 0.028 | NA | TRUE | TRUE | TRUE | FALSE |
| mmu_miR_1897_3p_121126_mat | NA | NA | FALSE | FALSE | FALSE | FALSE |
| mmu_miR_1897_5p_121199_mat | 0.349 | NA | FALSE | FALSE | TRUE | FALSE |
| mmu_miR_1898_121195_mat | NA | NA | FALSE | FALSE | FALSE | FALSE |
| mmu_miR_1899_121198_mat | NA | NA | FALSE | FALSE | FALSE | FALSE |
| mmu_miR_18a_002422 | 0.166 | 0.540 | TRUE | TRUE | TRUE | TRUE |
| mmu_miR_18a_002490 | 0.136 | 0.792 | TRUE | TRUE | TRUE | TRUE |
| mmu_miR_18b_002466 | NA | NA | FALSE | FALSE | FALSE | FALSE |
| mmu_miR_1900_121143_mat | NA | NA | FALSE | FALSE | FALSE | FALSE |
| mmu_miR_1901_121183_mat | NA | 0.702 | TRUE | TRUE | FALSE | TRUE |
| mmu_miR_1902_121197_mat | NA | NA | FALSE | FALSE | FALSE | FALSE |
| mmu_miR_1903_121153_mat | NA | NA | FALSE | FALSE | FALSE | FALSE |
| mmu_miR_1904_121162_mat | NA | NA | FALSE | FALSE | FALSE | FALSE |
| mmu_miR_1905_121196_mat | 0.216 | NA | TRUE | TRUE | TRUE | FALSE |
| mmu_miR_1906_121169_mat | NA | NA | FALSE | FALSE | FALSE | FALSE |
| mmu_miR_190_000489 | 0.647 | 0.542 | TRUE | TRUE | TRUE | TRUE |
| mmu_miR_191_002299 | 0.594 | 0.484 | TRUE | TRUE | TRUE | TRUE |
| mmu_miR_191_002576 | 0.486 | 0.810 | TRUE | TRUE | TRUE | TRUE |
| mmu_miR_1927_121193_mat | NA | NA | FALSE | TRUE | FALSE | TRUE |
| mmu_miR_1928_121164_mat | 0.263 | NA | TRUE | TRUE | TRUE | FALSE |
| mmu_miR_192_000491 | 0.702 | 0.588 | TRUE | TRUE | TRUE | TRUE |
| mmu_miR_1930_121201_mat | 0.275 | 0.527 | TRUE | TRUE | TRUE | TRUE |
| mmu_miR_1931_121168_mat | NA | NA | FALSE | FALSE | FALSE | FALSE |
| mmu_miR_1932_121172_mat | 0.845 | 0.944 | FALSE | TRUE | TRUE | TRUE |
| mmu_miR_1933_3p_121145_mat | NA | NA | FALSE | FALSE | FALSE | FALSE |
| mmu_miR_1933_5p_121133_mat | 0.326 | 0.800 | TRUE | FALSE | TRUE | TRUE |
| mmu_miR_1934_121185_mat | NA | NA | FALSE | TRUE | FALSE | FALSE |
| mmu_miR_1935_121192_mat | NA | NA | FALSE | FALSE | FALSE | FALSE |
| mmu_miR_1936_121158_mat | NA | NA | FALSE | FALSE | FALSE | FALSE |
| mmu_miR_1937b_241023_mat | 0.210 | NA | TRUE | FALSE | TRUE | FALSE |
| mmu_miR_1937c_241011_mat | 0.223 | NA | TRUE | FALSE | TRUE | FALSE |
| mmu_miR_1938_121194_mat | NA | NA | FALSE | FALSE | FALSE | FALSE |
| mmu_miR_1939_121180_mat | NA | NA | FALSE | FALSE | FALSE | TRUE |
| mmu_miR_193_002250 | NA | NA | FALSE | FALSE | FALSE | FALSE |
| mmu_miR_193_002577 | NA | 0.756 | TRUE | TRUE | FALSE | TRUE |
| mmu_miR_193b_002467 | 0.960 | 0.389 | TRUE | TRUE | TRUE | TRUE |
| mmu_miR_1940_121187_mat | 0.017 | NA | FALSE | FALSE | TRUE | TRUE |
| mmu_miR_1941_3p_121130_mat | NA | NA | FALSE | FALSE | FALSE | FALSE |
| mmu_miR_1941_5p_121140_mat | 0.251 | 0.973 | TRUE | TRUE | TRUE | TRUE |
| mmu_miR_1942_121136_mat | 0.013 | NA | TRUE | TRUE | TRUE | TRUE |
| mmu_miR_1943_121174_mat | NA | 0.436 | FALSE | TRUE | FALSE | TRUE |
| mmu_miR_1944_121189_mat | NA | NA | FALSE | FALSE | FALSE | FALSE |
| mmu_miR_1945_121166_mat | NA | NA | FALSE | FALSE | FALSE | TRUE |
| mmu_miR_1946a_121178_mat | 0.002 | NA | FALSE | FALSE | TRUE | FALSE |
| mmu_miR_1947_121156_mat | NA | NA | FALSE | FALSE | FALSE | TRUE |
| mmu_miR_1948_121171_mat | NA | 0.542 | TRUE | FALSE | FALSE | TRUE |
| mmu_miR_1949_121182_mat | NA | NA | FALSE | FALSE | FALSE | FALSE |
| mmu_miR_194_000493 | 0.438 | 0.602 | TRUE | TRUE | TRUE | TRUE |
| mmu_miR_1950_121146_mat | NA | NA | FALSE | FALSE | FALSE | FALSE |
| mmu_miR_1951_121165_mat | 0.001 | NA | TRUE | FALSE | TRUE | FALSE |
| mmu_miR_1952_121167_mat | NA | NA | FALSE | FALSE | FALSE | FALSE |

TABLE 4-continued

| Brain Stem miRNA data. | | | | | | |
|---|---|---|---|---|---|---|
| mmu_miR_1953_121159_mat | NA | NA | FALSE | FALSE | FALSE | FALSE |
| mmu_miR_1954_121137_mat | 0.022 | NA | TRUE | TRUE | TRUE | FALSE |
| mmu_miR_1956_121129_mat | NA | 0.181 | FALSE | FALSE | FALSE | TRUE |
| mmu_miR_1957_121163_mat | NA | NA | FALSE | FALSE | FALSE | FALSE |
| mmu_miR_1958_121181_mat | NA | NA | FALSE | FALSE | FALSE | TRUE |
| mmu_miR_1959_121132_mat | 0.065 | 0.996 | TRUE | TRUE | TRUE | TRUE |
| mmu_miR_195_000494 | 0.403 | 0.678 | TRUE | TRUE | TRUE | TRUE |
| mmu_miR_1960_121148_mat | NA | NA | FALSE | TRUE | FALSE | TRUE |
| mmu_miR_1961_197391_mat | 0.439 | NA | TRUE | FALSE | TRUE | FALSE |
| mmu_miR_1962_121173_mat | NA | NA | FALSE | FALSE | TRUE | FALSE |
| mmu_miR_1963_121191_mat | NA | NA | FALSE | FALSE | FALSE | FALSE |
| mmu_miR_1964_121138_mat | NA | NA | FALSE | FALSE | FALSE | FALSE |
| mmu_miR_1965_121186_mat | NA | NA | FALSE | FALSE | TRUE | FALSE |
| mmu_miR_1966_121134_mat | NA | NA | FALSE | FALSE | FALSE | FALSE |
| mmu_miR_1967_121151_mat | NA | NA | FALSE | FALSE | FALSE | FALSE |
| mmu_miR_1968_121179_mat | 0.788 | NA | TRUE | FALSE | TRUE | TRUE |
| mmu_miR_1969_121131_mat | 0.043 | 0.985 | TRUE | TRUE | TRUE | TRUE |
| mmu_miR_196a_002477 | NA | NA | FALSE | FALSE | FALSE | FALSE |
| mmu_miR_196b_002215 | 0.130 | 0.280 | FALSE | FALSE | TRUE | TRUE |
| mmu_miR_1970_121202_mat | 0.058 | NA | TRUE | FALSE | TRUE | FALSE |
| mmu_miR_1971_121161_mat | 0.354 | 0.702 | TRUE | FALSE | TRUE | TRUE |
| mmu_miR_197_000497 | 0.005 | NA | FALSE | TRUE | TRUE | FALSE |
| mmu_miR_1981_121200_mat | 0.867 | 0.289 | TRUE | TRUE | TRUE | TRUE |
| mmu_miR_1982.1_121157_mat | 0.655 | 0.343 | TRUE | TRUE | TRUE | TRUE |
| mmu_miR_1982.2_121154_mat | 0.220 | 0.729 | TRUE | TRUE | TRUE | TRUE |
| mmu_miR_199a_3p_002304 | 0.221 | 0.757 | TRUE | TRUE | TRUE | TRUE |
| mmu_miR_199a_5p_000498 | NA | 0.464 | FALSE | TRUE | FALSE | TRUE |
| mmu_miR_199b_001131 | NA | 0.475 | FALSE | FALSE | FALSE | TRUE |
| mmu_miR_19a_000395 | 0.312 | 0.638 | TRUE | TRUE | TRUE | TRUE |
| mmu_miR_19a_002544 | NA | NA | FALSE | FALSE | FALSE | FALSE |
| mmu_miR_19b_000396 | 0.351 | 0.477 | TRUE | TRUE | TRUE | TRUE |
| mmu_miR_1_002222 | 0.181 | 0.605 | TRUE | TRUE | TRUE | TRUE |
| mmu_miR_1_2_AS_002882 | 0.051 | 0.877 | TRUE | TRUE | TRUE | TRUE |
| mmu_miR_200a_000502 | NA | NA | TRUE | FALSE | FALSE | FALSE |
| mmu_miR_200b_002251 | NA | NA | FALSE | TRUE | FALSE | FALSE |
| mmu_miR_200c_002300 | 0.309 | NA | FALSE | FALSE | TRUE | FALSE |
| mmu_miR_201_002578 | NA | NA | FALSE | FALSE | FALSE | FALSE |
| mmu_miR_202_3p_001195 | NA | NA | FALSE | FALSE | FALSE | FALSE |
| mmu_miR_202_5p_002579 | NA | NA | FALSE | FALSE | FALSE | FALSE |
| mmu_miR_203_000507 | 0.397 | 0.965 | TRUE | TRUE | TRUE | TRUE |
| mmu_miR_203_002580 | NA | NA | FALSE | FALSE | TRUE | FALSE |
| mmu_miR_204_000508 | 0.545 | 0.838 | TRUE | TRUE | TRUE | TRUE |
| mmu_miR_205_000509 | NA | 0.296 | FALSE | FALSE | FALSE | TRUE |
| mmu_miR_207_001198 | NA | NA | FALSE | FALSE | FALSE | FALSE |
| mmu_miR_208_000511 | NA | NA | FALSE | TRUE | FALSE | FALSE |
| mmu_miR_208b_002290 | 0.353 | NA | TRUE | FALSE | TRUE | FALSE |
| mmu_miR_20a_000580 | 0.268 | 0.509 | TRUE | TRUE | TRUE | TRUE |
| mmu_miR_20a_002491 | 0.197 | 0.654 | FALSE | TRUE | TRUE | TRUE |
| mmu_miR_20b_001014 | 0.271 | 0.465 | TRUE | TRUE | TRUE | TRUE |
| mmu_miR_20b_002524 | NA | NA | FALSE | FALSE | FALSE | FALSE |
| mmu_miR_210_000512 | NA | 0.261 | FALSE | TRUE | FALSE | TRUE |

TABLE 4-continued

| Brain Stem miRNA data. | | | | | | |
|---|---|---|---|---|---|---|
| mmu_miR_211_001199 | 0.422 | 0.765 | TRUE | TRUE | TRUE | TRUE |
| mmu_miR_212_002551 | 0.876 | 0.141 | TRUE | TRUE | TRUE | TRUE |
| mmu_miR_2134_241120_mat | 0.216 | NA | TRUE | FALSE | TRUE | FALSE |
| mmu_miR_2135_241140_mat | NA | NA | FALSE | FALSE | FALSE | FALSE |
| mmu_miR_2136_241133_mat | NA | NA | FALSE | FALSE | FALSE | TRUE |
| mmu_miR_2138_241080_mat | 0.009 | NA | TRUE | TRUE | TRUE | TRUE |
| mmu_miR_2139_241130_mat | NA | NA | FALSE | FALSE | FALSE | FALSE |
| mmu_miR_2146_241082_mat | 0.257 | NA | TRUE | FALSE | TRUE | FALSE |
| mmu_miR_214_002306 | 0.199 | 0.912 | FALSE | TRUE | TRUE | TRUE |
| mmu_miR_215_001200 | NA | 0.669 | FALSE | TRUE | FALSE | TRUE |
| mmu_miR_216a_002220 | 0.645 | 0.111 | TRUE | FALSE | TRUE | TRUE |
| mmu_miR_216b_002326 | 0.761 | 0.125 | TRUE | TRUE | TRUE | TRUE |
| mmu_miR_217_001133 | 0.157 | 0.608 | TRUE | FALSE | TRUE | TRUE |
| mmu_miR_217_002556 | 0.315 | 0.345 | TRUE | TRUE | TRUE | TRUE |
| mmu_miR_2182_241119_mat | NA | NA | TRUE | FALSE | FALSE | FALSE |
| mmu_miR_2183_241095_mat | 0.086 | NA | TRUE | FALSE | TRUE | FALSE |
| mmu_miR_218_000521 | 0.920 | 0.437 | TRUE | TRUE | TRUE | TRUE |
| mmu_miR_218_1_002552 | 0.822 | 0.263 | TRUE | TRUE | TRUE | TRUE |
| mmu_miR_219_000522 | 0.801 | 0.125 | FALSE | TRUE | TRUE | TRUE |
| mmu_miR_21_000397 | 0.195 | 0.565 | TRUE | TRUE | TRUE | TRUE |
| mmu_miR_21_002493 | NA | 0.368 | FALSE | FALSE | FALSE | TRUE |
| mmu_miR_220_002468 | NA | NA | FALSE | FALSE | FALSE | FALSE |
| mmu_miR_221_000524 | 0.543 | 0.638 | TRUE | TRUE | TRUE | TRUE |
| mmu_miR_222_002276 | 0.475 | 0.579 | TRUE | TRUE | TRUE | TRUE |
| mmu_miR_223_002295 | 0.000 | NA | TRUE | FALSE | TRUE | FALSE |
| mmu_miR_224_002553 | NA | 0.524 | TRUE | TRUE | FALSE | TRUE |
| mmu_miR_23a_000399 | NA | NA | FALSE | FALSE | FALSE | FALSE |
| mmu_miR_23b_000400 | 0.547 | 0.601 | TRUE | TRUE | TRUE | TRUE |
| mmu_miR_24_000402 | 0.502 | 0.614 | TRUE | TRUE | TRUE | TRUE |
| mmu_miR_24_2_002494 | 0.406 | 0.889 | TRUE | TRUE | TRUE | TRUE |
| mmu_miR_25_000403 | 0.259 | 0.749 | TRUE | TRUE | TRUE | TRUE |
| mmu_miR_26a_000405 | 0.526 | 0.562 | TRUE | TRUE | TRUE | TRUE |
| mmu_miR_26b_000407 | 0.421 | 0.640 | TRUE | TRUE | TRUE | TRUE |
| mmu_miR_27a_000408 | 0.614 | 0.931 | TRUE | TRUE | TRUE | TRUE |
| mmu_miR_27b_000409 | 0.796 | 0.361 | TRUE | TRUE | TRUE | TRUE |
| mmu_miR_28_000411 | 0.415 | 0.978 | TRUE | TRUE | TRUE | TRUE |
| mmu_miR_28_002545 | 0.637 | 0.856 | TRUE | TRUE | TRUE | TRUE |
| mmu_miR_290_000187 | 0.000 | NA | FALSE | FALSE | TRUE | FALSE |
| mmu_miR_290_3p_002591 | NA | NA | FALSE | FALSE | FALSE | FALSE |
| mmu_miR_290_5p_002590 | NA | NA | FALSE | TRUE | FALSE | TRUE |
| mmu_miR_291_3p_001135 | NA | NA | FALSE | FALSE | FALSE | FALSE |
| mmu_miR_291_5p_001202 | NA | NA | FALSE | FALSE | FALSE | FALSE |
| mmu_miR_291a_3p_002592 | NA | NA | FALSE | FALSE | FALSE | FALSE |
| mmu_miR_291b_3p_002538 | NA | NA | FALSE | FALSE | FALSE | FALSE |
| mmu_miR_291b_5p_002537 | NA | NA | FALSE | FALSE | FALSE | FALSE |
| mmu_miR_292_3p_001054 | NA | NA | FALSE | FALSE | FALSE | FALSE |
| mmu_miR_292_3p_002593 | 0.190 | NA | FALSE | TRUE | TRUE | FALSE |
| mmu_miR_292_5p_001055 | NA | NA | FALSE | FALSE | FALSE | FALSE |
| mmu_miR_293_001794 | 0.055 | 0.854 | FALSE | FALSE | TRUE | TRUE |
| mmu_miR_293_002594 | NA | NA | FALSE | FALSE | FALSE | FALSE |
| mmu_miR_294_001056 | 0.128 | NA | FALSE | FALSE | TRUE | FALSE |

TABLE 4-continued

| Brain Stem miRNA data. | | | | | | |
|---|---|---|---|---|---|---|
| mmu_miR_294_002595 | NA | NA | FALSE | FALSE | FALSE | FALSE |
| mmu_miR_295_000189 | NA | NA | FALSE | FALSE | FALSE | FALSE |
| mmu_miR_295_002596 | 0.023 | NA | FALSE | FALSE | TRUE | FALSE |
| mmu_miR_296_3p_002101 | NA | NA | FALSE | FALSE | FALSE | FALSE |
| mmu_miR_296_5p_000527 | NA | 0.566 | TRUE | TRUE | FALSE | TRUE |
| mmu_miR_297a_002454 | 0.827 | 0.696 | TRUE | TRUE | TRUE | TRUE |
| mmu_miR_297b_5p_001626 | NA | NA | FALSE | TRUE | FALSE | FALSE |
| mmu_miR_297c_002480 | NA | NA | FALSE | TRUE | FALSE | TRUE |
| mmu_miR_298_002598 | NA | 0.016 | TRUE | TRUE | FALSE | TRUE |
| mmu_miR_299_002612 | NA | NA | FALSE | FALSE | FALSE | FALSE |
| mmu_miR_29a_002112 | 0.821 | 0.334 | TRUE | TRUE | TRUE | TRUE |
| mmu_miR_29b_000413 | 0.822 | 0.529 | TRUE | TRUE | TRUE | TRUE |
| mmu_miR_29b_002497 | 0.103 | NA | TRUE | FALSE | TRUE | FALSE |
| mmu_miR_29c_000587 | 0.864 | 0.412 | TRUE | TRUE | TRUE | TRUE |
| mmu_miR_300_000191 | NA | 0.271 | TRUE | TRUE | FALSE | TRUE |
| mmu_miR_300_002613 | NA | 0.494 | TRUE | FALSE | FALSE | TRUE |
| mmu_miR_301a_000528 | 0.660 | 0.502 | TRUE | TRUE | TRUE | TRUE |
| mmu_miR_301b_002600 | 0.824 | 0.423 | TRUE | TRUE | TRUE | TRUE |
| mmu_miR_302a_000529 | 0.163 | 0.631 | TRUE | TRUE | TRUE | TRUE |
| mmu_miR_302a_002615 | NA | NA | FALSE | FALSE | FALSE | FALSE |
| mmu_miR_302b_000531 | NA | NA | FALSE | TRUE | FALSE | FALSE |
| mmu_miR_302b_001307 | 0.053 | NA | FALSE | FALSE | TRUE | FALSE |
| mmu_miR_302c_002557 | NA | NA | FALSE | TRUE | FALSE | FALSE |
| mmu_miR_302c_002558 | 0.157 | NA | FALSE | FALSE | TRUE | FALSE |
| mmu_miR_302d_000535 | NA | NA | FALSE | FALSE | FALSE | FALSE |
| mmu_miR_30a_000417 | 0.554 | 0.562 | TRUE | TRUE | TRUE | TRUE |
| mmu_miR_30b_000602 | 0.624 | 0.519 | TRUE | TRUE | TRUE | TRUE |
| mmu_miR_30b_002498 | NA | 0.558 | FALSE | TRUE | FALSE | TRUE |
| mmu_miR_30c_000419 | 0.689 | 0.474 | TRUE | TRUE | TRUE | TRUE |
| mmu_miR_30d_000420 | 0.665 | 0.628 | TRUE | TRUE | TRUE | TRUE |
| mmu_miR_30e_002223 | 0.642 | 0.644 | TRUE | TRUE | TRUE | TRUE |
| mmu_miR_31_000185 | NA | NA | FALSE | FALSE | FALSE | FALSE |
| mmu_miR_31_002495 | 0.402 | 0.377 | TRUE | TRUE | TRUE | TRUE |
| mmu_miR_320_002277 | 0.720 | 0.642 | TRUE | TRUE | TRUE | TRUE |
| mmu_miR_322_001059 | 0.123 | 0.569 | TRUE | TRUE | TRUE | TRUE |
| mmu_miR_322_001076 | 0.324 | 0.261 | FALSE | TRUE | TRUE | TRUE |
| mmu_miR_322_002506 | 0.290 | 0.214 | TRUE | TRUE | TRUE | TRUE |
| mmu_miR_323_3p_002227 | 0.961 | 0.127 | TRUE | TRUE | TRUE | TRUE |
| mmu_miR_324_3p_002509 | 0.951 | 0.216 | TRUE | TRUE | TRUE | TRUE |
| mmu_miR_324_5p_000539 | 0.800 | 0.301 | TRUE | TRUE | TRUE | TRUE |
| mmu_miR_325_001060 | 0.031 | 0.537 | TRUE | TRUE | TRUE | TRUE |
| mmu_miR_325_002510 | NA | 0.187 | TRUE | TRUE | FALSE | TRUE |
| mmu_miR_326_001061 | 0.000 | 0.351 | FALSE | FALSE | TRUE | TRUE |
| mmu_miR_327_002481 | NA | NA | FALSE | FALSE | FALSE | FALSE |
| mmu_miR_328_000543 | 0.750 | 0.510 | TRUE | TRUE | TRUE | TRUE |
| mmu_miR_329_000192 | 0.951 | 0.264 | TRUE | TRUE | TRUE | TRUE |
| mmu_miR_32_002109 | 0.349 | 0.526 | FALSE | TRUE | TRUE | TRUE |
| mmu_miR_330_001062 | 0.511 | 0.641 | FALSE | FALSE | TRUE | TRUE |
| mmu_miR_330_002230 | 0.264 | 0.381 | TRUE | TRUE | TRUE | TRUE |
| mmu_miR_331_3p_000545 | 0.852 | 0.627 | TRUE | TRUE | TRUE | TRUE |
| mmu_miR_331_5p_002233 | 0.184 | 0.997 | TRUE | TRUE | TRUE | TRUE |

TABLE 4-continued

| Brain Stem miRNA data. | | | | | | |
|---|---|---|---|---|---|---|
| mmu_miR_335_3p_002185 | NA | 0.021 | TRUE | TRUE | FALSE | TRUE |
| mmu_miR_335_5p_000546 | 0.786 | 0.375 | TRUE | TRUE | TRUE | TRUE |
| mmu_miR_337_000193 | 0.919 | 0.434 | TRUE | TRUE | TRUE | TRUE |
| mmu_miR_337_3p_002532 | 0.938 | 0.358 | TRUE | TRUE | TRUE | TRUE |
| mmu_miR_337_5p_002515 | 0.913 | 0.650 | TRUE | TRUE | TRUE | TRUE |
| mmu_miR_338_3p_002252 | 0.936 | 0.152 | TRUE | TRUE | TRUE | TRUE |
| mmu_miR_339_3p_002533 | 0.222 | 0.673 | TRUE | TRUE | TRUE | TRUE |
| mmu_miR_339_5p_002257 | 0.505 | 0.432 | TRUE | TRUE | TRUE | TRUE |
| mmu_miR_340_3p_002259 | 0.740 | 0.542 | TRUE | TRUE | TRUE | TRUE |
| mmu_miR_340_5p_002258 | 0.858 | 0.439 | TRUE | TRUE | TRUE | TRUE |
| mmu_miR_342_3p_002260 | 0.541 | 0.380 | TRUE | TRUE | TRUE | TRUE |
| mmu_miR_342_5p_002527 | NA | 0.088 | TRUE | TRUE | FALSE | TRUE |
| mmu_miR_343_002483 | NA | NA | FALSE | FALSE | FALSE | FALSE |
| mmu_miR_344_001063 | 0.975 | 0.176 | TRUE | TRUE | TRUE | TRUE |
| mmu_miR_345_001137 | 0.770 | 0.687 | TRUE | TRUE | TRUE | TRUE |
| mmu_miR_345_3p_002529 | NA | 0.509 | FALSE | TRUE | FALSE | TRUE |
| mmu_miR_345_5p_002528 | 0.940 | 0.244 | TRUE | TRUE | TRUE | TRUE |
| mmu_miR_346_001064 | NA | 0.439 | FALSE | FALSE | FALSE | TRUE |
| mmu_miR_34a_000426 | 0.829 | 0.233 | TRUE | TRUE | TRUE | TRUE |
| mmu_miR_34b_001065 | 0.546 | 0.908 | TRUE | TRUE | TRUE | TRUE |
| mmu_miR_34b_3p_002618 | 0.901 | 0.715 | TRUE | TRUE | TRUE | TRUE |
| mmu_miR_34b_5p_002617 | NA | 0.933 | TRUE | TRUE | FALSE | TRUE |
| mmu_miR_34c_000428 | 0.999 | 0.610 | TRUE | TRUE | TRUE | TRUE |
| mmu_miR_34c_002584 | 0.850 | 0.816 | TRUE | TRUE | TRUE | TRUE |
| mmu_miR_350_002530 | 0.622 | 0.420 | TRUE | TRUE | TRUE | TRUE |
| mmu_miR_351_001067 | NA | NA | FALSE | FALSE | FALSE | TRUE |
| mmu_miR_361_000554 | 0.810 | 0.454 | TRUE | TRUE | TRUE | TRUE |
| mmu_miR_362_3p_002616 | 0.206 | 0.589 | TRUE | TRUE | TRUE | TRUE |
| mmu_miR_362_5p_002614 | 0.336 | 0.653 | TRUE | TRUE | TRUE | TRUE |
| mmu_miR_363_001271 | NA | 0.641 | FALSE | FALSE | FALSE | TRUE |
| mmu_miR_365_001020 | 0.933 | 0.383 | TRUE | TRUE | TRUE | TRUE |
| mmu_miR_367_000555 | 0.769 | 0.453 | TRUE | TRUE | TRUE | TRUE |
| mmu_miR_369_3p_000557 | 0.814 | 0.297 | TRUE | TRUE | TRUE | TRUE |
| mmu_miR_369_5p_001021 | 0.683 | 0.302 | TRUE | TRUE | TRUE | TRUE |
| mmu_miR_370_001068 | NA | 0.288 | FALSE | FALSE | FALSE | TRUE |
| mmu_miR_370_002275 | 0.993 | 0.041 | TRUE | TRUE | TRUE | TRUE |
| mmu_miR_374_002043 | NA | NA | TRUE | TRUE | FALSE | FALSE |
| mmu_miR_374_5p_001319 | 0.726 | 0.131 | TRUE | TRUE | TRUE | TRUE |
| mmu_miR_375_000564 | 0.932 | 0.639 | TRUE | TRUE | TRUE | TRUE |
| mmu_miR_376a_001069 | 0.862 | 0.281 | TRUE | TRUE | TRUE | TRUE |
| mmu_miR_376a_002482 | 0.706 | 0.317 | TRUE | TRUE | TRUE | TRUE |
| mmu_miR_376b_002451 | 0.865 | 0.305 | TRUE | TRUE | TRUE | TRUE |
| mmu_miR_376b_002452 | 0.976 | 0.193 | TRUE | TRUE | TRUE | TRUE |
| mmu_miR_376c_002450 | 0.866 | 0.423 | TRUE | TRUE | TRUE | TRUE |
| mmu_miR_376c_002523 | NA | NA | FALSE | FALSE | FALSE | FALSE |
| mmu_miR_377_000566 | NA | 0.672 | TRUE | TRUE | FALSE | TRUE |
| mmu_miR_379_001138 | 0.913 | 0.398 | TRUE | TRUE | TRUE | TRUE |
| mmu_miR_380_3p_001071 | NA | 0.427 | TRUE | FALSE | FALSE | TRUE |
| mmu_miR_380_5p_002601 | 0.833 | 0.324 | TRUE | TRUE | TRUE | TRUE |
| mmu_miR_381_000571 | 0.581 | 0.536 | TRUE | TRUE | TRUE | TRUE |
| mmu_miR_382_000572 | 0.998 | 0.051 | TRUE | TRUE | TRUE | TRUE |

TABLE 4-continued

| Brain Stem miRNA data. | | | | | | |
|---|---|---|---|---|---|---|
| mmu_miR_383_001767 | 0.876 | 0.172 | TRUE | TRUE | TRUE | TRUE |
| mmu_miR_384_3p_002603 | 0.811 | 0.322 | TRUE | TRUE | TRUE | TRUE |
| mmu_miR_384_5p_002602 | 0.809 | 0.249 | TRUE | TRUE | TRUE | TRUE |
| mmu_miR_409_3p_002332 | NA | 0.294 | TRUE | FALSE | FALSE | TRUE |
| mmu_miR_409_5p_002331 | NA | 0.132 | TRUE | TRUE | FALSE | TRUE |
| mmu_miR_410_001274 | 0.943 | 0.217 | TRUE | TRUE | TRUE | TRUE |
| mmu_miR_411_001610 | 0.895 | 0.366 | TRUE | TRUE | TRUE | TRUE |
| mmu_miR_412_002575 | 0.952 | 0.189 | TRUE | TRUE | TRUE | TRUE |
| mmu_miR_423_5p_002340 | 0.762 | 0.302 | TRUE | TRUE | TRUE | TRUE |
| mmu_miR_425_001516 | 0.075 | 1.000 | TRUE | TRUE | TRUE | TRUE |
| mmu_miR_429_001077 | 0.351 | NA | FALSE | FALSE | TRUE | TRUE |
| mmu_miR_431_001979 | NA | 0.003 | TRUE | TRUE | FALSE | TRUE |
| mmu_miR_432_241135_mat | NA | NA | FALSE | FALSE | FALSE | TRUE |
| mmu_miR_433_001028 | 0.898 | 0.237 | TRUE | TRUE | TRUE | TRUE |
| mmu_miR_433_5p_001078 | 0.291 | 0.502 | TRUE | FALSE | TRUE | TRUE |
| mmu_miR_434_3p_002604 | 0.750 | 0.246 | TRUE | TRUE | TRUE | TRUE |
| mmu_miR_434_5p_002581 | 0.853 | 0.255 | TRUE | TRUE | TRUE | TRUE |
| mmu_miR_448_001029 | 0.771 | 0.173 | TRUE | TRUE | TRUE | TRUE |
| mmu_miR_449a_001030 | 0.176 | 0.831 | TRUE | TRUE | TRUE | TRUE |
| mmu_miR_449b_001667 | 0.330 | 0.805 | TRUE | TRUE | TRUE | TRUE |
| mmu_miR_449b_002539 | NA | NA | FALSE | FALSE | FALSE | FALSE |
| mmu_miR_450B_3P_002632 | 0.042 | 0.468 | FALSE | TRUE | TRUE | TRUE |
| mmu_miR_450a_3p_002525 | NA | NA | FALSE | FALSE | FALSE | FALSE |
| mmu_miR_450a_5p_002303 | NA | 0.477 | FALSE | TRUE | FALSE | TRUE |
| mmu_miR_450b_5p_001962 | NA | NA | FALSE | FALSE | FALSE | FALSE |
| mmu_miR_451_001141 | 0.049 | NA | FALSE | FALSE | TRUE | FALSE |
| mmu_miR_452_001032 | 0.172 | 0.479 | FALSE | FALSE | TRUE | TRUE |
| mmu_miR_453_002484 | NA | NA | FALSE | FALSE | FALSE | FALSE |
| mmu_miR_455_002455 | 0.646 | 0.256 | FALSE | TRUE | TRUE | TRUE |
| mmu_miR_463_002582 | 0.108 | NA | TRUE | FALSE | TRUE | FALSE |
| mmu_miR_463_002662 | 0.063 | NA | FALSE | FALSE | TRUE | FALSE |
| mmu_miR_464_001081 | NA | NA | FALSE | FALSE | FALSE | FALSE |
| mmu_miR_465C_5P_002654 | 0.126 | NA | TRUE | FALSE | TRUE | FALSE |
| mmu_miR_465a_3p_002040 | NA | 0.376 | TRUE | TRUE | FALSE | TRUE |
| mmu_miR_465a_5p_001082 | NA | NA | FALSE | TRUE | TRUE | FALSE |
| mmu_miR_465b_5p_002485 | NA | 0.433 | FALSE | FALSE | FALSE | TRUE |
| mmu_miR_466E_5P_002718 | 0.009 | 0.948 | TRUE | TRUE | TRUE | TRUE |
| mmu_miR_466J_002817 | NA | 0.793 | TRUE | TRUE | FALSE | TRUE |
| mmu_miR_466a_3p_002586 | NA | 0.482 | TRUE | TRUE | FALSE | TRUE |
| mmu_miR_466b_3_3p_002500 | NA | 0.458 | TRUE | TRUE | FALSE | TRUE |
| mmu_miR_466d_5p_002534 | 0.586 | 0.617 | FALSE | TRUE | TRUE | TRUE |
| mmu_miR_466g_241015_mat | NA | NA | FALSE | FALSE | FALSE | FALSE |
| mmu_miR_466h_002516 | NA | 0.210 | FALSE | TRUE | FALSE | TRUE |
| mmu_miR_466k_240990_mat | 0.055 | 0.871 | TRUE | TRUE | TRUE | TRUE |
| mmu_miR_467F_002886 | 0.118 | NA | FALSE | FALSE | TRUE | FALSE |
| mmu_miR_467H_002809 | NA | 0.472 | FALSE | TRUE | FALSE | TRUE |
| mmu_miR_467a_001826 | 0.873 | 0.791 | TRUE | TRUE | TRUE | TRUE |
| mmu_miR_467a_002587 | 0.993 | 0.503 | TRUE | TRUE | TRUE | TRUE |
| mmu_miR_467b_001671 | NA | 0.329 | TRUE | TRUE | FALSE | TRUE |
| mmu_miR_467b_001684 | 0.165 | 0.988 | TRUE | TRUE | TRUE | TRUE |
| mmu_miR_467c_002517 | NA | 0.937 | TRUE | TRUE | FALSE | TRUE |

TABLE 4-continued

| Brain Stem miRNA data. | | | | | | |
|---|---|---|---|---|---|---|
| mmu_miR_467d_002518 | NA | 0.909 | TRUE | TRUE | FALSE | TRUE |
| mmu_miR_467e_002568 | 0.161 | 0.888 | TRUE | TRUE | TRUE | TRUE |
| mmu_miR_467e_002569 | NA | NA | FALSE | FALSE | FALSE | FALSE |
| mmu_miR_468_001085 | NA | NA | FALSE | FALSE | FALSE | FALSE |
| mmu_miR_469_001086 | NA | NA | FALSE | FALSE | FALSE | FALSE |
| mmu_miR_470_002588 | NA | NA | FALSE | FALSE | FALSE | FALSE |
| mmu_miR_470_002589 | 0.015 | NA | TRUE | TRUE | TRUE | TRUE |
| mmu_miR_471_002605 | NA | NA | FALSE | FALSE | FALSE | FALSE |
| mmu_miR_483_001291 | 0.017 | NA | FALSE | FALSE | TRUE | FALSE |
| mmu_miR_483_002560 | NA | NA | FALSE | FALSE | FALSE | FALSE |
| mmu_miR_484_001821 | 0.527 | 0.536 | TRUE | TRUE | TRUE | TRUE |
| mmu_miR_485_3p_001943 | 0.902 | 0.424 | TRUE | TRUE | TRUE | TRUE |
| mmu_miR_486_001278 | NA | 0.070 | TRUE | TRUE | FALSE | TRUE |
| mmu_miR_487b_001285 | 0.797 | 0.474 | TRUE | TRUE | TRUE | TRUE |
| mmu_miR_487b_001306 | 0.950 | 0.215 | TRUE | TRUE | TRUE | TRUE |
| mmu_miR_488_001659 | NA | 0.441 | TRUE | TRUE | FALSE | TRUE |
| mmu_miR_488_002014 | NA | NA | FALSE | FALSE | FALSE | FALSE |
| mmu_miR_489_001302 | 0.609 | 0.411 | TRUE | TRUE | TRUE | TRUE |
| mmu_miR_490_001037 | 0.344 | 0.026 | TRUE | FALSE | TRUE | TRUE |
| mmu_miR_491_001630 | 0.975 | 0.315 | TRUE | TRUE | TRUE | TRUE |
| mmu_miR_493_002519 | NA | NA | FALSE | FALSE | FALSE | FALSE |
| mmu_miR_494_001293 | NA | 0.440 | FALSE | TRUE | FALSE | TRUE |
| mmu_miR_494_002365 | NA | 0.522 | TRUE | TRUE | FALSE | TRUE |
| mmu_miR_495_001663 | 0.863 | 0.214 | TRUE | TRUE | TRUE | TRUE |
| mmu_miR_496_001953 | NA | 0.034 | TRUE | TRUE | FALSE | TRUE |
| mmu_miR_497_001346 | 0.587 | 0.625 | TRUE | TRUE | TRUE | TRUE |
| mmu_miR_499_001352 | 0.239 | 0.265 | TRUE | TRUE | TRUE | TRUE |
| mmu_miR_500_002606 | 0.276 | 0.422 | TRUE | TRUE | TRUE | TRUE |
| mmu_miR_501_001356 | NA | NA | FALSE | FALSE | FALSE | TRUE |
| mmu_miR_501_3p_001651 | 0.360 | 0.362 | TRUE | TRUE | TRUE | TRUE |
| mmu_miR_503_002456 | NA | 0.316 | FALSE | TRUE | FALSE | TRUE |
| mmu_miR_503_002536 | 0.148 | 0.657 | FALSE | TRUE | TRUE | TRUE |
| mmu_miR_504_002084 | NA | 0.402 | TRUE | TRUE | FALSE | TRUE |
| mmu_miR_505_001655 | NA | NA | FALSE | FALSE | FALSE | FALSE |
| mmu_miR_509_3p_002521 | 0.438 | NA | FALSE | FALSE | TRUE | FALSE |
| mmu_miR_509_5p_002520 | NA | NA | FALSE | FALSE | FALSE | FALSE |
| mmu_miR_511_002549 | 0.235 | NA | FALSE | FALSE | TRUE | FALSE |
| mmu_miR_532_3p_002355 | 0.357 | 0.654 | TRUE | TRUE | TRUE | TRUE |
| mmu_miR_532_5p_001518 | 0.378 | 0.545 | TRUE | TRUE | TRUE | TRUE |
| mmu_miR_539_001286 | 0.865 | 0.332 | TRUE | TRUE | TRUE | TRUE |
| mmu_miR_540_3p_001310 | NA | 0.445 | TRUE | FALSE | FALSE | TRUE |
| mmu_miR_540_5p_002561 | NA | 0.515 | TRUE | TRUE | FALSE | TRUE |
| mmu_miR_541_002562 | 0.825 | 0.094 | TRUE | TRUE | TRUE | TRUE |
| mmu_miR_542_3p_001284 | NA | 0.400 | FALSE | TRUE | FALSE | TRUE |
| mmu_miR_542_5p_002563 | NA | 0.474 | FALSE | FALSE | FALSE | TRUE |
| mmu_miR_543_001298 | 0.893 | 0.257 | TRUE | TRUE | TRUE | TRUE |
| mmu_miR_543_002376 | 0.880 | 0.304 | TRUE | TRUE | TRUE | TRUE |
| mmu_miR_544_002550 | NA | NA | FALSE | FALSE | FALSE | FALSE |
| mmu_miR_546_001312 | NA | 0.008 | FALSE | FALSE | FALSE | TRUE |
| mmu_miR_547_002564 | 0.211 | 0.502 | TRUE | TRUE | TRUE | TRUE |
| mmu_miR_551b_001535 | 0.312 | 0.786 | TRUE | TRUE | TRUE | TRUE |

TABLE 4-continued

| Brain Stem miRNA data. | | | | | | |
|---|---|---|---|---|---|---|
| mmu_miR_574_3p_002349 | 0.253 | 0.524 | TRUE | TRUE | TRUE | TRUE |
| mmu_miR_582_3p_002567 | 0.490 | 0.792 | TRUE | TRUE | TRUE | TRUE |
| mmu_miR_582_5p_002566 | NA | 0.328 | TRUE | TRUE | FALSE | TRUE |
| mmu_miR_590_5p_001984 | NA | 0.192 | FALSE | TRUE | FALSE | TRUE |
| mmu_miR_592_002017 | 0.941 | 0.117 | TRUE | TRUE | TRUE | TRUE |
| mmu_miR_598_002476 | 0.864 | 0.427 | TRUE | TRUE | TRUE | TRUE |
| mmu_miR_599_241117_mat | 0.692 | NA | TRUE | TRUE | TRUE | FALSE |
| mmu_miR_615_3p_001960 | NA | 0.494 | FALSE | FALSE | FALSE | TRUE |
| mmu_miR_615_5p_002353 | NA | NA | FALSE | FALSE | FALSE | FALSE |
| mmu_miR_652_002352 | 0.636 | 0.585 | TRUE | TRUE | TRUE | TRUE |
| mmu_miR_654_3p_002239 | NA | NA | FALSE | FALSE | FALSE | FALSE |
| mmu_miR_654_5p_002522 | NA | NA | FALSE | FALSE | FALSE | FALSE |
| mmu_miR_665_002607 | NA | 0.154 | FALSE | FALSE | FALSE | TRUE |
| mmu_miR_666_3p_002448 | NA | NA | FALSE | FALSE | TRUE | FALSE |
| mmu_miR_666_5p_001952 | NA | 0.342 | TRUE | TRUE | FALSE | TRUE |
| mmu_miR_667_001949 | 0.867 | 0.217 | TRUE | TRUE | TRUE | TRUE |
| mmu_miR_668_001947 | 0.817 | 0.107 | TRUE | TRUE | TRUE | TRUE |
| mmu_miR_669C_002646 | NA | 0.740 | FALSE | TRUE | FALSE | TRUE |
| mmu_miR_669D_002808 | NA | 0.721 | FALSE | TRUE | FALSE | TRUE |
| mmu_miR_669E_002774 | NA | 0.672 | FALSE | TRUE | FALSE | TRUE |
| mmu_miR_669G_002813 | NA | NA | FALSE | FALSE | FALSE | FALSE |
| mmu_miR_669H_5P_002906 | 0.253 | 0.519 | FALSE | FALSE | TRUE | TRUE |
| mmu_miR_669a_001683 | 0.908 | 0.490 | TRUE | TRUE | TRUE | TRUE |
| mmu_miR_669l_121149_mat | NA | 0.775 | TRUE | TRUE | FALSE | TRUE |
| mmu_miR_669m_121190_mat | NA | 0.783 | TRUE | TRUE | FALSE | TRUE |
| mmu_miR_669n_197143_mat | NA | 0.558 | FALSE | TRUE | FALSE | TRUE |
| mmu_miR_669o_121176_mat | NA | 0.944 | TRUE | TRUE | FALSE | TRUE |
| mmu_miR_670_002020 | 0.042 | 0.577 | FALSE | TRUE | TRUE | TRUE |
| mmu_miR_671_3p_002322 | NA | 0.270 | TRUE | TRUE | FALSE | TRUE |
| mmu_miR_672_002327 | NA | 0.014 | TRUE | TRUE | FALSE | TRUE |
| mmu_miR_673_001954 | 0.304 | NA | TRUE | TRUE | TRUE | FALSE |
| mmu_miR_673_3p_002449 | 0.640 | 0.273 | TRUE | TRUE | TRUE | TRUE |
| mmu_miR_674_001956 | 0.615 | 0.632 | TRUE | TRUE | TRUE | TRUE |
| mmu_miR_674_002021 | 0.728 | 0.253 | TRUE | TRUE | TRUE | TRUE |
| mmu_miR_675_3p_001941 | 0.003 | 0.752 | TRUE | TRUE | TRUE | TRUE |
| mmu_miR_675_5p_001940 | NA | NA | FALSE | TRUE | FALSE | TRUE |
| mmu_miR_676_001958 | 0.849 | 0.532 | TRUE | TRUE | TRUE | TRUE |
| mmu_miR_676_001959 | 0.763 | 0.531 | TRUE | TRUE | TRUE | TRUE |
| mmu_miR_677_001660 | NA | NA | FALSE | FALSE | FALSE | FALSE |
| mmu_miR_679_001662 | NA | 0.119 | FALSE | FALSE | FALSE | TRUE |
| mmu_miR_680_001664 | 0.020 | 0.677 | FALSE | FALSE | TRUE | TRUE |
| mmu_miR_682_001666 | NA | NA | FALSE | TRUE | FALSE | FALSE |
| mmu_miR_683_001668 | 0.198 | NA | FALSE | TRUE | TRUE | FALSE |
| mmu_miR_684_001669 | NA | NA | FALSE | FALSE | FALSE | FALSE |
| mmu_miR_685_001670 | 0.099 | NA | TRUE | FALSE | TRUE | FALSE |
| mmu_miR_686_001672 | NA | NA | FALSE | FALSE | TRUE | FALSE |
| mmu_miR_687_001674 | NA | NA | FALSE | FALSE | FALSE | FALSE |
| mmu_miR_688_001675 | NA | NA | TRUE | FALSE | FALSE | FALSE |
| mmu_miR_690_001677 | NA | NA | FALSE | FALSE | TRUE | FALSE |
| mmu_miR_691_001678 | 0.287 | NA | TRUE | FALSE | TRUE | TRUE |
| mmu_miR_692_001679 | NA | NA | FALSE | FALSE | TRUE | FALSE |

TABLE 4-continued

| Brain Stem miRNA data. | | | | | | |
|---|---|---|---|---|---|---|
| mmu_miR_693_001680 | 0.425 | NA | FALSE | TRUE | TRUE | FALSE |
| mmu_miR_693_3p_002036 | NA | NA | FALSE | FALSE | FALSE | FALSE |
| mmu_miR_694_001681 | 0.095 | NA | TRUE | TRUE | TRUE | TRUE |
| mmu_miR_695_001627 | NA | NA | TRUE | FALSE | FALSE | FALSE |
| mmu_miR_696_001628 | 0.017 | NA | TRUE | FALSE | TRUE | TRUE |
| mmu_miR_697_001631 | NA | NA | TRUE | FALSE | TRUE | TRUE |
| mmu_miR_698_001632 | NA | NA | FALSE | FALSE | TRUE | FALSE |
| mmu_miR_700_001634 | 0.933 | 0.389 | TRUE | TRUE | TRUE | TRUE |
| mmu_miR_701_001635 | 0.157 | 0.962 | TRUE | TRUE | TRUE | TRUE |
| mmu_miR_702_001636 | 0.418 | 0.448 | TRUE | TRUE | TRUE | TRUE |
| mmu_miR_704_001639 | NA | NA | FALSE | TRUE | FALSE | TRUE |
| mmu_miR_706_001641 | 0.537 | NA | TRUE | TRUE | TRUE | TRUE |
| mmu_miR_707_001642 | NA | NA | FALSE | FALSE | FALSE | FALSE |
| mmu_miR_708_002341 | 0.951 | 0.363 | TRUE | TRUE | TRUE | TRUE |
| mmu_miR_710_001645 | NA | NA | TRUE | FALSE | FALSE | FALSE |
| mmu_miR_711_001646 | NA | NA | TRUE | FALSE | TRUE | FALSE |
| mmu_miR_712_001961 | NA | NA | FALSE | FALSE | FALSE | FALSE |
| mmu_miR_712_002636 | NA | 0.971 | TRUE | TRUE | FALSE | TRUE |
| mmu_miR_713_001648 | NA | NA | TRUE | FALSE | FALSE | FALSE |
| mmu_miR_715_001649 | NA | NA | FALSE | FALSE | FALSE | FALSE |
| mmu_miR_717_001652 | 0.013 | NA | TRUE | FALSE | TRUE | FALSE |
| mmu_miR_718_001656 | NA | NA | TRUE | FALSE | FALSE | FALSE |
| mmu_miR_719_001673 | NA | NA | FALSE | FALSE | TRUE | FALSE |
| mmu_miR_720_001629 | 0.128 | NA | FALSE | FALSE | TRUE | FALSE |
| mmu_miR_721_001657 | 0.769 | 0.996 | TRUE | TRUE | TRUE | TRUE |
| mmu_miR_741_002457 | NA | 0.141 | FALSE | FALSE | FALSE | TRUE |
| mmu_miR_742_002038 | NA | NA | FALSE | FALSE | FALSE | FALSE |
| mmu_miR_742_002458 | NA | NA | TRUE | FALSE | FALSE | TRUE |
| mmu_miR_743a_002469 | 0.177 | 0.947 | TRUE | TRUE | TRUE | TRUE |
| mmu_miR_743b_3p_002471 | NA | NA | FALSE | FALSE | FALSE | FALSE |
| mmu_miR_743b_5p_002470 | NA | NA | FALSE | FALSE | FALSE | FALSE |
| mmu_miR_744_002324 | 0.751 | 0.544 | TRUE | TRUE | TRUE | TRUE |
| mmu_miR_758_002025 | NA | 0.566 | FALSE | FALSE | FALSE | TRUE |
| mmu_miR_759_002034 | 0.649 | NA | TRUE | TRUE | TRUE | FALSE |
| mmu_miR_761_002030 | 0.001 | NA | FALSE | TRUE | TRUE | TRUE |
| mmu_miR_762_002028 | NA | NA | FALSE | FALSE | FALSE | FALSE |
| mmu_miR_763_002033 | NA | NA | FALSE | FALSE | FALSE | FALSE |
| mmu_miR_764_3p_002032 | NA | 0.392 | FALSE | FALSE | FALSE | TRUE |
| mmu_miR_764_5p_002031 | 0.232 | 0.650 | TRUE | FALSE | TRUE | TRUE |
| mmu_miR_767_241081_mat | NA | NA | FALSE | FALSE | FALSE | FALSE |
| mmu_miR_770_3p_002027 | NA | 0.165 | TRUE | TRUE | FALSE | TRUE |
| mmu_miR_770_5p_002608 | NA | 0.444 | TRUE | FALSE | FALSE | TRUE |
| mmu_miR_7a_000268 | NA | 0.833 | TRUE | TRUE | FALSE | TRUE |
| mmu_miR_7b_002555 | NA | 0.424 | TRUE | FALSE | FALSE | TRUE |
| mmu_miR_802_002029 | NA | 0.354 | FALSE | TRUE | FALSE | TRUE |
| mmu_miR_804_002044 | 0.559 | 0.997 | TRUE | TRUE | TRUE | TRUE |
| mmu_miR_805_002045 | 0.099 | NA | TRUE | FALSE | TRUE | FALSE |
| mmu_miR_871_002354 | NA | NA | FALSE | FALSE | FALSE | FALSE |
| mmu_miR_872_002264 | 0.875 | 0.512 | TRUE | TRUE | TRUE | TRUE |
| mmu_miR_872_002542 | 0.909 | 0.442 | TRUE | TRUE | TRUE | TRUE |
| mmu_miR_873_002356 | NA | 0.371 | TRUE | TRUE | FALSE | TRUE |

TABLE 4-continued

Brain Stem miRNA data.

| | | | | | | |
|---|---|---|---|---|---|---|
| mmu_miR_874_002268 | NA | NA | FALSE | FALSE | FALSE | FALSE |
| mmu_miR_875_3p_002547 | 0.211 | NA | FALSE | TRUE | TRUE | FALSE |
| mmu_miR_876_3p_002464 | NA | NA | FALSE | FALSE | FALSE | FALSE |
| mmu_miR_876_5p_002463 | NA | NA | FALSE | FALSE | FALSE | FALSE |
| mmu_miR_877_002548 | 0.069 | 0.818 | TRUE | TRUE | TRUE | TRUE |
| mmu_miR_878_3p_002541 | NA | NA | FALSE | FALSE | FALSE | FALSE |
| mmu_miR_878_5p_002540 | NA | NA | FALSE | FALSE | FALSE | TRUE |
| mmu_miR_879_002472 | NA | 0.438 | FALSE | TRUE | FALSE | TRUE |
| mmu_miR_879_002473 | NA | 0.164 | TRUE | TRUE | FALSE | TRUE |
| mmu_miR_880_002665 | 0.113 | NA | FALSE | FALSE | TRUE | FALSE |
| mmu_miR_881_002475 | NA | NA | FALSE | FALSE | FALSE | FALSE |
| mmu_miR_881_002609 | NA | NA | TRUE | FALSE | FALSE | TRUE |
| mmu_miR_882_002610 | NA | NA | FALSE | FALSE | FALSE | FALSE |
| mmu_miR_883B_5P_002669 | NA | NA | TRUE | FALSE | FALSE | TRUE |
| mmu_miR_883a_3p_002461 | NA | NA | FALSE | FALSE | FALSE | FALSE |
| mmu_miR_883a_5p_002611 | NA | NA | FALSE | FALSE | FALSE | FALSE |
| mmu_miR_883b_3p_002565 | NA | NA | FALSE | FALSE | FALSE | FALSE |
| mmu_miR_92a_000430 | 0.220 | 0.912 | TRUE | TRUE | TRUE | TRUE |
| mmu_miR_92a_002496 | NA | NA | FALSE | FALSE | FALSE | FALSE |
| mmu_miR_93_001090 | 0.686 | 0.511 | TRUE | TRUE | TRUE | TRUE |
| mmu_miR_96_000186 | NA | 0.586 | TRUE | TRUE | FALSE | TRUE |
| mmu_miR_98_000577 | 0.947 | 0.082 | TRUE | TRUE | TRUE | TRUE |
| mmu_miR_99a_000435 | 0.753 | 0.508 | TRUE | TRUE | TRUE | TRUE |
| mmu_miR_99b_000436 | 0.883 | 0.624 | TRUE | TRUE | TRUE | TRUE |
| mmu_miR_9_000583 | 0.734 | 0.533 | TRUE | TRUE | TRUE | TRUE |

| | log2FC_ChATvsGFAP_bs | adj.p.value_ChATvsGFAP_bs | log2FC_ChATvsLyz2_bs | adj.p.value_ChATvsLyz2_bs | log2FC_ChATvsSyn_bs | adj.p.value_ChATvsSyn_bs |
|---|---|---|---|---|---|---|
| hsa_let_7b_002404 | 0.134 | 0.980 | 1.877 | 0.730 | 3.740 | 0.410 |
| hsa_let_7e_002407 | 0.641 | 0.670 | −0.354 | 0.911 | 0.538 | 0.782 |
| hsa_let_7f_1_002417 | −3.516 | 0.135 | 0.230 | 0.996 | −0.498 | 0.907 |
| hsa_let_7i_002172 | −3.519 | 0.001 | −1.352 | 0.236 | −0.322 | 0.858 |
| hsa_miR_106b_002380 | −3.233 | 0.009 | 0.102 | 0.996 | −4.424 | 0.001 |
| hsa_miR_10a_002288 | 0.796 | 0.770 | 0.765 | 0.858 | 1.640 | 0.558 |
| hsa_miR_1197_002810 | 4.126 | 0.011 | 2.303 | 0.207 | 1.380 | 0.528 |
| hsa_miR_124_002197 | 2.149 | 0.297 | 1.658 | 0.504 | 2.327 | 0.343 |
| hsa_miR_127_5p_002229 | 0.882 | 0.447 | −0.545 | 0.739 | −0.408 | 0.813 |
| hsa_miR_136_000592 | 3.378 | 0.000 | −1.021 | 0.307 | 0.305 | 0.834 |
| hsa_miR_136_002100 | 2.629 | 0.179 | 2.671 | 0.203 | 0.361 | 0.924 |
| hsa_miR_140_3p_002234 | −1.540 | 0.047 | −0.721 | 0.452 | −1.437 | 0.103 |
| hsa_miR_143_000466 | −0.504 | 0.925 | −0.985 | 0.905 | 2.048 | 0.672 |
| hsa_miR_144_002676 | 0.152 | 0.883 | 0.515 | 0.577 | 1.849 | 0.016 |
| hsa_miR_148a_002134 | 0.062 | 0.984 | 0.306 | 0.982 | −0.681 | 0.858 |
| hsa_miR_149_002255 | 1.998 | 0.002 | 1.753 | 0.006 | −0.269 | 0.792 |
| hsa_miR_151_5P_002642 | −4.985 | 0.000 | −3.436 | 0.002 | −4.303 | 0.000 |
| hsa_miR_154_000478 | 1.404 | 0.233 | 0.861 | 0.552 | −0.054 | 0.983 |
| hsa_miR_15b_002173 | 1.231 | 0.816 | −7.453 | 0.076 | 3.153 | 0.558 |
| hsa_miR_183_002270 | 6.642 | 0.002 | −0.580 | 0.917 | 0.871 | 0.801 |
| hsa_miR_189_000488 | −0.264 | 0.961 | −3.932 | 0.369 | 3.020 | 0.544 |
| hsa_miR_190b_002263 | −0.261 | 0.906 | 0.089 | 0.996 | 2.434 | 0.136 |
| hsa_miR_196a_241070_mat | 4.892 | 0.000 | 0.935 | 0.518 | −2.251 | 0.078 |

TABLE 4-continued

| Brain Stem miRNA data. | | | | | | |
|---|---|---|---|---|---|---|
| hsa_miR_200a_001011 | −2.540 | 0.089 | 0.250 | 0.967 | 0.202 | 0.944 |
| hsa_miR_200b_001800 | 5.661 | 0.040 | −1.138 | 0.830 | 5.689 | 0.066 |
| hsa_miR_200b_002274 | 3.366 | 0.478 | 4.446 | 0.378 | 4.573 | 0.395 |
| hsa_miR_200c_000505 | −1.721 | 0.304 | −6.687 | 0.000 | −0.535 | 0.846 |
| hsa_miR_200c_002286 | 0.568 | 0.751 | 1.179 | 0.477 | 0.937 | 0.617 |
| hsa_miR_206_000510 | −0.952 | 0.677 | −1.036 | 0.710 | −1.381 | 0.581 |
| hsa_miR_213_000516 | −2.900 | 0.006 | −1.988 | 0.074 | −1.986 | 0.093 |
| hsa_miR_214_000517 | 2.943 | 0.034 | −3.108 | 0.031 | 3.086 | 0.045 |
| hsa_miR_214_002293 | −0.578 | 0.739 | 0.267 | 0.956 | 2.087 | 0.158 |
| hsa_miR_218_2_002294 | 5.133 | 0.000 | 4.114 | 0.001 | 3.673 | 0.005 |
| hsa_miR_223_000526 | 1.305 | 0.727 | −12.248 | 0.000 | 7.317 | 0.017 |
| hsa_miR_22_000398 | −3.402 | 0.118 | 2.931 | 0.222 | −2.470 | 0.357 |
| hsa_miR_22_002301 | 0.205 | 0.869 | −0.196 | 0.949 | 0.779 | 0.491 |
| hsa_miR_23a_002439 | 0.498 | 0.931 | −10.183 | 0.011 | 3.159 | 0.545 |
| hsa_miR_26b_002444 | −1.548 | 0.571 | −2.336 | 0.414 | 0.296 | 0.951 |
| hsa_miR_27a_002445 | 1.358 | 0.571 | 1.242 | 0.682 | 3.305 | 0.154 |
| hsa_miR_27b_002174 | −0.939 | 0.293 | −0.797 | 0.443 | −0.057 | 0.976 |
| hsa_miR_28_3p_002446 | 0.604 | 0.813 | 0.223 | 0.995 | 0.653 | 0.841 |
| hsa_miR_299_5p_000600 | 7.871 | 0.003 | 2.336 | 0.458 | 6.276 | 0.024 |
| hsa_miR_29a_002447 | 1.189 | 0.659 | −2.001 | 0.453 | 0.783 | 0.830 |
| hsa_miR_29b_2_002166 | 3.504 | 0.193 | 2.386 | 0.448 | 3.947 | 0.181 |
| hsa_miR_30a_3p_000416 | −0.313 | 0.539 | −0.288 | 0.637 | 0.133 | 0.866 |
| hsa_miR_30c_1_002108 | −2.117 | 0.571 | 1.133 | 0.869 | 0.583 | 0.930 |
| hsa_miR_30c_2_002110 | 10.427 | 0.008 | 9.553 | 0.020 | 6.481 | 0.151 |
| hsa_miR_30d_002305 | −2.285 | 0.473 | −1.582 | 0.712 | −0.421 | 0.941 |
| hsa_miR_30e_3p_000422 | 0.183 | 0.766 | −1.308 | 0.006 | 0.486 | 0.408 |
| hsa_miR_324_3p_000579 | −2.827 | 0.195 | −2.918 | 0.211 | −2.712 | 0.279 |
| hsa_miR_338_000548 | −4.662 | 0.011 | −1.977 | 0.362 | −3.728 | 0.068 |
| hsa_miR_338_5P_002658 | −1.478 | 0.103 | 0.203 | 0.950 | −0.796 | 0.506 |
| hsa_miR_33a_002136 | −5.196 | 0.001 | −4.565 | 0.004 | −5.767 | 0.001 |
| hsa_miR_340_000550 | −0.057 | 0.963 | 0.733 | 0.479 | 0.141 | 0.932 |
| hsa_miR_363_001283 | −6.896 | 0.016 | −2.291 | 0.537 | −2.359 | 0.545 |
| hsa_miR_376a_001287 | 4.627 | 0.000 | 1.522 | 0.243 | 1.273 | 0.387 |
| hsa_miR_378_000567 | 1.558 | 0.421 | −1.968 | 0.338 | 3.679 | 0.061 |
| hsa_miR_411_002238 | 4.313 | 0.002 | 5.170 | 0.000 | 0.652 | 0.764 |
| hsa_miR_412_001023 | 4.539 | 0.009 | −5.829 | 0.001 | 0.574 | 0.848 |
| hsa_miR_421_002700 | 0.745 | 0.224 | 1.799 | 0.003 | 0.805 | 0.243 |
| hsa_miR_423_3P_002626 | −1.638 | 0.224 | −2.411 | 0.076 | −1.348 | 0.415 |
| hsa_miR_425_001104 | −1.341 | 0.550 | −5.675 | 0.004 | −3.025 | 0.169 |
| hsa_miR_431_002312 | 4.994 | 0.003 | 0.176 | 0.996 | 1.871 | 0.364 |
| hsa_miR_455_001280 | −4.316 | 0.007 | −5.324 | 0.001 | −3.030 | 0.089 |
| hsa_miR_485_5p_001036 | 0.820 | 0.586 | −1.207 | 0.448 | −0.077 | 0.979 |
| hsa_miR_493_3p_001282 | 5.980 | 0.207 | 2.014 | 0.800 | 6.580 | 0.211 |
| hsa_miR_590_3P_002677 | −0.772 | 0.221 | −0.424 | 0.594 | −0.911 | 0.185 |
| hsa_miR_653_002292 | 3.070 | 0.350 | −0.415 | 0.985 | 1.582 | 0.757 |
| hsa_miR_671_5p_197646_mat | 2.890 | 0.518 | 0.177 | 0.996 | 8.544 | 0.046 |
| hsa_miR_708_002342 | −0.236 | 0.938 | −3.628 | 0.109 | −0.564 | 0.886 |
| hsa_miR_744_002325 | 2.226 | 0.022 | −0.760 | 0.546 | 1.231 | 0.301 |
| hsa_miR_875_5p_002203 | 2.443 | 0.770 | −5.235 | 0.518 | 8.021 | 0.303 |
| hsa_miR_935_002178 | −0.434 | 0.875 | −0.276 | 0.981 | 0.088 | 0.983 |
| hsa_miR_93_002139 | −1.984 | 0.040 | −1.331 | 0.222 | −1.307 | 0.260 |

TABLE 4-continued

| Brain Stem miRNA data. | | | | | | |
|---|---|---|---|---|---|---|
| hsa_miR_99b_002196 | −2.889 | 0.042 | −0.798 | 0.710 | −1.351 | 0.472 |
| hsa_miR_9_002231 | −3.583 | 0.000 | −1.576 | 0.001 | −1.261 | 0.007 |
| mmu_let_7a_000377 | −2.915 | 0.046 | 1.303 | 0.477 | −2.293 | 0.175 |
| mmu_let_7a_002478 | −2.568 | 0.696 | −1.580 | 0.904 | −0.130 | 0.992 |
| mmu_let_7b_000378 | −1.751 | 0.000 | −0.499 | 0.307 | 0.163 | 0.816 |
| mmu_let_7c_000379 | −1.758 | 0.000 | −0.477 | 0.321 | −0.508 | 0.325 |
| mmu_let_7c_1_002479 | −1.257 | 0.754 | −1.369 | 0.789 | 0.836 | 0.880 |
| mmu_let_7d_001178 | −2.594 | 0.003 | −1.658 | 0.063 | −2.918 | 0.002 |
| mmu_let_7d_002283 | −0.795 | 0.156 | −0.051 | 0.996 | −0.073 | 0.946 |
| mmu_let_7e_002406 | −0.001 | 0.999 | −0.329 | 0.869 | 0.016 | 0.993 |
| mmu_let_7f_000382 | −5.103 | 0.077 | −1.713 | 0.694 | −3.931 | 0.249 |
| mmu_let_7g_002282 | 0.061 | 0.953 | 1.393 | 0.063 | 0.675 | 0.472 |
| mmu_let_7g_002492 | 1.942 | 0.221 | −0.542 | 0.868 | 2.155 | 0.219 |
| mmu_let_7i_002221 | −1.555 | 0.003 | 0.134 | 0.934 | 0.002 | 0.998 |
| mmu_miR_100_000437 | −2.745 | 0.000 | −0.358 | 0.722 | −1.122 | 0.137 |
| mmu_miR_101a_002253 | −0.491 | 0.349 | −0.552 | 0.333 | −0.379 | 0.575 |
| mmu_miR_101a_002507 | −1.365 | 0.079 | 0.338 | 0.803 | −1.168 | 0.190 |
| mmu_miR_101b_002531 | −0.082 | 0.931 | 1.036 | 0.107 | 0.211 | 0.833 |
| mmu_miR_103_000439 | 0.921 | 0.266 | 0.394 | 0.760 | 0.280 | 0.832 |
| mmu_miR_105_002465 | 0.811 | 0.925 | −6.741 | 0.243 | −1.367 | 0.886 |
| mmu_miR_106a_002459 | −5.175 | 0.022 | −5.425 | 0.021 | −4.665 | 0.066 |
| mmu_miR_106b_000442 | −1.965 | 0.004 | −1.017 | 0.173 | −1.080 | 0.162 |
| mmu_miR_107_000443 | 0.593 | 0.770 | 1.935 | 0.267 | 0.445 | 0.869 |
| mmu_miR_10a_000387 | 2.394 | 0.055 | 0.768 | 0.678 | 0.582 | 0.772 |
| mmu_miR_10b_001181 | 3.680 | 0.004 | 2.743 | 0.039 | −0.816 | 0.672 |
| mmu_miR_10b_002218 | 8.872 | 0.000 | 4.828 | 0.004 | −4.054 | 0.020 |
| mmu_miR_10b_002572 | 2.734 | 0.237 | −0.112 | 0.996 | 1.055 | 0.764 |
| mmu_miR_1186_002825 | 2.749 | 0.421 | 2.562 | 0.516 | 5.263 | 0.136 |
| mmu_miR_1188_002866 | 0.498 | 0.898 | 3.283 | 0.267 | 3.460 | 0.265 |
| mmu_miR_1191_002892 | 1.171 | 0.805 | −0.152 | 0.996 | 4.871 | 0.253 |
| mmu_miR_1192_002806 | −0.119 | 0.959 | 0.286 | 0.961 | −1.615 | 0.428 |
| mmu_miR_1193_002794 | 3.492 | 0.000 | 2.945 | 0.000 | 3.523 | 0.000 |
| mmu_miR_1194_002793 | 0.124 | 0.931 | 0.381 | 0.849 | −1.580 | 0.154 |
| mmu_miR_1195_002839 | 4.326 | 0.129 | 4.007 | 0.198 | 5.952 | 0.055 |
| mmu_miR_1198_002780 | −1.332 | 0.102 | 3.064 | 0.000 | −2.112 | 0.016 |
| mmu_miR_1199_240984_mat | −0.372 | 0.224 | −0.003 | 0.996 | −1.160 | 0.000 |
| mmu_miR_1224_240985_mat | −0.269 | 0.720 | 0.047 | 0.996 | −1.355 | 0.028 |
| mmu_miR_122_002245 | 1.410 | 0.798 | −4.121 | 0.408 | 1.982 | 0.763 |
| mmu_miR_124_001182 | 0.249 | 0.858 | 0.940 | 0.435 | −0.231 | 0.903 |
| mmu_miR_125a_3p_002199 | −0.486 | 0.786 | −0.614 | 0.798 | −0.165 | 0.953 |
| mmu_miR_125a_5p_002198 | 0.303 | 0.577 | 1.237 | 0.011 | 0.083 | 0.932 |
| mmu_miR_125b_002508 | 0.106 | 0.936 | 1.453 | 0.144 | 1.033 | 0.365 |
| mmu_miR_125b_3p_002378 | −0.845 | 0.404 | −1.164 | 0.267 | 0.902 | 0.455 |
| mmu_miR_125b_5p_000449 | −0.413 | 0.434 | 0.458 | 0.434 | 0.042 | 0.967 |
| mmu_miR_126_3p_002228 | 2.902 | 0.000 | −1.020 | 0.038 | 1.419 | 0.006 |
| mmu_miR_126_5p_000451 | 3.198 | 0.000 | −0.615 | 0.316 | 1.565 | 0.007 |
| mmu_miR_1274a_121150_mat | 0.502 | 0.881 | −7.287 | 0.002 | 1.461 | 0.672 |
| mmu_miR_127_000452 | 3.061 | 0.000 | 1.931 | 0.000 | 0.070 | 0.933 |
| mmu_miR_128a_002216 | −0.215 | 0.768 | −0.313 | 0.710 | −0.570 | 0.422 |
| mmu_miR_129_3p_001184 | 2.100 | 0.000 | 1.160 | 0.050 | −0.123 | 0.907 |
| mmu_miR_129_5p_000590 | 1.194 | 0.312 | 3.012 | 0.009 | 0.160 | 0.942 |

TABLE 4-continued

| Brain Stem miRNA data. | | | | | | |
|---|---|---|---|---|---|---|
| mmu_miR_1306_121155_mat | 0.151 | 0.938 | −0.294 | 0.956 | −0.740 | 0.744 |
| mmu_miR_130a_000454 | −6.115 | 0.000 | −0.138 | 0.996 | −3.947 | 0.016 |
| mmu_miR_130b_000456 | −2.850 | 0.002 | −3.366 | 0.000 | −0.758 | 0.527 |
| mmu_miR_130b_002460 | 3.232 | 0.062 | 1.192 | 0.615 | −0.208 | 0.953 |
| mmu_miR_132_000457 | 1.861 | 0.000 | 1.361 | 0.003 | −0.332 | 0.577 |
| mmu_miR_133a_001637 | 0.106 | 0.964 | 0.231 | 0.983 | −0.411 | 0.896 |
| mmu_miR_133a_002246 | 7.652 | 0.000 | 4.131 | 0.000 | 1.002 | 0.062 |
| mmu_miR_133b_002247 | 3.992 | 0.001 | 2.721 | 0.032 | 1.078 | 0.513 |
| mmu_miR_134_001186 | 3.961 | 0.000 | 3.851 | 0.000 | −0.506 | 0.701 |
| mmu_miR_135a_000460 | −0.576 | 0.311 | 0.651 | 0.289 | −1.072 | 0.076 |
| mmu_miR_135b_002261 | 0.443 | 0.739 | 2.467 | 0.016 | −0.290 | 0.869 |
| mmu_miR_136_002511 | 0.538 | 0.825 | 3.223 | 0.100 | −1.697 | 0.486 |
| mmu_miR_136_002512 | 5.426 | 0.014 | −1.258 | 0.710 | 5.303 | 0.028 |
| mmu_miR_137_001129 | 3.197 | 0.032 | 3.135 | 0.044 | 1.769 | 0.345 |
| mmu_miR_138_002284 | 3.822 | 0.000 | 3.600 | 0.000 | 0.966 | 0.144 |
| mmu_miR_138_002554 | 3.662 | 0.001 | 1.490 | 0.208 | 0.795 | 0.581 |
| mmu_miR_139_3p_002546 | 2.645 | 0.429 | −2.164 | 0.592 | −3.508 | 0.356 |
| mmu_miR_139_5p_002289 | 1.561 | 0.044 | −0.416 | 0.730 | 0.114 | 0.942 |
| mmu_miR_140_001187 | −0.310 | 0.758 | −0.352 | 0.786 | −0.066 | 0.967 |
| mmu_miR_141_000463 | 0.129 | 0.980 | −4.818 | 0.214 | 3.765 | 0.394 |
| mmu_miR_141_002513 | 4.718 | 0.152 | −3.772 | 0.303 | 6.974 | 0.048 |
| mmu_miR_142_3p_000464 | −1.100 | 0.613 | −10.290 | 0.000 | 2.841 | 0.179 |
| mmu_miR_142_5p_002248 | 0.751 | 0.889 | −6.751 | 0.076 | 6.880 | 0.089 |
| mmu_miR_143_002249 | 0.390 | 0.803 | −2.646 | 0.030 | 2.690 | 0.036 |
| mmu_miR_145_002278 | −0.353 | 0.840 | −3.792 | 0.004 | 1.842 | 0.210 |
| mmu_miR_145_002514 | 1.590 | 0.571 | 2.107 | 0.477 | 1.706 | 0.610 |
| mmu_miR_146a_000468 | 1.987 | 0.000 | −3.204 | 0.000 | 3.071 | 0.000 |
| mmu_miR_146b_001097 | −0.479 | 0.319 | −0.856 | 0.074 | −0.213 | 0.769 |
| mmu_miR_146b_002453 | −0.378 | 0.931 | −0.351 | 0.986 | 1.257 | 0.779 |
| mmu_miR_147_002262 | −2.217 | 0.524 | −2.429 | 0.531 | 2.800 | 0.486 |
| mmu_miR_148a_000470 | −1.732 | 0.169 | 4.039 | 0.001 | −0.272 | 0.906 |
| mmu_miR_148b_000471 | −2.242 | 0.022 | 3.307 | 0.001 | −0.860 | 0.515 |
| mmu_miR_150_000473 | 2.416 | 0.007 | −2.042 | 0.028 | 4.776 | 0.000 |
| mmu_miR_150_002570 | 3.493 | 0.205 | 0.741 | 0.916 | 3.491 | 0.265 |
| mmu_miR_151_3p_001190 | −6.402 | 0.000 | 0.223 | 0.926 | −4.723 | 0.000 |
| mmu_miR_152_000475 | −3.970 | 0.000 | −3.286 | 0.000 | 1.013 | 0.215 |
| mmu_miR_153_001191 | 0.654 | 0.687 | −0.260 | 0.956 | 0.297 | 0.903 |
| mmu_miR_154_000477 | 3.716 | 0.004 | 0.571 | 0.803 | −1.860 | 0.220 |
| mmu_miR_155_002571 | −2.424 | 0.008 | −3.969 | 0.000 | 4.448 | 0.000 |
| mmu_miR_15a_000389 | −4.698 | 0.000 | −3.961 | 0.002 | −2.170 | 0.120 |
| mmu_miR_15a_002488 | −0.803 | 0.347 | 0.022 | 0.996 | 0.633 | 0.558 |
| mmu_miR_15b_000390 | −2.732 | 0.000 | −2.828 | 0.000 | −1.180 | 0.020 |
| mmu_miR_16_000391 | −2.347 | 0.000 | −3.224 | 0.000 | −1.808 | 0.000 |
| mmu_miR_16_002489 | −5.569 | 0.000 | −8.574 | 0.000 | −1.863 | 0.185 |
| mmu_miR_17_002308 | −3.924 | 0.000 | −4.668 | 0.000 | −3.467 | 0.000 |
| mmu_miR_17_002543 | 6.842 | 0.043 | −3.158 | 0.448 | 3.420 | 0.436 |
| mmu_miR_181A_2_002687 | −0.438 | 0.798 | 0.075 | 0.996 | −0.994 | 0.577 |
| mmu_miR_181a_000480 | −3.329 | 0.000 | −0.872 | 0.169 | −2.383 | 0.000 |
| mmu_miR_181c_000482 | −1.654 | 0.020 | −0.979 | 0.223 | −1.240 | 0.130 |
| mmu_miR_182_002599 | 3.846 | 0.107 | 0.434 | 0.961 | 0.865 | 0.828 |
| mmu_miR_1839_3p_121203_mat | −0.365 | 0.770 | 0.693 | 0.576 | 0.385 | 0.805 |

TABLE 4-continued

| Brain Stem miRNA data. | | | | | | |
|---|---|---|---|---|---|---|
| mmu_miR_1839_5p_121135_mat | −0.205 | 0.931 | 3.908 | 0.017 | 0.252 | 0.934 |
| mmu_miR_183_002269 | 4.997 | 0.004 | 1.181 | 0.622 | 1.318 | 0.581 |
| mmu_miR_184_000485 | 4.315 | 0.033 | −3.489 | 0.110 | 1.426 | 0.618 |
| mmu_miR_185_002271 | 0.201 | 0.898 | 5.971 | 0.000 | −0.311 | 0.866 |
| mmu_miR_186_002285 | −1.973 | 0.061 | −1.216 | 0.318 | −0.463 | 0.789 |
| mmu_miR_186_002574 | 2.168 | 0.070 | −2.340 | 0.062 | 1.616 | 0.254 |
| mmu_miR_187_001193 | −7.593 | 0.000 | −1.878 | 0.039 | −5.659 | 0.000 |
| mmu_miR_188_3p_002106 | −0.180 | 0.894 | 0.419 | 0.788 | 0.202 | 0.906 |
| mmu_miR_188_5p_002320 | 0.663 | 0.754 | −3.285 | 0.045 | 2.172 | 0.244 |
| mmu_miR_1893_121170_mat | 1.297 | 0.655 | −2.403 | 0.388 | 0.771 | 0.849 |
| mmu_miR_1894_3p_241002_mat | 2.905 | 0.398 | −1.833 | 0.703 | 5.531 | 0.122 |
| mmu_miR_1894_5p_121144_mat | −1.917 | 0.185 | 0.435 | 0.901 | 1.341 | 0.457 |
| mmu_miR_1896_121128_mat | 2.365 | 0.589 | −3.588 | 0.435 | 8.147 | 0.051 |
| mmu_miR_1897_3p_121126_mat | −0.368 | 0.280 | 0.021 | 0.996 | −1.093 | 0.002 |
| mmu_miR_1897_5p_121199_mat | 3.092 | 0.145 | 0.271 | 0.986 | 4.853 | 0.031 |
| mmu_miR_1898_121195_mat | −0.624 | 0.077 | −0.002 | 0.997 | −1.132 | 0.003 |
| mmu_miR_1899_121198_mat | −0.346 | 0.756 | 0.235 | 0.916 | −0.493 | 0.707 |
| mmu_miR_18a_002422 | −4.165 | 0.001 | −6.068 | 0.000 | −3.367 | 0.014 |
| mmu_miR_18a_002490 | −1.723 | 0.293 | −4.454 | 0.006 | −0.168 | 0.957 |
| mmu_miR_18b_002466 | −1.908 | 0.518 | −0.327 | 0.986 | −0.697 | 0.885 |
| mmu_miR_1900_121143_mat | −0.366 | 0.724 | 0.141 | 0.961 | −0.756 | 0.457 |
| mmu_miR_1901_121183_mat | 1.469 | 0.737 | 5.081 | 0.154 | 3.194 | 0.452 |
| mmu_miR_1902_121197_mat | −0.369 | 0.349 | 0.064 | 0.963 | −0.986 | 0.014 |
| mmu_miR_1903_121153_mat | −3.568 | 0.430 | −5.116 | 0.275 | −0.246 | 0.979 |
| mmu_miR_1904_121162_mat | 3.692 | 0.000 | −0.950 | 0.227 | 5.508 | 0.000 |
| mmu_miR_1905_121196_mat | 2.626 | 0.472 | −0.689 | 0.956 | 5.843 | 0.117 |
| mmu_miR_1906_121169_mat | −2.045 | 0.275 | 0.084 | 0.996 | −2.083 | 0.352 |
| mmu_miR_190_000489 | −1.380 | 0.248 | −0.791 | 0.612 | −0.574 | 0.762 |
| mmu_miR_191_002299 | −0.443 | 0.259 | −0.657 | 0.101 | −0.402 | 0.398 |
| mmu_miR_191_002576 | −0.818 | 0.416 | −1.036 | 0.330 | 0.587 | 0.672 |
| mmu_miR_1927_121193_mat | −3.242 | 0.103 | 0.075 | 0.996 | −0.656 | 0.847 |
| mmu_miR_1928_121164_mat | 4.757 | 0.039 | 1.095 | 0.782 | 10.197 | 0.000 |
| mmu_miR_192_000491 | −2.050 | 0.012 | −0.834 | 0.388 | −0.581 | 0.612 |
| mmu_miR_1930_121201_mat | 0.732 | 0.720 | −2.053 | 0.236 | −0.267 | 0.932 |
| mmu_miR_1931_121168_mat | −1.566 | 0.252 | 0.132 | 0.996 | −1.990 | 0.185 |
| mmu_miR_1932_121172_mat | −3.469 | 0.345 | 1.538 | 0.798 | 2.520 | 0.595 |
| mmu_miR_1933_3p_121145_mat | −0.376 | 0.544 | 0.096 | 0.961 | −0.908 | 0.136 |
| mmu_miR_1933_5p_121133_mat | 4.857 | 0.429 | 0.560 | 0.996 | 3.868 | 0.623 |
| mmu_miR_1934_121185_mat | −8.183 | 0.006 | −0.089 | 0.996 | 0.792 | 0.886 |
| mmu_miR_1935_121192_mat | 2.233 | 0.246 | 2.840 | 0.158 | 0.548 | 0.866 |
| mmu_miR_1936_121158_mat | 1.302 | 0.366 | 1.767 | 0.241 | 1.327 | 0.447 |
| mmu_miR_1937b_241023_mat | 1.965 | 0.849 | −1.150 | 0.976 | 4.508 | 0.699 |
| mmu_miR_1937c_241011_mat | 2.194 | 0.000 | −1.016 | 0.109 | 4.590 | 0.000 |
| mmu_miR_1938_121194_mat | −0.151 | 0.952 | 0.429 | 0.934 | 0.683 | 0.808 |
| mmu_miR_1939_121180_mat | 0.269 | 0.951 | 0.112 | 0.996 | −1.169 | 0.808 |
| mmu_miR_193_002250 | −2.644 | 0.412 | 0.022 | 0.997 | 0.667 | 0.905 |
| mmu_miR_193_002577 | 0.370 | 0.705 | 1.458 | 0.063 | 1.439 | 0.087 |
| mmu_miR_193b_002467 | −1.069 | 0.106 | 2.010 | 0.003 | −0.317 | 0.762 |
| mmu_miR_1940_121187_mat | 1.123 | 0.734 | −5.814 | 0.023 | 1.321 | 0.749 |
| mmu_miR_1941_3p_121130_mat | −0.118 | 0.889 | 0.505 | 0.475 | 0.745 | 0.273 |
| mmu_miR_1941_5p_121140_mat | −1.315 | 0.524 | −2.371 | 0.239 | 1.517 | 0.528 |

TABLE 4-continued

| Brain Stem miRNA data. | | | | | | |
|---|---|---|---|---|---|---|
| mmu_miR_1942_121136_mat | −1.723 | 0.805 | −7.035 | 0.236 | 2.660 | 0.762 |
| mmu_miR_1943_121174_mat | −2.933 | 0.003 | −2.015 | 0.050 | −2.039 | 0.064 |
| mmu_miR_1944_121189_mat | −1.339 | 0.603 | 0.512 | 0.947 | −1.252 | 0.720 |
| mmu_miR_1945_121166_mat | 0.046 | 0.966 | 0.466 | 0.694 | −0.398 | 0.762 |
| mmu_miR_1946a_121178_mat | −0.105 | 0.982 | −11.509 | 0.001 | −2.903 | 0.515 |
| mmu_miR_1947_121156_mat | −2.911 | 0.154 | 0.221 | 0.996 | −0.490 | 0.896 |
| mmu_miR_1948_121171_mat | 2.891 | 0.169 | 2.181 | 0.362 | 1.539 | 0.581 |
| mmu_miR_1949_121182_mat | −0.291 | 0.766 | 0.177 | 0.942 | −1.530 | 0.061 |
| mmu_miR_194_000493 | −2.491 | 0.021 | −2.494 | 0.027 | −1.163 | 0.399 |
| mmu_miR_1950_121146_mat | −0.395 | 0.872 | 0.046 | 0.996 | −0.918 | 0.742 |
| mmu_miR_1951_121165_mat | 4.585 | 0.558 | −6.950 | 0.382 | 7.385 | 0.381 |
| mmu_miR_1952_121167_mat | −0.363 | 0.307 | 0.043 | 0.986 | −1.045 | 0.004 |
| mmu_miR_1953_121159_mat | −0.371 | 0.768 | 0.368 | 0.849 | 0.020 | 0.992 |
| mmu_miR_1954_121137_mat | 1.876 | 0.455 | −3.993 | 0.099 | 8.646 | 0.001 |
| mmu_miR_1956_121129_mat | −1.624 | 0.768 | −0.217 | 0.996 | −2.111 | 0.757 |
| mmu_miR_1957_121163_mat | −0.372 | 0.224 | −0.003 | 0.996 | −1.160 | 0.000 |
| mmu_miR_1958_121181_mat | 0.004 | 0.999 | 0.334 | 0.976 | −1.947 | 0.491 |
| mmu_miR_1959_121132_mat | 3.249 | 0.032 | −2.406 | 0.147 | 5.696 | 0.001 |
| mmu_miR_195_000494 | −3.796 | 0.000 | −3.314 | 0.000 | −1.388 | 0.038 |
| mmu_miR_1960_121148_mat | −2.957 | 0.091 | −0.064 | 0.996 | −0.141 | 0.971 |
| mmu_miR_1961_197391_mat | 6.588 | 0.104 | 4.267 | 0.369 | 14.437 | 0.001 |
| mmu_miR_1962_121173_mat | 1.085 | 0.387 | 0.396 | 0.878 | 0.956 | 0.543 |
| mmu_miR_1963_121191_mat | −0.372 | 0.224 | −0.003 | 0.996 | −1.160 | 0.000 |
| mmu_miR_1964_121138_mat | −0.515 | 0.710 | 0.431 | 0.831 | 1.957 | 0.100 |
| mmu_miR_1965_121186_mat | −0.385 | 0.285 | −0.429 | 0.271 | −1.146 | 0.002 |
| mmu_miR_1966_121134_mat | −0.315 | 0.571 | 0.020 | 0.996 | −1.040 | 0.047 |
| mmu_miR_1967_121151_mat | 0.380 | 0.445 | 0.757 | 0.118 | −0.348 | 0.577 |
| mmu_miR_1968_121179_mat | 6.513 | 0.033 | 6.387 | 0.045 | 7.395 | 0.027 |
| mmu_miR_1969_121131_mat | 3.784 | 0.042 | −2.933 | 0.152 | 5.471 | 0.007 |
| mmu_miR_196a_002477 | 3.428 | 0.616 | −0.873 | 0.978 | 6.203 | 0.396 |
| mmu_miR_196b_002215 | 3.477 | 0.060 | −3.329 | 0.091 | −1.558 | 0.529 |
| mmu_miR_1970_121202_mat | 8.207 | 0.003 | −1.514 | 0.714 | 8.331 | 0.005 |
| mmu_miR_1971_121161_mat | 8.928 | 0.006 | 2.115 | 0.637 | 5.341 | 0.144 |
| mmu_miR_197_000497 | 1.385 | 0.798 | −6.789 | 0.121 | 2.623 | 0.672 |
| mmu_miR_1981_121200_mat | 1.855 | 0.030 | 1.872 | 0.035 | 0.028 | 0.991 |
| mmu_miR_1982.1_121157_mat | 0.601 | 0.739 | −0.050 | 0.996 | −0.485 | 0.829 |
| mmu_miR_1982.2_121154_mat | 3.743 | 0.083 | −1.038 | 0.771 | 1.971 | 0.490 |
| mmu_miR_199a_3p_002304 | −1.730 | 0.248 | −3.254 | 0.028 | −0.244 | 0.932 |
| mmu_miR_199a_5p_000498 | −0.135 | 0.964 | 1.635 | 0.537 | 0.166 | 0.971 |
| mmu_miR_199b_001131 | 2.512 | 0.207 | 1.475 | 0.546 | 0.829 | 0.791 |
| mmu_miR_19a_000395 | −3.602 | 0.000 | −3.866 | 0.000 | −1.736 | 0.007 |
| mmu_miR_19a_002544 | −0.339 | 0.571 | 0.276 | 0.717 | −0.416 | 0.543 |
| mmu_miR_19b_000396 | −3.150 | 0.000 | −3.625 | 0.000 | −2.497 | 0.002 |
| mmu_miR_1_002222 | 5.722 | 0.001 | −1.308 | 0.551 | 1.307 | 0.577 |
| mmu_miR_1_2_AS_002882 | −6.864 | 0.051 | −9.227 | 0.011 | −0.364 | 0.959 |
| mmu_miR_200a_000502 | 5.944 | 0.020 | 5.222 | 0.050 | 8.234 | 0.003 |
| mmu_miR_200b_002251 | 0.510 | 0.931 | −1.205 | 0.904 | 3.688 | 0.472 |
| mmu_miR_200c_002300 | 4.514 | 0.116 | 0.584 | 0.956 | 5.586 | 0.078 |
| mmu_miR_201_002578 | 2.780 | 0.193 | 3.390 | 0.121 | 3.616 | 0.119 |
| mmu_miR_202_3p_001195 | −0.814 | 0.845 | −3.387 | 0.333 | 1.112 | 0.828 |
| mmu_miR_202_5p_002579 | −1.959 | 0.255 | 2.746 | 0.121 | 3.802 | 0.034 |

TABLE 4-continued

| Brain Stem miRNA data. | | | | | | |
|---|---|---|---|---|---|---|
| mmu_miR_203_000507 | −1.644 | 0.540 | −1.722 | 0.567 | 1.361 | 0.708 |
| mmu_miR_203_002580 | 1.534 | 0.655 | 2.087 | 0.565 | 4.806 | 0.130 |
| mmu_miR_204_000508 | −4.113 | 0.000 | −2.187 | 0.000 | −0.074 | 0.944 |
| mmu_miR_205_000509 | 3.238 | 0.267 | 0.911 | 0.890 | 0.034 | 0.995 |
| mmu_miR_207_001198 | −0.152 | 0.931 | 0.287 | 0.934 | −1.426 | 0.304 |
| mmu_miR_208_000511 | −5.307 | 0.268 | −0.707 | 0.976 | −0.085 | 0.993 |
| mmu_miR_208b_002290 | 7.014 | 0.072 | 1.825 | 0.782 | 6.154 | 0.164 |
| mmu_miR_20a_000580 | −2.905 | 0.000 | −3.985 | 0.000 | −2.274 | 0.001 |
| mmu_miR_20a_002491 | −4.750 | 0.011 | −5.535 | 0.004 | −2.513 | 0.261 |
| mmu_miR_20b_001014 | −4.875 | 0.002 | −5.541 | 0.001 | −4.212 | 0.014 |
| mmu_miR_20b_002524 | −0.203 | 0.945 | 0.159 | 0.996 | −1.103 | 0.742 |
| mmu_miR_210_000512 | −6.053 | 0.000 | −4.498 | 0.002 | −5.549 | 0.000 |
| mmu_miR_211_001199 | −1.331 | 0.860 | −1.666 | 0.904 | 0.119 | 0.992 |
| mmu_miR_212_002551 | 1.805 | 0.103 | 1.763 | 0.140 | −0.682 | 0.681 |
| mmu_miR_2134_241120_mat | 3.955 | 0.013 | −0.292 | 0.961 | 6.286 | 0.000 |
| mmu_miR_2135_241140_mat | 4.438 | 0.571 | 3.308 | 0.768 | 5.498 | 0.547 |
| mmu_miR_2136_241133_mat | 2.118 | 0.822 | −1.686 | 0.943 | −0.266 | 0.989 |
| mmu_miR_2138_241080_mat | −0.496 | 0.926 | −6.187 | 0.066 | 7.754 | 0.026 |
| mmu_miR_2139_241130_mat | 1.420 | 0.442 | 1.536 | 0.453 | 0.816 | 0.762 |
| mmu_miR_2146_241082_mat | 4.805 | 0.169 | 0.785 | 0.947 | 8.308 | 0.023 |
| mmu_miR_214_002306 | 0.621 | 0.758 | −2.198 | 0.194 | 1.687 | 0.379 |
| mmu_miR_215_001200 | −3.568 | 0.067 | −4.378 | 0.030 | −1.614 | 0.541 |
| mmu_miR_216a_002220 | 7.300 | 0.000 | 1.747 | 0.297 | −0.386 | 0.886 |
| mmu_miR_216b_002326 | 6.340 | 0.000 | 2.587 | 0.116 | −0.163 | 0.957 |
| mmu_miR_217_001133 | 3.765 | 0.022 | −1.984 | 0.296 | 0.794 | 0.763 |
| mmu_miR_217_002556 | 1.439 | 0.296 | −1.872 | 0.199 | −1.035 | 0.558 |
| mmu_miR_2182_241119_mat | 3.240 | 0.272 | 4.188 | 0.177 | 4.488 | 0.161 |
| mmu_miR_2183_241095_mat | 2.712 | 0.233 | −2.002 | 0.453 | 7.070 | 0.003 |
| mmu_miR_218_000521 | 4.253 | 0.000 | 4.294 | 0.000 | 2.276 | 0.000 |
| mmu_miR_218_1_002552 | 4.020 | 0.001 | 2.634 | 0.026 | 0.490 | 0.795 |
| mmu_miR_219_000522 | −7.843 | 0.000 | −3.710 | 0.001 | −7.528 | 0.000 |
| mmu_miR_21_000397 | −1.907 | 0.017 | −4.068 | 0.000 | −1.418 | 0.122 |
| mmu_miR_21_002493 | −0.866 | 0.571 | −0.497 | 0.854 | −0.936 | 0.613 |
| mmu_miR_220_002468 | −0.345 | 0.358 | 0.031 | 0.996 | −1.312 | 0.001 |
| mmu_miR_221_000524 | −2.408 | 0.000 | −1.736 | 0.000 | −0.691 | 0.154 |
| mmu_miR_222_002276 | −0.534 | 0.099 | −1.175 | 0.001 | −0.241 | 0.581 |
| mmu_miR_223_002295 | 2.907 | 0.001 | −11.143 | 0.000 | 6.409 | 0.000 |
| mmu_miR_224_002553 | −2.237 | 0.034 | −0.220 | 0.956 | −0.667 | 0.676 |
| mmu_miR_23a_000399 | −0.576 | 0.771 | 0.453 | 0.908 | 1.284 | 0.528 |
| mmu_miR_23b_000400 | −1.804 | 0.062 | −1.505 | 0.155 | −0.635 | 0.660 |
| mmu_miR_24_000402 | 0.270 | 0.352 | −0.614 | 0.028 | 0.275 | 0.434 |
| mmu_miR_24_2_002494 | −1.210 | 0.158 | −1.568 | 0.074 | 0.803 | 0.457 |
| mmu_miR_25_000403 | −2.922 | 0.013 | −3.569 | 0.004 | −0.661 | 0.735 |
| mmu_miR_26a_000405 | −1.266 | 0.001 | −1.376 | 0.000 | −0.595 | 0.144 |
| mmu_miR_26b_000407 | −2.100 | 0.000 | −2.253 | 0.000 | −0.712 | 0.144 |
| mmu_miR_27a_000408 | −1.662 | 0.144 | −0.624 | 0.710 | 1.224 | 0.380 |
| mmu_miR_27b_000409 | −0.919 | 0.093 | −0.012 | 0.996 | −0.811 | 0.194 |
| mmu_miR_28_000411 | −1.473 | 0.436 | −1.469 | 0.500 | 1.899 | 0.382 |
| mmu_miR_28_002545 | 3.058 | 0.084 | 2.205 | 0.270 | 3.695 | 0.060 |
| mmu_miR_290_000187 | 0.314 | 0.951 | −14.329 | 0.000 | 2.246 | 0.668 |
| mmu_miR_290_3p_002591 | −0.370 | 0.261 | 0.024 | 0.996 | −1.085 | 0.002 |

TABLE 4-continued

| Brain Stem miRNA data. | | | | | | |
|---|---|---|---|---|---|---|
| mmu_miR_290_5p_002590 | −1.247 | 0.782 | −3.363 | 0.414 | 0.758 | 0.906 |
| mmu_miR_291_3p_001135 | −0.315 | 0.750 | −0.003 | 0.997 | −1.874 | 0.018 |
| mmu_miR_291_5p_001202 | −0.315 | 0.546 | 0.028 | 0.996 | −1.045 | 0.032 |
| mmu_miR_291a_3p_002592 | −0.369 | 0.248 | 0.023 | 0.996 | −1.092 | 0.001 |
| mmu_miR_291b_3p_002538 | −0.356 | 0.586 | 0.181 | 0.895 | −0.653 | 0.353 |
| mmu_miR_291b_5p_002537 | −0.382 | 0.430 | −0.007 | 0.996 | −1.149 | 0.016 |
| mmu_miR_292_3p_001054 | 0.714 | 0.822 | 0.811 | 0.878 | 0.065 | 0.992 |
| mmu_miR_292_3p_002593 | −1.561 | 0.798 | −3.792 | 0.518 | −0.789 | 0.932 |
| mmu_miR_292_5p_001055 | −4.363 | 0.358 | −0.346 | 0.996 | 1.031 | 0.903 |
| mmu_miR_293_001794 | 0.789 | 0.916 | −4.503 | 0.427 | 1.154 | 0.896 |
| mmu_miR_293_002594 | −0.719 | 0.750 | 0.308 | 0.961 | −1.291 | 0.575 |
| mmu_miR_294_001056 | −2.344 | 0.571 | −4.387 | 0.284 | 1.310 | 0.828 |
| mmu_miR_294_002595 | −0.372 | 0.224 | −0.003 | 0.996 | −1.160 | 0.000 |
| mmu_miR_295_000189 | −0.091 | 0.965 | −1.183 | 0.532 | 0.804 | 0.742 |
| mmu_miR_295_002596 | −0.251 | 0.931 | −6.936 | 0.001 | −1.002 | 0.762 |
| mmu_miR_296_3p_002101 | −0.379 | 0.876 | −0.031 | 0.996 | 2.868 | 0.136 |
| mmu_miR_296_5p_000527 | 0.693 | 0.611 | 3.726 | 0.002 | 1.371 | 0.343 |
| mmu_miR_297a_002454 | −2.677 | 0.004 | 0.070 | 0.996 | 0.011 | 0.995 |
| mmu_miR_297b_5p_001626 | −1.452 | 0.278 | 0.430 | 0.881 | 1.392 | 0.389 |
| mmu_miR_297c_002480 | −1.118 | 0.571 | 0.254 | 0.978 | 1.448 | 0.524 |
| mmu_miR_298_002598 | 2.715 | 0.077 | 0.214 | 0.982 | −2.912 | 0.089 |
| mmu_miR_299_002612 | −0.372 | 0.224 | −0.003 | 0.996 | −1.160 | 0.000 |
| mmu_miR_29a_002112 | 0.647 | 0.172 | 1.052 | 0.026 | −0.223 | 0.762 |
| mmu_miR_29b_000413 | 2.488 | 0.013 | 2.316 | 0.026 | 1.441 | 0.219 |
| mmu_miR_29b_002497 | 1.053 | 0.339 | −2.628 | 0.013 | 4.191 | 0.000 |
| mmu_miR_29c_000587 | 1.071 | 0.007 | 1.737 | 0.000 | 0.364 | 0.491 |
| mmu_miR_300_000191 | 3.228 | 0.202 | 3.268 | 0.227 | 0.507 | 0.909 |
| mmu_miR_300_002613 | 5.413 | 0.000 | 2.912 | 0.025 | 2.426 | 0.084 |
| mmu_miR_301a_000528 | −1.211 | 0.018 | −0.743 | 0.196 | −0.623 | 0.333 |
| mmu_miR_301b_002600 | −0.651 | 0.339 | 0.415 | 0.641 | −0.375 | 0.708 |
| mmu_miR_302a_000529 | 4.747 | 0.330 | −1.620 | 0.869 | 1.237 | 0.885 |
| mmu_miR_302a_002615 | 2.577 | 0.348 | 2.287 | 0.473 | 2.762 | 0.395 |
| mmu_miR_302b_000531 | −0.729 | 0.815 | 1.897 | 0.520 | 0.389 | 0.932 |
| mmu_miR_302b_001307 | −0.076 | 0.986 | −5.224 | 0.116 | 0.345 | 0.957 |
| mmu_miR_302c_002557 | −1.620 | 0.532 | 2.283 | 0.388 | 1.799 | 0.552 |
| mmu_miR_302c_002558 | −0.911 | 0.859 | −3.469 | 0.434 | 1.404 | 0.813 |
| mmu_miR_302d_000535 | 0.758 | 0.847 | 1.501 | 0.730 | 1.325 | 0.771 |
| mmu_miR_30a_000417 | −1.562 | 0.000 | −1.434 | 0.000 | −0.682 | 0.114 |
| mmu_miR_30b_000602 | −0.095 | 0.840 | −0.334 | 0.422 | −0.120 | 0.833 |
| mmu_miR_30b_002498 | −1.245 | 0.509 | −0.011 | 0.997 | −0.226 | 0.944 |
| mmu_miR_30c_000419 | −0.149 | 0.696 | −0.188 | 0.658 | −0.225 | 0.581 |
| mmu_miR_30d_000420 | −1.632 | 0.007 | −0.767 | 0.267 | −0.293 | 0.763 |
| mmu_miR_30e_002223 | −1.257 | 0.000 | −0.647 | 0.027 | −0.121 | 0.796 |
| mmu_miR_31_000185 | 1.443 | 0.037 | 0.389 | 0.710 | 0.375 | 0.747 |
| mmu_miR_31_002495 | 1.153 | 0.612 | −1.314 | 0.615 | −0.680 | 0.832 |
| mmu_miR_320_002277 | −1.744 | 0.000 | −0.535 | 0.214 | −0.229 | 0.707 |
| mmu_miR_322_001059 | −0.136 | 0.980 | −3.889 | 0.362 | −0.522 | 0.942 |
| mmu_miR_322_001076 | −8.114 | 0.000 | −8.699 | 0.000 | −8.621 | 0.000 |
| mmu_miR_322_002506 | −3.161 | 0.050 | −5.285 | 0.002 | −5.118 | 0.004 |
| mmu_miR_323_3p_002227 | 2.604 | 0.002 | 3.423 | 0.000 | −0.342 | 0.803 |
| mmu_miR_324_3p_002509 | −1.827 | 0.061 | 1.304 | 0.235 | −1.570 | 0.157 |

TABLE 4-continued

| Brain Stem miRNA data. | | | | | | |
|---|---|---|---|---|---|---|
| mmu_miR_324_5p_000539 | −0.933 | 0.436 | −0.098 | 0.996 | −1.095 | 0.436 |
| mmu_miR_325_001060 | −2.040 | 0.617 | −7.618 | 0.032 | −2.003 | 0.713 |
| mmu_miR_325_002510 | 0.367 | 0.762 | 5.406 | 0.000 | −0.380 | 0.801 |
| mmu_miR_326_001061 | 1.352 | 0.844 | −16.729 | 0.001 | −2.900 | 0.709 |
| mmu_miR_327_002481 | 0.048 | 0.980 | 0.882 | 0.537 | −0.010 | 0.995 |
| mmu_miR_328_000543 | 1.228 | 0.003 | 1.075 | 0.010 | 0.602 | 0.195 |
| mmu_miR_329_000192 | 2.770 | 0.006 | 3.495 | 0.001 | 0.409 | 0.805 |
| mmu_miR_32_002109 | −7.009 | 0.004 | −6.669 | 0.008 | −5.342 | 0.047 |
| mmu_miR_330_001062 | 5.796 | 0.144 | 1.929 | 0.759 | 3.149 | 0.544 |
| mmu_miR_330_002230 | 1.510 | 0.229 | −2.120 | 0.099 | −0.846 | 0.616 |
| mmu_miR_331_3p_000545 | 0.663 | 0.244 | 1.637 | 0.004 | 1.074 | 0.077 |
| mmu_miR_331_5p_002233 | 0.272 | 0.936 | −2.070 | 0.488 | 3.882 | 0.152 |
| mmu_miR_335_3p_002185 | 3.410 | 0.006 | 5.704 | 0.000 | −1.500 | 0.327 |
| mmu_miR_335_5p_000546 | 3.450 | 0.000 | 2.261 | 0.000 | 0.822 | 0.200 |
| mmu_miR_337_000193 | 1.439 | 0.270 | 2.430 | 0.063 | 0.714 | 0.720 |
| mmu_miR_337_3p_002532 | 2.244 | 0.039 | 3.024 | 0.007 | 0.680 | 0.681 |
| mmu_miR_337_5p_002515 | 3.042 | 0.109 | 3.983 | 0.041 | 3.249 | 0.130 |
| mmu_miR_338_3p_002252 | −4.756 | 0.000 | −0.157 | 0.981 | −4.267 | 0.000 |
| mmu_miR_339_3p_002533 | −4.077 | 0.027 | −4.743 | 0.013 | −1.867 | 0.434 |
| mmu_miR_339_5p_002257 | −5.774 | 0.000 | −4.818 | 0.000 | −4.632 | 0.000 |
| mmu_miR_340_3p_002259 | −0.132 | 0.795 | 0.262 | 0.615 | 0.114 | 0.866 |
| mmu_miR_340_5p_002258 | −0.854 | 0.029 | 0.615 | 0.152 | −0.358 | 0.491 |
| mmu_miR_342_3p_002260 | 1.258 | 0.001 | −0.439 | 0.321 | −0.378 | 0.447 |
| mmu_miR_342_5p_002527 | −0.272 | 0.890 | −0.731 | 0.715 | −2.638 | 0.077 |
| mmu_miR_343_002483 | −0.364 | 0.582 | 0.001 | 0.999 | −1.103 | 0.085 |
| mmu_miR_344_001063 | −0.670 | 0.577 | 2.390 | 0.026 | −1.083 | 0.416 |
| mmu_miR_345_001137 | −1.475 | 0.120 | −0.086 | 0.996 | 0.102 | 0.957 |
| mmu_miR_345_3p_002529 | −2.160 | 0.053 | −0.871 | 0.546 | −0.965 | 0.524 |
| mmu_miR_345_5p_002528 | −3.890 | 0.000 | 0.407 | 0.704 | −2.754 | 0.000 |
| mmu_miR_346_001064 | 1.455 | 0.309 | 0.802 | 0.694 | 0.250 | 0.930 |
| mmu_miR_34a_000426 | 4.629 | 0.000 | 2.856 | 0.000 | 0.483 | 0.528 |
| mmu_miR_34b_001065 | −1.407 | 0.333 | −0.921 | 0.622 | 0.965 | 0.614 |
| mmu_miR_34b_3p_002618 | −0.861 | 0.066 | 1.723 | 0.001 | 0.983 | 0.060 |
| mmu_miR_34b_5p_002617 | 0.352 | 0.844 | 1.225 | 0.435 | 2.686 | 0.061 |
| mmu_miR_34c_000428 | −0.923 | 0.265 | 6.010 | 0.000 | 1.322 | 0.142 |
| mmu_miR_34c_002584 | −0.563 | 0.372 | 1.353 | 0.026 | 1.390 | 0.029 |
| mmu_miR_350_002530 | −3.701 | 0.000 | −2.524 | 0.000 | −2.613 | 0.000 |
| mmu_miR_351_001067 | −0.341 | 0.811 | 0.201 | 0.961 | −0.172 | 0.933 |
| mmu_miR_361_000554 | −0.007 | 0.999 | 0.771 | 0.710 | 0.014 | 0.995 |
| mmu_miR_362_3p_002616 | −3.097 | 0.001 | −4.602 | 0.000 | −1.997 | 0.054 |
| mmu_miR_362_5p_002614 | −1.194 | 0.154 | −2.181 | 0.009 | −0.368 | 0.779 |
| mmu_miR_363_001271 | 0.916 | 0.771 | 1.024 | 0.815 | 1.021 | 0.799 |
| mmu_miR_365_001020 | −5.714 | 0.000 | 0.223 | 0.922 | −2.269 | 0.011 |
| mmu_miR_367_000555 | −2.768 | 0.612 | −0.973 | 0.956 | −1.447 | 0.858 |
| mmu_miR_369_3p_000557 | 2.423 | 0.010 | 1.884 | 0.056 | 0.142 | 0.940 |
| mmu_miR_369_5p_001021 | 4.393 | 0.000 | 1.633 | 0.125 | 0.432 | 0.791 |
| mmu_miR_370_001068 | −0.252 | 0.931 | 0.228 | 0.986 | −0.818 | 0.778 |
| mmu_miR_370_002275 | 2.481 | 0.000 | 4.859 | 0.000 | −1.225 | 0.112 |
| mmu_miR_374_002043 | 0.632 | 0.931 | 1.079 | 0.952 | 5.713 | 0.345 |
| mmu_miR_374_5p_001319 | −9.452 | 0.006 | −6.096 | 0.094 | −9.210 | 0.014 |
| mmu_miR_375_000564 | −3.119 | 0.007 | 1.534 | 0.241 | 0.162 | 0.944 |

TABLE 4-continued

Brain Stem miRNA data.

| | | | | | | |
|---|---|---|---|---|---|---|
| mmu_miR_376a_001069 | 2.979 | 0.000 | 2.553 | 0.000 | 0.368 | 0.585 |
| mmu_miR_376a_002482 | 4.322 | 0.019 | 1.778 | 0.432 | 0.541 | 0.869 |
| mmu_miR_376b_002451 | 3.033 | 0.479 | 2.634 | 0.615 | 0.498 | 0.948 |
| mmu_miR_376b_002452 | 3.368 | 0.001 | 4.389 | 0.000 | 0.253 | 0.893 |
| mmu_miR_376c_002450 | 1.990 | 0.000 | 2.113 | 0.000 | 0.705 | 0.152 |
| mmu_miR_376c_002523 | 1.179 | 0.646 | 2.464 | 0.305 | 2.042 | 0.455 |
| mmu_miR_377_000566 | 0.361 | 0.888 | 0.750 | 0.803 | 0.835 | 0.762 |
| mmu_miR_379_001138 | 3.055 | 0.005 | 3.240 | 0.004 | 1.132 | 0.414 |
| mmu_miR_380_3p_001071 | 6.440 | 0.000 | 2.428 | 0.013 | 1.761 | 0.101 |
| mmu_miR_380_5p_002601 | 4.578 | 0.000 | 3.152 | 0.000 | 1.042 | 0.152 |
| mmu_miR_381_000571 | 1.783 | 0.253 | 0.281 | 0.961 | 0.496 | 0.847 |
| mmu_miR_382_000572 | 3.946 | 0.003 | 8.030 | 0.000 | −0.636 | 0.762 |
| mmu_miR_383_001767 | 4.785 | 0.000 | 3.581 | 0.000 | 0.227 | 0.830 |
| mmu_miR_384_3p_002603 | 1.619 | 0.004 | 1.442 | 0.013 | 0.019 | 0.991 |
| mmu_miR_384_5p_002602 | 2.058 | 0.000 | 1.614 | 0.000 | −0.196 | 0.751 |
| mmu_miR_409_3p_002332 | 3.235 | 0.002 | 2.887 | 0.006 | 0.540 | 0.753 |
| mmu_miR_409_5p_002331 | 4.707 | 0.000 | 2.407 | 0.013 | −0.202 | 0.907 |
| mmu_miR_410_001274 | 2.997 | 0.000 | 3.408 | 0.000 | 0.172 | 0.813 |
| mmu_miR_411_001610 | 2.330 | 0.001 | 2.541 | 0.000 | 0.636 | 0.457 |
| mmu_miR_412_002575 | 5.379 | 0.000 | 5.343 | 0.000 | 0.642 | 0.628 |
| mmu_miR_423_5p_002340 | −2.665 | 0.003 | −1.262 | 0.202 | −2.240 | 0.020 |
| mmu_miR_425_001516 | 2.811 | 0.170 | −2.190 | 0.342 | 6.783 | 0.002 |
| mmu_miR_429_001077 | 2.368 | 0.379 | −0.207 | 0.996 | 3.158 | 0.299 |
| mmu_miR_431_001979 | −0.969 | 0.381 | −2.156 | 0.042 | −6.434 | 0.000 |
| mmu_miR_432_241135_mat | 1.165 | 0.798 | 2.536 | 0.576 | 1.706 | 0.762 |
| mmu_miR_433_001028 | 3.646 | 0.000 | 3.261 | 0.000 | 0.427 | 0.496 |
| mmu_miR_433_5p_001078 | 5.590 | 0.067 | −0.587 | 0.961 | 0.762 | 0.896 |
| mmu_miR_434_3p_002604 | 3.014 | 0.000 | 1.573 | 0.002 | 0.003 | 0.997 |
| mmu_miR_434_5p_002581 | 3.972 | 0.001 | 2.968 | 0.012 | 0.512 | 0.782 |
| mmu_miR_448_001029 | 5.042 | 0.002 | 2.286 | 0.203 | 0.049 | 0.992 |
| mmu_miR_449a_001030 | 1.036 | 0.518 | −2.363 | 0.112 | 1.290 | 0.485 |
| mmu_miR_449b_001667 | 2.481 | 0.205 | −0.524 | 0.916 | 2.290 | 0.324 |
| mmu_miR_449b_002539 | −0.367 | 0.249 | 0.025 | 0.996 | −1.091 | 0.001 |
| mmu_miR_450B_3P_002632 | −0.001 | 0.999 | −6.200 | 0.039 | −1.498 | 0.757 |
| mmu_miR_450a_3p_002525 | −0.372 | 0.224 | −0.003 | 0.996 | −1.160 | 0.000 |
| mmu_miR_450a_5p_002303 | −2.349 | 0.097 | −1.004 | 0.588 | −1.216 | 0.519 |
| mmu_miR_450b_5p_001962 | −0.359 | 0.571 | 0.086 | 0.976 | −0.912 | 0.144 |
| mmu_miR_451_001141 | −2.489 | 0.500 | −5.487 | 0.115 | 4.678 | 0.215 |
| mmu_miR_452_001032 | −1.599 | 0.722 | −4.368 | 0.254 | −1.775 | 0.754 |
| mmu_miR_453_002484 | −0.193 | 0.925 | 0.386 | 0.896 | −0.626 | 0.755 |
| mmu_miR_455_002455 | −6.597 | 0.000 | −4.753 | 0.001 | −5.991 | 0.000 |
| mmu_miR_463_002582 | 2.723 | 0.037 | −1.776 | 0.227 | 6.352 | 0.000 |
| mmu_miR_463_002662 | 2.919 | 0.253 | −2.665 | 0.356 | 4.853 | 0.077 |
| mmu_miR_464_001081 | −0.284 | 0.804 | 0.160 | 0.961 | −0.651 | 0.581 |
| mmu_miR_465C_5P_002654 | 6.586 | 0.001 | −0.547 | 0.908 | 7.774 | 0.000 |
| mmu_miR_465a_3p_002040 | 3.324 | 0.209 | 3.128 | 0.277 | 1.026 | 0.805 |
| mmu_miR_465a_5p_001082 | −6.964 | 0.270 | −1.026 | 0.967 | 1.181 | 0.921 |
| mmu_miR_465b_5p_002485 | 3.129 | 0.483 | −3.099 | 0.546 | −0.399 | 0.960 |
| mmu_miR_466E_5P_002718 | −1.496 | 0.785 | −8.180 | 0.062 | 0.777 | 0.929 |
| mmu_miR_466J_002817 | −1.861 | 0.200 | −0.774 | 0.710 | 0.289 | 0.909 |
| mmu_miR_466a_3p_002586 | −3.636 | 0.000 | 0.631 | 0.498 | −0.966 | 0.273 |

TABLE 4-continued

| Brain Stem miRNA data. | | | | | | |
|---|---|---|---|---|---|---|
| mmu_miR_466b_3_3p_002500 | −3.268 | 0.004 | −0.099 | 0.996 | −1.269 | 0.365 |
| mmu_miR_466d_5p_002534 | 2.978 | 0.571 | 1.035 | 0.949 | 1.464 | 0.850 |
| mmu_miR_466g_241015_mat | −3.586 | 0.109 | 1.268 | 0.710 | 0.901 | 0.805 |
| mmu_miR_466h_002516 | −1.368 | 0.542 | −0.039 | 0.996 | −1.733 | 0.500 |
| mmu_miR_466k_240990_mat | 4.305 | 0.101 | −2.676 | 0.386 | 3.981 | 0.181 |
| mmu_miR_467F_002886 | −2.755 | 0.404 | −5.216 | 0.107 | −0.162 | 0.981 |
| mmu_miR_467H_002809 | −4.526 | 0.000 | −1.399 | 0.278 | −2.119 | 0.096 |
| mmu_miR_467a_001826 | −2.689 | 0.039 | 1.030 | 0.541 | 0.786 | 0.701 |
| mmu_miR_467a_002587 | −2.663 | 0.014 | 3.334 | 0.003 | −0.073 | 0.976 |
| mmu_miR_467b_001671 | −5.128 | 0.000 | −1.325 | 0.298 | −3.306 | 0.006 |
| mmu_miR_467b_001684 | 0.962 | 0.720 | −2.105 | 0.383 | 3.511 | 0.130 |
| mmu_miR_467c_002517 | −4.310 | 0.014 | −0.887 | 0.759 | 0.998 | 0.727 |
| mmu_miR_467d_002518 | −2.397 | 0.055 | −1.358 | 0.359 | 0.709 | 0.727 |
| mmu_miR_467e_002568 | −2.134 | 0.280 | −4.172 | 0.032 | 0.232 | 0.952 |
| mmu_miR_467e_002569 | 0.159 | 0.956 | −1.454 | 0.570 | −1.655 | 0.528 |
| mmu_miR_468_001085 | −0.104 | 0.964 | 0.095 | 0.996 | −0.576 | 0.828 |
| mmu_miR_469_001086 | 0.386 | 0.936 | 0.096 | 0.996 | −3.480 | 0.423 |
| mmu_miR_470_002588 | −0.099 | 0.954 | 0.452 | 0.850 | −0.059 | 0.983 |
| mmu_miR_470_002589 | −3.462 | 0.565 | −8.085 | 0.147 | 2.591 | 0.762 |
| mmu_miR_471_002605 | −0.325 | 0.571 | 0.145 | 0.908 | −1.157 | 0.029 |
| mmu_miR_483_001291 | 1.889 | 0.571 | −5.292 | 0.079 | 2.412 | 0.528 |
| mmu_miR_483_002560 | 0.587 | 0.687 | 0.376 | 0.890 | 2.825 | 0.023 |
| mmu_miR_484_001821 | −1.772 | 0.000 | −1.747 | 0.000 | −1.027 | 0.032 |
| mmu_miR_485_3p_001943 | 2.210 | 0.000 | 2.658 | 0.000 | 0.893 | 0.144 |
| mmu_miR_486_001278 | −5.954 | 0.000 | 1.667 | 0.303 | −6.271 | 0.000 |
| mmu_miR_487b_001285 | 2.351 | 0.000 | 1.938 | 0.001 | 0.961 | 0.119 |
| mmu_miR_487b_001306 | 1.379 | 0.009 | 2.508 | 0.000 | −0.265 | 0.762 |
| mmu_miR_488_001659 | −0.634 | 0.693 | 1.505 | 0.292 | −0.088 | 0.976 |
| mmu_miR_488_002014 | 0.863 | 0.786 | 0.065 | 0.996 | 1.830 | 0.581 |
| mmu_miR_489_001302 | 5.862 | 0.003 | 1.820 | 0.444 | 1.240 | 0.672 |
| mmu_miR_490_001037 | 2.790 | 0.016 | −2.910 | 0.015 | −4.682 | 0.000 |
| mmu_miR_491_001630 | 2.501 | 0.009 | 3.895 | 0.000 | 0.707 | 0.597 |
| mmu_miR_493_002519 | 2.745 | 0.237 | 1.497 | 0.624 | 3.131 | 0.231 |
| mmu_miR_494_001293 | −1.460 | 0.381 | −0.322 | 0.956 | −0.816 | 0.752 |
| mmu_miR_494_002365 | 1.669 | 0.189 | 1.365 | 0.333 | 0.848 | 0.618 |
| mmu_miR_495_001663 | 2.878 | 0.000 | 2.433 | 0.000 | 0.012 | 0.992 |
| mmu_miR_496_001953 | −1.968 | 0.454 | −1.027 | 0.805 | −4.476 | 0.092 |
| mmu_miR_497_001346 | −5.762 | 0.000 | −3.032 | 0.008 | −2.123 | 0.088 |
| mmu_miR_499_001352 | 1.748 | 0.415 | −2.549 | 0.243 | −1.700 | 0.516 |
| mmu_miR_500_002606 | −3.686 | 0.001 | −4.688 | 0.000 | −3.452 | 0.002 |
| mmu_miR_501_001356 | 1.764 | 0.418 | 1.319 | 0.627 | 1.268 | 0.672 |
| mmu_miR_501_3p_001651 | −2.203 | 0.001 | −3.171 | 0.000 | −2.517 | 0.001 |
| mmu_miR_503_002456 | −2.041 | 0.174 | −0.564 | 0.849 | −1.653 | 0.362 |
| mmu_miR_503_002536 | −2.287 | 0.019 | −4.675 | 0.000 | −1.163 | 0.343 |
| mmu_miR_504_002084 | 2.219 | 0.028 | −0.252 | 0.934 | −0.108 | 0.957 |
| mmu_miR_505_001655 | −0.039 | 0.981 | 0.445 | 0.849 | 1.044 | 0.494 |
| mmu_miR_509_3p_002521 | 4.056 | 0.463 | 1.737 | 0.875 | 6.753 | 0.253 |
| mmu_miR_509_5p_002520 | 4.724 | 0.279 | 5.066 | 0.288 | 4.867 | 0.351 |
| mmu_miR_511_002549 | −0.638 | 0.770 | −2.427 | 0.187 | 0.828 | 0.762 |
| mmu_miR_532_3p_002355 | −1.287 | 0.037 | −2.121 | 0.001 | −0.367 | 0.707 |
| mmu_miR_532_5p_001518 | −2.357 | 0.000 | −2.762 | 0.000 | −1.454 | 0.004 |

TABLE 4-continued

| Brain Stem miRNA data. | | | | | | |
|---|---|---|---|---|---|---|
| mmu_miR_539_001286 | 2.580 | 0.008 | 2.392 | 0.016 | 0.469 | 0.762 |
| mmu_miR_540_3p_001310 | 3.846 | 0.001 | 0.524 | 0.767 | 0.591 | 0.738 |
| mmu_miR_540_5p_002561 | 1.986 | 0.078 | 0.109 | 0.996 | 0.409 | 0.828 |
| mmu_miR_541_002562 | 4.400 | 0.000 | 2.458 | 0.000 | −0.416 | 0.610 |
| mmu_miR_542_3p_001284 | −2.752 | 0.034 | −0.934 | 0.588 | −1.687 | 0.280 |
| mmu_miR_542_5p_002563 | −0.364 | 0.931 | −0.184 | 0.996 | −0.272 | 0.964 |
| mmu_miR_543_001298 | 2.996 | 0.000 | 2.779 | 0.000 | 0.297 | 0.762 |
| mmu_miR_543_002376 | 3.032 | 0.000 | 2.765 | 0.000 | 0.537 | 0.367 |
| mmu_miR_544_002550 | 2.819 | 0.002 | 2.689 | 0.004 | 1.798 | 0.072 |
| mmu_miR_546_001312 | −0.111 | 0.991 | −5.906 | 0.500 | −8.405 | 0.327 |
| mmu_miR_547_002564 | 0.329 | 0.931 | −2.764 | 0.384 | −0.597 | 0.906 |
| mmu_miR_551b_001535 | 0.990 | 0.421 | −1.345 | 0.292 | 1.169 | 0.415 |
| mmu_miR_574_3p_002349 | −4.920 | 0.000 | −5.567 | 0.000 | −3.790 | 0.000 |
| mmu_miR_582_3p_002567 | 0.502 | 0.825 | −0.375 | 0.952 | 1.098 | 0.672 |
| mmu_miR_582_5p_002566 | 1.343 | 0.117 | 3.338 | 0.000 | 0.415 | 0.762 |
| mmu_miR_590_5p_001984 | −1.976 | 0.429 | 0.073 | 0.996 | −2.065 | 0.491 |
| mmu_miR_592_002017 | 2.714 | 0.000 | 3.129 | 0.000 | −0.384 | 0.755 |
| mmu_miR_598_002476 | 0.519 | 0.739 | 1.412 | 0.289 | 0.192 | 0.932 |
| mmu_miR_599_241117_mat | −2.759 | 0.298 | −0.177 | 0.996 | 2.255 | 0.501 |
| mmu_miR_615_3p_001960 | 2.235 | 0.020 | −1.367 | 0.204 | 0.000 | 1.000 |
| mmu_miR_615_5p_002353 | −0.096 | 0.898 | 0.385 | 0.548 | 0.571 | 0.361 |
| mmu_miR_652_002352 | −2.808 | 0.008 | −1.594 | 0.173 | −1.088 | 0.427 |
| mmu_miR_654_3p_002239 | −0.292 | 0.781 | 0.218 | 0.919 | −0.543 | 0.630 |
| mmu_miR_654_5p_002522 | 0.334 | 0.786 | 0.793 | 0.504 | −0.064 | 0.976 |
| mmu_miR_665_002607 | 0.063 | 0.967 | −0.915 | 0.514 | −2.116 | 0.085 |
| mmu_miR_666_3p_002448 | 1.465 | 0.530 | 1.131 | 0.710 | 3.135 | 0.176 |
| mmu_miR_666_5p_001952 | 4.053 | 0.000 | 0.336 | 0.788 | 0.127 | 0.932 |
| mmu_miR_667_001949 | 3.553 | 0.000 | 2.811 | 0.000 | 0.194 | 0.828 |
| mmu_miR_668_001947 | −0.243 | 0.931 | 0.026 | 0.996 | −2.123 | 0.367 |
| mmu_miR_669C_002646 | −3.075 | 0.017 | −1.327 | 0.387 | −0.273 | 0.909 |
| mmu_miR_669D_002808 | −2.712 | 0.034 | 0.084 | 0.996 | 0.080 | 0.979 |
| mmu_miR_669E_002774 | −2.568 | 0.096 | −0.027 | 0.996 | −0.117 | 0.974 |
| mmu_miR_669G_002813 | −0.356 | 0.518 | 0.106 | 0.952 | −0.842 | 0.122 |
| mmu_miR_669H_5P_002906 | 0.268 | 0.931 | −2.394 | 0.289 | −0.464 | 0.903 |
| mmu_miR_669a_001683 | −2.727 | 0.069 | 0.792 | 0.730 | −0.611 | 0.805 |
| mmu_miR_669l_121149_mat | −2.464 | 0.043 | 0.541 | 0.802 | 0.507 | 0.804 |
| mmu_miR_669m_121190_mat | −2.479 | 0.238 | 1.069 | 0.730 | 0.794 | 0.812 |
| mmu_miR_669n_197143_mat | −4.045 | 0.000 | −1.845 | 0.100 | −1.705 | 0.152 |
| mmu_miR_669o_121176_mat | 0.371 | 0.847 | 2.860 | 0.048 | 3.747 | 0.014 |
| mmu_miR_670_002020 | −0.920 | 0.876 | −6.319 | 0.161 | −1.006 | 0.896 |
| mmu_miR_671_3p_002322 | −0.584 | 0.571 | 3.076 | 0.001 | −0.399 | 0.782 |
| mmu_miR_672_002327 | 2.179 | 0.207 | 3.647 | 0.032 | −2.290 | 0.241 |
| mmu_miR_673_001954 | 4.239 | 0.103 | 1.025 | 0.843 | 7.736 | 0.006 |
| mmu_miR_673_3p_002449 | 3.693 | 0.179 | 0.981 | 0.857 | 0.021 | 0.996 |
| mmu_miR_674_001956 | −3.335 | 0.000 | −1.897 | 0.012 | −1.086 | 0.200 |
| mmu_miR_674_002021 | −4.089 | 0.008 | −2.310 | 0.174 | −3.655 | 0.029 |
| mmu_miR_675_3p_001941 | 0.765 | 0.931 | −9.187 | 0.166 | 0.445 | 0.976 |
| mmu_miR_675_5p_001940 | −3.345 | 0.290 | −0.261 | 0.996 | −0.264 | 0.967 |
| mmu_miR_676_001958 | 1.132 | 0.280 | 1.790 | 0.093 | 0.886 | 0.507 |
| mmu_miR_676_001959 | −3.330 | 0.010 | −0.996 | 0.548 | −1.237 | 0.463 |
| mmu_miR_677_001660 | 0.217 | 0.914 | 1.042 | 0.516 | 1.575 | 0.305 |

TABLE 4-continued

| Brain Stem miRNA data. | | | | | | |
|---|---|---|---|---|---|---|
| mmu_miR_679_001662 | 0.095 | 0.988 | −3.350 | 0.587 | −3.695 | 0.558 |
| mmu_miR_680_001664 | −4.104 | 0.474 | −9.232 | 0.092 | −2.377 | 0.774 |
| mmu_miR_682_001666 | −2.723 | 0.589 | −0.354 | 0.996 | 1.759 | 0.805 |
| mmu_miR_683_001668 | −5.047 | 0.195 | −5.160 | 0.214 | 1.136 | 0.864 |
| mmu_miR_684_001669 | −0.372 | 0.224 | −0.003 | 0.996 | −1.160 | 0.000 |
| mmu_miR_685_001670 | 3.451 | 0.352 | −1.634 | 0.782 | 7.053 | 0.068 |
| mmu_miR_686_001672 | −0.384 | 0.858 | −0.277 | 0.961 | −1.269 | 0.530 |
| mmu_miR_687_001674 | −0.317 | 0.768 | 0.230 | 0.916 | −0.879 | 0.394 |
| mmu_miR_688_001675 | 3.872 | 0.070 | 3.884 | 0.088 | 3.691 | 0.130 |
| mmu_miR_690_001677 | −0.055 | 0.980 | −1.821 | 0.217 | 0.659 | 0.762 |
| mmu_miR_691_001678 | 4.255 | 0.369 | 0.290 | 0.996 | 5.650 | 0.288 |
| mmu_miR_692_001679 | 0.559 | 0.850 | −2.257 | 0.373 | 0.375 | 0.932 |
| mmu_miR_693_001680 | −8.481 | 0.033 | −4.329 | 0.359 | 0.614 | 0.938 |
| mmu_miR_693_3p_002036 | −6.014 | 0.195 | −7.012 | 0.149 | −2.555 | 0.720 |
| mmu_miR_694_001681 | 3.703 | 0.338 | −1.383 | 0.850 | 9.143 | 0.020 |
| mmu_miR_695_001627 | 4.918 | 0.205 | 6.008 | 0.135 | 4.918 | 0.265 |
| mmu_miR_696_001628 | 6.364 | 0.231 | −3.873 | 0.552 | 5.103 | 0.436 |
| mmu_miR_697_001631 | 6.151 | 0.031 | 4.328 | 0.170 | 4.392 | 0.181 |
| mmu_miR_698_001632 | −0.379 | 0.750 | −0.732 | 0.516 | −0.678 | 0.577 |
| mmu_miR_700_001634 | 0.089 | 0.961 | 1.892 | 0.173 | 0.058 | 0.983 |
| mmu_miR_701_001635 | 0.327 | 0.931 | −2.738 | 0.362 | 2.200 | 0.520 |
| mmu_miR_702_001636 | 2.615 | 0.237 | −0.594 | 0.916 | 0.055 | 0.992 |
| mmu_miR_704_001639 | −1.496 | 0.322 | 0.361 | 0.934 | 0.292 | 0.912 |
| mmu_miR_706_001641 | 9.338 | 0.046 | 7.069 | 0.173 | 12.454 | 0.015 |
| mmu_miR_707_001642 | −0.374 | 0.550 | 0.137 | 0.934 | −0.798 | 0.199 |
| mmu_miR_708_002341 | −0.083 | 0.931 | 2.130 | 0.001 | −0.032 | 0.980 |
| mmu_miR_710_001645 | 4.157 | 0.571 | 6.486 | 0.387 | 8.286 | 0.273 |
| mmu_miR_711_001646 | 5.212 | 0.454 | 5.314 | 0.504 | 8.344 | 0.265 |
| mmu_miR_712_001961 | −1.209 | 0.370 | 0.594 | 0.782 | 0.116 | 0.964 |
| mmu_miR_712_002636 | 1.077 | 0.822 | −0.215 | 0.996 | 3.251 | 0.491 |
| mmu_miR_713_001648 | 5.907 | 0.421 | 5.525 | 0.516 | 6.757 | 0.434 |
| mmu_miR_715_001649 | 4.925 | 0.169 | 5.434 | 0.150 | 6.090 | 0.121 |
| mmu_miR_717_001652 | 2.233 | 0.754 | −4.823 | 0.458 | 4.822 | 0.491 |
| mmu_miR_718_001656 | 6.142 | 0.048 | 5.660 | 0.089 | 3.130 | 0.437 |
| mmu_miR_719_001673 | 1.389 | 0.463 | 0.733 | 0.809 | 1.479 | 0.520 |
| mmu_miR_720_001629 | 1.266 | 0.192 | −2.365 | 0.013 | 3.729 | 0.000 |
| mmu_miR_721_001657 | 2.863 | 0.750 | 3.955 | 0.694 | 7.751 | 0.354 |
| mmu_miR_741_002457 | 0.616 | 0.889 | 0.019 | 0.997 | −1.640 | 0.742 |
| mmu_miR_742_002038 | −0.071 | 0.980 | 0.499 | 0.916 | 0.396 | 0.905 |
| mmu_miR_742_002458 | 1.727 | 0.770 | 1.558 | 0.877 | 2.407 | 0.749 |
| mmu_miR_743a_002469 | 2.716 | 0.223 | −1.348 | 0.654 | 3.795 | 0.115 |
| mmu_miR_743b_3p_002471 | −0.318 | 0.822 | 0.267 | 0.934 | −0.286 | 0.885 |
| mmu_miR_743b_5p_002470 | 0.408 | 0.931 | −2.022 | 0.650 | 1.994 | 0.673 |
| mmu_miR_744_002324 | 1.344 | 0.103 | 1.190 | 0.190 | 0.819 | 0.437 |
| mmu_miR_758_002025 | 1.283 | 0.195 | −0.085 | 0.996 | 0.464 | 0.762 |
| mmu_miR_759_002034 | 1.390 | 0.768 | 2.011 | 0.710 | 6.720 | 0.092 |
| mmu_miR_761_002030 | −2.396 | 0.720 | −11.095 | 0.032 | 1.101 | 0.907 |
| mmu_miR_762_002028 | 4.114 | 0.272 | 3.653 | 0.388 | 5.672 | 0.164 |
| mmu_miR_763_002033 | 0.322 | 0.959 | 1.265 | 0.908 | 1.697 | 0.808 |
| mmu_miR_764_3p_002032 | 5.308 | 0.088 | 2.948 | 0.434 | 1.588 | 0.757 |
| mmu_miR_764_5p_002031 | 6.460 | 0.001 | −0.355 | 0.961 | 2.484 | 0.243 |

TABLE 4-continued

| Brain Stem miRNA data. | | | | | | |
|---|---|---|---|---|---|---|
| mmu_miR_767_241081_mat | −0.323 | 0.285 | 0.047 | 0.973 | −1.106 | 0.001 |
| mmu_miR_770_3p_002027 | 4.378 | 0.000 | 0.519 | 0.766 | −0.518 | 0.762 |
| mmu_miR_770_5p_002608 | 3.929 | 0.000 | 1.694 | 0.066 | 1.043 | 0.343 |
| mmu_miR_7a_000268 | −1.920 | 0.457 | −1.076 | 0.788 | 0.403 | 0.932 |
| mmu_miR_7b_002555 | 0.993 | 0.635 | 0.658 | 0.850 | 0.081 | 0.983 |
| mmu_miR_802_002029 | −1.709 | 0.307 | 0.030 | 0.996 | −1.179 | 0.585 |
| mmu_miR_804_002044 | −3.987 | 0.547 | −1.133 | 0.960 | 3.919 | 0.627 |
| mmu_miR_805_002045 | 3.480 | 0.360 | −1.735 | 0.768 | 5.887 | 0.144 |
| mmu_miR_871_002354 | −2.088 | 0.237 | 0.283 | 0.967 | 0.156 | 0.964 |
| mmu_miR_872_002264 | −2.157 | 0.000 | 0.458 | 0.516 | −0.470 | 0.527 |
| mmu_miR_872_002542 | −1.388 | 0.008 | 1.101 | 0.043 | −0.373 | 0.612 |
| mmu_miR_873_002356 | 2.253 | 0.043 | −0.076 | 0.996 | −0.122 | 0.957 |
| mmu_miR_874_002268 | 1.688 | 0.429 | 2.134 | 0.345 | 3.249 | 0.139 |
| mmu_miR_875_3p_002547 | −3.071 | 0.521 | −4.347 | 0.379 | −1.610 | 0.813 |
| mmu_miR_876_3p_002464 | −0.065 | 0.985 | 0.178 | 0.996 | 0.590 | 0.898 |
| mmu_miR_876_5p_002463 | −0.554 | 0.756 | 0.273 | 0.956 | 0.092 | 0.976 |
| mmu_miR_877_002548 | 3.823 | 0.146 | −2.859 | 0.337 | 3.031 | 0.343 |
| mmu_miR_878_3p_002541 | 2.607 | 0.534 | −3.815 | 0.375 | 6.147 | 0.136 |
| mmu_miR_878_5p_002540 | 0.752 | 0.876 | 0.093 | 0.996 | −0.695 | 0.909 |
| mmu_miR_879_002472 | −0.199 | 0.931 | 0.028 | 0.996 | −0.280 | 0.932 |
| mmu_miR_879_002473 | 1.294 | 0.387 | 2.905 | 0.042 | −0.459 | 0.847 |
| mmu_miR_880_002665 | 3.015 | 0.646 | −2.046 | 0.850 | 3.845 | 0.610 |
| mmu_miR_881_002475 | 3.117 | 0.463 | 3.037 | 0.537 | 3.914 | 0.428 |
| mmu_miR_881_002609 | 4.168 | 0.229 | 4.225 | 0.260 | 5.610 | 0.137 |
| mmu_miR_882_002610 | −0.372 | 0.224 | −0.003 | 0.996 | −1.160 | 0.000 |
| mmu_miR_883B_5P_002669 | 3.624 | 0.355 | 4.302 | 0.305 | 4.957 | 0.254 |
| mmu_miR_883a_3p_002461 | 0.289 | 0.929 | 0.391 | 0.956 | 1.643 | 0.524 |
| mmu_miR_883a_5p_002611 | −0.371 | 0.358 | 0.048 | 0.986 | −1.023 | 0.013 |
| mmu_miR_883b_3p_002565 | 1.944 | 0.559 | 1.585 | 0.710 | 1.710 | 0.701 |
| mmu_miR_92a_000430 | 1.009 | 0.013 | −1.840 | 0.000 | 1.970 | 0.000 |
| mmu_miR_92a_002496 | 1.889 | 0.159 | 2.243 | 0.107 | 1.463 | 0.368 |
| mmu_miR_93_001090 | −2.582 | 0.001 | −1.341 | 0.089 | −1.267 | 0.134 |
| mmu_miR_96_000186 | 5.180 | 0.004 | 2.498 | 0.213 | 2.701 | 0.190 |
| mmu_miR_98_000577 | −1.009 | 0.575 | 1.288 | 0.516 | −2.365 | 0.185 |
| mmu_miR_99a_000435 | −2.108 | 0.004 | −0.712 | 0.420 | −0.862 | 0.345 |
| mmu_miR_99b_000436 | −1.169 | 0.231 | 1.168 | 0.271 | 0.364 | 0.813 |
| mmu_miR_9_000583 | −2.581 | 0.000 | −1.007 | 0.009 | −1.042 | 0.011 |
| | log2FC_GFAPvsLyz2_bs | adj.p.value_GFAPvsLyz2_bs | log2FC_GFAPvsSyn_bs | adj.p.value_GFAPvsSyn_bs | log2FC_Lyz2vsSyn_bs | adj.p.value_Lyz2vsSyn_bs |
| hsa_let_7b_002404 | 1.743 | 0.711 | 3.606 | 0.383 | 1.863 | 0.671 |
| hsa_let_7e_002407 | −0.995 | 0.473 | −0.103 | 0.965 | 0.892 | 0.512 |
| hsa_let_7f_1_002417 | 3.746 | 0.128 | 3.018 | 0.237 | −0.728 | 0.817 |
| hsa_let_7i_002172 | 2.167 | 0.042 | 3.197 | 0.003 | 1.030 | 0.348 |
| hsa_miR_106b_002380 | 3.336 | 0.011 | −1.191 | 0.417 | −4.527 | 0.001 |
| hsa_miR_10a_002288 | −0.031 | 0.991 | 0.845 | 0.771 | 0.875 | 0.753 |
| hsa_miR_1197_002810 | −1.823 | 0.315 | −2.746 | 0.112 | −0.923 | 0.638 |
| hsa_miR_124_002197 | −0.491 | 0.875 | 0.179 | 0.963 | 0.669 | 0.810 |
| hsa_miR_127_5p_002229 | −1.427 | 0.208 | −1.289 | 0.278 | 0.138 | 0.937 |
| hsa_miR_136_000592 | −4.399 | 0.000 | −3.073 | 0.001 | 1.326 | 0.134 |
| hsa_miR_136_002100 | 0.042 | 0.990 | −2.268 | 0.285 | −2.310 | 0.238 |

TABLE 4-continued

| Brain Stem miRNA data. | | | | | | |
|---|---|---|---|---|---|---|
| hsa_miR_140_3p_002234 | 0.818 | 0.355 | 0.103 | 0.938 | −0.715 | 0.402 |
| hsa_miR_143_000466 | −0.480 | 0.939 | 2.552 | 0.513 | 3.033 | 0.388 |
| hsa_miR_144_002676 | 0.363 | 0.691 | 1.697 | 0.021 | 1.334 | 0.055 |
| hsa_miR_148a_002134 | 0.243 | 0.952 | −0.743 | 0.819 | −0.986 | 0.735 |
| hsa_miR_149_002255 | −0.245 | 0.784 | −2.267 | 0.001 | −2.023 | 0.001 |
| hsa_miR_151_5P_002642 | 1.549 | 0.172 | 0.682 | 0.611 | −0.867 | 0.459 |
| hsa_miR_154_000478 | −0.543 | 0.715 | −1.458 | 0.247 | −0.915 | 0.466 |
| hsa_miR_15b_002173 | −8.683 | 0.038 | 1.922 | 0.732 | 10.605 | 0.007 |
| hsa_miR_183_002270 | −7.222 | 0.001 | −5.771 | 0.009 | 1.451 | 0.542 |
| hsa_miR_189_000488 | −3.668 | 0.378 | 3.284 | 0.455 | 6.952 | 0.056 |
| hsa_miR_190b_002263 | 0.350 | 0.880 | 2.694 | 0.072 | 2.345 | 0.102 |
| hsa_miR_196a_241070_mat | −3.956 | 0.001 | −7.143 | 0.000 | −3.186 | 0.005 |
| hsa_miR_200a_001011 | 2.790 | 0.075 | 2.742 | 0.077 | −0.048 | 0.983 |
| hsa_miR_200b_001800 | −6.799 | 0.018 | 0.028 | 0.995 | 6.827 | 0.013 |
| hsa_miR_200b_002274 | 1.080 | 0.873 | 1.207 | 0.849 | 0.127 | 0.983 |
| hsa_miR_200c_000505 | −4.967 | 0.003 | 1.186 | 0.543 | 6.152 | 0.000 |
| hsa_miR_200c_002286 | 0.611 | 0.735 | 0.369 | 0.852 | −0.242 | 0.911 |
| hsa_miR_206_000510 | −0.083 | 0.980 | −0.429 | 0.874 | −0.345 | 0.911 |
| hsa_miR_213_000516 | 0.912 | 0.454 | 0.914 | 0.471 | 0.002 | 0.999 |
| hsa_miR_214_000517 | −6.051 | 0.000 | 0.142 | 0.955 | 6.194 | 0.000 |
| hsa_miR_214_002293 | 0.845 | 0.592 | 2.665 | 0.050 | 1.820 | 0.171 |
| hsa_miR_218_2_002294 | −1.019 | 0.468 | −1.460 | 0.287 | −0.441 | 0.796 |
| hsa_miR_223_000526 | −13.552 | 0.000 | 6.012 | 0.040 | 19.565 | 0.000 |
| hsa_miR_22_000398 | 6.334 | 0.005 | 0.932 | 0.761 | −5.402 | 0.011 |
| hsa_miR_22_002301 | −0.401 | 0.727 | 0.574 | 0.601 | 0.976 | 0.279 |
| hsa_miR_23a_002439 | −10.681 | 0.009 | 2.661 | 0.589 | 13.342 | 0.001 |
| hsa_miR_26b_002444 | −0.788 | 0.820 | 1.845 | 0.523 | 2.633 | 0.295 |
| hsa_miR_27a_002445 | −0.116 | 0.977 | 1.947 | 0.417 | 2.063 | 0.351 |
| hsa_miR_27b_002174 | 0.142 | 0.926 | 0.882 | 0.375 | 0.740 | 0.429 |
| hsa_miR_28_3p_002446 | −0.380 | 0.910 | 0.049 | 0.991 | 0.429 | 0.891 |
| hsa_miR_299_5p_000600 | −5.535 | 0.040 | −1.594 | 0.631 | 3.941 | 0.129 |
| hsa_miR_29a_002447 | −3.190 | 0.172 | −0.406 | 0.910 | 2.784 | 0.217 |
| hsa_miR_29b_2_002166 | −1.118 | 0.758 | 0.444 | 0.916 | 1.561 | 0.608 |
| hsa_miR_30a_3p_000416 | 0.025 | 0.977 | 0.445 | 0.383 | 0.420 | 0.376 |
| hsa_miR_30c_1_002108 | 3.250 | 0.363 | 2.700 | 0.477 | −0.550 | 0.918 |
| hsa_miR_30c_2_002110 | −0.874 | 0.895 | −3.946 | 0.389 | −3.072 | 0.490 |
| hsa_miR_30d_002305 | 0.702 | 0.879 | 1.863 | 0.610 | 1.161 | 0.766 |
| hsa_miR_30e_3p_000422 | −1.491 | 0.002 | 0.303 | 0.607 | 1.794 | 0.000 |
| hsa_miR_324_3p_000579 | −0.091 | 0.980 | 0.114 | 0.980 | 0.206 | 0.958 |
| hsa_miR_338_000548 | 2.685 | 0.172 | 0.934 | 0.722 | −1.752 | 0.378 |
| hsa_miR_338_5P_002658 | 1.681 | 0.076 | 0.682 | 0.533 | −0.999 | 0.293 |
| hsa_miR_33a_002136 | 0.631 | 0.772 | −0.571 | 0.803 | −1.202 | 0.484 |
| hsa_miR_340_000550 | 0.790 | 0.404 | 0.198 | 0.874 | −0.592 | 0.533 |
| hsa_miR_363_001283 | 4.606 | 0.138 | 4.537 | 0.141 | −0.069 | 0.983 |
| hsa_miR_376a_001287 | −3.105 | 0.011 | −3.354 | 0.006 | −0.249 | 0.899 |
| hsa_miR_378_000567 | −3.526 | 0.056 | 2.121 | 0.286 | 5.647 | 0.002 |
| hsa_miR_411_002238 | 0.857 | 0.611 | −3.662 | 0.010 | −4.518 | 0.001 |
| hsa_miR_412_001023 | −10.368 | 0.000 | −3.965 | 0.028 | 6.402 | 0.000 |
| hsa_miR_421_002700 | 1.055 | 0.089 | 0.060 | 0.955 | −0.994 | 0.086 |
| hsa_miR_423_3P_002626 | −0.773 | 0.629 | 0.291 | 0.878 | 1.063 | 0.459 |
| hsa_miR_425_001104 | −4.334 | 0.032 | −1.684 | 0.465 | 2.650 | 0.179 |

TABLE 4-continued

Brain Stem miRNA data.

| | | | | | | |
|---|---|---|---|---|---|---|
| hsa_miR_431_002312 | −4.818 | 0.005 | −3.124 | 0.068 | 1.695 | 0.337 |
| hsa_miR_455_001280 | −1.008 | 0.603 | 1.286 | 0.501 | 2.294 | 0.157 |
| hsa_miR_485_5p_001036 | −2.027 | 0.144 | −0.898 | 0.587 | 1.129 | 0.429 |
| hsa_miR_493_3p_001282 | −3.966 | 0.446 | 0.600 | 0.938 | 4.566 | 0.351 |
| hsa_miR_590_3P_002677 | 0.347 | 0.642 | −0.139 | 0.876 | −0.486 | 0.466 |
| hsa_miR_653_002292 | −3.485 | 0.304 | −1.488 | 0.732 | 1.998 | 0.575 |
| hsa_miR_671_5p_197646_mat | −2.712 | 0.557 | 5.655 | 0.177 | 8.367 | 0.028 |
| hsa_miR_708_002342 | −3.391 | 0.134 | −0.328 | 0.926 | 3.064 | 0.155 |
| hsa_miR_744_002325 | −2.986 | 0.004 | −0.995 | 0.383 | 1.991 | 0.038 |
| hsa_miR_875_5p_002203 | −7.678 | 0.272 | 5.578 | 0.465 | 13.257 | 0.034 |
| hsa_miR_935_002178 | 0.159 | 0.967 | 0.522 | 0.852 | 0.363 | 0.911 |
| hsa_miR_93_002139 | 0.653 | 0.578 | 0.677 | 0.585 | 0.024 | 0.983 |
| hsa_miR_99b_002196 | 2.091 | 0.172 | 1.538 | 0.355 | −0.552 | 0.785 |
| hsa_miR_9_002231 | 2.006 | 0.000 | 2.321 | 0.000 | 0.315 | 0.518 |
| mmu_let_7a_000377 | 4.218 | 0.006 | 0.623 | 0.767 | −3.595 | 0.013 |
| mmu_let_7a_002478 | 0.988 | 0.912 | 2.438 | 0.733 | 1.450 | 0.838 |
| mmu_let_7b_000378 | 1.252 | 0.005 | 1.914 | 0.000 | 0.662 | 0.124 |
| mmu_let_7c_000379 | 1.281 | 0.004 | 1.250 | 0.004 | −0.031 | 0.967 |
| mmu_let_7c_1_002479 | −0.112 | 0.980 | 2.093 | 0.582 | 2.205 | 0.513 |
| mmu_let_7d_001178 | 0.936 | 0.322 | −0.324 | 0.798 | −1.260 | 0.146 |
| mmu_let_7d_002283 | 0.744 | 0.204 | 0.723 | 0.229 | −0.021 | 0.979 |
| mmu_let_7e_002406 | −0.328 | 0.806 | 0.017 | 0.991 | 0.345 | 0.793 |
| mmu_let_7f_000382 | 3.390 | 0.284 | 1.172 | 0.771 | −2.218 | 0.492 |
| mmu_let_7g_002282 | 1.332 | 0.078 | 0.613 | 0.472 | −0.718 | 0.352 |
| mmu_let_7g_002492 | −2.484 | 0.123 | 0.213 | 0.934 | 2.697 | 0.070 |
| mmu_let_7i_002221 | 1.689 | 0.002 | 1.557 | 0.005 | −0.132 | 0.869 |
| mmu_miR_100_000437 | 2.387 | 0.001 | 1.623 | 0.019 | −0.764 | 0.274 |
| mmu_miR_101a_002253 | −0.062 | 0.948 | 0.112 | 0.878 | 0.173 | 0.800 |
| mmu_miR_101a_002507 | 1.703 | 0.036 | 0.197 | 0.863 | −1.506 | 0.048 |
| mmu_miR_101b_002531 | 1.118 | 0.078 | 0.292 | 0.732 | −0.825 | 0.179 |
| mmu_miR_103_000439 | −0.527 | 0.579 | −0.641 | 0.501 | −0.114 | 0.933 |
| mmu_miR_105_002465 | −7.552 | 0.172 | −2.178 | 0.767 | 5.374 | 0.329 |
| mmu_miR_106a_002459 | −0.250 | 0.953 | 0.510 | 0.878 | 0.760 | 0.814 |
| mmu_miR_106b_000442 | 0.948 | 0.193 | 0.885 | 0.242 | −0.062 | 0.960 |
| mmu_miR_107_000443 | 1.342 | 0.447 | −0.148 | 0.959 | −1.490 | 0.371 |
| mmu_miR_10a_000387 | −1.626 | 0.231 | −1.811 | 0.180 | −0.186 | 0.933 |
| mmu_miR_10b_001181 | −0.936 | 0.534 | −4.495 | 0.001 | −3.559 | 0.005 |
| mmu_miR_10b_002218 | −4.043 | 0.016 | −12.925 | 0.000 | −8.882 | 0.000 |
| mmu_miR_10b_002572 | −2.846 | 0.237 | −1.679 | 0.535 | 1.167 | 0.671 |
| mmu_miR_1186_002825 | −0.187 | 0.977 | 2.514 | 0.501 | 2.701 | 0.429 |
| mmu_miR_1188_002866 | 2.785 | 0.341 | 2.961 | 0.318 | 0.176 | 0.972 |
| mmu_miR_1191_002892 | −1.323 | 0.801 | 3.700 | 0.376 | 5.023 | 0.171 |
| mmu_miR_1192_002806 | 0.405 | 0.873 | −1.496 | 0.418 | −1.900 | 0.248 |
| mmu_miR_1193_002794 | −0.547 | 0.501 | 0.030 | 0.983 | 0.577 | 0.459 |
| mmu_miR_1194_002793 | 0.257 | 0.869 | −1.704 | 0.099 | −1.961 | 0.042 |
| mmu_miR_1195_002839 | −0.319 | 0.952 | 1.625 | 0.656 | 1.945 | 0.542 |
| mmu_miR_1198_002780 | 4.396 | 0.000 | −0.781 | 0.406 | −5.177 | 0.000 |
| mmu_miR_1199_240984_mat | 0.369 | 0.246 | −0.788 | 0.010 | −1.156 | 0.000 |
| mmu_miR_1224_240985_mat | 0.316 | 0.655 | −1.086 | 0.067 | −1.402 | 0.012 |
| mmu_miR_122_002245 | −5.532 | 0.217 | 0.572 | 0.936 | 6.103 | 0.147 |
| mmu_miR_124_001182 | 0.690 | 0.557 | −0.481 | 0.732 | −1.171 | 0.258 |

TABLE 4-continued

| Brain Stem miRNA data. | | | | | | |
|---|---|---|---|---|---|---|
| mmu_miR_125a_3p_002199 | −0.128 | 0.964 | 0.321 | 0.875 | 0.449 | 0.814 |
| mmu_miR_125a_5p_002198 | 0.934 | 0.059 | −0.220 | 0.742 | −1.154 | 0.013 |
| mmu_miR_125b_002508 | 1.347 | 0.172 | 0.927 | 0.383 | −0.420 | 0.731 |
| mmu_miR_125b_3p_002378 | −0.319 | 0.814 | 1.747 | 0.071 | 2.066 | 0.023 |
| mmu_miR_125b_5p_000449 | 0.871 | 0.089 | 0.455 | 0.418 | −0.416 | 0.430 |
| mmu_miR_126_3p_002228 | −3.922 | 0.000 | −1.483 | 0.004 | 2.439 | 0.000 |
| mmu_miR_126_5p_000451 | −3.813 | 0.000 | −1.633 | 0.004 | 2.180 | 0.000 |
| mmu_miR_1274a_121150_mat | −7.790 | 0.001 | 0.959 | 0.767 | 8.749 | 0.000 |
| mmu_miR_127_000452 | −1.130 | 0.013 | −2.991 | 0.000 | −1.860 | 0.000 |
| mmu_miR_128a_002216 | −0.098 | 0.921 | −0.355 | 0.613 | −0.257 | 0.727 |
| mmu_miR_129_3p_001184 | −0.940 | 0.123 | −2.223 | 0.000 | −1.283 | 0.022 |
| mmu_miR_129_5p_000590 | 1.818 | 0.129 | −1.034 | 0.436 | −2.853 | 0.010 |
| mmu_miR_1306_121155_mat | −0.445 | 0.821 | −0.890 | 0.610 | −0.446 | 0.814 |
| mmu_miR_130a_000454 | 5.977 | 0.000 | 2.168 | 0.182 | −3.809 | 0.011 |
| mmu_miR_130b_000456 | −0.516 | 0.642 | 2.092 | 0.023 | 2.608 | 0.004 |
| mmu_miR_130b_002460 | −2.040 | 0.285 | −3.440 | 0.057 | −1.400 | 0.467 |
| mmu_miR_132_000457 | −0.500 | 0.295 | −2.193 | 0.000 | −1.693 | 0.000 |
| mmu_miR_133a_001637 | 0.125 | 0.973 | −0.517 | 0.832 | −0.641 | 0.785 |
| mmu_miR_133a_002246 | −3.522 | 0.000 | −6.650 | 0.000 | −3.129 | 0.000 |
| mmu_miR_133b_002247 | −1.271 | 0.360 | −2.914 | 0.022 | −1.643 | 0.190 |
| mmu_miR_134_001186 | −0.110 | 0.948 | −4.467 | 0.000 | −4.357 | 0.000 |
| mmu_miR_135a_000460 | 1.227 | 0.030 | −0.496 | 0.438 | −1.723 | 0.002 |
| mmu_miR_135b_002261 | 2.024 | 0.053 | −0.733 | 0.553 | −2.756 | 0.005 |
| mmu_miR_136_002511 | 2.685 | 0.172 | −2.235 | 0.282 | −4.920 | 0.007 |
| mmu_miR_136_002512 | −6.684 | 0.004 | −0.124 | 0.980 | 6.560 | 0.003 |
| mmu_miR_137_001129 | −0.062 | 0.980 | −1.427 | 0.417 | −1.365 | 0.404 |
| mmu_miR_138_002284 | −0.222 | 0.791 | −2.857 | 0.000 | −2.635 | 0.000 |
| mmu_miR_138_002554 | −2.173 | 0.051 | −2.867 | 0.010 | −0.694 | 0.573 |
| mmu_miR_139_3p_002546 | −4.809 | 0.139 | −6.153 | 0.052 | −1.344 | 0.746 |
| mmu_miR_139_5p_002289 | −1.977 | 0.015 | −1.448 | 0.077 | 0.530 | 0.556 |
| mmu_miR_140_001187 | −0.042 | 0.977 | 0.245 | 0.827 | 0.287 | 0.791 |
| mmu_miR_141_000463 | −4.947 | 0.184 | 3.636 | 0.373 | 8.583 | 0.012 |
| mmu_miR_141_002513 | −8.490 | 0.011 | 2.256 | 0.578 | 10.746 | 0.001 |
| mmu_miR_142_3p_000464 | −9.190 | 0.000 | 3.941 | 0.039 | 13.130 | 0.000 |
| mmu_miR_142_5p_002248 | −7.502 | 0.047 | 6.129 | 0.108 | 13.631 | 0.000 |
| mmu_miR_143_002249 | −3.036 | 0.013 | 2.300 | 0.061 | 5.336 | 0.000 |
| mmu_miR_145_002278 | −3.439 | 0.009 | 2.195 | 0.100 | 5.634 | 0.000 |
| mmu_miR_145_002514 | 0.517 | 0.898 | 0.116 | 0.982 | −0.401 | 0.919 |
| mmu_miR_146a_000468 | −5.192 | 0.000 | 1.084 | 0.022 | 6.276 | 0.000 |
| mmu_miR_146b_001097 | −0.376 | 0.471 | 0.266 | 0.655 | 0.642 | 0.165 |
| mmu_miR_146b_002453 | 0.027 | 0.995 | 1.635 | 0.655 | 1.608 | 0.628 |
| mmu_miR_147_002262 | −0.212 | 0.975 | 5.018 | 0.117 | 5.229 | 0.081 |
| mmu_miR_148a_000470 | 5.770 | 0.000 | 1.459 | 0.286 | −4.311 | 0.001 |
| mmu_miR_148b_000471 | 5.548 | 0.000 | 1.382 | 0.194 | −4.166 | 0.000 |
| mmu_miR_150_000473 | −4.458 | 0.000 | 2.360 | 0.012 | 6.818 | 0.000 |
| mmu_miR_150_002570 | −2.752 | 0.355 | −0.002 | 1.000 | 2.750 | 0.329 |
| mmu_miR_151_3p_001190 | 6.625 | 0.000 | 1.679 | 0.053 | −4.946 | 0.000 |
| mmu_miR_152_000475 | 0.683 | 0.392 | 4.983 | 0.000 | 4.300 | 0.000 |
| mmu_miR_153_001191 | −0.915 | 0.543 | −0.358 | 0.850 | 0.557 | 0.746 |
| mmu_miR_154_000477 | −3.145 | 0.020 | −5.577 | 0.000 | −2.432 | 0.058 |
| mmu_miR_155_002571 | −1.545 | 0.117 | 6.872 | 0.000 | 8.417 | 0.000 |

TABLE 4-continued

Brain Stem miRNA data.

| | | | | | | |
|---|---|---|---|---|---|---|
| mmu_miR_15a_000389 | 0.737 | 0.629 | 2.528 | 0.048 | 1.792 | 0.152 |
| mmu_miR_15a_002488 | 0.825 | 0.360 | 1.436 | 0.087 | 0.612 | 0.493 |
| mmu_miR_15b_000390 | −0.096 | 0.907 | 1.552 | 0.002 | 1.648 | 0.001 |
| mmu_miR_16_000391 | −0.876 | 0.053 | 0.539 | 0.265 | 1.415 | 0.001 |
| mmu_miR_16_002489 | −3.005 | 0.018 | 3.707 | 0.004 | 6.712 | 0.000 |
| mmu_miR_17_002308 | −0.743 | 0.399 | 0.457 | 0.655 | 1.201 | 0.125 |
| mmu_miR_17_002543 | −10.000 | 0.005 | −3.422 | 0.387 | 6.578 | 0.049 |
| mmu_miR_181A_2_002687 | 0.513 | 0.783 | −0.555 | 0.767 | −1.069 | 0.459 |
| mmu_miR_181a_000480 | 2.458 | 0.000 | 0.946 | 0.121 | −1.512 | 0.008 |
| mmu_miR_181c_000482 | 0.675 | 0.409 | 0.414 | 0.661 | −0.261 | 0.796 |
| mmu_miR_182_002599 | −3.412 | 0.177 | −2.981 | 0.262 | 0.431 | 0.911 |
| mmu_miR_1839_3p_121203_mat | 1.059 | 0.313 | 0.751 | 0.512 | −0.308 | 0.814 |
| mmu_miR_1839_5p_121135_mat | 4.113 | 0.013 | 0.457 | 0.849 | −3.656 | 0.020 |
| mmu_miR_183_002269 | −3.816 | 0.038 | −3.679 | 0.042 | 0.137 | 0.966 |
| mmu_miR_184_000485 | −7.804 | 0.001 | −2.889 | 0.190 | 4.915 | 0.014 |
| mmu_miR_185_002271 | 5.770 | 0.000 | −0.512 | 0.732 | −6.282 | 0.000 |
| mmu_miR_186_002285 | 0.758 | 0.543 | 1.510 | 0.186 | 0.752 | 0.532 |
| mmu_miR_186_002574 | −4.508 | 0.001 | −0.553 | 0.746 | 3.956 | 0.001 |
| mmu_miR_187_001193 | 5.714 | 0.000 | 1.934 | 0.033 | −3.780 | 0.000 |
| mmu_miR_188_3p_002106 | 0.599 | 0.585 | 0.382 | 0.767 | −0.217 | 0.883 |
| mmu_miR_188_5p_002320 | −3.948 | 0.016 | 1.509 | 0.416 | 5.458 | 0.001 |
| mmu_miR_1893_121170_mat | −3.700 | 0.141 | −0.526 | 0.878 | 3.174 | 0.188 |
| mmu_miR_1894_3p_241002_mat | −4.738 | 0.164 | 2.626 | 0.492 | 7.364 | 0.017 |
| mmu_miR_1894_5p_121144_mat | 2.352 | 0.112 | 3.258 | 0.023 | 0.906 | 0.573 |
| mmu_miR_1896_121128_mat | −5.953 | 0.140 | 5.782 | 0.151 | 11.735 | 0.002 |
| mmu_miR_1897_3p_121126_mat | 0.388 | 0.274 | −0.726 | 0.031 | −1.114 | 0.001 |
| mmu_miR_1897_5p_121199_mat | −2.821 | 0.205 | 1.760 | 0.476 | 4.581 | 0.024 |
| mmu_miR_1898_121195_mat | 0.622 | 0.095 | −0.509 | 0.179 | −1.131 | 0.002 |
| mmu_miR_1899_121198_mat | 0.581 | 0.557 | −0.147 | 0.914 | −0.729 | 0.429 |
| mmu_miR_18a_002422 | −1.903 | 0.161 | 0.798 | 0.617 | 2.701 | 0.028 |
| mmu_miR_18a_002490 | −2.731 | 0.099 | 1.555 | 0.389 | 4.286 | 0.006 |
| mmu_miR_18b_002466 | 1.581 | 0.614 | 1.211 | 0.735 | −0.370 | 0.933 |
| mmu_miR_1900_121143_mat | 0.507 | 0.592 | −0.390 | 0.729 | −0.897 | 0.276 |
| mmu_miR_1901_121183_mat | 3.612 | 0.318 | 1.725 | 0.703 | −1.887 | 0.628 |
| mmu_miR_1902_121197_mat | 0.434 | 0.284 | −0.617 | 0.113 | −1.050 | 0.004 |
| mmu_miR_1903_121153_mat | −1.548 | 0.796 | 3.322 | 0.501 | 4.870 | 0.259 |
| mmu_miR_1904_121162_mat | −4.643 | 0.000 | 1.816 | 0.013 | 6.458 | 0.000 |
| mmu_miR_1905_121196_mat | −3.315 | 0.369 | 3.217 | 0.398 | 6.531 | 0.043 |
| mmu_miR_1906_121169_mat | 2.129 | 0.277 | −0.038 | 0.991 | −2.167 | 0.244 |
| mmu_miR_190_000489 | 0.589 | 0.691 | 0.806 | 0.578 | 0.217 | 0.911 |
| mmu_miR_191_002299 | −0.214 | 0.648 | 0.041 | 0.953 | 0.255 | 0.556 |
| mmu_miR_191_002576 | −0.218 | 0.885 | 1.405 | 0.151 | 1.624 | 0.073 |
| mmu_miR_1927_121193_mat | 3.317 | 0.115 | 2.586 | 0.237 | −0.731 | 0.793 |
| mmu_miR_1928_121164_mat | −3.662 | 0.139 | 5.441 | 0.023 | 9.102 | 0.000 |
| mmu_miR_192_000491 | 1.216 | 0.169 | 1.469 | 0.088 | 0.252 | 0.821 |
| mmu_miR_1930_121201_mat | −2.785 | 0.090 | −0.999 | 0.612 | 1.786 | 0.272 |
| mmu_miR_1931_121168_mat | 1.699 | 0.231 | −0.424 | 0.827 | −2.122 | 0.105 |
| mmu_miR_1932_121172_mat | 5.007 | 0.172 | 5.989 | 0.099 | 0.982 | 0.838 |
| mmu_miR_1933_3p_121145_mat | 0.472 | 0.441 | −0.532 | 0.389 | −1.004 | 0.056 |
| mmu_miR_1933_5p_121133_mat | −4.297 | 0.509 | −0.989 | 0.914 | 3.308 | 0.619 |
| mmu_miR_1934_121185_mat | 8.094 | 0.009 | 8.975 | 0.004 | 0.881 | 0.829 |

TABLE 4-continued

| Brain Stem miRNA data. | | | | | | |
|---|---|---|---|---|---|---|
| mmu_miR_1935_121192_mat | 0.607 | 0.821 | −1.685 | 0.439 | −2.292 | 0.231 |
| mmu_miR_1936_121158_mat | 0.465 | 0.814 | 0.025 | 0.991 | −0.440 | 0.814 |
| mmu_miR_1937b_241023_mat | −3.116 | 0.766 | 2.543 | 0.819 | 5.658 | 0.498 |
| mmu_miR_1937c_241011_mat | −3.210 | 0.000 | 2.396 | 0.000 | 5.606 | 0.000 |
| mmu_miR_1938_121194_mat | 0.579 | 0.816 | 0.834 | 0.732 | 0.254 | 0.933 |
| mmu_miR_1939_121180_mat | −0.157 | 0.977 | −1.439 | 0.732 | −1.281 | 0.746 |
| mmu_miR_193_002250 | 2.666 | 0.430 | 3.311 | 0.322 | 0.645 | 0.896 |
| mmu_miR_193_002577 | 1.088 | 0.175 | 1.069 | 0.187 | −0.019 | 0.983 |
| mmu_miR_193b_002467 | 3.080 | 0.000 | 0.753 | 0.313 | −2.327 | 0.001 |
| mmu_miR_1940_121187_mat | −6.937 | 0.007 | 0.198 | 0.967 | 7.135 | 0.004 |
| mmu_miR_1941_3p_121130_mat | 0.623 | 0.323 | 0.862 | 0.154 | 0.239 | 0.753 |
| mmu_miR_1941_5p_121140_mat | −1.056 | 0.636 | 2.832 | 0.138 | 3.888 | 0.027 |
| mmu_miR_1942_121136_mat | −5.311 | 0.373 | 4.383 | 0.494 | 9.695 | 0.063 |
| mmu_miR_1943_121174_mat | 0.918 | 0.416 | 0.894 | 0.445 | −0.025 | 0.983 |
| mmu_miR_1944_121189_mat | 1.851 | 0.463 | 0.087 | 0.985 | −1.764 | 0.467 |
| mmu_miR_1945_121166_mat | 0.420 | 0.672 | −0.444 | 0.672 | −0.864 | 0.299 |
| mmu_miR_1946a_121178_mat | −11.404 | 0.001 | −2.798 | 0.482 | 8.606 | 0.009 |
| mmu_miR_1947_121156_mat | 3.132 | 0.139 | 2.422 | 0.280 | −0.710 | 0.797 |
| mmu_miR_1948_121171_mat | −0.710 | 0.811 | −1.352 | 0.603 | −0.643 | 0.817 |
| mmu_miR_1949_121182_mat | 0.468 | 0.598 | −1.238 | 0.109 | −1.706 | 0.018 |
| mmu_miR_194_000493 | −0.003 | 0.998 | 1.328 | 0.281 | 1.331 | 0.240 |
| mmu_miR_1950_121146_mat | 0.441 | 0.869 | −0.523 | 0.832 | −0.964 | 0.632 |
| mmu_miR_1951_121165_mat | −11.535 | 0.105 | 2.800 | 0.767 | 14.335 | 0.028 |
| mmu_miR_1952_121167_mat | 0.406 | 0.271 | −0.682 | 0.052 | −1.088 | 0.002 |
| mmu_miR_1953_121159_mat | 0.739 | 0.502 | 0.391 | 0.771 | −0.348 | 0.796 |
| mmu_miR_1954_121137_mat | −5.869 | 0.013 | 6.770 | 0.005 | 12.639 | 0.000 |
| mmu_miR_1956_121129_mat | 1.408 | 0.815 | −0.487 | 0.948 | −1.894 | 0.731 |
| mmu_miR_1957_121163_mat | 0.369 | 0.246 | −0.788 | 0.010 | −1.156 | 0.000 |
| mmu_miR_1958_121181_mat | 0.330 | 0.935 | −1.951 | 0.439 | −2.281 | 0.318 |
| mmu_miR_1959_121132_mat | −5.655 | 0.001 | 2.447 | 0.128 | 8.102 | 0.000 |
| mmu_miR_195_000494 | 0.482 | 0.498 | 2.408 | 0.000 | 1.926 | 0.002 |
| mmu_miR_1960_121148_mat | 2.893 | 0.118 | 2.816 | 0.125 | −0.077 | 0.977 |
| mmu_miR_1961_197391_mat | −2.321 | 0.642 | 7.848 | 0.061 | 10.170 | 0.010 |
| mmu_miR_1962_121173_mat | −0.690 | 0.633 | −0.130 | 0.952 | 0.560 | 0.712 |
| mmu_miR_1963_121191_mat | 0.369 | 0.246 | −0.788 | 0.010 | −1.156 | 0.000 |
| mmu_miR_1964_121138_mat | 0.946 | 0.435 | 2.472 | 0.024 | 1.526 | 0.156 |
| mmu_miR_1965_121186_mat | −0.044 | 0.948 | −0.761 | 0.032 | −0.718 | 0.033 |
| mmu_miR_1966_121134_mat | 0.336 | 0.552 | −0.725 | 0.152 | −1.061 | 0.023 |
| mmu_miR_1967_121151_mat | 0.377 | 0.468 | −0.728 | 0.127 | −1.105 | 0.013 |
| mmu_miR_1968_121179_mat | −0.126 | 0.980 | 0.882 | 0.849 | 1.008 | 0.814 |
| mmu_miR_1969_121131_mat | −6.717 | 0.001 | 1.687 | 0.449 | 8.404 | 0.000 |
| mmu_miR_196a_002477 | −4.300 | 0.524 | 2.776 | 0.732 | 7.076 | 0.239 |
| mmu_miR_196b_002215 | −6.805 | 0.001 | −5.035 | 0.010 | 1.771 | 0.377 |
| mmu_miR_1970_121202_mat | −9.720 | 0.001 | 0.124 | 0.983 | 9.844 | 0.001 |
| mmu_miR_1971_121161_mat | −6.813 | 0.043 | −3.587 | 0.330 | 3.226 | 0.353 |
| mmu_miR_197_000497 | −8.174 | 0.056 | 1.238 | 0.836 | 9.412 | 0.019 |
| mmu_miR_1981_121200_mat | 0.017 | 0.990 | −1.826 | 0.040 | −1.844 | 0.028 |
| mmu_miR_1982.1_121157_mat | −0.651 | 0.715 | −1.086 | 0.501 | −0.435 | 0.815 |
| mmu_miR_1982.2_121154_mat | −4.781 | 0.034 | −1.772 | 0.494 | 3.009 | 0.170 |
| mmu_miR_199a_3p_002304 | −1.524 | 0.342 | 1.486 | 0.375 | 3.010 | 0.032 |
| mmu_miR_199a_5p_000498 | 1.770 | 0.458 | 0.301 | 0.930 | −1.469 | 0.533 |

TABLE 4-continued

| Brain Stem miRNA data. | | | | | | |
|---|---|---|---|---|---|---|
| mmu_miR_199b_001131 | −1.038 | 0.664 | −1.683 | 0.457 | −0.646 | 0.812 |
| mmu_miR_19a_000395 | −0.265 | 0.751 | 1.866 | 0.004 | 2.131 | 0.001 |
| mmu_miR_19a_002544 | 0.614 | 0.268 | −0.078 | 0.926 | −0.692 | 0.181 |
| mmu_miR_19b_000396 | −0.475 | 0.585 | 0.653 | 0.443 | 1.128 | 0.120 |
| mmu_miR_1_002222 | −7.030 | 0.000 | −4.415 | 0.013 | 2.615 | 0.130 |
| mmu_miR_1_2_AS_002882 | −2.363 | 0.579 | 6.500 | 0.079 | 8.863 | 0.011 |
| mmu_miR_200a_000502 | −0.722 | 0.858 | 2.290 | 0.454 | 3.012 | 0.262 |
| mmu_miR_200b_002251 | −1.715 | 0.753 | 3.178 | 0.501 | 4.893 | 0.227 |
| mmu_miR_200c_002300 | −3.930 | 0.197 | 1.073 | 0.798 | 5.002 | 0.074 |
| mmu_miR_201_002578 | 0.610 | 0.842 | 0.836 | 0.771 | 0.226 | 0.955 |
| mmu_miR_202_3p_001195 | −2.574 | 0.459 | 1.926 | 0.615 | 4.500 | 0.141 |
| mmu_miR_202_5p_002579 | 4.705 | 0.007 | 5.761 | 0.001 | 1.056 | 0.582 |
| mmu_miR_203_000507 | −0.078 | 0.983 | 3.005 | 0.243 | 3.084 | 0.192 |
| mmu_miR_203_002580 | 0.553 | 0.910 | 3.271 | 0.299 | 2.719 | 0.369 |
| mmu_miR_204_000508 | 1.927 | 0.001 | 4.040 | 0.000 | 2.113 | 0.000 |
| mmu_miR_205_000509 | −2.327 | 0.468 | −3.204 | 0.313 | −0.877 | 0.817 |
| mmu_miR_207_001198 | 0.439 | 0.789 | −1.274 | 0.326 | −1.713 | 0.138 |
| mmu_miR_208_000511 | 4.600 | 0.373 | 5.222 | 0.316 | 0.622 | 0.937 |
| mmu_miR_208b_002290 | −5.190 | 0.217 | −0.860 | 0.880 | 4.329 | 0.294 |
| mmu_miR_20a_000580 | −1.080 | 0.096 | 0.631 | 0.376 | 1.711 | 0.005 |
| mmu_miR_20a_002491 | −0.785 | 0.766 | 2.237 | 0.289 | 3.022 | 0.109 |
| mmu_miR_20b_001014 | −0.666 | 0.766 | 0.663 | 0.767 | 1.329 | 0.450 |
| mmu_miR_20b_002524 | 0.362 | 0.921 | −0.900 | 0.759 | −1.262 | 0.592 |
| mmu_miR_210_000512 | 1.555 | 0.318 | 0.504 | 0.809 | −1.052 | 0.503 |
| mmu_miR_211_001199 | −0.335 | 0.977 | 1.450 | 0.852 | 1.786 | 0.814 |
| mmu_miR_212_002551 | −0.041 | 0.980 | −2.487 | 0.028 | −2.446 | 0.023 |
| mmu_miR_2134_241120_mat | −4.248 | 0.011 | 2.331 | 0.179 | 6.578 | 0.000 |
| mmu_miR_2135_241140_mat | −1.130 | 0.926 | 1.059 | 0.926 | 2.190 | 0.815 |
| mmu_miR_2136_241133_mat | −3.803 | 0.670 | −2.384 | 0.819 | 1.420 | 0.908 |
| mmu_miR_2138_241080_mat | −5.691 | 0.095 | 8.250 | 0.013 | 13.941 | 0.000 |
| mmu_miR_2139_241130_mat | 0.116 | 0.975 | −0.604 | 0.809 | −0.720 | 0.750 |
| mmu_miR_2146_241082_mat | −4.020 | 0.274 | 3.504 | 0.375 | 7.523 | 0.023 |
| mmu_miR_214_002306 | −2.819 | 0.079 | 1.066 | 0.581 | 3.885 | 0.010 |
| mmu_miR_215_001200 | −0.809 | 0.768 | 1.954 | 0.389 | 2.763 | 0.165 |
| mmu_miR_216a_002220 | −5.553 | 0.001 | −7.686 | 0.000 | −2.133 | 0.152 |
| mmu_miR_216b_002326 | −3.753 | 0.018 | −6.503 | 0.000 | −2.750 | 0.070 |
| mmu_miR_217_001133 | −5.749 | 0.001 | −2.971 | 0.090 | 2.778 | 0.093 |
| mmu_miR_217_002556 | −3.312 | 0.015 | −2.474 | 0.070 | 0.837 | 0.582 |
| mmu_miR_2182_241119_mat | 0.948 | 0.816 | 1.247 | 0.760 | 0.300 | 0.956 |
| mmu_miR_2183_241095_mat | −4.714 | 0.039 | 4.358 | 0.055 | 9.072 | 0.000 |
| mmu_miR_218_000521 | 0.041 | 0.966 | −1.978 | 0.000 | −2.018 | 0.000 |
| mmu_miR_218_1_002552 | −1.386 | 0.270 | −3.529 | 0.004 | −2.144 | 0.057 |
| mmu_miR_219_000522 | 4.133 | 0.001 | 0.316 | 0.847 | −3.817 | 0.001 |
| mmu_miR_21_000397 | −2.161 | 0.010 | 0.489 | 0.640 | 2.650 | 0.001 |
| mmu_miR_21_002493 | 0.370 | 0.859 | −0.070 | 0.980 | −0.440 | 0.814 |
| mmu_miR_220_002468 | 0.376 | 0.339 | −0.968 | 0.009 | −1.343 | 0.000 |
| mmu_miR_221_000524 | 0.672 | 0.141 | 1.717 | 0.000 | 1.045 | 0.013 |
| mmu_miR_222_002276 | −0.641 | 0.056 | 0.292 | 0.439 | 0.934 | 0.004 |
| mmu_miR_223_002295 | −14.050 | 0.000 | 3.501 | 0.000 | 17.551 | 0.000 |
| mmu_miR_224_002553 | 2.017 | 0.073 | 1.570 | 0.168 | −0.448 | 0.753 |
| mmu_miR_23a_000399 | 1.029 | 0.572 | 1.860 | 0.278 | 0.831 | 0.648 |

TABLE 4-continued

| Brain Stem miRNA data. | | | | | | |
|---|---|---|---|---|---|---|
| mmu_miR_23b_000400 | 0.299 | 0.836 | 1.169 | 0.285 | 0.870 | 0.411 |
| mmu_miR_24_000402 | −0.884 | 0.002 | 0.005 | 0.991 | 0.889 | 0.001 |
| mmu_miR_24_2_002494 | −0.357 | 0.760 | 2.013 | 0.020 | 2.371 | 0.004 |
| mmu_miR_25_000403 | −0.647 | 0.664 | 2.262 | 0.068 | 2.908 | 0.013 |
| mmu_miR_26a_000405 | −0.110 | 0.836 | 0.671 | 0.075 | 0.781 | 0.027 |
| mmu_miR_26b_000407 | −0.153 | 0.806 | 1.388 | 0.003 | 1.540 | 0.001 |
| mmu_miR_27a_000408 | 1.038 | 0.409 | 2.887 | 0.012 | 1.848 | 0.093 |
| mmu_miR_27b_000409 | 0.907 | 0.117 | 0.108 | 0.899 | −0.799 | 0.147 |
| mmu_miR_28_000411 | 0.004 | 0.998 | 3.372 | 0.061 | 3.368 | 0.047 |
| mmu_miR_28_002545 | −0.854 | 0.715 | 0.637 | 0.809 | 1.490 | 0.446 |
| mmu_miR_290_000187 | −14.643 | 0.000 | 1.932 | 0.678 | 16.575 | 0.000 |
| mmu_miR_290_3p_002591 | 0.394 | 0.247 | −0.715 | 0.028 | −1.109 | 0.001 |
| mmu_miR_290_5p_002590 | −2.117 | 0.614 | 2.004 | 0.655 | 4.121 | 0.247 |
| mmu_miR_291_3p_001135 | 0.312 | 0.763 | −1.559 | 0.040 | −1.871 | 0.010 |
| mmu_miR_291_5p_001202 | 0.342 | 0.510 | −0.730 | 0.124 | −1.072 | 0.015 |
| mmu_miR_291a_3p_002592 | 0.392 | 0.237 | −0.723 | 0.023 | −1.115 | 0.001 |
| mmu_miR_291b_3p_002538 | 0.536 | 0.400 | −0.297 | 0.703 | −0.833 | 0.145 |
| mmu_miR_291b_5p_002537 | 0.375 | 0.462 | −0.767 | 0.100 | −1.142 | 0.009 |
| mmu_miR_292_3p_001054 | 0.098 | 0.980 | −0.649 | 0.852 | −0.746 | 0.817 |
| mmu_miR_292_3p_002593 | −2.230 | 0.715 | 0.772 | 0.921 | 3.003 | 0.575 |
| mmu_miR_292_5p_001055 | 4.017 | 0.431 | 5.394 | 0.282 | 1.377 | 0.820 |
| mmu_miR_293_001794 | −5.292 | 0.304 | 0.366 | 0.968 | 5.658 | 0.244 |
| mmu_miR_293_002594 | 1.027 | 0.615 | −0.573 | 0.819 | −1.600 | 0.376 |
| mmu_miR_294_001056 | −2.043 | 0.648 | 3.654 | 0.383 | 5.697 | 0.114 |
| mmu_miR_294_002595 | 0.369 | 0.246 | −0.788 | 0.010 | −1.156 | 0.000 |
| mmu_miR_295_000189 | −1.092 | 0.527 | 0.895 | 0.640 | 1.988 | 0.188 |
| mmu_miR_295_002596 | −6.685 | 0.002 | −0.751 | 0.803 | 5.934 | 0.003 |
| mmu_miR_296_3p_002101 | 0.348 | 0.907 | 3.247 | 0.066 | 2.899 | 0.084 |
| mmu_miR_296_5p_000527 | 3.034 | 0.011 | 0.678 | 0.655 | −2.355 | 0.037 |
| mmu_miR_297a_002454 | 2.748 | 0.005 | 2.689 | 0.006 | −0.059 | 0.972 |
| mmu_miR_297b_5p_001626 | 1.882 | 0.172 | 2.844 | 0.031 | 0.962 | 0.501 |
| mmu_miR_297c_002480 | 1.372 | 0.478 | 2.566 | 0.154 | 1.194 | 0.535 |
| mmu_miR_298_002598 | −2.500 | 0.127 | −5.626 | 0.001 | −3.126 | 0.038 |
| mmu_miR_299_002612 | 0.369 | 0.246 | −0.788 | 0.010 | −1.156 | 0.000 |
| mmu_miR_29a_002112 | 0.405 | 0.439 | −0.869 | 0.068 | −1.275 | 0.005 |
| mmu_miR_29b_000413 | −0.172 | 0.924 | −1.047 | 0.375 | −0.875 | 0.429 |
| mmu_miR_29b_002497 | −3.681 | 0.001 | 3.138 | 0.004 | 6.818 | 0.000 |
| mmu_miR_29c_000587 | 0.666 | 0.117 | −0.707 | 0.092 | −1.373 | 0.001 |
| mmu_miR_300_000191 | 0.040 | 0.991 | −2.722 | 0.323 | −2.761 | 0.277 |
| mmu_miR_300_002613 | −2.501 | 0.056 | −2.986 | 0.022 | −0.486 | 0.784 |
| mmu_miR_301a_000528 | 0.468 | 0.431 | 0.588 | 0.316 | 0.120 | 0.886 |
| mmu_miR_301b_002600 | 1.066 | 0.117 | 0.277 | 0.761 | −0.789 | 0.234 |
| mmu_miR_302a_000529 | −6.367 | 0.194 | −3.510 | 0.531 | 2.857 | 0.592 |
| mmu_miR_302a_002615 | −0.290 | 0.952 | 0.185 | 0.971 | 0.475 | 0.911 |
| mmu_miR_302b_000531 | 2.626 | 0.306 | 1.118 | 0.732 | −1.508 | 0.575 |
| mmu_miR_302b_001307 | −5.148 | 0.120 | 0.421 | 0.938 | 5.569 | 0.069 |
| mmu_miR_302c_002557 | 3.903 | 0.102 | 3.419 | 0.152 | −0.484 | 0.899 |
| mmu_miR_302c_002558 | −2.557 | 0.554 | 2.316 | 0.615 | 4.873 | 0.190 |
| mmu_miR_302d_000535 | 0.743 | 0.869 | 0.567 | 0.899 | −0.176 | 0.972 |
| mmu_miR_30a_000417 | 0.128 | 0.816 | 0.879 | 0.025 | 0.751 | 0.044 |
| mmu_miR_30b_000602 | −0.238 | 0.558 | −0.025 | 0.971 | 0.213 | 0.594 |

TABLE 4-continued

| Brain Stem miRNA data. | | | | | | |
|---|---|---|---|---|---|---|
| mmu__miR__30b__002498 | 1.235 | 0.520 | 1.019 | 0.632 | −0.216 | 0.937 |
| mmu__miR__30c__000419 | −0.039 | 0.948 | −0.075 | 0.864 | −0.037 | 0.944 |
| mmu__miR__30d__000420 | 0.864 | 0.186 | 1.338 | 0.034 | 0.474 | 0.488 |
| mmu__miR__30e__002223 | 0.610 | 0.040 | 1.137 | 0.000 | 0.527 | 0.059 |
| mmu__miR__31__000185 | −1.055 | 0.161 | −1.068 | 0.151 | −0.013 | 0.986 |
| mmu__miR__31__002495 | −2.466 | 0.237 | −1.833 | 0.416 | 0.634 | 0.814 |
| mmu__miR__320__002277 | 1.209 | 0.003 | 1.516 | 0.000 | 0.307 | 0.475 |
| mmu__miR__322__001059 | −3.753 | 0.360 | −0.386 | 0.954 | 3.367 | 0.393 |
| mmu__miR__322__001076 | −0.584 | 0.801 | −0.507 | 0.829 | 0.078 | 0.977 |
| mmu__miR__322__002506 | −2.125 | 0.227 | −1.958 | 0.285 | 0.167 | 0.956 |
| mmu__miR__323__3p__002227 | 0.819 | 0.378 | −2.946 | 0.001 | −3.765 | 0.000 |
| mmu__miR__324__3p__002509 | 3.130 | 0.002 | 0.257 | 0.856 | −2.873 | 0.004 |
| mmu__miR__324__5p__000539 | 0.835 | 0.510 | −0.162 | 0.928 | −0.997 | 0.402 |
| mmu__miR__325__001060 | −5.578 | 0.131 | 0.036 | 0.995 | 5.615 | 0.104 |
| mmu__miR__325__002510 | 5.039 | 0.000 | −0.746 | 0.498 | −5.785 | 0.000 |
| mmu__miR__326__001061 | −18.082 | 0.001 | −4.252 | 0.472 | 13.829 | 0.005 |
| mmu__miR__327__002481 | 0.834 | 0.520 | −0.059 | 0.980 | −0.892 | 0.468 |
| mmu__miR__328__000543 | −0.153 | 0.792 | −0.627 | 0.145 | −0.473 | 0.262 |
| mmu__miR__329__000192 | 0.725 | 0.538 | −2.362 | 0.023 | −3.087 | 0.002 |
| mmu__miR__32__002109 | 0.341 | 0.943 | 1.667 | 0.590 | 1.327 | 0.652 |
| mmu__miR__330__001062 | −3.867 | 0.373 | −2.647 | 0.589 | 1.219 | 0.817 |
| mmu__miR__330__002230 | −3.631 | 0.004 | −2.357 | 0.061 | 1.274 | 0.322 |
| mmu__miR__331__3p__000545 | 0.974 | 0.092 | 0.412 | 0.535 | −0.562 | 0.336 |
| mmu__miR__331__5p__002233 | −2.341 | 0.385 | 3.610 | 0.155 | 5.951 | 0.011 |
| mmu__miR__335__3p__002185 | 2.294 | 0.078 | −4.909 | 0.000 | −7.204 | 0.000 |
| mmu__miR__335__5p__000546 | −1.189 | 0.041 | −2.628 | 0.000 | −1.439 | 0.009 |
| mmu__miR__337__000193 | 0.991 | 0.493 | −0.725 | 0.656 | −1.716 | 0.179 |
| mmu__miR__337__3p__002532 | 0.780 | 0.547 | −1.564 | 0.187 | −2.344 | 0.029 |
| mmu__miR__337__5p__002515 | 0.941 | 0.703 | 0.207 | 0.953 | −0.734 | 0.784 |
| mmu__miR__338__3p__002252 | 4.599 | 0.000 | 0.489 | 0.756 | −4.110 | 0.000 |
| mmu__miR__339__3p__002533 | −0.666 | 0.804 | 2.210 | 0.287 | 2.876 | 0.123 |
| mmu__miR__339__5p__002257 | 0.956 | 0.468 | 1.142 | 0.389 | 0.187 | 0.921 |
| mmu__miR__340__3p__002259 | 0.394 | 0.363 | 0.247 | 0.613 | −0.147 | 0.785 |
| mmu__miR__340__5p__002258 | 1.469 | 0.001 | 0.496 | 0.262 | −0.973 | 0.012 |
| mmu__miR__342__3p__002260 | −1.697 | 0.000 | −1.636 | 0.000 | 0.061 | 0.925 |
| mmu__miR__342__5p__002527 | −0.459 | 0.814 | −2.366 | 0.092 | −1.907 | 0.160 |
| mmu__miR__343__002483 | 0.365 | 0.598 | −0.738 | 0.246 | −1.103 | 0.049 |
| mmu__miR__344__001063 | 3.060 | 0.005 | −0.413 | 0.780 | −3.473 | 0.001 |
| mmu__miR__345__001137 | 1.389 | 0.169 | 1.577 | 0.109 | 0.188 | 0.908 |
| mmu__miR__345__3p__002529 | 1.289 | 0.298 | 1.195 | 0.362 | −0.094 | 0.963 |
| mmu__miR__345__5p__002528 | 4.297 | 0.000 | 1.137 | 0.127 | −3.161 | 0.000 |
| mmu__miR__346__001064 | −0.653 | 0.715 | −1.205 | 0.455 | −0.552 | 0.766 |
| mmu__miR__34a__000426 | −1.773 | 0.003 | −4.146 | 0.000 | −2.373 | 0.000 |
| mmu__miR__34b__001065 | 0.486 | 0.806 | 2.372 | 0.100 | 1.885 | 0.177 |
| mmu__miR__34b__3p__002618 | 2.585 | 0.000 | 1.844 | 0.000 | −0.741 | 0.116 |
| mmu__miR__34b__5p__002617 | 0.872 | 0.575 | 2.333 | 0.086 | 1.461 | 0.282 |
| mmu__miR__34c__000428 | 6.933 | 0.000 | 2.245 | 0.007 | −4.688 | 0.000 |
| mmu__miR__34c__002584 | 1.916 | 0.002 | 1.952 | 0.002 | 0.037 | 0.972 |
| mmu__miR__350__002530 | 1.177 | 0.033 | 1.088 | 0.048 | −0.089 | 0.919 |
| mmu__miR__351__001067 | 0.542 | 0.698 | 0.169 | 0.926 | −0.373 | 0.804 |
| mmu__miR__361__000554 | 0.778 | 0.642 | 0.021 | 0.992 | −0.757 | 0.639 |

TABLE 4-continued

| Brain Stem miRNA data. | | | | | | |
|---|---|---|---|---|---|---|
| mmu_miR_362_3p_002616 | −1.504 | 0.134 | 1.101 | 0.297 | 2.605 | 0.005 |
| mmu_miR_362_5p_002614 | −0.987 | 0.268 | 0.825 | 0.383 | 1.812 | 0.023 |
| mmu_miR_363_001271 | 0.107 | 0.980 | 0.105 | 0.983 | −0.002 | 0.999 |
| mmu_miR_365_001020 | 5.937 | 0.000 | 3.445 | 0.000 | −2.492 | 0.003 |
| mmu_miR_367_000555 | 1.795 | 0.787 | 1.322 | 0.849 | −0.474 | 0.956 |
| mmu_miR_369_3p_000557 | −0.539 | 0.648 | −2.281 | 0.020 | −1.742 | 0.061 |
| mmu_miR_369_5p_001021 | −2.760 | 0.008 | −3.961 | 0.000 | −1.201 | 0.244 |
| mmu_miR_370_001068 | 0.480 | 0.869 | −0.566 | 0.829 | −1.046 | 0.627 |
| mmu_miR_370_002275 | 2.378 | 0.001 | −3.706 | 0.000 | −6.084 | 0.000 |
| mmu_miR_374_002043 | 0.447 | 0.964 | 5.081 | 0.370 | 4.634 | 0.376 |
| mmu_miR_374_5p_001319 | 3.356 | 0.386 | 0.242 | 0.971 | −3.114 | 0.404 |
| mmu_miR_375_000564 | 4.653 | 0.000 | 3.281 | 0.008 | −1.372 | 0.261 |
| mmu_miR_376a_001069 | −0.426 | 0.454 | −2.610 | 0.000 | −2.184 | 0.000 |
| mmu_miR_376a_002482 | −2.544 | 0.203 | −3.781 | 0.050 | −1.237 | 0.565 |
| mmu_miR_376b_002451 | −0.399 | 0.957 | −2.535 | 0.606 | −2.135 | 0.643 |
| mmu_miR_376b_002452 | 1.021 | 0.363 | −3.115 | 0.004 | −4.135 | 0.000 |
| mmu_miR_376c_002450 | 0.123 | 0.856 | −1.285 | 0.005 | −1.408 | 0.001 |
| mmu_miR_376c_002523 | 1.285 | 0.618 | 0.863 | 0.771 | −0.422 | 0.908 |
| mmu_miR_377_000566 | 0.389 | 0.893 | 0.475 | 0.852 | 0.086 | 0.977 |
| mmu_miR_379_001138 | 0.184 | 0.924 | −1.924 | 0.091 | −2.108 | 0.047 |
| mmu_miR_380_3p_001071 | −4.013 | 0.000 | −4.679 | 0.000 | −0.667 | 0.541 |
| mmu_miR_380_5p_002601 | −1.426 | 0.034 | −3.536 | 0.000 | −2.110 | 0.001 |
| mmu_miR_381_000571 | −1.501 | 0.373 | −1.287 | 0.472 | 0.214 | 0.933 |
| mmu_miR_382_000572 | 4.084 | 0.003 | −4.582 | 0.001 | −8.666 | 0.000 |
| mmu_miR_383_001767 | −1.204 | 0.071 | −4.559 | 0.000 | −3.355 | 0.000 |
| mmu_miR_384_3p_002603 | −0.177 | 0.833 | −1.600 | 0.007 | −1.423 | 0.011 |
| mmu_miR_384_5p_002602 | −0.444 | 0.274 | −2.254 | 0.000 | −1.811 | 0.000 |
| mmu_miR_409_3p_002332 | −0.348 | 0.816 | −2.696 | 0.012 | −2.348 | 0.020 |
| mmu_miR_409_5p_002331 | −2.300 | 0.018 | −4.909 | 0.000 | −2.609 | 0.005 |
| mmu_miR_410_001274 | 0.411 | 0.413 | −2.825 | 0.000 | −3.236 | 0.000 |
| mmu_miR_411_001610 | 0.212 | 0.825 | −1.693 | 0.013 | −1.905 | 0.004 |
| mmu_miR_412_002575 | −0.036 | 0.980 | −4.737 | 0.000 | −4.700 | 0.000 |
| mmu_miR_423_5p_002340 | 1.403 | 0.139 | 0.424 | 0.733 | −0.978 | 0.298 |
| mmu_miR_425_001516 | −5.001 | 0.015 | 3.972 | 0.053 | 8.973 | 0.000 |
| mmu_miR_429_001077 | −2.575 | 0.362 | 0.790 | 0.829 | 3.365 | 0.188 |
| mmu_miR_431_001979 | −1.187 | 0.294 | −5.465 | 0.000 | −4.278 | 0.000 |
| mmu_miR_432_241135_mat | 1.371 | 0.783 | 0.542 | 0.926 | −0.829 | 0.883 |
| mmu_miR_433_001028 | −0.385 | 0.478 | −3.219 | 0.000 | −2.834 | 0.000 |
| mmu_miR_433_5p_001078 | −6.177 | 0.053 | −4.828 | 0.136 | 1.350 | 0.746 |
| mmu_miR_434_3p_002604 | −1.441 | 0.004 | −3.012 | 0.000 | −1.570 | 0.001 |
| mmu_miR_434_5p_002581 | −1.005 | 0.446 | −3.460 | 0.004 | −2.456 | 0.029 |
| mmu_miR_448_001029 | −2.756 | 0.109 | −4.992 | 0.004 | −2.237 | 0.174 |
| mmu_miR_449a_001030 | −3.399 | 0.018 | 0.254 | 0.910 | 3.653 | 0.008 |
| mmu_miR_449b_001667 | −3.005 | 0.134 | −0.191 | 0.955 | 2.814 | 0.138 |
| mmu_miR_449b_002539 | 0.391 | 0.237 | −0.725 | 0.022 | −1.116 | 0.000 |
| mmu_miR_450B_3P_002632 | −6.199 | 0.041 | −1.497 | 0.716 | 4.702 | 0.105 |
| mmu_miR_450a_3p_002525 | 0.369 | 0.246 | −0.788 | 0.010 | −1.156 | 0.000 |
| mmu_miR_450a_5p_002303 | 1.345 | 0.397 | 1.133 | 0.501 | −0.212 | 0.932 |
| mmu_miR_450b_5p_001962 | 0.445 | 0.478 | −0.552 | 0.386 | −0.997 | 0.065 |
| mmu_miR_451_001141 | −2.998 | 0.419 | 7.167 | 0.033 | 10.165 | 0.002 |
| mmu_miR_452_001032 | −2.770 | 0.478 | −0.177 | 0.980 | 2.593 | 0.494 |

TABLE 4-continued

| Brain Stem miRNA data. | | | | | | |
|---|---|---|---|---|---|---|
| mmu_miR_453_002484 | 0.579 | 0.715 | −0.434 | 0.809 | −1.012 | 0.450 |
| mmu_miR_455_002455 | 1.844 | 0.207 | 0.606 | 0.759 | −1.238 | 0.402 |
| mmu_miR_463_002582 | −4.499 | 0.001 | 3.630 | 0.009 | 8.129 | 0.000 |
| mmu_miR_463_002662 | −5.584 | 0.030 | 1.934 | 0.513 | 7.518 | 0.002 |
| mmu_miR_464_001081 | 0.444 | 0.691 | −0.367 | 0.767 | −0.811 | 0.389 |
| mmu_miR_465C_5P_002654 | −7.133 | 0.000 | 1.188 | 0.611 | 8.321 | 0.000 |
| mmu_miR_465a_3p_002040 | −0.197 | 0.971 | −2.298 | 0.443 | −2.101 | 0.457 |
| mmu_miR_465a_5p_001082 | 5.938 | 0.384 | 8.145 | 0.218 | 2.207 | 0.796 |
| mmu_miR_465b_5p_002485 | −6.227 | 0.143 | −3.527 | 0.457 | 2.700 | 0.556 |
| mmu_miR_466E_5P_002718 | −6.684 | 0.134 | 2.273 | 0.690 | 8.957 | 0.028 |
| mmu_miR_466J_002817 | 1.086 | 0.501 | 2.150 | 0.146 | 1.063 | 0.493 |
| mmu_miR_466a_3p_002586 | 4.266 | 0.000 | 2.670 | 0.001 | −1.596 | 0.027 |
| mmu_miR_466b_3_3p_002500 | 3.169 | 0.007 | 1.999 | 0.090 | −1.170 | 0.329 |
| mmu_miR_466d_5p_002534 | −1.943 | 0.760 | −1.513 | 0.819 | 0.430 | 0.958 |
| mmu_miR_466g_241015_mat | 4.854 | 0.037 | 4.487 | 0.052 | −0.368 | 0.920 |
| mmu_miR_466h_002516 | 1.329 | 0.564 | −0.365 | 0.909 | −1.694 | 0.428 |
| mmu_miR_466k_240990_mat | −6.981 | 0.010 | −0.324 | 0.942 | 6.657 | 0.010 |
| mmu_miR_467F_002886 | −2.461 | 0.478 | 2.593 | 0.472 | 5.054 | 0.093 |
| mmu_miR_467H_002809 | 3.127 | 0.009 | 2.407 | 0.040 | −0.720 | 0.585 |
| mmu_miR_467a_001826 | 3.718 | 0.007 | 3.475 | 0.011 | −0.243 | 0.911 |
| mmu_miR_467a_002587 | 5.996 | 0.000 | 2.590 | 0.023 | −3.407 | 0.002 |
| mmu_miR_467b_001671 | 3.803 | 0.001 | 1.822 | 0.123 | −1.981 | 0.072 |
| mmu_miR_467b_001684 | −3.066 | 0.161 | 2.549 | 0.263 | 5.615 | 0.005 |
| mmu_miR_467c_002517 | 3.423 | 0.067 | 5.308 | 0.005 | 1.884 | 0.320 |
| mmu_miR_467d_002518 | 1.039 | 0.471 | 3.106 | 0.018 | 2.067 | 0.100 |
| mmu_miR_467e_002568 | −2.038 | 0.332 | 2.366 | 0.263 | 4.404 | 0.017 |
| mmu_miR_467e_002569 | −1.612 | 0.475 | −1.814 | 0.436 | −0.201 | 0.956 |
| mmu_miR_468_001085 | 0.199 | 0.948 | −0.472 | 0.841 | −0.671 | 0.753 |
| mmu_miR_469_001086 | −0.289 | 0.966 | −3.866 | 0.314 | −3.576 | 0.322 |
| mmu_miR_470_002588 | 0.550 | 0.727 | 0.040 | 0.988 | −0.510 | 0.748 |
| mmu_miR_470_002589 | −4.623 | 0.431 | 6.052 | 0.293 | 10.676 | 0.033 |
| mmu_miR_471_002605 | 0.471 | 0.396 | −0.832 | 0.106 | −1.303 | 0.007 |
| mmu_miR_483_001291 | −7.182 | 0.016 | 0.523 | 0.910 | 7.704 | 0.007 |
| mmu_miR_483_002560 | −0.211 | 0.917 | 2.238 | 0.061 | 2.449 | 0.029 |
| mmu_miR_484_001821 | 0.025 | 0.977 | 0.745 | 0.109 | 0.720 | 0.102 |
| mmu_miR_485_3p_001943 | 0.448 | 0.470 | −1.317 | 0.019 | −1.765 | 0.001 |
| mmu_miR_486_001278 | 7.621 | 0.000 | −0.317 | 0.878 | −7.938 | 0.000 |
| mmu_miR_487b_001285 | −0.413 | 0.511 | −1.390 | 0.013 | −0.977 | 0.069 |
| mmu_miR_487b_001306 | 1.130 | 0.042 | −1.643 | 0.004 | −2.773 | 0.000 |
| mmu_miR_488_001659 | 2.139 | 0.110 | 0.546 | 0.761 | −1.593 | 0.218 |
| mmu_miR_488_002014 | −0.798 | 0.821 | 0.967 | 0.780 | 1.765 | 0.521 |
| mmu_miR_489_001302 | −4.043 | 0.047 | −4.622 | 0.022 | −0.579 | 0.829 |
| mmu_miR_490_001037 | −5.700 | 0.000 | −7.472 | 0.000 | −1.772 | 0.133 |
| mmu_miR_491_001630 | 1.394 | 0.177 | −1.794 | 0.077 | −3.187 | 0.001 |
| mmu_miR_493_002519 | −1.247 | 0.654 | 0.386 | 0.916 | 1.634 | 0.515 |
| mmu_miR_494_001293 | 1.139 | 0.529 | 0.645 | 0.767 | −0.494 | 0.817 |
| mmu_miR_494_002365 | −0.304 | 0.875 | −0.821 | 0.596 | −0.517 | 0.753 |
| mmu_miR_495_001663 | −0.444 | 0.295 | −2.866 | 0.000 | −2.422 | 0.000 |
| mmu_miR_496_001953 | 0.941 | 0.783 | −2.507 | 0.366 | −3.449 | 0.152 |
| mmu_miR_497_001346 | 2.729 | 0.018 | 3.639 | 0.002 | 0.910 | 0.461 |
| mmu_miR_499_001352 | −4.297 | 0.036 | −3.448 | 0.092 | 0.849 | 0.747 |

TABLE 4-continued

| Brain Stem miRNA data. | | | | | | |
|---|---|---|---|---|---|---|
| mmu_miR_500_002606 | −1.002 | 0.395 | 0.234 | 0.878 | 1.236 | 0.253 |
| mmu_miR_501_001356 | −0.445 | 0.893 | −0.496 | 0.864 | −0.051 | 0.983 |
| mmu_miR_501_3p_001651 | −0.968 | 0.172 | −0.313 | 0.733 | 0.654 | 0.356 |
| mmu_miR_503_002456 | 1.477 | 0.363 | 0.388 | 0.852 | −1.089 | 0.501 |
| mmu_miR_503_002536 | −2.388 | 0.018 | 1.124 | 0.313 | 3.512 | 0.001 |
| mmu_miR_504_002084 | −2.471 | 0.018 | −2.326 | 0.026 | 0.145 | 0.933 |
| mmu_miR_505_001655 | 0.485 | 0.766 | 1.083 | 0.424 | 0.598 | 0.675 |
| mmu_miR_509_3p_002521 | −2.319 | 0.727 | 2.697 | 0.693 | 5.016 | 0.351 |
| mmu_miR_509_5p_002520 | 0.342 | 0.968 | 0.142 | 0.988 | −0.199 | 0.977 |
| mmu_miR_511_002549 | −1.790 | 0.334 | 1.466 | 0.457 | 3.256 | 0.046 |
| mmu_miR_532_3p_002355 | −0.835 | 0.214 | 0.919 | 0.167 | 1.754 | 0.005 |
| mmu_miR_532_5p_001518 | −0.405 | 0.452 | 0.902 | 0.065 | 1.307 | 0.005 |
| mmu_miR_539_001286 | −0.188 | 0.912 | −2.111 | 0.035 | −1.923 | 0.043 |
| mmu_miR_540_3p_001310 | −3.321 | 0.003 | −3.254 | 0.004 | 0.067 | 0.972 |
| mmu_miR_540_5p_002561 | −1.877 | 0.118 | −1.578 | 0.195 | 0.300 | 0.856 |
| mmu_miR_541_002562 | −1.942 | 0.002 | −4.816 | 0.000 | −2.874 | 0.000 |
| mmu_miR_542_3p_001284 | 1.819 | 0.193 | 1.065 | 0.500 | −0.753 | 0.628 |
| mmu_miR_542_5p_002563 | 0.179 | 0.977 | 0.092 | 0.989 | −0.087 | 0.983 |
| mmu_miR_543_001298 | −0.217 | 0.804 | −2.700 | 0.000 | −2.483 | 0.000 |
| mmu_miR_543_002376 | −0.267 | 0.654 | −2.495 | 0.000 | −2.228 | 0.000 |
| mmu_miR_544_002550 | −0.130 | 0.941 | −1.021 | 0.316 | −0.891 | 0.356 |
| mmu_miR_546_001312 | −5.794 | 0.468 | −8.293 | 0.286 | −2.499 | 0.796 |
| mmu_miR_547_002564 | −3.094 | 0.294 | −0.926 | 0.819 | 2.167 | 0.466 |
| mmu_miR_551b_001535 | −2.334 | 0.047 | 0.180 | 0.926 | 2.514 | 0.022 |
| mmu_miR_574_3p_002349 | −0.647 | 0.445 | 1.130 | 0.151 | 1.777 | 0.014 |
| mmu_miR_582_3p_002567 | −0.877 | 0.691 | 0.596 | 0.818 | 1.473 | 0.432 |
| mmu_miR_582_5p_002566 | 1.996 | 0.023 | −0.928 | 0.341 | −2.923 | 0.001 |
| mmu_miR_590_5p_001984 | 2.049 | 0.431 | −0.089 | 0.985 | −2.138 | 0.386 |
| mmu_miR_592_002017 | 0.415 | 0.654 | −3.098 | 0.000 | −3.512 | 0.000 |
| mmu_miR_598_002476 | 0.893 | 0.510 | −0.328 | 0.850 | −1.221 | 0.329 |
| mmu_miR_599_241117_mat | 2.582 | 0.363 | 5.015 | 0.056 | 2.433 | 0.374 |
| mmu_miR_615_3p_001960 | −3.602 | 0.001 | −2.235 | 0.025 | 1.367 | 0.165 |
| mmu_miR_615_5p_002353 | 0.480 | 0.396 | 0.667 | 0.226 | 0.186 | 0.793 |
| mmu_miR_652_002352 | 1.214 | 0.300 | 1.720 | 0.127 | 0.507 | 0.717 |
| mmu_miR_654_3p_002239 | 0.510 | 0.597 | −0.250 | 0.829 | −0.761 | 0.376 |
| mmu_miR_654_5p_002522 | 0.460 | 0.711 | −0.398 | 0.767 | −0.858 | 0.402 |
| mmu_miR_665_002607 | −0.978 | 0.437 | −2.179 | 0.056 | −1.201 | 0.301 |
| mmu_miR_666_3p_002448 | −0.334 | 0.926 | 1.669 | 0.494 | 2.004 | 0.358 |
| mmu_miR_666_5p_001952 | −3.717 | 0.000 | −3.926 | 0.000 | −0.209 | 0.838 |
| mmu_miR_667_001949 | −0.742 | 0.193 | −3.359 | 0.000 | −2.617 | 0.000 |
| mmu_miR_668_001947 | 0.269 | 0.942 | −1.880 | 0.389 | −2.149 | 0.277 |
| mmu_miR_669C_002646 | 1.748 | 0.212 | 2.802 | 0.037 | 1.054 | 0.466 |
| mmu_miR_669D_002808 | 2.796 | 0.038 | 2.791 | 0.036 | −0.005 | 0.999 |
| mmu_miR_669E_002774 | 2.541 | 0.119 | 2.451 | 0.128 | −0.090 | 0.973 |
| mmu_miR_669G_002813 | 0.462 | 0.396 | −0.486 | 0.383 | −0.948 | 0.044 |
| mmu_miR_669H_5P_002906 | −2.661 | 0.214 | −0.732 | 0.804 | 1.930 | 0.369 |
| mmu_miR_669a_001683 | 3.519 | 0.025 | 2.117 | 0.193 | −1.402 | 0.390 |
| mmu_miR_669l_121149_mat | 3.005 | 0.018 | 2.971 | 0.020 | −0.034 | 0.983 |
| mmu_miR_669m_121190_mat | 3.548 | 0.097 | 3.273 | 0.125 | −0.275 | 0.937 |
| mmu_miR_669n_197143_mat | 2.199 | 0.046 | 2.340 | 0.031 | 0.140 | 0.937 |
| mmu_miR_669o_121176_mat | 2.489 | 0.093 | 3.376 | 0.020 | 0.888 | 0.584 |

TABLE 4-continued

| Brain Stem miRNA data. | | | | | | |
|---|---|---|---|---|---|---|
| mmu_miR_670_002020 | −5.399 | 0.226 | −0.086 | 0.991 | 5.313 | 0.210 |
| mmu_miR_671_3p_002322 | 3.660 | 0.000 | 0.184 | 0.894 | −3.476 | 0.000 |
| mmu_miR_672_002327 | 1.468 | 0.438 | −4.469 | 0.010 | −5.937 | 0.001 |
| mmu_miR_673_001954 | −3.214 | 0.250 | 3.497 | 0.217 | 6.711 | 0.009 |
| mmu_miR_673_3p_002449 | −2.712 | 0.363 | −3.672 | 0.201 | −0.960 | 0.796 |
| mmu_miR_674_001956 | 1.438 | 0.063 | 2.249 | 0.004 | 0.812 | 0.298 |
| mmu_miR_674_002021 | 1.780 | 0.295 | 0.434 | 0.850 | −1.345 | 0.429 |
| mmu_miR_675_3p_001941 | −9.952 | 0.123 | −0.320 | 0.980 | 9.632 | 0.112 |
| mmu_miR_675_5p_001940 | 3.084 | 0.363 | 3.081 | 0.381 | −0.003 | 0.999 |
| mmu_miR_676_001958 | 0.659 | 0.585 | −0.245 | 0.866 | −0.904 | 0.408 |
| mmu_miR_676_001959 | 2.334 | 0.090 | 2.093 | 0.127 | −0.241 | 0.911 |
| mmu_miR_677_001660 | 0.825 | 0.587 | 1.358 | 0.353 | 0.533 | 0.753 |
| mmu_miR_679_001662 | −3.445 | 0.527 | −3.790 | 0.501 | −0.345 | 0.967 |
| mmu_miR_680_001664 | −5.128 | 0.377 | 1.727 | 0.819 | 6.855 | 0.192 |
| mmu_miR_682_001666 | 2.369 | 0.664 | 4.482 | 0.376 | 2.113 | 0.710 |
| mmu_miR_683_001668 | −0.113 | 0.984 | 6.183 | 0.116 | 6.296 | 0.089 |
| mmu_miR_684_001669 | 0.369 | 0.246 | −0.788 | 0.010 | −1.156 | 0.000 |
| mmu_miR_685_001670 | −5.085 | 0.172 | 3.602 | 0.375 | 8.687 | 0.011 |
| mmu_miR_686_001672 | 0.107 | 0.975 | −0.885 | 0.655 | −0.992 | 0.573 |
| mmu_miR_687_001674 | 0.548 | 0.576 | −0.561 | 0.587 | −1.109 | 0.182 |
| mmu_miR_688_001675 | 0.012 | 0.998 | −0.181 | 0.965 | −0.193 | 0.960 |
| mmu_miR_690_001677 | −1.766 | 0.217 | 0.714 | 0.693 | 2.480 | 0.057 |
| mmu_miR_691_001678 | −3.965 | 0.432 | 1.395 | 0.829 | 5.360 | 0.244 |
| mmu_miR_692_001679 | −2.816 | 0.224 | −0.184 | 0.965 | 2.632 | 0.238 |
| mmu_miR_693_001680 | 4.152 | 0.360 | 9.096 | 0.028 | 4.943 | 0.235 |
| mmu_miR_693_3p_002036 | −0.999 | 0.893 | 3.458 | 0.523 | 4.457 | 0.353 |
| mmu_miR_694_001681 | −5.086 | 0.191 | 5.440 | 0.158 | 10.526 | 0.004 |
| mmu_miR_695_001627 | 1.089 | 0.846 | 0.000 | 1.000 | −1.089 | 0.833 |
| mmu_miR_696_001628 | −10.237 | 0.055 | −1.261 | 0.864 | 8.976 | 0.074 |
| mmu_miR_697_001631 | −1.824 | 0.600 | −1.760 | 0.636 | 0.064 | 0.983 |
| mmu_miR_698_001632 | −0.353 | 0.782 | −0.299 | 0.819 | 0.055 | 0.972 |
| mmu_miR_700_001634 | 1.802 | 0.180 | −0.031 | 0.991 | −1.834 | 0.152 |
| mmu_miR_701_001635 | −3.065 | 0.271 | 1.873 | 0.553 | 4.938 | 0.048 |
| mmu_miR_702_001636 | −3.209 | 0.161 | −2.560 | 0.285 | 0.649 | 0.822 |
| mmu_miR_704_001639 | 1.857 | 0.229 | 1.788 | 0.263 | −0.069 | 0.977 |
| mmu_miR_706_001641 | −2.269 | 0.715 | 3.116 | 0.606 | 5.385 | 0.277 |
| mmu_miR_707_001642 | 0.511 | 0.403 | −0.423 | 0.515 | −0.934 | 0.080 |
| mmu_miR_708_002341 | 2.213 | 0.000 | 0.051 | 0.964 | −2.162 | 0.000 |
| mmu_miR_710_001645 | 2.329 | 0.801 | 4.129 | 0.610 | 1.800 | 0.838 |
| mmu_miR_711_001646 | 0.101 | 0.991 | 3.132 | 0.729 | 3.030 | 0.712 |
| mmu_miR_712_001961 | 1.804 | 0.179 | 1.326 | 0.368 | −0.478 | 0.789 |
| mmu_miR_712_002636 | −1.292 | 0.804 | 2.175 | 0.640 | 3.466 | 0.371 |
| mmu_miR_713_001648 | −0.382 | 0.977 | 0.850 | 0.940 | 1.232 | 0.911 |
| mmu_miR_715_001649 | 0.510 | 0.939 | 1.165 | 0.819 | 0.655 | 0.911 |
| mmu_miR_717_001652 | −7.056 | 0.217 | 2.589 | 0.732 | 9.645 | 0.065 |
| mmu_miR_718_001656 | −0.482 | 0.935 | −3.012 | 0.411 | −2.530 | 0.466 |
| mmu_miR_719_001673 | −0.657 | 0.789 | 0.090 | 0.980 | 0.747 | 0.746 |
| mmu_miR_720_001629 | −3.631 | 0.000 | 2.464 | 0.010 | 6.095 | 0.000 |
| mmu_miR_721_001657 | 1.092 | 0.927 | 4.888 | 0.556 | 3.796 | 0.636 |
| mmu_miR_741_002457 | −0.597 | 0.910 | −2.256 | 0.539 | −1.658 | 0.646 |
| mmu_miR_742_002038 | 0.570 | 0.821 | 0.467 | 0.852 | −0.102 | 0.973 |

TABLE 4-continued

| Brain Stem miRNA data. | | | | | | |
|---|---|---|---|---|---|---|
| mmu_miR_742_002458 | −0.169 | 0.980 | 0.680 | 0.928 | 0.849 | 0.911 |
| mmu_miR_743a_002469 | −4.064 | 0.069 | 1.079 | 0.722 | 5.143 | 0.013 |
| mmu_miR_743b_3p_002471 | 0.585 | 0.659 | 0.032 | 0.989 | −0.553 | 0.672 |
| mmu_miR_743b_5p_002470 | −2.430 | 0.509 | 1.586 | 0.727 | 4.016 | 0.218 |
| mmu_miR_744_002324 | −0.153 | 0.917 | −0.525 | 0.614 | −0.371 | 0.735 |
| mmu_miR_758_002025 | −1.368 | 0.177 | −0.819 | 0.471 | 0.549 | 0.628 |
| mmu_miR_759_002034 | 0.622 | 0.924 | 5.330 | 0.161 | 4.709 | 0.197 |
| mmu_miR_761_002030 | −8.699 | 0.105 | 3.498 | 0.585 | 12.197 | 0.014 |
| mmu_miR_762_002028 | −0.461 | 0.948 | 1.558 | 0.761 | 2.018 | 0.638 |
| mmu_miR_763_002033 | 0.943 | 0.894 | 1.375 | 0.827 | 0.433 | 0.956 |
| mmu_miR_764_3p_002032 | −2.360 | 0.510 | −3.720 | 0.285 | −1.360 | 0.746 |
| mmu_miR_764_5p_002031 | −6.814 | 0.001 | −3.976 | 0.033 | 2.839 | 0.117 |
| mmu_miR_767_241081_mat | 0.370 | 0.237 | −0.783 | 0.010 | −1.153 | 0.000 |
| mmu_miR_770_3p_002027 | −3.859 | 0.001 | −4.896 | 0.000 | −1.036 | 0.363 |
| mmu_miR_770_5p_002608 | −2.235 | 0.015 | −2.885 | 0.002 | −0.650 | 0.512 |
| mmu_miR_7a_000268 | 0.844 | 0.804 | 2.323 | 0.389 | 1.479 | 0.585 |
| mmu_miR_7b_002555 | −0.335 | 0.912 | −0.912 | 0.704 | −0.577 | 0.814 |
| mmu_miR_802_002029 | 1.739 | 0.322 | 0.530 | 0.820 | −1.209 | 0.494 |
| mmu_miR_804_002044 | 2.854 | 0.703 | 7.906 | 0.201 | 5.052 | 0.419 |
| mmu_miR_805_002045 | −5.215 | 0.172 | 2.407 | 0.596 | 7.622 | 0.029 |
| mmu_miR_871_002354 | 2.372 | 0.191 | 2.245 | 0.229 | −0.127 | 0.967 |
| mmu_miR_872_002264 | 2.615 | 0.000 | 1.687 | 0.004 | −0.928 | 0.091 |
| mmu_miR_872_002542 | 2.489 | 0.000 | 1.015 | 0.064 | −1.474 | 0.005 |
| mmu_miR_873_002356 | −2.329 | 0.048 | −2.375 | 0.041 | −0.045 | 0.979 |
| mmu_miR_874_002268 | 0.446 | 0.890 | 1.560 | 0.501 | 1.115 | 0.628 |
| mmu_miR_875_3p_002547 | −1.275 | 0.836 | 1.461 | 0.818 | 2.737 | 0.573 |
| mmu_miR_876_3p_002464 | 0.243 | 0.961 | 0.655 | 0.852 | 0.412 | 0.919 |
| mmu_miR_876_5p_002463 | 0.826 | 0.614 | 0.646 | 0.732 | −0.180 | 0.937 |
| mmu_miR_877_002548 | −6.682 | 0.012 | −0.792 | 0.832 | 5.890 | 0.019 |
| mmu_miR_878_3p_002541 | −6.422 | 0.095 | 3.540 | 0.401 | 9.962 | 0.006 |
| mmu_miR_878_5p_002540 | −0.658 | 0.910 | −1.447 | 0.761 | −0.789 | 0.883 |
| mmu_miR_879_002472 | 0.227 | 0.943 | −0.081 | 0.981 | −0.308 | 0.911 |
| mmu_miR_879_002473 | 1.612 | 0.289 | −1.753 | 0.258 | −3.365 | 0.013 |
| mmu_miR_880_002665 | −5.061 | 0.409 | 0.830 | 0.926 | 5.891 | 0.301 |
| mmu_miR_881_002475 | −0.080 | 0.990 | 0.797 | 0.893 | 0.877 | 0.888 |
| mmu_miR_881_002609 | 0.056 | 0.991 | 1.441 | 0.761 | 1.385 | 0.755 |
| mmu_miR_882_002610 | 0.369 | 0.246 | −0.788 | 0.010 | −1.156 | 0.000 |
| mmu_miR_883B_5P_002669 | 0.678 | 0.917 | 1.334 | 0.809 | 0.655 | 0.913 |
| mmu_miR_883a_3p_002461 | 0.103 | 0.977 | 1.354 | 0.578 | 1.251 | 0.574 |
| mmu_miR_883a_5p_002611 | 0.419 | 0.318 | −0.652 | 0.102 | −1.071 | 0.005 |
| mmu_miR_883b_3p_002565 | −0.360 | 0.948 | −0.235 | 0.966 | 0.125 | 0.977 |
| mmu_miR_92a_000430 | −2.849 | 0.000 | 0.961 | 0.023 | 3.809 | 0.000 |
| mmu_miR_92a_002496 | 0.354 | 0.866 | −0.426 | 0.826 | −0.780 | 0.613 |
| mmu_miR_93_001090 | 1.241 | 0.117 | 1.315 | 0.092 | 0.074 | 0.958 |
| mmu_miR_96_000186 | −2.682 | 0.166 | −2.479 | 0.204 | 0.204 | 0.953 |
| mmu_miR_98_000577 | 2.296 | 0.172 | −1.357 | 0.466 | −3.653 | 0.017 |
| mmu_miR_99a_000435 | 1.396 | 0.070 | 1.246 | 0.106 | −0.150 | 0.907 |
| mmu_miR_99b_000436 | 2.337 | 0.016 | 1.533 | 0.122 | −0.804 | 0.435 |
| mmu_miR_9_000583 | 1.574 | 0.000 | 1.539 | 0.000 | −0.035 | 0.960 |

REFERENCES FOR THE EXAMPLES

1. Sayed D & Abdellatif M (2011) MicroRNAs in development and disease. *Physiol Rev* 91(3):827-887.
2. Ardekani A M & Naeini M M (2010) The Role of MicroRNAs in Human Diseases. *Avicenna J Med Biotechnol* 2(4):161-179.
3. O'Connell R M, Rao D S, Chaudhuri A A, & Baltimore D (2010) Physiological and pathological roles for microRNAs in the immune system. *Nat Rev Immunol* 10(2): 111-122.
4. Koval E D, et al. (2013) Method for widespread microRNA-155 inhibition prolongs survival in ALS-model mice. *Human Molecular Genetics* 22(20):4127-4135.
5. Chen X, et al. (2008) Characterization of microRNAs in serum: a novel class of biomarkers for diagnosis of cancer and other diseases. *Cell Res* 18(10):997-1006.
6. Butovsky O, et al. (2014) Targeting miR-155 restores abnormal microglia and attenuates disease in SOD1 mice. *Ann Neurol.*

Ilieva H, Polymenidou M, & Cleveland D W (2009) Non-cell autonomous toxicity in neurodegenerative disorders: ALS and beyond. *The Journal of Cell Biology* 187(6): 761-772.

8. Boillee S, et al. (2006) Onset and progression in inherited ALS determined by motor neurons and microglia. *Science* 312(5778):1389-1392.
9. Doyle J P, et al. (2008) Application of a Translational Profiling Approach for the Comparative Analysis of CNS Cell Types. *Cell* 135(4):749-762.
10. He M, et al. (2012) Cell-type-based analysis of microRNA profiles in the mouse brain. *Neuron* 73(1):35-48.
11. Dougherty J D, Schmidt E F, Nakajima M, & Heintz N (2010) Analytical approaches to RNA profiling data for the identification of genes enriched in specific cells. *Nucleic Acids Research* 38(13):4218-4230.
12. Gaughwin P, Ciesla M, Yang H, Lim B, & Brundin P (2011) Stage-specific modulation of cortical neuronal development by Mmu-miR-134. *Cereb Cortex* 21(8): 1857-1869.
13. Kocerha J, et al. (2009) MicroRNA-219 modulates NMDA receptor-mediated neurobehavioral dysfunction. *Proc Natl Acad Sci USA* 106(9):3507-3512.
14. Ying Z, et al. (2013) Loss of miR-204 expression enhances glioma migration and stem cell-like phenotype. *Cancer Res* 73(2):990-999.
15. Lu X, et al. (2013) miR-142-3p regulates the formation and differentiation of hematopoietic stem cells in vertebrates. *Cell Res* 23(12):1356-1368.
16. Peltier H J & Latham G J (2008) Normalization of microRNA expression levels in quantitative RT-PCR assays: identification of suitable reference RNA targets in normal and cancerous human solid tissues. *RNA* 14(5): 844-852.
17. Xu X, Wells A B, O'Brien D R, Nehorai A, & Dougherty J D (2014) Cell Type-Specific Expression Analysis to Identify Putative Cellular Mechanisms for Neurogenetic Disorders. *Journal of Neuroscience* 34(4):1420-1431.
18. Wooley C M, et al. (2005) Gait analysis detects early changes in transgenic SOD1(G93A) mice. *Muscle Nerve* 32(1):43-50.
19. Howland D S, et al. (2002) Focal loss of the glutamate transporter EAAT2 in a transgenic rat model of SOD1 mutant-mediated amyotrophic lateral sclerosis (ALS). *Proc Natl Acad Sci USA* 99(3):1604-1609.
20. Smith R A, et al. (2006) Antisense oligonucleotide therapy for neurodegenerative disease. *J Clin Invest* 116 (8):2290-2296.
21. Thiebes K P, et al. (2015) miR-218 is essential to establish motor neuron fate as a downstream effector of IsI1-Lhx3. *Nat Commun* 6:7718.
22. Amin N D, et al. (2015) Loss of motoneuron-specific microRNA-218 causes systemic neuromuscular failure. *Science* 350(6267):1525-1529.
23. Aluise C D, Sowell R A, & Butterfield D A (2008) Peptides and proteins in plasma and cerebrospinal fluid as biomarkers for the prediction, diagnosis, and monitoring of therapeutic efficacy of Alzheimer's disease. *Biochim Biophys Acta* 1782(10):549-558.
24. Su Z, et al. (2014) Discovery of a biomarker and lead small molecules to target r(GGGGCC)-associated defects in c9FTD/ALS. *Neuron* 83(5):1043-1050.
25. Mitchell P S, et al. (2008) Circulating microRNAs as stable blood-based markers for cancer detection. *Proc Natl Acad Sci USA* 105(30):10513-10518.
26. Arroyo J D, et a/. (2011) Argonaute2 complexes carry a population of circulating microRNAs independent of vesicles in human plasma. *Proc Natl Acad Sci USA* 108(12):5003-5008.
27. Valadi H, et a/. (2007) Exosome-mediated transfer of mRNAs and microRNAs is a novel mechanism of genetic exchange between cells. *Nat Cell Biol* 9(6):654-659.
28. Wang K, Zhang S, Weber J, Baxter D, & Galas D J (2010) Export of microRNAs and microRNA-protective protein by mammalian cells. *Nucleic Acids Res* 38(20): 7248-7259.
29. Risso D, Massa M S, Chiogna M, & Romualdi C (2009) A modified LOESS normalization applied to microRNA arrays: a comparative evaluation. *Bioinformatics* 25(20): 2685-2691.
30. Smyth G K (2004) Linear models and empirical bayes methods for assessing differential expression in microarray experiments. *Stat Appl Genet Mol Biol* 3:Article3.
31. Klipper-Aurbach Y, et al. (1995) Mathematical formulae for the prediction of the residual beta cell function during the first two years of disease in children and adolescents with insulin-dependent diabetes mellitus. *Med Hypotheses* 45(5):486-490.

What is claimed is:

1. A method to improve motor neuron function in a subject diagnosed with a motor neuron disease, suspected of having a motor neuron disease or at risk for a motor neuron disease, the method comprising administering a miR-218, miR-133a, miR-133b, miR-1193, miR-34b, miR-380, or miR-379 composition, or combination thereof, to the subject, wherein the miR-218 composition decreases the expression of miR-218 and wherein improvement in motor neuron function results in an improvement of a symptom associated with a motor neuron disease.

2. A method to improve motor neuron function in a subject diagnosed with a motor neuron disease, suspected of having a motor neuron disease or at risk for a motor neuron disease, the method comprising administering a composition comprising a miR-218 agent capable of decreasing the amount or expression of miR-218, wherein the miR-218 agent is an antisense oligonucleotide and wherein improvement in motor neuron function results in an improvements of a symptom associated with a motor neuron disease.

3. The method of claim 2, wherein the miR-218 agent comprises nucleic acid sequences complementary to a mature miR218.

4. The method of claim 3, wherein the miR-218 agent consists of 8-25 nucleotides at least 90% complementary to a mature miR-218.

5. The method of claim 2, wherein the miR-218 agent comprises nucleic acid sequences complementary to a seed region of miR-218.

* * * * *